(12) United States Patent
Wittrup et al.

(10) Patent No.: US 12,227,559 B2
(45) Date of Patent: Feb. 18, 2025

(54) COLLAGEN-LOCALIZED IMMUNOMODULATORY MOLECULES AND METHODS THEREOF

(71) Applicant: MASSACHUSETTS INSTITUTE OF TECHNOLOGY, Cambridge, MA (US)

(72) Inventors: Karl Dane Wittrup, Boston, MA (US); Noor Momin, Cambridge, MA (US); Joseph Palmeri, Cambridge, MA (US); Magnolia Chinn, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 18/056,825

(22) Filed: Nov. 18, 2022

(65) Prior Publication Data
US 2023/0174623 A1    Jun. 8, 2023

Related U.S. Application Data

(63) Continuation of application No. 16/523,965, filed on Jul. 26, 2019, now abandoned.

(60) Provisional application No. 62/738,981, filed on Sep. 28, 2018.

(51) Int. Cl.
| | |
|---|---|
| *A61K 39/00* | (2006.01) |
| *C07K 14/00* | (2006.01) |
| *C07K 14/47* | (2006.01) |
| *C07K 14/705* | (2006.01) |
| *C07K 14/715* | (2006.01) |
| *C07K 14/725* | (2006.01) |
| *C07K 14/78* | (2006.01) |
| *C12N 5/0783* | (2010.01) |
| *A61K 38/00* | (2006.01) |

(52) U.S. Cl.
CPC .......... *C07K 14/78* (2013.01); *A61K 39/0011* (2013.01); *A61K 39/4611* (2023.05); *A61K 39/4631* (2023.05); *A61K 39/4636* (2023.05); *A61K 39/464499* (2023.05); *C07K 14/473* (2013.01); *C07K 14/4741* (2013.01); *C07K 14/7051* (2013.01); *C07K 14/70521* (2013.01); *C07K 14/70532* (2013.01); *C07K 14/7155* (2013.01); *C12N 5/0636* (2013.01); *A61K 38/00* (2013.01); *A61K 2239/31* (2023.05); *A61K 2239/38* (2023.05); *A61K 2239/57* (2023.05); *C07K 2317/92* (2013.01); *C07K 2319/03* (2013.01); *C07K 2319/30* (2013.01); *C07K 2319/74* (2013.01)

(58) Field of Classification Search
None
See application file for complete search history.

(56) References Cited

U.S. PATENT DOCUMENTS

| | | |
|---|---|---|
| 9,879,062 B2 | 1/2018 | Hubbell et al. |
| 2002/0177571 A1 | 11/2002 | Gordon et al. |
| 2009/0305352 A1 | 12/2009 | Dai et al. |
| 2014/0010832 A1 | 1/2014 | Hubbell et al. |
| 2015/0031625 A1 | 1/2015 | Gordon et al. |
| 2015/0071926 A1 | 3/2015 | Fertala et al. |
| 2015/0132254 A1 | 5/2015 | Wittrup et al. |
| 2018/0179274 A1 | 6/2018 | Lanzavecchia et al. |
| 2018/0222959 A1 | 8/2018 | Hall et al. |
| 2019/0358277 A1 | 11/2019 | Yun et al. |
| 2020/0010539 A1 | 1/2020 | Bleck |
| 2024/0101630 A1 | 3/2024 | Mehta et al. |

FOREIGN PATENT DOCUMENTS

| | | | |
|---|---|---|---|
| CN | 102115495 A | * | 7/2011 |
| CN | 111683687 A | | 9/2020 |
| WO | 2000049159 A1 | | 8/2000 |
| WO | 2007/102736 | | 9/2007 |
| WO | 2012/112690 | | 8/2012 |
| WO | 2014160956 | | 3/2014 |
| WO | 2016054107 | | 7/2016 |
| WO | 2018/112394 | | 6/2018 |
| WO | 2019/173289 | | 9/2019 |
| WO | 2020068261 | | 4/2020 |

OTHER PUBLICATIONS

Mehta et al. 1093 CLN-617 combines IL-2 and IL-12 in a single molecule to optimally balance safety and efficacy upon intratumoral injection. Abstract 1093. Journal for ImmunoTherapy of Cancer 2023 (Year: 2023).*
Zhao J, Si Y, Cheng M, Yang Y, Niu Y, Li X, et al. (2013) Albumin Fusion of Interleukin-28B: Production and Characterization of Its Biological Activities and Protein Stability. PLoS One 8(5): e64301. (Year: 2013).*
Allen, E. et al., "Combined antiangiogenic and anti-PD-L 1 therapy stimulates tumor immunity through HEV formation," Science Translational Medicine, vol. 9 (385): 14 pages (2017).
Aloisi, F. et al., "Lymphoid neogenesis in chronic inflammatory diseases," Nat Rev Immunol., vol. 6: 205-217 (2006).
An. B., et al., "Collagen interactions: Drug design and delivery ," Adv Drug Deliv Rev., vol. 97:69-84 (2016).
Aper, S. et al., "Colorful Protein-Based Fluorescent Probes for Collagen Imaging," PLoS One, DOI: 10.1371/journal.pone. 0114983, 21 pages (2014).
Aumailley, M. et al., Nidogen mediates the formation of ternary complexes of basement membrane components, Kidney International, vol. 43: 7-12 (1993).
Bauer, R. et al., "Structural Comparison of ColH and ColG Collagen-Binding Domain from Clostridium histolyticum," J_ Bacterial., vol. 195 (2):318-327(2013).

(Continued)

*Primary Examiner* — Maher M Haddad
(74) *Attorney, Agent, or Firm* — MCDONNELL BOEHNEN HULBERT & BERGHOFF LLP

(57) ABSTRACT

The present disclosure provides immunomodulatory fusion proteins comprising a collagen-binding domain operably linked to an immunomodulatory domain. The disclosure also features compositions and methods of using the same, for example, to treat cancer.

10 Claims, 26 Drawing Sheets

Figure 1A:
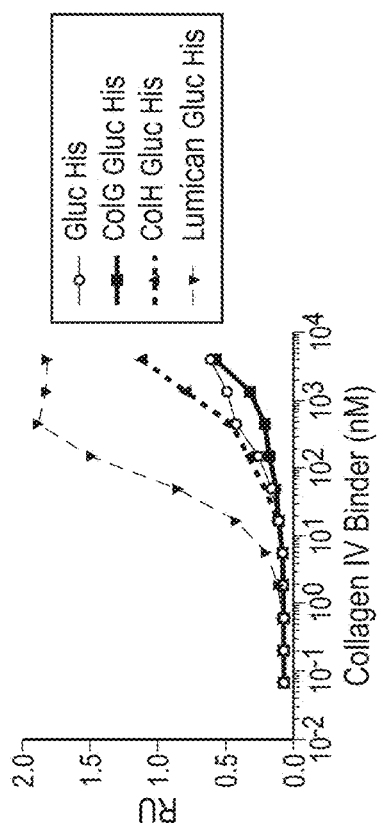

Specification includes a Sequence Listing.

(56) References Cited

OTHER PUBLICATIONS

Brewitz, A. et al., "CD8+ T Cells Orchestrate pDC-XCR1+ Dendritic Cell Spatial and Functional Cooperativity to Optimize Priming," Immunity, vol. 46: 205-219 (2017).

Brown, E. et al., "Dynamic imaging of collagen and its modulation in tumors in vivo using second-harmonic peneration," Nat Med., vol. 9(6):796-800 (2003).

Chao, Y. et al., "Combined local immunostimulatory radioisotope therapy and systemic immune checkpoint blockade Imparts potent antitumour responses," Nature Biomedical Engineering, vol. 2: 611-621 (2018).

Chen, S. et al., "The regulatory roles of small leucine-rich proteoglycans in extracellular matrix assembly," FEBS Journal, vol. 280: 2120-2137 (2013).

Dranoff, G. et al., "Vaccination with irradiated tumor cells engineered to secrete murine granulocyte-macrophage polony-stimulating factor stimulates potent, specific, and long-lasting antitumor immunity," PNAS, vol. 90:3539-3543 (1993).

Fang, M. et al., "Collagen as a double-edged sword in tumor progression," Tumour Biol., vol. 35:2871-2882 (2014).

Frantz, C. et al., "The extracellular matrix at a glance," J Cell Sci., vol. 123 (24):4195-4200 (2010).

Hisada, Y. et al., "Discovery of an uncovered region in fibrin clots and its clinical significance," Scientific Reports, vol. 3 2604: 7 pages {2013).

Ishihara, J. et al., "Laminin heparin-binding peptides bind to several growth factors and enhance diabetic wound healing," Nature Communications, vol. 9:2163: 14 pages {2018).

Ishihara, J. et al., "Matrix-binding checkpoint immunotherapies enhance antitumor efficacy and reduce adverse events," Science translational Medicine, vol. 9: 14 pages {2017).

Kalamajski, S. et al., Homologous Sequence in Lumican and Fibromodulin Leucine-rich Repeat 5-7 Competes for Collagen Binding, Journal of Biological Chemistry, vol. 284(1 ):534-539(2009).

Kar, U. et al., "Novel CCL21-Vault Nanocapsule Intratumoral Delivery Inhibits Lung Cancer Growth," PLoS One, vol. 6 (5): e18758: 8 pages (2011).

Karamanour, K. et al., "Lumican effectively regulates the estrogen receptors-associated functional properties of breast cancer cells, expression of matrix effectors and epithelial-to-mesenchymal transition," Scientific Reports, vol. 7:45138 15 pages (2017).

Kwong, B. et al., Localized Immunotherapy via Liposome-Anchored Anti-CD137 + IL-2 Prevents Lethal Toxicity and Elicits Local and Systemic Antitumor Immunity, Cancer Res., vol. 73:1547-1558 (2013).

Liang, C-M., et al., "Local Expression of Secondary Lymphoid Tissue Chemokine Delivered by Adena-Associated Virus Within the Tumor Bed Stimulates Strong Anti-Liver Tumor Immunity," Journal of Virology, vol. 81(17):9502-9511 (2007).

Iang, H et al., "A collagen-binding EGFR antibody fragment targeting tumors with a collagen-rich extracellular matrix," Sci. Rep., vol. 6: 14 pages {2016).

Lin, Y et al., "CCL21 Cancer Immunotherapy," Cancers, vol. 6: 1098-1110 (2014).

In, Y et al., "A Cytokine-Delivering Polymer Is Effective in Reducing Tumor Burden in a Head and Neck Squamous Cell Carcinoma Murine Model," otolaryngology-Head and Neck Surgery, vol. 151(3):447-453 (2014).

Lu, P et al., "The extracellular matrix: A dynamic niche in cancer progression," J Cell Biol, vol. 196(4): 395-406: (2012.

Marabelle, A et al., "Intratumoral Immunization: A New Paradigm for Cancer Therapy," Clin Cancer Res., vol. 20:1747-1756 (2014).

Mariathasan, S et al., "TGF-beta attenuates tumour response to PD-L 1 blockade by contributing to exclusion of T cells," Nature, vol. 554(7693): 544-548 (2018).

Marsland, B et al., "CCL 19 and CCL21 Induce a Potent Proinflammatory Differentiation Program in Licensed Dendritic Cells," Immunity, vol. 22:493-505 {2005).

Martino, M et al., "Growth Factors Engineered for Super-Affinity to the Extracellular Matrix Enhance Tissue Healing," Science, vol. 343(6173):885-888 (2014).

Momin, N et al., "Collagen anchoring of locally administered cytokines safely potentiates systemic cancer Immunotherapy ," Poster presentation- Disclosure, 1 page (2018).

Naba, A et al., "The Matrisome: In Silica Definition and In Vivo Characterization by Proteomics of Normal and Tumor Extracellular Matrices," Molecular & Cellular Proteomics 11: 10.107 4/mcp. M111.01464 7, 1-18 (2012).

Nishi, N et al., "Collagen-binding growth factors: Production and characterization of functional fusion proteins having ? collagen-binding domain," PNAS, vol_ 95: 7018-7023(1998).

Novak, L. et al., "Characterization of the CCL21-mediated melanoma-specific immune responses and in situ melanoma eradication," Mal Cancer Ther., vol. 6(6):1755-1764 (2007).

Obonai, T. et al., "Tumour imaging by the detection of fibrin clots in tumour stroma using an anti-fibrin Fab fragment," Scientific Reports, vol. 6:23613, 10 pages (2016).

Ponnapakkam, T. et al., "A Single Injection of the Anabolic Bone Agent, Parathyroid Hormone-Collagen Binding Domain (PTH-CBD), Results in Sustained Increases in Bone Mineral Density for up to 12 Months in Normal Female Mice" Calcif Tissue Int., vol. 91:196-203 (2012).

Riedil, K. et al., "Overexpression of CCL-21/Secondary Lymphoid Tissue Chemokine in Human Dendritic Cells Augments Chemotactic Activities for Lymphocytes and Antigen Presenting Cells," Molecular Cancer, vol. 2:35: 13 pages (2003).

Schaefer, L. et al., "Biological Functions of the Small Leucine-rich Proteoglycans: From Genetics to Signal Transduction," Journal of Biological Chemistry, vol. 283(31):21305-21309 (2008).

Schmidt and Wittrup, "A modeling analysis of the effects of molecular size and binding affinity on tumor targeting," Mol Cancer Ther., vol. 8(10): 2861-2871 (2009).

Schumann, K. et al., "Immobilized Chemokine Fields and Soluble Chemokine Gradients Cooperatively Shape Migration Patterns of Dendritic Cells," Immunity, vol. 32:703-713 (2010).

Sharma, S. et al., "CCL21 Chemokine Therapy for Lung Cancer," Int Trends Immun., vol. 1(1): 10-15 (2013).

Sharma, S. et al., "Secondary Lymphoid Tissue Chemokine Mediates T Cell-Dependent Antitumor Responses In Vivo," J. Immunol., vol. 164:4558-4563 (2000).

Shields, J. et al., "Induction of Lymphoidlike Stroma and Immune Escape by Tumors That Express the Chemokine CCL21," Science, vol. 328(5979): 749-752 (2010).

Steplewski, A. et al., "Matrix-Specific Anchors: A New Concept for Targeted Delivery and Retention of Therapeutic Cells," Tissue Engineering Part A, vol. 21 (7 and 8): 10 pages (2015).

Sudhamsu, J. et al., "Dimerization of L TbetaR by L Talpha1beta2 is necessary and sufficient for signal transduction," DNAS, vol. 110(49): 19896-19901 (2013).

Sudhamsu, S. et al., "SI Materials and Methods Protein Expression and Purication," Supporting Information, PNAS, 7 pages (2013).

Trang, H. et al., "Facilitating T Cell Infiltration in Tumor Microenvironment Overcomes Resistance to PD-L 1 Blockade," Cancer Cell, vol. 29:285-296 (2016).

Trust, T. et al., "High-Affinity Binding of the Basement Membrane Proteins Collagen Type IV and Laminin to the Gastric Pathogen Helicobacter pylori," Infect Immun., vol. 59(12):4398-4404 (1991).

Yousefieh, N. et al., "Regulated Expression of CCL21 in the Prostate Tumor Microenvironment Inhibits Tumor Growth and Metastasis in an Orthotopic Model of Prostate Cancer," Cancer Microenvironment, vol. 2:59-67 (2009).

Zou, Y. et al., "CCL21 as an independent favorable prognostic factor for stage III/IV colorectal cancer," Oncology Reports, vol. 30: 659-666 (2013).

Willems, S. et al., "Running GAGs: myxoid matrix in tumor pathology revisited; What's in it for the pathologist?," Virchows Archiv., vol. 456(2):181-192 (2009).

Lebbink et al. "The soluble leukocyte-associated Ig-like receptor (LAIR)-2 antagonizes the collagen/LAIR-1 inhibitory immune interaction". J Immunol. 180(3): 1662-9, (Feb. 2008).

(56) References Cited

OTHER PUBLICATIONS

Tandon et al. "Identification of glycoprotein IV (CD36) as a primary receptor for platelet-collagen adhesion". J Biol Chem. 264(13):7576-83, (May 1989).
Harma, et al. "Crystal structure and collagen-binding site of immune inhibitory receptor LAIR-1: unexpected implications for collagen binding by platelet receptor GPVI," Blood, Dec. 100, 2009, vol. 115, No. 7, pp. 1364-1373.
Kalamajski, et al., "Fibromodulin Binds collagen type 1 via Glu-353 and Lys-355 in leucine-rich Repeasr 11," J Biol Chem, Jul. 10, 2007, vol. 282, No. 37, pp. 26740-26745.
Ohlund, et al. (2009) "Type IV collagen is a tumor stroma-derived biomarker for pancrease cancer." Cancer Research. 101:91-97.
Ono (1991) "Distribution of Collagen Types I, III, IV, and V in Lung Cancers and Expression of Procollagen III Peptide in Cancer cells," Japanese Journal of Lung Cancer, vol. 31, No. 3, pp. 319-326.—English Abstract.
Rygiel, T. et al., "Tumor-expressed collagens can modulate immune cell function through the inhibitory collage receptor LAIR-1," Molecular Immunology, vol. 49:402-406 (2011).
Reed, C. et al., "Decorin prevents metastatic spreading of breast cancer," Oncogene, vol. 24(6):1104-1110 (2005).
Plde Nordkamp, M. et al., "Inhibition of the Classical and Lectin Pathway of the Complement System by Recombinant LAIR-2," Innate Immun., vol. 6:284-292 (2014).
Momin, N. et al., "Anchoring of intratumorally administered cytokines to collagen safely potentiates systemic cancer Immunotherapy," Science Translational Medicine, vol. 11(498): eaaw2614 (2019).
Yasunaga, M. et al., "Cancer-Strama Targeting Therapy by Cytotoxic Immunoconjugate Bound to the Collagen 4 Network in the Tumor Tissue," Bioconjugate Chemistry, vol. 22: 1776-1783 (2011).
Jang, H. et al., "A collagen-binding EGFR single-chain Fv antibody fragment for the targeted cancer therapy," Journal of Controlled Release, vol. 209:101-109 (2015).
Lebbink, J_ et al., "Collagens are functional, high affinity ligands for the inhibitory immune receptor LAIR-1," JEM, vol. 203(6):1419-1425 (2006).
Koninger J_ et al., "Overexpressed decorin in pancreatic cancer: potential tumor growth inhibition and attenuation of chemotherapeutic action," Clinical Cancer Research, US, vol. 10(14): 4776-4783 (2004).
Shihara, J_ et al., "Targeted antibody and cytokine cancer immunotherapies through collagen affinity," Science Translational Medicine, vol. 11(487): eaau3259(2019).
International Search Report and Written Opinion, PCT/US2019/043805, dated Jan. 21, 2020, 16 pages.
Addi et al. Design and Use of Chimeric Proteins Containing a Collagen-Binding Domain for Wound Healing and Bone Regeneration . Tissue Engineering: Part B vol. 23, No. 2, 2017, p. 163-182 (Year: 2017).
Andrades et al. "A recombinant human TGF-beta1 fusion protein with collagen-binding domain promotes migration, growth, and differentiation of bone marrow mesenchymal cells." Exp Cell Res 250(2): 485-98, 1999. (Year: 1999).
Karamanou et al. Lumican as a multivalent effector in wound healing. Advanced Drug Delivery Reviews 129 (2018) 344-351. Avaliable online Mar. 1, 2018. (Year: 2018).
Pietraszek et al. Lumican—derived peptides inhibit melanoma cell growth and migration, PLoS One 8 (2013), e76232. (Year: 2013).

Svensson et al. Fibromodulin and lumican bind to the same region on collagen type I fibrils. FEBS Letters 470 (2000) 178 182 ( Year: 2000).
Zhou et al. Reorganized Collagen in the Tumor Microenvironment of Gastric Cancer and Its Association with Prognosis. Journal of Cancer. 2017; 8(8): 1466-1476. (Year: 2017).
Counterpoint Biomedica: Cancer therapeutics & Diagnostics: Proven Tumor-Targeting Platforms: For ProActive Delivery of Anti-Cancer Agents, Antibodies, and Cytokines; Targeted cancer Diagnostics: for Capture and Characterization of Circulating Tumor Cells. Mar. 14, 2017, pp. 1-29. (Year: 2017).
Counterpoint Biomedica: Lesion Targeted Cytokines: GM-CSF/VWF fusion protein for immune modulation in cancers & focal lesions of viral hepatitis. Dec. 9, 2016, pp. 1-11 . (Year: 2016).
Fang and DeClerck. Targeting the Tumor Microenvironment: From Understanding Pathways to Effective Clinical Trials. Cancer Res; 73(16); 4965-77. (Year: 2013).
Zhu et al. Synergistic innate and adaptive immune response to combination immunotherapy with anti-tumor antigen antibodies and extended serum half-life IL-2. Cancer Cell, 2015, 27(4)489-501. (Year: 2015).
International Preliminary Report on Patentability, PCT/US2019/043805, dated Mar. 23, 2021, 6 pages.
Iozzo et al. Proteoglycan form and function: A comprehensive nomenclature of proteoglycans. Matrix Biology, 42:11-55m 2015. ( Year: 2015).
Miyakawa et al. Gene Delivery of Albumin Binding Peptide-Interferon-gamma Fusion Protein with Improved Pharmacokinetic Properties andSustained Biological Activity. J Pharm Sci. Sep. 2013; 102(9):3110-8. (Year: 2013).
Nilsen et al. Human and mouse albumin bind their respective neonatal Fe receptors diferently. Scientific Reports (2018) 8: 14648. ( Year: 2018).
Nilsen et al. Animal models for evaluation of albumin-based therapeutics. Current Opinion in Chemical Engineering 2018, 19:68-76. Available on line Jan. 2018 (Year: 2018).
Tzeng et al. Antigen specificity can be irrelevant to immunocytokine efficacy and biodistribution. Proc Natl Acad Sci USA. Mar. 17, 2015; 112(11): 3320-3325. (Year: 2015).
Schliemann C, et al. Complete eradication of human B-cell lymphoma xenografts using rituximab in combination with the immunocytokine L 19-IL2. Blood. 2009; 113(10):2275-2283. (Year: 2009).
Edwards et al., The remarkable flexibility of the human antibody repertoire; isolation of over one thousand different antibodies to a single protein, BLyS. J Mol Biol. Nov. 14, 2003;334(1): 103-18. (Year: 2003).
Lloyd et al., Modelling the human immune response: performance of a 1011 human antibody repertoire against a broad panel of therapeutically relevant antigens. Protein Eng Des Sel. Mar. 2009;22(3): 159-68. (Year: 2009).
Goel et al., Plasticity within the antigen-combining site may manifest as molecular mimicry in the humoral immune response. J Immunol. Dec. 15, 2004; 173(12):7358-67. (Year: 2004).
Kanyavuz et al., Breaking the law: unconventional strategies for antibody diversification. Nat Rev Immunol. Jun. 2019; 19(6):355-368. (Year: 2019).
Qianqian H. et al., "Functional collagen biomaterials and tissue regeneration," China Medical Device Information, vol. 18(2), (2012). [English machine translation of abstract provided].

* cited by examiner

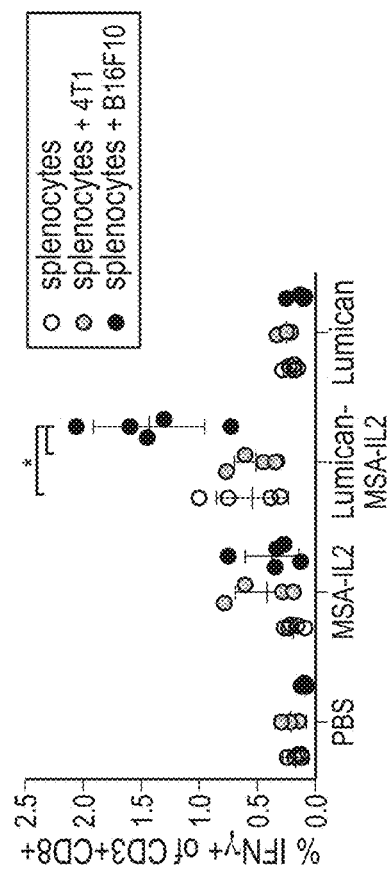
FIG. 5A
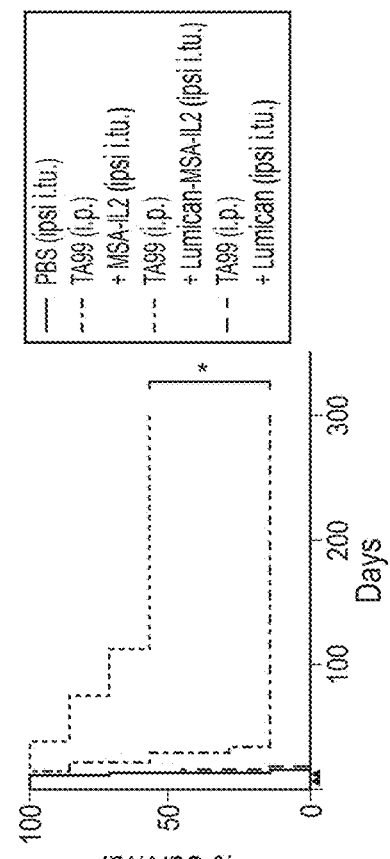
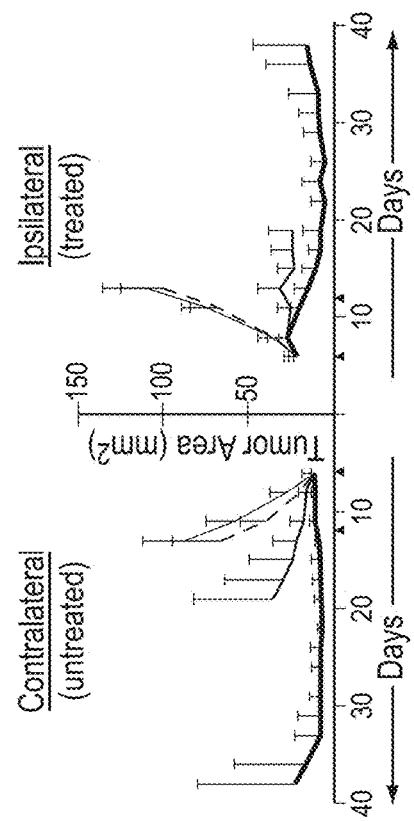
FIG. 5B

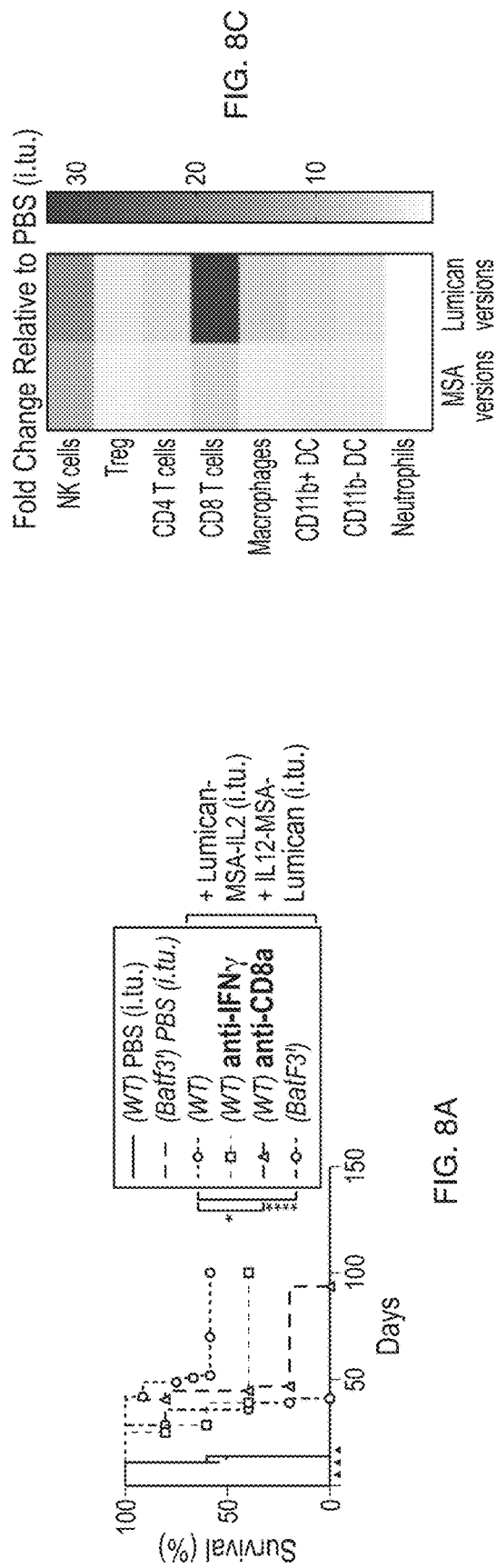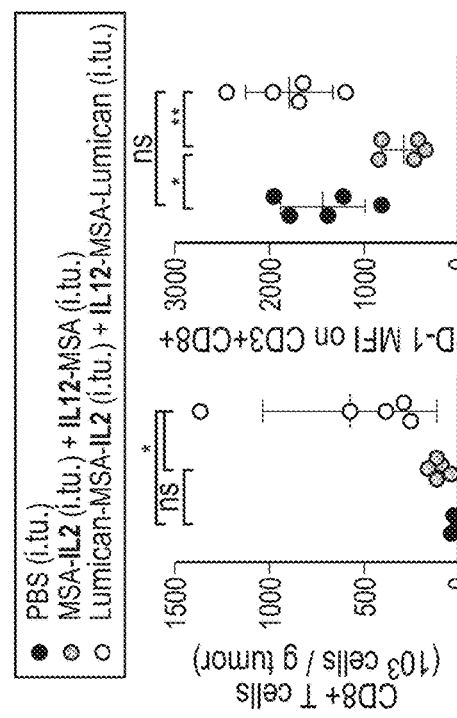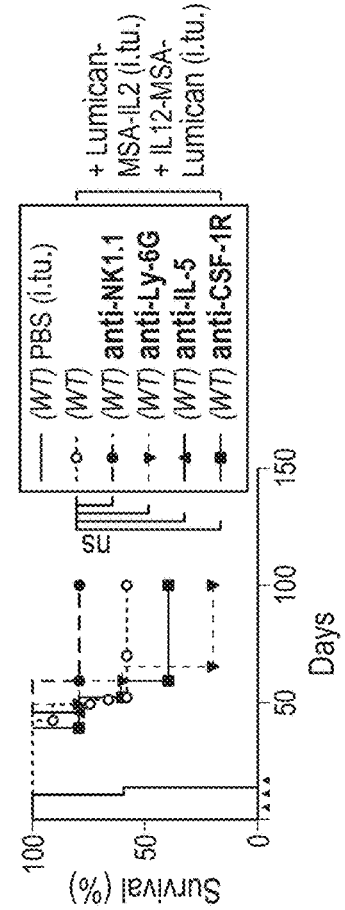
FIG. 8A
FIG. 8B
FIG. 8C
FIG. 8D
FIG. 8E

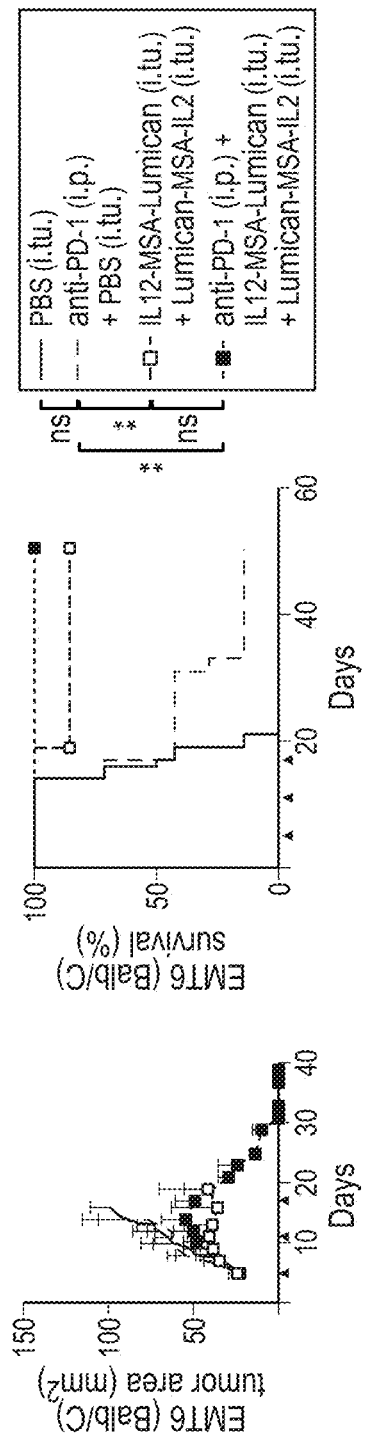
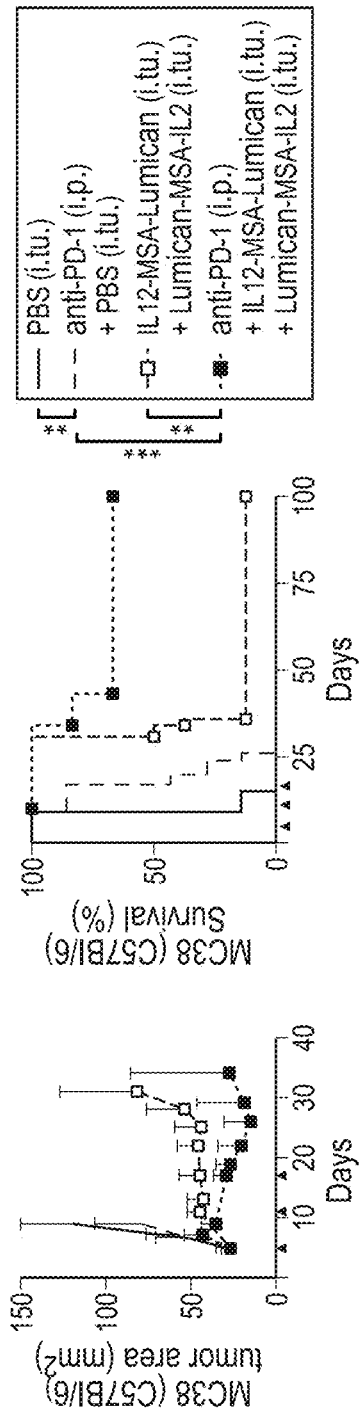
FIG. 10A
FIG. 10B

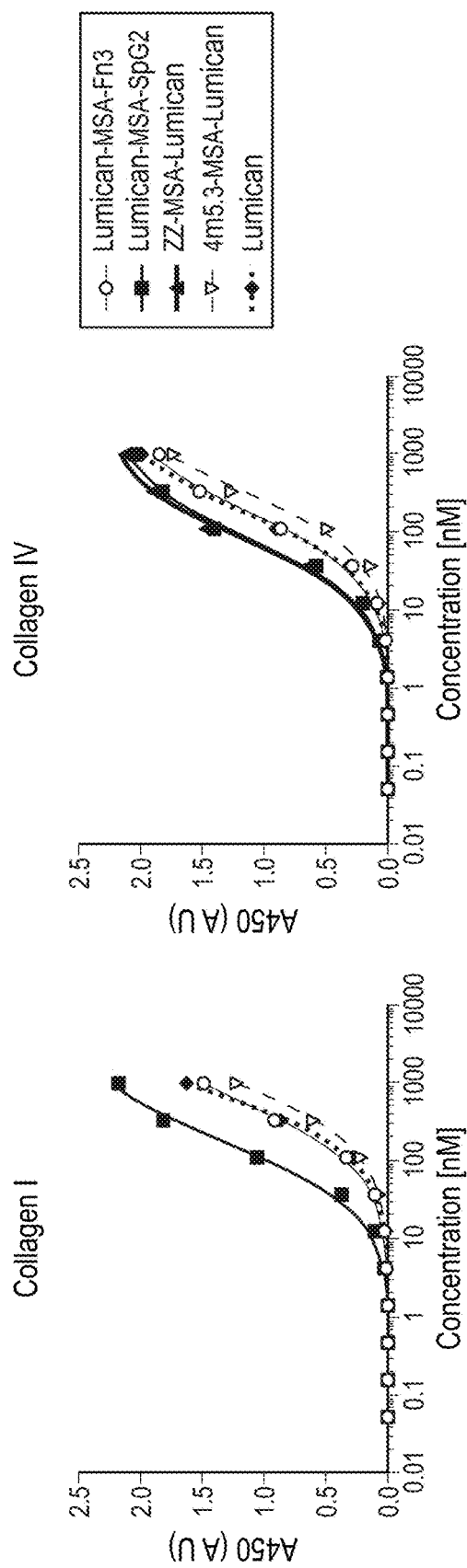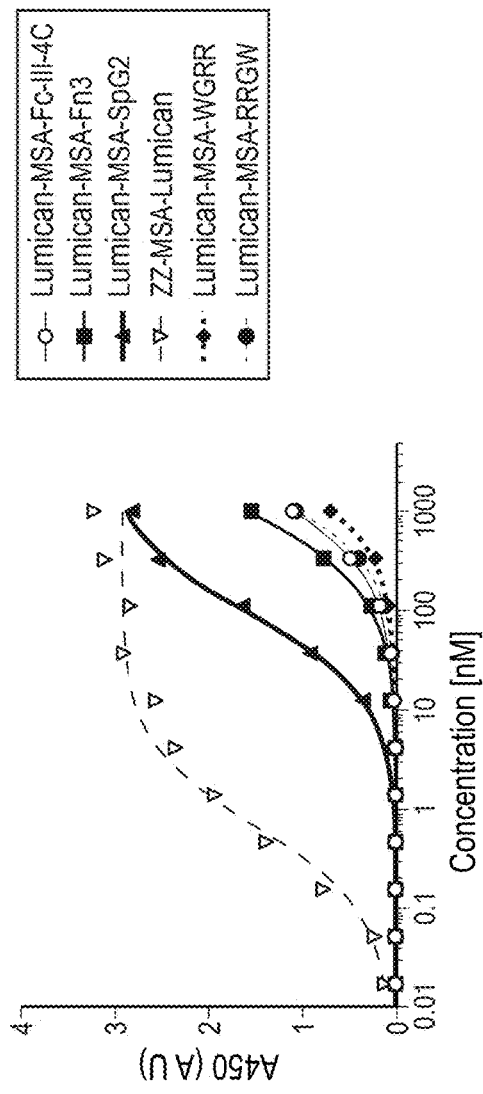
FIG. 18A
FIG. 18B

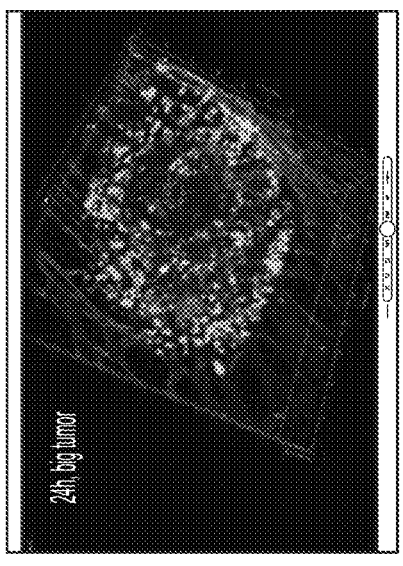
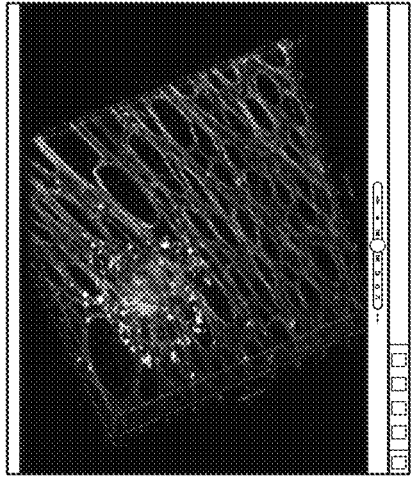
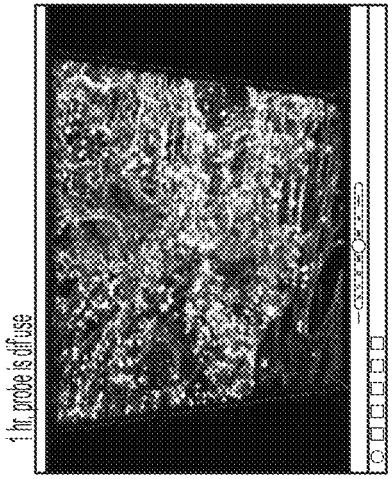
FIG. 19

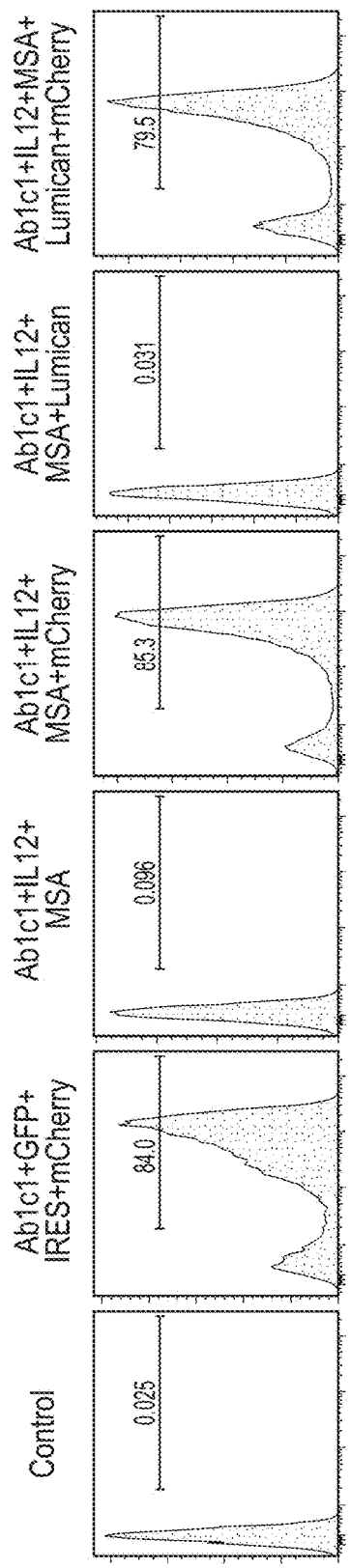
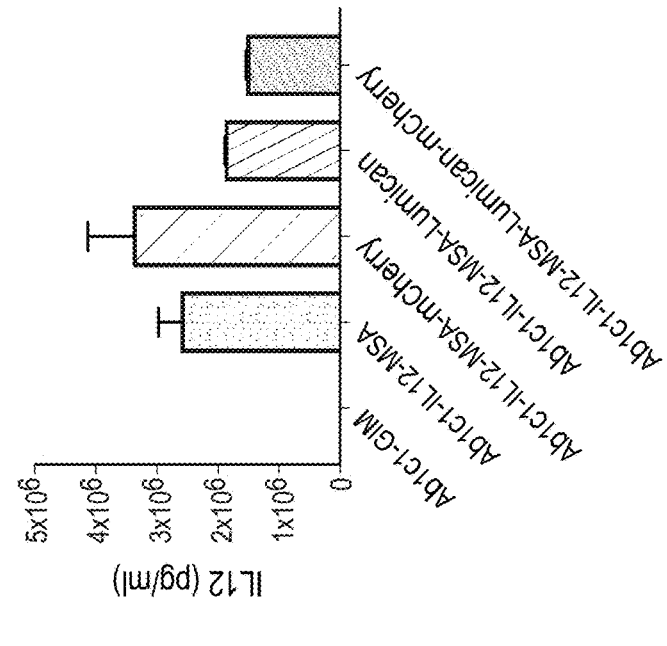
FIG. 20A
FIG. 20B

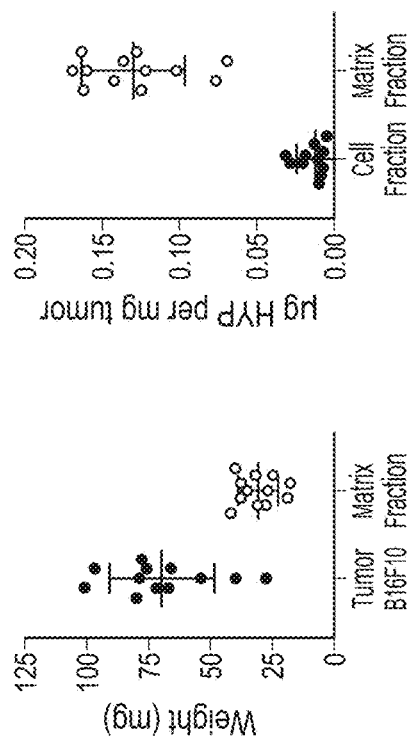
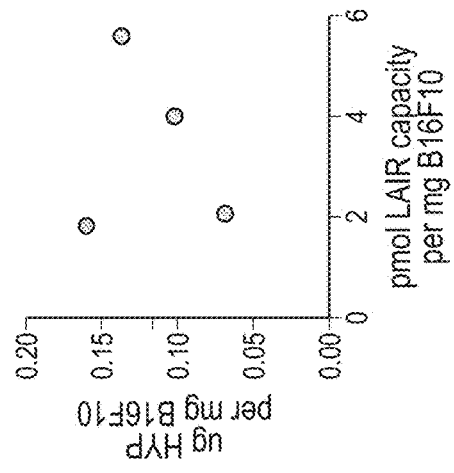
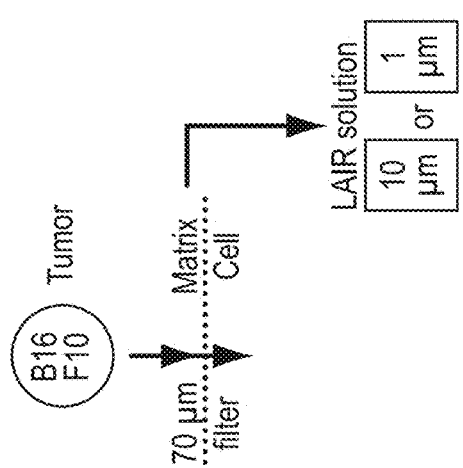
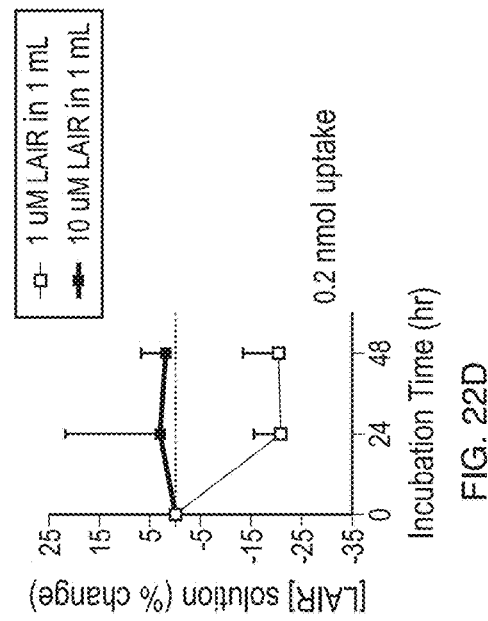
FIG. 22A  FIG. 22B  FIG. 22C  FIG. 22D  FIG. 22E

|          |    |    | 27 |    |    | 43 | 45 |    | 49 | 51 |    |
|----------|----|----|----|----|----|----|----|----|----|----|----|
| LAIR30.w.A | QEGSLPDITIFPNSSLM | ISQGTFVTVACSYSDKHDLYNMVRLEKGGSTFMEKSTE |
| LAIR30.w.B | QEGSLPDITIFPNSSLM | ISQGTFVTVVCSYSDKHDLYNMVRLEKDGSTSMEKSTE |
| LAIR30.w.C | QEGSLPDITIFPNSSLM | ISQGTFVTVVCSYSDKHDLYNMVRLEKDGSTFMGKSTE |
| LAIR30.d.D | QEGSLPDITIFPNSSLM | ISQGTFVTVVCSYSDKHDLYNMARLAKDGSTFMEKSTE |
| LAIR | QEGSLPDITIFPNSSLM | ISQGTFVTVVCSYSDKHDLYNMVRLEKDGSTFMEKSTE |

| LAIR30.w.A | PYKTEDEFEIGPVNETITGHYSCIYSKGITWSERSKTLELKVIKENVIQTPAPGPTSD |
| LAIR30.w.B | PYKTEDEFEIGPVNETITGHYSCIYSKGITWSERSKTLELKVIKENVIQTPAPGPTSD |
| LAIR30.w.C | PYKTEDEFEIGPVNETITGHYSCIYSKGITWSERSKTLELKVIKENVIQTPAPGPTSD |
| LAIR30.d.D | PYKTEDEFEIGPVNETITGHYSCIYSKGITWSERSKTLELKVIKENVIQTPAPGPTSD |
| LAIR | PYKTEDEFEIGPVNETITGHYSCIYSKGITWSERSKTLELKVIKENVIQTPAPGPTSD |

| LAIR30.w.A | TSWLKTYSIY |
| LAIR30.w.B | TSWLKTYSIY |
| LAIR30.w.C | TSWLKTYSIY |
| LAIR30.d.D | TSWLKTYSIY |
| LAIR | TSWLKTYSIY |

FIG. 24A

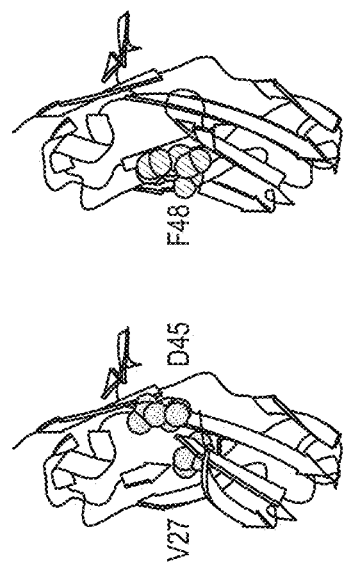

FIG. 24B

FIG. 24C

FIG. 24E

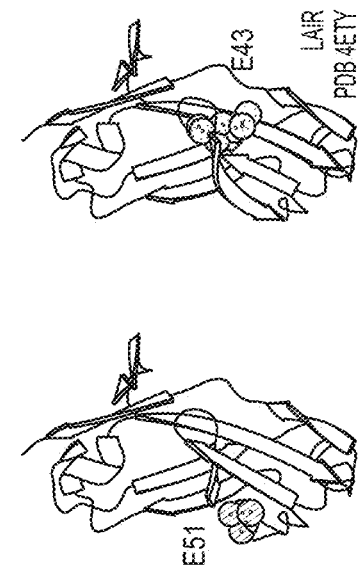

FIG. 24D

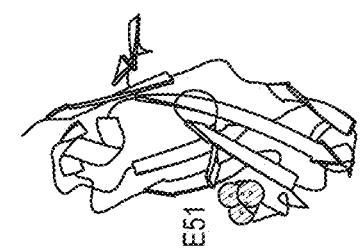

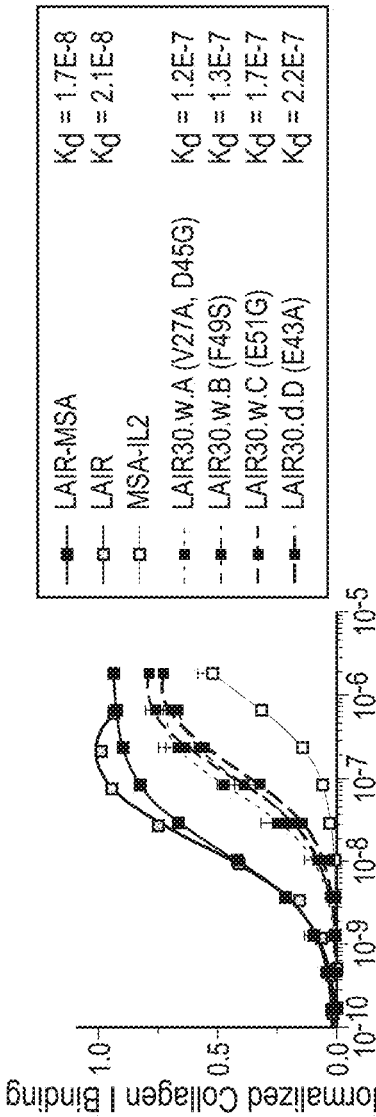

FIG. 24F

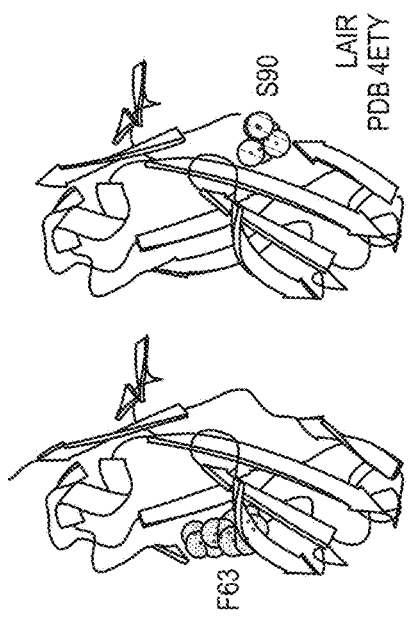

FIG. 25B

FIG. 25C

```
           QEGSLPDITIFPNSSLM ISQGTFVTVCSYSDKHDLYNMVRLEKDGSTFMEKSTE
LAIR30.w.E QEGSLPDITIFPNSSLM ISQGTFVTVCSYSDKHDLYNMVRLEKDGSTFMEKSTE
LAIR30.w.F QEGSLPDITIFPNSSLM ISQGTFVTVCSYSDKHDLYNMVRLEKDGSTFMEKSTE
LAIR 63                                      90
LAIR30.w.E PYKTEDELEIGPVNETITGHYSCIYSKGITWSERSKTLELKVIKENVIQTPAPGPTSD
LAIR30.w.F PYKTEDEFEIGPVNETITGHYSCIYSKGITWSERAKTLELKVIKENVIQTPAPGPTSD
LAIR       PYKTEDEFEIGPVNETITGHYSCIYSKGITWSERSKTLELKVIKENVIQTPAPGPTSD

LAIR30.w.E TSWLKTYSIY
LAIR30.w.F TSWLKTYSIY
LAIR       TSWLKTYSIY
```

FIG. 25A

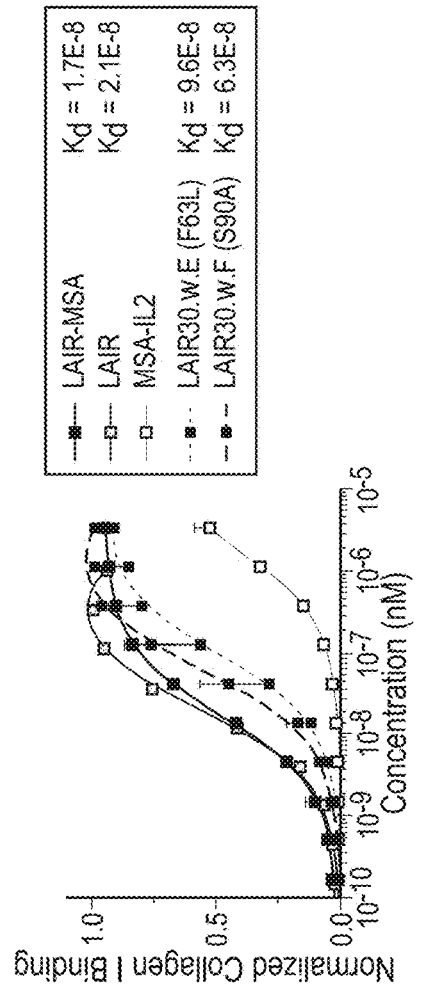

FIG. 25D

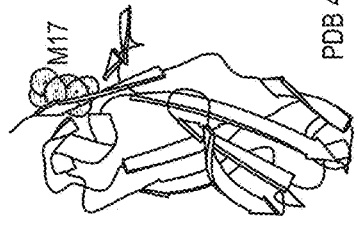
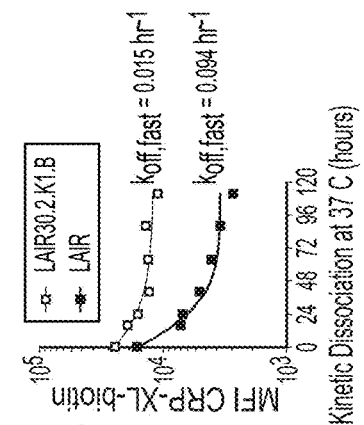
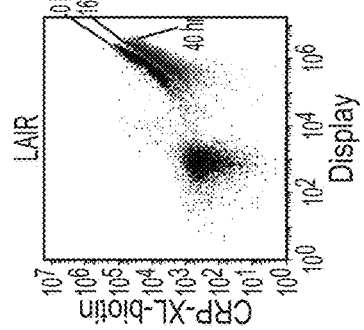
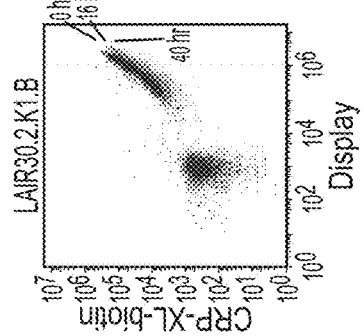
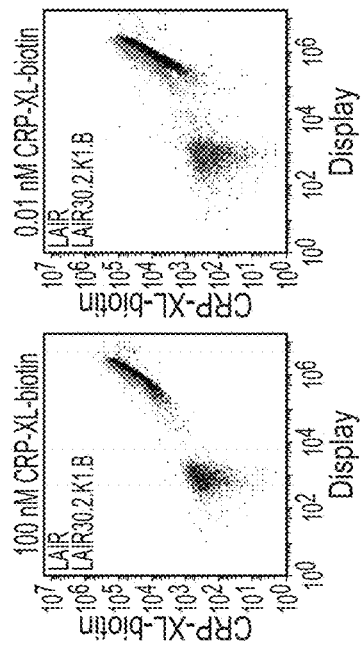
FIG. 26A
FIG. 26B
FIG. 26C
FIG. 26D
FIG. 26E
FIG. 26F
FIG. 26G

COLLAGEN-LOCALIZED IMMUNOMODULATORY MOLECULES AND METHODS THEREOF

RELATED INFORMATION

This application is a Continuation of U.S. patent application Ser. No. 16/523,965, filed Jul. 26, 2019, which claims priority to U.S. Provisional Application No. 62/738,981, filed Sep. 28, 2018, both of which are incorporated by reference herein in their entirety.

GOVERNMENT FUNDING

This invention was made with Government support under Grants No. R01 CA096504 and R01 CA174795 awarded by the National Institutes of Health (NIH). The Government has certain rights in this invention.

SEQUENCE LISTING STATEMENT

A computer readable form of the Sequence Listing is filed with this application by electronic submission and is incorporated into this application by reference in its entirety. The Sequence Listing is contained in the file created on Nov. 16, 2022 having the file name "21-0851-US-CON.xml" and is 354 kb in size.

BACKGROUND

While immunotherapy has transformed oncology with durable curative responses in a minority of patients, immune-related adverse events (irAEs) limit its broadest application (Michot et al. 2016, *Eur J Cancer,* 54:139-148). It is desired to restrict the most potent immune activation events to tumor tissue, while sparing non-tumor healthy tissue. An accepted objective of new immunotherapies is to "heat up" immunologically "cold" tumors, driving inflammation and immune cell infiltration (Chen and Mellman 2017, *Nature,* 541:321-330). Various tumor-localization approaches have been proposed: linking immunomodulatory agents to tumor-targeting modules in immunocytokines (Hutmacher and Neri 2018, *Adv Drug Deliv Rev*); masking agent activity systemically, with tumor-localized proteolytic activation (Thomas and Daugherty 2009, *Protein Sci* 18:2053-2059); intratumoral injection of the agents (Singh and Overwijk 2015, *Nat Commun* 8:1447; Ager et al. 2017, *Cancer Immunol Res* 5:676-684; Bommareddy et al. 2017, *Cancer J* 23:40-47; Milling et al. 2017, *Adv Drug Deliv Rev* 114:79-101; Singh et al. 2017, *Nat Commun* 8:1447; Sagiv-Barfi et al. 2018, *Sci Transl Med* 10:eaan4488); peritumoral injection of a solid biomaterial to entrap the agent (Park et al. 2018, *Sci Transl Med,* 10: eaar1916); conjugation to a solid particle (Kwong et al. 2013, *Cancer Res* 73:1547-1558) or conjugation of basic charged peptides to drive some nonspecific sticking of the agent to tumor extracellular matrix (Ishihara et al. 2017, *Sci Transl Med* 9:eaan0401; Ishihara et al. 2018, *Mol Cancer Ther* 17:2399-2411). A related but distinct approach is to localize growth factors in tissue to drive tissue regeneration (Nishi et al. 1998, *Proc Natl Acad Sci* 95:7018-7023; Martino et al. 2014, *Science* 343:885-888; Mitchell et al. 2016, *Acta Biomater* 30:1-12).

Significant problems exist with each of the current approaches above. Immunocytokines systemically expose immune cells to the immunomodulatory agent (Tzeng et al. 2015, *Proc Natl Acad Sci* 112:3320-3325). Masking agents may be unmasked outside target tissues, and the masking agent may complicate manufacturing and immunogenicity. Intratumoral injection often leads to rapid diffusion out of the tumor compartment. Conjugation of peptides at random sites is difficult to reproduce, can negatively impact specific activity, doesn't fully prevent tumor exit, and creates significant CMC issues due to the heterogeneous products of random conjugation methods.

Accordingly, there remains a need for novel immunotherapy approaches to promote tumor-localization and increase efficacy, while preventing systemic toxicity.

SUMMARY OF THE DISCLOSURE

The present disclosure is based, at least in part, on the discovery that an immunomodulatory domain (e.g., cytokine, anti-immune receptor antibody, anti-tumor associated-antigen antibody, etc.) can be conjugated to a collagen-binding domain, resulting in enhanced anti-tumor efficacy relative to the unconjugated immunomodulatory domain. Without wishing to be bound by theory, collagen localization of an immunomodulatory domain results in enhanced anti-tumor efficacy because T cells become entrapped in collagen-rich zones around tumors, thus making such sites desirable for targeting of immunomodulatory agents. Almost half of human tumors exhibit an immune-excluded phenotype, wherein CD8+ T cells are apparently trapped within collagen-rich desmoplastic stroma (Mariathasan, et al., Nature, 2018, 554:544-548). Given the primary importance of CD8+ T cells in immunotherapeutic efficacy, there is a desire to localize immunomodulatory agents to this collagen-rich, CD8+ T cell-rich compartment of tumors. Specificity is of significance because prior agents which utilize nonspecific electrostatic interactions in small unstructured peptides for retention (Martino, et al., Science, 2014, 343: 885-888), bind promiscuously to the great majority of negatively-charged extracellular matrix components rather than within the particular collagen-rich compartment of interest. Such unstructured, positively charged peptides also lead to relatively weak retention kinetics, wherein in some cases half of the injected conjugate payload leaking into systemic circulation (Ishihara, et al. *Mol Cancer Ther.* 2018, 17:2399-2411).

Accordingly, provided herein are immunomodulatory fusions to structured proteins with specific affinity for collagen, leading to greater retention within the particular collagen-rich compartments of interest. In some aspects described herein, the immunomodulatory fusion proteins comprise a cytokine, wherein the collagen-binding domain increases tumor retention and prevents systemic exposure to the cytokine following intratumoral administration in preclinical animal models, thereby reducing treatment-related toxicity. Furthermore, the immunomodulatory fusion proteins have increased anti-tumor efficacy and reduced toxicity compared to equivalent fusion proteins lacking collagen-binding domains when combined with one or more additional immunotherapies (e.g., tumor-targeting antibodies, checkpoint blockade, cancer vaccines, and T cell therapy.

As provided herein, these immunomodulatory fusion proteins demonstrate durable and systemic antitumor responses, enabling localized immunity against injected tumor and systemic immunity for effective treatment of a contralateral noninjected tumor. Neoadjuvant administration of the immunomodulatory fusion proteins also improved survival by preventing metastases following surgical excision of residual primary tumor, further demonstrating that the immunomodulatory fusion proteins promote systemic anti-tumor immunity. Thus, the immunomodulatory fusion proteins of the disclosure are useful for treating metastatic tumors and/or mediating abscopal effect in therapeutic (e.g., anti-cancer) modalities.

Also provided herein, are variant collagen-binding domains that have altered (e.g., increased or decreased) binding affinities for collagen. By disclosing a selection of variant collagen-binding domains with different collagen-binding affinities, the disclosures herein provide options for selecting immunomodulatory fusion proteins with different binding affinities for collagen-rich compartments (e.g., collagen-expressing tumors).

The collagen-binding compositions and methods provided herein allow for tumor- and payload-agnostic local targeting of active therapeutics. The collagen-binding compositions also demonstrate increase efficacy with concomitant decrease in toxicity associated with systemic immunotherapies.

In some aspects, the disclosure provides an immunomodulatory fusion protein comprising:
  (i) an immunomodulatory domain;
  (ii) a collagen-binding domain, wherein the collagen-binding domain specifically binds type I and/or type IV collagen and binds type I collagen with a $K_D \leq 500$ nM, and wherein the collagen-binding domain has an isoelectric point pI<10 and a molecular weight (MW) of ≥5 kDa; and
  (iii) optionally, a linker,
wherein the immunomodulatory domain is operably linked with or without the linker to the collagen-binding domain.

In some aspects, the $K_D$ of the collagen-binding domain for type I and/or type IV collagen is less than the $K_D$ of the collagen-binding domain for an extracellular matrix component selected from fibronectin, vitronectin, osteopontin, tenascin C, or fibrinogen. In some aspects, the collagen-binding domain has a MW of about 5-100 kDa, about 10-80 kDa, about 20-60 kDa, about 30-50 kDa, or about 10 kDa, about 20 kDa, about 30 kDa, about 40 kDa, about 50 kDa, about 60 kDa, about 70 kDa, about 80 kDa, about 90 kDa or about 100 kDa.

In some aspects, the immunomodulatory fusion protein comprises a collagen-binding domain comprising one or more leucine-rich repeats which bind collagen. In some aspects, the collagen-binding domain comprises two, three, four, five, six, seven, eight, nine or ten leucine-rich repeats which bind collagen. In some aspects, the collagen-binding domain comprises one or more leucine-rich repeats from a human proteoglycan Class II member of the small leucine-rich proteoglycan (SLRP) family. In some aspects, the SLRP is selected from lumican, decorin, biglycan, fibromodulin, chondroadherin, asporin, PRELP, osteoadherin/osteomodulin, opticin, osteoglycin/mimecan, podocan, perlecan, and nidogen. In some aspects, the SLRP is lumican.

In some aspects, the immunomodulatory fusion protein comprises a collagen-binding domain comprising a human SLRP. In some aspects, the SLRP is selected from lumican, decorin, biglycan, fibromodulin, chondroadherin, asporin, PRELP, osteoadherin/osteomodulin, opticin, osteoglycin/ mimecan, podocan, perlecan, and nidogen. In some aspects, the SLRP is lumican. In some aspects, lumican comprises the amino acid sequence as set forth in SEQ ID NO: 107.

In some aspects, the immunomodulatory fusion protein comprises a collagen-binding domain comprising a human type I glycoprotein having an Ig-like domain, or an extracellular portion thereof which binds collagen. In some aspects, the type I glycoprotein competes with lumican for binding for binding to collagen type I. In some aspects, the human type I glycoprotein is selected from LAIR1, LAIR2, and Glycoprotein IV. In some aspects, the human type I glycoprotein is LAIR1. In some aspects, the human type I glycoprotein is LAIR1 and the collagen-binding domain comprises amino acid residues 22-122 of the amino acid sequence as set forth in SEQ ID NO: 98. In some embodiments, the LAIR1 is a variant comprising one or more amino acid substitutions, additions or deletions, optionally two, three, four, five, six, seven, eight, nine, ten or more amino acid substitutions, additions or deletions relative to a LAIR1 protein comprising the amino acid sequence of SEQ ID NO: 98. In some embodiment, the LAIR1 variant has increased binding affinity to collagen relative to a collagen binding affinity of a LAIR1 protein comprising the amino acid sequence of SEQ ID NO: 98. In other further embodiments, the LAIR1 variant has decreased binding affinity to collagen relative to a collagen binding affinity of a LAIR1 protein comprising the amino acid sequence of SEQ ID NO: 98.

In any of the foregoing aspects, the immunomodulatory domain comprises a polypeptide that activates, enhances or promotes a response by an immune cell. In other aspects, the immunomodulatory domain comprises a polypeptide that inhibits, reduces or suppresses a response by an immune cell.

In some aspects, the immune cell is a lymphoid cell selected from an innate lymphoid cell, a T cell, a B cell, an NK cell, and a combination thereof. In other aspects, the immune cell is a myeloid cell selected from a monocyte, a neutrophil, a granulocyte, a mast cell, a macrophage, a dendritic cell, and a combination thereof.

In some aspects, the response by the immune cell comprises cytokine production, antibody production, production of antigen-specific immune cells, increased effector function and/or cytotoxicity, and a combination thereof.

In any of the foregoing aspects, the immunomodulatory domain comprises one or more selected from a cytokine, a chemokine, an activating ligand/receptor, an inhibitory ligand/receptor, or a combination thereof. In some aspects, the immunomodulatory domain comprises one or more cytokines.

In some aspects, the cytokine is a human gamma common chain receptor interleukin selected from IL-2, IL-4, IL-7, IL-9, IL-13, IL-15, IL-15/IL-15RA, IL-21, and a combination thereof. In some aspects, the cytokine is IL-2.

In some aspects, the cytokine is a human IL-12 family member selected from IL-12 (p35), IL-12 (p40), IL-12(p35)/IL-12(p40), IL-23, IL-27 IL-35, and a combination thereof. In some aspects, the cytokine is a single chain fusion of IL-12(p35)/IL-12(p40).

In other aspects, the cytokine is a human IL-1 family member selected from IL-1, IL-18, IL-33, and a combination thereof. In some aspects, the cytokine is IL-18.

In yet other aspects, the cytokine is selected from TNFα, INFα, IFN-γ, GM-CSF, FLT3L, G-CSF, M-CSF, and a combination thereof.

In some aspects, the immunomodulatory domain comprises one or more chemokines. In some aspects, the chemokine is selected from LIF, MIP-2, MIP-1α, MIP-1β, CXCL1, CXCL9, CXCL10, MCP-1, Eotaxin, RANTES, LIX and a combination thereof. In other aspects, the chemokine is selected from CCL3, CCL4, CCL5, Eotaxin and a combination thereof.

In any of the foregoing aspects, the immunomodulatory domain comprises one or more activating ligands/receptors. In some aspects, the activating ligand/receptor is selected from a TNF superfamily, a CD28 receptor superfamily, a B7 ligand family, and a T cell receptor. In other aspects, the activating ligand/receptor is a TNF superfamily ligand selected from TNF-alpha, CD40L, 4-1BBL, OX40, and a combination thereof. In yet other aspects, the activating ligand/receptor is a TNF superfamily receptor and the immunomodulatory domain comprises an antibody or antigen binding fragment thereof selected from an anti-TNFR1 antibody, an anti-TNFR2 antibody, an anti-CD40 antibody, an anti-4-1BB antibody and an anti-OX40 antibody. In other aspects, the activating ligand/receptor is a CD28 superfamily member or a B7 family member selected from ICOS ligand, CD80, and CD86, and a combination thereof. In yet other aspects, the activating ligand/receptor is a CD28 superfamily member and the immunomodulatory domain comprises an antibody or antigen binding fragment thereof selected from an anti-ICOS antibody and an anti-CD28 antibody. In further aspects, the activating ligand/receptor is a T cell receptor and the immunomodulatory domain comprises an antibody or antigen binding fragment thereof selected from an anti-CD3γ antibody, an anti-CD3δ antibody, an anti-CD3ζ antibody, and an anti-CD3ε antibody.

In some aspects, the activating ligand/receptor is selected from a TNF superfamily, a CD28 receptor superfamily, a B7 ligand family, a T cell receptor, a Killer Cell Ig-Like receptor, a Leukocyte Ig-Like receptor, a CD94/NKG2 receptor family, and an Fc receptor. In other aspects, the activating ligand/receptor is a Killer Cell Ig-Like Receptor Ligand and the immunomodulatory domain comprises antibody or antigen binding fragment thereof selected from an anti-KIR 2DS1 antibody, an anti-KIR 2DS2 antibody, an anti-KIR 2DS3 antibody, an anti-KIR 2DS4 antibody, an anti-KIR 2DS5 antibody and an anti-KIR 3DS1 antibody. In further aspects, the activating ligand/receptor is a Leukocyte Ig-Like receptor and the immunomodulatory domain comprises an anti-LIRA2 antibody or antigen binding fragment thereof. In other aspects, the activating ligand/receptor is an CD94/NKG2 receptor family member selected from MICA, MICB, ULBP1, ULBP2, ULBP3, ULBP4, ULBP5 (isoform 1) ULBP5 (isoform 2), and ULBP6. In yet other aspects, the activating ligand/receptor is an CD94/NKG2 receptor family member and the immunomodulatory domain comprises an antibody or antigen binding fragment thereof selected from an anti-CD94/NKG2D antibody, an anti-CD94/NKG2C antibody, an anti-CD94/NKG2E antibody, and an anti-CD94/NKG2H antibody. In further aspects, the activating ligand/receptor is an Fc receptor family member and the immunomodulatory domain comprises an antibody or antigen binding fragment thereof selected from anti-FcγRI antibody, an anti-FcγRIIC antibody, an anti-FcγRIIIA antibody, an anti-FcγRIIIB antibody, an anti-FcεRI antibody, an anti-FcεRII antibody, an anti-FcαR antibody, and an anti-FcμR antibody.

In any of the foregoing aspects, the immunomodulatory domain comprises one or more inhibitory ligands/receptors. In some aspects, the inhibitory ligand/receptor is selected from a CD28 receptor superfamily, a TNF superfamily, and a checkpoint inhibitor. In other aspects, the inhibitory ligand/receptor is a CD28 superfamily member and the immunomodulatory domain comprises an antibody or antigen binding fragment thereof selected from an anti-PD-1 antibody, an anti-PD-L1 antibody, an anti-PD-L2 antibody, an anti-CTLA4 antibody. In yet further aspects, the inhibitory ligand/receptor is a TNF superfamily member and the immunomodulatory domain comprises an antibody or antigen binding fragment selected from an anti-TIGIT antibody and an anti-BTLA antibody. In some aspects, the inhibitory ligand/receptor is a checkpoint inhibitor and the immunomodulatory domain comprises an antibody or antigen binding fragment selected from an anti-VISTA antibody, an anti-TIM-3 antibody, an anti-LAG-3 antibody, an anti-CD47 antibody, and an anti-SIRPα antibody.

In some aspects, the inhibitory ligand/receptor is selected from a CD28 receptor superfamily, a TNF superfamily, a Siglec family, a CD94/NKG2A family, a Leukocyte Ig-Like receptor family, Killer Cell Ig-Like Receptor Ligand, an Fc Receptor, an adenosine pathway molecule, and a checkpoint inhibitor. In other aspects, the inhibitory ligand/receptor comprises a Siglec family member and the immunomodulatory domain comprises an antibody or antigen binding fragment selected from an anti-Siglec 1 antibody, an anti-Siglec 2 antibody, an anti-Siglec 3 antibody, an anti-Siglec 4a antibody, an anti-Siglec 5 antibody, an anti-Siglec 6 antibody, an anti-Siglec 7 antibody, an anti-Siglec 8 antibody, an anti-Siglec 9 antibody, an anti-Siglec 10 antibody, an anti-Siglec 11 antibody and an anti-Siglec 12 antibody. In yet other aspects, the inhibitory ligand/receptor comprises a CD94/NKG2 receptor family inhibitory receptor or inhibitory ligand and the immunomodulatory domain comprises an antibody or antigen binding fragment selected from an anti-CD94/NKG2A antibody and an anti-CD94/NKG2B antibody. In some aspects, the inhibitory ligand/receptor comprises a Leukocyte Ig-Like Receptor and the immunomodulatory domain comprises an antibody or antigen binding fragment selected from an anti-LIRB1 antibody, an anti-LIRB2 antibody, an anti-LIRB3 antibody, an anti-LIRB4 antibody. In other aspects, the inhibitory ligand/receptor comprises a Killer Cell Ig-Like Receptor Ligand and the immunomodulatory domain comprises antibody or antigen binding fragment thereof selected from an anti-KIR 2DL1 antibody, an anti-KIR 2DL2 antibody, an anti-KIR 2DL3 antibody, an anti-KIR 2DL4 antibody, an anti-KIR 2DL5A antibody, an anti-KIR 2DL5B antibody, an anti-KIR 3DL1 antibody, an anti-KIR 3DL2 antibody and an anti-KIR 3DL3 antibody. In yet other aspects, the inhibitory ligand/receptor comprises an Fc receptor and the immunomodulatory domain comprises an anti-FcγRIIB antibody or antigen binding fragment. In some aspects, the inhibitory ligand/receptor comprises an adenosine pathway molecule and the immunomodulatory domain comprises an antibody or antigen binding fragment selected from an anti-CD39 antibody and anti-CD73 antibody. In other aspects, the inhibitory ligand/receptor comprises a checkpoint inhibitor and the immunomodulatory domain comprises an antibody or antigen binding fragment selected from is an anti-VISTA antibody, an anti-TIM-3 antibody an anti-LAG-3 antibody, an anti-CD47 antibody, and an anti-SIRPα antibody.

In any of the foregoing aspects, the immunomodulatory domain is operably linked to the collagen-binding domain via a linker. In some aspects, the linker is of sufficient length or mass to reduce adsorption of the immunomodulatory domain onto collagen fibrils. In some aspects, the linker provides sufficient molecular weight to the fusion protein reduce diffusion from a tissue. In some aspects, the linker allows for steric separation of the immunomodulatory domain from collagen fibrils to promote receptor/ligand engagement. In some aspects, the linker is a hydrophilic polypeptide comprising "N" amino acids in length, wherein 1-1000, 10-900, 30-800, 40-700, 50-600, 100-500, or 200-400. In some aspects, the linker is human serum albumin or fragment thereof. In other aspects, the linker comprises an Fc domain or a mutant Fc domain with reduced FcR interaction.

In any of the foregoing aspects, the immunomodulatory fusion protein is of sufficient mass to reduce size dependent escape by diffusion or convection upon administration in vivo. In some aspects, the fusion protein is ≥60 kDa. In some aspects, the immunomodulatory fusion protein binds type I and/or type IV collagen upon administration in vivo, thereby reducing systemic exposure of the immunomodulatory fusion protein.

In some aspects, the disclosure provides an immunomodulatory fusion protein comprising:
(i) at least one cytokine;
(ii) a collagen-binding domain, wherein the collagen-binding domain specifically binds type I and/or type IV collagen and binds type I collagen with a $K_D$≤500 nM, and wherein the collagen-binding domain has an isoelectric point pI<10 and a molecular weight (MW) of ≥5 kDa; and
(iii) a linker, wherein the linker is a hydrophilic polypeptide comprising "N" amino acids in length, wherein N=1-1000, 10-900, 30-800, 40-700, 50-600, 100-500, or 200-400, wherein the cytokine is operably linked via the linker to the collagen-binding domain, and wherein the fusion protein is ≥60 kDa. In some aspects, the $K_D$ of the collagen-binding domain for type I and/or type IV collagen is less than the $K_D$ of the collagen-binding domain for an extracellular matrix component selected from fibronectin, vitronectin, osteopontin, tenascin C, or fibrinogen. In some aspects, the collagen-binding domain comprises a human SLRP selected from lumican, decorin, biglycan, fibromodulin, chondroadherin, asporin, PRELP, osteoadherin/osteomodulin, opticin, osteoglycin/mimecan, podocan, perlecan, and nidogen. In some aspects, the SLRP is lumican. In some aspects, the lumican comprises the amino acid sequence as set forth in SEQ ID NO: 107. In other aspects, the collagen-binding domain is selected from LAIR1, LAIR2, and Glycoprotein IV. In some aspects, the collagen-binding domain is LAIR1. In some aspects, the collagen-binding domain comprises amino acid residues 22-122 of the amino acid sequence as set forth in SEQ ID NO: 98. In some embodiments, the LAIR1 is a variant comprising one or more amino acid substitutions, additions or deletions, optionally two, three, four, five, six, seven, eight, nine, ten or more amino acid substitutions, additions or deletions relative to a LAIR1 protein comprising the amino acid sequence of SEQ ID NO: 98. In some embodiment, the LAIR1 variant has increased binding affinity to collagen relative to a collagen binding affinity of a LAIR1 protein comprising the amino acid sequence of SEQ ID NO: 98. In other further embodiments, the LAIR1 variant has decreased binding affinity to collagen relative to a collagen binding affinity of a LAIR1 protein comprising the amino acid sequence of SEQ ID NO: 98.

In some aspects, the cytokine is a human gamma common chain receptor interleukin selected from IL-2, IL-4, IL-7, IL-9, IL-13, IL-15, IL-15/IL-15RA, IL-21, and a combination thereof. In some aspects, the cytokine is IL-2. In some aspects, the cytokine is a human IL-12 family member selected from IL-12 (p35), IL-12 (p40), IL-12(p35)/IL-12 (p40), IL-23, IL-27, IL-35, and a combination thereof. In some aspects, the cytokine is a single chain fusion of IL-12(p35)/IL-12(p40). In some aspects, the immunomodulatory fusion protein comprises a second cytokine. In some aspects, the second cytokine is IL-2.

In other aspects, the cytokine is a human IL-1 family member selected from IL-1, IL-18, IL-33, and a combination thereof. In yet other aspects, the cytokine is selected from TNFα, INFα, IFN-γ, GM-CSF, FLT3L, G-CSF, M-CSF, and a combination thereof.

In some aspects, the linker is of sufficient length or mass to reduce adsorption of the immunomodulatory domain onto collagen fibrils, and/or provides sufficient molecular weight to the fusion protein reduce diffusion from a tissue and/or allows for steric separation of the immunomodulatory domain from collagen fibrils to promote receptor/ligand engagement. In some aspects, the linker is human serum albumin or fragment thereof. In other aspects, the linker comprises an Fc domain or a mutant Fc domain with reduced FcR interaction.

In some aspects, the fusion protein is of sufficient mass to reduce size dependent escape by diffusion or convection upon administration in vivo. In some aspects, the fusion protein binds type I and/or type IV collagen upon administration in vivo, thereby reducing systemic exposure of the immunomodulatory fusion protein.

In other aspects, the disclosure provides an immunomodulatory fusion protein comprising:
(i) at least one chemokine;
(ii) a collagen-binding domain, wherein the collagen-binding domain specifically binds type I and/or type IV collagen and binds type I collagen with a $K_D$≤500 nM, and wherein the collagen-binding domain has an isoelectric point pI<10 and a molecular weight (MW) of ≥5 kDa; and
(iii) a linker, wherein the linker is a hydrophilic polypeptide comprising "N" amino acids in length, wherein N=1-1000, 10-900, 30-800, 40-700, 50-600, 100-500, or 200-400, wherein the chemokine is operably linked via the linker to the collagen-binding domain, and wherein the fusion protein is ≥60 kDa. In some aspects, the $K_D$ of the collagen-binding domain for type I and/or type IV collagen is less than the $K_D$ of the collagen-binding domain for an extracellular matrix component selected from fibronectin, vitronectin, osteopontin, tenascin C, or fibrinogen. In some aspects, the collagen-binding domain comprises a human SLRP selected from lumican, decorin, biglycan, fibromodulin, chondroadherin, asporin, PRELP, osteoadherin/osteomodulin, opticin, osteoglycin/mimecan, podocan, perlecan, and nidogen. In some aspects, the SLRP is lumican. In some aspects, the lumican comprises the amino acid sequence as set forth in SEQ ID NO: 107. In other aspects, the collagen-binding domain is selected from LAIR1, LAIR2, and Glycoprotein IV. In some aspects, the collagen-binding domain is LAIR1. In some aspects, the collagen-binding domain comprises amino acid residues 22-122 of the amino acid sequence as set forth in SEQ ID NO: 98. In some embodiments, the LAIR1 is a variant comprising one or more amino acid substitutions, additions or deletions, optionally two, three, four, five, six, seven, eight, nine, ten or more amino acid substitutions, additions or deletions relative to a LAIR1 protein comprising the amino acid sequence of SEQ ID NO: 98. In some embodiment, the LAIR1 variant has increased binding affinity to collagen relative to a collagen binding affinity of a LAIR1 protein comprising the amino acid sequence of SEQ ID NO: 98. In other further embodiments, the LAIR1 variant has decreased binding affinity to collagen relative to a collagen binding affinity of a LAIR1 protein comprising the amino acid sequence of SEQ ID NO: 98.

In some aspects, the chemokine is selected from LIF, MIP-2, MIP-1α, MIP-1β, CXCL1, CXCL9, CXCL10, MCP-1, Eotaxin, RANTES, LIX, and a combination thereof.

In some aspects, the chemokine is selected from CCL3, CCL4, CCL5, Eotaxin and a combination thereof.

In some aspects, the linker is of sufficient length or mass to reduce adsorption of the immunomodulatory domain onto collagen fibrils, and/or provides sufficient molecular weight to the fusion protein reduce diffusion from a tissue and/or allows for steric separation of the immunomodulatory domain from collagen fibrils to promote receptor/ligand engagement. In some aspects, the linker is human serum albumin or fragment thereof. In other aspects, the linker comprises an Fc domain or a mutant Fc domain with reduced FcR interaction.

In some aspects, the fusion protein is of sufficient mass to reduce size dependent escape by diffusion or convection upon administration in vivo. In some aspects, the fusion protein binds type I and/or type IV collagen upon administration in vivo, thereby reducing systemic exposure of the immunomodulatory fusion protein.

In yet other aspects, the disclosure provides an immunomodulatory fusion protein comprising:

(i) an agonist antibody which binds an activating ligand/receptor comprising an Fc domain or a mutant Fc domain with reduced FcR interaction; and (ii) a collagen-binding domain, wherein the collagen-binding domain specifically binds type I and/or type IV collagen and binds type I collagen with a $K_D \leq 500$ nM, and wherein the collagen-binding domain has an isoelectric point pI<10 and a molecular weight (MW) of ≥5 kDa, wherein the collagen-binding domain is operably linked to the C-terminus of the Fc domain or mutant Fc domain. In some aspects, the $K_D$ of the collagen-binding domain for type I and/or type IV collagen is less than the $K_D$ of the collagen-binding domain for an extracellular matrix component selected from fibronectin, vitronectin, osteopontin, tenascin C, or fibrinogen. In some aspects, the collagen-binding domain comprises a human SLRP selected from lumican, decorin, biglycan, fibromodulin, chondroadherin, asporin, PRELP, osteoadherin/osteomodulin, opticin, osteoglycin/mimecan, podocan, perlecan, and nidogen. In some aspects, the SLRP is lumican. In some aspects, the lumican comprises the amino acid sequence as set forth in SEQ ID NO: 107. In other aspects, the collagen-binding domain is selected from LAIR1, LAIR2, and Glycoprotein IV. In some aspects, the collagen-binding domain is LAIR1. In some aspects, the collagen-binding domain comprises amino acid residues 22-122 of the amino acid sequence as set forth in SEQ ID NO: 98. In some embodiments, the LAIR1 is a variant comprising one or more amino acid substitutions, additions or deletions, optionally two, three, four, five, six, seven, eight, nine, ten or more amino acid substitutions, additions or deletions relative to a LAIR1 protein comprising the amino acid sequence of SEQ ID NO: 98. In some embodiment, the LAIR1 variant has increased binding affinity to collagen relative to a collagen binding affinity of a LAIR1 protein comprising the amino acid sequence of SEQ ID NO: 98. In other further embodiments, the LAIR1 variant has decreased binding affinity to collagen relative to a collagen binding affinity of a LAIR1 protein comprising the amino acid sequence of SEQ ID NO: 98.

In some aspects, the agonist antibody is selected from an anti-TNFR1 antibody, an anti-TNFR2 antibody, an anti-CD40 antibody, an anti-4-1BB antibody and an anti-OX40 antibody. In other aspects, the agonist antibody is selected from an anti-ICOS antibody and an anti-CD28 antibody. In some aspects, the agonist antibody is selected from an anti-CD3γ antibody, an anti-CD3δ antibody, an anti-CD3ζ antibody, and an anti-CD3ε antibody.

In some aspects, the fusion protein is of sufficient mass to reduce size dependent escape by diffusion or convection upon administration in vivo. In some aspects, the fusion protein binds type I and/or type IV collagen upon administration in vivo, thereby reducing systemic exposure of the immunomodulatory fusion protein.

In further aspects, the disclosure provides an immunomodulatory fusion protein comprising:

(i) an antagonist antibody which binds an inhibitory ligand/receptor comprising an Fc domain or a mutant Fc domain with reduced FcR interaction; and (ii) a collagen-binding domain, wherein the collagen-binding domain specifically binds type I and/or type IV collagen and binds type I collagen with a $K_D \leq 500$ nM, and wherein the collagen-binding domain has an isoelectric point pI<10 and a molecular weight (MW) of ≥5 kDa, wherein the collagen-binding domain is operably linked to the C-terminus of the Fc domain or mutant Fc domain. In some aspects, the $K_D$ of the collagen-binding domain for type I and/or type IV collagen is less than the $K_D$ of the collagen-binding domain for an extracellular matrix component selected from fibronectin, vitronectin, osteopontin, tenascin C, or fibrinogen. In some aspects, the collagen-binding domain comprises a human SLRP selected from lumican, decorin, biglycan, fibromodulin, chondroadherin, asporin, PRELP, osteoadherin/osteomodulin, opticin, osteoglycin/mimecan, podocan, perlecan, and nidogen. In some aspects, the SLRP is lumican. In some aspects, the lumican comprises the amino acid sequence as set forth in SEQ ID NO: 107. In other aspects, the collagen-binding domain is selected from LAIR1, LAIR2, and Glycoprotein IV. In some aspects, the collagen-binding domain is LAIR1. In some aspects, the collagen-binding domain comprises amino acid residues 22-122 of the amino acid sequence as set forth in SEQ ID NO: 98. In some embodiments, the LAIR1 is a variant comprising one or more amino acid substitutions, additions or deletions, optionally two, three, four, five, six, seven, eight, nine, ten or more amino acid substitutions, additions or deletions relative to a LAIR1 protein comprising the amino acid sequence of SEQ ID NO: 98. In some embodiment, the LAIR1 variant has increased binding affinity to collagen relative to a collagen binding affinity of a LAIR1 protein comprising the amino acid sequence of SEQ ID NO: 98. In other further embodiments, the LAIR1 variant has decreased binding affinity to collagen relative to a collagen binding affinity of a LAIR1 protein comprising the amino acid sequence of SEQ ID NO: 98.

In some aspects, the antagonist antibody is selected from an anti-PD-1 antibody, an anti-PD-L1 antibody, an anti-PD-L2 antibody, an anti-CTLA4 antibody, an anti-TIGIT antibody, an anti-BTLA antibody, an anti-VISTA antibody, an anti-TIM-3 antibody, an anti-LAG-3 antibody, an anti-CD47 antibody, and an anti-SIRPα antibody.

In some aspects, the fusion protein is of sufficient mass to reduce size dependent escape by diffusion or convection upon administration in vivo. In some aspects, the fusion protein binds type I and/or type IV collagen upon administration in vivo, thereby reducing systemic exposure of the immunomodulatory fusion protein.

In other aspects, the disclosure provides an immunomodulatory fusion protein comprising:

(i) human IL-2;

(ii) human lumican, human LAIR1, or human LAIR1 variant; and (iii) a linker, wherein the linker is a hydrophilic polypeptide comprising "N" amino acids in length, wherein N=1-1000, 10-900, 30-800, 40-700, 50-600, 100-500, or 200-400,
wherein IL-2 is operably linked via the linker to lumican or LAIR1, and wherein the fusion protein is ≥60 kDa.

In further aspects, the disclosure provides an immunomodulatory fusion protein comprising:
(i) a single chain fusion of human IL-12(p35)/IL-12(p40);
(ii) human lumican, human LAIR1, or human LAIR1 variant; and
(iii) a linker, wherein the linker is a hydrophilic polypeptide comprising "N" amino acids in length, wherein N=1-1000, 10-900, 30-800, 40-700, 50-600, 100-500, or 200-400,
wherein the single chain fusion of IL-12(p35)/IL-12(p40) is operably linked via the linker to lumican or LAIR1, and wherein the fusion protein is ≥60 kDa.

In yet further aspects, the disclosure provides an immunomodulatory fusion protein comprising:
(i) human CCL-3;
(ii) human lumican, human LAIR1, or human LAIR1 variant; and
(iii) a linker, wherein the linker is a hydrophilic polypeptide comprising "N" amino acids in length, wherein N=1-1000, 10-900, 30-800, 40-700, 50-600, 100-500, or 200-400,
wherein CCL-3 is operably linked via the linker to lumican or LAIR1, and wherein the fusion protein is ≥60 kDa.

In other aspects, the disclosure provides an immunomodulatory fusion protein comprising:
(i) human CCL-4;
(ii) human lumican, human LAIR1, or human LAIR1 variant; and
(iii) a linker, wherein the linker is a hydrophilic polypeptide comprising "N" amino acids in length, wherein N=1-1000, 10-900, 30-800, 40-700, 50-600, 100-500, or 200-400,
wherein CCL-4 is operably linked via the linker to lumican or LAIR1, and wherein the fusion protein is ≥60 kDa.

In some aspects, the disclosure provides an immunomodulatory fusion protein comprising:
(i) human CCL-5;
(ii) human lumican, human LAIR1, or human LAIR1 variant; and
(iii) a linker, wherein the linker is a hydrophilic polypeptide comprising "N" amino acids in length, wherein N=1-1000, 10-900, 30-800, 40-700, 50-600, 100-500, or 200-400,
wherein CCL-5 is operably linked via the linker to lumican or LAIR1, and wherein the fusion protein is ≥60 kDa.

In other aspects, the disclosure provides an immunomodulatory fusion protein comprising:
(i) human Eotaxin;
(ii) human lumican, human LAIR1, or human LAIR1 variant; and
(iii) a linker, wherein the linker is a hydrophilic polypeptide comprising "N" amino acids in length, wherein N=1-1000, 10-900, 30-800, 40-700, 50-600, 100-500, or 200-400,
wherein Eotaxin is operably linked via the linker to lumican or LAIR1, and wherein the fusion protein is ≥60 kDa.

In any of the foregoing aspects, lumican comprises the amino acid sequence as set forth in SEQ ID NO: 107.

In any of the foregoing aspects, LAIR1 comprises the amino acid sequence as set forth in SEQ ID NO: 98. In some embodiments, the LAIR1 is a variant comprising one or more amino acid substitutions, additions or deletions, optionally two, three, four, five, six, seven, eight, nine, ten or more amino acid substitutions, additions or deletions relative to a LAIR1 protein comprising the amino acid sequence of SEQ ID NO: 98. In some embodiment, the LAIR1 variant has increased binding affinity to collagen relative to a collagen binding affinity of a LAIR1 protein comprising the amino acid sequence of SEQ ID NO: 98. In other further embodiments, the LAIR1 variant has decreased binding affinity to collagen relative to a collagen binding affinity of a LAIR1 protein comprising the amino acid sequence of SEQ ID NO: 98.

In any of the foregoing aspects, the linker is of sufficient length or mass to reduce adsorption of the immunomodulatory domain onto collagen fibrils, and/or provides sufficient molecular weight to the fusion protein reduce diffusion from a tissue and/or allows for steric separation of the immunomodulatory domain from collagen fibrils to promote receptor/ligand engagement. In some aspects, the linker is human serum albumin or fragment thereof. In other aspects, the linker comprises an Fc domain or a mutant Fc domain with reduced FcR interaction.

In some aspects, the fusion protein is of sufficient mass to reduce size dependent escape by diffusion or convection upon administration in vivo. In some aspects, the fusion protein binds type I and/or type IV collagen upon administration in vivo, thereby reducing systemic exposure of the immunomodulatory fusion protein.

In yet other aspects, the disclosure provides an immunomodulatory fusion protein comprising:

(i) an agonist antibody comprising an Fc domain or a mutant Fc domain with reduced FcR interaction, wherein the agonist antibody is selected from an anti-CD3 antibody, an anti-4 BB antibody, an anti-CD40 antibody and an anti-OX40 antibody; and (ii) human lumican, human LAIR1, or human LAIR1 variant;

wherein lumican or LAIR1 is operably linked to the C-terminus of the Fc domain or mutant Fc domain.

In some aspects, the fusion protein is of sufficient mass to reduce size dependent escape by diffusion or convection upon administration in vivo. In some aspects, the fusion protein binds type I and/or type IV collagen upon administration in vivo, thereby reducing systemic exposure of the immunomodulatory fusion protein.

In some aspects, the disclosure provides a pharmaceutical composition comprising an immunomodulatory fusion protein disclosed herein, and a pharmaceutically acceptable carrier.

In other aspects, the disclosure provides a nucleotide sequence encoding an immunomodulatory fusion protein disclosed herein. In some aspects, the disclosure provides an expression vector comprising a nucleic acid disclosed herein. In other aspects, the disclosure provides a cell transformed with an expression vector disclosed herein.

In another aspects, the disclosure provides a method for producing an immunomodulatory fusion protein, the method comprising maintaining a cell described herein under conditions permitting expression of the immunomodulatory fusion protein. In further aspects, the method comprises obtaining the immunomodulatory fusion protein.

In other aspects, the disclosure provides a method for activating, enhancing or promoting a response by an immune cell in a subject, comprising administering to a subject in need thereof, an effective amount of an immunomodulatory fusion protein or pharmaceutical composition disclosed herein In yet further aspects, the disclosure provides a method for inhibiting, reducing or suppressing a response by an immune cell in a subject, comprising administering to a subject in need thereof, an effective amount of an immunomodulatory fusion protein or pharmaceutical composition disclosed herein In any of the foregoing aspects, the immune cell is a lymphoid cell selected from an innate lymphoid cell, a T cell, a B cell, an NK cell, and a combination thereof. In other aspects, the immune cell is a myeloid cell selected from a monocyte, a neutrophil, a granulocyte, a mast cell, a macrophage, a dendritic cell, and a combination thereof. In some aspects, the response by the immune cell comprises cytokine production, antibody production, production of antigen-specific immune cells, increased effector function and/or cytotoxicity, and a combination thereof. In some aspects, the immune cell occurs in a tumor microenvironment.

In other aspects, the disclosure provides a method for reducing or inhibiting tumor growth, comprising administering to a subject in need thereof, an effective amount an immunomodulatory fusion protein or pharmaceutical composition disclosed herein.

In further aspects, the disclosure provides a method for treating cancer in a subject, comprising administering to a subject in need thereof, an effective amount of an immunomodulatory fusion protein or pharmaceutical composition disclosed herein.

In any of the foregoing aspects, an anti-tumor immune response is induced in the subject after administration of the immunomodulatory fusion protein or the pharmaceutical composition. In some aspects, the anti-tumor immune response is a T cell response comprising the production of IFNγ and/or IL-2 by one or both of CD4+ T cells and CD8+ T cells.

In any of the foregoing aspects, infiltration of immune cells into a tumor microenvironment is increased after administration of the immunomodulatory fusion protein or the pharmaceutical composition.

In any of the foregoing aspects, the quantity of T regulatory (Treg) cells is reduced in a tumor microenvironment after administration of the immunomodulatory fusion protein or the pharmaceutical composition. In any of the foregoing aspects, T cell exhaustion is reduced in a tumor microenvironment after administration of the immunomodulatory fusion protein or the pharmaceutical composition.

In any of the foregoing aspects, the immunomodulatory fusion protein or pharmaceutical composition is administered intratumorally.

In any of the foregoing aspects, the immunomodulatory fusion protein or pharmaceutical composition is administered by viral vectors, electroporation, transplantation of cells expressing the immunomodulatory fusion protein, or replicons.

In other aspects, the disclosure provides a kit comprising a container comprising an immunomodulatory fusion protein described herein, and an optional pharmaceutically acceptable carrier, or a pharmaceutical composition described herein, and a package insert comprising instructions for administration of the fusion protein or pharmaceutical composition, for treating or delaying progression of cancer or reducing or inhibiting tumor growth in a subject in need thereof.

In yet further aspects, the disclosure provides a kit comprising a container comprising an immunomodulatory fusion protein described herein, and an optional pharmaceutically acceptable carrier, or a pharmaceutical composition described herein, and a package insert comprising instructions for administration of the antibody or pharmaceutical composition alone or in combination with another agent, for treating or delaying progression of cancer or reducing or inhibiting tumor growth in a subject in need thereof.

In some aspects, the disclosure provides use of an immunomodulatory fusion protein described herein, and an optional pharmaceutically acceptable carrier, or a pharmaceutical composition described herein, for the manufacture of a medicament for treating or delaying progression of cancer or reducing or inhibiting tumor growth in a subject in need thereof.

In other aspects, the disclosure provides an immunomodulatory fusion protein described herein, and an optional pharmaceutically acceptable carrier, or a pharmaceutical composition described herein, in the manufacture of a medicament for treating or delaying progression of cancer or reducing or inhibiting tumor growth in a subject in need thereof.

In yet further aspects, the disclosure provides an immunomodulatory fusion protein described herein, and an optional pharmaceutically acceptable carrier, or a pharmaceutical composition described herein, for use as a medicament.

In other aspects, the disclosure provides a method for reducing or inhibiting tumor growth or treating cancer in a subject, the method comprising administering to a subject in need thereof, an effective amount an immunomodulatory fusion protein or pharmaceutical composition described herein, and an effective amount of a second composition comprising a tumor antigen-targeting antibody, or antigen-binding fragment thereof, thereby reducing or inhibiting tumor growth or treating cancer in the subject. In some aspects, the tumor antigen is a tumor-associated antigen (TAA), a tumor-specific antigen (TSA), or a tumor neoantigen. In other aspects, the tumor antigen-targeting antibody specifically binds human HER-2/neu, EGFR, VEGFR, CD20, CD33, or CD38.

In yet other aspects, the disclosure provides a method for reducing or inhibiting tumor growth or treating cancer in a subject, the method comprising administering to a subject in need thereof, an effective amount an immunomodulatory fusion protein or pharmaceutical composition described herein, and an effective amount of a second composition comprising a cancer vaccine, thereby reducing or inhibiting tumor growth or treating cancer in the subject. In some aspects, the cancer vaccine is a population of cells immunized in vitro with a tumor antigen and administered to the subject. In other aspects, the cancer vaccine is a peptide comprising one or more tumor-associated antigens. In some aspects, cancer vaccine is an amphiphilic peptide conjugate comprising a tumor-associated antigen, a lipid, and optionally a linker, wherein the amphiphilic peptide conjugate binds albumin under physiological conditions. In some aspects, the cancer vaccine further comprises an adjuvant.

In some aspects, the disclosure provides a method for reducing or inhibiting tumor growth or treating cancer in a subject, the method comprising administering to a subject in need thereof, an effective amount an immunomodulatory fusion protein or pharmaceutical composition described herein, and an effective amount of a second composition comprising an immune checkpoint inhibitor, thereby reducing or inhibiting tumor growth or treating cancer in the subject. In some aspects, the immune checkpoint inhibitor comprises an antibody or antigen binding fragment thereof which binds PD-1, PD-L1, CTLA-4, LAG3, or TIM3.

In further aspects, the disclosure provides a method for reducing or inhibiting tumor growth or treating cancer in a subject, the method comprising administering to a subject in need thereof, an effective amount an immunomodulatory fusion protein or pharmaceutical composition described herein, and an effective amount of a second composition comprising an adoptive cell therapy, thereby reducing or inhibiting tumor growth or treating cancer in the subject. In some aspects, the adoptive cell therapy comprises an immune effector cell comprising a chimeric antigen receptor (CAR) molecule which binds to a tumor antigen. In some aspects, the CAR molecule comprises an antigen binding domain, a transmembrane domain, and an intracellular domain comprising a costimulatory domain and/or a primary signaling domain. In some aspects, the antigen binding domain binds to the tumor antigen associated with the disease. In some aspects, the tumor antigen is selected from CD19, EGFR, Her2/neu, CD30 and BCMA. In some aspects, the immune effector cell is a T cell, such as a CD8+ T cell. In some aspects, the immune effector cell is a natural killer (NK) cell.

In any of the foregoing methods, the immunomodulatory fusion protein or the pharmaceutical composition are administered intratumorally. In some aspects, the immunomodulatory fusion protein or the pharmaceutical composition and the second composition are administered concurrently or sequentially.

In other aspects, the disclosure provides a method for reducing or inhibiting tumor growth or treating cancer in a subject, the method comprising administering to a subject in need thereof, an effective amount of immunomodulatory fusion protein comprising:
  (i) human IL-2;
  (ii) human lumican, human LAIR1, or human LAIR1 variant; and
  (iii) a linker, wherein the linker is a hydrophilic polypeptide comprising "N" amino acids in length, wherein N=1-1000, 10-900, 30-800, 40-700, 50-600, 100-500, or 200-400, wherein IL-2 is operably linked via the linker to lumican or LAIR1, and wherein the fusion protein is >60 kDa, thereby reducing or inhibiting tumor growth or treating cancer in the subject.

In some aspects, the disclosure provides a method for reducing or inhibiting tumor growth or treating cancer in a subject, the method comprising administering to a subject in need thereof, an effective amount of an immunomodulatory fusion protein comprising:
  (i) a single chain fusion of human IL-12(p35)/IL-12(p40);
  (ii) human lumican, human LAIR1, or human LAIR1 variant; and
  (iii) a linker, wherein the linker is a hydrophilic polypeptide comprising "N" amino acids in length, wherein N=1-1000, 10-900, 30-800, 40-700, 50-600, 100-500, or 200-400, wherein the single chain fusion of IL-12 (p35)/IL-12(p40) is operably linked via the linker to lumican or LAIR1, and wherein the fusion protein is ≥60 kDa,
thereby reducing or inhibiting tumor growth or treating cancer in the subject.

In some aspects, the disclosure provides a method for reducing or inhibiting tumor growth or treating cancer in a subject, the method comprising administering to a subject in need thereof, an effective amount of a first composition comprising an immunomodulatory fusion protein comprising:
  (i) human IL-2;
  (ii) human lumican, human LAIR1, or human LAIR1 variant; and
  (iii) a linker, wherein the linker is a hydrophilic polypeptide comprising "N" amino acids in length, wherein N=1-1000, 10-900, 30-800, 40-700, 50-600, 100-500, or 200-400, wherein IL-2 is operably linked via the linker to lumican or LAIR1, and wherein the fusion protein is >60 kDa, and a second composition comprising an effective amount of an immunomodulatory fusion protein comprising:
  (i) a single chain fusion of human IL-12(p35)/IL-12(p40);
  (ii) human lumican, human LAIR1, or; and
  (iii) a linker, wherein the linker is a hydrophilic polypeptide comprising "N" amino acids in length, wherein N=1-1000, 10-900, 30-800, 40-700, 50-600, 100-500, or 200-400, wherein the single chain fusion of IL-12 (p35)/IL-12(p40) is operably linked via the linker to lumican or LAIR1, and wherein the fusion protein is ≥60 kDa,
thereby reducing or inhibiting tumor growth or treating cancer in the subject.

In some aspects, the method further comprises administering a second (or third, or fourth) composition comprising an effective amount of a tumor antigen-targeting antibody, or antigen-binding fragment thereof. In other aspects, the method further comprises administering a second composition comprising an effective amount of composition comprising a cancer vaccine. In yet other aspects, the method further comprises administering a second composition comprising an effective amount of a second composition comprising an immune checkpoint inhibitor. In some aspects, the immune checkpoint inhibitor comprises an antibody or antigen binding fragment thereof which binds PD-1, PD-L1, CTLA-4, LAG3, or TIM3.

In another aspects, the method further comprises administering a second composition comprising an effective amount of a second composition comprising an adoptive cell therapy, thereby reducing or inhibiting tumor growth or treating cancer in the subject. In some aspects, the adoptive cell therapy comprises an immune effector cell comprising a chimeric antigen receptor (CAR) molecule which binds to a tumor antigen. In some aspects, the immune effector cell is a T cell, such as a CD8+ T cell or an NK cell.

In any of the foregoing aspects, the immunomodulatory fusion protein or the pharmaceutical composition are administered intratumorally.

In any of the foregoing aspects, the immunomodulatory fusion protein or the pharmaceutical composition and the second composition are administered concurrently or sequentially.

BRIEF DESCRIPTIONS OF THE FIGURES

FIG. 1A provides a graph showing the binding of *Gaussia* luciferase alone (Gluc) or fused to collagen-binding polypeptides (Lumican-Gluc, ColG s3a/s3b-Gluc, ColH s3-Gluc) to collagen type I as a function of concentration. Binding was determined by ELISA.

Figure 1C:
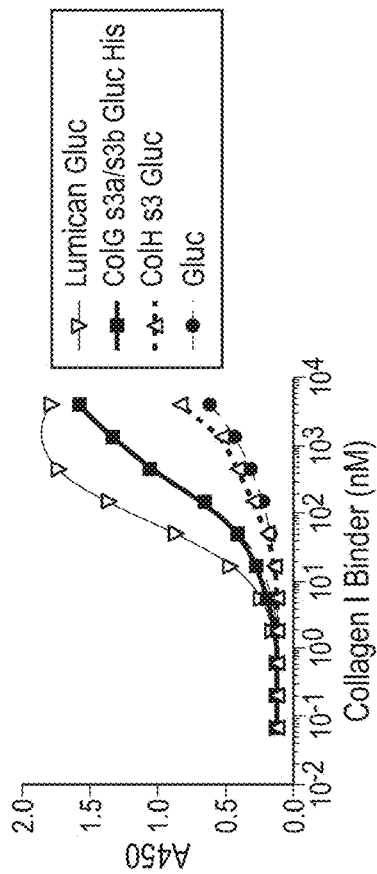
Figure 1B:
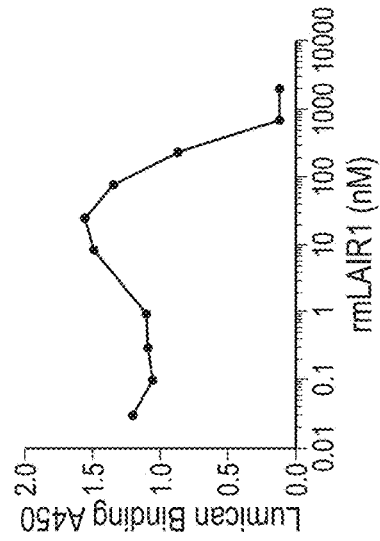

FIG. 1B provides a graph showing the binding of *Gaussia* luciferase alone (Gluc) or fused to collagen-binding polypeptides (Lumican-Gluc, ColG s3a/s3b-Gluc, ColH s3-Glue) to collagen type IV as a function of concentration. Binding was determined by ELISA.

FIG. 1C provides a graph showing the binding of His-tagged murine LAIR-1 (mLAIR1-His) and His-tagged biotinylated lumican (Lwt-HIS-b) to collagen type I as a function of concentration. Binding was determined by ELISA using an anti-HIS antibody conjugated to horseradish peroxidase (HRP).

Figure 1D:
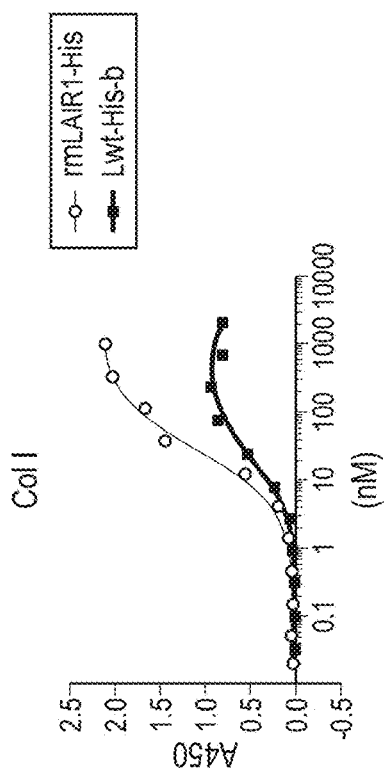

FIG. 1D provides a graph showing the competitive binding between His-tagged murine LAIR-1 (mLAIR1) and His-tagged biotinylated lumican to collagen type I as a function of mLAIR1 concentration. Lumican binding to collagen type I was determined by competition ELISA in the presence of varying concentrations of mLAIR1 using Streptavidin conjugated to horseradish perioxidate (HRP).

Figure 2B:
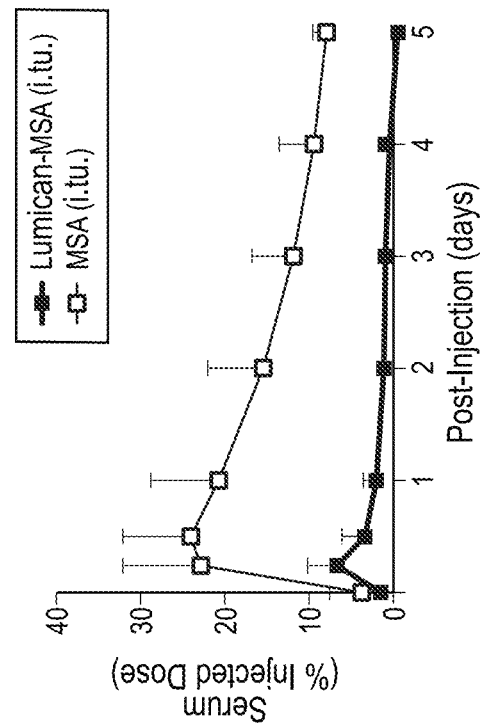
Figure 2A:
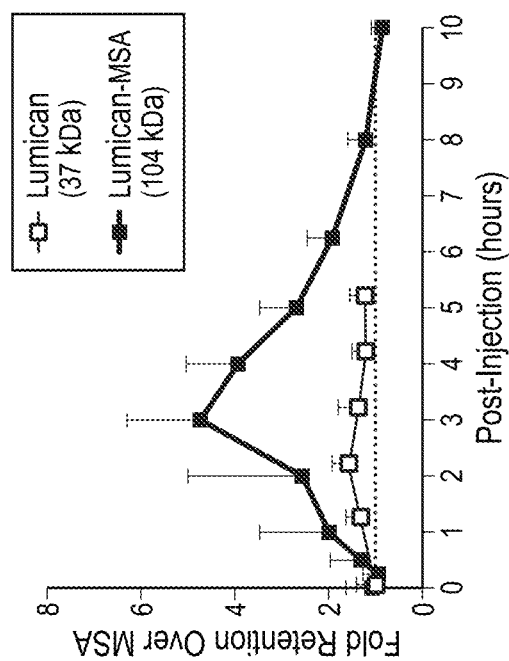

FIG. 2A provides a graph quantifying relative tumor fluorescence over time of fluorescently-labeled lumican or lumican-MSA compared to fluorescently-labeled MSA following intratumoral injection in B16F10-Trp2KO tumors as determined by in vivo fluorescence imaging.

FIG. 2B provides a graph quantifying fluorescence of serum from B16F10-Trp2KO tumor-bearing mice injected with fluorescently-labeled lumican-MSA or fluorescently-labeled MSA as a percentage of injected dose. Serum fluorescence was determined by fluorescent imaging of micro-hematocrit heparin-coated tubes containing mouse blood samples.

Figure 3A:
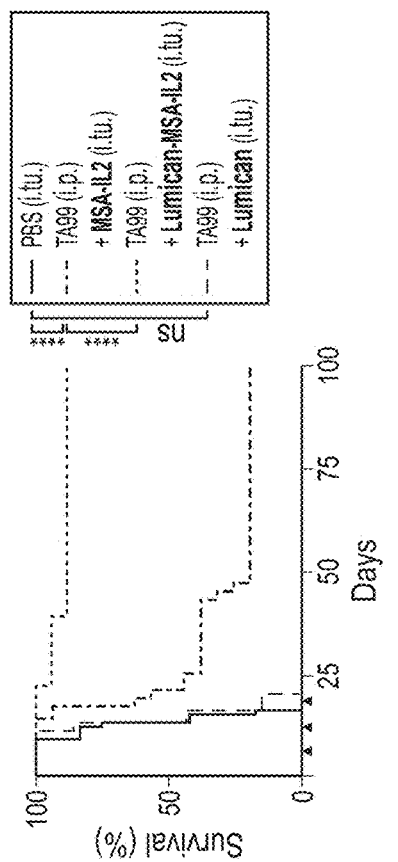

FIG. 3A provides a Mantel-Cox survival curve of B16F10 melanoma tumor-bearing mice treated with PBS (control) (i.tu.), MSA-IL2 (i.tu.), Lumican-MSA-IL2 (i.tu.), or Lumican (i.tu.). Mice (n=5 or 7 per treatment group) were treated as indicated (arrows) on day 6 and 12. Survival statistics determined by log-rank Mantel-Cox test. Significance indicated with **($P<0.002$).

Figure 3B:
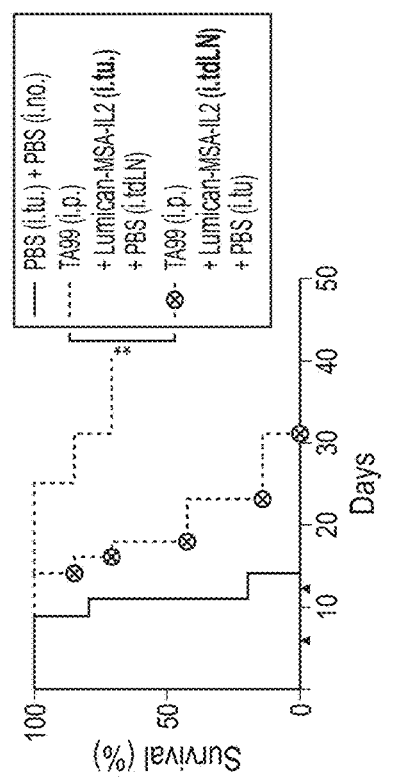

FIG. 3B provides a Mantel-Cox survival curve of B16F10 melanoma tumor-bearing mice treated intratumorally with PBS (n=7, i.tu.), anti-TYRP1 antibody (TA99) (i.p.) in combination with MSA-IL2 (n=17, i.tu.), Lumican-MSA-IL2 (n=17, i.tu.), or with Lumican (n=17, i.tu.). Mice were treated as indicated (arrows) on day 6, 12 and 18. Survival statistics determined by log-rank Mantel-Cox test. Significance indicated with *($P<0.03$), ($P<0.002$), *($P<0.0002$), ****($P<0.0001$), n.s., not significant.

Figure 3C:
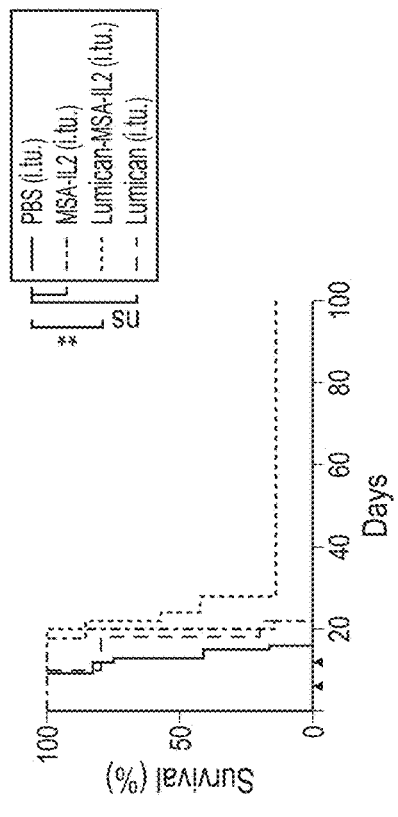

FIG. 3C provides a Mantel-Cox survival curve B16F10 melanoma tumor-bearing mice treated with PBS (control) (i.tu.) or with a combination of anti-TYRP1 antibody (TA99) (i.p.) and Lumican-MSA-IL2 administered intratumorally (i.tu.), peritumorally (peri.tu) (i.e. adjacent to the tumor), or subcutaneously near the base of the tail (s.c. tail base) Mice were treated as indicated (arrows) on day 6, 12 and 18. Survival statistics determined by log-rank Mantel-Cox test. Significance indicated with *($P<0.03$), ($P<0.002$), *($P<0.0002$), ****($P<0.0001$), n.s., not significant.

Figure 3D:
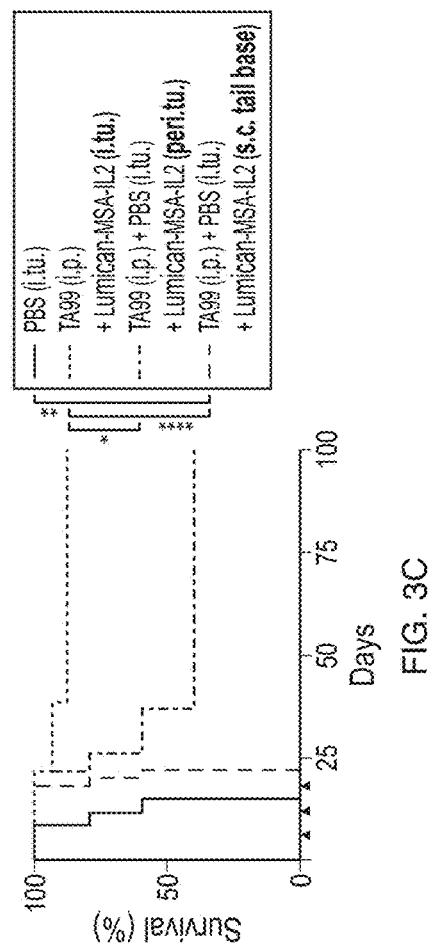

FIG. 3D provides a Mantel-Cox survival curve of B16F10 melanoma tumor-bearing mice treated with PBS (control) both (i.tu.) and into the inguinal tumor draining lymph node (i.tdLN), with anti-TYRP1 antibody (TA99) (i.p) in combination with Lumican-MSA-IL2 (i.tu.) and PBS (i.tdLN), or with anti-TYRP1 antibody (TA99) (i.p) in combination with Lumican-MSA-IL2 (i.tdLN) and PBS (i.tu). Mice (n=7 per treatment group) were treated as indicated (arrows) on day 6 and day 12. Survival statistics determined by log-rank Mantel-Cox test. Significance indicated with **($P<0.002$).

Figure 4:
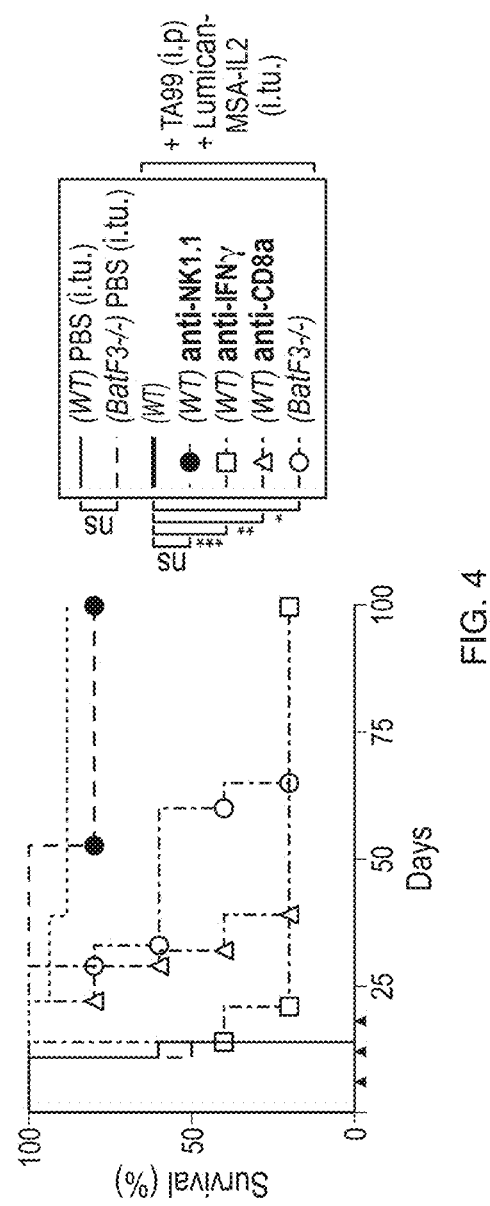

FIG. 4 provides a Mantel-Cox survival curve of B16F10 melanoma tumor-bearing BatF3$^{-/-}$ or wild-type (WT) mice treated with PBS (control) (i.tu.) or anti-TYRP1 antibody (TA99) (i.p.) in combination with Lumican-MSA-IL2 (i.tu) and immune cell depleting or cytokine neutralizing antibodies as indicated. Mice (n=5 per treatment group) were treated as indicated on day 6, 12 and 18. Survival statistics determined by log-rank Mantel-Cox test. Significance indicated with *($P<0.03$), ($P<0.002$), *($P<0.0002$), ****($P<0.0001$), n.s., not significant.

FIG. 5A provides a graph quantifying IFNγ+ cells among live CD45+CD3+CD8+ T cells derived from splenocytes, excised on day 10 of mice (treated as described in FIG. 3B), stimulated with irradiated B16F10 or 4T1 cells for 12 hours in the presence of brefeldin A and subsequently stained for surface markers and intracellular IFNγ (n=5 mice per treatment group). Data analyzed by one-way ANOVA with Tukey's multiple comparison test.

FIG. 5B provides a graph quantifying mean tumor areas of the contralateral (untreated) (left panel) and ipsilateral (treated) (middle panel) lesions from B16F10 melanoma tumor-bearing mice treated and percent survival (right panel) monitored over time (n=7/group). Mice were inoculated with B16F10 cells on the right flank (ipsilateral) and with B16F10 cells on the left flank (contralateral) on day 0. Intratumoral treatments were administered to the ipsilateral tumor alongside TA99 (i.p.) on day 6 and day 12. Tumor area (mean+S.D.) of the contralateral (untreated) and ipsilateral (treated) lesions (left) and survival (right) monitored over time (n=7/group). For each group, tumor area shown until a mouse reaches the euthanasia criterion. Survival statistics determined by log-rank Mantel-Cox test. Significance assumed with *, $P<0.03$; , $P<0.002$; *, $P<0.0002$; ****, $P<0.0001$; n.s., not significant.

Figure 6B:
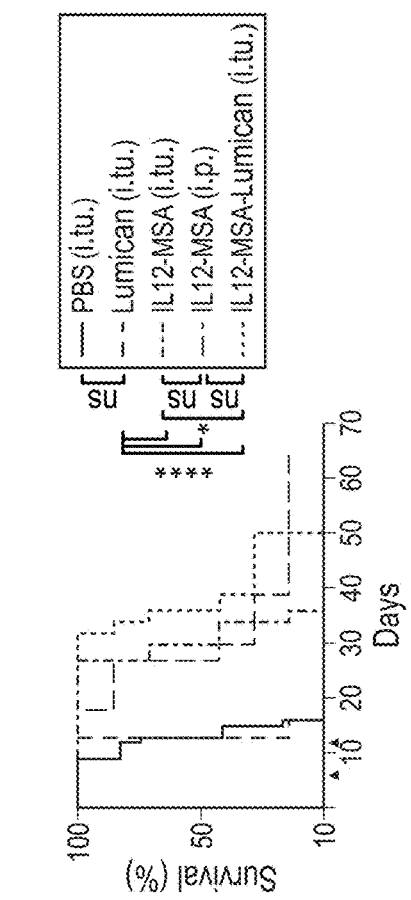
Figure 6A:
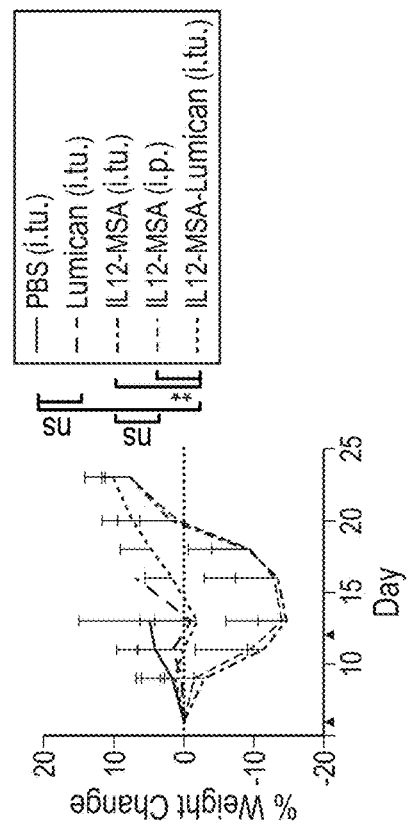

FIG. 6A provides a graph quantifying weight change of B16F10 melanoma tumor-bearing mice after treatment with PBS (i.tu.) (n=6), lumican (i.tu.) (n=7), IL12-MSA (i.tu.) (n=7), IL12-MSA-Lumican (i.tu.) (n=7), or IL12-MSA (i.p.) (n=7). Mice were treated as indicated (arrows) on day 6 and day 12.

FIG. 6B provides a survival curve for mice inoculated with B16F10 melanoma tumors on day 0 and treated with PBS (control), lumican (i.tu.), IL12-MSA (i.tu), IL12-MSA (i.p.) or IL12-MSA-Lumican (i.tu) on days 6 and 12.

Figure 7:
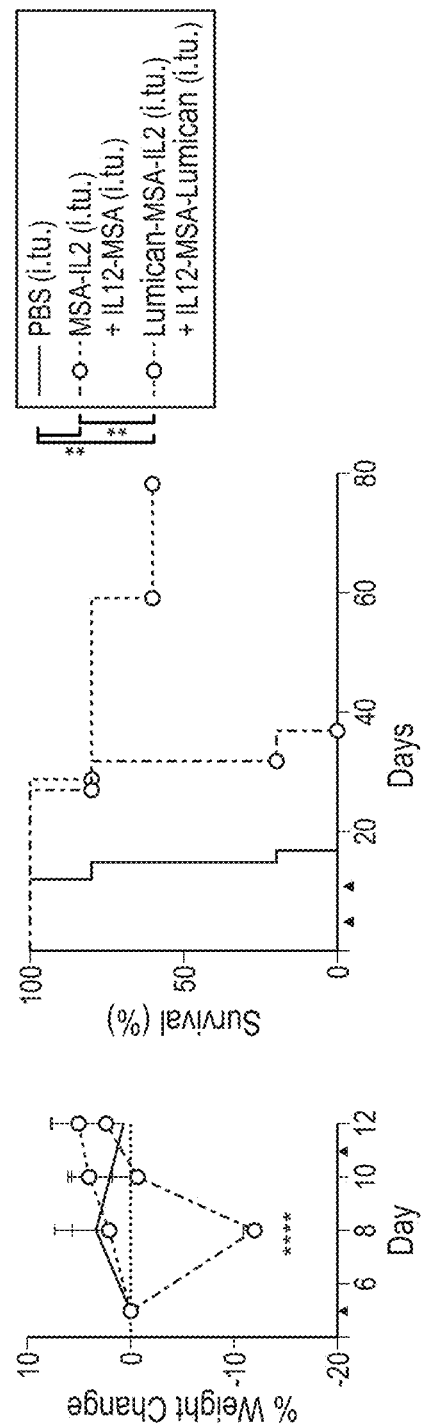

FIG. 7 provides graphs depicting weight change from baseline (left panel) and corresponding survival over time (right panel) of B16F10 tumor-bearing mice treated with intratumoral (i.tu.) injections of PBS (n=5), MSA-IL2 and IL12-MSA (n=5), or Lumican-MSA-IL2 and IL12-MSA-Lumican (n=5) on day 5 and day 11. Arrows indicate time of treatment. Survival statistics determined by log-rank Mantel-Cox test. Significance indicated with *($P<0.03$), ($P<0.002$), *($P<0.0002$), ****($P<0.0001$), n.s., not significant.

FIG. 8A provides a Mantel-Cox survival curve of B16F10 melanoma tumor-bearing BatF3$^{-/-}$ or wild-type (WT) mice treated with PBS (control) (i.tu.) or Lumican-MSA-IL2 (i.tu.) in combination with IL12-MSA-Lumican (i.tu.) and immune cell depleting or cytokine neutralizing antibodies as indicated. Mice (n=5 per treatment group) were treated as indicated on day 6, 12 and 18. Survival statistics determined by log-rank Mantel-Cox test. Significance indicated with *($P<0.03$), ($P<0.002$), *($P<0.0002$), ****($P<0.0001$), n.s., not significant.

FIG. 8B provides a Mantel-Cox survival curve of B16F10 melanoma tumor-bearing BatF3−/− or wild-type (WT) mice treated with PBS (control) (i.tu.) or Lumican-MSA-IL2 (i.tu.) in combination with IL12-MSA-Lumican (i.tu.) and immune cell depleting antibodies as indicated. Mice (n=5 per treatment group) were treated as indicated on day 6, 12 and 18. Survival statistics determined by log-rank Mantel-Cox test. Significance indicated with *(P<0.03), (P<0.002), *(P<0.0002), ****(P<0.0001), n.s., not significant.

FIG. 8C provides a heat map showing the fold change of immune cells in tumor infiltrates from B16F10 melanoma tumor-bearing mice treated intratumorally with a combination of IL12-MSA-Lumican and Lumican-MSA-IL2 (Lumican versions) or a combination of IL12-MSA+MSA-IL2 (MSA versions) of relative to treatment with PBS.

FIGS. 8D-8E provide graphs quantifying tumor-infiltrating CD8+ T cells isolated from B16F10 melanoma tumor-bearing mice on day 11 post-tumor cell injection (FIG. 8D) and their corresponding median fluorescence intensity (MFI) of surface PD-1 (FIG. 8E), after treatment as in FIG. 8C on day 5 post-tumor cell injection.

Figure 9:
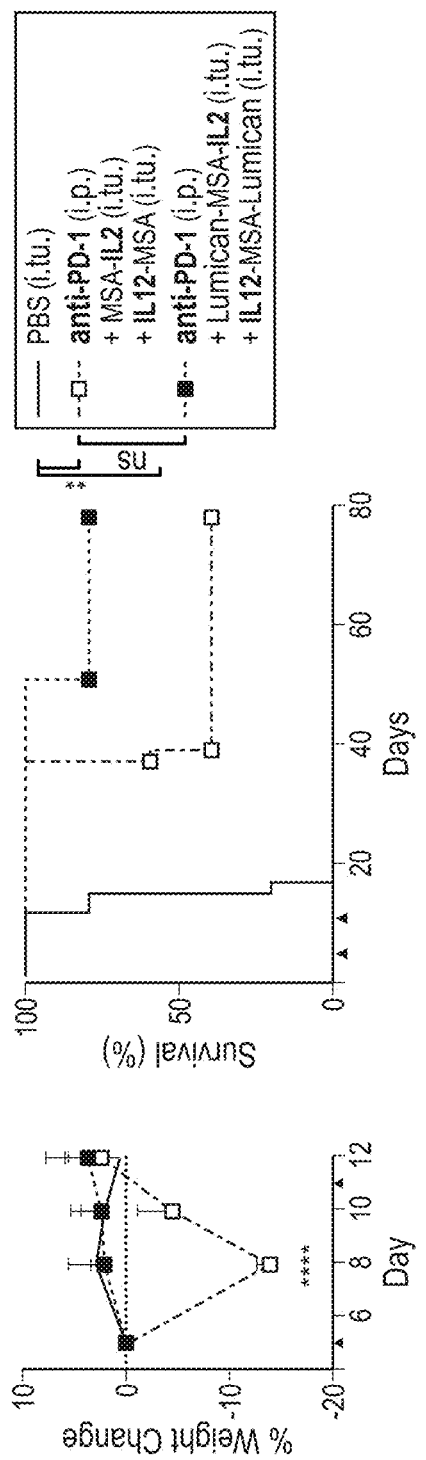

FIG. 9 provides graphs depicting weight change from baseline (left panel) and corresponding survival over time (right panel) of B16F10 melanoma tumor-bearing mice treated with intratumoral (i.tu.) injections of PBS (n=5), anti-PD-1 antibody in combination with MSA-IL2 and IL12-MSA (n=5), or anti-PD-1 antibody in combination with Lumican-MSA-IL2 and IL12-MSA-Lumican (n=5) on day 5 and day 11. Arrows indicate time of treatment. Weight change and comparison statistics determined by one-way ANOVA with Tukey's multiple comparison test. Survival statistics determined by log-rank Mantel-Cox test. Significance indicated with *(P<0.03), (P<0.002), * (P<0.0002), ****(P<0.0001), n.s., not significant.

FIGS. 10A-10B provides a graph depicting tumor area (left panel) and percent survival (right panel) of EMT6 tumor-bearing mice (FIG. 10A) or MC38 tumor-bearing mice (FIG. 10B) and treated as indicated (arrows) on day 5, 11, and 17 as indicated (arrows). Weight change and comparison statistics determined by one-way ANOVA with Tukey's multiple comparison test. Survival statistics determined by log-rank Mantel-Cox test. Significance indicated with *, P<0.03; , P<0.002; *, P<0.0002; ****, P<0.0001; n.s., not significant.

Figure 11:
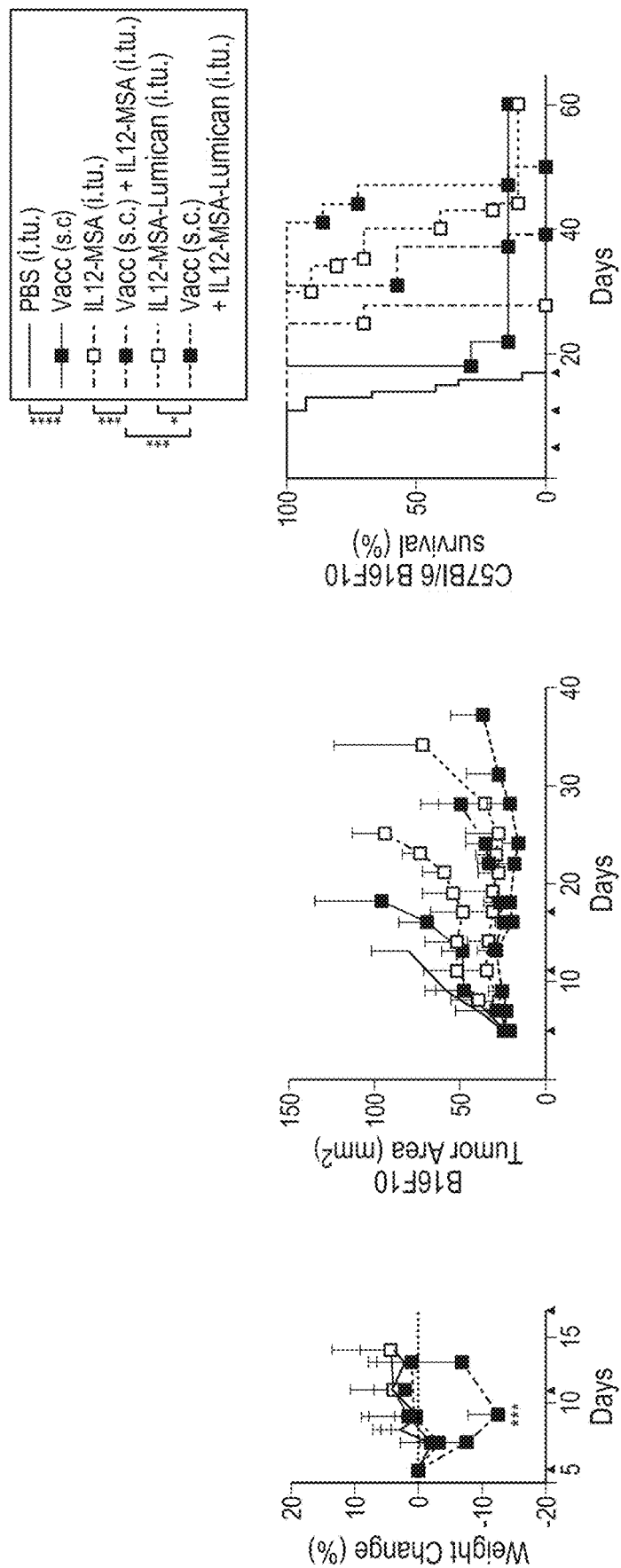
Figure 12:
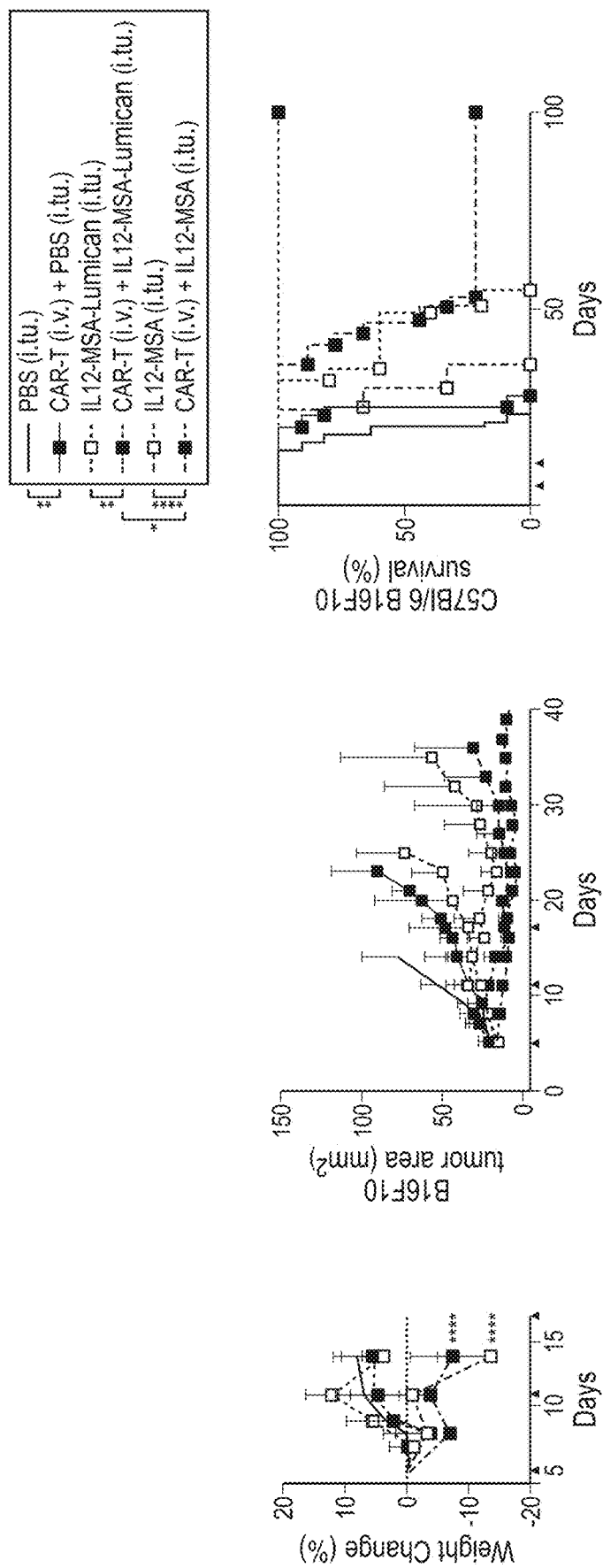
Figure 13:
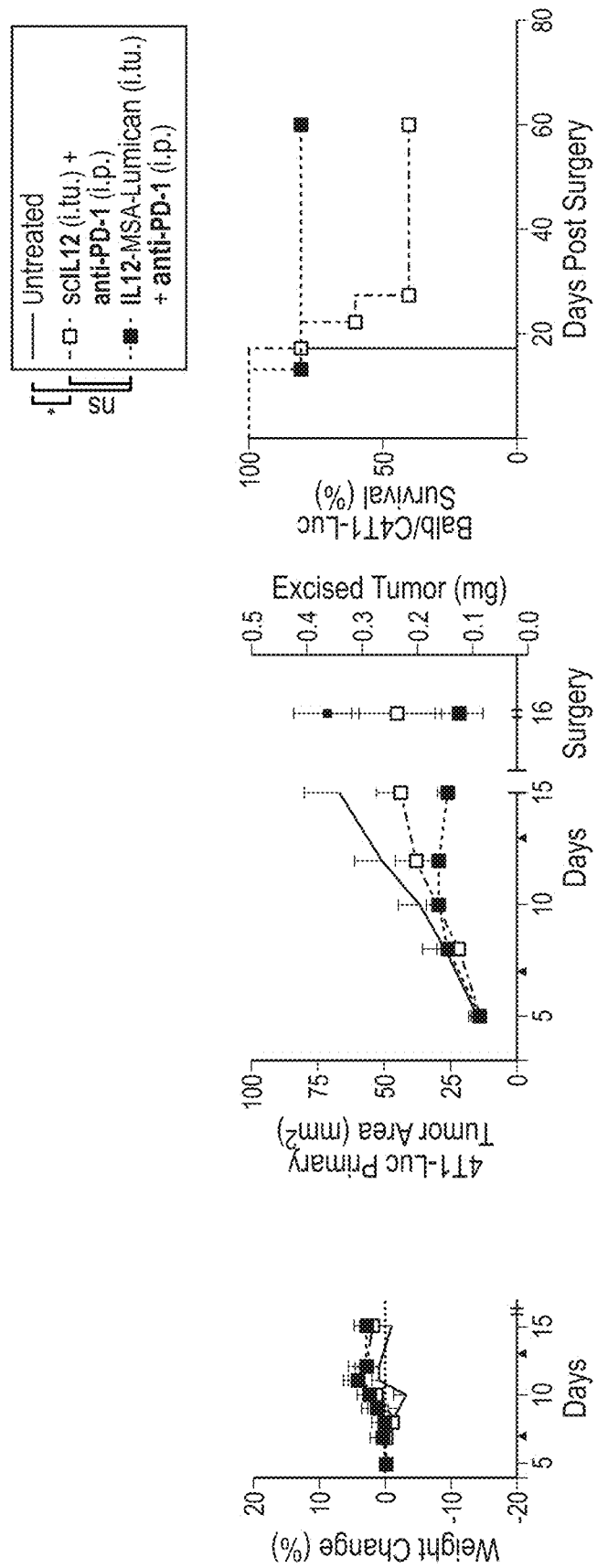
Figure 14A:
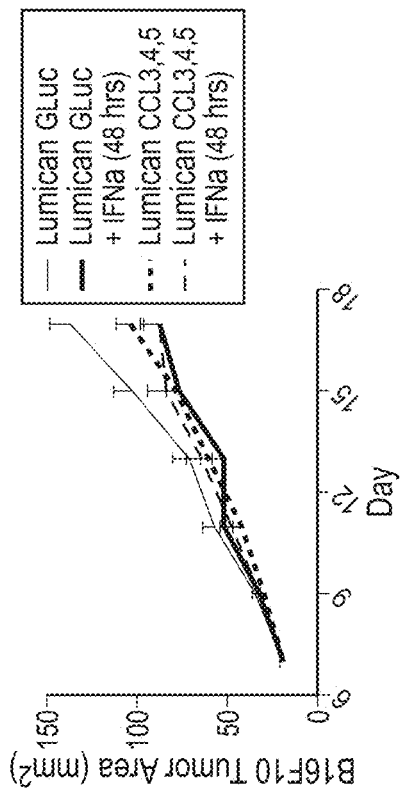

FIG. 11 provides graphs depicting weight change from baseline (left, mean+S.D.), corresponding tumor area (middle, mean+S.D.) and survival (right) of B16F10 melanoma tumor-bearing mice treated with intratumoral (i.tu.) injections of PBS (n=12) or IL-12 (n=10 for IL12-MSA; n=10 for IL12-MSA-Lumican), or cancer vaccine (n=7) alone, or cancer vaccine and IL12 (n=7 for IL12-MSA; n=7 for IL12-MSA-Lumican) on days 5, 11 and 17 as indicated (arrows). Tumor area shown until a mouse reaches the euthanasia criterion (>100 mm²). Weight change statistics, shown within plot, determined by one-way ANOVA with Tukey's multiple comparison test. Survival statistics, adjacent to the legend, determined by log-rank Mantel-Cox test. Significance assumed with *, P<0.03; , P<0.002; *, P<0.0002; ****, P<0.0001; n.s., not significant FIG. 12 provides graphs depicting weight change from baseline (left, mean+S.D.), corresponding tumor area (middle, mean+S.D.) and percent survival (right) of B16F10 melanoma tumor-bearing mice treated with intratumoral (i.tu.) injections of PBS (n=11) or IL-12 (n=9 for IL12-MSA; n=5 for IL12-MSA-Lumican), or CAR-T (n=11) alone, or CAR-T and IL12 (n=9 for IL12-MSA; n=5 for IL12-MSA-Lumican) on days 5 and 11 as indicated (arrows). Mice were inoculated with B16F10 cells on day 0 and lymphodepleted by total body irradiation on day 4. CAR-T treatments were administered in a single bolus tail vein injection (i.v.) on day 5. Tumor area shown until a mouse reaches the euthanasia criterion (>100 mm²). Weight change statistics, shown within plot, determined by one-way ANOVA with Tukey's multiple comparison test. Survival statistics, adjacent to the legend, determined by log-rank Mantel-Cox test. Significance assumed with *, P<0.03; , P<0.002; *, P<0.0002; ****, P<0.0001; n.s., not significant FIG. 13 provides graphs depicting total body weight change during neoadjuvant treatment (left), primary tumor growth and weight (middle) and survival (right) of 4T1 mammary carcinoma tumor-bearing mice treated with intratumoral (i.tu.) injections of IL-12 (n=5 for IL12; n=5 for IL12-MSA-Lumican) and intraperitoneal (i.p.) injection of anti-PD-1 on day 7 and 13. Arrows indicate time of treatment and cross indicates time of surgery. Mice were inoculated 4T1-Luc cells in the mammary fat pad on day 0. Neoadjuvant therapy was administered on day 7 and 13 and the primary tumors was surgically excised on day 16. Post-operation mice were monitored by in vivo imaging (IVIS) for metastases. For each group, tumor area shown until the primary tumor is excised. Weight change statistics, shown within plot, determined by one-way ANOVA with Tukey's multiple comparison test. Survival statistics, adjacent to the legend, determined by log-rank Mantel-Cox test. Significance assumed with *, P<0.03; , P<0.002; *, P<0.0002; ****, P<0.0001; n.s., not significant FIG. 14A provides a graph depicting mean tumor area of 4T1 mammary carcinoma tumor-bearing mice treated intratumorally with Lumican-GLuc or a combination of Lumican-CCL3, Lumican-CCL4 and Lumican-CCL on day 7 and day 13. Administration of IFNα intraperitoneally occurred on day 9 and day 15. Tumor growth (mean+SEM) monitored over time every other day.

Figure 14B:
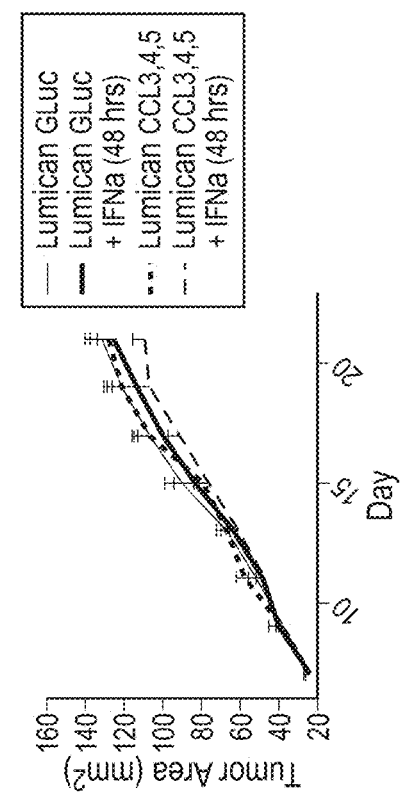

FIG. 14B provides a graph depicting mean tumor area of B16F10 melanoma tumor-bearing mice treated intratumorally with Lumican-GLuc or a combination of Lumican-CCL3, Lumican-CCL4 and Lumican-CCL5 on day 7 and day 13. Administration of IFNα intraperitoneally on day 9 and day 15. Tumor growth (mean+SEM) monitored over time every other day.

Figure 14C:
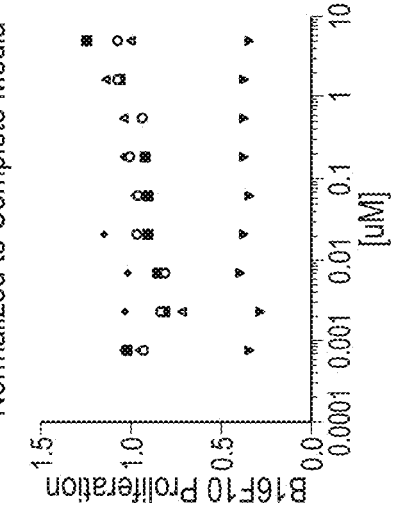

FIG. 14C provides a graph depicting the effect of various concentrations of fusion proteins Lumican-GLuc (Lum GLuc), Lumican-CCL3 (Lum CCL3), Lumican-CCL5 (Lum CCL5) on the proliferation of 4T1 breast tumor cells in vitro. Proliferation was determined by measurement of WST-1 proliferation reagent by absorbance at 450 nm.

Figure 14D:
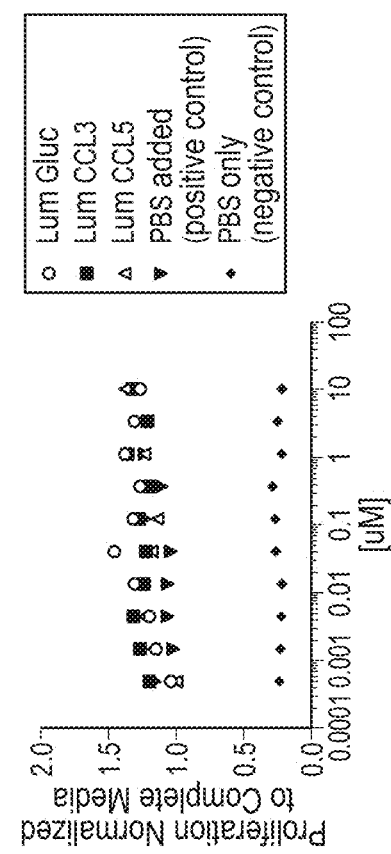

FIG. 14D provides a graph depicting the effect of various concentrations of fusion proteins Lumican-GLuc (Lum GLuc), Lumican-CCL3 (Lum CCL3), Lumican-CCL5 (Lum CCL5) on the proliferation of B16F10 melanoma tumor cells in vitro. Proliferation was determined by measurement of WST-1 proliferation reagent by absorbance at 450 nm.

Figure 15:
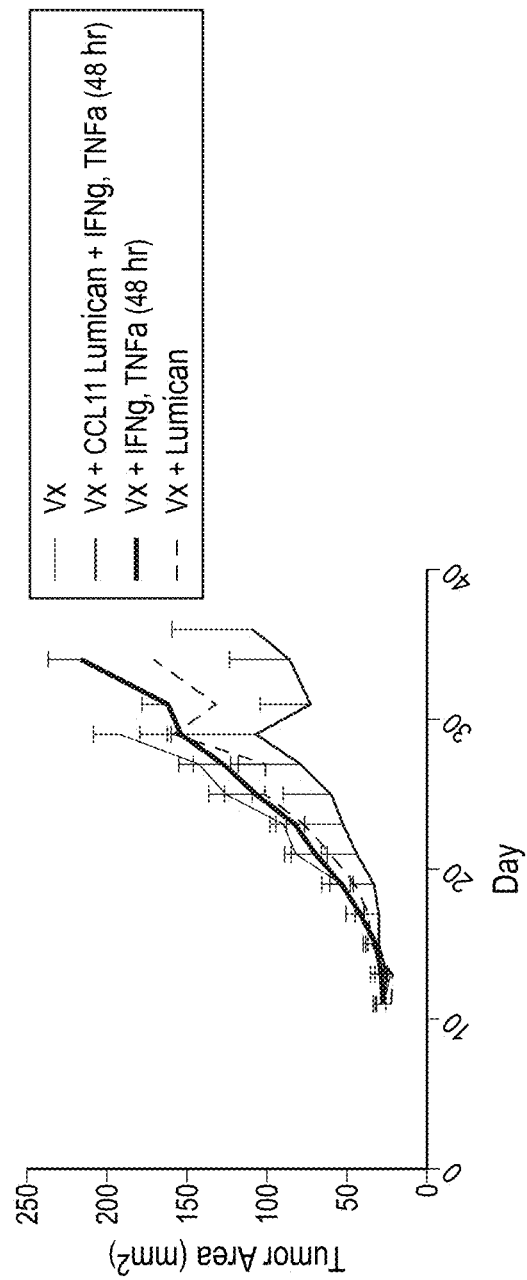

FIG. 15 provides a graph depicting mean tumor areas of tumor lesions in B16F10 melanoma tumor-bearing mice treated with a cancer vaccine administered subcutaneously (s.c.) at the tail base with a prime on day 5 and boosts on day 11 and 17 post-tumor cell injection. Cancer vaccine was administered alone or in combination with CCL11-lumican, TNFα, IFNγ, or Lumican, as indicated, administered intratumorally on days 11, 17, 23, and 29. Tumor area (mean+SD) was measured over time every other day.

Figure 16A:
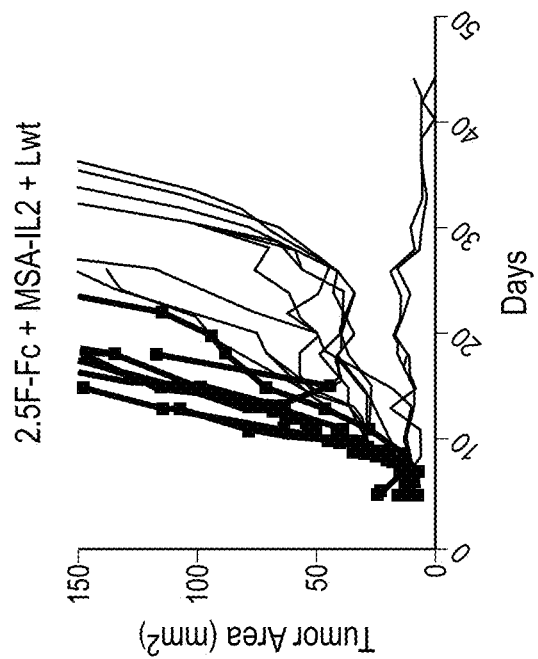
Figure 16B:
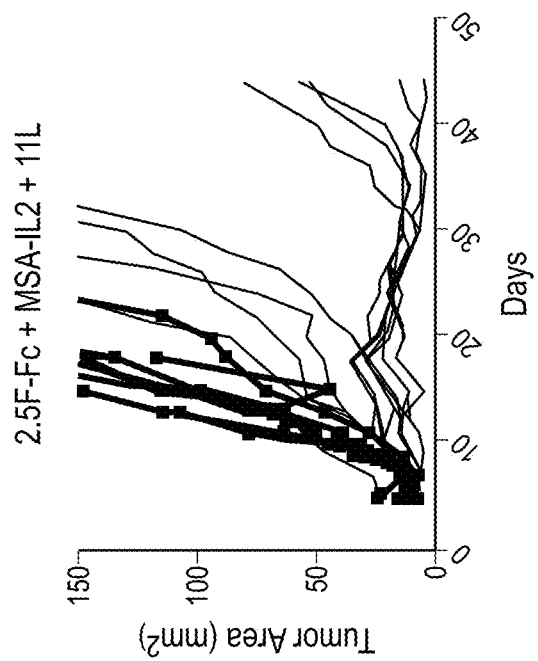

FIGS. 16A-16B provides a graph depicting individual tumor areas of tumor lesions in B16F10 melanoma tumor-bearing mice treated with a tumor-targeting antibody 2.5F-Fc (i.p.) and MSA-IL2 (i.p.) on days 5, 11, and 17 post-tumor cell injection in combination with either lumican (Lwt) (i.tu.) (FIG. 16B) or CCL11-lumican (11 L) (i.tu.)

(FIG. 16A) administered on days 5 and 11. Tumor area monitored over time every other day.

Figure 17A:
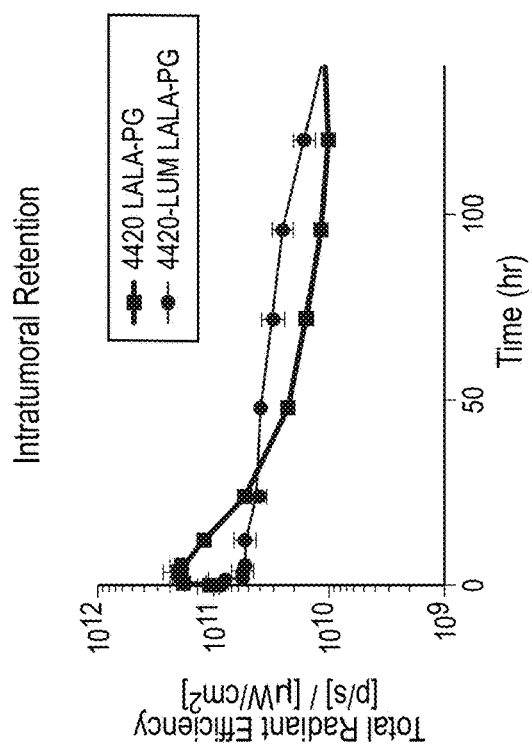

FIG. 17A provides a graph showing the binding of agonist antibody-lumican fusion proteins to collagen type I as a function of concentration. Binding was determined by ELISA.

Figure 17B:
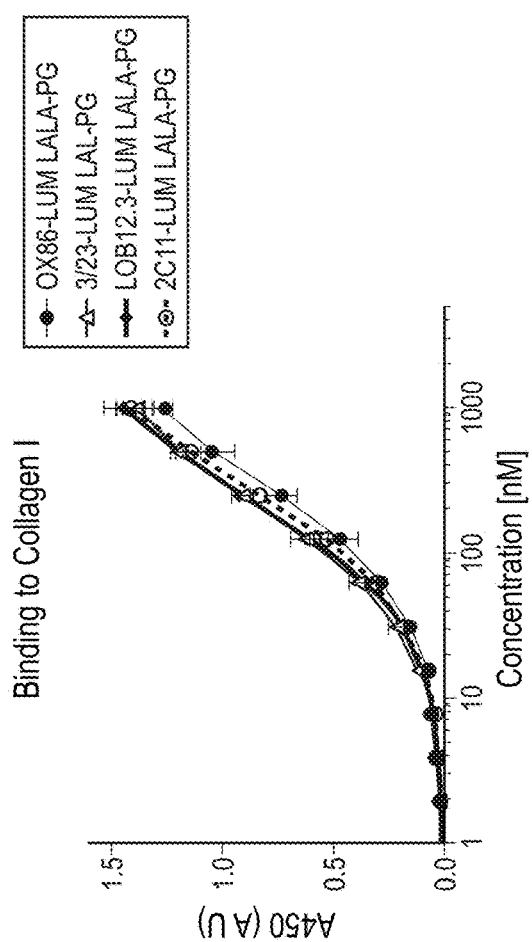

FIG. 17B provides a graph quantifying the in vivo fluorescence of a mouse anti-FITC antibody (4420) alone or fused to Lumican fluorescently-labeled with Alexa Fluor® 647 after intratumoral injection into 4T1 tumors of mic over time as determined by in vivo fluorescence imaging. Measurement of in vivo fluorescence is provided in units of total radiant efficiency (p/s)/(μW/cm2).

FIG. 18A provides a graph showing the binding of a subset of His-tagged lumican-IgG binding fusion proteins, as indicated, to collagen type I (left panel) or collagen IV (right panel) as a function of concentration. Binding was determined by ELISA.

FIG. 18B provides a graph depicting the binding of His-tagged lumican-IgG binding fusion proteins to mouse IgG2a isotype control (Clone C1.18.4) as a function of concentration. Binding was determined by ELISA. Anti-His (Clone ab1187) was used to detect each construct.

FIG. 19 provides 3D microscopy images of mouse omental tissue from OVCA433 human ovarian tumor-bearing mice showing specific accumulation of Alexa Fluor 647-labeled lumican (yellow) around RFP-expressing OVCA433 human ovarian tumor cell microcolonies (Red) in the mouse omental tissue, with collagen imaged by SHG microscopy in grey. Labeled lumican was injected intraperitoneally in tumor-bearing mice.

FIG. 20A provides graphs depicting the expression of IL-12 fusion proteins alone or fused to a fluorescent protein (mCherry), as indicated, from a self-replicating RNA in B16F10 cells as determined by flow cytometry.

FIG. 20B provides a graph depicting the expression of IL-12 fusion proteins alone or fused to a fluorescent protein (mCherry), as indicted, from a self-replicating RNA in B16F10 cells as determined by an IL-12 ELISA.

Figure 21A:
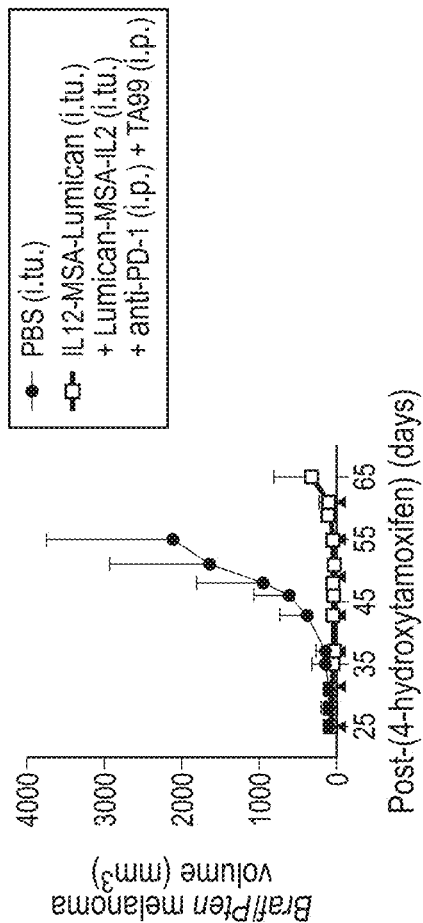

FIG. 21A provides a graph showing tumor volume (mean+SD) of tumor-bearing mice treated either with an intratumoral injection of PBS (n=4) or with intratumoral collagen-anchoring cytokines Lumican-MSA-IL2 and IL12-MSA-Lumican and intraperitoneal TA99 and anti-PD-1 (n=5) on days 25, 31, 37, 43, 49, 55, and 61. For each group, tumor volume shown until a mouse reaches the euthanasia criterion (>1200 mm$^3$).

Figure 21B:
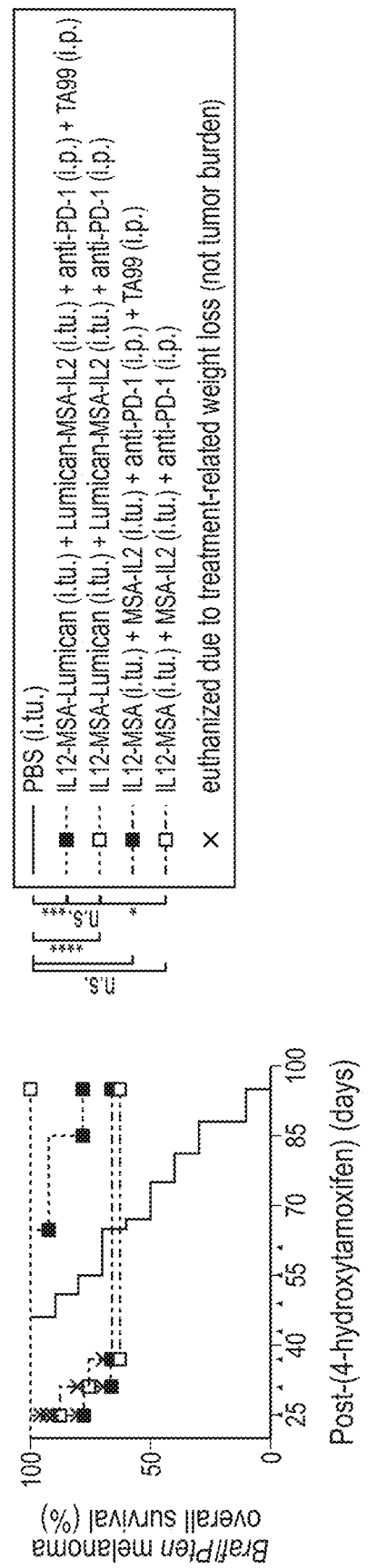

FIG. 21B provides a Mantel-Cox survival curve of tumor-bearing mice treated with intratumoral PBS (n=10), with intratumoral Lumican-MSA-IL2 and IL12-MSA-Lumican and intraperitoneal TA99 and anti-PD-1 (n=14), with intratumoral Lumican-MSA-IL2 and IL12-MSA-Lumican and intraperitoneal anti-PD-1 (n=10), with intratumoral MSA-IL2 and IL12-MSA and intraperitoneal TA99 and anti-PD-1 (n=9), or with intratumoral MSA-IL2 and IL12-MSA and intraperitoneal anti-PD-1 (n=8) on days 25, 31, 37, 43, 49, 55, and 61. Arrowheads indicate times of treatment. Overall survival graph enumerates mice that succumbed to tumor burden (>1200 mm$^3$) or to treatment-related weight loss (>20%); the latter is indicated by a blue "x" for each mouse. Survival was compared by log-rank Mantel-Cox test. *P<0.03, *P<0.0002, **P<0.0001.

FIG. 22A provides a schematic for measuring LAIR binding capacity in B16F10 tumors.

FIG. 22B provides a graph showing the weight of an excised tumor and its extracellular matrix.

FIG. 22C provides a graph showing the hydroxyproline content of the B16F10 cell fraction compared to matrix fraction.

FIG. 22D provides a graph showing depletion of LAIR-fluorescence as a B16F10 derived-matrix fraction was placed in a 1 mL of AF647-labeled LAIR.

FIG. 22E provides a graph showing the correlation between the matrix fraction hydroxyproline content and the LAIR-binding capacity of B16F10-derived matrix fraction.

Figure 23B:
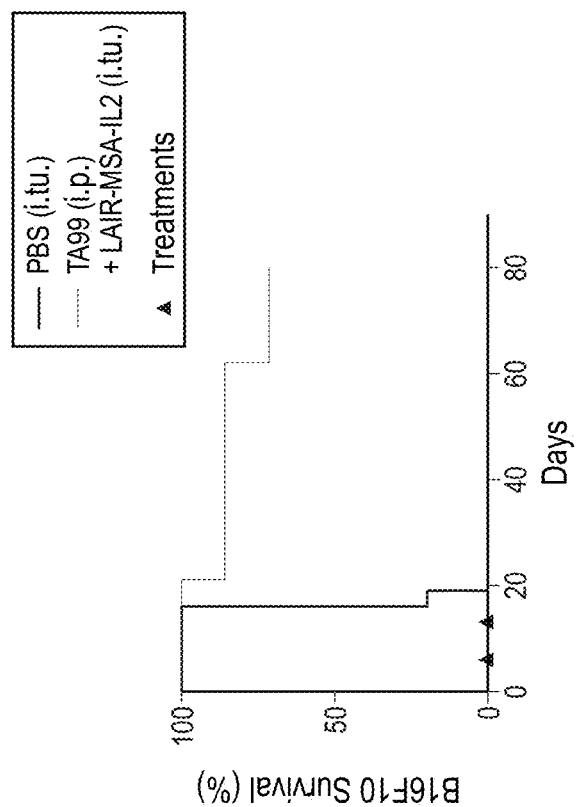
Figure 23A:
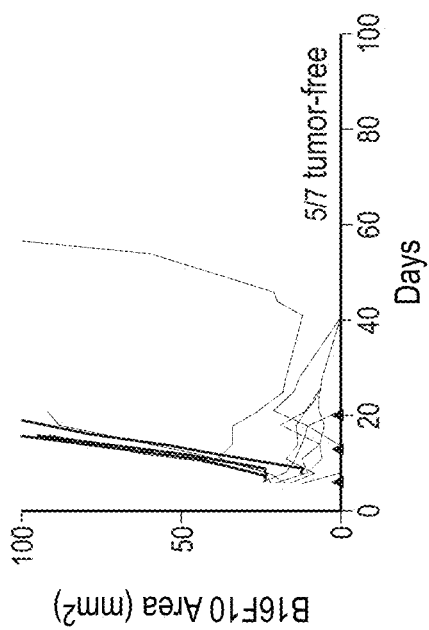

FIG. 23A provides a graph showing tumor area of B16F10 melanoma tumors (1×10$^6$ cells inoculated on day 0) treated with PBS control (i.tu) (n=5) or LAIR-MSA-IL2 (i.tu) TA99 (i.p.) (n=7) on days 6, and 13.

FIG. 23B provides a Mantel-Cox survival curve of B16F10 melanoma tumor-bearing mice (1×10$^6$ cells inoculated on day 0) treated with PBS control (i.tu) (n=5) or LAIR-MSA-IL2 (i.tu)+TA99 (i.p.) (n=7) on days 6 and 13.

FIG. 24A provides a sequence alignment of low affinity collagen binders, LAIR.30.w.A, LAIR.30.w.B, LAIR.30.w.C, and LAIR.30.w. D, compared to wild-type LAIR (LAIR).

FIGS. 24B-E provide depictions of the crystal structures of wild-type LAIR (PDB 4ETY) shown as a gray ribbon, with selected mutated amino acid residues of low affinity collagen binders, LAIR.30.w.A (FIG. 24B), LAIR.30.w.B (FIG. 24C), LAIR.30.w.C (FIG. 24D), and LAIR.30.d. D (FIG. 24E), highlighted as bonded spheres.

FIG. 24F provides a graph showing binding of WT LAIR, WT LAIR-MSA, MSA-IL-2 (non-specific binding control), and mutant LAIR-MSA fusions to collagen type 1 in an ELISA assay (n=2). The binding-affinity (Kd) of each LAIR construct, calculated on a non-linear one-site binding fit, is also shown.

FIG. 25A provides a sequence alignment of low affinity collagen binders, LAIR.30.w.E and LAIR.30.w.F compared to wild-type LAIR.

FIGS. 25B-C provide depictions of the crystal structures of wild-type LAIR (PDB 4ETY) shown as a gray ribbon, with selected mutated amino acid residues of low affinity collagen binders, LAIR.30.w.E (FIG. 25B) and LAIR.30.w. F (FIG. 25C), highlighted as bonded spheres.

FIG. 25D provides a graph showing binding of WT LAIR, WT LAIR-MSA, MSA-IL-2 (non-specific binding control), and mutant LAIR-MSA fusions to collagen type 1 in an ELISA assay (n=2). The binding-affinity (Kd) of each LAIR construct, modeled on a non-linear one-site binding fit, is also shown.

FIG. 26A provides a sequence alignment of high affinity collagen binder, LAIR.30.2.K1.B, compared to wild-type LAIR.

FIG. 26B provides a depiction of the crystal structure of wild-type LAIR (PDB 4ETY) shown as a gray ribbon, with selected mutated amino acid residues of high affinity collagen binder, LAIR.30.2.K1.B, highlighted as bonded spheres.

FIGS. 26C-D provide flow cytometry plots showing CRP-XL-biotin binding (Strepravidin-AF647) versus protein display (goat anti-chicken AF488) of yeast bearing wild-type LAIR (black) or LAIR30.2.K1.B (cyan) incubated in either 100 nM (FIG. 26C) or 0.01 nM (FIG. 26D) of CRP-XL-biotin.

FIGS. 26E-F provide flow cytometry plots showing remaining surface CRP-XL-biotin signal (Streptatividn-AF647) versus protein display (goat anti-chicken AF488) of yeast bearing LAIR30.2.K1.B (FIG. 26E) or wild-type LAIR (FIG. 26F) at different time points (0 hours, 16 hours and 40 hours of competition) after competition with an excess of non-biotinylated CRP-XL.

FIG. 26G provides a graph showing the median fluorescence intensity of bound CRP-XL-biotin over time in the kinetic dissociation experiment depicted in FIGS. 26E-F. The estimated off-rates, modeled on a one-phase exponential decay fit, are also shown.

DETAILED DESCRIPTION

Provided herein are immunomodulatory fusion proteins comprising an immunomodulatory domain operably linked to a collagen-binding domain. Such fusion proteins localize the immunomodulatory domain (e.g., cytokine, antibody), such that it is not systemically disseminated. Systemic dissemination of an immunomodulatory domain can result in reduced efficacy due to rapid clearance from the site of interest (e.g., tumor), and/or toxicity due to effects on non-target cells outside the tumor. Accordingly, the linking of an immunomodulatory domain to a collagen-binding protein localizes the immunomodulatory domain to prevent systemic dissemination, thereby maintaining the immunomodulatory domain at the site of interest and reducing potential off-target effects that could lead to toxicity.

Definitions

Terms used in the claims and specification are defined as set forth below unless otherwise specified. In the case of direct conflict with a term used in a parent provisional patent application, the term used in the instant application shall control.

It must be noted that, as used in the specification and the appended claims, the singular forms "a," "an" and "the" include plural referents unless the context clearly dictates otherwise.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

As used herein, the term "agonist" refers to any molecule (e.g., an antibody or antigen binding fragment thereof) that partially or fully promotes, increases, or activates a biological activity of a native polypeptide disclosed herein. Suitable agonist molecules specifically include agonist antibodies or antibody fragments, fragments or amino acid sequence variants of native polypeptides, peptides, antisense oligonucleotides, small organic molecules, etc. In some embodiments, activation in the presence of the agonist is observed in a dose-dependent manner. In some embodiments, the measured signal (e.g., biological activity) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% higher than the signal measured with a negative control under comparable conditions. Also disclosed herein, are methods of identifying agonists suitable for use in the methods of the disclosure. For example, these methods include, but are not limited to, binding assays such as enzyme-linked immuno-absorbent assay (ELISA), Forte Bio© systems, and radioimmunoassay (MA). These assays determine the ability of an agonist to bind the polypeptide of interest (e.g., a receptor or ligand) and therefore indicate the ability of the agonist to promote, increase or activate the activity of the polypeptide. Efficacy of an agonist can also be determined using functional assays, such as the ability of an agonist to activate or promote the function of the polypeptide. For example, a functional assay may comprise contacting a polypeptide with a candidate agonist molecule and measuring a detectable change in one or more biological activities normally associated with the polypeptide. The potency of an agonist is usually defined by its $EC_{50}$ value (concentration required to activate 50% of the agonist response). The lower the $EC_{50}$ value the greater the potency of the agonist and the lower the concentration that is required to activate the maximum biological response.

The term "albumin" refers to a protein having the same, or very similar three dimensional structure as human albumin (SEQ ID NO: 42) and having a long serum half-life. Exemplary albumin proteins include human serum albumin (HSA; SEQ ID NOs: 42 and 43), primate serum albumin (such as chimpanzee serum albumin), gorilla serum albumin or macaque serum albumin, rodent serum albumin (such as hamster serum albumin), guinea pig serum albumin, mouse serum albumin and rat serum albumin, bovine serum albumin (such as cow serum albumin), equine serum albumin (such as horse serum albumin or donkey serum albumin), rabbit serum albumin, goat serum albumin, sheep serum albumin, dog serum albumin, chicken serum albumin and pig serum albumin.

The term "ameliorating" refers to any therapeutically beneficial result in the treatment of a disease state, e.g., cancer, including prophylaxis, lessening in the severity or progression, remission, or cure thereof.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups {e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, larger "peptide insertions," can also be made, e.g. insertion of about three to about five or even up to about ten, fifteen, or twenty amino acid residues. The inserted residue(s) may be naturally occurring or non-naturally occurring as disclosed above. An "amino acid deletion"

refers to the removal of at least one amino acid residue from a predetermined amino acid sequence.

As used herein, the term "antagonist" refers to any molecule (e.g., antibody or antigen-binding fragment thereof) that partially or fully blocks, inhibits, or neutralizes a biological activity of a native polypeptide disclosed herein. Suitable antagonist molecules specifically include antagonist antibodies or antibody fragments, fragments or amino acid sequence variants of native polypeptides, peptides, antisense oligonucleotides, small organic molecules, etc. In some embodiments, inhibition in the presence of the antagonist is observed in a dose-dependent manner. In some embodiments, the measured signal (e.g., biological activity) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% lower than the signal measured with a negative control under comparable conditions. Also disclosed herein, are methods of identifying antagonists suitable for use in the methods of the disclosure. For example, these methods include, but are not limited to, binding assays such as enzyme-linked immuno-absorbent assay (ELISA), Forte Bio© systems, and radioimmunoassay (RIA). These assays determine the ability of an antagonist to bind the polypeptide of interest (e.g., a receptor or ligand) and therefore indicate the ability of the antagonist to inhibit, neutralize or block the activity of the polypeptide. Efficacy of an antagonist can also be determined using functional assays, such as the ability of an antagonist to inhibit the function of the polypeptide or an agonist. For example, a functional assay may comprise contacting a polypeptide with a candidate antagonist molecule and measuring a detectable change in one or more biological activities normally associated with the polypeptide. The potency of an antagonist is usually defined by its $IC_{50}$ value (concentration required to inhibit 50% of the agonist response). The lower the $IC_{50}$ value the greater the potency of the antagonist and the lower the concentration that is required to inhibit the maximum biological response.

As used herein, the term "antibody" refers to a whole antibody comprising two light chain polypeptides and two heavy chain polypeptides. Whole antibodies include different antibody isotypes including IgM, IgG, IgA, IgD, and IgE antibodies. The term "antibody" includes a polyclonal antibody, a monoclonal antibody, a chimerized or chimeric antibody, a humanized antibody, a primatized antibody, a deimmunized antibody, and a fully human antibody. The antibody can be made in or derived from any of a variety of species, e.g., mammals such as humans, non-human primates (e.g., orangutan, baboons, or chimpanzees), horses, cattle, pigs, sheep, goats, dogs, cats, rabbits, guinea pigs, gerbils, hamsters, rats, and mice. The antibody can be a purified or a recombinant antibody.

As used herein, the term "antibody fragment," "antigen-binding fragment," or similar terms refer to a fragment of an antibody that retains the ability to bind to a target antigen(s) and promote, induce, and/or increase the activity of the target antigen. Such fragments include, e.g., a single chain antibody, a single chain Fv fragment (scFv), an Fd fragment, an Fab fragment, an Fab' fragment, or an F(ab')2 fragment. An scFv fragment is a single polypeptide chain that includes both the heavy and light chain variable regions of the antibody from which the scFv is derived. In addition, intrabodies, minibodies, triabodies, and diabodies are also included in the definition of antibody and are compatible for use in the methods described herein. See, e.g., Todorovska et al. (2001) *J Immunol Methods* 248(1):47-66; Hudson and Kortt (1999) *J Immunol Methods* 231(1):177-189; Poljak (1994) *Structure* 2(12): 1121-1123; Rondon and Marasco (1997) *Annual Review of Microbiology* 51:257-283, the disclosures of each of which are incorporated herein by reference in their entirety.

As used herein, the term "antibody fragment" also includes, e.g., single domain antibodies such as camelized single domain antibodies. See, e.g., Muyldermans et al. (2001) *Trends Biochem Sci* 26:230-235; Nuttall et al. (2000) *Curr Pharm Biotech* 1:253-263; Reichmann et al. (1999) *J Immunol Meth* 231:25-38; PCT application publication nos. WO 94/04678 and WO 94/25591; and U.S. Pat. No. 6,005,079, all of which are incorporated herein by reference in their entireties. In some embodiments, the disclosure provides single domain antibodies comprising two VH domains with modifications such that single domain antibodies are formed.

The "B7 family" refers to activating and inhibitory ligands. The B7 family encompasses at least activating ligands B7-1 and B7-2, and inhibitory ligands B7-H1, B7-H2, B7-H3 and B7-H4. B7-1 and B7-2 bind to CD28, B7-H1 (i.e., PD-L1) binds to PD-1, and B7-H2 binds to ICOS. B7-H3 and B7-H4 bind unknown receptors. Further, B7-H3 and B7-H4 have been shown to be upregulated on tumor cells and tumor infiltrating cells. The complete hB7-H3 and hB7-H4 sequence can be found under GenBank Accession Nos. Q5ZPR3 and AAZ17406 (SEQ ID NOs: 49 and 50) respectively.

As used herein, the term "chimeric antigen receptor (CAR)" refers to an artificial transmembrane protein receptor comprising (i) an extracellular domain capable of binding to at least one predetermined CAR ligand or antigen, or a predetermined CAR ligand and an antigen, (ii) an intracellular segment comprising one or more cytoplasmic domains derived from signal transducing proteins different from the polypeptide from which the extracellular domain is derived, and (iii) a transmembrane domain. The "chimeric antigen receptor (CAR)" is sometimes called a "chimeric receptor", a "T-body", or a "chimeric immune receptor (CIR)."

The phrase "CAR ligand" used interchangeably with "CAR antigen" means any natural or synthetic molecule (e.g., small molecule, protein, peptide, lipid, carbohydrate, nucleic acid) or part or fragment thereof that can specifically bind to a CAR (e.g., the extracellular domain of a CAR). In some embodiments, the CAR ligand is a tumor-associated antigen, or fragment thereof. In some embodiments, the CAR ligand is a tag.

The "intracellular signaling domain" means any oligopeptide or polypeptide domain known to function to transmit a signal causing activation or inhibition of a biological process in a cell, for example, activation of an immune cell such as a T cell or a NK cell. Examples include ILR chain, CD28 and/or CD3ζ.

As used herein, "cancer antigen" refers to (i) tumor-specific antigens, (ii) tumor-associated antigens, (iii) cells that express tumor-specific antigens, (iv) cells that express tumor-associated antigens, (v) embryonic antigens on tumors, (vi) autologous tumor cells, (vii) tumor-specific membrane antigens, (viii) tumor-associated membrane antigens, (ix) growth factor receptors, (x) growth factor ligands, and (xi) any other type of antigen or antigen-presenting cell or material that is associated with a cancer.

As used herein, "cancer vaccine" refers to a treatment that induces the immune system to attack cells with one or more tumor associated antigens. The vaccine can treat existing cancer (e.g., therapeutic cancer vaccine) or prevent the development of cancer in certain individuals (e.g., prophylactic cancer vaccine). The vaccine creates memory cells that will recognize tumor cells with the antigen and therefore prevent tumor growth.

As used herein, the term "chemokine" refers to a member of the family of small cytokines, or signaling proteins, that induce directed chemotaxis. Chemokines are grouped into four subfamilies: CXC, CC, (X)C, and CX3C.

As used herein, the term "collagen" refers to the predominant structural protein located within the extracellular space, and maintains the mechanical integrity of many different tissues. Collagen's molecular organization determines its function. There are more than 20 types of collagen currently identified, with type I being the most common.

As used herein, the term "collagen-binding domain" refers to a polypeptide, or a portion thereof, that binds to collagen. A collagen-binding domain may be part of a larger fusion protein, bioactive agent, or pharmaceutical agent. The binding of a composition, polypeptide or portion thereof, fusion protein, or pharmaceutical or bioactive agent to collagen can determined by methods known in the art (e.g., collagen-binding assay; see e.g., Turecek et al., (2002) Semin Thromb Hemost 28(2):149-160). In some embodiments, a collagen-binding domain is determined by its ability to compete with a known or reference collagen-binding protein for binding to collagen. In some embodiments, a collagen-binding domains is derived from a naturally-occurring collagen-binding protein or collagen receptor. Collagen-binding proteins and collagen receptors comprising collagen-binding domains are known in the art (see e.g., Svensson et al., (2001) Osteoarthritis Cartilage 9 Suppl A:S23-28; Leitinger and Hohenester E (2007) Matrix Biol 26(3):146-155). In some embodiments, the collagen-binding domain is derived from a prokaryotic collagen-binding protein. Prokaryotic collagen-binding proteins are known in the art (see e.g., Symersky et al., (1997) Nat Struct Biol 4:833-838). In some embodiments, a collagen-binding domain comprises one or more mutations that increases its affinity for collagen.

As used herein, "combination therapy" embraces administration of each agent or therapy in a sequential or simultaneous manner in a regimen that will provide beneficial effects of the combination, and co-administration of these agents or therapies in a substantially simultaneous manner, such as in a single capsule having a fixed ratio of these active agents or in multiple, separate capsules for each agent. Combination therapy also includes combinations where individual elements may be administered at different times and/or by different routes but which act in combination to provide a beneficial effect by co-action or pharmacokinetic and pharmacodynamics effect of each agent or tumor treatment approaches of the combination therapy.

A "co-stimulatory signal", as used herein, refers to a signal, which in combination with a primary signal, such as TCR/CD3 ligation, leads to T cell proliferation and/or upregulation or downregulation of key molecules "Cytotoxic T Lymphocyte Associated Antigen-4 (CTLA-4)" is a T cell surface molecule and is a member of the immunoglobulin superfamily. This protein downregulates the immune system by binding to CD80 and CD86. The term "CTLA-4" as used herein includes human CTLA-4 (hCTLA-4), variants, isoforms, and species homologs of hCTLA-4, and analogs having at least one common epitope with hCTLA-4. The complete hCTLA-4 sequence can be found under GenBank Accession No. P16410 (SEQ ID NO: 46):

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence. Polypeptides derived from another peptide may have one or more mutations relative to the starting polypeptide, e.g., one or more amino acid residues which have been substituted with another amino acid residue or which has one or more amino acid residue insertions or deletions. A polypeptide can comprise an amino acid sequence which is not naturally occurring. Such variants necessarily have less than 100% sequence identity or similarity with the starting molecule. In certain embodiments, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule.

In certain embodiments, there is one amino acid difference between a starting polypeptide sequence and the sequence derived therefrom. Identity or similarity with respect to this sequence is defined herein as the percentage of amino acid residues in the candidate sequence that are identical (i.e., same residue) with the starting amino acid residues, after aligning the sequences and introducing gaps, if necessary, to achieve the maximum percent sequence identity. In certain embodiments, a polypeptide consists of, consists essentially of, or comprises an amino acid sequence selected from the Sequence Summary Table. In certain embodiments, a polypeptide includes an amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence selected from the Sequence Summary Table. In certain embodiments, a polypeptide includes a contiguous amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous amino acid sequence selected from the Sequence Summary Table. In certain embodiments, a polypeptide includes an amino acid sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous amino acids of an amino acid sequence selected from the Sequence Summary Table.

In certain embodiments, the peptides of the disclosure are encoded by a nucleotide sequence. Nucleotide sequences of the disclosure can be useful for a number of applications, including: cloning, gene therapy, protein expression and purification, mutation introduction, DNA vaccination of a host in need thereof, antibody generation for, e.g., passive immunization, PCR, primer and probe generation, and the like. In certain embodiments, the nucleotide sequence of the disclosure comprises, consists of, or consists essentially of, a nucleotide sequence selected from SEQ ID NOs: 3, 5, 7, 9, 11, 15, 17, 19, 21, 23, 25, 27, 29, 31, and 33. In certain embodiments, a nucleotide sequence includes a nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence set forth in the Sequence Summary Table. In certain embodiments, a nucleotide sequence includes a contiguous nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous nucleotide sequence set forth in the Sequence Summary Table. In certain embodiments, a nucleotide sequence includes a nucleotide sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous nucleotides of a nucleotide sequence set forth in the Sequence Summary Table.

It will also be understood by one of ordinary skill in the art that the polypeptides suitable for use in the immunomodulatory fusion proteins disclosed herein may be altered such that they vary in sequence from the naturally occurring or native sequences from which they were derived, while retaining the desirable activity of the native sequences. For example, nucleotide or amino acid substitutions leading to conservative substitutions or changes at "non-essential" amino acid residues may be made. Mutations may be introduced by standard techniques, such as site-directed mutagenesis and PCR-mediated mutagenesis.

The polypeptides suitable for use in the immunomodulatory fusion proteins disclosed herein may comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a binding polypeptide is preferably replaced with another amino acid residue from the same side chain family. In certain embodiments, a string of amino acids can be replaced with a structurally similar string that differs in order and/or composition of side chain family members. Alternatively, in certain embodiments, mutations may be introduced randomly along all or part of a coding sequence, such as by saturation mutagenesis, and the resultant mutants can be incorporated into binding polypeptides of the disclosure and screened for their ability to bind to the desired target.

As used herein, the term "effector cell" or "effector immune cell" refers to a cell involved in an immune response, e.g., in the promotion of an immune effector response. In some embodiments, immune effector cells specifically recognize an antigen. Examples of immune effector cells include, but are not limited to, Natural Killer (NK) cells, B cells, monocytes, macrophages, T cells (e.g., cytotoxic T lymphocytes (CTLs). In some embodiments, the effector cell is a T cell. As used herein, the term "immune effector function" or "immune effector response" refers to a function or response of an immune effector cell that promotes an immune response to a target.

As used herein, the term "Fc region" refers to the portion of a native immunoglobulin formed by the respective Fc domains (or Fc moieties) of its two heavy chains. In some embodiments, the term "Fc domain" refers to a portion of a single immunoglobulin (Ig) heavy chain wherein the Fc domain does not comprise an Fv domain. In some embodiments, the term "Fc domain" refers to a portion of a single immunoglobulin (Ig) heavy chain also comprising an Fv domain. As such, an Fc domain can also be referred to as "Ig" or "IgG." In certain embodiments, an Fc domain begins in the hinge region just upstream of the papain cleavage site and ends at the C-terminus of the antibody. Accordingly, a complete Fc domain comprises at least a hinge domain, a CH2 domain, and a CH3 domain. In certain embodiments, an Fc domain comprises at least one of: a hinge (e.g., upper, middle, and/or lower hinge region) domain, a CH2 domain, a CH3 domain, a CH4 domain, or a variant, portion, or fragment thereof. In certain embodiments, an Fc domain comprises a complete Fc domain (i.e., a hinge domain, a CH2 domain, and a CH3 domain). In certain embodiments, an Fc domain comprises a hinge domain (or portion thereof) fused to a CH3 domain (or portion thereof). In certain embodiments, an Fc domain comprises a CH2 domain (or portion thereof) fused to a CH3 domain (or portion thereof). In certain embodiments, an Fc domain consists of a CH3 domain or portion thereof. In certain embodiments, an Fc domain consists of a hinge domain (or portion thereof) and a CH3 domain (or portion thereof). In certain embodiments, an Fc domain consists of a CH2 domain (or portion thereof) and a CH3 domain. In certain embodiments, an Fc domain consists of a hinge domain (or portion thereof) and a CH2 domain (or portion thereof). In certain embodiments, an Fc domain lacks at least a portion of a CH2 domain (e.g., all or part of a CH2 domain). An Fc domain herein generally refers to a polypeptide comprising all or part of the Fc domain of an immunoglobulin heavy-chain. This includes, but is not limited to, polypeptides comprising the entire CH1, hinge, CH2, and/or CH3 domains as well as fragments of such peptides comprising only, e.g., the hinge, CH2, and CH3 domain. The Fc domain may be derived from an immunoglobulin of any species and/or any subtype, including, but not limited to, a human IgG1, IgG2, IgG3, IgG4, IgD, IgA, IgE, or IgM antibody. A human IgG1 constant region can be found at Uniprot P01857 and SEQ ID NO: 114. The Fc domain of human IgG1 can be found in SEQ ID NO: 115. The Fc domain encompasses native Fc and Fc variant molecules. As with Fc variants and native Fc's, the term Fc domain includes molecules in monomeric or multimeric form, whether digested from whole antibody or produced by other means. The assignment of amino acid residue numbers to an Fc domain is in accordance with the definitions of Kabat. See, e.g., Sequences of Proteins of Immunological Interest (Table of Contents, Introduction and Constant Region Sequences sections), 5th edition, Bethesda, MD: NIH vol. 1:647-723 (1991); Kabat et al., "Introduction" Sequences of Proteins of Immunological Interest, US Dept of Health and Human Services, NIH, 5th edition, Bethesda, MD vol. 1: xiii-xcvi (1991); Chothia & Lesk, J. Mol. Biol. 196:901-917 (1987); Chothia et al., Nature 342:878-883 (1989), each of which is herein incorporated by reference for all purposes.

As set forth herein, it will be understood by one of ordinary skill in the art that any Fc domain may be modified such that it varies in amino acid sequence from the native Fc domain of a naturally occurring immunoglobulin molecule. In certain embodiments, the Fc domain has reduced effector function (e.g., FcγR binding).

The Fc domains suitable for use in the immunomodulatory fusion proteins disclosed herein may be derived from different immunoglobulin molecules. For example, an Fc domain of a polypeptide may comprise a CH2 and/or CH3 domain derived from an IgG1 molecule and a hinge region derived from an IgG3 molecule. In another example, an Fc domain can comprise a chimeric hinge region derived, in part, from an IgG1 molecule and, in part, from an IgG3 molecule. In another example, an Fc domain can comprise a chimeric hinge derived, in part, from an IgG1 molecule and, in part, from an IgG4 molecule.

As used herein, the term "gly-ser polypeptide linker" or "gly-ser linker" refers to a peptide that consists of glycine and serine residues. An exemplary gly-ser polypeptide linker comprises the amino acid sequence Ser(Gly$_4$Ser)n. In certain embodiments, n=1. In certain embodiments, n=2. In certain embodiments, n=3, i.e., Ser(Gly$_4$Ser)3. In certain embodiments, n=4, i.e., Ser(Gly$_4$Ser)4. In certain embodiments, n=5. In certain embodiments, n=6. In certain embodiments, n=7. In certain embodiments, n=8. In certain embodiments, n=9. In certain embodiments, n=10. Another exemplary gly-ser polypeptide linker comprises the amino acid sequence (Gly$_4$Ser)n. In certain embodiments, n=1. In certain embodiments, n=2. In certain embodiments, n=3. In certain embodiments, n=4. In certain embodiments, n=5. In certain embodiments, n=6. Another exemplary gly-ser polypeptide linker comprises the amino acid sequence (Gly$_3$Ser)n. certain embodiments, n=1. In certain embodiments, n=2. In certain embodiments, n=3. In certain embodiments, n=4. In certain embodiments, n=5. In certain embodiments, n=6.

As used herein, the term "human antibody" includes antibodies having variable and constant regions (if present) of human germline immunoglobulin sequences. Human antibodies of the disclosure can include amino acid residues not encoded by human germline immunoglobulin sequences (e.g., mutations introduced by random or site-specific mutagenesis in vitro or by somatic mutation in vivo) (see, Lonberg, N. et al. (1994) *Nature* 368(6474): 856-859); Lonberg, N. (1994) *Handbook of Experimental Pharmacology* 113:49-101; Lonberg, N. and Huszar, D. (1995) *Intern. Rev. Immunol.* Vol. 13: 65-93, and Harding, F. and Lonberg, N. (1995) *Ann. N.Y. Acad. Sci* 764:536-546). However, the term "human antibody" does not include antibodies in which CDR sequences derived from the germline of another mammalian species, such as a mouse, have been grafted onto human framework sequences (i.e., humanized antibodies).

As used herein, the term a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

As used herein, "immune cell" is a cell of hematopoietic origin and that plays a role in the immune response. Immune cells include lymphocytes (e.g., B cells and T cells), natural killer cells, and myeloid cells (e.g., monocytes, macrophages, eosinophils, mast cells, basophils, and granulocytes).

As used herein, "immune checkpoint" refers to co-stimulatory and inhibitory signals that regulates immune cells \. In certain embodiments, the immune checkpoint is an inhibitory signal. In certain embodiments, the inhibitory signal is the interaction between PD-1 and PD-L1. In certain embodiments, the inhibitory signal is the interaction between CTLA-4 and CD80 or CD86 to displace CD28 binding. In certain embodiments the inhibitory signal is the interaction between LAG3 and MHC class II molecules. In certain embodiments, the inhibitory signal is the interaction between TIM3 and galectin 9.

As used herein, "immune checkpoint blocker" refers to a molecule that totally or partially reduces, inhibits, interferes with or modulates one or more checkpoint proteins. In certain embodiments, the immune checkpoint blocker prevents inhibitory signals associated with the immune checkpoint. In certain embodiments, the immune checkpoint blocker is an antibody, or fragment thereof that disrupts inhibitory signaling associated with the immune checkpoint. In certain embodiments, the immune checkpoint blocker is a small molecule that disrupts inhibitory signaling. In certain embodiments, the immune checkpoint blocker is an antibody, fragment thereof, or antibody mimic, that prevents the interaction between checkpoint blocker proteins, e.g., an antibody, or fragment thereof, that prevents the interaction between PD-1 and PD-L1. In certain embodiments, the immune checkpoint blocker is an antibody, or fragment thereof, that prevents the interaction between CTLA-4 and CD80 or CD86. In certain embodiments, the immune checkpoint blocker is an antibody, or fragment thereof, that prevents the interaction between LAG3 and its ligands, or TIM-3 and its ligands.

As used herein, the term "immunomodulatory fusion protein" refers to a polypeptide comprising a collagen-binding domain operably linked to at least one immunomodulatory domain. In some embodiments, the collagen-binding domain is operably linked to the immunomodulatory domain via a linker.

As used herein, the term "immunomodulatory domain" refers to a polypeptide (e.g., cytokine, agonist or antagonistic antibody) that confers an activity resulting in activation or suppression of an immune response (e.g., stimulation of CD8+ T cells). In some embodiments, the immunomodulatory domain refers to a polypeptide that binds to its cognate ligand or receptor, thereby resulting in activation or suppression of an immune response.

The terms "inducing an immune response" and "enhancing an immune response" are used interchangeably and refer to the stimulation of an immune response (i.e., either passive or adaptive) to a particular antigen. The term "induce" as used with respect to inducing CDC or ADCC refer to the stimulation of particular direct cell killing mechanisms.

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a composition comprising a fusion protein described herein).

The term "in vivo" refers to processes that occur in a living organism.

As used herein, "interleukin (IL)-2," refers to a pleiotropic cytokine that activates and induces proliferation of T cells and natural killer (NK) cells. IL-2 signals by binding its receptor, IL-2R, which is comprised of alpha, beta, and gamma subunits. IL-2 signaling stimulates proliferation of antigen-activated T cells.

As used herein, the term "isolated antibody" is intended to refer to an antibody which is substantially free of other antibodies having different antigenic specificities (e.g., an isolated antibody that binds to immune checkpoint blockers or co-stimulatory molecules) is substantially free of antibodies that specifically bind antigens other than the target of interest. An isolated antibody that specifically binds to an epitope may, however, have cross-reactivity to other targets from different species. In addition, an isolated antibody is typically substantially free of other cellular material and/or chemicals.

As used herein, the term "isolated nucleic acid molecule" refers to nucleic acids encoding fusion proteins, polypeptides, antibodies or antibody portions disclosed herein, is intended to refer to a nucleic acid molecule in which the nucleotide sequences encoding the fusion protein, polypeptide, antibody or antibody portion are free of other nucleotide sequences, which other sequences may naturally flank the nucleic acid in human genomic DNA.

As used herein, "isotype" refers to the antibody class (e.g., IgM or IgG1) that is encoded by heavy chain constant region genes. In some embodiments, an antibody of the disclosure is of the IgG1 isotype. In some embodiments, an antibody of the disclosure is of the IgG2 isotype. In some embodiments, an antibody of the disclosure is of the IgG3 isotype. In some embodiments, an antibody of the disclosure is of the IgG4 isotype.

As used herein the term "KD" or "$K_D$" refers to the equilibrium dissociation constant of a binding reaction between e.g., a ligand and a receptor, an antigen and an antibody, or a collagen-binding protein and collagen. The value of $K_D$ is a numeric representation of the ratio of the binding protein off-rate constant (kd) to the binding protein on-rate constant (ka). The value of $K_D$ is inversely related to the binding affinity of the binding protein to its binding partner. The smaller the $K_D$ value the greater the affinity of the binding protein for its binding partner. Affinity is the strength of binding of a single molecule to its ligand and is typically measured and reported by the equilibrium dissociation constant ($K_D$), which is used to evaluate and rank order strengths of bimolecular interactions.

As used herein, the term "kd" or "$k_d$" (alternatively "koff" or "$k_{off}$") is intended to refer to the off-rate constant for the dissociation of a binding protein from binding protein/partner complex. The value of kd is a numeric representation of the fraction of complexes that decay or dissociate per second, and is expressed in units $sec^{-1}$.

As used herein, the term "ka" or "$k_a$" (alternatively "kon" or "$k_{on}$") is intended to refer to the on-rate constant for the association of a binding protein with a binding partner. The value of ka is a numeric representation of the number of antibody/antigen complexes formed per second in a 1 molar (1M) solution of binding partners, and is expressed in units $M^{-1} sec^{-1}$.

As used herein, the terms "linked," "operably linked," "fused" or "fusion", are used interchangeably. These terms refer to the joining together of two more elements or components or domains, by whatever means including chemical conjugation, noncovalent complex formation or recombinant means. Methods of chemical conjugation (e.g., using heterobifunctional crosslinking agents) are known in the art.

As used herein, "local administration" or "local delivery," refers to delivery that does not rely upon transport of the composition or agent to its intended target tissue or site via the vascular system. For example, the immunomodulatory fusion protein or composition comprising the fusion protein may be delivered by injection or implantation of the fusion protein or composition, or by injection or implantation of a device containing the fusion protein or composition. Following local administration in the vicinity of a target tissue or site, the composition or agent, or one or more components thereof, may diffuse to the intended target tissue or site. In some embodiments, an immunomodulatory fusion protein is locally administered by viral vectors, electroporation, transplantation of cells expressing the immunomodulatory fusion protein, or replicons.

"Lymphocyte Activation Gene-3 (LAG3)" is an inhibitory receptor associated with inhibition of lymphocyte activity by binding to MHC class II molecules. This receptor enhances the function of Treg cells and inhibits CD8+ effector T cell function. The term "LAG3" as used herein includes human LAG3 (hLAG3), variants, isoforms, and species homologs of hLAG3, and analogs having at least one common epitope. The complete hLAG3 sequence can be found under GenBank Accession No. P 18627 (SEQ ID NO: 47).

The term "mammal" or "subject" or "patient" as used herein includes both humans and non-humans and includes, but is not limited to, humans, non-human primates, canines, felines, murines, bovines, equines, and porcines.

"Nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081, 1991; Ohtsuka et al., Biol. Chem. 260:2605-2608, 1985; and Cassol et al, 1992; Rossolini et al, Mol. Cell. Probes 8:91-98, 1994). For arginine and leucine, modifications at the second base can also be conservative. The term nucleic acid is used interchangeably with gene, cDNA, and mRNA encoded by a gene.

Polynucleotides used herein can be composed of any polyribonucleotide or polydeoxribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

As used herein, "parenteral administration," "administered parenterally," and other grammatically equivalent phrases, refer to modes of administration other than enteral and topical administration, usually by injection, and include, without limitation, intravenous, intranasal, intraocular, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid, intracolonic/intraintestinal, intravervical/intravaginal, and intrasternal injection and infusion.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

As generally used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Polypeptide," "peptide", and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The "Programmed Death-1 (PD-1)" receptor refers to an immuno-inhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. AAC51773 (SEQ ID NO: 44).

"Programmed Death Ligand-1 (PD-L1)" is one of two cell surface glycoprotein ligands for PD-1 (the other being PD-L2) that downregulates T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7 (SEQ ID NO: 45).

As used herein, the term "purified" or "isolated" as applied to any of the proteins (fusion proteins, antibodies or fragments) described herein refers to a polypeptide that has been separated or purified from components (e.g., proteins or other naturally-occurring biological or organic molecules) which naturally accompany it, e.g., other proteins, lipids, and nucleic acid in a prokaryote expressing the proteins. Typically, a polypeptide is purified when it constitutes at least 60 (e.g., at least 65, 70, 75, 80, 85, 90, 92, 95, 97, or 99) %, by weight, of the total protein in a sample.

As used herein, the terms "specifically binds" and "selectively binds" refers to binding by a collagen-binding domain to collagen, or binding by an antibody to an epitope on a predetermined antigen. In some embodiments, a collagen-binding domain specifically binds or selectively binds to collagen based on the $K_D$ for collagen (i.e., the $K_D$ for binding to collagen is lower than the $K_D$ for at least fibronectin, vitronectin, osteopontin, tenascin C or fibrinogen).

The term "sufficient amount" or "amount sufficient to" means an amount sufficient to produce a desired effect, e.g., an amount sufficient to reduce the size of a tumor.

The term "T cell" refers to a type of white blood cell that can be distinguished from other white blood cells by the presence of a T cell receptor on the cell surface. There are several subsets of T cells, including, but not limited to, T helper cells (a.k.a. $T_H$ cells or CD4$^+$ T cells) and subtypes, including $T_H1$, $T_H2$, $T_H3$, $T_H17$, $T_H9$, and $T_{FH}$ cells, cytotoxic T cells (a.k.a Tc cells, CD8$^+$ T cells, cytotoxic T lymphocytes, T-killer cells, killer T cells), memory T cells and subtypes, including central memory T cells ($T_{CM}$ cells), effector memory T cells ($T_{EM}$ and $T_{EMRA}$ cells), and resident memory T cells ($T_{RM}$ cells), regulatory T cells (a.k.a. $T_{reg}$ cells or suppressor T cells) and subtypes, including CD4$^+$FOXP3$^+$ $T_{reg}$ cells, CD4$^+$FOXP3$^-$ $T_{reg}$ cells, Tr1 cells, Th3 cells, and $T_{reg}17$ cells, natural killer T cells (a.k.a. NKT cells), mucosal associated invariant T cells (MAITs), and gamma delta T cells (γδ T cells), including Vγ9/Vδ2 T cells. Any one or more of the aforementioned or unmentioned T cells may be the target cell type for a method as disclosed herein.

The term "T cell cytotoxicity" includes any immune response that is mediated by CD8+ T cell activation. Exemplary immune responses include cytokine production, CD8+ T cell proliferation, granzyme or perforin production, and clearance of an infectious agent.

"T Cell Membrane Protein-3 (TIM3)" is an inhibitory receptor involved in the inhibition of lymphocyte activity by inhibition of $T_H1$ cells responses. Its ligand is galectin 9, which is upregulated in various types of cancers. The term "TIM3" as used herein includes human TIM3 (hTIM3), variants, isoforms, and species homologs of hTIM3, and analogs having at least one common epitope. The complete hTIM3 sequence can be found under GenBank Accession No. Q8TDQo (SEQ ID NO: 48).

A "therapeutic antibody" is an antibody, fragment of an antibody, or construct that is derived from an antibody, and can bind to a cell-surface antigen on a target cell to cause a therapeutic effect. Such antigens can be chimeric, humanized or fully human antibodies. Methods are known in the art for producing such antibodies. Such antibodies include single chain Fc fragments of antibodies, minibodies and diabodies. Any of the therapeutic antibodies known in the art to be useful for cancer therapy can be used in the combination therapy suitable for use in the methods disclosed herein. Therapeutic antibodies may be monoclonal antibodies or polyclonal antibodies. In preferred embodiments, the therapeutic antibodies target cancer antigens.

The term "therapeutically effective amount" is an amount that is effective to ameliorate a symptom of a disease. A therapeutically effective amount can be a "prophylactically effective amount" as prophylaxis can be considered therapy.

As used herein, the term "vector" is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

Immunomodulatory Fusion Protein

In some aspects, the disclosure provides an immunomodulatory fusion protein comprising a collagen-binding domain operably linked to an immunomodulatory domain. In some embodiments, the immunomodulatory fusion protein further comprises a linker, such that the collagen-binding domain is operably linked to a linker, and the linker is operably linked to the immunomodulatory domain.

I. Collagen-Binding Domains

In some embodiments, the disclosure provides immunomodulatory fusion proteins comprising a collagen-binding domain. In some embodiments, the collagen-binding domain has a MW of about 5-100 kDa, about 10-80 kDa, about 20-60 kDa, about 30-50 kDa, or about 10 kDa, about 20 kDa, about 30 kDa, about 40 kDa, about 50 kDa, about 60 kDa, about 70 kDa, about 80 kDa, about 90 kDa or about 100 kDa. In some embodiments, the collagen-binding domain is about 5 kDa, about 10 kDa, about 20 kDa, about 30 kDa, about 40 kDa, about 50 kDa, about 60 kDa, about 70 kDa, about 80 kDa, about 90 kDa, or about 100 kDa. In some embodiments, the collagen-binding domain is about 30 kDa. In some embodiments, the collagen-binding domain is about 40 kDa.

In some embodiments, the collagen-binding domain is about 10-350, about 10-300, about 10-250, about 10-200, about 10-150, about 10-100, about 10-50, or about 10-20 amino acids in length. In some embodiments, the collagen-binding domain is about 10 amino acids in length. In some embodiments, the collagen-binding domain is about 15 amino acids in length. In some embodiments, the collagen-binding domain is about 20 amino acids in length. In some embodiments, the collagen-binding domain is about 30 amino acids in length. In some embodiments, the collagen-binding domain is about 40 amino acids in length. In some embodiments, the collagen-binding domain is about 50 amino acids in length. In some embodiments, the collagen-binding domain is about 60 amino acids in length. In some embodiments, the collagen-binding domain is about 70 amino acids in length. In some embodiments, the collagen-binding domain is about 80 amino acids in length. In some embodiments, the collagen-binding domain is about 90 amino acids in length. In some embodiments, the collagen-binding domain is about 100 amino acids in length. In some embodiments, the collagen-binding domain is about 120 amino acids in length. In some embodiments, the collagen-binding domain is about 150 amino acids in length. In some embodiments, the collagen-binding domain is about 200 amino acids in length. In some embodiments, the collagen-binding domain is about 250 amino acids in length. In some embodiments, the collagen-binding domain is about 300 amino acids in length. In some embodiments, the collagen-binding domain is about 350 amino acids in length.

A. Isoelectric Point

The isoelectric point (pI, pH(I), IEP), is the pH at which a particular molecule (e.g., a collagen-binding domain) carries no net electrical charge or is electrically neutral. Table 1 provides the calculated pI for exemplary collagen-binding domains, described herein. The ExPASy tool from Swiss Institute of Bioinformatics (https://web.expasy.org/computepi/) was used to calculate the isoelectric points (pI) of the collagen-binding domains shown in Table 1.

In some embodiments, the collagen-binding domain has an isoelectric point pI less than (<) about 10, about 8, about 6, about 4, about 2, or about 1. In some embodiments, the collagen-binding domain has an isoelectric point pI of less than (<) 10. In some embodiments, the collagen-binding domain has an isoelectric point pI of less than (<) 10 and a molecular weight (MW) of greater than (>) 5 kDa.

TABLE 1

Calculated pI for Exemplary Collagen-Binding Domains

| Collagen-Binding Domain | Calculated pI | SEQ ID NO |
|---|---|---|
| LAIR1 | 5.23 | 98 |
| LAIR2 | 4.88 | 99 |
| Glycoprotein IV | 7.68 | 100 |
| Nidogen | 5.05 | 101 |
| Perlecan | 6.03 | 102 |
| Biglycan | 8.13 | 103 |
| Decorin | 8.76 | 104 |
| Asporin | 6.1 | 105 |
| Fibromodulin | 5.66 | 106 |
| Lumican | 6.17 | 107 |
| PRELP | 9.45 | 108 |
| Osteoadherin/Osteomodulin | 5.22 | 109 |
| Opticin | 5.38 | 110 |
| Osteoglycin/Mimecan | 5.22 | 111 |
| Chondroadherin | 9.14 | 112 |
| Podcan | 6.41 | 113 |
| Lumican (murine) | 6.01 | 195 |

B. Type I Collagen

Collagen is the predominant structural protein located within the extracellular space and type I collagen is the most abundant protein in mammals (Di Lullo et al., (2002) J Biol Chem 277(6):4223-4231). The fundamental structural unit of type I collagen is a long (300-nm), thin (1.5-nm-diameter) protein that consists of three coiled subunits: two α1 (I) chains and one α2(I). Each chain contains 1050 amino acids wound around one another in a characteristic right-handed triple helix. In humans, type I collagen is encoded by the COL1A1 and COL1A2 genes. The COL1A1 gene encodes the pro-alpha1 chain of type I collagen. The COL1A2 gene pro-alpha2 chain of type I collagen, whose triple helix comprises two alpha1 chains and one alpha2 chain. Type I is a fibril-forming collagen found in most connective tissues and is abundant in bone, cornea, dermis and tendon.

An exemplary amino acid sequence for the human alpha1 chain precursor of type I collagen is set forth in SEQ ID NO: 90 (NCBI Reference Sequence: NP_000079.2).

An exemplary amino acid sequence for the human alpha2 chain precursor of type I collagen is set forth in SEQ ID NO: 91 (NCBI Reference Sequence: NP_000080.2).

C. Type IV Collagen

Type IV collagen is comprised of a family of polypeptides and is a major constituent of mammalian basement membranes (Timpl (1989) Eur J Biochem 180:487-502; Paulsson (1992) Crit Rev Biochem Mol Biol 27:93-127). The α1(IV) and α2(IV) chains are products of distinct genes (COL4A1 and COL4A2, respectively) located pairwise in a head-to-head fashion on chromosome 13 in humans (Hudson et al., (1993) J Biol Chem 268:26033-26036). The α3(IV) and α4(IV) chains (encoded by the COL4A3 and COL4A4 genes, respectively) are present in the same orientation on chromosome 2 in humans, and the α5(IV) and α6(IV) chains (encoded by the COL4A5 and COL4A6 genes, respectively) are located on the X chromosome in humans (Hudson et al., (1991) in Pathobiochemistry, ed Kang A. (CRC Press, Boca Raton, FL), pp 17-30).

An exemplary amino acid sequence for the human alpha1 chain of type IV collagen is set forth in SEQ ID NO: 92 (NCBI Reference Sequence: XP_011519350.1).

An exemplary amino acid sequence for the human alpha2 chain of type IV collagen is set forth in SEQ ID NO: 93 (NCBI Reference Sequence: NP_001837.2).

An exemplary amino acid sequence for the human alpha3 chain of type IV collagen is set forth in SEQ ID NO: 94 (NCBI Reference Sequence: NP_000082.2).

An exemplary amino acid sequence for the human alpha4 chain of type IV collagen is set forth in SEQ ID NO: 95 (NCBI Reference Sequence: NP_000083.3).

An exemplary amino acid sequence for the human alpha5 chain of type IV collagen is set forth in SEQ ID NO: 96 (NCBI Reference Sequence: XP_011529151.2).

An exemplary amino acid sequence for the human alpha6 chain of type IV collagen is set forth in SEQ ID NO: 97 (NCBI Reference Sequence: XP_006724680.1).

Accordingly, in some embodiments, the disclosure provides immunomodulatory fusion proteins comprising a collagen-binding domain that specifically binds collagen. In some embodiments, the collagen-binding domain specifically binds human type I collagen and/or human type IV collagen. In some embodiments, the collagen-binding domain binds human type I collagen. In some embodiments, the collagen-binding domain binds human type IV collagen. In some embodiments, the collagen-binding domain specifically binds human type I collagen and human type IV collagen. In some embodiments, the collagen-binding domain specifically binds human type I collagen or human type IV collagen.

D. Binding Affinity to Collagen

In some embodiments, the disclosure provide immunomodulatory fusion proteins comprising a collagen-binding domain that specifically binds collagen with an affinity ($K_D$) of less than about 0.5 nM as determined by a collagen-binding assay. In some embodiments, the disclosure provide immunomodulatory fusion proteins comprising a collagen-binding domain that specifically binds collagen with an affinity ($K_D$) of less than about 5 nM as determined by a collagen-binding assay. In some embodiments, the disclosure provide immunomodulatory fusion proteins comprising a collagen-binding domain that specifically binds collagen with an affinity ($K_D$) of less than about 50 nM as determined by a collagen-binding assay. In some embodiments, the disclosure provide immunomodulatory fusion proteins comprising a collagen-binding domain that specifically binds collagen with an affinity ($K_D$) of less than about 500 nM as determined by a collagen-binding assay. In some embodiments, the collagen-binding domain specifically binds collagen with an affinity ($K_D$) of about 0.5-5 nM, 5-50 nM, or 50-500 nM as determined by a collagen-binding assay. In some embodiments, the collagen-binding domain specifically binds collagen with an affinity ($K_D$) of about 50-100 nM, 100-200 nM, 200-300 nM, 300-400 nM, or 400-500 nM as determined by a collagen-binding assay.

In some embodiments, the collagen-binding assay determines a binding affinity of the collagen-binding domain for collagen. In some embodiments, the collagen-binding assay determines a binding affinity of the collagen-binding domain for type I collagen. In some embodiments, the collagen-binding assay determines a binding affinity for type IV collagen.

In some embodiments, the collagen-binding assay is an ELISA. Methods and techniques to perform a collagen-binding ELISA are known in the art (see e.g., Smith et al., (2000) J Biol Chem 275:4205-4209). Accordingly, in some embodiments, the disclosure provides an immunomodulatory fusion protein comprising a collagen-binding domain that specifically binds collagen with an affinity ($K_D$) of less than about 0.5 nM as determined by an ELISA. Accordingly, in some embodiments, the disclosure provides an immunomodulatory fusion protein comprising a collagen-binding domain that specifically binds collagen with an affinity ($K_D$) of less than about 5 nM as determined by an ELISA. Accordingly, in some embodiments, the disclosure provides an immunomodulatory fusion protein comprising a collagen-binding domain that specifically binds collagen with an affinity ($K_D$) of less than about 50 nM as determined by an ELISA. Accordingly, in some embodiments, the disclosure provides an immunomodulatory fusion protein comprising a collagen-binding domain that specifically binds collagen with an affinity ($K_D$) of less than about 500 nM as determined by an ELISA. In some embodiments, the collagen-binding domain specifically binds collagen with an affinity ($K_D$) of about 0.5-5 nM, 4-40 nM, 50-500 nM as determined by an ELISA. In some embodiments, the collagen-binding domain specifically binds collagen with an affinity ($K_D$) of about 50-100 nM, 100-200 nM, 200-300 nM, 300-400 nM, or 400-500 nM as determined by an ELISA.

In some embodiments, the collagen-binding assay is a surface plasmon resonance (SPR) assay. Methods and techniques to perform a collagen-binding SPR assay are known in the art (see e.g., Saenko et al., (2002) Anal Biochem 302(2):252-262). Accordingly, in some embodiments, the disclosure provides an immunomodulatory fusion protein comprising a collagen-binding domain that specifically binds collagen with an affinity ($K_D$) of less than about 500 nM as determined by an SPR assay. In some embodiments, the collagen-binding domain specifically binds collagen with an affinity ($K_D$) of about 50-500 nM as determined by an SPR assay. In some embodiments, the collagen-binding domain specifically binds collagen with an affinity ($K_D$) of about 50-100 nM, 100-200 nM, 200-300 nM, 300-400 nM, or 400-500 nM as determined by an SPR assay.

The phrase "surface plasmon resonance" includes an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jönsson, U., et al. (1993) Ann. Biol. Clin. 51:19-26; Jönsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

E. Binding Specificity to Collagen

In some embodiments, the disclosure provides immunomodulatory fusion proteins comprising a collagen-binding domain that specifically binds collagen and does not specifically bind to one or more non-collagen extracellular matrix (ECM) components including, but not limited to, fibronectin, vitronectin, tenascin C, osteopontin and fibrinogen. In some embodiments, the collagen-binding domain binds to collagen with a lower $K_D$ than to one or more non-collagen ECM components. In some embodiments, the $K_D$ of the collagen-binding domain for type I collagen is less than the $K_D$ of the collagen-binding domain for an extracellular matrix component selected from fibronectin, vitronectin, osteopontin, tenascin C, or fibrinogen. In some embodiments, the collagen-binding domain binds to collagen with about 10%, about 20%, about 30%, about 40%, about 50%, about 60%, about 70%, about 80%, about 90%, about 99% lower $K_D$ than to one or more non-collagen ECM components. In some embodiments, the collagen-binding domain binds to collagen with about 2-fold, about 3-fold, about 4-fold, about 5-fold, about 10-fold lower $K_D$ than to one or more non-collagen ECM components.

In some embodiments, the collagen-binding domain is not a promiscuous binder of ECM components. In some embodiments, the collagen-binding domain does not comprise a heparin-binding domain. In some embodiments, the collagen-binding domain is not a growth factor or portion thereof which binds extracellular matrix.

In some embodiments, the collagen-binding domain binds to type I collagen with a lower $K_D$ than to type IV collagen. In some embodiments, the collagen-binding domain binds to type IV collagen with a lower $K_D$ than to type I collagen.

In some embodiments, the collagen-binding domain competes with a reference collagen-binding domain for binding to collagen. In some embodiments, the collagen-binding domain competes with a reference collagen-binding domain for binding to type I collagen. In some embodiments, the collagen-binding domain competes with a reference collagen-binding domain for binding to type IV collagen. In some embodiments, the collagen-binding domain competes with a reference collagen-binding domain for binding to type I collagen and type IV collagen. In some embodiments, the collagen-binding domain competes with a reference collagen-binding domain for binding to type I collagen but not to type IV collagen. In some embodiments, the collagen-binding domain competes with a reference collagen-binding domain for binding to type IV collagen but not to type I collagen.

In some embodiments, the reference collagen-binding domain comprises one or more (e.g., two, three, four, five, six, seven, eight, nine, ten or more) leucine-rich repeats which bind collagen. In some embodiments, the reference collagen-binding domain comprises a proteoglycan. In some embodiments, the reference collagen-binding domain comprises a proteoglycan, wherein the proteoglycan is selected from the group consisting of: decorin, biglycan, fibromodulin, lumican, chondroadherin, asporin, PRELP, osteoadherin/osteomodulin, opticin, osteoglycin/mimecan, podocan, perlecan, nidogen. In some embodiments, the reference collagen-binding domain is lumican. In some embodiments, the reference collagen-binding domain comprises a class I small leucine-rich proteoglycan (SLRP). SLRPs are known to bind collagen (Chen and Birk (2013) FEBS Journal 2120-2137). In some embodiments, the reference collagen-binding domain comprises a class II SLRP. In some embodiments, the reference collagen-binding domain comprises a class III SLRP. In some embodiments, the reference collagen-binding domain comprises a class IV SLRP. In some embodiments, the reference collagen-binding domain comprises a class V SLRP. Further description of SLRP classes is disclosed in Schaefer & Iozzo (2008) J Biol Chem 283(31):21305-21309, which is incorporated herein by reference it its entirety.

In some embodiments, the reference collagen-binding domain comprises the leukocyte-associated immunoglobulin-like receptor 1 (LAIR-1) protein. In some embodiments, the reference collagen-binding domain comprises the leukocyte-associated immunoglobulin-like receptor 2 (LAIR-2) protein. In some embodiments, the reference collagen-binding domain comprises Glycoprotein IV.

F. Exemplary Collagen-Binding Domains

In some embodiments, the collagen-binding domain comprises one or more (e.g., two, three, four, five, six, seven, eight, nine, ten or more) leucine-rich repeats which bind collagen. In some embodiments, the collagen-binding domain comprises a proteoglycan. In some embodiments, the collagen-binding domain comprises a proteoglycan, wherein the proteoglycan is selected from the group consisting of: decorin, biglycan, testican, bikunin, fibromodulin, lumican, chondroadherin, keratin, ECM2, epiphycan, asporin, PRELP, keratocan, osteoadherin, opticin, osteoglycan, nyctalopin, Tsukushi, podocan, podocan-like protein 1 versican, perlecan, nidogen, neurocan, aggrecan, and brevican.

In some embodiments, the collagen-binding domain comprises a class I small leucine-rich proteoglycan (SLRP). In some embodiments, the collagen-binding domain comprises a class II SLRP. In some embodiments, the collagen-binding domain comprises a class III SLRP. In some embodiments, the collagen-binding domain comprises a class IV SLRP. In some embodiments, the collagen-binding domain comprises a class V SLRP. Further description of SLRP classes is disclosed in Schaefer & Iozzo (2008) J Biol Chem 283(31): 21305-21309, which is incorporated herein by reference it its entirety.

In some embodiments, the collagen-binding domain comprises one or more leucine-rich repeats from a human proteoglycan Class II member of the small leucine-rich proteoglycan (SLRP) family. In some embodiments, the SLRP is selected from lumican, decorin, biglycan, fibromodulin, keratin, epiphycan, asporin and osteoglycin. In some embodiments, the SLRP is lumican. In some embodiments, lumican comprises the amino acid sequence as set forth in SEQ ID NO: 107.

Lumican

Lumican, also known as LUM, is an extracellular matrix protein that, in humans, is encoded by the LUM gene on chromosome 12 (Chakravarti et al., (1995) Genomics 27(3): 481-488). Lumican is a proteoglycan Class II member of the small leucine-rich proteoglycan (SLRP) family that includes decorin, biglycan, fibromodulin, keratocan, epiphycan, and osteoglycin (Iozzo & Schaefer (2015) Matrix Biology 42:11-55).

Like the other SLRPs, lumican has a molecular weight of about 40 kDa and has four major intramolecular domains: 1) a signal peptide of 16 amino acid residues, 2) a negatively-charged N-terminal domain containing sulfated tyrosine and disulfide bond(s), 3) ten tandem leucine-rich repeats allowing lumican to bind to collagen, and 4) a carboxyl terminal domain of 50 amino acid residues containing two conserved cysteines 32 residues apart. Kao et al., (2006) Experimental Eye Research 82(1):3-4). There are four N-linked sites within the leucine-rich repeat domain of the protein core that can be substituted with keratan sulfate. The core protein of lumican (like decorin and fibromodulin) is horseshoe shaped. This enables it bind to collagen molecules within a collagen fibril, thus helping keep adjacent fibrils apart Scott (1996) Biochemistry 35(27): 8795-8799.

Leukocyte-Associated Immunoglobulin-Like Receptors (LAIR-1 and LAIR-2)

Leukocyte-associated Ig-like receptor (LAIR)-1 is a collagen-receptor that inhibits immune cell function upon collagen binding. Next to LAIR-1, the human genome encodes LAIR-2, a soluble homolog. Human (h) LAIR-1 is expressed on the majority of PBMC and thymocytes (Maasho et al., (2005) Mol Immunol 42: 1521-1530). Cross-linking of hLAIR-1 by mAbs in vitro delivers a potent inhibitory signal that is capable of inhibiting immune cell function (4, 10-15). Collagens are known to be natural, high-affinity ligands for the LAIR molecules. Interaction of hLAIR-1 with collagens directly inhibits immune cell activation in vitro (Meyaard et al., (1997) Immunity 7:283-290; Poggi (1998) Eur J Immunol 28:2086-2091; Van der Vuurst de Vries et al., (1999) Eur J Immunol 29:3160-3167; Lebbink et al., (2006) J Exp Med 203:1419-1425).

In some embodiments, the collagen-binding domain comprises a human type I glycoprotein having an Ig-like domain, or an extracellular portion thereof which binds collagen. In some embodiments, the type I glycoprotein competes with lumican for binding for binding to collagen type I. In some embodiments, the human type I glycoprotein is selected from LAIR1, LAIR2, and Glycoprotein IV. In some embodiments, the human type I glycoprotein is LAIR1. In some embodiments, the human type I glycoprotein is LAIR1 and the collagen-binding domain comprises amino acid residues 22-122 of the amino acid sequence as set forth in SEQ ID NO: 98.

In some embodiments, the collagen-binding domain is a variant of LAIR1, LAIR2, or Glycoprotein IV. In some embodiments, the LAIR1 variant, LAIR2 variant, or Glycoprotein IV variant comprises one or more amino acid substitutions, additions or deletions (e.g., two, three, four, five, six, seven, eight, nine, ten or more) relative to the wild-type LAIR1, LAIR 2 or Glycoprotein IV protein sequence. In some embodiments, the collagen-binding domain is a LAIR1 variant comprising one or more amino acid substitutions, additions or deletions (e.g., two, three, four, five, six, seven, eight, nine, ten or more) relative to a LAIR1 protein comprising the amino acid sequence of SEQ ID NO: 98. In some embodiments, the collagen-binding domain is a LAIR1 variant comprising one or more amino acid substitutions, additions or deletions (e.g., two, three, four, five, six, seven, eight, nine, ten or more) in the LAIR1 binding pocket (e.g., a LAIR1 binding site comprising one or more residues E61, S66, Y68, I102, W109, Y115, R59, E63, R100, E111 and Q112, and combinations thereof) (Brondijk et al., (2010) Blood 115:1364-1373). In some embodiments, the collagen-binding domain is a LAIR1 variant comprising one or more amino acid substitutions, additions or deletions (e.g., two, three, four, five, six, seven, eight, nine, ten or more) outside the LAIR1 binding pocket.

In some embodiments, the collagen-binding domain is a LAIR1 variant having increased binding affinity to collagen relative to the collagen binding affinity of a wild-type LAIR1 protein. In some embodiments, the LAIR1 variant demonstrates an increase in binding affinity to collagen relative to the collagen binding affinity of a LAIR1 protein comprising the amino acid sequence of SEQ ID NO: 98. In some embodiments, the LAIR1 variant having decreased binding affinity to collagen relative to the collagen binding affinity of wild-type LAIR1 protein. In some embodiments, the LAIR1 variant demonstrates a decrease in binding affinity to collagen relative to the collagen binding affinity of a LAIR1 protein comprising the amino acid sequence of SEQ ID NO: 98.

Glycoprotein IV (CD36)

In some embodiments, the collagen-binding domain comprises Glycoprotein IV (GPIV). Glycoprotein IV binds many ligands including collagen (Tandon (1989) J Biol Chem 264(13): 7576-7583). A multifunctional glycoprotein, GPIV acts as receptor for a broad range of ligands, including thrombospondin, fibronectin, collagen or amyloid-beta as well as of lipidic nature such as oxidized low-density lipoprotein (oxLDL), anionic phospholipids, long-chain fatty acids and bacterial diacylated lipopeptides. GPIV is a protein that in humans is encoded by the CD36 gene. The CD36 antigen is an integral membrane protein found on the surface of many cell types in vertebrate animals. It imports fatty acids inside cells and is a member of the class B scavenger receptor family of cell surface proteins. In some embodiments, the CD36 comprises the amino acid sequence set forth in SEQ ID NO: 100.

II. Immunomodulatory Domain

The immunomodulatory fusion proteins disclosed herein comprise at least one immunomodulatory domain operably linked to a collagen-binding domain. In some embodiments, the immunomodulatory fusion protein comprises one, two, three, four, or five immunomodulatory domains. In some embodiments, when more than one immunomodulatory domain is present in the fusion protein, the immunomodulatory domains are the same. In some embodiments, when more than one immunomodulatory domain is present in the fusion protein, the immunomodulatory domains are different. In some embodiments, when more than one immunomodulatory domain is present in the fusion protein, each domain is located at the N terminus of a collagen-binding domain. In some embodiments, when more than one immunomodulatory domain is present in the fusion protein, each domain is located at the C terminus of a collagen-binding domain. In some embodiments, when more than one immunomodulatory domain is present in the fusion protein, at least one domain is located at the N terminus of a collagen-binding domain and at least one domain is located at the C terminus of the collagen-binding domain.

In some embodiments, the immunomodulatory domain activates the activity of a cell of the immune system. For example, in some embodiments the immunomodulatory domain is an immune response stimulatory, such as, but not limited to, a cytokine, such as an interleukin, a chemokine, a member of the TNF family, an agonistic antibody, an immune checkpoint blocker, or a combination thereof. In some embodiments, the immunomodulatory domain enhances an immune response. In some embodiments, enhancement of an immune response includes stimulation of T cells, stimulation of B cells, stimulation of dendritic cell responses, or a combination thereof. In some embodiments, enhancement of an immune response results in cytokine production, antibody production, antigen-specific immune cell (e.g., CD8+ T cells or CD4+ T cells) production, stimulation of Type I interferon responses, or combinations thereof.

In some embodiments, the immunomodulatory domain comprises a polypeptide that activates, enhances or promotes a response by an immune cell. In some embodiments, the immunomodulatory domain comprises a polypeptide that inhibits, reduces or suppresses a response by an immune cell. In some embodiments, the immune cell is a lymphoid cell, including but not limited to T cells, B cells, NK cells and innate lymphoid cells. In some embodiments, the immune cell is a myeloid cell, including but not limited to monocytes, neutrophils, macrophages, dendritic cells, mast cells and granulocytes.

In some embodiments, the response of the immune cell is cytokine production, antibody production, production of antigen-specific immune cells, or a combination thereof.

A. Interleukins

In some embodiments, the immunomodulatory domain suitable for use in the immunomodulatory fusion proteins of the present disclosure, is an interleukin (IL). Interleukins are secreted proteins that bind to their specific receptors and play a role in the communication among leukocytes. Interleukins suitable for use as an immunomodulatory domain of the immunomodulatory fusion proteins include, but are not limited to: IL-2, IL-12, IL-15, IL-15 superagonist (IL-15SA), IL-21, IL-6, IL-5, IL-8, IL-7, IL-17, IL-23, IL-18, IL-1, IL-4, IL-3, IL-10, IL-13, and IL-9. In some embodiments, the interleukin suitable for use as an immunomodulatory domain comprises an amino acid sequence selected from SEQ ID NOs: 1-5 and 9-24. In some embodiments, the immunomodulatory domain is an IL-2 polypeptide. In some embodiments, the immunomodulatory domain is an IL-12 polypeptide. In some embodiments, the immunomodulatory domain is an IL-15 polypeptide. In some embodiments, the immunomodulatory domain is an IL-15SA polypeptide.

In some embodiments, the immunomodulatory domain is an interleukin polypeptide that binds to a common gamma chain receptor. Interleukins that bind the common gamma chain receptor include, but are not limited to, IL-2, IL-4, IL-7, IL-9, IL-13, IL-15, IL-15/IL-15Rα and IL-21.

In some embodiments, the immunomodulatory domain is a polypeptide belonging to the IL-12 family. The IL-12 family comprises heterodimeric ligands comprised of an α subunit with helical structure (e.g., IL-12p35, IL-23p19, IL-27p28) and a β subunit (e.g., IL-12p40, IL-23p40 (which is identical to IL-12p40), EBI3). Exemplary members include IL-12, IL-23, IL-27 and IL-35.

In some embodiments, the immunomodulatory domain is a polypeptide belonging to the IL-1 superfamily. The Interleukin-1 (IL-1) family consists of 11 structurally related family members (IL-1α, IL-1-β, IL-1Ra, IL-18, IL-33 and IL-1F5 to IL-1 F10), that are among the most potent immune system signaling molecules, acting through a group of closely related receptors. All IL-1 receptors have a similar mode of activation: upon binding of ligand to the primary receptor subunit (i.e. IL-1R1 for IL-1α and β, IL-18R for IL-18 and ST2 for IL-33), a second receptor subunit is recruited (i.e. IL-1RAP for IL-1α and β, IL-18RAP for IL-18 and IL-1RAP for IL-33) and signaling is initiated via juxtaposition of the receptor subunits' cytoplasmic Toll/IL-1 receptor (TIR) domains. The dimerized TIR domains provide a docking platform for the MYD88 adaptor protein, which via recruitment of other intermediates leads to activation of the pro-inflammatory nuclear factor-κB (NF-κB) and mitogen-activated protein kinase (MAPK) pathways. The IL-1 family members are primarily produced by innate immune cells and act on a variety of cell types during the immune response. Accordingly, in some embodiments the immunomodulatory domain is an IL-18 polypeptide.

Interleukin-2 (IL-2)

In some embodiments, the immunomodulatory fusion protein comprises a member of the IL-2 family operably linked to a collagen binding domain, optionally via a linker. In some embodiments, the member of the IL-2 family is IL-2. Interleukin-2 (IL-2) is a cytokine that induces proliferation of antigen-activated T cells and stimulates natural killer (NK) cells. The biological activity of IL-2 is mediated through a multi-subunit IL-2 receptor complex (IL-2R) of three polypeptide subunits that span the cell membrane: p55 (IL-2Rα, the alpha subunit, also known as CD25 in humans), p75 (IL-2RP, the beta subunit, also known as CD 122 in humans) and p64 (IL-2Rγ, the gamma subunit, also known as CD 132 in humans). T cell response to IL-2 depends on a variety of factors, including: (1) the concentration of IL-2; (2) the number of IL-2R molecules on the cell surface; and (3) the number of IL-2R occupied by IL-2 (i.e., the affinity of the binding interaction between IL-2 and IL-2R (Smith, "Cell Growth Signal Transduction is Quantal" In Receptor Activation by Antigens, Cytokines, Hormones, and Growth Factors 766:263-271, 1995)). The IL-2:IL-2R complex is internalized upon ligand binding and the different components undergo differential sorting. IL-2Rα is recycled to the cell surface, while IL-2 associated with the IL-2:IL-2RPγ complex is routed to the lysosome and degraded. When administered as an intravenous (i.v.) bolus, IL-2 has a rapid systemic clearance (an initial clearance phase with a half-life of 12.9 minutes followed by a slower clearance phase with a half-life of 85 minutes) (Konrad et al., Cancer Res. 50:2009-2017, 1990).

Outcomes of systemic IL-2 administration in cancer patients are far from ideal. While 15 to 20 percent of patients respond objectively to high-dose IL-2, the great majority do not, and many suffer severe, life-threatening side effects, including nausea, confusion, hypotension, and septic shock. The severe toxicity associated with high-dose IL-2 treatment is largely attributable to the activity of natural killer (NK) cells. NK cells express the intermediate-affinity receptor, IL-2RPγ$_c$, and thus are stimulated at nanomolar concentrations of IL-2, which do in fact result in patient sera during high-dose IL-2 therapy. Attempts to reduce serum concentration, and hence selectively stimulate IL-2RaPγ$_c$-bearing cells, by reducing dose and adjusting dosing regimen have been attempted, and while less toxic, such treatments were also less efficacious. Given the toxicity issues associated with high dose IL-2 cancer therapy, numerous groups have attempted to improve anti-cancer efficacy of IL-2 by simultaneously administering therapeutic antibodies. Yet, such efforts have been largely unsuccessful, yielding no additional or limited clinical benefit compared to IL-2 therapy alone. Accordingly, novel IL-2 therapies are needed to more effectively combat various cancers.

In some embodiments, the linking of IL-2 to a collagen-binding domain localizes the cytokine to a cell, and therefore prevents systemic toxicity. Further, in some embodiments, when administered directly to a tumor or lesion, the collagen-binding domain localizes the cytokine to the tumor or lesion microenvironment, thereby preventing systemic toxicity associated with IL-2 treatment.

In some embodiments, the IL-2 is a human recombinant IL-2 such as Proleukin® (aldesleukin). Proleukin® is a human recombinant interleukin-2 product produced in *E. coli*. Proleukin® differs from the native interleukin-2 in the following ways: a) it is not glycosylated; b) it has no N-terminal alanine; and c) it has serine substituted for cysteine at amino acid positions 125. Proleukin® exists as biologically active, non-covalently bound microaggregates with an average size of 27 recombinant interleukin-2 molecules. Proleukin® (aldesleukin) is administered by intravenous infusion. In some embodiments, IL-2 is wild-type IL-2 (e.g., human IL-2 in its precursor form or mature IL-2. In some embodiments, IL-2 comprises the amino acid sequence set forth in SEQ ID NO: 1.

In certain embodiments, IL-2 is mutated such that it has an altered affinity (e.g., a higher affinity) for the IL-2R alpha receptor compared with unmodified IL-2. Site-directed mutagenesis can be used to isolate IL-2 mutants that exhibit high affinity binding to CD25, i.e., IL-2Rα, as compared to wild-type IL-2. Increasing the affinity of IL-2 for IL-2Rα at the cell surface will increase receptor occupancy within a limited range of IL-2 concentration, as well as raise the local concentration of IL-2 at the cell surface.

In some embodiments, the disclosure features IL-2 mutants, which may be, but are not necessarily, substantially purified and which can function as high affinity CD25 binders. IL-2 is a T cell growth factor that induces proliferation of antigen-activated T cells and stimulation of NK cells. Exemplary IL-2 mutants which are high affinity binders include those described in WO2013/177187A2 (herein incorporated by reference in its entirety). Further exemplary IL-2 mutants with increased affinity for CD25 are disclosed in U.S. Pat. No. 7,569,215, the contents of which are incorporated herein by reference.

In some embodiments, the disclosure features IL-2 mutants with reduced binding affinity to CD25 relative to wild-type IL-2. In some embodiments, the IL-2 mutant does not bind to CD25.

In some embodiments, IL-2 mutants comprise an amino acid sequence that is at least 80% identical to SEQ ID NO: 1 that bind CD25. For example, some embodiments an IL-2 mutant has at least one mutation (e.g., a deletion, addition, or substitution of 1, 2, 3, 4, 5, 6, 7, 8, 9, 10, 11, 12, 13, 14, 15, 16, 17, 18, 19, 20, or more amino acid residues) that increases the affinity for the alpha subunit of the IL-2 receptor relative to wild-type IL-2. It should be understood that mutations identified in mouse IL-2 may be made at corresponding residues in full length human IL-2 (nucleic acid sequence (accession: NM000586); amino acid sequence (accession: P60568)) or human IL-2 without the signal peptide. Accordingly, in some embodiments, the IL-2 is human IL-2. In other embodiments, the IL-2 is a mutant human IL-2.

In some embodiments, IL-2 mutants are at least or about 50%, at least or about 65%, at least or about 70%, at least or about 80%, at least or about 85%, at least or about 87%, at least or about 90%, at least or about 95%, at least or about 97%, at least or about 98%, or at least or about 99% identical in amino acid sequence to wild-type IL-2 (in its precursor form or, preferably, the mature form). The mutation can consist of a change in the number or content of amino acid residues. For example, the IL-2 mutants can have a greater or a lesser number of amino acid residues than wild-type IL-2. Alternatively, or in addition, IL-2 mutants can contain a substitution of one or more amino acid residues that are present in the wild-type IL-2.

By way of illustration, a polypeptide that includes an amino acid sequence that is at least 95% identical to a reference amino acid sequence of SEQ ID NO: 1 is a polypeptide that includes a sequence that is identical to the reference sequence except for the inclusion of up to five alterations of the reference amino acid of SEQ ID NO: 1. For example, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino (N—) or carboxy (C–) terminal positions of the reference amino acid sequence or anywhere between those terminal positions, interspersed either individually among residues in the reference sequence or in one or more contiguous groups within the reference sequence.

The substituted amino acid residue(s) can be, but are not necessarily, conservative substitutions, which typically include substitutions within the following groups: glycine, alanine; valine, isoleucine, leucine; aspartic acid, glutamic acid; asparagine, glutamine; serine, threonine; lysine, arginine; and phenylalanine, tyrosine. These mutations can be at amino acid residues that contact IL-2Rα.

Interleukin-12 (IL-12)

In some embodiments, the immunomodulatory fusion protein comprises an IL-12 polypeptide operably linked to a collagen binding domain, optionally via a linker. Interleukin-12 (IL-12) is a pro-inflammatory cytokine that plays an important role in innate and adaptive immunity. Gately, M K et al., *Annu Rev Immunol.* 16: 495-521 (1998). IL-12 functions primarily as a 70 kDa heterodimeric protein consisting of two disulfide-linked p35 and p40 subunits. The precursor form of the IL-12 p40 subunit (NM_002187; P29460; also referred to as IL-12B, natural killer cell stimulatory factor 2, cytotoxic lymphocyte maturation factor 2) is 328 amino acids in length, while its mature form is 306 amino acids long. The precursor form of the IL-12 p35 subunit (NM_000882; P29459; also referred to as IL-12A, natural killer cell stimulatory factor 1, cytotoxic lymphocyte maturation factor 1) is 219 amino acids in length and the mature form is 197 amino acids long. Id. The genes for the IL-12 p35 and p40 subunits reside on different chromosomes and are regulated independently of each other. Gately, M K et al., *Annu Rev Immunol.* 16: 495-521 (1998). Many different immune cells (e.g., dendritic cells, macrophages, monocytes, neutrophils, and B cells) produce IL-12 upon antigenic stimuli. The active IL-12 heterodimer is formed following protein synthesis. Id.

Due to its ability to activate both NK cells and cytotoxic T cells, IL-12 protein has been studied as a promising anti-cancer therapeutic since 1994. See Nastala, C. L. et al., *J Immunol* 153: 1697-1706 (1994). But despite high expectations, early clinical studies did not yield satisfactory results. Lasek W. et al., *Cancer Immunol Immunother* 63: 419-435, 424 (2014). Repeated administration of IL-12, in most patients, led to adaptive response and a progressive decline of IL-12-induced interferon gamma (IFNγ) levels in blood. Id. Moreover, while it was recognized that IL-12-induced anti-cancer activity is largely mediated by the secondary secretion of IFNγ, the concomitant induction of IFNγ along with other cytokines (e.g., TNF-α) or chemokines (IP-10 or MIG) by IL-12 caused severe toxicity. Id.

In addition to the negative feedback and toxicity, the marginal efficacy of the IL-12 therapy in clinical settings may be caused by the strong immunosuppressive environment in humans. Id. To minimize IFNγ toxicity and improve IL-12 efficacy, scientists tried different approaches, such as different dose and time protocols for IL-12 therapy. See Sacco, S. et al., *Blood* 90: 4473-4479 (1997); Leonard, J. P. et al., *Blood* 90: 2541-2548 (1997); Coughlin, C. M. et al., *Cancer Res.* 57: 2460-2467 (1997); Asselin-Paturel, C. et al., *Cancer* 91: 113-122 (2001); and Saudemont, A. et al., *Leukemia* 16: 1637-1644 (2002). Nonetheless, these approaches have not significantly impacted patient survival. Kang, W. K., et al., *Human Gene Therapy* 12: 671-684 (2001).

Membrane-anchored versions of IL-12 have been studied as a means of reducing toxicity associated with systemic administration, using retroviral and adenoviral vectors for expression in tumor cells. See Pan, W-Y. et al., *Mol. Ther.* 20(5): 927-937 (2012). But, the use of viral vectors presents a potential health risk, since the underlying viruses can act as oncogenes and the viral vectors can be immunogenic.

Accordingly, in some embodiments, the immunomodulatory fusion proteins disclosed herein comprise an IL-12 polypeptide operably linked to a collagen-binding domain. In some embodiments, the linking of an IL-12 polypeptide to a collagen-binding domain localizes the cytokine to a cell, and therefore prevents systemic toxicity. Further, in some embodiments, when administered directly to a tumor or lesion, the collagen-binding domain localizes the cytokine to the tumor or lesion microenvironment, thereby preventing systemic toxicity.

In some embodiments, the IL-12 polypeptide comprises IL-12A (e.g., SEQ ID NO: 3). In some embodiments, the IL-12 polypeptide comprises IL-12B (e.g., SEQ ID NO: 2). In some embodiments, the IL-12 polypeptide comprises both IL-12A and IL-12B.

In some embodiments, IL-12B is located N-terminal to IL-12A in the IL-12 polypeptide. In some embodiments, IL-12A is located N-terminal to IL-12B in the IL-12 polypeptide. The phrase "located N-terminal to" indicates location in a polypeptide with respect to other sequences in the polypeptide in relation to the N-terminus of the polypeptide. For example, IL-12B that is "N-terminal to" IL-12A means that IL-12B is located closer to the N-terminus of the IL-12 polypeptide than IL-12A.

In some embodiments, the IL-12 polypeptide comprises a single polypeptide chain comprising IL-12B and IL-12A, which are fused directly to one another or are linked to one another by a linker (referred to herein as an "subunit linker"). Non-limiting examples of linkers are disclosed elsewhere herein.

In some embodiments, the IL-12 polypeptide of the disclosure comprises IL-12A and/or IL-12B that is a variant, that is a functional fragment, or that contains a substitution, an insertion and/or an addition, a deletion, and/or a covalent modification with respect to a wild-type IL-12A or IL-12B sequence. In some embodiments, amino acid residues located at the carboxy, amino terminal, or internal regions of the IL-12 polypeptide are deleted, thereby providing for fragments.

In some embodiments, the IL-12 polypeptide comprises a substitutional variant of an IL-12A and/or IL-12B amino acid sequence, which can comprise one, two, three or more than three substitutions. In some embodiments, the substitutional variant can comprise one or more conservative amino acids substitutions. In other embodiments, the variant is an insertional variant. In other embodiments, the variant is a deletional variant.

As recognized by those skilled in the art, IL-12 protein fragments, functional protein domains, variants, and homologous proteins (orthologs) are also considered to be within the scope of the IL-12 polypeptides of the disclosure. Nonlimiting examples of IL-12 polypeptides suitable for use in the immunomodulatory fusion proteins disclosed herein are set forth in SEQ ID NOs: 2-3.

In some embodiments, the immunomodulatory fusion protein comprises an IL-12 polypeptide comprising the amino acid sequence set forth in SEQ ID NO: 2. In some embodiments, the immunomodulatory fusion protein comprises an IL-12 polypeptide comprising the amino acid sequence set forth in SEQ ID NO: 3. In some embodiments, the immunomodulatory fusion protein comprises an IL-12 polypeptide comprising the amino acid sequences set forth in SEQ ID NOs: 2 and 3.

Interleukin-15 (IL-15)

In some embodiments, the immunomodulatory fusion protein comprises an IL-15 polypeptide operably linked to a collagen binding domain, optionally via a linker. IL-15 is a member of the 4α-helix bundle family of cytokines and plays an important role in the development of an effective immune response. Waldmann, T. A., Cancer Immunol. Res. 3: 219-227 (2015). IL-15 is essential for the proper development of NK cells and long-term maintenance of memory CD8+ T cells. The IL-15 gene encodes a 162 amino acid preprotein having a signal peptide of 48 amino acids, with the mature protein being 114 amino acids in length. Bamford, R. N., et al., Proc. Natl. Acad. Sci. USA 93: 2897-2902 (1996). See also, e.g., GenBank Accession Numbers NM_000585 for the *Homo sapiens* IL15 transcript variant 3 mRNA sequence and NP_000576 for the corresponding IL15 isoform 1 preproprotein.

IL-15 shares certain structural similarity to interleukin-2 (IL-2). Like IL-2, IL-15 signals through the IL-2 receptor beta chain (CD122) and the common gamma chain (CD132). But, unlike IL-2, IL-15 cannot effectively bind CD122 and CD132 on its own. IL-15 must first bind to the IL-15 alpha receptor subunit (IL-15Rα). The IL-15Rα gene encodes a 267 amino acid preprotein having a signal peptide of 30 amino acids, with the mature protein being 237 amino acids in length. See, e.g., GenBank Accession Numbers NM_002189 for the *Homo sapiens* IL-15Rα transcript variant 1 mRNA and NP_002180 for the *Homo sapiens* IL-15Rα isoform 1 precursor amino acid sequence.

Human IL-15Rα is predominantly a transmembrane protein that binds to IL-15 on the surface of cells such as activated dendritic cells and monocytes. Waldmann, T. A., Cancer Immunol. Res. 3: 219-227 (2015). The membrane bound complex of IL-15/IL-15Rα then presents IL-15 in trans to CD122 and CD132 subunits. Accordingly, IL-15Rα is an essential component of IL-15 activity.

To overcome the short half-life of systemically injected IL-15, pre-complexation of IL-15 with soluble recombinant IL-15Ra, resulting in IL-15 superagonist (IL-15SA) has been shown to enhance the systemic potency of IL-15 by ~50 fold, and also raises the half-life of the cytokine in serum following systemic injection to ~20 hrs. (Stoklasek et al., J Immunol 177(9): 6072, 2006; Dubois et al., J Immunol 180(4): 2099, 2008; Rubinstein et. al. Proc Natl Acad Sci USA 103(24): 9166, 2006.)

Accordingly, in some embodiments, the immunomodulatory domain of the immunomodulatory fusion protein is an IL-15 polypeptide. In some embodiments, the IL-15 polypeptide comprises the amino acid sequence set forth in SEQ ID NO: 5. In some embodiments, the IL-15 polypeptide comprises the amino acid sequence set forth in SEQ ID NO: 4. In some embodiments, the IL-15 polypeptide is an IL-15 superagonist, comprising IL-15 and IL-15Rα. In some embodiments, the IL-15 superagonist comprises the amino acid sequences set forth in SEQ ID NOs: 4 and 5.

B. Interferons

In some embodiments, the immunomodulatory domain suitable for use in the immunomodulatory fusion proteins of the present disclosure, is an interferon (IFN). Interferons comprise a family of secretory proteins induced in response to specific extracellular stimuli through stimulation of toll-like receptors (TLRs). In some embodiments, interferons heighten anti-viral defenses of the immune system (e.g., antigen presentation). Through high-affinity cell surface receptors, IFNs stimulate genes using signaling molecules. Interferons suitable for use as an immunomodulatory domain of the immunomodulatory fusion proteins include, but are not limited to: IFN-gamma and IFN-alpha.

In some embodiments, the immunomodulatory fusion protein comprises an IFN-gamma polypeptide operably linked to a collagen-binding domain. IFN-gamma is produced by a variety of immune cells, such as activated T cells and NK cells. IFN-gamma interacts with a specific receptor at the cell surface and activates signal transduction pathways that produce immunomodulatory effects. Accordingly, in some embodiments, the immunomodulatory domain is an IFN-gamma polypeptide. In some embodiments, the IFN-gamma polypeptide comprises the amino acid sequence set forth in SEQ ID NO: 7.

In some embodiments, the immunomodulatory fusion protein comprises an IFN-alpha polypeptide operably linked to a collagen-binding domain. IFN-alpha is produced by B lymphocytes, null lymphocytes and macrophages, and activates NK cells, along with having antiviral and antitumor activities. Accordingly, in some embodiments, the immunomodulatory domain is an IFN-alpha polypeptide. In some embodiments, the IFN-alpha polypeptide comprises the amino acid sequence set forth in SEQ ID NO: 6.

C. Immune Cell Differentiation Stimulating Factors

In some embodiments, the immunomodulatory domain suitable for use in the immunomodulatory fusion proteins of the present disclosure, is an immune cell differentiation stimulating factor. In some embodiments, immune cell differentiation stimulating factors activate intracellular signaling pathways that drive hematopoietic progenitor cell differentiation, development and proliferation into specific subtypes of immune cells. Immune cell differentiation stimulating factors suitable for use in the immunomodulatory fusion proteins disclosed herein include, but are not limited to: GM-CSF (granulocyte-macrophage colony-stimulating factor), G-CSF (granulocyte colony-stimulating factor) and FLT3L (FMS-like tyrosine kinase 3 ligand).

In some embodiments, the immunomodulatory domain is a GM-CSF polypeptide. GM-CSF is a monomeric glycoprotein secreted by macrophages, T cells, mast cells, NK cells, endothelial cells and fibroblasts. In addition to having a function of growth stimulation and differentiation on hematopoietic precursor cells, GM-CSF has a variety of effects on immune cells expressing the GM-CSF receptor. In some embodiments, the GM-CSF polypeptide comprises the amino acid sequence set forth in SEQ ID NO: 27.

In some embodiments, the immunomodulatory domain is a FLT3L polypeptide. FLT3 is a receptor tyrosine kinase (RTK) which is expressed by immature hematopoietic precursor cells. FLT3L is a transmembrane protein or soluble protein and is expressed by a large number of cells, including hematopoietic cells and stroma cells in the bone marrow. In combination with other growth factors, FLT3L stimulates proliferation and development of various cells types, including myeloid and lymphoid precursor cells, dendritic cells and NK cells. In some embodiments, the FLT3L polypeptide comprises the amino acid sequence set forth in SEQ ID NO: 28.

In some embodiments, the immunomodulatory domain is an G-CSF polypeptide. In some embodiments, G-CSF regulates proliferation, differentiation and functional activation of neutrophilic granulocytes. In some embodiments, the G-CSF polypeptide comprises the amino acid sequence set forth in SEQ ID NO: 29.

D. Chemokines

In some embodiments, the immunomodulatory domain suitable for use in the immunomodulatory fusion proteins of the present disclosure, is a chemokine. In some embodiments, chemokines are proteins that induce directed chemotaxis of a responsive cell (e.g., leukocytes). In general, chemokines are grouped into four subfamilies: CXC, CC, (X)C, and CX3C. In the CXC chemokines, one amino acid separates the first two cysteines ("the CXC motif"). ELR+ CXC chemokines are ligands for CXCR1 and/or CXCR2 chemokine receptors, which are G-protein coupled seven transmembrane domain-type receptors that specifically bind ELR+ CXC chemokines. The seven human ELR+ CXC chemokines are human Gro-alpha (also known as CXCL1), human Gro-beta (also known as CXCL2), human Gro-gamma (also known as CXCL3), human ENA-78 (also known as CXCL5), human GCP-2 (also known as CXCL6), human NAP-2 (also known as CXCL7), and human IL-8 (also known as CXCL8). All ELR+ CXC chemokines bind the CXCR2 receptor; moreover, some ELR+ CXC chemokines bind both CXCR1 and CXCR2 receptors (i.e., CXCL6 and CXCL8), all of which contributes to redundancy in the activation pathways. The five murine ELR+ CXC chemokines are keratinocyte chemoattractant (KC) (also known as CXCL1), Macrophage Inflammatory Protein-2 (MIP-2) (also known as CXCL2), dendritic cell inflammatory protein-1 (DCIP-1) (also known as CXCL3), lipopolysaccharide-induced CXC chemokine (LIX) (also known as CXCL5), and neutrophil activating peptide-2 (NAP-2) (also known as CXCL7).

Chemokines suitable for use in the immunomodulatory fusion protein disclosed herein include, but are not limited to: LIF, M-CSF, MIP-2, MIP-1beta, KP (CXLC1), MIG (CXCL9), IP-10 (CXCL10), MCP-1, eotaxin, RANTES, LIX and MIP-1 alpha.

Amino acids encoding exemplary chemokines suitable for use as an immunomodulatory domain for the immunomodulatory fusion protein disclosed herein, are set forth below:

| Chemokine | Amino acid sequence (SEQ ID NO) |
|---|---|
| LIF | 30 |
| M-CSF | 31 |
| MIP-2 | 32 |
| MIP-1beta | 33 |
| KP (CXCL1) | 34 |
| MIG (CXCL9) | 35 |
| IP-10 (CXCL10) | 36 |
| MCP-1 | 37 |
| Eotaxin | 38 |
| RANTES | 39 |
| LIX | 40 |
| MIP-1alpha | 41 |

E. Tumor Necrosis Factor (TNF) Superfamily

In some embodiments, the immunomodulatory domain suitable for use in the immunomodulatory fusion proteins of the present disclosure, is an extracellular domain of a member of the tumor necrosis factor (TNF) superfamily. The tumor necrosis factor super family of ligands and receptors are a series of structurally homologous cell surface proteins that signal via forming trimeric clusters of ligand-receptor complexes. Ligation of activating TNF superfamily receptors can lead to a wide range of pro-immune responses, including proliferation, enhanced effector function, and production of chemokines and cytokines. Some ligands, such as Fas, can lead to the induction of apoptosis and are expressed on the surface of immune cells. Additionally, other ligands function as inhibitory receptors which weaken the immune response. In some embodiments, the extracellular domain is derived from: TNF-alpha, LIGHT, LT-alpha, LT-beta, BTLA, CD160, CD40L, FasL, CD30L, 4-1BBL, CD27L, OX40L, TWEAK, APRIL, BAFF, RANKL, TRAIL, EDA1, EDA2 or GITRL. The extracellular domain is capable of binding the selected TNF superfamily member's receptor, thereby inducing or stimulating an immune response.

The following table shows the receptor corresponding to the derived extracellular domain:

| Ligand | Receptor | Amino acid sequence of ligand extracellular domain (SEQ ID NO) |
|---|---|---|
| TNF-alpha | TNFR1, TNFR2 | 51 |
| LIGHT | HEVM, LT-betaR | 52 |
| LT-alpha | TNFR1, TNFR2, HEVM | 53 |
| LT-beta | LT-BetaR | 54 |
| CD160 | HVEM | 56 |
| CD40L | CD40 | 57 |
| FasL | Fas | 58 |
| CD30L | CD30 | 59 |
| 4-1BBL | 4-1BB | 60 |
| CD27L | CD27 | 61 |
| OX40L | OX40 | 62 |
| TWEAK | Fn14 | 63 |
| APRIL | BCMA, TACI | 64 |
| BAFF | BCMA, TACI, BAFFR | 65 |
| RANKL | RANK, OPG | 66 |
| TRAIL | OPG, TRAIL R1 (DR4), TRAIL R2 (DR5), DcR1, DcR2 | 67 |
| EDA1 | EDAR | 68 |
| EDA2 | XEDAR | 69 |
| GITRL | GITR | 70 |

F. CD28 Family

In some embodiments, the immunomodulatory domain suitable for use in the immunomodulatory fusion proteins of the present disclosure, is an extracellular domain of a member of the CD28 family. The CD28 family is a family of inhibitory (PD1, CTLA-4) and activating (CD28, ICOS) receptors that bind to members of the B7 family of ligands. CD28 is a co-stimulatory receptor that provides the second signal required to activate naive T cells (along with ligation of the TCR) and has two natural ligands, CD80 and CD86. CD28 signaling can serve to increase proliferation, effector function, and anti-apoptotic signaling. CD28 signaling has recently been shown to be required in effective PD1/PDL1 blockade. ICOS (Inducible T cell Costimulator) is a closely related surface receptor that is expressed on activated T cells and displays similar functions as CD28.

Accordingly, in some embodiments, the immunomodulatory domain is an extracellular domain of CD80 (B7-1). In some embodiments, the immunomodulatory domain comprises the amino acid sequence set forth in SEQ ID NO: 71.

Accordingly, in some embodiments, the immunomodulatory domain is an extracellular domain of CD86 (B7-2), capable of binding CD28. In some embodiments, the immunomodulatory domain comprises the amino acid sequence set forth in SEQ ID NO: 72.

Accordingly, in some embodiments, the immunomodulatory domain is an extracellular domain of ICOSLG. In some embodiments, the immunomodulatory domain comprises the amino acid sequence set forth in SEQ ID NO: 73.

G. Agonistic Antibodies

In some embodiments, the immunomodulatory domain suitable for use in the immunomodulatory fusion proteins of the present disclosure, is an agonistic antibody, or antigen binding fragment thereof. Agonistic antibodies activate their target of interest, in contrast to antagonistic antibodies which block the function of their target. In some embodiments, the agonistic antibodies, or antigen binding fragments thereof, bind to immune activating receptors. In some embodiments, immune activating receptors include, but are not limited to: tumor necrosis factor (TNF) receptors, CD28 family members, T-cell receptors (TCRs), Killer cell Ig-Like receptors (KIRs), Leukocyte Ig-Like receptors (LIRs), CD94/NKG2 receptors, Fc receptors, signaling lymphocytic activation molecules (SLAMs), and activating Siglec receptors.

Tumor Necrosis Factor (TNF) Superfamily

In some embodiments, the immunomodulatory domain suitable for use in the immunomodulatory fusion proteins of the present disclosure, is an agonistic antibody, or antigen binding fragment thereof, that binds to a tumor necrosis factor (TNF) superfamily member receptor. The TNF superfamily is described supra. For example, in some embodiments, the immunomodulatory domain is an agonistic antibody, or antigen binding fragment, that binds to TNFR1, thereby activating the receptor.

The following table provides a list of TNF superfamily member receptors that agonistic antibodies, or antigen binding fragments thereof, can be generated to target, suitable for use in the immunomodulatory fusion protein described herein:

| Ligand | Receptor | Receptor Uniprot KB |
|---|---|---|
| TNF-alpha | TNFR1 | P19438 |
|  | TNFR2 | P20333 |
| LIGHT | HEVM | Q92956 |
|  | LT-betaR | Q06643 |
| LT-alpha | TNFR1 | P19438 |
|  | TNFR2 | P20333 |
|  | HEVM | Q92956 |
| LT-beta | LT-BetaR | Q06643 |
| CD160 | HVEM | Q92956 |
| CD40L | CD40 | P25942 |
| FasL | Fas | P25445 |
| CD30L | CD30 | P28908 |
| 4-1BBL | 4-1BB | Q07011 |
| CD27L | CD27 | P26842 |
| OX40L | OX40 | P43489 |
| TWEAK | Fn14 | Q9NP84 |
| APRIL | BCMA | Q02223 |
|  | TACI | O14836 |
| BAFF | BCMA | Q02223 |
|  | TACI | O14836 |
|  | BAFFR | Q96RJ3 |
| RANKL | RANK | Q9Y6Q6 |
|  | OPG | O00300 |
| TRAIL | OPG | O00300 |
|  | TRAIL R1 (DR4) | O00220 |
|  | TRAIL R2 (DR5) | O14763 |
|  | DcR1 | O14798 |
|  | DcR2 | Q9UBN6 |
| EDA1 | EDAR | Q9UNE0 |
| EDA2 | XEDAR | Q9HAV5 |
| GITRL | GITR | Q9Y5U5 |

In some embodiments, the immunomodulatory domain is an anti-4-1BB agonist antibody. In some embodiments, the immunomodulatory domain is an anti-OX40 agonist antibody. In some embodiments, the immunomodulatory domain is a CD40 agonist antibody.

CD28 Receptor Superfamily

In some embodiments, the immunomodulatory domain suitable for use in the immunomodulatory fusion proteins of the present disclosure, is an agonistic antibody, or antigen binding fragment thereof, that binds to a CD28 superfamily receptor. The CD28 superfamily is described supra. For example, in some embodiments, the immunomodulatory domain is an agonistic antibody, or antigen binding fragment, that binds to CD28, thereby activating the receptor.

The following table provides a list of CD28 superfamily member receptors that agonistic antibodies, or antigen binding fragments thereof, can be generated to target, suitable for use in the immunomodulatory fusion protein described herein:

| Ligand | Receptor | Receptor Uniprot KB |
|---|---|---|
| CD80 (B7-1) | CD28 | P10747 |
| CD86 (B7-2) | CD28 | P10747 |
| ICOSLG | ICOS | Q9Y6W8 |

T Cell Receptor (TCR) Complex

In some embodiments, the immunomodulatory domain suitable for use in the immunomodulatory fusion proteins of the present disclosure, is an agonistic antibody, or antigen binding fragment thereof, that binds to a T-cell Receptor (TCR) complex. The T-cell Receptor (TCR) is the cell surface receptor responsible for imparting antigen specificity to T-cells. Each TCR is specific for a particular peptide presented either by MHC Class I (for CD8+ T cells) or MEW Class II (for CD4+ T cells). For naive T cells, ligation of the TCR provides the first of two signals required to activate the T cell. TCR ligation of CD8+ T cells leads to death of the cell displaying the cognate pMHC (and potentially bystander cells) via release of soluble factors, such as perforin and granzyme B, as well as upregulation of apoptosis inducing ligands, such as Fas ligand. For CD4+ helper T cells, ligation of the TCR with its cognate pMHC results in the release of cytokines, Accordingly, in some embodiments, the immunomodulatory domain is an agonistic antibody, or antigen binding fragment thereof, that binds to a TCR. For example, in some embodiments, the immunomodulatory domain is an agonistic antibody, or antigen binding fragment, that binds to CD3γ, thereby activating the receptor.

The following table provides a list of members of TCR complexes that agonistic antibodies, or antigen binding fragments thereof, can be generated to target, suitable for use in the immunomodulatory fusion protein described herein:

| TCR Binder | TCR Complex Member | Member Uniprot KB |
|---|---|---|
| pMHC | CD3γ | P09693 |
| pMHC | CD3δ | P04234 |
| pMHC | CD3ζ | P20963 |
| pMHC | CD3ε | P07766 |

Killer Cell Ig-Like Receptor (KIR)

In some embodiments, the immunomodulatory domain suitable for use in the immunomodulatory fusion proteins of the present disclosure, is an agonistic antibody, or antigen binding fragment thereof, that binds to a Killer Cell Ig-Like Receptor (KIR). The killer cell immunoglobulin like receptor (KIR) is a family of receptors expressed mainly on NK cells and on some subsets of T cells. These receptors are primarily responsible through recognition of self (and therefore inhibitory function), by binding to MHC class I (HLA-A, HLA-B, and HLA-C) molecules. These receptors can be either activating or inhibitory, depending on the length of the cytoplasmic tail. Inhibitory receptors have a longer tail and contain an ITIM domain. Activating KIRs have a shorter cytoplasmic domain and associate with DAP12 to mediate signaling.

Activating KIRs are provided in the table below, in which agonistic antibodies, or antigen binding fragments thereof, can be generated to target, suitable for use in the immunomodulatory fusion protein described herein:

| Ligand | Receptor | Receptor Uniprot KB |
|---|---|---|
| HLA molecules | KIR 2DS1 | Q14954 |
| HLA molecules | KIR 2DS2 | P43631 |
| HLA molecules | KIR 2DS3 | Q14952 |
| HLA molecules | KIR 2DS4 | P43632 |
| HLA molecules | KIR 2DS5 | Q14953 |
| HLA molecules | KIR 3DS1 | Q14943 |

Leukocyte Ig-Like Receptor (LIR)

In some embodiments, the immunomodulatory domain suitable for use in the immunomodulatory fusion proteins of the present disclosure, is an agonistic antibody, or antigen binding fragment thereof, that binds to a leukocyte Ig-Like receptor (LIR). LIR receptors are a class of immune receptors expressed primarily on innate immune cells. Their primary ligand is MHC Class I molecules and they largely exhibit inhibitory functions, although some have activating functions. LIRA2, for example, acts as an innate sensor of immunoglobulin fragments that have been cleaved by microbial proteases.

In some embodiments, the immunomodulatory domain is an agonistic antibody, or antigen binding fragment thereof, that binds to LIRA2. In some embodiments, antibodies capable of binding to LIRA2 can be generated based on Uniprot ID Q8N149.

CD94/NKG2 Receptor Family

In some embodiments, the immunomodulatory domain suitable for use in the immunomodulatory fusion proteins of the present disclosure, is an agonistic antibody, or antigen binding fragment thereof, that binds to a CD94/NKG2 receptor. CD94/NKG2 are heterodimer C-type lectin receptors that are expressed on the surface of NK cells and some subsets of CD8 T cells. They bind to HLA-E molecules (non-classical MHC Class I molecules) and can transmit both inhibitory and activating signals to NK Cells. Inhibitory receptors contain ITIM domains in their cytoplasmic tails, while activating receptors associate with DAP12 and DAP10 which contain ITAM domains.

Activating CD94/NKG2 receptors are provided in the table below, in which agonistic antibodies, or antigen binding fragments thereof, can be generated to target, suitable for use in the immunomodulatory fusion protein described herein.

In some embodiments, the immunomodulatory domain suitable for use in the immunomodulatory fusion proteins of the present disclosure is an extracellular domain of a CD94/NKG2 ligand. The following table shows the receptor corresponding to the derived extracellular domain.

| Ligand | Receptor | Receptor Uniprot KB | Amino acid sequence of ligand extracellular domain (SEQ ID NO) |
|---|---|---|---|
| MICA | CD94 | Q13241 | 74 |
|  | NKG2D | P26718 |  |
| MICB | CD94 | Q13241 | 75 |
|  | NKG2D | P26718 |  |
| ULBP1 | CD94 | Q13241 | 76 |
|  | NKG2D | P26718 |  |
| ULBP2 | CD94 | Q13241 | 77 |
|  | NKG2D | P26718 |  |
| ULBP3 | CD94 | Q13241 | 78 |
|  | NKG2D | P26718 |  |
| ULBP4 | CD94 | Q13241 | 79 |
|  | NKG2D | P26718 |  |
| ULBP5, isoform 1 | CD94 | Q13241 | 80 |
|  | NKG2D | P26718 |  |
| ULBP5, isoform 2 | CD94 | Q13241 | 81 |
|  | NKG2D | P26718 |  |
| ULBP6 | NKG2D | P26718 | 82 |
|  | NKG2C | P26717 |  |
|  | NKG2E | Q07444 |  |
|  | NKG2H | O43908 |  |
|  | CD94 | Q13241 |  |

Fc Receptors

In some embodiments, the immunomodulatory domain suitable for use in the immunomodulatory fusion proteins of the present disclosure, is an agonistic antibody, or antigen binding fragment thereof, that binds to an Fc receptor. Fc receptors are immune cell receptors expressed primarily on innate immune cells which bind to the constant region of antibodies and elicit a wide range of functions. Fc receptors are almost exclusively activating (except for Fc γ RIIB, which transmits inhibitory signals). Fc receptor ligation can lead to ADCC, phagocytosis, degranulation, and the transmission of activating signals which increase effector function.

The following table provides a list of Fc receptors that agonistic antibodies, or antigen binding fragments thereof, can be generated to target, suitable for use in the immunomodulatory fusion protein described herein:

| Ligand | Receptor | Receptor Uniprot KB |
|---|---|---|
| IgG | FcγRI | P12314 |
| IgG | FcγRIIC | P31995 |
| IgG | FcγRIIIA | P12318 |
| IgG | FcγRIIIB | P31994 |
| IgE | FcεRI | P30273 |
| IgE | FcεRII | P06734 |
| IgA | FcαR | P24071 |
| IgA/IgM | FcµR | Q8WWV6 |

Signaling Lymphocytic Activation Molecules (SLAM)

In some embodiments, the immunomodulatory domain suitable for use in the immunomodulatory fusion proteins of the present disclosure, is an agonistic antibody, or antigen binding fragment thereof, that binds to a signaling lymphocytic activation molecule (SLAM) receptor. SLAM receptors are a series of molecules that function both as receptors and ligands. SLAM molecules interact with one another on adjacent cells to send either activating or inhibitory signals. SLAM molecules contain Immunoreceptor Tyrosine based Swith motifs in their cytoplasmic tails, allowing them to associate with both activating and inhibitory signaling molecules intracellularly.

The following table provides a list of SLAM receptors that agonistic antibodies, or antigen binding fragments thereof, can be generated to target, suitable for use in the immunomodulatory fusion protein described herein.

In some embodiments, the immunomodulatory domain suitable for use in the immunomodulatory fusion proteins of the present disclosure is an extracellular domain of a SLAM ligand. The following table shows the receptor corresponding to the derived extracellular domain.

| Ligand | Receptor | Receptor Uniprot KB | Amino acid sequence of ligand extracellular domain (SEQ ID NO) |
|---|---|---|---|
| SLAMF1 | SLAMF1 | Q13291 | 83 |
| SLAMF2 | SLAMF2 | P09326 | 84 |
| SLAMF3 | SLAMF3 | Q9HBG7 | 85 |
| SLAMF4 | SLAMF4 | Q9BZW8 | 86 |
| SLAMF5 | SLAMF5 | Q9UIB8 | 87 |
| SLAMF6 | SLAMF6 | Q96DU3 | 88 |
| SLAMF7 | SLAMF7 | Q9NQ25 | 89 |

Siglec Family Receptors

In some embodiments, the immunomodulatory domain suitable for use in the immunomodulatory fusion proteins of the present disclosure, is an agonistic antibody, or antigen binding fragment thereof, that binds to a Siglec family receptor. Siglecs are a family of surface receptors found mainly on immune cells that are part of the lectin family (sugar binding proteins). These receptors bind to sialic acid containing ligands. These receptors function mainly as inhibitory receptors on a wide range of immune cell types, although some (siglec 14, 15, and 16) contain an ITAM activating domain.

Activating Siglec receptors are provided in the table below, in which agonistic antibodies, or antigen binding fragments thereof, can be generated to target, suitable for use in the immunomodulatory fusion protein described herein:

| Receptor | Receptor Uniprot KB |
|---|---|
| Siglec 14 | Q08ET2 |
| Siglec 15 | Q6ZMC9 |
| Siglec 16 | A6NMB1 |

H. Antagonistic Antibodies

In some embodiments, the immunomodulatory domain suitable for use in the immunomodulatory fusion proteins of the present disclosure, is an antagonistic antibody, or antigen binding fragment thereof. Antagonistic antibodies block the function of their target. In some embodiments, the antagonistic antibodies, or antigen binding fragments thereof, bind to immune inhibitory receptors, thereby allowing for the induction of an immune response. In some embodiments, the antagonistic antibodies, or antigen binding fragments thereof, bind to immune inhibitory ligands, thereby allowing for the induction of an immune response. In some embodiments, immune inhibitor receptors and ligands include, but are not limited to: CD28 receptors, tumor necrosis factor (TNF) superfamily receptors, Siglec receptors, CD94/NKG2 receptors, Leukocyte Ig-Like receptors (LIRs), Killer Cell Ig-Like receptors (KIRs), Fc receptors, adenosine pathway molecules, other checkpoint inhibitors, and LAIR1.

CD28 Molecules

In some embodiments, the immunomodulatory domain suitable for use in the immunomodulatory fusion proteins of the present disclosure, is an antagonistic antibody, or antigen binding fragment thereof, that binds a CD28 molecule. As described supra, the CD28 family includes both activating and inhibitory molecules. Accordingly, in some embodiments, antagonizing the inhibitory molecules results in an induction or stimulation of immune responses.

The following table provides a list of CD28 molecules that antagonistic antibodies, or antigen binding fragments thereof, can be generated to target, suitable for use in the immunomodulatory fusion protein described herein.

| Molecule | Molecule Uniprot KB |
|---|---|
| PD1 | Q15116 |
| PDL1 | Q9NZQ7 |
| PDL2 | Q9BQ51 |
| CTLA-4 | P16410 |
| B7-H4 | Q7Z7D3 |
| B7-H3 | Q5ZPR3 |

In some embodiments, the immunomodulatory domain is an antagonistic antibody, or antigen binding fragment thereof, that binds PD-1. In some embodiments, the immunomodulatory domain is an antagonistic antibody, or antigen binding fragment thereof, that binds PD-L1. In some embodiments, the immunomodulatory domain is an antagonistic antibody, or antigen binding fragment thereof, that binds CTLA-4.

TNF Superfamily Molecules

In some embodiments, the immunomodulatory domain suitable for use in the immunomodulatory fusion proteins of the present disclosure, is an antagonistic antibody, or antigen binding fragment thereof, that binds a TNF superfamily member. As described supra, the TNF superfamily includes both activating and inhibitory molecules. Accordingly, in some embodiments, antagonizing the inhibitory molecules results in an induction or stimulation of immune responses.

The following table provides a list of TNF superfamily molecules that antagonistic antibodies, or antigen binding fragments thereof, can be generated to target, suitable for use in the immunomodulatory fusion protein described herein.

| Molecule | Molecule Uniprot KB |
|---|---|
| TIGIT | Q495A1 |
| BTLA | Q7Z6A9 |

Siglec Receptors

In some embodiments, the immunomodulatory domain suitable for use in the immunomodulatory fusion proteins of the present disclosure, is an antagonistic antibody, or antigen binding fragment thereof, that binds a Siglec receptor. As described supra, the Siglec family includes both activating and inhibitory molecules. Accordingly, in some embodiments, antagonizing the inhibitory molecules results in an induction or stimulation of immune responses.

The following table provides a list of Siglec receptors that antagonistic antibodies, or antigen binding fragments thereof, can be generated to target, suitable for use in the immunomodulatory fusion protein described herein.

| Receptor | Receptor Uniprot KB |
|---|---|
| Siglec 1 (siualoadhesion) | Q9BZZ2 |
| Siglec 2 (CD22) | P20273 |
| Siglec 3 (CD33) | P20138 |
| Siglec 4a (MAG) | P20916 |
| Siglec 5 | O15389 |
| Siglec 6 | O43699 |

-continued

| Receptor | Receptor Uniprot KB |
|---|---|
| Siglec 7 | Q9Y286 |
| Siglec 8 | Q9NYZ4 |
| Siglec 9 | Q9Y336 |
| Siglec 10 | Q96LC7 |
| Siglec 11 | Q96RL6 |
| Siglec 12 | Q96PQ1 |

CD94/NKG2 Receptors

In some embodiments, the immunomodulatory domain suitable for use in the immunomodulatory fusion proteins of the present disclosure, is an antagonistic antibody, or antigen binding fragment thereof, that binds a CD94/NKG2 receptors. As described supra, the CD94/NKG2 family includes both activating and inhibitory molecules. Accordingly, in some embodiments, antagonizing the inhibitory molecules results in an induction or stimulation of immune responses.

Accordingly, in some embodiments, the immunomodulatory domain is an antagonistic antibody, or antigen binding fragment thereof, that binds CD94/NKG2A. In some embodiments, such antibodies are generated based on UniProt ID P26715.

In some embodiments, the immunomodulatory domain is an antagonistic antibody, or antigen binding fragment thereof, that binds CD94/NKG2B. In some embodiments, such antibodies are generated based on UniProt ID Q13241.

Leukocyte Ig-Like Receptors (LIRs)

In some embodiments, the immunomodulatory domain suitable for use in the immunomodulatory fusion proteins of the present disclosure, is an antagonistic antibody, or antigen binding fragment thereof, that binds a Leukocyte Ig-Like Receptors (LIR). As described supra, the LIR family includes both activating and inhibitory molecules. Accordingly, in some embodiments, antagonizing the inhibitory molecules results in an induction or stimulation of immune responses.

The following table provides a list of LIRs that antagonistic antibodies, or antigen binding fragments thereof, can be generated to target, suitable for use in the immunomodulatory fusion protein described herein.

| Receptor | Receptor Uniprot KB |
|---|---|
| LIRB1 | Q8NHL6 |
| LIRB2 | Q8N423 |
| LIRB3 | O75022 |
| LIRB4 | Q8NHJ6 |

Killer Cell Ig-Like Receptors (KIRs)

In some embodiments, the immunomodulatory domain suitable for use in the immunomodulatory fusion proteins of the present disclosure, is an antagonistic antibody, or antigen binding fragment thereof, that binds a Killer Cell Ig-Like Receptor (KIR). As described supra, the KIR family includes both activating and inhibitory molecules. Accordingly, in some embodiments, antagonizing the inhibitory molecules results in an induction or stimulation of immune responses.

The following table provides a list of KIRs that antagonistic antibodies, or antigen binding fragments thereof, can be generated to target, suitable for use in the immunomodulatory fusion protein described herein.

| Receptor | Receptor Uniprot KB |
|---|---|
| KIR 2DL1 | P43626 |
| KIR 2DL2 | P43627 |
| KIR 2DL3 | P43628 |
| KIR 2DL4 | Q99706 |
| KIR 2DL5A | Q8N109 |
| KIR 2DL5B | Q8NHK3 |
| KIR 3DL1 | P43629 |
| KIR 3DL2 | P43630 |
| KIR 3DL3 | Q8N743 |

Fc Receptors

In some embodiments, the immunomodulatory domain suitable for use in the immunomodulatory fusion proteins of the present disclosure, is an antagonistic antibody, or antigen binding fragment thereof, that binds an Fc receptor. As described supra, the family of Fc receptors includes both activating and inhibitory molecules. Accordingly, in some embodiments, antagonizing the inhibitory molecules results in an induction or stimulation of immune responses.

In some embodiments, the inhibitor Fc receptor is Fc γ RIM In some embodiments, the immunomodulatory domain is an antagonistic antibody, or antigen binding fragment thereof, that binds Fc γ RIIB In some embodiments, such antibodies are generated based on UniProt ID P31994.

Adenosine Pathway Molecules

In some embodiments, the immunomodulatory domain suitable for use in the immunomodulatory fusion proteins of the present disclosure, is an antagonistic antibody, or antigen binding fragment thereof, that binds a member of the adenosine pathway. For example, CD39 and CD73 are enzymes expressed on the surface of cells which catalyze the transformation of ATP into adenosine. Extracellular ATP is a danger molecule which elicits an immune response, while adenosine is immunosuppressive. These molecules contribute to a locally immunosuppressive environment by generating adenosine.

Accordingly, in some embodiments, the immunomodulatory domain is an antagonistic antibody, or antigen binding fragment thereof, that binds CD39. In some embodiments, such antibodies are generated based on UniProt ID P49961.

In some embodiments, the immunomodulatory domain is an antagonistic antibody, or antigen binding fragment thereof, that binds CD73. In some embodiments, such antibodies are generated based on UniProt ID P21589.

Other Checkpoint Inhibitors

In some embodiments, the immunomodulatory domain suitable for use in the immunomodulatory fusion proteins of the present disclosure, is an antagonistic antibody, or antigen binding fragment thereof, that binds an immune checkpoint inhibitor. In some embodiments, by antagonizing such immune checkpoint inhibitors, an immune response is induced or stimulated.

The following table provides a list of immune checkpoint inhibitors that antagonistic antibodies, or antigen binding fragments thereof, can be generated to target, suitable for use in the immunomodulatory fusion protein described herein.

| Molecule | Molecule Uniprot KB |
|---|---|
| VISTA | Q9H7M9 |
| TIM-3 | Q8TDQ0 |
| LAG-3 | P18627 |
| CD47 | Q08722 |
| SIRPα | P78324 |

III. Linkers

In some embodiments, the immunomodulatory fusion protein comprises an immunomodulatory domain operably linked to a collagen-binding protein via a linker. In some embodiments, the linker between the immunomodulatory domain and the collagen-binding protein provides a steric separation such that the immunomodulatory domain retains its activity (e.g., promote receptor/ligand engagement). In some embodiments, the linker between the immunomodulatory domain and the collagen-binding protein is of sufficient length or mass to reduce adsorption of the immunomodulatory domain onto collagen fibrils. Methods for measuring adsorption are known to those of skill in the art. For example, adsorption can be measured by ellipsometry (ELM), surface plasmon resonance (SPR), optical waveguide lightmode spectroscopy (OWLS), attenuated total internal reflectance-infrared spectroscopy (ATR-IR), circular dichroism spectroscopy (CD), total internal reflectance-infrared spectroscopy (TIRF), and other high resolution microscopy techniques. In some embodiments, these methods show the spatial arrangement between the domains of the immunomodulatory fusion protein.

In some embodiments, the linker between the immunomodulatory domain and the collagen-binding protein provides sufficient molecular weight to slow or reduce diffusion from the tissue. Methods for measuring diffusion from the tissue are known to those of skill in the art. For example, diffusion can be measured by in vivo imagining, or via microscopy of tissue sections over time. Exemplary methods are described in at least Schmidt & Wittrup, Mol Canc Ther. 2009' and Wittrup et al., Methods in Enzymol 2012, each of which is herein incorporated by reference in their entirety.

In some embodiments, the linker is a hydrophilic polypeptide comprising "N" amino acids in length, wherein N=1-1000, 50-800, 100-600, or 200-500.

A. Serum Albumin

In some embodiments, the linker is a serum albumin, or fragments thereof. Methods of fusing serum albumin to proteins are disclosed in, e.g., US2010/0144599, US2007/0048282, and US2011/0020345, which are herein incorporated by reference in their entirety. In some embodiments, the linker is human serum albumin (HSA), or variants or fragments thereof, such as those disclosed in U.S. Pat. No. 5,876,969, WO 2011/124718, WO 2013/075066, and WO 2011/0514789.

Suitable albumins for use in the immunomodulatory fusion proteins can be from human, primate, rodent, bovine, equine, donkey, rabbit, goat, sheep, dog, chicken, or pig. In some embodiments, the albumin is a serum albumin, for example, a human serum albumin (SEQ ID NO: 42, primate serum albumin (e.g., chimpanzee serum albumin, gorilla serum albumin), rodent serum albumin (e.g., hamster serum albumin, guinea pig serum albumin, mouse albumin and rat serum albumin), bovine serum albumin, equine serum albumin, donkey serum albumin, rabbit serum albumin, goat serum albumin, sheep serum albumin, dog serum albumin, chicken serum albumin and pig serum albumin.

In some embodiments, the albumin, or a variant or fragment thereof, has a sequence identity to the sequence of wild-type HSA as set forth in SEQ ID NO: 42 of at least 50%, such as at least 60%, at least 70%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

In some embodiments, the number of alterations, e.g., substitutions, insertions, or deletions, in an albumin variants is 1-20, e.g., 1-10 and 1-5, such as 1, 2, 3, 4, 5, 6, 7, 8, 9 or 10 alterations compared to the corresponding wild-type albumin (e.g., HSA).

In some embodiments, fragments of albumin, or fragments of variants thereof, are suitable for use in the immunomodulatory fusion proteins. Exemplary albumin fragments are disclosed in WO 2011/124718. In some embodiments, a fragment of albumin (e.g., a fragment of HSA) is at least 20 amino acids in length, such as at least 40 amino acids, at least 60 amino acids, at least 80 amino acids, at least 100 amino acids, at least 150 amino acids, at least 200 amino acids, at least 300 amino acids, at least 400 amino acids, or at least 500 amino acids in length.

In some embodiments, an albumin fragment may comprise at least one whole sub-domain of albumin. Domains of HSA have been expressed as recombinant proteins (Dockal et al., *JBC* 1999; 274:9303-10), where domain I was defined as consisting of amino acids 1-197 (SEQ ID NO: 116), domain II was defined as consisting of amino acids 189-385 (SEQ ID NO: 117), and domain III was defined as consisting of amino acids 381-585 (SEQ ID NO: 118) of HSA (SEQ ID NO: 42). Partial overlap of the domains occurs given the extended α-helix structure (h10-h1) which exists between domains I and II, and between domains II and III (Peters, 1996, op. cit, Table 2-4). HSA also comprises six sub-domains (sub-domains IA, IB, NA, NB, INA and NIB). Sub-domain IA comprises amino acids 6-105, sub-domain IB comprises amino acids 120-177, sub-domain NA comprises amino acids 200-291, sub-domain NB comprises amino acids 316-369, sub-domain INA comprises amino acids 392-491 and sub-domain NIB comprises amino acids 512-583 of SEQ ID NO: 42

In some embodiments, a fragment comprises a whole or part of one or more domains or sub-domains as defined above, or any combination of those domains and/or sub-domains. In some embodiments, an albumin fragment comprises at least 50, 60, 70, 75, 80, 85, 90, 95, 96, 97, 98, or 99% of an albumin or of a domain of an albumin, or a variant or fragment thereof.

B. Fc Domains

In some embodiments, the linker suitable for use in the immunomodulatory fusion protein described herein is an Fc domain. In some embodiments, the Fc domain is a component of the agonist or antagonist antibodies described supra, and therefore a separate Fc domain is not needed.

In certain embodiments, the Fc domain comprises the amino acid sequence set forth in SEQ ID NO: 115. In some embodiments, the Fc domain does not contain a variable region that binds to antigen. In some embodiments, the Fc domain contains a variable region that binds to antigen. Fc domains suitable for the immunomodulatory fusion proteins disclosed herein may be obtained from a number of different sources. In certain embodiments, an Fc domain is derived from a human immunoglobulin. In certain embodiments, the Fc domain is from a human IgG1 constant region. The Fc domain of human IgG1 is set forth in SEQ ID NO: 115. It is understood, however, that the Fc domain may be derived from an immunoglobulin of another mammalian species, including for example, a rodent (e.g. a mouse, rat, rabbit, guinea pig) or non-human primate (e.g. chimpanzee, macaque) species. Moreover, the Fc domain or portion thereof may be derived from any immunoglobulin class, including IgM, IgG, IgD, IgA, and IgE, and any immunoglobulin isotype, including IgG1, IgG2, IgG3, and IgG4.

In some embodiments, the immunomodulatory fusion protein comprises a mutant Fc domain. In some embodiments, the immunomodulatory fusion protein comprises a mutant, IgG1 Fc domain. In some embodiments, a mutant Fc domain comprises one or more mutations in the hinge, CH2, and/or CH3 domains. In some aspects, a mutant Fc domain includes a D265A mutation.

A variety of Fc domain gene sequences (e.g., mouse and human constant region gene sequences) are available in the form of publicly accessible deposits. Constant region domains comprising an Fc domain sequence can be selected lacking a particular effector function and/or with a particular modification to reduce immunogenicity. Many sequences of antibodies and antibody-encoding genes have been published and suitable Fc domain sequences (e.g. hinge, CH2, and/or CH3 sequences, or portions thereof) can be derived from these sequences using art recognized techniques. The genetic material obtained using any of the foregoing methods may then be altered or synthesized to obtain polypeptides suitable for use in the methods disclosed herein. It will further be appreciated that the scope of this disclosure encompasses alleles, variants and mutations of constant region DNA sequences.

Fc domain sequences can be cloned, e.g., using the polymerase chain reaction and primers which are selected to amplify the domain of interest. To clone an Fc domain sequence from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif (1990); Ho et al. 1989. Gene 77:51; Horton et al. 1993. Methods Enzymol. 217:270. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7: 1509); rapid amplification of cDNA ends (Ruberti, F. et al. 1994. J. Immunol. Methods 173:33); antibody leader sequences (Larrick et al. Biochem Biophys Res Commun 1989; 160: 1250). The cloning of antibody sequences is further described in Newman et al., U.S. Pat. No. 5,658,570, filed Jan. 25, 1995, which is herein incorporated by reference.

In some embodiments, the immunomodulatory fusion protein disclosed comprises one or more Fc domains (e.g., 2, 3, 4, 5, 6, 7, 8, 9, 10, or more Fc domains). In certain embodiments, the Fc domains may be of different types. In certain embodiments, at least one Fc domain present in the immunomodulatory fusion protein comprises a hinge domain or portion thereof. In certain embodiments, the immunomodulatory fusion protein comprises at least one Fc domain which comprises at least one CH2 domain or portion thereof. In certain embodiments, the immunomodulatory fusion protein comprises at least one Fc domain which comprises at least one CH3 domain or portion thereof. In certain embodiments, the immunomodulatory fusion protein comprises at least one Fc domain which comprises at least one CH4 domain or portion thereof. In certain embodiments, the immunomodulatory fusion protein comprises at least one Fc domain which comprises at least one hinge domain or portion thereof and at least one CH2 domain or portion thereof (e.g., in the hinge-CH2 orientation). In certain embodiments, the immunomodulatory fusion protein comprises at least one Fc domain which comprises at least one CH2 domain or portion thereof and at least one CH3 domain or portion thereof (e.g., in the CH2-CH3 orientation). In certain embodiments, the immunomodulatory fusion protein comprises at least one Fc domain comprising at least one hinge domain or portion thereof, at least one CH2 domain or portion thereof, and least one CH3 domain or portion thereof, for example in the orientation hinge-CH2-CH3, hinge-CH3-CH2, or CH2-CH3-hinge.

In certain embodiments, immunomodulatory fusion protein comprises at least one complete Fc region derived from one or more immunoglobulin heavy chains (e.g., an Fc domain including hinge, CH2, and CH3 domains, although these need not be derived from the same antibody). In certain embodiments, immunomodulatory fusion protein comprises at least two complete Fc domains derived from one or more immunoglobulin heavy chains. In certain embodiments, the complete Fc domain is derived from a human IgG immunoglobulin heavy chain (e.g., human IgG1).

In certain embodiments, the immunomodulatory fusion protein comprises at least one Fc domain comprising a complete CH3 domain. In certain embodiments, the immunomodulatory fusion protein comprises at least one Fc domain comprising a complete CH2 domain. In certain embodiments, the immunomodulatory fusion protein comprises at least one Fc domain comprising at least a CH3 domain, and at least one of a hinge region, and a CH2 domain. In certain embodiments, the immunomodulatory fusion protein comprises at least one Fc domain comprising a hinge and a CH3 domain. In certain embodiments, the immunomodulatory fusion protein comprises at least one Fc domain comprising a hinge, a CH2, and a CH3 domain. In certain embodiments, the Fc domain is derived from a human IgG immunoglobulin heavy chain (e.g., human IgG1).

The constant region domains or portions thereof making up an Fc domain of the immunomodulatory fusion protein may be derived from different immunoglobulin molecules. For example, a polypeptide suitable for use in the immunomodulatory fusion proteins disclosed herein may comprise a CH2 domain or portion thereof derived from an IgG1 molecule and a CH3 region or portion thereof derived from an IgG3 molecule. In some embodiments, the immunomodulatory fusion protein comprises an Fc domain comprising a hinge domain derived, in part, from an IgG1 molecule and, in part, from an IgG3 molecule. As set forth herein, it will be understood by one of ordinary skill in the art that an Fc domain may be altered such that it varies in amino acid sequence from a naturally occurring antibody molecule.

In certain embodiments, the immunomodulatory fusion protein lacks one or more constant region domains of a complete Fc region, i.e., they are partially or entirely deleted. In certain embodiments, the immunomodulatory fusion protein lacks an entire CH2 domain. In certain embodiments, the immunomodulatory fusion protein comprises CH2 domain-deleted Fc regions derived from a vector (e.g., from IDEC Pharmaceuticals, San Diego) encoding an IgG1 human constant region domain (see, e.g., WO02/060955A2 and WO02/096948A2). This exemplary vector is engineered to delete the CH2 domain and provide a synthetic vector expressing a domain-deleted IgG1 constant region. It will be noted that these exemplary constructs are preferably engineered to fuse a binding CH3 domain directly to a hinge region of the respective Fc domain.

In other constructs it may be desirable to provide a peptide spacer between one or more constituent Fc domains. For example, a peptide spacer may be placed between a hinge region and a CH2 domain and/or between a CH2 and a CH3 domain. For example, compatible constructs could be expressed wherein the CH2 domain has been deleted and the remaining CH3 domain (synthetic or unsynthetic) is joined to the hinge region with a 1-20, 1-10, or 1-5 amino acid peptide spacer. Such a peptide spacer may be added, for instance, to ensure that the regulatory elements of the constant region domain remain free and accessible or that the hinge region remains flexible. Preferably, any linker peptide compatible used in the instant disclosure will be relatively non-immunogenic and not prevent proper folding of the Fc.

In certain embodiments, an Fc domain employed in the immunomodulatory fusion protein is altered or modified, e.g., by amino acid mutation (e.g., addition, deletion, or substitution). As used herein, the term "Fc domain variant" refers to an Fc domain having at least one amino acid modification, such as an amino acid substitution, as compared to the wild-type Fc from which the Fc domain is derived. For example, wherein the Fc domain is derived from a human IgG1 antibody, a variant comprises at least one amino acid mutation (e.g., substitution) as compared to a wild type amino acid at the corresponding position of the human IgG1 Fc region.

In certain embodiments, the Fc variant comprises a substitution at an amino acid position located in a hinge domain or portion thereof. In certain embodiments, the Fc variant comprises a substitution at an amino acid position located in a CH2 domain or portion thereof. In certain embodiments, the Fc variant comprises a substitution at an amino acid position located in a CH3 domain or portion thereof. In certain embodiments, the Fc variant comprises a substitution at an amino acid position located in a CH4 domain or portion thereof.

In certain embodiments, the immunomodulatory fusion protein comprises an Fc variant comprising more than one amino acid substitution. The immunomodulatory fusion protein may comprise, for example, 2, 3, 4, 5, 6, 7, 8, 9, 10 or more amino acid substitutions in the Fc domain. Preferably, the amino acid substitutions are spatially positioned from each other by an interval of at least 1 amino acid position or more, for example, at least 2, 3, 4, 5, 6, 7, 8, 9, or 10 amino acid positions or more. More preferably, the engineered amino acids are spatially positioned apart from each other by an interval of at least 5, 10, 15, 20, or 25 amino acid positions or more.

In some embodiments, an Fc domain includes changes in the region between amino acids 234-238, including the sequence LLGGP at the beginning of the CH2 domain. In some embodiments, an Fc variant alters Fc mediated effector function, particularly ADCC, and/or decrease binding avidity for Fc receptors. In some aspects, sequence changes closer to the CH2-CH3 junction, at positions such as K322 or P331 can eliminate complement mediated cytotoxicity and/or alter avidity for FcR binding. In some embodiments, an Fc domain incorporates changes at residues P238 and P331, e.g., changing the wild type prolines at these positions to serine. In some embodiments, alterations in the hinge region at one or more of the three hinge cysteines, to encode CCC, SCC, SSC, SCS, or SSS at these residues can also affect FcR binding and molecular homogeneity, e.g., by elimination of unpaired cysteines that may destabilize the folded protein.

Other amino acid mutations in the Fc domain are contemplated to reduce binding to the Fc gamma receptor and Fc gamma receptor subtypes. For example, mutations at positions 238, 239, 248, 249, 252, 254, 255, 256, 258, 265, 267, 268, 269, 270, 272, 279, 280, 283, 285, 298, 289, 290, 292, 293, 294, 295, 296, 298, 301, 303, 305, 307, 312, 315, 322, 324, 327, 329, 330, 331, 333, 334, 335, 337, 338, 340, 356, 360, 373, 376, 378, 379, 382, 388, 389, 398, 414, 416, 419, 430, 434, 435, 437, 438 or 439 of the Fc region can alter binding as described in U.S. Pat. No. 6,737,056, issued May 18, 2004, incorporated herein by reference in its entirety. This patent reported that changing Pro331 in IgG3 to Ser resulted in six fold lower affinity as compared to unmutated IgG3, indicating the involvement of Pro331 in Fc gamma RI binding. In addition, amino acid modifications at positions 234, 235, 236, and 237, 297, 318, 320 and 322 are disclosed as potentially altering receptor binding affinity in U.S. Pat. No. 5,624,821, issued Apr. 29, 1997 and incorporated herein by reference in its entirety.

Further mutations contemplated for use include, e.g., those described in U.S. Pat. App. Pub. No. 2006/0235208, published Oct. 19, 2006 and incorporated herein by reference in its entirety. Additionally, mutations described in U.S. Pat. App. Pub. No. 2006/0235208, incorporated herein by reference in its entirety, are contemplated for use. The mutant L234A/L235A is described, e.g., in U.S. Pat. App. Pub. No. 2003/0108548, published Jun. 12, 2003 and incorporated herein by reference in its entirety. In embodiments, the described modifications are included either individually or in combination. In certain embodiments, the mutation is D265A in human IgG1.

In certain embodiments, the immunomodulatory fusion protein comprises an Fc variant comprising an amino acid substitution which alters the antigen-dependent effector functions of the polypeptide, in particular ADCC or complement activation, e.g., as compared to a wild type Fc region. Such immunomodulatory fusion protein exhibit decreased binding to FcR gamma when compared to wild-type polypeptides and, therefore, mediate reduced effector function. Fc variants with decreased FcR gamma binding affinity are expected to reduce effector function, and such molecules are also useful, for example, for treatment of conditions in which target cell destruction is undesirable, e.g., where normal cells may express target molecules, or where chronic administration of the polypeptide might result in unwanted immune system activation.

In certain embodiments, the immunomodulatory fusion protein exhibits altered binding to an activating FcγR (e.g. FcγI, FcγIIa, or FcγRIIIa). In certain embodiments, the immunomodulatory fusion protein exhibits altered binding affinity to an inhibitory FcγR (e.g. FcγRIIb). Exemplary amino acid substitutions which altered FcR or complement binding activity are disclosed in International PCT Publication No. WO05/063815 which is incorporated by reference herein.

In some embodiments, the immunomodulatory fusion protein comprises an amino acid substitution which alters the glycosylation of the fusion protein. For example, in some embodiments, the Fc domain comprises a mutation leading to reduced glycosylation (e.g., N- or O-linked glycosylation) or comprises an altered glycoform of the wild-type Fc domain (e.g., a low fucose or fucose-free glycan). In certain embodiments, the immunomodulatory fusion protein has an amino acid substitution near or within a glycosylation motif, for example, an N-linked glycosylation motif that contains the amino acid sequence NXT or NXS. Exemplary amino acid substitutions which reduce or alter glycosylation are disclosed in WO05/018572 and US2007/0111281, the contents of which are incorporated by reference herein. In certain embodiments, the immunomodulatory fusion protein comprises at least one Fc domain having engineered cysteine residue or analog thereof which is located at the solvent-exposed surface. In certain embodiments, the immunomodulatory fusion protein comprise an Fc domain comprising at least one engineered free cysteine residue or analog thereof that is substantially free of disulfide bonding with a second cysteine residue. Any of the above engineered cysteine residues or analogs thereof may subsequently be conjugated to a functional domain using art-recognized techniques (e.g., conjugated with a thiol-reactive heterobifunctional linker).

In certain embodiments, the immunomodulatory fusion protein comprises a genetically fused Fc domain having two or more of its constituent Fc domains independently selected from the Fc domains described herein. In certain embodiments, the Fc domains are the same. In certain embodiments, at least two of the Fc domains are different. For example, the Fc domains comprise the same number of amino acid residues or they may differ in length by one or more amino acid residues (e.g., by about 5 amino acid residues (e.g., 1, 2, 3, 4, or 5 amino acid residues), about 10 residues, about 15 residues, about 20 residues, about 30 residues, about 40 residues, or about 50 residues). In certain embodiments, the Fc domains differ in sequence at one or more amino acid positions. For example, at least two of the Fc domains may differ at about 5 amino acid positions (e.g., 1, 2, 3, 4, or 5 amino acid positions), about 10 positions, about 15 positions, about 20 positions, about 30 positions, about 40 positions, or about 50 positions).

C. Additional Linkers

In some embodiments, the linker suitable for use in the immunomodulatory fusion protein described herein is a polyethylene glycol (PEG) domain. PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, and can be represented by the formula: $X\text{-}0(CH_2CH_20)_{n\text{-}1}CH_2CH_2OH$, where n is 20 to 2300 and X is H or a terminal modification, e.g., a $C_{1\text{-}4}$ alkyl. In certain embodiments, the PEG suitable for use in the methods disclosed herein terminates on one end with hydroxy or methoxy, i.e., X is H or $CH_3$ ("methoxy PEG"). PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and USS, 932,462, both of which are hereby incorporated by reference. One form of PEGs includes two PEG side-chains (PEG2) linked via the primary amino groups of a lysine (Monfardini et al., Bioconjugate Chem 1995; 6:62-9).

In certain embodiments, PEG is conjugated to a cysteine moiety at the N- or C-terminus of the domains of the immunomodulatory fusion protein (e.g., immunomodulatory domain and collagen-binding domain). A PEG moiety may also be attached by other chemistry, including by conjugation to amines. PEG conjugation to peptides or proteins generally involves the activation of PEG and coupling of the activated PEG-intermediates directly to target proteins/peptides or to a linker, which is subsequently activated and coupled to target proteins/peptides (see Abuchowski et al., JBC 1977; 252:3571 and JBC 1977; 252: 3582, and Harris et. al., in: Poly(ethylene glycol) Chemistry: Biotechnical and Biomedical Applications; (J. M. Harris ed.) Plenum Press: New York, 1992; Chap. 21 and 22). A variety of molecular mass forms of PEG can be selected, e.g., from about 1,000 Daltons (Da) to 100,000 Da (n is 20 to 2300). The number of repeating units "n" in the PEG is approximated for the molecular mass described in Daltons.

One skilled in the art can select a suitable molecular mass for PEG, e.g., based on at least the molecular mass of the immunomodulatory fusion protein without PEG.

In certain embodiments, PEG molecules may be activated to react with amino groups on the domains such as with lysines (Bencham C. O. et al., Anal. Biochem., 131, 25 (1983); Veronese, F. M. et al., Appl. Biochem., 11, 141 (1985); Zalipsky, S. et al., Polymeric Drugs and Drug Delivery Systems, adrs 9-110 ACS Symposium Series 469 (1999); Zalipsky, S. et al., Europ. Polym. J., 19, 1177-1183 (1983); Delgado, C. et al., Biotechnology and Applied Biochemistry, 12, 119-128 (1990)).

In certain embodiments, carbonate esters of PEG are used to conjugate PEG. N,N'-disuccinimidylcarbonate (DSC) may be used in the reaction with PEG to form active mixed PEG-succinimidyl carbonate that may be subsequently reacted with a nucleophilic group of a linker or an amino group of IL-2 (see U.S. Pat. Nos. 5,281,698 and 5,932,462). In a similar type of reaction, 1,1'-(dibenzotriazolyl)carbonate and di-(2-pyridyl)carbonate may be reacted with PEG to form PEG-benzotriazolyl and PEG-pyridyl mixed carbonate (U.S. Pat. No. 5,382,657), respectively. Pegylation can be performed according to the methods of the state of the art, for example by reaction of IL-2 with electrophilically active PEGs (Shearwater Corp., USA, www.shearwatercorp.com). Preferred PEG reagents suitable for use in the methods disclosed herein are, e.g., N-hydroxysuccinimidyl propionates (PEG-SPA), butanoates (PEG-SBA), PEG-succinimidyl propionate or branched N-hydroxysuccinimides such as mPEG2-NHS (Monfardini, C, et al., Bioconjugate Chem. 6 (1995) 62-69).

In some embodiments, the linker suitable for use in the immunomodulatory fusion protein described herein is transferrin, as disclosed in U.S. Pat. Nos. 7,176,278 and 8,158, 579, which are herein incorporated by reference in their entirety.

In some embodiments, the linker suitable for use in the immunomodulatory fusion protein described herein is a serum immunoglobulin binding protein such as those disclosed in US2007/0178082, which is herein incorporated by reference in its entirety.

In some embodiments, the linker suitable for use in the immunomodulatory fusion protein described herein is a globulin such as thyroxine-binding globulin, a2 macroglobulin, or haptoglobulin.

In some embodiments, the linker suitable for use in the immunomodulatory fusion protein described herein is a fibronectin (Fn)-based scaffold domain protein, such as those disclosed in US2012/0094909, which is herein incorporated by reference in its entirety. Methods of making fibronectin-based scaffold domain proteins are also disclosed in US2012/0094909. A non-limiting example of an Fn3-based extended-PK group is Fn3(HSA).

D. Other Linkers

In some embodiments, the immunomodulatory domain is operably linked to a collagen-binding domain via a linker, e.g., a gly-ser linker. In some embodiments, the immunomodulatory domain is operably linked to a collagen-binding domain via a linker (e.g., serum albumin), wherein the linker is linked to the collagen-binding domain and immunomodulatory domain via additional linkers (e.g. gly-ser linker). Linkers suitable for fusing the collagen-binding domain and immunomodulatory domain, or for fusing the collagen-binding domain, the immunomodulatory domain, and the linker (e.g., serum albumin) are well known in the art, and are disclosed in, e.g., US2010/0210511 US2010/0179094, and US2012/0094909, which are herein incorporated by reference in its entirety. Exemplary linkers include gly-ser polypeptide linkers, glycine-proline polypeptide linkers, and proline-alanine polypeptide linkers. In certain embodiments, the linker is a gly-ser polypeptide linker, i.e., a peptide that consists of glycine and serine residues.

Exemplary gly-ser polypeptide linkers comprise the amino acid sequence Ser(Gly$_4$Ser)n. In certain embodiments, n=1. In certain embodiments, n=2. In certain embodiments, n=3, i.e., Ser(Gly$_4$Ser)3. In certain embodiments, n=4, i.e., Ser(Gly$_4$Ser)4. In certain embodiments, n=5. In certain embodiments, n=6. In certain embodiments, n=7. In certain embodiments, n=8. In certain embodiments, n=9. In certain embodiments, n=10. Another exemplary gly-ser polypeptide linker comprises the amino acid sequence Ser(Gly$_4$Ser)n. In certain embodiments, n=1. In certain embodiments, n=2. In certain embodiments, n=3. In certain embodiments, n=4. In certain embodiments, n=5. In certain embodiments, n=6. Another exemplary gly-ser polypeptide linker comprises (Gly$_4$Ser)n. In certain embodiments, n=1. In certain embodiments, n=2. In certain embodiments, n=3. In certain embodiments, n=4. In certain embodiments, n=5. In certain embodiments, n=6. Another exemplary gly-ser polypeptide linker comprises (Gly$_3$Ser)n. In certain embodiments, n=1. In certain embodiments, n=2. In certain embodiments, n=3. In certain embodiments, n=4. In certain embodiments, n=5. In certain embodiments n=6.

Other linkers that are suitable for use in the immunomodulatory fusion proteins are known in the art, for example, the serine-rich linkers disclosed in U.S. Pat. No. 5,525,491, the helix forming peptide linkers (e.g., A(EAAAK)nA (n=2-5)) disclosed in Arai et al., *Protein Eng* 2001; 14:529-32, and the stable linkers disclosed in Chen et al., *Mol Pharm* 2011; 8:457-65, i.e., the dipeptide linker LE, a thrombin-sensitive disulfide cyclopeptide linker, and the alpha-helix forming linker LEA(EAAAK)$_4$ALEA(EAAAK)$_4$ALE (SEQ ID NO: 119).

Other exemplary linkers include GS linkers (i.e., (GS)n), GGSG linkers (i.e., (GGSG)n), GSAT linkers, SEG linkers, and GGS linkers (i.e., (GGSGGS)n), wherein n is a positive integer (e.g., 1, 2, 3, 4, or 5). Other suitable linkers for use in the hybrid nuclease-albumin molecules can be found using publicly available databases, such as the Linker Database (ibi.vu.nl/programs/linkerdbwww). The Linker Database is a database of inter-domain linkers in multi-functional enzymes which serve as potential linkers in novel fusion proteins (see, e.g., George et al., *Protein Engineering* 2002; 15:871-9).

It will be understood that variant forms of these exemplary polypeptide linkers can be created by introducing one or more nucleotide substitutions, additions or deletions into the nucleotide sequence encoding a polypeptide linker such that one or more amino acid substitutions, additions or deletions are introduced into the polypeptide linker. Mutations may be introduced by standard techniques, such as site-directed mutagenesis and PCR-mediated mutagenesis.

Polypeptide linkers of the disclosure are at least one amino acid in length and can be of varying lengths. In one embodiment, a polypeptide linker of the disclosure is from about 1 to about 50 amino acids in length. As used in this context, the term "about" indicates+/−two amino acid residues. Since linker length must be a positive integer, the length of from about 1 to about 50 amino acids in length, means a length of from 1 to 48-52 amino acids in length. In another embodiment, a polypeptide linker of the disclosure is from about 10-20 amino acids in length. In another embodiment, a polypeptide linker of the disclosure is from about 15 to about 50 amino acids in length.

In another embodiment, a polypeptide linker of the disclosure is from about 20 to about 45 amino acids in length. In another embodiment, a polypeptide linker of the disclosure is from about 15 to about 25 amino acids in length. In another embodiment, a polypeptide linker of the disclosure is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or 61 or more amino acids in length.

Polypeptide linkers can be introduced into polypeptide sequences using techniques known in the art. Modifications can be confirmed by DNA sequence analysis. Plasmid DNA can be used to transform host cells for stable production of the polypeptides produced.

IV. Exemplary Immunomodulatory Fusion Proteins

The disclosure provides immunomodulatory fusion proteins comprising an immunomodulatory domain and a collagen-binding domain, optionally a linker, wherein the immunomodulatory domain is operably linked with or without the linker to the collagen-binding domain. The immunomodulatory fusion proteins of the disclosure are modular and can be configured to incorporate various individual domains.

A. IL-2 Fusion Proteins

In some embodiments, the immunomodulatory fusion protein comprises IL-2 and lumican, wherein IL-2 is operably linked to lumican. In some embodiments, IL-2 is operably linked to lumican with albumin. In some embodiments, IL-2 is operably linked to the N-terminus of lumican. In some embodiments, IL-2 is operably linked to the C-terminus of lumican.

In some embodiments, the immunomodulatory fusion protein comprises the human IL-2 sequence set forth in SEQ ID NO: 1 operably linked to the human lumican sequence set forth in SEQ ID NO: 107. In some embodiments, the immunomodulatory fusion protein comprises the human IL-2 sequence set forth in SEQ ID NO: 1 operably linked to the human lumican sequence set forth in SEQ ID NO: 107 with a human serum albumin sequence selected from SEQ ID NO: 42 and SEQ ID NO: 43.

In some embodiments, the immunomodulatory fusion protein comprises IL-2 and LAIR-1, wherein IL-2 is operably linked to LAIR-1. In some embodiments, IL-2 is operably linked to LAIR-1 with albumin. In some embodiments, IL-2 is operably linked to the N-terminus of LAIR-1. In some embodiments, IL-2 is operably linked to the C-terminus of LAIR-1.

In some embodiments, the immunomodulatory fusion protein comprises the human IL-2 sequence set forth in SEQ ID NO: 1 operably linked to the human LAIR-1 sequence set forth in SEQ ID NO: 98. In some embodiments, the immunomodulatory fusion protein comprises the human IL-2 sequence set forth in SEQ ID NO: 1 operably linked to the human LAIR-1 sequence set forth in SEQ ID NO: 98 with a human serum albumin sequence selected from SEQ ID NO: 42 and SEQ ID NO: 43.

B. IL-12 Fusion Proteins

In some embodiments, the immunomodulatory fusion protein comprises IL-12 and lumican, wherein IL-12 is operably linked to lumican. In some embodiments, IL-12 is operably linked to lumican with albumin. In some embodiments, IL-12 is operably linked to the N-terminus of lumican. In some embodiments, IL-12 is operably linked to the C-terminus of lumican.

In some embodiments, the immunomodulatory fusion protein comprises the human IL-12 sequences set forth in SEQ ID NO: 2 and SEQ ID NO: 3 operably linked to the human lumican sequence set forth in SEQ ID NO: 107. In some embodiments, the immunomodulatory fusion protein comprises the human IL-12 sequences set forth in SEQ ID NO: 2 and SEQ ID NO: 3 operably linked to the human lumican sequence set forth in SEQ ID NO: 107 with a human serum albumin sequence selected from SEQ ID NO: 42 and SEQ ID NO: 43.

In some embodiments, the immunomodulatory fusion protein comprises IL-12 and LAIR-1, wherein IL-12 is operably linked to LAIR-1. In some embodiments, IL-12 is operably linked to LAIR-1 with albumin. In some embodiments, IL-12 is operably linked to the N-terminus of LAIR-1. In some embodiments, IL-12 is operably linked to the C-terminus of LAIR-1.

In some embodiments, the immunomodulatory fusion protein comprises the human IL-12 sequences set forth in SEQ ID NO: 2 and SEQ ID NO: 3, operably linked to the human LAIR-1 sequence set forth in SEQ ID NO: 98. In some embodiments, the immunomodulatory fusion protein comprises the human IL-12 sequences set forth in SEQ ID NO: 2 and SEQ ID NO: 3 operably linked to the human LAIR-1 sequence set forth in SEQ ID NO: 98 with a human serum albumin sequence selected from SEQ ID NO: 42 and SEQ ID NO: 43.

C. CCL-3 Fusion Proteins

In some embodiments, the immunomodulatory fusion protein comprises CCL-3 and lumican, wherein CCL-3 is operably linked to lumican. In some embodiments, CCL-3 is operably linked to lumican with albumin. In some embodiments, CCL-3 is operably linked to the N-terminus of lumican. In some embodiments, CCL-3 is operably linked to the C-terminus of lumican.

In some embodiments, the immunomodulatory fusion protein comprises the human CCL-3 sequence set forth in SEQ ID NO: 41 operably linked to the human lumican sequence set forth in SEQ ID NO: 107. In some embodiments, the immunomodulatory fusion protein comprises the human CCL-3 sequence set forth in SEQ ID NO: 41 operably linked to the human lumican sequence set forth in SEQ ID NO: 107 with a human serum albumin sequence selected from SEQ ID NO: 42 and SEQ ID NO: 43.

In some embodiments, the immunomodulatory fusion protein comprises CCL-3 and LAIR-1, wherein CCL-3 is operably linked to LAIR-1. In some embodiments, CCL-3 is operably linked to LAIR-1 with albumin. In some embodiments, CCL-3 is operably linked to the N-terminus of LAIR-1. In some embodiments, CCL-3 is operably linked to the C-terminus of LAIR-1.

In some embodiments, the immunomodulatory fusion protein comprises the human CCL-3 sequence set forth in SEQ ID NO: 41 operably linked to the human LAIR-1 sequence set forth in SEQ ID NO: 98. In some embodiments, the immunomodulatory fusion protein comprises the human CCL-3 sequence set forth in SEQ ID NO: 41 operably linked to the human LAIR-1 sequence set forth in SEQ ID NO: 98 with a human serum albumin sequence selected from SEQ ID NO: 42 and SEQ ID NO: 43.

D. CCL-4 Fusion Proteins

In some embodiments, the immunomodulatory fusion protein comprises CCL-4 and lumican, wherein CCL-4 is operably linked to lumican. In some embodiments, CCL-4 is operably linked to lumican with albumin. In some embodiments, CCL-4 is operably linked to the N-terminus of lumican. In some embodiments, CCL-4 is operably linked to the C-terminus of lumican.

In some embodiments, the immunomodulatory fusion protein comprises the human CCL-4 sequence set forth in SEQ ID NO: 33 operably linked to the human lumican sequence set forth in SEQ ID NO: 107. In some embodiments, the immunomodulatory fusion protein comprises the human CCL-4 sequence set forth in SEQ ID NO: 33 operably linked to the human lumican sequence set forth in SEQ ID NO: 107 with a human serum albumin sequence selected from SEQ ID NO: 42 and SEQ ID NO: 43.

In some embodiments, the immunomodulatory fusion protein comprises CCL-4 and LAIR-1, wherein CCL-4 is operably linked to LAIR-1. In some embodiments, CCL-4 is operably linked to LAIR-1 with albumin. In some embodiments, CCL-4 is operably linked to the N-terminus of LAIR-1. In some embodiments, CCL-4 is operably linked to the C-terminus of LAIR-1.

In some embodiments, the immunomodulatory fusion protein comprises the human CCL-4 sequence set forth in SEQ ID NO: 33 operably linked to the human LAIR-1 sequence set forth in SEQ ID NO: 98. In some embodiments, the immunomodulatory fusion protein comprises the human CCL-4 sequence set forth in SEQ ID NO: 33 operably linked to the human LAIR-1 sequence set forth in SEQ ID NO: 98 with a human serum albumin sequence selected from SEQ ID NO: 42 and SEQ ID NO: 43.

E. CCL-5 Fusion Proteins

In some embodiments, the immunomodulatory fusion protein comprises CCL-5 and lumican, wherein CCL-5 is operably linked to lumican. In some embodiments, CCL-5 is operably linked to lumican with albumin. In some embodiments, CCL-5 is operably linked to the N-terminus of lumican. In some embodiments, CCL-5 is operably linked to the C-terminus of lumican.

In some embodiments, the immunomodulatory fusion protein comprises the human CCL-5 sequence set forth in SEQ ID NO: 39 operably linked to the human lumican sequence set forth in SEQ ID NO: 107. In some embodiments, the immunomodulatory fusion protein comprises the human CCL-5 sequence set forth in SEQ ID NO: 39 operably linked to the human lumican sequence set forth in SEQ ID NO: 107 with a human serum albumin sequence selected from SEQ ID NO: 42 and SEQ ID NO: 43.

In some embodiments, the immunomodulatory fusion protein comprises CCL-5 and LAIR-1, wherein CCL-5 is operably linked to LAIR-1. In some embodiments, CCL-5 is operably linked to LAIR-1 with albumin. In some embodiments, CCL-5 is operably linked to the N-terminus of LAIR-1. In some embodiments, CCL-5 is operably linked to the C-terminus of LAIR-1.

In some embodiments, the immunomodulatory fusion protein comprises the human CCL-5 sequence set forth in SEQ ID NO: 39 operably linked to the human LAIR-1 sequence set forth in SEQ ID NO: 98. In some embodiments, the immunomodulatory fusion protein comprises the human CCL-5 sequence set forth in SEQ ID NO: 39 operably linked to the human LAIR-1 sequence set forth in SEQ ID NO: 98 with a human serum albumin sequence selected from SEQ ID NO: 42 and SEQ ID NO: 43.

F. Eotaxin Fusion Proteins

In some embodiments, the immunomodulatory fusion protein comprises Eotaxin and lumican, wherein Eotaxin is operably linked to lumican. In some embodiments, Eotaxin is operably linked to lumican with albumin. In some embodiments, Eotaxin is operably linked to the N-terminus of lumican. In some embodiments, Eotaxin is operably linked to the C-terminus of lumican.

In some embodiments, the immunomodulatory fusion protein comprises the human Eotaxin sequence set forth in SEQ ID NO: 38 operably linked to the human lumican sequence set forth in SEQ ID NO: 107. In some embodiments, the immunomodulatory fusion protein comprises the human Eotaxin sequence set forth in SEQ ID NO: 38 operably linked to the human lumican sequence set forth in SEQ ID NO: 107 with a human serum albumin sequence selected from SEQ ID NO: 42 and SEQ ID NO: 43.

In some embodiments, the immunomodulatory fusion protein comprises Eotaxin and LAIR-1, wherein Eotaxin is operably linked to LAIR-1. In some embodiments, Eotaxin is operably linked to LAIR-1 with albumin. In some embodiments, Eotaxin is operably linked to the N-terminus of LAIR-1. In some embodiments, Eotaxin is operably linked to the C-terminus of LAIR-1.

In some embodiments, the immunomodulatory fusion protein comprises the human Eotaxin sequence set forth in SEQ ID NO: 38 operably linked to the human LAIR-1 sequence set forth in SEQ ID NO: 98. In some embodiments, the immunomodulatory fusion protein comprises the human Eotaxin sequence set forth in SEQ ID NO: 38 operably linked to the human LAIR-1 sequence set forth in SEQ ID NO: 98 with a human serum albumin sequence selected from SEQ ID NO: 42 and SEQ ID NO: 43.

G. Antibody Fusion Proteins

In some embodiments, the immunomodulatory fusion protein comprises an anti-CD3 antibody and lumican, wherein the anti-CD3 antibody is operably linked to lumican. In some embodiments, the anti-CD3 antibody is operably linked to the N-terminus of lumican. In some embodiments, anti-CD3 antibody is operably linked to the C-terminus of lumican.

In some embodiments, the immunomodulatory fusion protein comprises an anti-CD3 antibody and LAIR-1, wherein the anti-CD3 antibody is operably linked to LAIR-1. In some embodiments, the anti-CD3 antibody is operably linked to the N-terminus of LAIR-1. In some embodiments, the anti-CD3 antibody is operably linked to the C-terminus of LAIR-1.

In some embodiments, the immunomodulatory fusion protein comprises an anti-4-1-BB antibody and lumican, wherein the anti-4-1-BB antibody is operably linked to lumican. In some embodiments, the anti-4-1-BB antibody is operably linked to the N-terminus of lumican. In some embodiments, anti-4-1-BB antibody is operably linked to the C-terminus of lumican.

In some embodiments, the immunomodulatory fusion protein comprises an anti-4-1-BB antibody and LAIR-1, wherein the anti-4-1-BB antibody is operably linked to LAIR-1. In some embodiments, the anti-4-1-BB antibody is operably linked to the N-terminus of LAIR-1. In some embodiments, the anti-4-1-BB antibody is operably linked to the C-terminus of LAIR-1.

In some embodiments, the immunomodulatory fusion protein comprises an anti-CD40 antibody and lumican, wherein the anti-CD40 antibody is operably linked to lumican. In some embodiments, the anti-CD40 antibody is operably linked to the N-terminus of lumican. In some embodiments, anti-CD40 antibody is operably linked to the C-terminus of lumican.

In some embodiments, the immunomodulatory fusion protein comprises an anti-CD40 antibody and LAIR-1, wherein the anti-CD40 antibody is operably linked to LAIR-1. In some embodiments, the anti-CD40 antibody is operably linked to the N-terminus of LAIR-1. In some embodiments, the anti-CD40 antibody is operably linked to the C-terminus of LAIR-1.

In some embodiments, the immunomodulatory fusion protein comprises an anti-OX40 antibody and lumican, wherein the anti-OX40 antibody is operably linked to lumican. In some embodiments, the anti-OX40 antibody is operably linked to the N-terminus of lumican. In some embodiments, anti-OX40 antibody is operably linked to the C-terminus of lumican.

In some embodiments, the immunomodulatory fusion protein comprises an anti-OX40 antibody and LAIR-1, wherein the anti-OX40 antibody is operably linked to LAIR-1. In some embodiments, the anti-OX40 antibody is operably linked to the N-terminus of LAIR-1. In some embodiments, the anti-OX40 antibody is operably linked to the C-terminus of LAIR-1.

V. Methods for Making Immunomodulatory Fusion Proteins

In some aspects, the polypeptides described herein (e.g., collagen-binding domains, cytokines, antibodies) are made in transformed host cells using recombinant DNA techniques. To do so, a recombinant DNA molecule coding for the peptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidate method. Also, a combination of these techniques could be used.

The methods of making polypeptides also include a vector capable of expressing the peptides in an appropriate host. The vector comprises the DNA molecule that codes for the peptides operatively linked to appropriate expression control sequences. Methods of affecting this operative linking, either before or after the DNA molecule is inserted into the vector, are well known. Expression control sequences include promoters, activators, enhancers, operators, ribosomal nuclease domains, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be suitable for use in the methods disclosed herein. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial hosts include bacteria (such as *E. coli* sp.), yeast (such as *Saccharomyces* sp.) and other fungi, insects, plants, mammalian (including human) cells in culture, or other hosts known in the art.

Next, the transformed host is cultured and purified. Host cells may be cultured under conventional fermentation conditions so that the desired compounds are expressed. Such fermentation conditions are well known in the art. Finally, the peptides are purified from culture by methods well known in the art.

The compounds may also be made by synthetic methods. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527. Solid phase synthesis is the preferred technique of making individual peptides since it is the most cost-effective method of making small peptides. Compounds that contain derivatized peptides or which contain non-peptide groups may be synthesized by well-known organic chemistry techniques.

Other methods are of molecule expression/synthesis are generally known in the art to one of ordinary skill.

The nucleic acid molecules described above can be contained within a vector that is capable of directing their expression in, for example, a cell that has been transduced with the vector. Accordingly, in addition to polypeptide mutants, expression vectors containing a nucleic acid molecule encoding a mutant and cells transfected with these vectors are among the certain embodiments.

Vectors suitable for use include T7-based vectors for use in bacteria (see, for example, Rosenberg et al., Gene 56: 125, 1987), the pMSXND expression vector for use in mammalian cells (Lee and Nathans, J. Biol. Chem. 263:3521, 1988), and baculovirus-derived vectors (for example the expression vector pBacPAKS from Clontech, Palo Alto, Calif.) for use in insect cells. The nucleic acid inserts, which encode the polypeptide of interest in such vectors, can be operably linked to a promoter, which is selected based on, for example, the cell type in which expression is sought. For example, a T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance (neo$^r$) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that are suitable for use include, for example, retroviral, adenoviral, and adeno-associated vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.).

Prokaryotic or eukaryotic cells that contain and express a nucleic acid molecule that encodes a polypeptide mutant are also suitable for use. A cell is a transfected cell, i.e., a cell into which a nucleic acid molecule, for example a nucleic acid molecule encoding a mutant polypeptide, has been introduced by means of recombinant DNA techniques. The progeny of such a cell are also considered suitable for use in the methods disclosed herein.

The precise components of the expression system are not critical. For example, a polypeptide mutant can be produced in a prokaryotic host, such as the bacterium E. coli, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

The expressed polypeptides can be purified from the expression system using routine biochemical procedures, and can be used, e.g., as therapeutic agents, as described herein.

Pharmaceutical Compositions and Modes of Administration

In certain embodiments, the disclosure provides for a pharmaceutical composition comprising an immunomodulatory fusion protein with a pharmaceutically acceptable diluent, carrier, solubilizer, emulsifier, preservative and/or adjuvant.

In certain embodiments, acceptable formulation materials preferably are nontoxic to recipients at the dosages and concentrations employed. In certain embodiments, the formulation material(s) are for s.c. and/or I.V. administration. In certain embodiments, the formulation material(s) are for local administration, e.g., intratumoral administration. In certain embodiments, the pharmaceutical composition can contain formulation materials for modifying, maintaining or preserving, for example, the pH, osmolality, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In certain embodiments, the formulation comprises PBS; 20 mM NaOAC, pH 5.2, 50 mM NaCl; and/or 10 mM NAOAC, pH 5.2, 9% Sucrose. In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and rate of in vivo clearance of the immunomodulatory fusion protein.

In some embodiments, the formulations comprising an immunomodulatory fusion protein described herein are 4° C. to 37° C. when administered to a subject.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In certain embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising an immunomodulatory fusion protein is prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising an immunomodulatory fusion protein is formulated as a lyophilizate using appropriate excipients such as sucrose.

In certain embodiments, the pharmaceutical composition is selected for parenteral delivery. In certain embodiments, the compositions are selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition is in the form of a pyrogen-free, parenterally acceptable aqueous solution comprising an immunomodulatory fusion protein, in a pharmaceutically acceptable vehicle. In certain embodiments, a vehicle for parenteral injection is sterile distilled water in which the immunomodulatory fusion protein is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition is formulated for inhalation. In certain embodiments, an immunomodulatory fusion protein is formulated as a dry powder for inhalation. In certain embodiments, an inhalation solution comprising an immunomodulatory fusion protein is formulated with a propellant for aerosol delivery. In certain embodiments, solutions can be nebulized. Pulmonary administration is further described in PCT application No. PCT/US94/001875, which describes pulmonary delivery of chemically modified proteins.

In certain embodiments, it is contemplated that formulations are administered orally. In certain embodiments, an immunomodulatory fusion protein administered in this fashion is formulated with or without those carriers customarily used in the compounding of solid dosage forms such as tablets and capsules. In certain embodiments, a capsule is designed to release the active portion of the formulation at the point in the gastrointestinal tract when bioavailability is maximized and pre-systemic degradation is minimized. In certain embodiments, at least one additional agent is included to facilitate absorption of the immunomodulatory fusion protein. In certain embodiments, diluents, flavorings, low melting point waxes, vegetable oils, lubricants, suspending agents, tablet disintegrating agents, and binders can also be employed.

In certain embodiments, a pharmaceutical composition comprises an effective quantity of immunomodulatory fusion protein in a mixture with non-toxic excipients which are suitable for the manufacture of tablets. In certain embodiments, by dissolving the tablets in sterile water, or another appropriate vehicle, solutions are prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving an immunomodulatory fusion protein, in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15: 167-277 (1981) and Langer, Chem. Tech., 12:98-105 (1982)), ethylene vinyl acetate (Langer et al., supra) or poly-D(−)-3-hydroxybutyric acid (EP 133,988). In certain embodiments, sustained release compositions include liposomes, which can be prepared by any of several methods known in the art. See, e.g., Eppstein et al, Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this is accomplished by filtration through sterile filtration membranes. In certain embodiments, where the composition is lyophilized, sterilization using this method is conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising immunomodulatory fusion protein to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which the immunomodulatory fusion protein is being used, the route of administration, and the size (body weight, body surface or organ size) and/or condition (the age and general health) of the patient. In certain embodiments, the clinician can titer the dosage and modify the route of administration to obtain the optimal therapeutic effect.

In certain embodiments, the frequency of dosing will take into account the pharmacokinetic parameters of the immunomodulatory fusion protein in the formulation used. In certain embodiments, a clinician will administer the composition until a dosage is reached that achieves the desired effect. In certain embodiments, the composition can therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intraocular, intraarterial, intraportal, or intralesional routes; by sustained release systems or by implantation devices. In certain embodiments, the compositions can be administered by bolus injection or continuously by infusion, or by implantation device. In certain embodiments, individual elements of the combination therapy may be administered by different routes.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration. In certain embodiments, it can be desirable to use a pharmaceutical composition comprising an immunomodulatory fusion protein in an ex vivo manner. In such instances, cells, tissues and/or organs that have been removed from the patient are exposed to a pharmaceutical composition comprising the immunomodulatory fusion protein after which the cells, tissues and/or organs are subsequently implanted back into the patient.

In certain embodiments, an immunomodulatory fusion protein is delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semipermeable polymeric enclosures or membranes that allow the release of the protein product(s) but prevent the destruction of the cells by the patient's immune system or by other detrimental factors from the surrounding tissues.

Methods of Treating

The immunomodulatory fusion proteins and/or nucleic acids expressing them, described herein, are useful for treating a disorder associated with abnormal apoptosis or a differentiative process (e.g., cellular proliferative disorders (e.g., hyperproliferaetive disorders) or cellular differentiative disorders, such as cancer). Non-limiting examples of cancers that are amenable to treatment with the methods of the present disclosure are described below.

Examples of cellular proliferative and/or differentiative disorders include cancer (e.g., carcinoma, sarcoma, metastatic disorders or hematopoietic neoplastic disorders, e.g., leukemias). A metastatic tumor can arise from a multitude of primary tumor types, including but not limited to those of prostate, colon, lung, breast and liver. Accordingly, the compositions used herein, comprising, e.g., immunomodulatory fusion protein, can be administered to a patient who has cancer.

As used herein, the terms "cancer" (or "cancerous"), "hyperproliferative," and "neoplastic" refer to cells having the capacity for autonomous growth (i.e., an abnormal state or condition characterized by rapidly proliferating cell growth). Hyperproliferative and neoplastic disease states may be categorized as pathologic (i.e., characterizing or constituting a disease state), or they may be categorized as non-pathologic (i.e., as a deviation from normal but not associated with a disease state). The terms are meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasm" are used to refer to malignancies of the various organ systems, including those affecting the lung, breast, thyroid, lymph glands and lymphoid tissue, gastrointestinal organs, and the genitourinary tract, as well as to adenocarcinomas which are generally considered to include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The immunomodulatory fusion proteins can be used to treat patients who have, who are suspected of having, or who may be at high risk for developing any type of cancer, including renal carcinoma or melanoma, or any viral disease. Exemplary carcinomas include those forming from tissue of the cervix, lung, prostate, breast, head and neck, colon and ovary. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias (e.g., erythroblastic leukemia and acute megakaryoblastic leukemia). Additional exemplary myeloid disorders include, but are not limited to, acute promyeloid leukemia (APML), acute myelogenous leukemia (AML) and chronic myelogenous leukemia (CIVIL) (reviewed in Vaickus, L. (1991) Crit. Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macro globulinemia (WM). Additional forms of malignant lymphomas include, but are not limited to non-Hodgkin lymphoma and variants thereof, peripheral T cell lymphomas, adult T cell leukemia/lymphoma (ATL), cutaneous T cell lymphoma (CTCL), large granular lymphocytic leukemia (LGF), Hodgkin's disease and Reed-Sternberg disease.

It will be appreciated by those skilled in the art that amounts of an immunomodulatory fusion protein sufficient to reduce tumor growth and size, or a therapeutically effective amount, will vary not only on the particular compounds or compositions selected, but also with the route of administration, the nature of the condition being treated, and the age and condition of the patient, and will ultimately be at the discretion of the patient's physician or pharmacist. The length of time during which the compounds used in the instant method will be given varies on an individual basis.

It will be appreciated by those skilled in the art that the B16 melanoma model used herein is a generalized model for solid tumors. That is, efficacy of treatments in this model is also predictive of efficacy of the treatments in other non-melanoma solid tumors. For example, as described in Baird et al. (J Immunology 2013; 190:469-78; Epub Dec. 7, 2012), efficacy of cps, a parasite strain that induces an adaptive immune response, in mediating anti-tumor immunity against B16F10 tumors was found to be generalizable to other solid tumors, including models of lung carcinoma and ovarian cancer. In another example, results from a line of research into VEGF targeting lymphocytes also shows that results in B16F10 tumors were generalizable to the other tumor types studied (Chinnasamy et al., *JCI* 2010; 120:3953-68; Chinnasamy et al., *Clin Cancer Res* 2012; 18:1672-83). In yet another example, immunotherapy involving LAG-3 and PD-fled to reduced tumor burden, with generalizable results in a fibrosarcoma and colon adenocarcinoma cell lines (Woo et al., *Cancer Res* 2012; 72:917-27).

In certain embodiments, the immunomodulatory fusion proteins disclosed herein are used to treat cancer. In certain embodiments, the immunomodulatory fusion proteins disclosed herein are used to treat melanoma, leukemia, lung cancer, breast cancer, prostate cancer, ovarian cancer, colon cancer, and brain cancer.

In certain embodiments, the immunomodulatory fusion proteins disclosed herein inhibit the growth and/or proliferation of tumor cells. In certain embodiments, the immunomodulatory fusion proteins disclosed herein reduce tumor size. In certain embodiments, the immunomodulatory fusion proteins disclosed herein inhibit metastases of a primary tumor.

It will be appreciated by those skilled in the art that reference herein to treatment extends to prophylaxis as well as the treatment of the noted cancers and symptoms.

Combination Therapy

In some embodiments, the immunomodulatory fusion proteins are used in combination with other therapies. For example, in some embodiments the immunomodulatory fusion proteins are used in combination with another immunotherapy. Exemplary immunotherapies include, but are not limited to, chimeric antigen receptor (CAR) T cell therapy, tumor-associated antigen targeting antibodies, immune checkpoint inhibitors, and cancer vaccines.

I. Chimeric Antigen Receptor (CAR) Effector Cells

In some aspects, the disclosure provides immunomodulatory fusion proteins to be used or performed in conjunction with chimeric antigen receptor (CAR) effector cell therapy (e.g., CAR T cells).

Chimeric antigen receptors (CARs) are genetically-engineered, artificial transmembrane receptors, which confer an arbitrary specificity for a ligand onto an immune effector cell (e.g. a T cell, natural killer cell or other immune cell) and which results in activation of the effector cell upon recognition and binding to the ligand. Typically these receptors are used to impart the antigen specificity of a monoclonal antibody onto a T cell.

In some embodiments, CARs contain three domains: 1) an ectodomain typically comprising a signal peptide, a ligand or antigen recognition region (e.g. scFv), and a flexible spacer; 2) a transmembrane (TM) domain; 3) an endodomain (alternatively known as an "activation domain") typically comprising one or more intracellular signaling domains. The ectodomain of the CAR resides outside of the cell and is exposed to the extracellular space, whereby it is accessible for interaction with its cognate ligand. The TM domain allows the CAR to be anchored into the cell membrane of the effector cell. The third endodomain (also known as the "activation domain") aids in effector cell activation upon binding of the CAR to its specific ligand. In some embodiments, effector cell activation comprises induction of cytokine and chemokine production, as well as activation of the cytolytic activity of the cells. In some embodiments, the CARs redirect cytotoxicity toward tumor cells.

In some embodiments, CARs comprise a ligand- or antigen-specific recognition domain that binds to a specific target ligand or antigen (also referred to as a binding domain). In some embodiments, the binding domain is a single-chain antibody variable fragment (scFv), a tethered ligand or the extracellular domain of a co-receptor, fused to a transmembrane domain, which is linked, in turn, to a signaling domain. In some embodiments, the signaling domain is derived from CD3ζ or FcRγ. In some embodiments, the CAR comprises one or more co-stimulatory domains derived from a protein such as CD28, CD137 (also known as 4-1BB), CD134 (also known as OX40) and CD278 (also known as ICOS).

Engagement of the antigen binding domain of the CAR with its target antigen on the surface of a target cell results in clustering of the CAR and delivers an activation stimulus to the CAR-containing cell. In some embodiments, the main characteristic of CARs are their ability to redirect immune effector cell specificity, thereby triggering proliferation, cytokine production, phagocytosis or production of molecules that can mediate cell death of the target antigen expressing cell in a major histocompatibility (MHC) independent manner, exploiting the cell specific targeting abilities of monoclonal antibodies, soluble ligands or cell specific co-receptors. Although scFv-based CARs engineered to contain a signaling domain from CD3ζ or FcRγ have been shown to deliver a potent signal for T cell activation and effector function, they are not sufficient to elicit signals that promote T cell survival and expansion in the absence of a concomitant co-stimulatory signal. A new generation of CARs containing a binding domain, a hinge, a transmembrane and the signaling domain derived from CD3ζ or FcRγ together with one or more co-stimulatory signaling domains (e.g., intracellular co-stimulatory domains derived from CD28, CD137, CD134 and CD278) has been shown to more effectively direct antitumor activity as well as increased cytokine secretion, lytic activity, survival and proliferation in CAR expressing T cells in vitro, in animal models and cancer patients (Milone et al., Molecular Therapy, 2009; 17: 1453-1464; Zhong et al., Molecular Therapy, 2010; 18: 413-420; Carpenito et al., PNAS, 2009; 106:3360-3365).

In some embodiments, chimeric antigen receptor-expressing effector cells (e.g. CAR-T cells) are cells that are derived from a patient with a disease or condition and genetically modified in vitro to express at least one CAR with an arbitrary specificity to a ligand. The cells perform at least one effector function (e.g. induction of cytokines) that is stimulated or induced by the specific binding of the ligand to the CAR and that is useful for treatment of the same patient's disease or condition. The effector cells may be T cells (e.g. cytotoxic T cells or helper T cells). One skilled in the art would understand that other cell types (e.g. a natural killer cell or a stem cell) may express CARs and that a chimeric antigen receptor effector cell may comprise an effector cell other than a T cell. In some embodiments, the effector cell is a T cell (e.g. a cytotoxic T cell) that exerts its effector function (e.g. a cytotoxic T cell response) on a target cell when brought in contact or in proximity to the target or target cell (e.g. a cancer cell) (see e.g., Chang and Chen (2017) Trends Mol Med 23(5):430-450).

Prolonged exposure of T cells to their cognate antigen can result in exhaustion of effector functions, enabling the persistence of infected or transformed cells. Recently developed strategies to stimulate or rejuvenate host effector function using agents that induce an immune checkpoint blockade have resulted in success towards the treatment of several cancers. Emerging evidence suggests that T cell exhaustion may also represent a significant impediment in sustaining long-lived antitumor activity by chimeric antigen receptor-expressing T cells (CAR-T cells. In some embodiments, the differentiation status of the patient-harvested T cells prior to CAR transduction and the conditioning regimen a patient undergoes before reintroducing the CAR-T cells (e.g., addition or exclusion of alkylating agents, fludarabine, total-body irradiation) can profoundly affect the persistence and cytotoxic potential of CAR-T cells. In vitro culture conditions that stimulate (via anti-CD3/CD28 or stimulator cells) and expand (via cytokines, such as IL-2) T cell populations can also alter the differentiation status and effector function of CAR-T cells (Ghoneim et al., (2016) Trends in Molecular Medicine 22(12):1000-1011).

In some embodiments, in particular for the treatment of ALL and/or NHL, suitable CARs target CD19 or CD20. Non-limiting examples include CARs comprising a structure: (i) an anti-CD19 scFv, a CD8 H/TM domain, an 4-1BB CS domain and a CD3ζ TCR signaling domain; (ii) an anti-CD19 scFv, a CD28 hinge and transmembrane domain, a CD28 co-stimulatory domain and a CD3ζ TCR signaling domain; and (iii) an anti-CD20 scFv, an IgG hinge and transmembrane domain, a CD28/4-1BB co-stimulatory domain and a CD3ζ TCR signaling domain. In some embodiments, a CAR effector cell suitable for combination with the combinations and methods disclosed herein targets CD19 or CD20, including but not limited to Kymriah™ (tisagenlecleucel; Novartis; formerly CTL019) and Yescarta™ (axicabtagene ciloleucel; Kite Pharma).

A. Re-Targeted CAR T Cells

In some embodiments, the CAR-T therapy suitable for use in combination with the immunomodulatory fusion proteins is a re-targeted CAR-T cell. In some embodiments, effector cells (e.g., T cells) modified to express a CAR which binds to a universal immune receptor, a tag, a switch or an Fc region on an immunoglobulin are suitable for the methods described herein.

In some embodiments, effector cells (e.g., T cells) are modified to express a universal immune receptor or UnivIR. One type of UnivIR is a biotin-binding immune receptor (BBIR) (see e.g., US Patent Publication US20140234348 A1 incorporated herein by reference in its entirety). Other examples of methods and compositions relating to universal chimeric receptors and/or effector cells expressing universal chimeric receptors are described in International Patent Applications WO2016123122A1, WO2017143094A1, WO2013074916A1, US Patent Application US20160348073A1, all of which are incorporated herein by reference in their entirety.

In some embodiments, effector cells (e.g., T cells) are modified to express a universal, modular, anti-tag chimeric antigen receptor (UniCAR). This system allows for retargeting of UniCAR engrafted immune cells against multiple antigens (see e.g., US Patent Publication US20170240612 A1 incorporated herein by reference in its entirety; Cartellieri et al., (2016) Blood Cancer Journal 6, e458 incorporated herein by reference in its entirety).

In some embodiments, effector cells (e.g., T cells) are modified to express a switchable chimeric antigen receptor and chimeric antigen receptor effector cell (CAR-EC) switches. In this system, the CAR-EC switches have a first region that is bound by a chimeric antigen receptor on the CAR-EC and a second region that binds a cell surface molecule on target cell, thereby stimulating an immune response from the CAR-EC that is cytotoxic to the bound target cell. In some embodiments, the CAR-EC is a T cell, wherein the CAR-EC switch may act as an "on-switch" for CAR-EC activity. Activity may be "turned off" by reducing or ceasing administration of the switch. These CAR-EC switches may be used with CAR-ECs disclosed herein, as well as existing CAR T-cells, for the treatment of a disease or condition, such as cancer, wherein the target cell is a malignant cell. Such treatment may be referred to herein as switchable immunotherapy (US Patent Publication U.S. Pat. No. 9,624,276 B2 incorporated herein by reference in its entirety).

In some embodiments, effector cells (e.g., T cells) are modified to express a receptor that binds the Fc portion of human immunoglobulins (e.g., CD16V-BB-ζ)(Kudo et al., (2014) Cancer Res 74(1):93-103 incorporated herein by reference in its entirety).

In some embodiments, effector cells (e.g., T cells) are modified to express a universal immune receptor (e.g., switchable CAR, sCAR) that binds a peptide neo-epitope (PNE). In some embodiments, the peptide neo-epitope (PNE), has been incorporated at defined different locations within an antibody targeting an antigen (antibody switch). Therefore, sCAR-T-cell specificity is redirected only against PNE, not occurring in the human proteome, thus allowing an orthogonal interaction between the sCAR-T-cell and the antibody switch. In this way, sCAR-T cells are strictly dependent on the presence of the antibody switch to become fully activated, thus excluding CAR T-cell off-target recognition of endogenous tissues or antigens in the absence of the antibody switch (Arcangeli et al., (2016) Transl Cancer Res 5(Suppl 2):S174-S177 incorporated herein by reference in its entirety). Other examples of switchable CARs is provided by US Patent Application US20160272718A1 incorporated herein by reference in its entirety.

As used herein, the term "tag" encompasses a universal immune receptor, a tag, a switch, or an Fc region of an immunoglobulin as described supra. In some embodiments, an effector cell is modified to express a CAR comprising a tag binding domain. In some embodiments, the CAR binds fluorescein isothiocyanate (FITC), streptavidin, biotin, dinitrophenol, peridinin chlorophyll protein complex, green fluorescent protein, phycoerythrin (PE), horse radish peroxidase, palmitoylation, nitrosylation, alkalanine phosphatase, glucose oxidase, or maltose binding protein.

B. Anti-TAG Chimeric Antigen Receptors (AT-CAR)

In some embodiments, the CAR-T therapy suitable for use in combination with the immunomodulatory fusion proteins is an anti-tag CAR T cell. There are several limitations to the generalized clinical application of CAR T cells. For example, as there is no single tumor antigen universally expressed by all cancer types, each scFv in a CAR needs to be engineered with specificity for the desired tumor antigen. In addition, tumor antigens targeted by a CAR may be down-regulated or mutated in response to treatment resulting in tumor evasion.

As an alternative, universal, anti-tag chimeric antigen receptors (AT-CAR) and CAR-T cells have been developed. For example, human T cells have been engineered to express an anti-fluorescein isothiocyanate (FITC) CAR (referred to anti-FITC-CAR). This platform takes advantage of the high affinity interaction between the anti-FITC scFv (on the cell's surface) and FITC as well as the ability conjugate FITC molecules (or other tags) to any anti-cancer-based monoclonal antibody such as cetuximab (anti-EGFR), retuximab (anti-CD20) and herceptin (anti-Her2).

Accordingly, in some embodiments, effector cells (e.g., T cells) are modified to express a universal anti-tag chimeric antigen receptor (AT-CAR), as described at least in WO 2012082841 and US20160129109A1, incorporated herein by reference in its entirety. In such AT-CAR systems, T cells recognize and bind tagged proteins, such as antibodies. For example, in some embodiments an AT-CAR T cell recognizes tag-labeled antibodies, such as FITC-labeled antibodies. In some embodiments, an anti-tumor antigen antibody is conjugated to a tag (e.g., FITC), and administered prior to, concurrently, or after AT-CAR therapy. Anti-tumor antigen antibodies are known to those of skill in the art.

As indicated, the binding specificity of the tag-binding domain depends on the identity of the tag that is conjugated to the protein that is used to bind target cells. For example, in some aspects of the disclosure, the tag is FITC, the tag-binding domain is an anti-FITC scFv. Alternatively, in some aspects of the disclosure, the tag is biotin or PE (phycoerythrin) and the tag-binding domain is an anti-biotin scFv or an anti-PE scFv.

In some embodiments, the protein of each formulation of tagged proteins is the same or different and the protein is an antibody or an antigen-binding fragment thereof. In some aspects, the antibody or antigen-binding fragment thereof is cetuximab (anti-EGFR), nimotuzumab (anti-EGFR), panitumumab (anti-EGFR), retuximab (anti-CD20), omalizumab (anti-CD20), tositumomab (anti-CD20), trastuzumab (anti-Her2), gemtuzumab (anti-CD33), alemtuzumab (anti-CD52), and bevacuzimab (anti-VEGF).

Thus, in some embodiments, the tagged proteins include FITC-conjugated antibodies, biotin-conjugated antibodies, PE-conjugated antibodies, histidine-conjugated antibodies and streptavidin-conjugated antibodies, where the antibody binds to a TAA or a TSA expressed by the target cells. For example, the tagged proteins include, but are not limited to, FITC-conjugated cetuximab, FITC-conjugated retuximab, FITC-conjugated herceptin, biotin-conjugated cetuximab, biotin-conjugated retuximab, biotin-conjugated herceptin, PE-conjugated cetuximab, PE-conjugated retuximab, PE-conjugated herceptin, histidine-conjugated cetuximab, histidine-conjugated retuximab, histidine-conjugated herceptin, streptavidin-conjugated cetuximab, streptavidin-conjugated retuximab, and streptavidin-conjugated herceptin.

In some embodiments, the AT-CAR of each population of AT-CAR-expressing T cells is the same or different and the AT-CAR comprises a tag-binding domain, a transmembrane domain, and an activation domain. In some embodiments, the tag-binding domain is an antibody or an antigen-binding fragment thereof. In some aspects, the tag-binding domain specifically binds FITC, biotin, PE, histidine or streptavidin. In some embodiments the tag-binding domain is antigen-binding fragment and the antigen-binding fragment is a single chain variable fragment (scFv), such as a scFv that specifically binds FITC, biotin, PE, histidine or streptavidin. In some embodiments the transmembrane domain is the hinge and transmembrane regions of the human CD8a chain. In some embodiments, the activation domain comprises one or more of the cytoplasmic region of CD28, the cytoplasmic region of CD137 (41BB), OX40, HVEM, CD3ζ and FcRε.

In some embodiments, the tag of each formulation of tagged proteins is the same or different and the tag is selected from the group consisting of fluorescein isothiocyanate (FITC), streptavidin, biotin, histidine, dinitrophenol, peridinin chlorophyll protein complex, green fluorescent protein, phycoerythrin (PE), horse radish peroxidase, palmitoylation, nitrosylation, alkalanine phosphatase, glucose oxidase, and maltose binding protein.

The tag may be conjugated to the proteins using techniques such as chemical coupling and chemical cross-linkers. Alternatively, polynucleotide vectors can be prepared that encode the tagged proteins as fusion proteins. Cell lines can then be engineered to express the tagged proteins, and the tagged proteins can be isolated from culture media, purified and used in the methods disclosed herein.

In some embodiments, tagged proteins are administered to a subject prior to, or concurrent with, or after administration of the AT-CAR-expressing T cells. In some embodiments, the disclosure provide a method of treating cancer in a subject, comprising: (a) administering a formulation of tagged proteins to a subject in need of treatment, wherein the tagged proteins bind a cancer cell in the subject, and (b) administering a therapeutically-effective population of anti-tag chimeric antigen receptor (AT-CAR)-expressing T cells to the subject, wherein the AT-CAR-expressing T cells bind the tagged proteins and induce cancer cell death, thereby treating cancer in a subject.

C. Tandem CAR (TanCAR) Effector Cells

In some embodiments, the CAR-T therapy suitable for use in combination with the immunomodulatory fusion proteins is a tandem CAR effector cell. It has been observed that using a CAR approach for cancer treatment, tumor heterogeneity and immunoediting can cause escape from CAR treatment (Grupp et al., New Eng. J. Med (2013) 368:1509-1518). As an alternative approach, bispecific CARs, known as tandem CARs or TanCARs, have been developed in an attempt to target multiple cancer specific markers simultaneously. In a TanCAR, the extracellular domain comprises two antigen binding specificities in tandem, joined by a linker. The two binding specificities (scFvs) are thus both linked to a single transmembrane portion: one scFv being juxtaposed to the membrane and the other being in a distal position. As an exemplary TanCAR, Grada et al. (Mol Ther Nucleic Acids (2013) 2, e105) describes a TanCAR which includes a CD19-specific scFv, followed by a Gly-Ser linker and a HER2-specific scFv. The HER2-scFv was in the juxta-membrane position, and the CD19-scFv in the distal position. The TanCAR was shown to induce distinct T cell reactivity against each of the two tumor restricted antigens.

Accordingly, some aspects of the disclosure relate to a tandem chimeric antigen receptor that mediates bispecific activation and targeting of T cells. Although the present disclosure refers to bispecificity for the CAR, in some aspects the CARs are able to target three, four, or more tumor antigens. Targeting multiple antigens using CAR T cells may enhance T cell activation and/or offset tumor escape by antigen loss. TanCARs may also target multiple expressed antigens, target various tumors using the same cellular product with a broad specificity, and/or provide a better toxicity profile with a less intensely signaling CAR achieving the same results due to multiple specificity.

In some embodiments, the disclosure provides a TanCAR that includes two targeting domains. In some embodiments, the disclosure provides a multispecific TanCAR that includes three or more targeting domains. In another embodiment, the disclosure provides a first CAR and second CAR at the cell surface, each CAR comprising an antigen-binding domain, wherein the antigen-binding domain of the first CAR binds to a first tumor antigen (e.g., CD19, CD20, CD22, HER2) and the antigen-binding domain of the second CAR binds to another (different) tumor antigen. TanCARs are described in US20160303230A1 and US20170340705A1, incorporated herein by reference.

In some embodiments, the TanCAR of the disclosure targets two or more tumor antigens. Exemplary tumor antigens include one or more of CD19, CD20, CD22, k light chain, CD30, CD33, CD123, CD38, ROR1, ErbB2, ErbB3/4, EGFR vIII, carcinoembryonic antigen, EGP2, EGP40, mesothelin, TAG72, PSMA, NKG2D ligands, B7-H6, IL-13 receptor α2, MUC1, MUC16, CA9, GD2, GD3, HMW-MAA, CD171, Lewis Y, G250/CALX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, and/or TEM8.

In some embodiments, the disclosure provides a bispecific TanCAR that targets CD19 and another tumor antigen. In some embodiments, the disclosure provides a bispecific TanCAR that targets CD22 and another tumor antigen. In some embodiments, the disclosure provides a bispecific TanCAR that targets HER2 and another tumor antigen. In some embodiments, the disclosure provides a bispecific TanCAR that targets IL13R-alpha2 and another tumor antigen. In some embodiments, the disclosure provides a bispecific TanCAR that targets VEGF-A and another tumor antigen. In some embodiments, the disclosure provides a bispecific TanCAR that targets Tem8 and another tumor antigen. In some embodiments, the disclosure provides a bispecific TanCAR that targets FAP and another tumor antigen. In some embodiments, the disclosure provides a bispecific TanCAR that targets EphA2 and another tumor antigen. In some embodiments, the disclosure provides a bispecific TanCAR that targets one or more, two or more, three or more, or four or more of the following tumor antigens: CD19, CD22, HER2, IL13R-alpha2, VEGF-A, Tem8, FAP, or EphA2, and any combination thereof. In some embodiments, the disclosure provides a bispecific TanCAR that targets HER2 and IL13R-alpha2. In some embodiments, the disclosure provides a bispecific TanCAR that targets CD19 and CD22.

D. Methods for Generating Chimeric Antigen Receptors and CAR Effector Cells

In some embodiments, a subject's effectors cells (e.g., T cells) are genetically modified with a chimeric antigen receptor (Sadelain et al., *Cancer Discov.* 3:388-398, 2013). For example, an effector cell (e.g., T cell) is provided and a recombinant nucleic acid encoding a chimeric antigen receptor is introduced into the patient-derived effector cell (e.g., T cell) to generate a CAR cell. In some embodiments, effector cells (e.g., T cells) not derived from the subject are genetically modified with a chimeric antigen receptor. For example, in some embodiments, effector cells (e.g., T cells) are allogeneic cells that have been engineered to be used as an "off the shelf" adoptive cell therapy, such as Universal Chimeric Antigen Receptor T cells (UCARTs), as developed by Cellectis. UCARTs are allogeneic CAR T cells that have been engineered to be used for treating the largest number of patients with a particular cancer type. Non-limiting examples of UCARTs under development by Cellectis include those that target the following tumor antigens: CD19, CD123, CD22, CS1 and CD38.

A variety of different methods known in the art can be used to introduce any of the nucleic acids or expression vectors disclosed herein into an effector cell (e.g., T cell). Non-limiting examples of methods for introducing nucleic acid into a an effector cell (e.g., T cell) include: lipofection, transfection (e.g., calcium phosphate transfection, transfection using highly branched organic compounds, transfection using cationic polymers, dendrimer-based transfection, optical transfection, particle-based transfection (e.g., nanoparticle transfection), or transfection using liposomes (e.g., cationic liposomes)), microinjection, electroporation, cell squeezing, sonoporation, protoplast fusion, impalefection, hydrodynamic delivery, gene gun, magnetofection, viral transfection, and nucleofection. Furthermore, the CRISPR/Cas9 genome editing technology known in the art can be used to introduce CAR nucleic acids into effector cells (e.g., T cells) and/or to introduce other genetic modifications (e.g., as described below) into effector cells (e.g., T cells) to enhance CAR cell activity (for use of CRISPR/Cas9 technology in connection with CART cells, see e.g., U.S. Pat. Nos. 9,890,393; 9,855,297; US 2017/0175128; US 2016/0184362; US 2016/0272999; WO 2015/161276; WO 2014/191128; CN 106755088; CN 106591363; CN 106480097; CN 106399375; CN 104894068).

Provided herein are methods that can be used to generate any of the cells or compositions described herein where each cell can express a CAR (e.g., any of the CARs described herein).

Chimeric antigen receptors (CARs) include an antigen-binding domain, a transmembrane domain, and an cytoplasmic signaling domain that includes a cytoplasmic sequence of CD3ζ sequence sufficient to stimulate a T cell when the antigen-binding domain binds to the antigen, and optionally, a cytoplasmic sequence of one or more (e.g., two, three, or four) co-stimulatory proteins (e.g., a cytoplasmic sequence of one or more of B7-H3, BTLA, CD2, CD7, CD27, CD28, CD30, CD40, CD40L, CD80, CD160, CD244, ICOS, LAG3, LFA-1, LIGHT, NKG2C, 4-1BB, OX40, PD-1, PD-L1, TIM3, and a ligand that specifically binds to CD83) that provides for co-stimulation of the T cell when the antigen-binding domain binds to the antigen. In some embodiments, a CAR can further include a linker. Non-limiting aspects and features of CARs are described below. Additional aspects of CARs and CAR cells, including exemplary antigen-binding domains, linkers, transmembrane domains, and cytoplasmic signaling domains, are described in, e.g., Kakarla et al., *Cancer J.* 20:151-155, 2014; Srivastava et al., *Trends Immunol.* 36:494-502, 2015; Nishio et al., *Oncoimmunology* 4(2): e988098, 2015; Ghorashian et al., *Br. J. Haematol.* 169:463-478, 2015; Levine, *Cancer Gene Ther.* 22:79-84, 2015; Jensen et al., *Curr. Opin. Immunol.* 33:9-15, 2015; Singh et al., *Cancer Gene Ther.* 22:95-100, 2015; Li et al., *Zhongguo Shi Yan Xue Ye Xue Za Zhi* 22:1753-1756, 2014; Gill et al., *Immunol. Rev.* 263:68-89, 2015; Magee et al., *Discov. Med.* 18:265-271, 2014; Gargett et al., *Front. Pharmacol.* 5:235, 2014; Yuan et al., *Zhongguo Shi Yan Xue Ye Xue Za Zhi* 22:1137-1141, 2014; Pedgram et al., *Cancer J.* 20:127-133, 2014; Eshhar et al., *Cancer J.* 20:123-126, 2014; Ramos et al., *Cancer J.* 20:112-118, 2014; Maus et al., *Blood* 123:2625-2635, 2014; Jena et al., *Curr. Hematol. Malig. Rep.* 9:50-56, 2014; Maher et al., *Curr. Gene Ther.* 14:35-43, 2014; Riches et al., *Discov. Med.* 16:295-302, 2013; Cheadle et al., *Immunol. Rev.* 257:83-90, 2014; Davila et al., *Int. J. Hematol.* 99:361-371, 2014; Xu et al., *Cancer Lett.* 343:172-178, 2014; Kochenderfer et al., *Nat. Rev. Clin. Oncol.* 10:267-276, 2013; Hosing et al., *Curr. Hematol. Malig. Rep.* 8:60-70, 2013; Hombach et al., *Curr. Mol. Med.* 13:1079-1088, 2013; Xu et al., *Leuk. Lymphoma* 54:255-260, 2013; Gilham et al., *Trends Mol. Med.* 18:377-384, 2012; Lipowska-Bhalla et al., *Cancer Immunol. Immunother.* 61:953-962, 2012;

Chmielewski et al., *Cancer Immunol. Immunother.* 61:1269-1277, 2013; Jena et al., *Blood* 116:1035-1044, 2010; Dotti et al, *Immunology Reviews* 257(1): 107-126, 2013; Dai et al., *Journal of the National Cancer Institute* 108(7): djv439, 2016; Wang and Riviere, *Molecular Therapy-Oncolytics* 3: 16015, 2016; U.S. Patent Application Publication Nos. 2018/0057609; 2018/0037625; 2017/0362295; 2017/0137783; 2016/0152723; 2016/0206656; 2016/0199412; 2016/0208018; 2015/0232880; 2015/0225480; 2015/0224143; 2015/0224142; 2015/0190428; 2015/0196599; 2015/0152181; 2015/0140023; 2015/0118202; 2015/0110760; 2015/0099299; 2015/0093822; 2015/0093401; 2015/0051266; 2015/0050729; 2015/0024482; 2015/0023937; 2015/0017141; 2015/0017136; 2015/0017120; 2014/0370045; 2014/0370017; 2014/0369977; 2014/0349402; 2014/0328812; 2014/0322275; 2014/0322216; 2014/0322212; 2014/0322183; 2014/0314795; 2014/0308259; 2014/0301993; 2014/0296492; 2014/0294784; 2014/0286973; 2014/0274909; 2014/0274801; 2014/0271635; 2014/0271582; 2014/0271581; 2014/0271579; 2014/0255363; 2014/0242701; 2014/0242049; 2014/0227272; 2014/0219975; 2014/0170114; 2014/0134720; 2014/0134142; 2014/0120622; 2014/0120136; 2014/0106449; 2014/0106449; 2014/0099340; 2014/0086828; 2014/0065629; 2014/0050708; 2014/0024809; 2013/0344039; 2013/0323214; 2013/0315884; 2013/0309258; 2013/0288368; 2013/0287752; 2013/0287748; 2013/0280221; 2013/0280220; 2013/0266551; 2013/0216528; 2013/0202622; 2013/0071414; 2012/0321667; 2012/0302466; 2012/0301448; 2012/0301447; 2012/0060230; 2011/0213288; 2011/0158957; 2011/0104128; 2011/0038836; 2007/0036773; and 2004/0043401. Additional aspects of CARs and CAR cells, including exemplary antigen-binding domains, linkers, transmembrane domains, and cytoplasmic signaling domains, are described in WO 2016/168595; WO 12/079000; 2015/0141347; 2015/0031624; 2015/0030597; 2014/0378389; 2014/0219978; 2014/0206620; 2014/0037628; 2013/0274203; 2013/0225668; 2013/0116167; 2012/0230962; 2012/0213783; 2012/0093842; 2012/0071420; 2012/0015888; 2011/0268754; 2010/0297093; 2010/0158881; 2010/0034834; 2010/0015113; 2009/0304657; 2004/0043401; 2014/0322253; 2015/0118208; 2015/0038684; 2014/0024601; 2012/0148552; 2011/0223129; 2009/0257994; 2008/0160607; 2008/0003683; 2013/0121960; 2011/0052554; and 2010/0178276.

Antigen Binding Domains

Antigen binding domains included in the chimeric antigen receptor (CAR) can specifically bind to an antigen (e.g., a tumor associated antigen (TAA) or an antigen that is not expressed on a non-cancerous cell) or a universal receptor (e.g., a tag). Non-limiting examples of an antigen binding domain include: a monoclonal antibody (e.g., IgG1, IgG2, IgG3, IgG4, IgM, IgE, and IgD) (e.g., a fully human or a chimeric (e.g., a humanized) antibody), an antigen binding fragment of an antibody (e.g., Fab, Fab', or F(ab')$_2$ fragments) (e.g., a fragment of a fully human or a chimeric (e.g., humanized) antibody), a diabody, a triabody, a tetrabody, a minibody, a scFv, scFv-Fc, (scFv)$_2$, scFab, bis-scFv, hc-IgG, a BiTE, a single domain antibody (e.g., a V-NAR domain or a VhH domain), IgNAR, and a multispecific (e.g., bispecific antibody) antibody. Methods of making these antigen-binding domains are known in the art.

In some embodiments, an antigen binding domain includes at least one (e.g., one, two, three, four, five, or six) CDR (e.g., any of the three CDRs from an immunoglobulin light chain variable domain or any of the three CDRs from an immunoglobulin heavy chain variable domain) of an antibody that is capable of specifically binding to the target antigen, such as immunoglobulin molecules (e.g., light or heavy chain immunoglobulin molecules) and immunologically-active (antigen-binding) fragments of immunoglobulin molecules.

In some embodiments, an antigen binding domain is a single-chain antibody (e.g., a V-NAR domain or a V$_H$H domain, or any of the single-chain antibodies as described herein). In some embodiments, an antigen binding domain is a whole antibody molecule (e.g., a human, humanized, or chimeric antibody) or a multimeric antibody (e.g., a bi-specific antibody).

In some embodiments, antigen-binding domains include antibody fragments and multispecific (e.g., bi-specific) antibodies or antibody fragments. Examples of antibodies and antigen-binding fragments thereof include, but are not limited to: single-chain Fvs (sdFvs), Fab fragments, Fab' fragments, F(ab')$_2$, disulfide-linked Fvs (sdFvs), Fvs, and fragments containing either a VL or a VH domain.

Additional antigen binding domains provided herein are polyclonal, monoclonal, multispecific (multimeric, e.g., bi-specific), human antibodies, chimeric antibodies (e.g., human-mouse chimera), single-chain antibodies, intracellularly-made antibodies (i.e., intrabodies), and antigen-binding fragments thereof. The antibodies or antigen-binding fragments thereof can be of any type (e.g., IgG, IgE, IgM, IgD, IgA, and IgY), class (e.g., IgG$_1$, IgG$_2$, IgG$_3$, IgG$_4$, IgA$_1$, and IgA$_2$), or subclass. In some embodiments, the antigen binding domain is an IgG$_1$ antibody or antigen-binding fragment thereof. In some examples, the antigen binding domain is an IgG$_4$ antibody or antigen-binding fragment thereof. In some embodiments, the antigen binding domain is an immunoglobulin comprising a heavy and light chain.

Additional examples of antigen binding domains are antigen-binding fragments of an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4), an antigen-binding fragment of an IgA (e.g., an antigen-binding fragment of IgA1 or IgA2) (e.g., an antigen-binding fragment of a human or humanized IgA, e.g., a human or humanized IgA1 or IgA2), an antigen-binding fragment of an IgD (e.g., an antigen-binding fragment of a human or humanized IgD), an antigen-binding fragment of an IgE (e.g., an antigen-binding fragment of a human or humanized IgE), or an antigen-binding fragment of an IgM (e.g., an antigen-binding fragment of a human or humanized IgM).

In some embodiments, an antigen binding domain can bind to a particular antigen (e.g., a tumor-associated antigen) with an affinity ($K_D$) about or less than $1\times10^{-7}$M (e.g., about or less than $1\times10^{-8}$M, about or less than $5\times10^{-9}$M, about or less than $2\times10^{-9}$M, or about or less than $1\times10^{-9}$M), e.g., in saline or in phosphate buffered saline.

In some embodiments, CAR effector cells (e.g., CAR T cells) comprise a CAR molecule that binds to a tumor antigen (e.g., comprises a tumor antigen binding domain). In some embodiments, the CAR molecule comprises an antigen binding domain that recognizes a tumor antigen of a solid tumor (e.g., breast cancer, colon cancer, etc.). In some embodiments, the CAR molecule is a tandem CAR molecule as described supra, which comprises at least two antigen binding domains. In some embodiments, the CAR molecule comprises an antigen binding domain that recognizes a tumor antigen of a hematologic malignancy (e.g., leukemia, acute lymphocytic leukemia, acute myelocytic leukemia, acute promyelocytic leukemia, chronic leukemia, chronic myelocytic (granulocytic) leukemia, chronic lymphocytic leukemia, mantle cell lymphoma, primary central nervous system lymphoma, Burkitt's lymphoma and marginal zone B cell lymphoma, Polycythemia vera, Hodgkin's disease, non-Hodgkin's disease, multiple myeloma, etc.).

In some embodiments, the tumor antigen is a tumor-specific antigen (TSA). A TSA is unique to tumor cells and does not occur on other cells in the body. In some embodiments, the tumor antigen is a tumor-associated antigen (TAA). A TAA is not unique to a tumor cell and instead is also expressed on a normal cell under conditions that fail to induce a state of immunologic tolerance to the antigen. The expression of the antigen on the tumor may occur under conditions that enable the immune system to respond to the antigen. In some embodiments, a TAA is expressed on normal cells during fetal development when the immune system is immature and unable to respond or is normally present at extremely low levels on normal cells but which are expressed at much higher levels on tumor cells.

In certain embodiments, the tumor-associated antigen is determined by sequencing a patient's tumor cells and identifying mutated proteins only found in the tumor. These antigens are referred to as "neoantigens." Once a neoantigen has been identified, therapeutic antibodies can be produced against it and used in the methods described herein.

In some embodiments, the tumor antigen is an epithelial cancer antigen, (e.g., breast, gastrointestinal, lung), a prostate specific cancer antigen (PSA) or prostate specific membrane antigen (PSMA), a bladder cancer antigen, a lung (e.g., small cell lung) cancer antigen, a colon cancer antigen, an ovarian cancer antigen, a brain cancer antigen, a gastric cancer antigen, a renal cell carcinoma antigen, a pancreatic cancer antigen, a liver cancer antigen, an esophageal cancer antigen, a head and neck cancer antigen, or a colorectal cancer antigen. In certain embodiments, the tumor antigen is a lymphoma antigen (e.g., non-Hodgkin's lymphoma or Hodgkin's lymphoma), a B-cell lymphoma cancer antigen, a leukemia antigen, a myeloma (e.g., multiple myeloma or plasma cell myeloma) antigen, an acute lymphoblastic leukemia antigen, a chronic myeloid leukemia antigen, or an acute myelogenous leukemia antigen.

Tumor antigens, (e.g. tumor-associated antigens (TAAs) and tumor-specific antigens (TSAs)) that may be targeted by CAR effector cells (e.g., CAR T cells), include, but are not limited to, 1GH-IGK, 43-9F, 5T4, 791Tgp72, acyclophilin C-associated protein, alphafetoprotein (AFP), α-actinin-4, A3, antigen specific for A33 antibody, ART-4, B7, Ba 733, BAGE, BCR-ABL, beta-catenin, beta-HCG, BrE3-antigen, BCA225, BTAA, CA125, CA15-3\CA 27.29\BCAA, CA195, CA242, CA-50, CAM43, CAMEL, CAP-1, carbonic anhydrase IX, c-Met, CA19-9, CA72-4, CAM 17.1, CASP-8/m, CCCL19, CCCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD66a-e, CD67, CD68, CD70, CD70L, CD74, CD79a, CD79b, CD80, CD83, CD95, CD126, CD132, CD133, CD138, CD147, CD154, CDC27, CDK4, CDK4m, CDKN2A, CO-029, CTLA4, CXCR4, CXCR7, CXCL12, HIF-1a, colon-specific antigen-p (CSAp), CEA (CEACAM5), CEACAM6, c-Met, DAM, E2A-PRL, EGFR, EGFRvIII, EGP-1 (TROP-2), EGP-2, ELF2-M, Ep-CAM, fibroblast growth factor (FGF), FGF-5, Flt-1, Flt-3, folate receptor, G250 antigen, Ga733VEpCAM, GAGE, gp100, GRO-β, H4-RET, HLA-DR, HM1.24, human chorionic gonadotropin (HCG) and its subunits, HER2/neu, HMGB-1, hypoxia inducible factor (HIF-1), HSP70-2M, HST-2, HTgp-175, Ia, IGF-1R, IFN-γ, IFN-α, IFN-β, IFN-λ, IL-4R, IL-6R, IL-13R, IL-15R, IL-17R, IL-18R, IL-2, IL-6, IL-8, IL-12, IL-15, IL-17, IL-18, IL-23, IL-25, insulin-like growth factor-1 (IGF-1), KC4-antigen, KSA, KS-1-antigen, KS1-4, LAGE-1a, Le-Y, LDR/FUT, M344, MA-50, macrophage migration inhibitory factor (MIF), MAGE, MAGE-1, MAGE-3, MAGE-4, MAGE-5, MAGE-6, MART-1, MART-2, TRAG-3, mCRP, MCP-1, MIP-1A, MIP-1B, MIF, MG7-Ag, MOV18, MUC1, MUC2, MUC3, MUC4, MUC5ac, MUC13, MUC16, MUM-1/2, MUM-3, MYL-RAR, NB/70K, Nm23H1, NuMA, NCA66, NCA95, NCA90, NY-ESO-1, p15, p16, p185erbB2, p180erbB3, PAM4 antigen, pancreatic cancer mucin, PD1 receptor (PD-1), PD-1 receptor ligand 1 (PD-L1), PD-1 receptor ligand 2 (PD-L2), PI5, placental growth factor, p53, PLAGL2, Pmel17 prostatic acid phosphatase, PSA, PRAME, PSMA, P1GF, ILGF, ILGF-1R, IL-6, IL-25, RCAS1, RS5, RAGE, RANTES, Ras, T101, SAGE, S100, survivin, survivin-2B, SDDCAG16, TA-90\Mac2 binding protein, TAAL6, TAC, TAG-72, TLP, tenascin, TRAIL receptors, TRP-1, TRP-2, TSP-180, TNF-α, Tn antigen, Thomson-Friedenreich antigens, tumor necrosis antigens, tyrosinase, VEGFR, ED-B fibronectin, WT-1, 17-1A-antigen, complement factors C3, C3a, C3b, C5a, C5, an angiogenesis marker, bcl-2, bcl-6, and K-ras, an oncogene marker and an oncogene product (see, e.g., Sensi et al., Clin Cancer Res 2006, 12:5023-32; Parmiani et al., J Immunol 2007, 178:1975-79; Novellino et al. Cancer Immunol Immunother 2005, 54:187-207).

In some embodiments, the tumor antigen is a viral antigen derived from a virus associated with a human chronic disease or cancer (such as cervical cancer). For example, in some embodiments, the viral antigen is derived from Epstein-Barr virus (EBV), HPV antigens E6 and/or E7, hepatitis C virus (HCV), hepatitis B virus (HBV), or cytomegalovirus (CMV).

Exemplary cancers or tumors and specific tumor antigens associated with such tumors (but not exclusively), include acute lymphoblastic leukemia (etv6, aml1, cyclophilin b), B cell lymphoma (Ig-idiotype), glioma (E-cadherin, α-catenin, β-catenin, γ-catenin, p120ctn), bladder cancer (p21ras), biliary cancer (p21ras), breast cancer (MUC family, HER2/neu, c-erbB-2), cervical carcinoma (p53, p21ras), colon carcinoma (p21ras, HER2/neu, c-erbB-2, MUC family), colorectal cancer (Colorectal associated antigen (CRC)-0017-1A/GA733, APC), choriocarcinoma (CEA), epithelial cell cancer (cyclophilin b), gastric cancer (HER2/neu, c-erbB-2, ga733 glycoprotein), hepatocellular cancer (α-fetoprotein), Hodgkins lymphoma (Imp-1, EBNA-1), lung cancer (CEA, MAGE-3, NY-ESO-1), lymphoid cell-derived leukemia (cyclophilin b), melanoma (p5 protein, gp75, oncofetal antigen, GM2 and GD2 gangliosides, Melan-A/MART-1, cdc27, MAGE-3, p21ras, gp100), mycloma (MUC family, p21ras), non-small cell lung carcinoma (HER2/neu, c-erbB-2), nasopharyngeal cancer (Imp-1, EBNA-1), ovarian cancer (MUC family, HER2/neu, c-erbB-2), prostate cancer (Prostate Specific Antigen (PSA) and its antigenic epitopes PSA-1, PSA-2, and PSA-3, PSMA, HER2/neu, c-erbB-2, ga733 glycoprotein), renal cancer (HER2/neu, c-erbB-2), squamous cell cancers of the cervix and esophagus, testicular cancer (NY-ESO-1), and T cell leukemia (HTLV-1 epitopes), and viral products or proteins.

In some embodiments, the immune effector cell comprising a CAR molecule (e.g., CAR T cell) useful in the methods disclosed herein expresses a CAR comprising a mesothelin binding domain (i.e., the CAR T cell specifically recognizes mesothelin). Mesothelin is a tumor antigen that is overexpressed in a variety of cancers including ovarian, lung and pancreatic cancers.

In some embodiments, the immune effector cell comprising a CAR molecule (e.g., CAR T cell) useful in the methods disclosed herein expresses a CAR comprising a CD19 binding domain. In some embodiments, the immune effector cell comprising a CAR molecule (e.g., CAR T cell) useful in the methods disclosed herein expresses a CAR comprising a HER2 binding domain. In some embodiments, the immune effector cell comprising a CAR molecule (e.g., CAR T cell) useful in the methods disclosed herein expresses a CAR comprising an EGFR binding domain.

In some embodiments, the CAR effector cell expressing a CAR comprising a CD19 targeting or binding domain is Kymriah™ (tisagenlecleucel; Novartis; see WO 2016109410, herein incorporated by reference in its entirety) or Yescarta™ (axicabtagene ciloleucel; Kite; see US 20160346326, herein incorporated by reference in its entirety).

Linker

Provided herein are CARs that can optionally include a linker (1) between the antigen binding domain and the transmembrane domain, and/or (2) between the transmembrane domain and the cytoplasmic signaling domain. In some embodiments, the linker can be a polypeptide linker. For example, the linker can have a length of between about 1 amino acid and about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, about 18 amino acids, about 16 amino acids, about 14 amino acids, about 12 amino acids, about 10 amino acids, about 8 amino acids, about 6 amino acids, about 4 amino acids, or about 2 amino acids; about 2 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, about 18 amino acids, about 16 amino acids, about 14 amino acids, about 12 amino acids, about 10 amino acids, about 8 amino acids, about 6 amino acids, or about 4 amino acids; about 4 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, about 18 amino acids, about 16 amino acids, about 14 amino acids, about 12 amino acids, about 10 amino acids, about 8 amino acids, or about 6 amino acids; about 6 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, about 18 amino acids, about 16 amino acids, about 14 amino acids, about 12 amino acids, about 10 amino acids, or about 8 amino acids; about 8 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, about 18 amino acids, about 16 amino acids, about 14 amino acids, about 12 amino acids, or about 10 amino acids; about 10 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, about 18 amino acids, about 16 amino acids, about 14 amino acids, or about 12 amino acids; about 12 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, about 18 amino acids, about 16 amino acids, or about 14 amino acids; about 14 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, about 18 amino acids, or about 16 amino acids; about 16 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, or about 18 amino acids; about 18 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, or about 20 amino acids; about 20 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, or about 25 amino acids; about 25 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, or about 30 amino acids; about 30 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, or about 35 amino acids; about 35 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, or about 40 amino acids; about 40 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, or about 50 amino acids; about 50 amino acids to about 500 amino acids, about 400 amino acids, about 300 amino acids, about 200 amino acids, about 100 amino acids, about 90 amino acids, about 80 amino acids, about 70 amino acids, or about 60 amino acids; about 60 amino acids to about 500 amino acids, about 400 amino acids, about 300 amino acids, about 200 amino acids, about 150 amino acids, about 100 amino acids, about 90 amino acids, about 80 amino acids, or about 70 amino acids; about 70 amino acids to about 500 amino acids, about 400 amino acids, about 300 amino acids, about 200 amino acids, about 100 amino acids, about 90 amino acids, or about 80 amino acids; about 80 amino acids to about 500 amino acids, about 400 amino acids, about 300 amino acids, about 200 amino acids, about 100 amino acids, or about 90 amino acids; about 90 amino acids to about 500 amino acids, about 400 amino acids, about 300 amino acids, about 200 amino acids, or about 100 amino acids; about 100 amino acids to about 500 amino acids, about 400 amino acids, about 300 amino acids, or about 200 amino acids; about 200 amino acids to about 500 amino acids, about 400 amino acids, or about 300 amino acids; about 300 amino acids to about 500 amino acids or about 400 amino acids; or about 400 amino acids to about 500 amino acids.

Additional examples and aspects of linkers are described in the references cited herein, and are thus incorporated in their entirety herein.

Transmembrane Domains

In some embodiments, the CARs described herein also include a transmembrane domain. In some embodiments, the transmembrane domain is naturally associated with a sequence in the cytoplasmic domain. In some embodiments, the transmembrane domain can be modified by one or more (e.g., two, three, four, five, six, seven, eight, nine, or ten) amino acid substitutions to avoid the binding of the domain to other transmembrane domains (e.g., the transmembrane domains of the same or different surface membrane proteins) to minimize interactions with other members of the receptor complex.

In some embodiments, the transmembrane domain may be derived from a natural source. In some embodiments, the transmembrane domain may be derived from any membrane-bound or transmembrane protein. Non-limiting examples of transmembrane domains that may be used herein may be derived from (e.g., comprise at least the transmembrane sequence or a part of the transmembrane sequence of) the alpha, beta, or zeta chain of the T-cell receptor, CD28, CD3 epsilon, CD33, CD37, CD64, CD80, CD45, CD4, CD5, CD8, CD9, CD16, CD22, CD86, CD134, CD137 or CD154.

In some embodiments, the transmembrane domain may be synthetic. For example, in some embodiments where the transmembrane domain is from a synthetic source, the transmembrane domain may include (e.g., predominantly include) hydrophobic residues (e.g., leucine and valine). In some embodiments, the synthetic transmembrane domain will include at least one (e.g., at least two, at least three, at least four, at least five, or at least six) triplet of phenylalanine, tryptophan, and valine at the end of a synthetic transmembrane domain. In some embodiments, the transmembrane domain of a CAR can include a CD8 hinge domain.

Additional specific examples of transmembrane domains are described in the references cited herein.

Cytoplasmic Domains

Also provided herein are CAR molecules that comprise, e.g., a cytoplasmic signaling domain that includes a cytoplasmic sequence of CD3 sufficient to stimulate a T cell when the antigen binding domain binds to the antigen, and optionally, a cytoplasmic sequence of one or more of costimulatory proteins (e.g., a cytoplasmic sequence of one or more of CD27, CD28, 4-1BB, OX40, CD30, CD40L, CD40, PD-1, PD-L1, ICOS, LFA-1, CD2, CD7, CD160, LIGHT, BTLA, TIM3, CD244, CD80, LAG3, NKG2C, B7-H3, a ligand that specifically binds to CD83, and any of the ITAM sequences described herein or known in the art) that provides for co-stimulation of the T cell. The stimulation of a CAR immune effector cell can result in the activation of one or more anti-cancer activities of the CAR immune effector cell. For example, in some embodiments, stimulation of a CAR immune effector cell can result in an increase in the cytolytic activity or helper activity of the CAR immune effector cell, including the secretion of cytokines. In some embodiments, the entire intracellular signaling domain of a co-stimulatory protein is included in the cytoplasmic signaling domain. In some embodiments, the cytoplasmic signaling domain includes a truncated portion of an intracellular signaling domain of a co-stimulatory protein (e.g., a truncated portion of the intracellular signaling domain that transduces an effector function signal in the CAR immune effector cell). Non-limiting examples of intracellular signaling domains that can be included in a cytoplasmic signaling domain include the cytoplasmic sequences of the T cell receptor (TCR) and co-receptors that act in concert to initiate signal transduction following antigen receptor engagement, as well as any variant of these sequences including at least one (e.g., one, two, three, four, five, six, seven, eight, nine, or ten) substitution and have the same or about the same functional capability.

In some embodiments, a cytoplasmic signaling domain can include two distinct classes of cytoplasmic signaling sequences: signaling sequences that initiate antigen-dependent activation through the TCR (primary cytoplasmic signaling sequences) (e.g., a CD3ζ cytoplasmic signaling sequence) and a cytoplasmic sequence of one or more of co-stimulatory proteins that act in an antigen-independent manner to provide a secondary or co-stimulatory signal (secondary cytoplasmic signaling sequences).

In some embodiments, the cytoplasmic domain of a CAR can be designed to include the CD3ζ signaling domain by itself or combined with any other desired cytoplasmic signaling sequence(s) useful in the context of a CAR. In some examples, the cytoplasmic domain of a CAR can include a CD3ζ chain portion and a costimulatory cytoplasmic signaling sequence. The costimulatory cytoplasmic signaling sequence refers to a portion of a CAR including a cytoplasmic signaling sequence of a costimulatory protein (e.g., CD27, CD28, 4-1BB (CD 137), OX40, CD30, CD40, PD-1, ICOS, lymphocyte function-associated antigen-1 (LFA-1), CD2, CD7, LIGHT, NKG2C, B7-H3, and a ligand that specifically binds with CD83).

In some embodiments, the cytoplasmic signaling sequences within the cytoplasmic signaling domain of a CAR are positioned in a random order. In some embodiments, the cytoplasmic signaling sequences within the cytoplasmic signaling domain of a CAR are linked to each other in a specific order. In some embodiments, a linker (e.g., any of the linkers described herein) can be used to form a linkage between different cytoplasmic signaling sequences.

In some embodiments, the cytoplasmic signaling domain is designed to include the cytoplasmic signaling sequence of CD3 and the cytoplasmic signaling sequence of the costimulatory protein CD28. In some embodiments, the cytoplasmic signaling domain is designed to include the cytoplasmic signaling sequence of CD3 and the cytoplasmic signaling sequence of costimulatory protein 4-1BB. In some embodiments, the cytoplasmic signaling domain is designed to include the cytoplasmic signaling sequence of CD3ζ and the cytoplasmic signaling sequences of costimulatory proteins CD28 and 4-1BB. In some embodiments, the cytoplasmic signaling domain does not include the cytoplasmic signaling sequences of 4-1BB.

Additional Modification of CAR T Cells

In another embodiment, the therapeutic efficacy of CAR effector cells (e.g., CAR T cells) is enhanced by disruption of a methylcytosine dioxygenase gene (e.g., Tet1, Tet2, Tet3), which leads to decreased total levels of 5-hydroxymethylcytosine in association with enhanced proliferation, regulation of effector cytokine production and degranulation, and thereby increases CAR effector cell (e.g., CAR T cell) proliferation and/or function, as described in PCT Publication WO 2017/049166. Thus, an effector cell (e.g., T cell) can be engineered to express a CAR and wherein expression and/or function of Tet1, Tet2 and/or Tet3 in said effector cell (e.g., T cell) has been reduced or eliminated.

In another embodiment, the therapeutic efficacy of CAR effector cells (e.g., CAR T cells) is enhanced by using an effector cell (e.g., T cell) that constitutively expresses a CAR (referred to as a nonconditional CAR) and conditionally expresses another agent useful for treating cancer, as described in PCT Publication WO 2016/126608 and US Publication No. 2018/0044424. In such embodiments, the conditionally expressed agent is expressed upon activation of the effector cell (e.g., T cell), e.g., the binding of the nonconditional CAR to its target. In one embodiment, the conditionally expressed agent is a CAR (referred to herein as a conditional CAR). In another embodiment, the conditionally expressed agent inhibits a checkpoint inhibitor of the immune response. In another embodiment, the conditionally expressed agent improves or enhances the efficacy of a CAR, and can include a cytokine.

In another embodiment, the therapeutic efficacy of CAR T cells is enhanced by modifying the CAR. T cell with a nucleic acid that is capable of altering (e.g., downmodulating) expression of an endogenous gene selected from the group consisting of TCR α chain, TCR β chain, beta-2 microglobulin, a HLA molecule, CTLA-4, PD1, and FAS, as described in PCT Publication WO 2016/069282 and US Publication No. 2017/0335331.

In another embodiment, the therapeutic efficacy of CAR T cells is enhanced by co-expressing in the T cells the CAR and one or more enhancers of T cell priming ("ETPs"), as described in PCT Publication WO 2015/112626 and US Publication No. 2016/0340406. The addition of an ETP component to the CAR T cell confers enhanced "professional" antigen-presenting cell (APC) function. In an embodiment, the CAR and one or more ETPs are transiently co-expressed in the T cell. Thus, the engineered T cells are safe (given the transient nature of the CAR/ETP expression), and induce prolonged immunity via APC function.

In another embodiment, the therapeutic efficacy of CART cells is enhanced by co-expressing in the T cells a CAR and an inhibitory membrane protein (IMP) comprising a binding (or dimerization) domain, as described in PCT Publication WO 2016/055551 and US Publication No. 2017/0292118. The CAR and the IMP are made both reactive to a soluble compound, especially through a second binding domain comprised within the CAR, thereby allowing the co-localization, by dimerization or ligand recognition, of the inhibitory signaling domain borne by the IMP and of the signal transducing domain borne by the CAR, having the effect of turning down the CAR activation. The inhibitory signaling domain is preferably the programmed death-1 (PD-1), which attenuates I-cell receptor (TCR)-mediated activation of IL-2 production and T-cell proliferation.

In another embodiment, the therapeutic efficacy of CART cells is enhanced using a system where controlled variations in the conformation of the extracellular portion of a CAR containing the antigen-binding domain is obtained upon addition of small molecules, as described in PCT Publication WO 2017/032777, This integrated system switches the interaction between the antigen and the antigen binding domain between on/off states. By being able to control the conformation of the extracellular portion of a CAR, downstream functions of the CAR cell, such as cytotoxicity, can be directly modulated. Thus, a CAR can be characterized in that it comprises: a) at least one ectodomain which comprises: 0 an extracellular antigen binding domain; and ii) a switch domain comprising at least a first multimerizing ligand-binding, domain and a second multimerizing ligand-binding domain which are capable of binding to a predetermined multivalent ligand to form a multimer comprising said two binding domains and the multivalent ligand to which they are capable of binding; b) at least one transmembrane domain; and c) at least one endodomain comprising a signal transducing domain and optionally a co-stimulatory domain; wherein the switch domain is located between the extracellular antigen binding domain and the transmembrane domain.

II. Tumor-Associated Antigen Targeting Antibodies

In some aspects, the disclosure provides immunomodulatory fusion proteins to be used or performed in conjunction with antibodies that target tumor antigens.

Therapeutic monoclonal antibodies have been conceived as a class of pharmaceutically active agents which should allow tumor selective treatment by targeting tumor selective antigens or epitopes.

Methods of producing antibodies, and antigen-binding fragments thereof, are well known in the art and are disclosed in, e.g., U.S. Pat. Nos. 7,247,301, 7,923,221, and U.S. Patent Application 2008/0138336, all of which are herein incorporated by reference in their entirety.

Therapeutic antibodies that can be used in the methods of the present disclosure include, but are not limited to, any of the art-recognized anti-cancer antibodies that are approved for use, in clinical trials, or in development for clinical use. In certain embodiments, more than one anti-cancer antibody can be included in the combination therapy of the present disclosure.

Non-limiting examples of anti-cancer antibodies include the following, without limitation: trastuzumab (HERCEPTIN™ by Genentech), South San Francisco, Calif.), which is used to treat HER-2/neu positive breast cancer or metastatic breast cancer; bevacizumab (AVASTIN™ by Genentech), which are used to treat colorectal cancer, metastatic colorectal cancer, breast cancer, metastatic breast cancer, non-small cell lung cancer, or renal cell carcinoma; rituximab (RITUXAN™ by Genentech), which is used to treat non-Hodgkin's lymphoma or chronic lymphocytic leukemia; pertuzumab (OMNITARG™ by Genentech), which is used to treat breast cancer, prostate cancer, non-small cell lung cancer, or ovarian cancer; cetuximab (ERBITUX™ by ImClone Systems Incorporated, New York, N.Y.), which can be used to treat colorectal cancer, metastatic colorectal cancer, lung cancer, head and neck cancer, colon cancer, breast cancer, prostate cancer, gastric cancer, ovarian cancer, brain cancer, pancreatic cancer, esophageal cancer, renal cell cancer, prostate cancer, cervical cancer, or bladder cancer; IMC-1C11 (ImClone Systems Incorporated), which is used to treat colorectal cancer, head and neck cancer, as well as other potential cancer targets; tositumomab and tositumomab and iodine I 131 (BEXXAR XM by Corixa Corporation, Seattle, Wash.), which is used to treat non-Hodgkin's lymphoma, which can be CD20 positive, follicular, non-Hodgkin's lymphoma, with and without transformation, whose disease is refractory to Rituximab and has relapsed following chemotherapy; $In^{111}$ ibirtumomab tiuxetan; $Y^{90}$ ibirtumomab tiuxetan; ibirtumomab tiuxetan and $Y^{90}$ ibirtumomab tiuxetan (ZEVALIN™ by Biogen Idee, Cambridge, Mass.), which is used to treat lymphoma or non-Hodgkin's lymphoma, which can include relapsed follicular lymphoma; relapsed or refractory, low grade or follicular non-Hodgkin's lymphoma; or transformed B-cell non-Hodgkin's lymphoma; EMD 7200 (EMD Pharmaceuticals, Durham, N.C.), which is used for treating non-small cell lung cancer or cervical cancer; SGN-30 (a genetically engineered monoclonal antibody targeted to CD30 antigen by Seattle Genetics, Bothell, Wash.), which is used for treating Hodgkin's lymphoma or non-Hodgkin's lymphoma; SGN-15 (a genetically engineered monoclonal antibody targeted to a Lewisy-related antigen that is conjugated to doxorubicin by Seattle Genetics), which is used for treating non-small cell lung cancer; SGN-33 (a humanized antibody targeted to CD33 antigen by Seattle Genetics), which is used for treating acute myeloid leukemia (AML) and myelodysplasia syndromes (MDS); SGN-40 (a humanized monoclonal antibody targeted to CD40 antigen by Seattle Genetics), which is used for treating multiple myeloma or non-Hodgkin's lymphoma; SGN-35 (a genetically engineered monoclonal antibody targeted to a CD30 antigen that is conjugated to auristatin E by Seattle Genetics), which is used for treating non-Hodgkin's lymphoma; SGN-70 (a humanized antibody targeted to CD70 antigen by Seattle Genetics), which is used for treating renal cancer and nasopharyngeal carcinoma; SGN-75 (a conjugate comprised of the SGN70 antibody and an Auristatin derivative by Seattle Genetics); and SGN-17/19 (a fusion protein containing antibody and enzyme conjugated to melphalan prodrug by Seattle Genetics), which is used for treating melanoma or metastatic melanoma.

It should be understood that the therapeutic antibodies to be used in the methods of the present disclosure are not limited to those described supra. For example, the following approved therapeutic antibodies can also be used in the methods of the disclosure: brentuximab vedotin (ADCETRIS™) for anaplastic large cell lymphoma and Hodgkin lymphoma, ipilimumab (MDX-101; YERVOY™) for melanoma, ofatumumab (ARZERRA™) for chronic lymphocytic leukemia, panitumumab (VECTIBIX™) for colorectal cancer, alemtuzumab (CAMPATH™) for chronic lymphocytic leukemia, ofatumumab (ARZERRA™) for chronic lymphocytic leukemia, gemtuzumab ozogamicin (MYLOTARG™) for acute myelogenous leukemia.

Antibodies suitable for use in the methods disclosed herein can also target molecules expressed by immune cells, such as, but not limited to, OX86 which targets OX40 and increases antigen-specific CD8+ T cells at tumor sites and enhances tumor rejection; BMS-663513 which targets CD137 and causes regression of established tumors, as well as the expansion and maintenance of CD8+ T cells, and daclizumab (ZENAPAX™) which targets CD25 and causes transient depletion of CD4+CD25+FOXP3+ Tregs and enhances tumor regression and increases the number of effector T cells. A more detailed discussion of these antibodies can be found in, e.g., Weiner et al., Nature Rev. Immunol 2010; 10:317-27.

Other therapeutic antibodies can be identified that target tumor antigens (e.g., tumor antigens associated with different types of cancers, such as carcinomas, sarcomas, myelomas, leukemias, lymphomas, and combinations thereof). For example, the following tumor antigens can be targeted by therapeutic antibodies in the methods disclosed herein.

The tumor antigen may be an epithelial cancer antigen, (e.g., breast, gastrointestinal, lung), a prostate specific cancer antigen (PSA) or prostate specific membrane antigen (PSMA), a bladder cancer antigen, a lung (e.g., small cell lung) cancer antigen, a colon cancer antigen, an ovarian cancer antigen, a brain cancer antigen, a gastric cancer antigen, a renal cell carcinoma antigen, a pancreatic cancer antigen, a liver cancer antigen, an esophageal cancer antigen, a head and neck cancer antigen, or a colorectal cancer antigen. In certain embodiments, the tumor antigen is a lymphoma antigen (e.g., non-Hodgkin's lymphoma or Hodgkin's lymphoma), a B-cell lymphoma cancer antigen, a leukemia antigen, a myeloma (e.g., multiple myeloma or plasma cell myeloma) antigen, an acute lymphoblastic leukemia antigen, a chronic myeloid leukemia antigen, or an acute myelogenous leukemia antigen. It should be understood that the described tumor antigens are only exemplary and that any tumor antigen can be targeted for use in the methods disclosed herein.

In certain embodiments, the tumor antigen is a mucin-1 protein or peptide (MUC-1) that is found on most or all human adenocarcinomas: pancreas, colon, breast, ovarian, lung, prostate, head and neck, including multiple myelomas and some B cell lymphomas. Patients with inflammatory bowel disease, either Crohn's disease or ulcerative colitis, are at an increased risk for developing colorectal carcinoma. MUC-1 is a type I transmembrane glycoprotein. The major extracellular portion of MUC-1 has a large number of tandem repeats consisting of 20 amino acids which comprise immunogenic epitopes. In some cancers it is exposed in an unglycosylated form that is recognized by the immune system (Gendler et al., *J Biol Chem* 1990; 265:15286-15293).

In certain embodiments, the tumor antigen is a mutated B-Raf antigen, which is associated with melanoma and colon cancer. The vast majority of these mutations represent a single nucleotide change of T-A at nucleotide 1796 resulting in a valine to glutamic acid change at residue 599 within the activation segment of B-Raf. Raf proteins are also indirectly associated with cancer as effectors of activated Ras proteins, oncogenic forms of which are present in approximately one-third of all human cancers. Normal non-mutated B-Raf is involved in cell signaling, relaying signals from the cell membrane to the nucleus. The protein is usually only active when needed to relay signals. In contrast, mutant B-Raf has been reported to be constantly active, disrupting the signaling relay (Mercer and Pritchard, Biochim Biophys Acta (2003) 1653(1):25-40; Sharkey et al., Cancer Res. (2004) 64(5):1595-1599).

In certain embodiments, the tumor antigen is a human epidermal growth factor receptor-2 (HER-2/neu) antigen. Cancers that have cells that overexpress HER-2/neu are referred to as HER-2/neu$^+$ cancers. Exemplary HER-2/neu$^+$ cancers include prostate cancer, lung cancer, breast cancer, ovarian cancer, pancreatic cancer, skin cancer, liver cancer (e.g., hepatocellular adenocarcinoma), intestinal cancer, and bladder cancer.

HER-2/neu has an extracellular binding domain (ECD) of approximately 645 aa, with 40% homology to epidermal growth factor receptor (EGFR), a highly hydrophobic transmembrane anchor domain (TMD), and a carboxyterminal intracellular domain (ICD) of approximately 580 aa with 80% homology to EGFR. The nucleotide sequence of HER- 2/neu is available at GENBANK™. Accession Nos. AH002823 (human HER-2 gene, promoter region and exon 1); M16792 (human HER-2 gene, exon 4): M16791 (human HER-2 gene, exon 3); M16790 (human HER-2 gene, exon 2); and M16789 (human HER-2 gene, promoter region and exon 1). The amino acid sequence for the HER-2/neu protein is available at GENBANK™. Accession No. AAA58637. Based on these sequences, one skilled in the art could develop HER-2/neu antigens using known assays to find appropriate epitopes that generate an effective immune response. Exemplary HER-2/neu antigens include p369-377 (a HER-2/neu derived HLA-A2 peptide); dHER2 (Corixa Corporation); li-Key MHC class II epitope hybrid (Generex Biotechnology Corporation); peptide P4 (amino acids 378-398); peptide P7 (amino acids 610-623); mixture of peptides P6 (amino acids 544-560) and P7; mixture of peptides P4, P6 and P7; HER2 [9754]; and the like.

In certain embodiments, the tumor antigen is an epidermal growth factor receptor (EGFR) antigen. The EGFR antigen can be an EGFR variant 1 antigen, an EGFR variant 2 antigen, an EGFR variant 3 antigen and/or an EGFR variant 4 antigen. Cancers with cells that overexpress EGFR are referred to as EGFR$^+$ cancers. Exemplary EGFR$^+$ cancers include lung cancer, head and neck cancer, colon cancer, colorectal cancer, breast cancer, prostate cancer, gastric cancer, ovarian cancer, brain cancer and bladder cancer.

In certain embodiments, the tumor antigen is a vascular endothelial growth factor receptor (VEGFR) antigen. VEGFR is considered to be a regulator of cancer-induced angiogenesis. Cancers with cells that overexpress VEGFR are called VEGFR$^+$ cancers. Exemplary VEGFR$^+$ cancers include breast cancer, lung cancer, small cell lung cancer, colon cancer, colorectal cancer, renal cancer, leukemia, and lymphocytic leukemia.

In certain embodiments, the tumor antigen is prostate-specific antigen (PSA) and/or prostate-specific membrane antigen (PSMA) that are prevalently expressed in androgen-independent prostate cancers.

In certain embodiments, the tumor antigen is Glycoprotein 100 (gp 100), a tumor-specific antigen associated with melanoma.

In certain embodiments, the tumor antigen is a carcinoembryonic (CEA) antigen. Cancers with cells that overexpress CEA are referred to as CEA$^+$ cancers. Exemplary CEA$^+$ cancers include colorectal cancer, gastric cancer and pancreatic cancer. Exemplary CEA antigens include CAP-1 (i.e., CEA aa 571-579), CAP1-6D, CAP-2 (i.e., CEA aa 555-579), CAP-3 (i.e., CEA aa 87-89), CAP-4 (CEA aa 1-11), CAP-5 (i.e., CEA aa 345-354), CAP-6 (i.e., CEA aa 19-28) and CAP-7.

In certain embodiments, the tumor antigen is carbohydrate antigen 10.9 (CA 19.9). CA 19.9 is an oligosaccharide related to the Lewis A blood group substance and is associated with colorectal cancers.

In certain embodiments, the tumor antigen is a melanoma cancer antigen. Melanoma cancer antigens are useful for treating melanoma. Exemplary melanoma cancer antigens include MART-1 (e.g., MART-1 26-35 peptide, MART-1 27-35 peptide); MART-1/Melan A; pMel 17; pMel 17/gp100; gp100 (e.g., gp 100 peptide 280-288, gp 100 peptide 154-162, gp 100 peptide 457-467); TRP-1; TRP-2; NY-ESO-1; p16; beta-catenin; mum-1; and the like.

In certain embodiments, the tumor antigen is a mutant or wild type ras peptide. The mutant ras peptide can be a mutant K-ras peptide, a mutant N-ras peptide and/or a mutant H-ras peptide. Mutations in the ras protein typically occur at positions 12 (e.g., arginine or valine substituted for glycine), 13 (e.g., asparagine for glycine), 61 (e.g., glutamine to leucine) and/or 59. Mutant ras peptides can be useful as lung cancer antigens, gastrointestinal cancer antigens, hepatoma antigens, myeloid cancer antigens (e.g., acute leukemia, myelodysplasia), skin cancer antigens (e.g., melanoma, basal cell, squamous cell), bladder cancer antigens, colon cancer antigens, colorectal cancer antigens, and renal cell cancer antigens.

In certain embodiments, the tumor antigen is a mutant and/or wildtype p53 peptide. The p53 peptide can be used as colon cancer antigens, lung cancer antigens, breast cancer antigens, hepatocellular carcinoma cancer antigens, lymphoma cancer antigens, prostate cancer antigens, thyroid cancer antigens, bladder cancer antigens, pancreatic cancer antigens and ovarian cancer antigens.

Further tumor antigens are well known in the art and include, for example, a glioma-associated antigen, carcinoembryonic antigen (CEA), β-human chorionic gonadotropin, alphafetoprotein (AFP), lectin-reactive AFP, thyroglobulm, RAGE-1, MN-CA IX, human telomerase reverse transcriptase, RU1, RU2 (AS), intestinal carboxy esterase, mut hsp70-2, M-CSF, prostase, prostate-specific antigen (PSA), PAP, NY-ESO-1, LAGE-1a, p53, tyrosinase, prostein, PSMA, ras, Her2/neu, TRP-1, TRP-2, TAG-72, KSA, CA-125, PSA, BRCI, BRC-II, bcr-ab1, pax3-fkhr, ews-fli-1, survivin and telomerase, prostate-carcinoma tumor antigen-1 (PCTA-1), MAGE, GAGE, GP-100, MUC-1, MUC-2, ELF2M, neutrophil elastase, ephrinB2, CD22, insulin growth factor (IGF)-I, IGF-II, IGF-I receptor, and mesothelin, In certain embodiments, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The tumor antigen may also be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/MelanA (MART-1), Pmel 17, tyrosinase, TRP-1, TRP-2 and tumor-specific multilineage antigens such as MAGE-1, MAGE-3, BAGE, GAGE-1, GAGE-2, pi 5; overexpressed embryonic antigens such as CEA; overexpressed oncogenes and mutated tumor-suppressor genes such as p53, Ras, HER-2/neu; unique tumor antigens resulting from chromosomal translocations such as BCR-ABL, E2A-PRL, H4-RET, 1GH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p 1 80erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4(791Tgp72}, alpha-fetoprotem, beta-HCG, BCA225, BTAA, CA 125, CA 15-3\CA 27.29\BCAA, CA 195, CA 242, CA-50, CAM43, CD68\I, CO-029, FGF-5, G250, Ga733VEpCAM, HTgp-175, M344, MA-50, MG7-Ag, MOV 18, NB/70K, NY-CO-1, RCAS 1, SDCCAG16, TA-90\Mac-2 binding protein, Acyclophilin C-associated protein, TAAL6, TAG72, TLP, and TPS.

In certain embodiments, the tumor-associated antigen is determined by sequencing a patient's tumor cells and identifying mutated proteins only found in the tumor. These antigens are referred to as "neoantigens." Once a neoantigen has been identified, therapeutic antibodies can be produced against it and used in the methods described herein.

The therapeutic antibody can be a fragment of an antibody; a complex comprising an antibody; or a conjugate comprising an antibody. The antibody can optionally be chimeric or humanized or fully human.

III. Immune Checkpoint Blockade

In some aspects, the disclosure provides immunomodulatory fusion proteins to be used or performed in conjunction with immune checkpoint inhibitors or immune checkpoint blockers.

T cell activation and effector functions are balanced by co-stimulatory and inhibitory signals, referred to as "immune checkpoints." Inhibitory ligands and receptors that regulate T cell effector functions are overexpressed on tumor cells. Subsequently, agonists of co-stimulatory receptors or antagonists of inhibitory signals, result in the amplification of antigen-specific T cell responses. In contrast to therapeutic antibodies which target tumor cells directly, immune checkpoint blocker enhances endogenous anti-tumor activity. In certain embodiments, the immune checkpoint blocker suitable for use in the methods disclosed herein, is an antagonist of inhibitory signals, e.g., an antibody which targets, for example, PD-1, PD-L1, CTLA-4, LAG3, B7-H3, B7-H4, or TIM3. These ligands and receptors are reviewed in Pardoll, D., Nature. 12: 252-264, 2012.

In certain embodiments, the immune checkpoint blocker is an antibody or an antigen-binding portion thereof, that disrupts or inhibits signaling from an inhibitory immunoregulator. In certain embodiments, the immune checkpoint blocker is a small molecule that disrupts or inhibits signaling from an inhibitory immunoregulator.

In certain embodiments, the inhibitory immunoregulator (immune checkpoint blocker) is a component of the PD-1/PD-L1 signaling pathway. Accordingly, certain embodiments of the disclosure provide methods for immunotherapy of a subject afflicted with cancer, which methods comprise administering to the subject a therapeutically effective amount of an antibody or an antigen-binding portion thereof that disrupts the interaction between the PD-1 receptor and its ligand, PD-L1. Antibodies known in the art which bind to PD-1 and disrupt the interaction between the PD-1 and its ligand, PD-L1, and stimulates an anti-tumor immune response, are suitable for use in the methods disclosed herein. In certain embodiments, the antibody or antigen-binding portion thereof binds specifically to PD-1. For example, antibodies that target PD-1 and are in clinical trials include, e.g., nivolumab (BMS-936558, Bristol-Myers Squibb) and pembrolizumab (lambrolizumab, MK03475, Merck). Other suitable antibodies for use in the methods disclosed herein are anti-PD-1 antibodies disclosed in U.S. Pat. No. 8,008,449, herein incorporated by reference. In certain embodiments, the antibody or antigen-binding portion thereof binds specifically to PD-L1 and inhibits its interaction with PD-1, thereby increasing immune activity. Antibodies known in the art which bind to PD-L1 and disrupt the interaction between the PD-1 and PD-L1, and stimulates an anti-tumor immune response, are suitable for use in the methods disclosed herein. For example, antibodies that target PD-L1 and are in clinical trials, include BMS-936559 (Bristol-Myers Squibb) and MPDL3280A (Genetech). Other suitable antibodies that target PD-L1 are disclosed in U.S. Pat. No. 7,943,743. It will be understood by one of ordinary skill that any antibody which binds to PD-1 or PD-L1, disrupts the PD-1/PD-L1 interaction, and stimulates an anti-tumor immune response, is suitable for use in the methods disclosed herein.

In certain embodiments, the inhibitory immunoregulator is a component of the CTLA-4 signaling pathway. Accordingly, certain embodiments of the disclosure provide methods for immunotherapy of a subject afflicted with cancer, which methods comprise administering to the subject a therapeutically effective amount of an antibody or an antigen-binding portion thereof that targets CTLA-4 and disrupts its interaction with CD80 and CD86. Exemplary antibodies that target CTLA-4 include ipilimumab (MDX-010, MDX-101, Bristol-Myers Squibb), which is FDA approved, and tremelimumab (ticilimumab, CP-675, 206, Pfizer), currently undergoing human trials. Other suitable antibodies that target CTLA-4 are disclosed in WO 2012/120125, U.S. Pat. Nos. 6,984,720, 6,682,7368, and U.S. Patent Applications 2002/0039581, 2002/0086014, and 2005/0201994, herein incorporated by reference. It will be understood by one of ordinary skill that any antibody which binds to CTLA-4, disrupts its interaction with CD80 and CD86, and stimulates an anti-tumor immune response, is suitable for use in the methods disclosed herein.

In certain embodiments, the inhibitory immunoregulator is a component of the LAG3 (lymphocyte activation gene 3) signaling pathway. Accordingly, certain embodiments of the disclosure provide methods for immunotherapy of a subject afflicted with cancer, which methods comprise administering to the subject a therapeutically effective amount of an antibody or an antigen-binding portion thereof that targets LAG3 and disrupts its interaction with MEW class II molecules. An exemplary antibody that targets LAG3 is IMP321 (Immutep), currently undergoing human trials. Other suitable antibodies that target LAG3 are disclosed in U.S. Patent Application 2011/0150892, herein incorporated by reference. It will be understood by one of ordinary skill that any antibody which binds to LAG3, disrupts its interaction with MHC class II molecules, and stimulates an anti-tumor immune response, is suitable for use in the methods disclosed herein.

In certain embodiments, the inhibitory immunoregulator is a component of the B7 family signaling pathway. In certain embodiments, the B7 family members are B7-H3 and B7-H4. Accordingly, certain embodiments of the disclosure provide methods for immunotherapy of a subject afflicted with cancer, which methods comprise administering to the subject a therapeutically effective amount of an antibody or an antigen-binding portion thereof that targets B7-H3 or H4. The B7 family does not have any defined receptors but these ligands are upregulated on tumor cells or tumor-infiltrating cells. Preclinical mouse models have shown that blockade of these ligands can enhance anti-tumor immunity. An exemplary antibody that targets B7-H3 is MGA271 (Macrogenics), currently undergoing human trials. Other suitable antibodies that target LAG3 are disclosed in U.S. Patent Application 2013/0149236, herein incorporated by reference. It will be understood by one of ordinary skill that any antibody which binds to B7-H3 or H4, and stimulates an anti-tumor immune response, is suitable for use in the methods disclosed herein.

In certain embodiments, the inhibitory immunoregulator is a component of the TIM3 (T cell membrane protein 3) signaling pathway. Accordingly, certain embodiments of the disclosure provide methods for immunotherapy of a subject afflicted with cancer, which methods comprise administering to the subject a therapeutically effective amount of an antibody or an antigen-binding portion thereof that targets LAG3 and disrupts its interaction with galectin 9. Suitable antibodies that target TIM3 are disclosed in U.S. Patent Application 2013/0022623, herein incorporated by reference. It will be understood by one of ordinary skill that any antibody which binds to TIM3, disrupts its interaction with galectin 9, and stimulates an anti-tumor immune response, is suitable for use in the methods disclosed herein.

It should be understood that antibodies targeting immune checkpoints suitable for use in the methods disclosed herein are not limited to those described supra. Moreover, it will be understood by one of ordinary skill in the art that other immune checkpoint targets can also be targeted by antagonists or antibodies in the methods described herein, provided that the targeting results in the stimulation of an anti-tumor immune response as reflected in, e.g., an increase in T cell proliferation, enhanced T cell activation, and/or increased cytokine production (e.g., IFN-γ, IL-2).

IV. Cancer Vaccine

In some aspects, the disclosure provides immunomodulatory fusion proteins to be used or performed in conjunction with a cancer vaccine. In certain embodiments, the cancer vaccine stimulates a specific immune response against a specific target, such as a tumor-associated antigen.

In certain embodiments, the cancer vaccine includes viral, bacterial or yeast vectors to deliver recombinant genes to antigen presenting cells (APCs).

In certain embodiments the cancer vaccine uses autologous or allogeneic tumor cells. In certain embodiments, these tumor cells may be modified for expression of MEW, costimulatory molecules, or cytokines.

In certain embodiments, the tumor-associated antigen is determined by sequencing a patient's tumor cells and identifying mutated proteins only found in the tumor. These antigens are referred to as "neoantigens." Once a neoantigen has been identified, it can be used as the antigen for a vaccine or for developing monoclonal antibodies specifically reactive with the neoantigen.

In certain embodiments, the vaccine includes irradiated tumor cells transduced with cytokines such as GM-CSF or loaded with adjuvant compounds, such as the GM-CSF-secreting tumor cell vaccine GVAX (*Immunological Reviews*, 222(1): 287-298, 2008). In certain embodiments the vaccine includes one or more tumor-associated antigens in the form of an immunogenic composition, optionally in combination with an adjuvant. For example, vaccination against HPV-16 oncoproteins resulted in positive clinical outcomes for vulvar intraepithelial neoplasia (*The New England Journal of Medicine*, 361(19), 1838-1847, 2012). Also, multipeptide immune response to cancer vaccine IMA901 after single-dose cyclophosphamide associates with longer patient survival (*Nature Medicine*, 18(8): 1254-61, 2012). Alternatively, a DNA-based approach can be used to immunize a patient with one or more tumor-associated antigens. Improved tumor immunity is observed using a DNA vaccine in combination with an anti-tyrosinase related protein-1 monoclonal antibody in murine melanoma (*Cancer Research*, 68(23), 9884-9891,2008).

Other vaccine approaches utilize patient immune cells, such as dendritic cells which can be cultured with a tumor-associated antigen to produce antigen presenting cells that will stimulate the immune system and target the antigen of interest. A current FDA approved cancer treatment vaccine using this approach is Provenge® (Dendreon), approved for use in some men with metastatic prostate cancer. This vaccine stimulates an immune response to prostatic acid phosphatase (PAP), an antigen found on most prostate cancer cells. The vaccine is created by isolating a specific patient's immune cells and culturing dendritic cells with PAP to produce antigen presenting cells that will stimulate the immune system and target PAP. These and other cancer vaccines can be used in combination with other treatments as described herein.

A. Amphiphile Vaccines

In some embodiments, the cancer vaccine suitable for use with the immunomodulatory fusion proteins described herein is an amphiphile vaccine, as described in US 2013/0295129, herein incorporated by reference. An amphiphile vaccine combines an albumin-binding lipid and a peptide antigen or molecular adjuvant to efficiently target the peptide or adjuvant to lymph nodes in vivo. Lipid conjugates bind to endogenous albumin, which targets them to lymphatics and draining lymph nodes where they accumulate due to the filtering of albumin by antigen presenting cells. When the lipid conjugate includes an antigenic peptide or molecular adjuvant, the conjugates induce or enhance a robust immune response.

Lymph node-targeting conjugates typically include three domains: a highly lipophilic, albumin-binding domain (e.g., an albumin-binding lipid), a cargo such as a molecular adjuvant or a peptide antigen, and a polar block linker, which promotes solubility of the conjugate and reduces the ability of the lipid to insert into cellular plasma membranes. Accordingly, in certain embodiments, the general structure of the conjugate is L-P-C, where "L" is an albumin-binding lipid, "P" is a polar block, and "C" is a cargo such as a molecular adjuvant or a polypeptide. In some embodiments, the cargo itself can also serve as the polar block domain, and a separate polar block domain is not required. Therefore, in certain embodiments the conjugate has only two domains: an albumin-binding lipid and a cargo.

The cargo of the conjugates suitable for use in the methods disclosed herein is typically a molecular adjuvant such as an immunostimulatory oligonucleotide, or a peptide antigen. However, the cargo can also be other oligonucleotides, peptides, Toll-like receptor agonists or other immunomodulatory compounds, dyes, MM contrast agents, fluorophores or small molecule drugs that require efficient trafficking to the lymph nodes.

In certain embodiments, a lipid-oligonucleotide conjugates includes an immunostimulatory oligonucleotide which is conjugated directly to a lipid, or is linked to a linker which is conjugated to a lipid. Other embodiments are directed to lipid-peptide conjugates which include an antigenic peptide conjugated directly to a lipid, or is linked to a linker which is conjugated to a lipid.

Lipids

The lipid conjugates typically include a hydrophobic lipid. The lipid can be linear, branched, or cyclic. The lipid is preferably at least 17 to 18 carbons in length, but may be shorter if it shows good albumin binding and adequate targeting to the lymph nodes. Lymph node-targeting conjugates include lipid-oligonucleotide conjugates and lipid-peptide conjugates that can be trafficked from the site of delivery through the lymph to the lymph node. In certain embodiments, the activity relies, in-part, on the ability of the conjugate to associate with albumin in the blood of the subject. Therefore, lymph node-targeted conjugates typically include a lipid that can bind to albumin under physiological conditions. Lipids suitable for targeting the lymph node can be selected based on the ability of the lipid or a lipid conjugate including the lipid to bind to albumin. Suitable methods for testing the ability of the lipid or lipid conjugate to bind to albumin are known in the art.

For example, in certain embodiments, a plurality of lipid conjugates is allowed to spontaneously form micelles in aqueous solution. The micelles are incubated with albumin, or a solution including albumin such as Fetal Bovine Serum (FBS). Samples can be analyzed, for example, by ELISA, size exclusion chromatography or other methods to determine if binding has occurred. Lipid conjugates can be selected as lymph node-targeting conjugates if in the presence of albumin, or a solution including albumin such as Fetal Bovine Serum (FBS), the micelles dissociate and the lipid conjugates bind to albumin as discussed above.

Examples of preferred lipids for use in lymph node targeting lipid conjugates include, but are not limited to, fatty acids with aliphatic tails of 8-30 carbons including, but not limited to, linear unsaturated and saturated fatty acids, branched saturated and unsaturated fatty acids, and fatty acids derivatives, such as fatty acid esters, fatty acid amides, and fatty acid thioesters, diacyl lipids, cholesterol, cholesterol derivatives, and steroid acids such as bile acids, Lipid A or combinations thereof.

In certain embodiments, the lipid is a diacyl lipid or two-tailed lipid. In some embodiments, the tails in the diacyl lipid contain from about 8 to about 30 carbons and can be saturated, unsaturated, or combinations thereof. The tails can be coupled to the head group via ester bond linkages, amide bond linkages, thioester bond linkages, or combinations thereof. In a particular embodiment, the diacyl lipids are phosphate lipids, glycolipids, sphingolipids, or combinations thereof.

Preferably, lymph node-targeting conjugates include a lipid that is 8 or more carbon units in length. It is believed that increasing the number of lipid units can reduce insertion of the lipid into plasma membrane of cells, allowing the lipid conjugate to remain free to bind albumin and traffic to the lymph node.

For example, the lipid can be a diacyl lipid composed of two C18 hydrocarbon tails. In certain embodiments, the lipid for use in preparing lymph node targeting lipid conjugates is not a single chain hydrocarbon (e.g., C18), or cholesterol. Cholesterol conjugation has been explored to enhance the immunomodulation of molecular adjuvants such as CpG and immunogenicity of peptides, but cholesterol conjugates, which associate well with lipoproteins but poorly with albumin, show poor lymph node targeting and low immunogenicity in vaccines compared to optimal albumin-binding conjugates.

Molecular Adjuvants

In certain embodiments, lipid-oligonucleotide conjugates are used in the vaccine. The oligonucleotide conjugates typically contain an immunostimulatory oligonucleotide.

In certain embodiments, the immunostimulatory oligonucleotide can serve as a ligand for pattern recognition receptors (PRRs). Examples of PRRs include the Toll-like family of signaling molecules that play a role in the initiation of innate immune responses and also influence the later and more antigen specific adaptive immune responses. Therefore, the oligonucleotide can serve as a ligand for a Toll-like family signaling molecule, such as Toll-Like Receptor 9 (TLR9).

For example, unmethylated CpG sites can be detected by TLR9 on plasmacytoid dendritic cells and B cells in humans (Zaida, et al., *Infection and Immunity*, 76(5):2123-2129, (2008)). Therefore, the sequence of oligonucleotide can include one or more unmethylated cytosine-guanine (CG or CpG, used interchangeably) dinucleotide motifs. The 'p' refers to the phosphodiester backbone of DNA, as discussed in more detail below, some oligonucleotides including CG can have a modified backbone, for example a phosphorothioate (PS) backbone. In certain embodiments, an immunostimulatory oligonucleotide can contain more than one CG dinucleotide, arranged either contiguously or separated by intervening nucleotide(s). The CpG motif(s) can be in the interior of the oligonucleotide sequence. Numerous nucleotide sequences stimulate TLR9 with variations in the number and location of CG dinucleotide(s), as well as the precise base sequences flanking the CG dimers.

Typically, CG ODNs are classified based on their sequence, secondary structures, and effect on human peripheral blood mononuclear cells (PBMCs). The five classes are Class A (Type D), Class B (Type K), Class C, Class P, and Class S (Vollmer, J & Krieg, A M, *Advanced drug delivery reviews* 61(3): 195-204 (2009), incorporated herein by reference). CG ODNs can stimulate the production of Type I interferons (e.g., IFNα) and induce the maturation of dendritic cells (DCs). Some classes of ODNs are also strong activators of natural killer (NK) cells through indirect cytokine signaling. Some classes are strong stimulators of human B cell and monocyte maturation (Weiner, G L, PNAS USA 94(20): 10833-7 (1997); Dalpke, A H, Immunology 106(1): 102-12 (2002); Hartmann, G, J of Immun. 164(3): 1617-2 (2000), each of which is incorporated herein by reference).

According to some embodiments, a lipophilic-CpG oligonucleotide conjugate is used to enhance an immune response to a peptide antigen. The lipophilic-CpG oligonucleotide is represented by the following, wherein "L" is a lipophilic compound, such as diacyl lipid, "$G_n$" is a guanine repeat linker and "n" represents 1, 2, 3, 4, or 5.

$$5'\text{-}L\text{-}G_n\text{TCCATGACGTTCCTGACGTT-}3'$$

Other PRR Toll-like receptors include TLR3, and TLR7 which may recognize double-stranded RNA, single-stranded and short double-stranded RNAs, respectively, and retinoic acid-inducible gene I (RIG-I)-like receptors, namely RIG-I and melanoma differentiation-associated gene 5 (MDA5), which are best known as RNA-sensing receptors in the cytosol. Therefore, in certain embodiments, the oligonucleotide contains a functional ligand for TLR3, TLR7, or RIG-I-like receptors, or combinations thereof.

Examples of immunostimulatory oligonucleotides, and methods of making them are known in the art, see for example, Bodera, P. *Recent Pat Inflamm Allergy Drug Discov.* 5(1):87-93 (2011), incorporated herein by reference.

In certain embodiments, the oligonucleotide cargo includes two or more immunostimulatory sequences.

The oligonucleotide can be between 2-100 nucleotide bases in length, including for example, 5 nucleotide bases in length, 10 nucleotide bases in length, 15 nucleotide bases in length, 20 nucleotide bases in length, 25 nucleotide bases in length, 30 nucleotide bases in length, 35 nucleotide bases in length, 40 nucleotide bases in length, 45 nucleotide bases in length, 50 nucleotide bases in length, 60 nucleotide bases in length, 70 nucleotide bases in length, 80 nucleotide bases in length, 90 nucleotide bases in length, 95 nucleotide bases in length, 98 nucleotide bases in length, 100 nucleotide bases in length or more.

The 3' end or the 5' end of the oligonucleotides can be conjugated to the polar block or the lipid. In certain embodiments the 5' end of the oligonucleotide is linked to the polar block or the lipid.

The oligonucleotides can be DNA or RNA nucleotides which typically include a heterocyclic base (nucleic acid base), a sugar moiety attached to the heterocyclic base, and a phosphate moiety which esterifies a hydroxyl function of the sugar moiety. The principal naturally-occurring nucleotides comprise uracil, thymine, cytosine, adenine and guanine as the heterocyclic bases, and ribose or deoxyribose sugar linked by phosphodiester bonds. In certain embodiments, the oligonucleotides are composed of nucleotide analogs that have been chemically modified to improve stability, half-life, or specificity or affinity for a target receptor, relative to a DNA or RNA counterpart. The chemical modifications include chemical modification of nucleobases, sugar moieties, nucleotide linkages, or combinations thereof. As used herein 'modified nucleotide" or "chemically modified nucleotide" defines a nucleotide that has a chemical modification of one or more of the heterocyclic base, sugar moiety or phosphate moiety constituents. In certain embodiments, the charge of the modified nucleotide is reduced compared to DNA or RNA oligonucleotides of the same nucleobase sequence. For example, the oligonucleotide can have low negative charge, no charge, or positive charge.

Typically, nucleoside analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). In certain embodiments, the analogs have a substantially uncharged, phosphorus containing backbone.

Peptide Antigens

The peptide conjugates suitable for use in the methods disclosed herein typically include an antigenic protein or polypeptide, such as a tumor-associated antigen or portion thereof.

The peptide can be 2-100 amino acids, including for example, 5 amino acids, 10 amino acids, 15 amino acids, 20 amino acids, 25 amino acids, 30 amino acids, 35 amino acids, 40 amino acids, 45 amino acids, or 50 amino acids. In some embodiments, a peptide can be greater than 50 amino acids. In some embodiments, the peptide can be >100 amino acids. A protein/peptide can be linear, branched or cyclic. The peptide can include D amino acids, L amino acids, or a combination thereof. The peptide or protein can be conjugated to the polar block or lipid at the N-terminus or the C-terminus of the peptide or protein.

The protein or polypeptide can be any protein or peptide that can induce or increase the ability of the immune system to develop antibodies and T-cell responses to the protein or peptide. A cancer antigen is an antigen that is typically expressed preferentially by cancer cells (i.e., it is expressed at higher levels in cancer cells than on non-cancer cells) and in some instances it is expressed solely by cancer cells. The cancer antigen may be expressed within a cancer cell or on the surface of the cancer cell. The cancer antigen can be, but is not limited to, TRP-1, TRP-2, MART-1/Melan-A, gp100, adenosine deaminase-binding protein (ADAbp), FAP, cyclophilin b, colorectal associated antigen (CRC)—0017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain, and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-1, GAGE-2, GAGE-3, GAGE-4, GAGE-5, GAGE-6, GAGE-7, GAGE-8, GAGE-9, BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100Pmel117, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, 1mp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20, or c-erbB-2. Additional cancer antigens include the tumor antigens described herein.

Suitable antigens are known in the art and are available from commercial government and scientific sources. In certain embodiments, the antigens are whole inactivated or irradiated tumor cells. The antigens may be purified or partially purified polypeptides derived from tumors. The antigens can be recombinant polypeptides produced by expressing DNA encoding the polypeptide antigen in a heterologous expression system. The antigens can be DNA encoding all or part of an antigenic protein. The DNA may be in the form of vector DNA such as plasmid DNA.

In certain embodiments, antigens may be provided as single antigens or may be provided in combination. Antigens may also be provided as complex mixtures of polypeptides or nucleic acids.

Polar Block/Linker

For the conjugate to be trafficked efficiently to the lymph node, the conjugate should remain soluble. Therefore, a polar block linker can be included between the cargo and the lipid to increase solubility of the conjugate. The polar block reduces or prevents the ability of the lipid to insert into the plasma membrane of cells, such as cells in the tissue adjacent to the injection site. The polar block can also reduce or prevent the ability of cargo, such as synthetic oligonucleotides containing a PS backbone, from non-specifically associating with extracellular matrix proteins at the site of administration. The polar block increases the solubility of the conjugate without preventing its ability to bind to albumin. It is believed that this combination of characteristics allows the conjugate to bind to albumin present in the serum or interstitial fluid, and remain in circulation until the albumin is trafficked to, and retained in a lymph node. The length and composition of the polar block can be adjusted based on the lipid and cargo selected. For example, for oligonucleotide conjugates, the oligonucleotide itself may be polar enough to insure solubility of the conjugate, for example, oligonucleotides that are 10, 15, 20 or more nucleotides in length. Therefore, in certain embodiments, no additional polar block linker is required. However, depending on the amino acid sequence, some lipidated peptides can be essentially insoluble. In these cases, it can be desirable to include a polar block that mimics the effect of a polar oligonucleotide.

A polar block can be used as part of any of lipid conjugates suitable for use in the methods disclosed herein, for example, lipid-oligonucleotide conjugates and lipid-peptide conjugates, which reduce cell membrane insertion/preferential portioning onto albumin. Suitable polar blocks include, but are not limited to, oligonucleotides such as those discussed above, a hydrophilic polymer including but not limited to poly(ethylene glycol) (MW: 500 Da to 20,000 Da), polyacrylamide (MW: 500 Da to 20,000 Da), polyacrylic acid; a string of hydrophilic amino acids such as serine, threonine, cysteine, tyrosine, asparagine, glutamine, aspartic acid, glutamic acid, lysine, arginine, histidine, or combinations thereof polysaccharides, including but not limited to, dextran (MW: 1,000 Da to 2,000,000 Da), or combinations thereof.

The hydrophobic lipid and the linker/cargo are covalently linked. The covalent bond may be a non-cleavable linkage or a cleavable linkage. The non-cleavable linkage can include an amide bond or phosphate bond, and the cleavable linkage can include a disulfide bond, acid-cleavable linkage, ester bond, anhydride bond, biodegradable bond, or enzyme-cleavable linkage.

a. Ethylene Glycol Linkers

In certain embodiments, the polar block is one or more ethylene glycol (EG) units, more preferably two or more EG units (i.e., polyethylene glycol (PEG)). For example, in certain embodiments, a peptide conjugate includes a protein or peptide (e.g., peptide antigen) and a hydrophobic lipid linked by a polyethylene glycol (PEG) molecule or a derivative or analog thereof.

In certain embodiments, protein conjugates suitable for use in the methods disclosed herein contain protein antigen linked to PEG which is in turn linked to a hydrophobic lipid, or lipid-Gn-ON conjugates, either covalently or via formation of protein-oligo conjugates that hybridize to oligo micelles. The precise number of EG units depends on the lipid and the cargo, however, typically, a polar block can have between about 1 and about 100, between about 20 and about 80, between about 30 and about 70, or between about 40 and about 60 EG units. In certain embodiments, the polar block has between about 45 and 55 EG, units. For example, in certain embodiments, the polar block has 48 EG units.

b. Oligonucleotide Linkers

As discussed above, in certain embodiments, the polar block is an oligonucleotide. The polar block linker can have any sequence, for example, the sequence of the oligonucleotide can be a random sequence, or a sequence specifically chosen for its molecular or biochemical properties (e.g., highly polar). In certain embodiments, the polar block linker includes one or more series of consecutive adenine (A), cytosine (C), guanine (G), thymine (T), uracil (U), or analog thereof. In certain embodiments, the polar block linker consists of a series of consecutive adenine (A), cytosine (C), guanine (G), thymine (T), uracil (U), or analog thereof.

In certain embodiments, the linker is one or more guanines, for example between 1-10 guanines. It has been discovered that altering the number of guanines between a cargo such as a CpG oligonucleotide, and a lipid tail controls micelle stability in the presence of serum proteins. Therefore, the number of guanines in the linker can be selected based on the desired affinity of the conjugate for serum proteins such as albumin. When the cargo is a CpG immunostimulatory oligonucleotide and the lipid tail is a diacyl lipid, the number of guanines affects the ability of micelles formed in aqueous solution to dissociate in the presence of serum: 20% of the non-stabilized micelles (lipo-$G_0T_{10}$-CG) were intact, while the remaining 80% were disrupted and bonded with FBS components. In the presence of guanines, the percentage of intact micelles increased from 36% (lipo-$G_2T8$-CG) to 73% (lipo-$G_4T_6$-CG), and finally reached 90% (lipo-$G_6T_4$-CG). Increasing the number of guanines to eight (lipo-$G_8T_2$-CG) and ten (lipo-$G_{10}T_0$-CG) did not further enhance micelle stability.

Therefore, in certain embodiments, the linker in a lymph node-targeting conjugate suitable for use in the methods disclosed herein can include 0, 1, or 2 guanines. As discussed in more detail below, linkers that include 3 or more consecutive guanines can be used to form micelle-stabilizing conjugates with properties that are suitable for use in the methods disclosed herein.

B. Immunogenic Compositions

The conjugates suitable for use in the methods disclosed herein can be used in immunogenic compositions or as components in vaccines. Typically, immunogenic compositions disclosed herein include an adjuvant, an antigen, or a combination thereof. The combination of an adjuvant and an antigen can be referred to as a vaccine. When administered to a subject in combination, the adjuvant and antigen can be administered in separate pharmaceutical compositions, or they can be administered together in the same pharmaceutical composition. When administered in combination, the adjuvant can be a lipid conjugate, the antigen can be a lipid conjugate, or the adjuvant and the antigen can both be lipid conjugates.

An immunogenic composition suitable for use in the methods disclosed herein can include a lipid conjugate that is an antigen such as an antigenic polypeptide-lipid conjugate, administered alone, or in combination with an adjuvant. The adjuvant may be without limitation alum (e.g., aluminum hydroxide, aluminum phosphate); saponins purified from the bark of the *Q. saponaria* tree such as QS21 (a glycolipid that elutes in the 21 st peak with HPLC fractionation; Antigenics, Inc., Worcester, Mass.); poly[di(carboxylatophenoxy)phosphazene (PCPP polymer; Virus Research Institute, USA), Flt3 ligand, *Leishmania* elongation factor (a purified *Leishmania* protein; Corixa Corporation, Seattle, Wash.), ISCOMS (immunostimulating complexes which contain mixed saponins, lipids and form virus-sized particles with pores that can hold antigen; CSL, Melbourne, Australia), Pam3Cys, SB-AS4 (SmithKline Beecham adjuvant system #4 which contains alum and MPL; SBB, Belgium), non-ionic block copolymers that form micelles such as CRL 1005 (these contain a linear chain of hydrophobic polyoxypropylene flanked by chains of polyoxyethylene, Vaxcel, Inc., Norcross, Ga.), and Montanide IMS (e.g., IMS 1312, water-based nanoparticles combined with a soluble immunostimulant, Seppic).

Adjuvants may be TLR ligands, such as those discussed above. Adjuvants that act through TLR3 include, without limitation, double-stranded RNA. Adjuvants that act through TLR4 include, without limitation, derivatives of lipopolysaccharides such as monophosphoryl lipid A (MPLA; Ribi ImmunoChem Research, Inc., Hamilton, Mont.) and muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland). Adjuvants that act through TLR5 include, without limitation, flagellin. Adjuvants that act through TLR7 and/or TLR8 include single-stranded RNA, oligoribonucleotides (ORN), synthetic low molecular weight compounds such as imidazoquinolinamines (e.g., imiquimod (R-837), resiquimod (R-848)). Adjuvants acting through TLR9 include DNA of viral or bacterial origin, or synthetic oligodeoxynucleotides (ODN), such as CpG ODN. Another adjuvant class is phosphorothioate containing molecules such as phosphorothioate nucleotide analogs and nucleic acids containing phosphorothioate backbone linkages.

The adjuvant can also be oil emulsions (e.g., Freund's adjuvant); saponin formulations; virosomes and viral-like particles; bacterial and microbial derivatives; immunostimulatory oligonucleotides; ADP-ribosylating toxins and detoxified derivatives; alum; BCG; mineral-containing compositions (e.g., mineral salts, such as aluminium salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

Adjuvants may also include immunomodulators such as cytokines, interleukins (e.g., IL-1, IL-2, IL-4, IL-5, IL-6, IL-7, IL-12, etc.), interferons (e.g., interferon-.gamma.), macrophage colony stimulating factor, and tumor necrosis factor.

Kits

In some aspects, the disclosure provides kits comprising at least an immunomodulatory fusion protein described herein and instructions for use. In some embodiments, the kits comprise, in a suitable container, an immunomodulatory fusion protein, one or more controls, and various buffers, reagents, enzymes and other standard ingredients well known in the art. In some embodiments, the kits further comprise instructions for use in combination with an immunotherapy.

In some embodiments, the container is at least one vial, well, test tube, flask, bottle, syringe, or other container means, into which an immunomodulatory fusion protein may be placed, and in some instances, suitably aliquoted. When an additional component is provided, the kit can contain additional containers into which this compound may be placed. The kits can also include a means for containing an immunomodulatory fusion protein, and any other reagent containers in close confinement for commercial sale. Such containers may include injection or blow-molded plastic containers into which the desired vials are retained. Containers and/or kits can include labeling with instructions for use and/or warnings.

In some embodiments, the disclosure provides a kit comprising a container comprising an immunomodulatory fusion protein described herein, an optional pharmaceutically acceptable carrier, and a package insert comprising instructions for administration of the composition for treating or delaying progression of cancer in an individual receiving an immunotherapy (e.g., CAR-T cells, cancer vaccine, anti-tumor associated antigen antibody, and/or immune checkpoint blockade).

In some embodiments, the disclosure provides a kit comprising a medicament comprising an immunomodulatory fusion protein described herein, an optional pharmaceutically acceptable carrier, and a package insert comprising instructions for administration of the medicament alone or in combination with an immunotherapy (e.g., CAR-T cells, cancer vaccine, anti-tumor associated antigen antibody, and/ or immune checkpoint blockade), for treating or delaying progression of cancer in an individual receiving CAR-T cell therapy.

Other Embodiments—Collagen-Binding IgG-Binding Fusion Proteins

In another aspect, the disclosure provides collagen-binding IgG-binding fusion proteins comprising an Ig-binding domain and a collagen-binding domain. The collagen-binding IgG-binding fusion proteins provided by the disclosure bind to an IgG (e.g., an immunomodulatory IgG) and to collagen, thereby localizing or sequestering the IgG within a tumor when administered.

In some embodiments, the collagen-binding domain is a collagen-binding domain as described supra. Exemplary IgG binding domains include a dimerized Z domain (one of the five IgG binding domains of protein A, herein referred to as "ZZ") (Jendeberg et al., (1995) J Mol Recognit 8:270-278), a dimerized IgG binding domain of protein G (herein referred to as "SpG2") (Jung et al., (2009) Anal Chem 81:936-942), an IgG binder isolated from a Sso7d yeast display library (Gera et al., (2011) J Mol Biol 409:601-616), an IgG binder isolated from a Fibronectin type III domain (Fn3) yeast display library (Hackel et al., (2010) J Mol Biol 401:84-96), and two small peptides designed to bind IgG Fc regions (herein referred to as "Fc-III-4C" and "RRGW) (Gong et al., (2015) Bioconjug Chem 27:1569-1573; Tsai et al., (2014) Anal Chem 86:2931-2938).

In some embodiments, the collagen-binding IgG-binding fusion protein is suitable for use in any of the methods described herein. In some embodiments, the collagen-binding IgG-binding fusion protein is used in combination with a therapeutic antibody (e.g., an immunomodulatory antibody). In some embodiments, the collagen-binding IgG-binding fusion protein is administered in combination with a therapeutic antibody for the treatment of cancer.

EXAMPLES

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

Example 1: Recombinant Expression of Collagen-Binding Fusion Proteins in Mammalian Cells To evaluate the ability to express collagen-binding immunomodulatory molecules in mammalian cells, five His-tagged collagen-binding polypeptides fused to *Gaussia* Luciferase (Gluc) (collagen imaging probe (CNA35-Gluc), bacterial collagenase ColG domains s3a/s3b (ColG s3a/s3b-Gluc), heparin binding domain of murine placenta growth factor-2 (PLGF2HBD-Gluc), bacterial collagenase ColH domain s3 (ColH s3-Gluc), and murine protein lumican (Lumican-Gluc)) were transiently expressed in human embryonic kidney 293 (HEK293) cells. The amino acid sequences for these constructs are set forth in SEQ ID NOs: 128-132. Briefly, HEK293 cells (at 1 million cells/mL density) were transfected with sterile-filtered plasmid DNA (1 mg per liter cell culture) using polyethylenimine (2 mg per liter cell culture) in OptiPro serum-free media (20 mL per liter cell culture) (Thermo Fisher). TA99 was purified using rProtein A Sepharose Fast Flow resin (GE Healthcare) as previously described (Zhu et al. 2015). His-tagged proteins were isolated from HEK293 supernatant using TALON Metal Affinity Resin (Takara Bio Inc.). Cytokine-fusion proteins were then further purified by size exclusion chromatrography using a HiLoad 16/600 Superdex 200 pg column on an ÂKTA FPLC system (GE Healthcare) that had been pretreated for 4 hours with 1 M NaOH to remove endotoxin and subsequently equilibrated in sterile PBS (Corning). Following purification, all proteins were buffer exchanged into sterile PBS (Corning), 0.2 micron sterile-filtered (Pall Corporation) and confirmed to contain minimal levels of endotoxin (<0.1 EU per injection) using an chromogenic LAL assay (Lonza). To confirm their molecular weights, proteins were run alongside a Novex Prestained Sharp Protein Ladder on a 4-12% NuPAGE Bis-Tris protein gel (Life Technologies) with 1% IVIES running buffer. All proteins were stored at 4° C. but, prior to therapeutic injection, cytokine fusion proteins were warmed to room temperature to rescue lumican which demonstrates reversible cold denaturation. The relative expression levels of the His-tagged collagen-binding fusion proteins in the resulting eluates was evaluated by SDS-PAGE and by absorption spectrophotometry following size-exclusion chromatography of TALON-purification eluates.

Transient expression of Gluc (19.8 kDa) alone as well as Gluc-fused collagen-binding polypeptides ColG s3a/s3b-Gluc (46.1 kDa), ColH s3-Gluc (32.8 kDa), and Lumican-Gluc (56.6 kDa) in HEK293 cells was achieved, as determined by SDS-PAGE analysis of His-tagged proteins purified from HEK cell lysates. Protein staining at or near the respective expected molecular weight of each fusion protein was observed (data not shown). However, no expression was observed for CNA35-Gluc (54.4 kDa) or PLGF2HBD-Gluc (22.8 kDa) as measured by SDS-PAGE of protein purified from HEK cell lysates (data not shown).

Transient expression of Gluc, ColG s3a/s3b-Gluc, ColH s3-Gluc, and Lumican-Gluc in HEK293 cells was achieved, as determined by absorption spectrophotometry during size exclusion chromatography of recombinantly expressed and purified His-tagged proteins. A monomeric peak of UV radiation absorption at 280 nm (A280) was observed for each fusion protein (data not shown). No absorbance peaks were detected for CNA35-Gluc or PLGF2HBD-Gluc.

In addition to lumican, other mammalian collagen-binding polypeptides can be expressed as collagen-binding fusion proteins. The extracellular domain of the mammalian leukocyte-associated immunoglobulin-like receptor 1 (LAIR-1) protein is known to bind collagen (Lebbink et al., (2006) J Exp Med 203(6):1419-1425). Transient expression of the extracellular domain of His-tagged murine LAIR-1 (amino acid sequence set forth in SEQ ID NO: 181) in HEK293 as described above was achieved, as determined by absorption spectrophotometry during size exclusion chromatography of recombinantly expressed protein. LAIR-1 eluted as a monomeric peak as measured by UV radiation absorption at 280 nm (A280) (data not shown).

These results demonstrate that collagen-binding fusion proteins comprising prokaryotic or mammalian collagen-binding polypeptides express in mammalian cells. Expression of the His-tagged collagen-binding fusion proteins ColG s3a/s3b-Gluc, ColH s3-Gluc, and Lumican-Gluc as well as Gluc alone in HEK293 cells was achieved, while expression of CNA35-Gluc or PLGF2HBD-Gluc was not observed. Further, the extracellular domain of His-tagged LAIR-1 in HEK293 cells was expressed and purified. These results suggest that collagen-binding immunomodulatory molecules comprising a prokaryotic or mammalian collagen-binding polypeptide (e.g., ColG s3a/s3b, ColH s3, Lumican or LAIR) will express in mammalian cells.

Example 2: Recombinant Collagen-Binding Fusion Proteins Bind Collagen In Vitro

To evaluate the ability of collagen-binding immunomodulatory molecules to bind collagen, the collagen-binding fusion proteins expressed and purified as described in Example 1 were tested for their ability to bind to collagen I- and collagen IV-coated plates by ELISA. Briefly, collagen I (Gibco) and collagen IV (Corning) coated 96 well-plates were blocked at room temperature for 1 hour with PBS+ 0.1% wt/vol bovine serum albumin (BSA)+0.05% wt/vol Tween-20 (PBSTA) and then incubated with various concentrations of lumican in PBSTA for 3 hours at room temperature. The lumican had been prewarmed for 10 minutes at 37 C to reverse its denaturation mediated by cold temperatures. Wells were washed with PBSTA and then incubated with a horseradish peroxidase-conjugated polyclonal anti-6×His (ab1187, Abcam) at a 1:4000 dilution in PBSTA for 1 hour at room temperature. Wells were washed again with PB STA and then 1-Step Ultra TMB-ELISA Substrate Solution (Thermo Fisher Scientific) was added for 10 mins followed by 1 M sulfuric acid to stop the chromogenic reaction. Absorbance at 450 nm (corrected with a reference absorbance at 570 nm) measured using an Infinite M1000 microplate reader (Tecan). Wells with titrations of MSA served as a negative control.

Purified His-tagged collagen-binding fusion proteins Lumican-Gluc, ColG s3a/s3b-Gluc, and ColH s3-Gluc were evaluated by ELISA on a collagen I coated plate. As shown in FIG. 1A, only Lumican-Gluc and ColG s3a/s3b-Gluc bound to collagen I with a $K_D$ of 130 nM and 139 nM, respectively. ColH s3-Gluc did not bind collagen I specifically over Gluc background binding.

Purified His-tagged collagen-binding fusion proteins Lumican-Gluc, ColG s3a/s3b-Gluc, and ColH s3-Gluc were evaluated by ELISA on a collagen IV coated plate. As shown in FIG. 1B, Lumican-Gluc bound to collagen IV with a $K_D$ of 600 nM. ColG s3a/s3b-Gluc or ColH s3-Gluc did not bind collagen IV specifically over Gluc background binding.

Purified His-tagged murine LAIR-1 (denoted as mLAIR1-His) and His-tagged biotinylated lumican (denoted Lwt-His-b) were evaluated for binding to collagen type I by ELISA as a function of concentration. Binding was determined by ELISA using an anti-His antibody conjugated to horseradish peroxidase (HRP). As shown in FIG. 1C, LAIR-1 and lumican had similar binding affinity to collagen type I. Binding to a plate blocked with bovine serum albumin was also evaluated by ELISA. No binding was observed for either protein, indicating that measured binding to collagen type I was specific.

To further demonstrate the collagen-binding activity of the mammalian collagen-binding polypeptides described above, the ability of the purified His-tagged LAIR-1 and lumican collagen-binding polypeptides described in Example 1 to competitively bind collagen was tested.

Briefly, collagen I (Gibco) 96 well-plates was blocked at room temperature for 1 hour with PBS+0.1% wt/vol bovine serum albumin (BSA)+0.05% wt/vol Tween-20 (PBSTA) and then incubated with various concentrations of LAIR in the presence of 50 nM of biotinylated lumican in PBSTA for 3 hours at room temperature. The lumican and LAIR had been prewarmed for 10 minutes at 37 C to reverse its denaturation mediated by cold temperatures. Wells were washed with PBSTA and then incubated with a horseradish peroxidase-conjugated polyclonal Streptavidin-HRP at a 1:400 dilution in PBSTA for 1 hour at room temperature. Wells were washed again with PBSTA and then 1-Step Ultra TMB-ELISA Substrate Solution (Thermo Fisher Scientific) was added for 10 mins followed by 1 M sulfuric acid to stop the chromogenic reaction. Absorbance at 450 nm (corrected with a reference absorbance at 570 nm) measured using an Infinite M1000 microplate reader (Tecan). Wells with titrations of MSA served as a negative control. The results of a competition ELISA detecting lumican binding in the presence of varying concentration of LAIR on a collagen coated plate is shown in FIG. 1D.

To evaluate the stability of a collagen-binding polypeptide following purification, the collagen-binding activity of lumican after thawing from a frozen state in solution was tested. Briefly, collagen I Affinity ($K_D$) of lumican incubated with various excipients (trehalose (T), BSA (B), collagen (C), protein alone (P)) in different conditions after thawing from frozen: 37 C for 3 weeks (blue), 4 C for 3 weeks (gray), 4 C for 2 weeks followed by 37 for 1 week (red). The binding affinity of lumican, in the presence of excipient (trehalose, bovine serum albumin, and collagen), to collagen I after thawing from frozen was determined by ELISA as described previously. The binding of affinity ($K_D$) remained similar regardless of which excipient was used. However, the binding affinity was reduced by approximately 50-fold if lumican was not warmed to 37° C. prior to measurement (data not shown).

These results demonstrate that collagen-binding fusion proteins comprising prokaryotic (e.g., ColG s3a/s3b) or mammalian (e.g., lumican) collagen-binding polypeptides bind to collagen I (FIG. 1A). These results also demonstrate that a collagen-binding fusion protein comprising a mammalian collagen-binding polypeptide (e.g., lumican) binds to both collagen I and IV (FIG. 1B). Further, these results demonstrate that the extracellular domain of LAIR-1 and lumican compete for binding to collagen I (FIG. 1C, 1D). These results suggest that collagen-binding immunomodulatory molecules comprising prokaryotic or mammalian collagen-binding polypeptides (e.g., ColG s3a/s3b, lumican, and LAIR-1) will bind to collagen.

Example 3: Recombinant Collagen-Binding Fusion Proteins are Retained Following Intratumoral Injection Collagens type I and IV are components of the thick fibrotic capsule surrounding tumors and the perivascular basement membrane, respectively. To evaluate expression of collagen types I and IV in mouse tumors, mice were inoculated with 1 million 4T1, MC38 or B16F10 tumor cells on day 0. Tumors were excised on day 10 and fixed in 10% neutral buffered formalin overnight, then embedded in paraffin and section to 5 micron thickness (CryoStar NX70). The tumor cross-sections were assessed for presence of collagen types I and IV by immunohistochemistry. Briefly, sections were stained with rabbit antibodies against collagen type I (ab34710, Abcam) and collagen type IV (ab6586, Abcam) at a 1:500 dilution in Tris-buffered saline with 0.1% vol/vol Tween-20, followed by a secondary staining using goat HRP-conjugated anti-rabbit antibody (ab6721, Abcam). Cross-sections of 4T1 (left), MC38 (middle), and B16F10 (right) tumors showed positive staining for collagen type I (top) and collagen type IV (bottom) (data not shown). Thus, collagen types I and IV are abundantly expressed in several syngeneic murine tumor models.

To evaluate the intratumoral retention of collagen-binding immunomodulatory molecules, the collagen-binding fusion proteins that bound to collagen I in Example 2 (Lumican-Gluc and ColG s3a/s3b-Gluc) were tested for their ability to remain associated at the site of intratumoral injection by in vivo fluorescence imaging. Briefly, $5 \times 10^5$ 4T1 cells (murine mammary carcinoma cells) were injected into the mammary fat pad of BALB/c mice followed by intratumoral injection of Gluc alone, GolG s3a/s3b-Gluc, or Lumican-Gluc on day 7 post-tumor cell injection. Immediately after intratumoral injection, each mouse was monitored by in vivo bioluminescence imaging (epi-illumination, autoexposure settings).

The bioluminescent signal from the mouse injected Gluc alone decreased to a background level approximately 36 hrs. post injection (data not shown). The signal from the mouse injected with ColG s3a/s3b-Gluc decreased to a background level approximately 8.5 days and post-injection (data not shown). The signal from the mouse injected with Lumican-Gluc did not decrease below background level for the duration of the experiment (approximately 16.5 days post injection, data not shown).

These results demonstrate that the collagen-binding fusion proteins ColG s3a/s3b-Gluc and Lumican-Gluc are physically retained at the site of intratumoral injection over time. These results suggest that collagen-binding immunomodulatory molecules comprising a prokaryotic or mammalian collagen-binding polypeptide (e.g., ColG s3a/s3b or Lumican) will exhibit intratumoral retention and limited systemic dissemination.

Example 4: Intratumoral Retention of Collagen-Binding Fusion Proteins Depend on Molecular Weight and Collagen Binding Activity Several factors may dictate the intratumoral retention of a collagen-binding fusion protein: affinity for collagen, collagen concentration, size-dependent escape by diffusion or convection, and protein turnover. As a protein under 60 kDa, lumican (37 kDa) faces high permeability across vascular endothelium and is vulnerable to absorption into circulation, which may contribute to distribution away from the injection site and a decrease in intratumoral retention (McLennan et al., (2005) Drug Discov Today Technol 2:89-96; Egawa et al., (2013) Sci Rep 3:1932).

To evaluate the effect of molecular weight on the intratumoral retention and systemic distribution of collagen-binding immunomodulatory molecules, the retention of the collagen-binding polypeptide lumican fused to the 67 kDa mouse serum albumin (MSA) protein after intratumoral injection was determined by in vivo fluorescence imaging. Briefly, for tumor inoculation of B16F10-Trp2KO, $10^6$ cells resuspended in 50 uL of sterile PBS were injected subcutaneously into the right flanks of C57BL/6 female mice. Fusion proteins were labeled with five-molar excess of Alexa Fluor 647 NHS Ester (Life Technologies) for 30 minutes in PBS adjusted to pH 8. Excess dye was removed using a PD10 Desalting Column (GE Healthcare) and degree of labeling (DOL) for each protein calculated. Proteins compared in retention studies contained equimolar amount of dye. For Lumican-MSA (SEQ ID NO: 126) and MSA (SEQ ID NO: 183), 0.11 nmol of each construct (110 ug of Lumican-MSA and 71.7 ug of MSA was administered) was injected intratumorally into mice bearing B16F10-Trp2KO tumors five days after inoculation.

For assessing fusion protein retention, mice were imaged with a Xenogen IVIS Imaging System 100 (Xenogen) at indicated time points under auto-exposure epi-illumination fluorescence settings. During this time, mice were maintained on an alfalfa-free casein chow (Test Diet) to minimize gastrointestinal background fluorescence. Image analysis to determine total radiant efficiency was performed using Living Image (Caliper Life Sciences). B16F10 cells lacking tyrosinase-related protein-2, B16F10-Trp2KO, were used to inoculate tumors without pigmentation in order to maximize the fluorescence signal-to-noise.

Fluorescently-labeled Lumican, Lumican-MSA, or MSA were intratumorally injected and mice were monitored for total radiant efficiency over time. The fluorescent signal from lumican (37 kDa) was retained to a greater extent than the fluorescent signal from MSA (67 kDa) during the first 5 hours post-injection (data not shown) despite the smaller molecular weight of lumican. These data suggest that the intratumoral retention of lumican is dependent, at least in part, on its collagen binding activity. The fluorescent signal from lumican-MSA was also retained to a greater extent than the fluorescent signal from MSA (FIG. 2A). Lumican-MSA (104 kDa) is significantly larger than lumican (37 kDa), and although they each possess an identical collagen binding site, lumican-MSA is retained to a greater extent than lumican alone (FIG. 2A), presumably due to more rapid clearance of the smaller lumican construct.

To further evaluate the effect of molecular weight on the systemic distribution, the amount of fluorescence from serum of mice injected with fluorescently-labeled lumican fused to MSA over time was determined. Fluorescently-labeled MSA was used as a comparator. For assessing serum fluorescence after injection, a small volume of blood (<10 uL) was drawn by capillary action into glass micro-hematocrit heparin coated tubes (VWR) from the tip of the tail at indicated time points. Tubes were sealed at one end with parafilm and stored upright protected from the light at 4 C to allow serum separation from clotted blood by gravity. Tubes were scanned using a flatbed Typhoon Trio Variable Mode Imager (GE Healthcare) (excitation laser: 633 nm; emission filter: 670 BP; PMT: 450-500 V) and serum fluorescence quantified using Fiji image analysis software.

As shown in FIG. 2B, the fluorescence signal from serum of mice injected with lumican-MSA was lower over time compared to the fluorescence signal from serum of mice injected with MSA as a % of injected dose. These results demonstrate that lumican-MSA exhibits less systemic distribution than MSA alone.

Lumican co-localization with collagen types I and IV was assessed following intratumoral administration by immunofluorescence imaging. Briefly, B16F10 tumors were excised following intratumoral injection of fluorescently-labeled lumican. The tumors were preserved overnight in periodate-lysine-paraformaldehyde at 4° C., then cryoprotected with 30% sucrose in PBS for 8 hours at 4° C., and then frozen slowly in a cryomold containing 100% OCT compound (Sakura Finetek USA Inc.) on dry ice. Frozen tumor molds were sectioned to 50 micron thickness (CryStar NX70), and sections were dried at room temperature for an hour prior to antigen retrieval. For antigen retrieval, tissue sections were heated at 60° C. in 10 mM sodium citrate with 0.05% Tween20 for 1 hour, washed in PBS, and then treated with 2 mg/mL of hyaluronidase for 30 minutes at room temperature. Sections were washed in immunomix (PBS containing 0.2% wt/vol bovine serum albumin, 0.05% wt/vol sodium azide, 0.3% vol/vol Triton X-10, 10% vol/vol donkey serum), then permeabilized with cold acetone for 10 minutes at −20° C., and then blocked in Immunomix for 1 hour at room temperature. Staining was performed with rabbit antibodies against collagen type I (ab34710, Abcam) and collagen type IV (ab6586, Abcam) at a 1:200 dilution in Immunomix overnight at room temperature in a humidifying chamber. After several PBS washes, sections were stained with secondary AF488-conjugated goat anti-rabbit antibody at 1:500 dilution in Immunomix overnight at room temperature in a humidifying chamber. After several washes, sections were fixed in 1% neutral buffered formalin in PBS and mounted in VECTASHIELD anti-fade mounting medium. Sections were imaged by confocal microscopy. By overlaying fluorescent signal of collagen type I or type IV with fluorescent signal of lumican, it was determined that lumican co-localized with both collagen type I and type IV in B16F10 tumors to a high extent (data not shown).

These results demonstrate that both affinity to collagen and increased molecular weight contribute the intratumoral retention and systemic distribution of collagen-binding fusion proteins. These results suggest that increasing the affinity to collagen and the molecular weight of a collagen-binding immunomodulatory molecule will increase intratumoral retention and decrease systemic distribution, thereby increasing therapeutic effect.

Example 5: Proximity to Bound Collagen Decreases Payload Activity of Collagen-Binding Fusion Proteins To evaluate the effect of collagen-binding on payload activity, the intratumoral bioluminencence of Lumican-Gluc compared to ColG-Gluc was compared in vivo. Briefly, equimolar amounts (0.3 nmol) of Lumican-Gluc or GolG-Gluc were intratumorally injected into B16F10 melanoma tumor-bearing mice. Less intratumoral bioluminescence was observed with Lumican-Gluc compared to ColG-Gluc despite an equimolar (0.3 nmol) injection. Specifically, ⅘ mice injected with ColG-Gluc had detectable bioluminescence over background, while only ⅕ mice injected with Lumican-Gluc had detectable bioluminescence over background (data not shown). Interestingly, bioluminescence signal was only detected outside the tumor, presumably from construct that was leaking out of the tumor. The lack of intratumoral bioluminescence from collagen-bound constructs suggests that the enzyme is not optimally functional when forced into close proximity to collagen. This result informs the need for a spacer protein, like MSA, to help better separate collagen from any future payload.

Since collagen is an insoluble protein and thus susceptible to solid-phase behavior like surface adsorption of proximal soluble proteins, the MSA acts as a large hydrophilic spacer protein between the payload and lumican to protect the payload from adsorption and functional denatuation. For our localization approach, any soluble payload is forced into the solid-liquid interface by lumican and can be adsorbed onto a collagen fiber potentially rendering it functionally inert (as seen with Gluc). To prevent adsorption of our payload onto collagen, we operably link mouse serum albumin (MSA) to lumican as a large spacer protein between the payload and collagen.

Example 6: Synergistic Effect of Immunomodulatory Collagen-Binding Molecules and Anti-Tumor Antigen Antibody in Mouse Melanoma Tumor Model The synergy between anti-tumor antigen antibody and interleukin-2 (IL-2) is well characterized (Zhu et al., (2015) Cancer Cell 27:489-501). The effect of fusing IL-2 to collagen-binding molecules was evaluated by preparing IL-2 fused to the C-terminus of Lumican-MSA. MSA was incorporated to ensure steric access of receptors to IL-2 when bound to collagen fibrils and also to increase the construct's molecular weight and thereby reduce diffusive flux from the tumor. As an equivalently bioactive comparator, IL-2 was expressed as a fusion to MSA (MSA-IL2), allowing the effects of collagen binding to be largely separated from size-based improvements in tumor retention of small cytokines like wild-type IL-2. Thus, IL-2 was expressed as a fusion to MSA alone or as a fusion to the C-terminus of Lumican-MSA using the methods described in Example 1. His-tagged cytokine-fusion proteins were purified by TALON metal affinity resin as described in Example 1. Cytokine-fusion proteins were further purified by FPLC (AKTA, GE Healthcare) using a size exclusion chromatography column (HiLoad 16/600 Superdex 200 pg) that had been pre-treated for 4 hours with 1M NaOH to remove endotoxin, then subsequently equilibrated in sterile PBS. After purification, the proteins were buffer exchanged into sterile PBS, sterile filtered by a 0.2 micron membrane filter (Pall Corporation) and confirmed to contain minimal endotoxin (<0.1EU per dose) using a chromogenic LAL assay (Lonza).

The proteins demonstrated >90% monomeric expression when evaluated by absorbance at 280 nm during size exclusion chromatography (data not shown). Additionally, the ability of the proteins to induce cell proliferation was evaluated. CTLL-2 cells were seeded on tissue culture plates either uncoated or coated with collagen type IV at a density of 5000 cells/well. The cells were stimulated with various concentrations of MSA-IL2, Lumican-MSA-IL2, or Lumican for 48 hours. Cell proliferation was determined by WST-1 based colorimetric assay (Roche) according to manufacturer's instructions. While Lumican resulted in no proliferation, treatment with MSA-IL2 and Lumican-MSA-IL2 resulted in similar levels of cell proliferation, regardless of the presence or absence of collagen type IV (data not shown). Thus, MSA-IL2 and Lumican-MSA-IL2 have equivalent bioactivity.

Additionally, serum levels of the IL-2 fusions following intratumoral injection were quantified as described in Example 4. Fluorescently-labeled lumican-MSA-IL2 and MSA-IL2 were injected into B16F10-Trp2KO tumors, and serum fluorescence levels were quantified following injection at different time points. The fluorescence signal from serum of mice injected with lumican-MSA-IL2 was lower as over time as compared to the fluorescence signal from serum of mice injected with MSA-IL2 when measured as a % of injected dose (data not shown). These results demonstrate that lumican-MSA-IL2 binds to intratumoral collagen in vivo and as a result, exhibits less systemic distribution than MSA-IL2 alone.

To characterize the anti-tumor efficacy of combinations of immunomodulatory collagen-binding molecules with tumor antigen-targeting antibodies, fusion proteins comprising a collagen-binding polypeptide fused to the cytokine IL-2 were assessed for synergy with a mouse monoclonal anti-TYRP1 antibody (TY99) in a B16-F10 melanoma model.

Briefly, C57BL/6 mice aged 6-8 weeks were injected subcutaneously into the right flanks with $1\times10^6$ B16-F10 mouse melanoma cells (ATCC) in 50 µL sterile PBS. Mice with established B16-F10 melanoma tumors were treated systemically with 100m/dose anti-TYRP-1 antibody (TA99) via intraperitoneal (i.p.) injection and with 13 µl, g/dose of the collagen-binding IL-2 fusion protein lumican-MSA-IL2 via intratumoral injection (i.tu.). Mice injected with MSA-IL2 (SEQ ID NO: 121) (9m/dose) or lumican (SEQ ID NO: 182) (4 µg/dose) were used as comparators. Mice injected with IL-2 fusion proteins (lumican-MSA-IL2 (SEQ ID NO: 120) or MSA-IL2) received the equivalent of 0.11 nmol/dose of IL-2. Animals were euthanized at a euthanasia endpoint, which was either 20% total body weight loss or tumor area exceeding 100 mm² (length×width).

Percent survival of mice with tumors treated with MSA-IL2, lumican-MSA-IL2, lumican alone or in combination with TA99 is shown in FIG. 3A-3B. Monotherapy of mice administered lumican-MSA-IL2 or MSA-IL2 alone imparted a limited survival benefit (FIG. 3A). The combination of TA99 and lumican provided no survival benefit (FIG. 3B), however, administration of a combination of TA99 and either MSA-IL-2 or lumican-MSA-IL2 showed a synergistic survival benefit to mice (FIG. 3B). The combination with lumican-MSA-IL2 imparted a greater survival benefit compared to the combination with MSA-IL2 (FIG. 3B).

After cessation of treatment, several mice developed localized skin depigmentation or vitiligo which is indicative of a melanocyte-specific T cell response. Nearly all mice injected with lumican-MSA-IL2 and TA99 developed a patch of vitiligo localized to the site of injection (16 out of 17 mice) whereas only one out of 17 mice treated with MSA-IL2 and TA99 displayed this side effect. Together, these observations indicate that lumincan-MSA-IL2 anchors IL-2 intratumorally and enhances IL-2's synergy with TA99 by increasing anti-tumor T cell responses and overall survival.

To determine if intratumoral injection of lumican-MSA-IL-2 was necessary for the improved outcomes when used in combination with TA99, we evaluated the efficacy of this combination when lumican-MSA-IL2 was injected into other corporeal sites. When lumican-MSA-IL2 was administered peritumorally (peri.tu) (i.e. adjacent to the lesion) (FIG. 3C) or intranodally (i.e. into the tumor draining inguinal lymph node) (FIG. 3D), efficacy was attenuated. All survival benefit of the combination diminished when lumican-MSA-IL2 was administered subcutaneously at the tail base, 2 cm distal to the tumor site (FIG. 3C).

These results show that treatment of tumor-bearing mice with lumican-MSA-IL2 in combination with TA99 provides a synergistic anti-tumor effect and that intratumoral localization of IL-2 is required for maximal efficacy of this combination therapy.

Example 7: Synergistic Effect of Immunomodulatory Collagen-Binding Molecules and Anti-Tumor Antigen Antibody is Dependent on CD8+ T Cells, Dendritic Cells, and IFNγ

High dose IL-2 supports the proliferation and effector functions of T cells and NK cells, but also promotes neutrophilia and eosinophilia (Macdonald et al., (1990) Br J Haematol 76(2):168-173; Li et al., (1996) Inflammation 20(4):361-372). Given the known diverse effects of IL-2 on immune cells, the contribution of distinct leukocytes types to the therapeutic efficacy of lumican-MSA-IL2 was determined by antibody-mediated cellular depletions. Immune cell subsets or IFNγ were depleted by intraperitoneal (i.p.) administration of depleting antibody beginning one day before the first treatment until one week after the last treatment. TA99 and lumican-MSA-IL2 were administered as described for FIG. 3B. CD8+ T cells, NK cells or neutrophils were depleted using 400 µg of anti-CD8a (2.43, BioXCell), anti-NK1.1 (PK136, BioXCell), or anti-Ly6G (1A8, BioXCell) antibody every four days, respectively. Macrophages or soluble IFNγ were depleted using 300 µg of anti-CSF1R (AFS98, BioXCell) or 200 µg of anti-IFNγ (XMG1.2, BioXCell) every other day, respectively. Eosinophils were depleted using 1 mg of anti-IL-5 (TRFK5, BioXCell).

To assess contribution of immune cell subsets, 6-8 week old C57BL/6 wildtype (WT) or BatF3$^{-/-}$ mice (B6.129S(C)-Batf3$^{tm1Kmm}$/J Jackson Laboratory), which are deficient in cross-presenting dendritic cells (DCs), were injected subcutaneously into the right flanks with $1\times10^6$ B16-F10 mouse melanoma cells (ATCC) in 50 µL sterile PBS. Depletion of natural killer (NK) in WT mice did not alter efficacy of lumican-MSA-IL2 in combination with TA99 (FIG. 4). Depletion of neutrophils, eosinophils, or macrophages in wildtype mice also did not alter efficacy of lumican-MSA-IL2 in combination with TA99 (data not shown), indicating that no single innate cell population was solely responsible for tumor control. However, depletion of CD8+ T cells (anti-CD8α), cross-presenting DCs (BatF3$^{-/-}$), and IFNγ (anti-IFNγ) did alter efficacy of treatment indicating that they were indispensable for tumor rejection (FIG. 4). Survival statistics were determined by log-rank Mantel-Cox test.

These results show that treatment of tumor-bearing mice with lumican-MSA-IL2 in combination with TA99 provides a synergistic anti-tumor effect that is dependent on CD8+ T cells, dendritic cells and IFNγ.

Example 8: Combination of Immunomodulatory Collagen-Binding Molecules and Anti-Tumor Antigen Antibody Establishes Protective Memory and Induces Systemic Tumor-Specific Cellular Immunity The durable disease-free survival and the reliance on components of adaptive immunity observed after treatment with lumican-MSA-IL2 in combination with TA99 as shown above suggested that cured tumor-free mice might be resistant to tumor re-challenge. To determine if cured tumor-free mice treated with lumican-MSA-IL2 in combination with TA99, cured C57BL/6 mice from the experiment shown in FIG. 3B were re-challenged on day 100 with $1\times10^6$ B16-F10 cells inoculated on the contralateral flank. A majority of long-term survivors treated with lumican-MSA-IL2 in combination with TA99 rejected a rechallenge with B16-F10 inoculated on the contralateral flank (9/15 mice).

Although tumor eradication by cell-mediated immunity requires systemic immune activation (Spitzer et al., (2017) Cell 168:487-502), the strictly localized patch of vitiligo observed following treatment with lumican-MSA-IL2 in combination with TA99 (see Example 6) prompted an evaluation of tumor-specific T cell responses outside the treated tumor lesion. To determine if treatment with lumican-MSA-IL2 in combination with TA99 induces a systemic anti-tumor T cell response, an IFNγ ELISPOT was performed using splenocytes harvested four days after treatment of mice as described in FIG. 3B. Treatment with TA99 in combination with MSA-IL2 or lumican were used as comparators. The number of IFNγ spot forming units (SFUs) in response to stimulation with B16F10 target cells was quantified. Treatment with TA99 in combination with lumican-MSA-IL2 yielded more peripheral splenocytes expressing IFNγ than in combination with MSA-IL2. Specifically, treatment with TA99+Lumican-MSA-IL2 resulted in approximately 20 SFUs per 1 million splenocytes, while treatment with TA99+MSA-IL2, with TA99+lumican, or no treatment resulted in less than approximately 7 SFUs per 1 million splenocytes.

To confirm the intracellular IFNγ staining on splenocytes was generated by tumor-specific CD8+ T cells, splenocytes were harvested four days after treatment of mice as described in FIG. 3B. Harvested splenocytes were simulated with irradiated B16-F10 or 4T1 for 12 hours in the presence of brefeldin A and subsequently stained for surface markers (CD4, CD3 and CD8) and intracellular IFNγ (n=5 mice/group). FIG. 5A shows the quantification of IFNγ+ cells among live CD45+CD3+CD8+ T cells as determined by flow cytometry. Data were analyzed by one-way ANOVA with Tukey's multiple comparison test.

The results shown in FIG. 5A demonstrate that stimulation with irradiated B16-F10 tumor cells, but not 4T1 tumor cells, induced the expression of IFNγ in splenocytes, confirming that peripheral B16F10-specific CD8+ T cell responses in spleen were induced by treatment of tumor-bearing mice with lumican-MSA-IL2 in combination with TA99. These results also show that treatment of tumor-bearing mice with TA99 in combination with tumor collagen-anchored lumican-MSA-IL2 induced a greater tumor-specific systemic response than in combination with unanchored MSA-IL2.

To determine the ability of peripheral effectors (e.g., peripheral tumor-specific T cells) induced by treatment with TA99 in combination with lumican-MSA-IL2 to control a distant untreated tumor lesion where exogenous cytokine support is limited, mice were inoculated $1\times10^6$ B16-F10 cells subcutaneously to establish tumors on both flanks and administered TA99 systemically (i.p) and IL-2 (as lumican-MSA-IL2 or MSA-IL2) intratumorally (i.tu) into only the right, or ipsilateral, tumor. FIG. 5B shows the mean tumor areas for uninjected contralateral tumors and for intratumorally-injected ipsilateral tumors over time. The results shown in FIG. 5B demonstrate that the combination of TA99 with MSA-IL2, which can leak out of the ipsilateral tumor and to the contralateral lesion after injection, imparted some contralateral tumor control but most mice succumbed to tumor burden. In contrast, the combination of TA99 with lumican-MSA-IL2, which is isolated to the ipsilateral tumor, halted both ipsilateral and contralateral tumor growth leading to durable cures in several mice. These results show systemic anti-tumor response elicited by anchoring IL-2 via tumor collagen-binding is superior to diffuse IL-2 stimulation in controlling and eradicating disseminated disease.

Example 9: Treatment of Tumor-Bearing Mice with a Collagen-Binding IL-12 Fusion Protein Does Not Induce IL-12-Related Weight Loss After observing improvement of anti-tumor therapeutic effects by collagen-anchoring of IL-2 as shown in the Examples above, the effect(s) of anchoring IL-12, another dose-limited cytokine, to collagen was evaluated. IL-12 acts as a key regulator in type-1 cell mediated immunity, a pathway known to be critical for effective anti-tumor responses (Green et al., (2017) J Biol Chem 292:13925-13933). Despite promising preclinical work, severe toxicities and fatalities halted an early clinical trial administering systemic IL-12 (Lasek et al., (2014) Cancer Immunol Immunother 63(5):419-435). IFNγ, induced by IL-12 stimulation of NK cells and T cells, was implicated in the toxicity, however, IL-12 is also inextricably coupled to its efficacy (Leonard et al., (1997) Blood 90:2541-2548).

Thus, IL-12 was expressed and purified as a fusion to MSA alone or as a fusion to the N-terminus of Lumican-MSA (IL12-MSA-Lumican) using the methods described in Examples 1 and 6. Briefly, murine IL-12 was expressed in a single chain format with a 15 amino acid glycine-serine linker between the p40 and p35 subunits (scIL12). To generate a collagen-anchoring version of IL-12, scIL12 was fused to the N-terminus of lumican with an MSA spacer, henceforth referred to as IL12-MSA-Lumican (SEQ ID NO: 123). IL12-MSA (SEQ ID NO: 122), a non-anchoring version of IL-12, was used as a comparator. The IL12-MSA and IL12-MSA-Lumican proteins demonstrated >90% monomeric expression when evaluated by absorbance at 280 nm during size exclusion chromatography (data not shown).

Additionally, serum levels of the IL-12 fusions following intratumoral injection were quantified as described in Example 4. Fluorescently-labeled IL12-MSA-lumican and IL12-MSA were injected into B16F10-Trp2KO tumors, and serum fluorescence levels were quantified following injection at different time points. The fluorescence signal from serum of mice injected with IL12-MSA-lumican was lower as over time as compared to the fluorescence signal from serum of mice injected with IL12-MSA when measured as a % of injected dose (data not shown). These results demonstrate that IL12-MSA-lumican binds to intratumoral collagen in vivo and as a result, exhibits less systemic distribution than IL12-MSA alone.

To determine if retaining IL-12 to the tumor via collagen-binding would ameliorate IL-12-mediated toxicities, IL-12 fused to lumican-MSA was evaluated in a mouse melanoma tumor model. C57BL/6 mice, aged 6-8 weeks, were inoculated with 1×10⁶ B16-F10 melanoma cells on day 0. Weight change from baseline of these mice was monitored after treatment with either intratumoral (i.tu.) injections of PBS (n=6), 17.8 μg/dose IL12-MSA (n=7), or 23.1 μg/dose IL12-MSA-Lumican (n=7), or intraperitoneal (i.p.) injection of 17.8 μg/dose IL12-MSA (n=7) on day 6 and day 12. Mice injected with IL-12 fusion proteins (IL12-MSA-lumican or IL12-MSA) received the equivalent of 140 pmol/dose of IL-12.

As shown in FIG. 6A, intratumoral administration of IL12-MSA in B16-F10 tumor-bearing mice lead to significant weight loss, a noninvasive readout for systemic cytokine (e.g., IFNγ) toxicity. Systemic administration of IL12-MSA by intraperitoneal injection resulted in an identical weight loss profile. In contrast, an equimolar intratumoral injection of IL12-MSA-Lumican did not cause weight loss. Collectively, these results demonstrate that local administration in the absence of an effort towards intratumoral retention via collagen binding is insufficient in alleviating IL-12-mediated toxicity and that collagen-anchoring provided sufficient intratumoral confinement to curb overt systemic toxicities of IL-12, resulting in improved therapeutic index.

The survival of animals treated as in FIG. 6A was also evaluated. Mice were euthanized according to the criteria described in Example 6. As shown in FIG. 6B, treatment with an IL12 fusion improved survival over untreated control mice or mice treated with lumican. Treatment with IL12-MSA-Lumican resulted in a modest improvement in survival compared to IL12-MSA.

The dose of IL12 used to treat B16F10 tumors was titrated to determine dose-dependent effects on toxicity and anti-tumor efficacy. Mice inoculated with B16F10 tumors on day 0 as described above were treated on day 5 with an intratumoral injection of IL12-MSA or IL12-MSA-Lumican at different doses. Untreated control mice received an intratumoral injection of PBS. The effect of dose was evaluated on tumor area (e.g., measure of efficacy) and % weight change (e.g., measure of toxicity). The doses of IL12-MSA and IL12-MSA-Lumican that were evaluated included the mass equivalent of 140 pmol IL12, 14 pmol IL12, 1.4 pmol IL12, or 0.14 pmol IL12. IL12-MSA-Lumican showed no toxicity at any dose tested, but demonstrated reduced efficacy at a 1.4 or 0.14 pmol dose of IL12 (data not shown). While IL12-MSA demonstrated both reduced toxicity and reduced efficacy with decreased dose (data not shown). Thus to evaluate IL12 fusions in combination with other therapeutic agents, a 14 pmol IL12 dose was identified as having a tolerable toxicity index while maintaining therapeutic efficacy.

Example 10: Synergistic Anti-Tumor Effect of Collagen-Binding IL-2 and IL-12 Fusion Proteins In a Mouse Tumor Model Combinations to potentiate the anti-tumor effects of IL-12 have been theorized but safety concerns have largely precluded their actualization (Lasek et al., (2014) Cancer Immunol Immunother 63(5):419-435). The improved therapeutic index of IL12-MSA-lumican, as indicated by the absence of treatment-related weight loss in Example 9, prompted the evaluation of this cytokine in combination with other therapeutic agents. IL-2 and IL-12 are known to engage complementary signaling pathways to stimulate NK cells and T cells (Wigginton & Wiltrout (2002) Expert Opin Biol Ther 2:513-524) Additionally, IL-2 upregulates the expression of a IL-12 receptor subunit beta 2 (Wang et al., (2000) Blood 95:3183) and IL-12 sustains surface expression the high-affinity IL-2 receptor CD25 (Starbeck-Miller et al., (2013) J Exp Med 211:105-120). By reciprocal positive feedback, IL-2 and IL-12 augment and prolong the effect of each other (Wigginton et al., (1996) J Natl Cancer Inst 88:38-43). Despite promising efficacy, several clinical trials around this combination have been terminated (Wigginton & Wiltrout (2002) Expert Opin Biol Ther 2:513-524; Gollob et al., (2003) J Clin Oncol 21:2564-2573; Addison et al., (1998) Gene Ther 5:1400-1409; Wigginton et al., (2001) J Immunol 166:1156-1168). Notably, the combination of IL-2 and IL-12 also significantly enhances the production of IFN-γ by T cells and NK cells (Wigginton & Wiltrout (2002) Expert Opin Biol Ther 2:513-524).

To evaluate the therapeutic effect(s) of a combination of immunomodulatory collagen-binding molecules comprising IL-2 or IL-12, lumican-MSA-IL2 and IL12-MSA-lumican were tested in combination in a mouse melanoma tumor model essentially as described in Example 9. However, given the known toxicities arising from administration of non-collagen-anchored cytokines in combination described above, the dosages of IL12-MSA-lumican and IL12-MSA-IL-12 were reduced to ¹⁄₁₀ of what was previously administered in Example 9 to 14 pmol/dose. As in Example 6, mice administered lumican-MSA-IL2 received 13 μg/dose. Mice administered MSA-IL2 received 9 μg/dose. Mice injected with IL-2 fusion proteins (lumican-MSA-IL2 or MSA-IL2) received the equivalent of 0.11 nmol/dose of IL-2.

Intratumoral administration of the reduced dose (14 pmol/dose) of IL12-MSA alone or MSA-IL2 alone did not result in weight loss or significant tumor growth delay in B16-F10 tumor-bearing mice (data not shown). In contrast, the administration of IL12-MSA in combination with MSA-IL2 resulted in weight loss and increased survival (FIG. 7). In contrast, combination treatment using the collagen-anchoring versions, IL12-MSA-Lumican and Lumican-MSA-IL2, increased survival to a greater extent than combination of IL12-MSA and MSA-IL2 and did not result in concomitant weight loss (FIG. 7).

These results demonstrate that treatment of tumor-bearing mice with a combination of collagen-binding IL12-MSA-lumican and lumican-MSA-IL2 resulted in increased survival of mice to a greater extent than treatment with a combination of non-collagen-binding IL12-MSA and MSA-IL2. Furthermore, these results show that treatment of mice with a combination of collagen-binding IL12-MSA-lumican and lumican-MSA-IL2 prevented treatment-related toxicity associated with co-administration of IL-12 and IL-2, thereby providing a therapeutic modality for this cytokine combination.

Example 11: Synergistic Effect of Collagen-Binding IL-2 and IL-12 Fusion Proteins is Dependent on CD8+ T Cells and Dendritic Cells The immune cell types responsible for the efficacy of intratumoral IL12-MSA-Lumican and Lumican-MSA-IL2 combination therapy was determined by antibody-mediated cellular depletions essentially as described in Example 7. As shown in FIG. 8A, CD8+ T cells and cross-presenting dendritic cells are indispensable for efficacy, as depletion of these cell types reduces survival of tumor-bearing mice treated intratumorally with a combination of IL12-MSA-Lumican and Lumican-MSA-IL2. In contrast, depletion of NK cells, neutrophils, eosinophils, or macrophages did not significantly affect the survival outcome (FIG. 8B). Antibody-mediated depletion of IFNγ, a cytokine known to be amplified by concurrent IL-2 and IL-12 stimulation (Gollob et al., (1999) J Immunol 162(8):4472-4481), also did not significantly alter survival (FIG. 8A), however, the lack of effect might be attributed to insufficient depletion of IFNγ.

To further evaluate the contribution of immune cell types toward the anti-tumor efficacy provided by the combination of IL12-MSA-lumican and lumican-MSA-IL2 in tumor-bearing mice, immunophenotyping of tumor-infiltrating immune cells was performed. Mice were inoculated with 1 million B16F10 tumor cells on day 0 and treated with either intratumoral injection of PBS, IL12-MSA and MSA-IL2, or IL12-MSA-Lumican and Lumican-MSA-IL2 on day 5. Tumors were excised on day 11. Immune cell infiltrates of tumors were analyzed as previously described. (Moynihan et al., (2016) Nat Med 22:1402-1410); Zhu et al., (2015) Cancer Cell 27:489-501). Briefly, resected tumors were weighed, dissociated into small pieces, incubated in RPMI-1640 containing 1 mg/mL collagenase and dispase (Roche) and 25 ug/mL DNase I (Roche) for 30 minutes at 37C. Further mechanical dissociation was used to generate a single cell suspension for staining. Cells were analyzed on BD FACS LSRFortessa™ and data was analyzed using FlowJo® (FlowJo, Inc). Cells were stained for surface and intracellular markers to delineate cell types as follows:

NK cells (live $CD45^+CD3^-NK1.1^+$)
Treg cells (live $CD45^+CD3^+NK1.1^-CD4^+CD8^-CD25^+FoxP3^+$)
CD4 cells (live $CD45^+CD3^+NK1.1^-CD4^+CD8^-CD25^{+/-}FoxP3^-$)
CD8 T cells (live $CD45^+CD3^+NK1.1^-CD4^-CD8^+$)

Monocytes/Macrophages (live $CD45^+CD11b^+Ly6G^-CD11c^-F4/80^+$)
$CD11b^+$ DC (live $CD45^+CD11b^+MHCII^+CD11c^+$)
$CD11b^-$ DC (live $CD45^+CD11b^-MHCII^+CD11c^+$)
Neutrophil (live $CD45^+CD11b^+Ly6G^+$)

As shown in FIG. 8C, the fold change of CD8+ T cells in tumor infiltrates from mice treated with a combination of IL12-MSA-Lumican and Lumican-MSA-IL2 (Lumican versions) relative to treatment with PBS is higher than the fold change from mice treated with IL12-MSA+MSA-IL2 (MSA versions) relative to treatment with PBS. Furthermore, tumors treated with the lumican-MSA cytokine fusions had more infiltrating CD8+ T cells compared to tumors treated with the MSA cytokines fusions six days after initial treatment (FIG. 8D) and had higher surface expression of PD-1 (FIG. 8E).

The production of tumor-specific T cells in response to treatment was further evaluated in splenocytes isolated at six days following treatment by IFNγ ELISPOT. The number of IFNγ spot-forming units (SFU) in response to stimulation with B16F10 target cells was quantified. Treatment with lumican-MSA cytokine fusions yielded approximately 20 SFU per 1 million splenocytes, compared to approximately 15 SFU per 1 million splenocytes for MSA cytokine fusions or approximately 2 SFU per 1 million splenocytes for untreated animals. Thus, treatment with lumican-MSA cytokine fusions resulted in an increase in the number of peripheral tumor-specific T cells compared to no treatment or treatment with MSA-cytokine fusions.

These results demonstrate that the anti-tumor efficacy (e.g., increased survival) provided by the combination of IL12-MSA-Lumican and Lumican-MSA-IL2 is dependent on CD8+ T cells and dendritic cells. Furthermore, these results demonstrate that intratumoral treatment of tumor-bearing mice with a combination of IL12-MSA-Lumican and Lumican-MSA-IL2 provides anti-tumor efficacy, at least in part, by inducing the infiltration of activated CD8+ T cells into the tumor and inducing production of peripheral tumor-specific T cells.

Example 12: Synergistic Effect of Collagen-Binding IL-2 and IL-12 Fusion Proteins and Anti-PD-1 Antibody Combination In a Mouse Melanoma Tumor Model The upregulation of surface PD-1 on tumor infiltrating CD8 T cells in response to lumican-cytokine treatment as described in Example 11 prompted an evaluation of the anti-tumor efficacy of a combination of an anti-PD-1 antibody (clone 29F.1A12, BioXCell), IL12-MSA-lumican, and lumican-MSA-IL2 in a mouse melanoma tumor model. Briefly, C57BL/6 mice aged 6-8 weeks were inoculated with $1 \times 10^6$ B16-F10 tumor cells subcutaneously into the right flank on day 0. Tumor-bearing mice were treated with a combination of Lumican-MSA-IL2 and IL12-MSA-Lumican or a combination of MSA-IL2 and IL12-MSA intratumorally at dosages as described in Example 10 and with anti-PD-1 antibody (200 μg/dose) intraperitoneally on day 5 and day 11. Percent weight change from baseline and percent survival was monitored and is shown in FIG. 9.

As shown in FIG. 9, the inclusion of anti-PD-1 antibody in combination with IL12-MSA and MSA-IL2 or with IL12-MSA-Lumican and Lumican-MSA-IL2 did not alter the weight loss trends observed previously (FIG. 7). However, the addition of anti-PD-1 antibody improved survival outcomes for mice treated with the IL12-MSA+MSA-IL2 combination but did not further improve survival for mice treated with the IL12-MSA-Lumican+Lumican-MSA-IL2 combination.

Localized vitiligo occurred more frequently in mice treated with anti-PD-1 antibody, IL12-MSA-Lumican, and Lumican-MSA-IL2 (4/5 mice with vitiligo at injection site) compared to mice treated with anti-PD-1 antibody, IL12-MSA, and MSA-IL2 (1/5 mice with vitiligo at injection site). Furthermore, more survivors from cytokine (IL12-MSA+MSA-IL2 or IL12-MSA-Lumican+Lumican-MSA-IL2) and anti-PD-1 treatment compared to survivors from IL12-MSA-Lumican+Lumican-MSA-IL2 treatment in the absence of anti-PD-1 treatment were protected against a subsequent tumor re-challenge with B16-F10 tumor cells. While 4/4 mice treated with Lumican-MSA cytokines+anti-PD-1 and 2/2 mice treated with MSA cytokines+anti-PD-1 rejected re-challenge tumors, only 1/3 mice treated with Lumican-MSA cytokines only rejected re-challenge.

These results demonstrate treatment of tumor-bearing mice with a combination of anti-PD-1, IL12-MSA-Lumican, and Lumican-MSA-IL2 increased the occurrence of treatment-induced vitiligo and effective immunological memory thus demonstrating a synergistic effect in enhancing T cell responses generated from localized IL-2 and IL-12 treatment.

Example 13: Synergistic Effect of Collagen-Binding IL-2 and IL-12 Fusion Proteins and Anti-PD-1 Antibody Combination In Mouse Mammary and Colon Carcinoma Tumor Models The anti-tumor effect(s) of a combinations of collagen-binding IL-2 and IL-12 fusion proteins with an anti-PD-1 antibody were further assessed in an EMT6 mammary carcinoma model. Briefly, 1×10$^6$ EMT6 mouse mammary carcinoma cells (ATCC) or 1×10$^6$ MC38 mouse colon carcinoma cells (National Cancer Institute, Bethesda, MD) were resuspended in 50 µL of sterile PBS were injected subcutaneously into the right flanks of C57BL/6 female mice on day 0. EMT6 tumor-bearing mice were treated with Lumican-MSA-IL2+IL12-MSA-Lumican (i.tu.), anti-PD-1 antibody alone (i.p., 200 µg/dose) or anti-PD-1 antibody in combination with Lumican-MSA-IL2 and IL12-MSA-Lumican (i.tu) at dosages as described in Example 10 on day 5, day 11 and day 17. MC38 tumor-bearing mice were treated with a combination of Lumican-MSA-IL2+IL12-MSA-Lumican (i.tu.), anti-PD-1 antibody alone (i.p., 200 µg/dose) or in combination with Lumican-MSA-IL2+IL12-MSA-Lumican (i.tu.) at dosages as described in Example 10 on day 5, day 11 and day 17. For each tumor model, tumor area (mm$^2$) and percent survival was monitored over time and is shown in FIG. 10A-10B. Survival statistics determined by log-rank Mantel-Cox test.

As shown in FIG. 10A, treatment of mice bearing EMT6 mammary carcinoma tumors with an anti-PD-1 antibody in combination with Lumican-MSA-IL2 and IL12-MSA-Lumican resulted in resolution of tumor lesions (as indicated by absence of measurable tumor area) and increase survival to a greater extent than treatment of tumor-bearing mice with anti-PD-1 antibody alone.

As shown in FIG. 10B, treatment of mice bearing MC38 colon carcinoma tumors with an anti-PD-1 antibody in combination with Lumican-MSA-IL2 and IL12-MSA-Lumican resulted in a decrease in tumor area and increased survival to a greater extent than treatment of tumor-bearing mice with anti-PD-1 antibody alone or with the IL12-MSA-Lumican+Lumican-MSA-IL2 combination alone.

These results show that treatment of tumor-bearing mice with an anti-PD-1 antibody in combination with IL12-MSA-Lumican+Lumican-MSA-IL2 results in a synergistic anti-tumor effect in both EMT6 mammary carcinoma and MC38 colon carcinoma models.

Example 14: Synergistic Effect of Collagen-Binding IL-12 Fusion Protein and Cancer Vaccine in a Mouse Melanoma Tumor Model To further evaluate the ability of a collagen-binding IL-12 fusion protein to synergistically potentiate anti-tumor treatments, the anti-tumor effect(s) of the collagen-binding IL-12 fusion protein IL12-MSA-Lumican in combination with a cancer vaccine was assessed in an B16-F10 mouse melanoma model. Briefly, 1×10$^6$ B16-F10 cells (ATCC), resuspended in 50 µL of sterile PBS, were inoculated subcutaneously into the right flank of 6-8 week old C57BL/6 female mice on day 0. A cancer vaccine, comprising 90 µg of a lymph node-targeting moiety fused to peptides derived from B16-F10-associated antigens TYRP-1 and a modified gp100 peptide (EGP) and 50 µg of cyclic dinucleotides adjuvants (Invivogen), was administered subcutaneously at the base of the tail with a prime dose on day 5 and boost dose on day 11 and day 17. Subcutaneous administration of the cyclic dinucleotide adjuvant and the cancer vaccine was evaluated for priming of an antigen-specific CD8 T cell response. Briefly, peripheral blood was collected on day 16 and stimulated for 6 hours with peptide antigens Trp1 and EGP. Brefeldin A was included for the final 4 hours of incubation. Peripheral blood cells were subsequently stained for surface markers and intracellular IFNγ and analyzed by flow cytometry. The percentage of IFNγ$^+$ cells among live CD45$^+$ CD3$^+$ CD8$^+$ T cells was evaluated. Vaccination alone or in combination with IL12-MSA-Lumican improved priming of antigen-specific CD8 T cells (data not shown).

Weight change from baseline of each mouse, tumor area, and survival of mice treated with intratumoral (i.tu.) injections of PBS (n=12) or IL-12 (n=10 for IL12-MSA; n=10 for IL12-MSA-Lumican), or vaccine (n=7) alone, or vaccine and IL12 (n=7 for IL12-MSA; n=7 for IL12-MSA-Lumican) on days 5, 11, and 17 were monitored over time (FIG. 11, left to right).

As shown in FIG. 11, vaccination alone did not affect weight relative to mice treated with PBS (left panel), modestly delayed B16F10 tumor growth (middle panel), and modestly increased survival of mice (right panel). In contrast, co-administration of the cancer vaccine with IL-12, using either IL12-MSA or IL12-MSA-Lumican, resulted in a synergistic reduction in tumor growth (middle panel) and increase in survival (right panel). The cancer vaccine administered in combination with IL12-MSA-Lumican extended survival longer than combination with IL12-MSA. Additionally, the vaccine with IL12-MSA lead to treatment-induced weight loss that was undetected with IL12-MSA-Lumican (right panel).

These results demonstrate that administration of a cancer vaccine in combination with collagen anchored IL-12 (IL12-MSA-lumican) to tumor-bearing mice results in a synergistic anti-tumor effect, decreasing tumor growth and increasing percent survival to a greater extent that administration of the cancer vaccine or IL12-MSA-lumican alone. These results show that intratumoral collagen-anchoring of a cytokine (e.g., IL-12) synergistically improves the tumor control of a cancer vaccine.

Example 15: Synergistic Effect of Collagen-Binding IL12 Fusion Protein and CAR-T Cells in a Mouse Melanoma Tumor Model To further evaluate the ability of a collagen-binding IL-12 fusion protein to synergistically potentiate anti-tumor treatments, the anti-tumor effect(s) of the collagen-binding IL-12 fusion protein IL12-MSA-Lumican in combination with CAR-T cells was assessed in an B16-F10 mouse melanoma model. Briefly, $0.5 \times 10^6$ B16-F10 cells (ATCC), resuspended in 50 µL of sterile PBS, were inoculated subcutaneously into the right flank of 6-8 week old C57BL/6 female mice on day 0. B16F10-specific CAR-T cells were generated by transducing CD3+ splenocytes to express a CAR composed of single-chain variable fragment (scFv) of TA99 fused to costimulatory CD28 and CD3 ζ signaling domains. To ensure CAR-T cell engraftment, all mice were preconditioned with total body irradiation the day prior to a bolus injection of 10 million CAR-T cells intravenously (i.v.). Weight change from baseline, tumor area, and survival of mice treated with intratumoral (i.tu.) injections of PBS (n=9) or IL-12 (n=6 for IL12-MSA; n=5 for IL12-MSA-Lumican), or CAR-T (n=12) alone, or CAR-T and IL12 (n=7 for IL12-MSA; n=5 for IL12-MSA-Lumican) on days 5 and 11 were monitored over time (FIG. 12, left to right).

As shown in FIG. 12, treatment with CAR-T cells and IL12-MSA-Lumican (2.3 ug/dose) alone decreased tumor area (middle panel) and increased survival (right panel). However, administration of a combination of CAR-T cells and IL12-MSA-Lumican to tumor-bearing mice resulted in a durable tumor regression, reducing tumor area and increasing survival to a greater extent that treatment with either CAR-T cells or IL12-MSA-Lumican alone. Treatment with CAR-T cells in combination with IL12-MSA also resulted in tumor regression and modest improvement in survival. However, the combination treatment demonstrated significant toxicity as shown by the large reduction in animal body weight loss following treatment. Such toxicity was not observed for the combination of CAR-T cells and IL-12-MSA-lumican.

These results demonstrate that administration of tumor-antigen specific CAR-T cells in combination with collagen anchored IL-12 (IL12-MSA-lumican) to tumor-bearing mice results in a synergistic anti-tumor effect, decreasing tumor growth and increasing percent survival to a greater extent that administration of the CAR-T cells or IL12-MSA-lumican alone. These results show that intratumoral collagen-anchoring of a cytokine (e.g., IL-12) synergistically improves the tumor control of tumor-antigen specific CAR-T cells.

Example 16: Neoadjuvant Administration of a Collagen-Binding IL-12 Fusion Protein in Combination with PD-1 Checkpoint Blockade Prevents Metastatic Recurrence in a Mouse Breast Tumor Resection Model To further evaluate the ability of a collagen-binding IL-12 fusion protein to synergistically potentiate anti-tumor treatments, the anti-tumor effect(s) of the collagen-binding IL-12 fusion protein IL12-MSA-Lumican in combination with an anti-PD-1 antibody (clone 29F.1A12, BioXCell) was assessed in an 4T1 mouse breast tumor resection model and compared to scIL12 combined with anti-PD-1. Briefly, $0.5 \times 10^6$ luciferase-expressing 4T1-Luc cells (MIT, Cambridge, MA), resuspended in 100 µL of sterile PBS, were injected into the mammary fat pad of 6-8 week old BALB/c female mice on day 0. Prior to surgical resection of primary lesions, mice were treated with IL12-MSA-Lumican or scIL12 intratumorally and anti-PD-1 systemically (neoadjuvant therapy). Neoadjuvant therapy (anti-PD-1, 200 µg/dose, administered i.p.+IL12-MSA-lumican, 4.6 µg/dose (30 pmol IL12/dose) or scIL12, 1.9 µg/dose (30 pmol IL12/dose)), administered i.tu.) was administered on day 7 and 13 and primary tumors were surgically excised on day 16. Post-operation mice were monitored by in vivo imaging (IVIS) for metastases. FIG. 13 shows total body weight change during neoadjuvant treatment (left panel), primary tumor growth and weight (middle panel) and percent survival (right panel) of mice treated with intratumoral (i.tu.) injections of IL-12 (n=5 for scIL12; n=5 for IL12-MSA-Lumican) and intraperitoneal (i.p.) injection of anti-PD-1 on day 7 and 13. Arrows indicate time of treatment and cross indicates time of surgery.

As shown in FIG. 13, the combination of either version of IL-12 (scIL12 or IL12-MSA-Lumican) and anti-PD-1 antibody was not overtly toxic based on the absence of weight loss (left panel). However, the neoadjuvant therapy with IL12-MSA-Lumican led to more primary tumor shrinkage than the non-anchoring version scIL-12 (middle panel). After surgery, mice were monitored for metastases by in vivo bioluminescence imaging. IL12-MSA-Lumican completely protected mice from metastatic growth while several mice treated with scIL-12 relapsed.

These results demonstrate that administration of anti-PD-1 antibody in combination with collagen anchored IL-12 (IL12-MSA-lumican) to tumor-bearing mice results in a synergistic anti-tumor effect, decreasing primary tumor growth and increasing percent survival after surgical resection of tumor to a greater extent that administration of the a combination of non-collagen-binding IL-12 (scIL12) and anti-PD-1 antibody. These results demonstrate that collagen-anchoring IL-12 in a neoadjuvant setting improves postoperative outcomes.

Example 17: Collagen-Binding Chemokine Fusion Proteins Induce Immune Cell Migration and Tumor Infiltration T cell infiltration is critical for durable anti-tumor immunity. A correlation exists between T-cell infiltration and tumor-cell derived expression of CCL3, CCL4, and CCL5. Spranger et al., (2015) Nature 523:231-235 (2015); Spranger et al. (2016) Proc Natl Acad Sci USA 113, E7759-E7768 (2016). CCL3 (MIP-1a) binds with high affinity to CCR1, and low affinity to CCR5 thereby mediating the recruitment of T cells, B cells and monocytes. CCL4 (MIP-1b) binds to CCR5 mediating general lymphocyte recruitment. CCL5 (RANTES) binds several chemokine receptors (CCR1, CCR3, CCR4, CCR5) and thereby attracts monocytes, T cells, eosinophils, and other immune cells. T-cell recruiting chemokines are also more prevalent in tumors undergoing productive immune-mediated regression. Liang et al., (2016) Proc Natl Acad Sci USA 113:5000-5005; Schlecker et al., (2012) J Immunol 189:5602-5611; Brewitz et al., (2017) Immunity 46:205-219; Kanegasaki et al., (2014) Cancer Res 74:5070-5078; Wittrup (2017) Trends Cancer Res 3:615-620.

To evaluate the ability to express collagen-binding chemokines in mammalian cells, three His-tagged collagen-binding cytokines comprising lumican fused to CCL3, CCL4 or CCL5 were transiently expressed in human embryonic kidney 293 (HEK293) cells. Briefly, HEK293 cells (at 1 million cells/mL density) were transfected with sterile-filtered plasmid DNA (1 mg per liter cell culture) using polyethylenimine (2 mg per liter cell culture) in OptiPro serum-free media (20 mL per liter cell culture) (Thermo Fisher). TA99 was purified using rProtein A Sepharose Fast Flow resin (GE Healthcare) as previously described (Zhu et al. 2015). His-tagged proteins were isolated from HEK293 supernatant using TALON Metal Affinity Resin (Takara Bio Inc.). Cytokine-fusion proteins were then further purified by size exclusion chromatrography using a HiLoad 16/600 Superdex 200 pg column on an AKTA FPLC system (GE Healthcare) that had been pretreated for 4 hours with 1 M NaOH to remove endotoxin and subsequently equilibrated in sterile PBS (Corning). Following purification, all proteins were buffer exchanged into sterile PBS (Corning), 0.2 micron sterile-filtered (Pall Corporation) and confirmed to contain minimal levels of endotoxin (<0.1 EU per injection) using an chromogenic LAL assay (Lonza). To confirm their molecular weights, proteins were run alongside a Novex Prestained Sharp Protein Ladder on a 4-12% NuPAGE Bis-Tris protein gel (Life Technologies) with 1% IVIES running buffer. The relative expression levels of the His-tagged collagen-binding fusion proteins in the resulting eluates was evaluated by SDS-PAGE (not shown).

Transient expression of Lumican, Lumican D213A (SEQ ID NO: 125), Lumican-Gluc, Lumican-CCL3 (SEQ ID NO: 153), Lumican-CCL4 (SEQ ID NO: 156), and Lumican-CCL5 (SEQ ID NO: 160) in HEK293 cells was achieved, as determined by SD S-PAGE analysis showing by presence of protein staining at or near the respective expected molecular weight of each fusion protein.

These results demonstrate that collagen-binding fusion proteins comprising chemokines are able to express and be purified from mammalian cells.

To evaluate the ability of the lumican-chemokine fusion proteins generated as described above to induce inflammation (e.g., immune cell migration), an in vivo inflammatory peritonitis assay was performed as previously described (Proudfoot et al., (2003) Proc Natl Acad Sci USA 100:1885-1890. Briefly, the peritoneal cavity is lined by a collagen- and vasculature-rich mesothelium. When injected intraperitoneally, matrix-binding constructs (e.g. collagen-binding chemokine fusion proteins) adhere to this lining. In the case of lumican-chemokines, mesothelial localization can create a concentration gradient that mediates immune cell extravasation out of nearby blood vessels and into the peritoneal cavity. These infiltrates are retrieved by intraperitoneal lavage for ex vivo immunophenotyping. Accordingly, BALB/c mice were injected intraperitoneally with 1 nmol equivalent in 200 uL sterile PBS of either Lumican-Gluc, Lumican-CCL3, Lumican-CCL4, or Lumican-CCL5 and sacrificed 18 hours post-injection. The peritoneal cavity was washed three-times by gently massaging 5 mL of ice cold PBS in the cavity and the pooling the lavages. The collected cells were enumerated using Accuri Flow Cytometer.

Lumican-chemokine fusion proteins comprising CCL3, CCL4, or CCL5 were capable of mediating overall cell infiltration compared to an injection of Lumican-GLuc (data not shown). When infiltrates were immunophenotyped by surface marker staining, lavages from mice treated with Lumican-CCL3, Lumican-CCL4 or Lumican-CCL5 contained a greater abundance of macrophages, followed by neutrophils, NK cells, DCs, B cells, and T cells relative to lavages from mice treated with PBS or Lumican-Gluc (data not shown).

These results demonstrate that i.p. administration of collagen-binding chemokines (e.g., Lumican-CCL3, Lumican-CCL4 or Lumican-CCL5) induce immune cell migration, including T cells, into the peritoneal cavity of mice. These results suggest that intratumoral administration of lumican-chemokine fusion proteins will induce inflammation (e.g., immune cell infiltration), thereby mimicking immune-responding tumors.

To assess the therapeutic effect of inducing inflammation using lumican-chemokines in a tumor setting, Lumican-CCL3 (Lum CCL3) and Lumican-CCL5 (Lum CCL5) were tested in both the 4T1 breast tumor model and B16F10 melanoma model as described herein. Intratumoral treatment of tumor-bearing mice with Lumican-GLuc (20 ug/dose) or a combination of Lumican-CCL3 (5.5 ug/dose), Lumican-CCL4 (5.4 ug/dose) and Lumican-CCL5 (5.5 ug/dose) in the presence or absence of IFNα occurred on day 7 and day 13. Intraperitoneal administration of IFNα (50 ug/dose) occurred on day 9 and day 15.

As shown in FIG. 14A, intratumoral injection of a combination of Lumican-CCL3, Lumican-CCL4 and Lumican-CCL5 in the presence of systemic IFNα slightly delayed 4T1 tumor growth. The same treatment administered in B16F10 tumor-bearing mice conclusively showed that IFNα and lumican-chemokines, administered separately or in combination, delays growth equivalently (FIG. 14B). To determine if lumican-chemokines are directly impact the viability of tumor cells, increasing concentrations of fusion proteins Lumican-GLuc (Lum GLuc), Lumican-CCL3 (Lum CCL3), Lumican-CCL5 (Lum CCL5) were incubated with 4T1 cells or B16F10 in cell culture for 48 hours. After an additional 4 hour incubation with 10 uL of the cell proliferation detection reagent WST-1 (Sigma Aldrich), proliferation was measured by absorbance at 450 nm (reference 700 nm). As shown in FIGS. 14C and 14D, lumican cytokines had no effect on proliferation on 4T1 cells or B16F10 cells indicating any tumor growth delay observed in vivo arose from an immune-mediated and not from direct tumoricidal effect.

Example 18: Synergistic Effect of Collagen-Binding CCL11 Chemokine Fusion Protein and Cancer Vaccine in a Mouse Melanoma Tumor Model Eosinophils are known to secrete T-cell chemoattractants and normalize tumor vasculature thereby easing intratumoral infiltration. Carretero, et al., (2015) Nat Immunol 16:609-617. The chemokine CCL11 (eoxtaxin) is known to recruit eosinophils (Menzies-Gow et al., (2002) J Immunol 169(5):2712-2718). Accordingly, a CCL11-lumican fusion protein (SEQ ID NO: 172), in combination with the cancer vaccine described in Example 14 was tested for its ability to recruit eosinophils into a tumor and thereby mediate subsequent tumor control in the presence of systemic TNFα and IFNγ. Briefly, C57BL/6 mice were inoculated with $3\times10^5$ B16F10 cells into the right flank on day 0. Vaccinations were administered subcutaneously (s.c.) at the tail base with a prime on day 5 and boosts on day 11 and 17. The vaccination was comprised of 90 ug of TTR-Trp1-EGP and 50 ug of cyclic di-nucleotide to prime a tumor-specific CD8+ T cell response. Intratumoral treatments with CCL11-lumican (5 ug/dose/mouse), TNFα (5.8 pmol/dose/mouse) and IFNγ (6.3 pmol/dose/mouse) were administered on days 11, 17, 23, and 29. Tumor area (mean+SD) was measured over time every other day As shown in FIG. 15, treatment of tumor-bearing mice with CCL11-Lumican in combination with a B16F10-specific cancer vaccine TNFα and IFNγ decreased tumor area to a greater extent than the cancer vaccine alone or in combination with systemic TNFα and IFNγ.

Example 19: Synergistic Effect of Collagen-Binding CCL11 Chemokine Fusion Protein and Cancer Vaccine in a Mouse Melanoma Tumor Model To further evaluate the ability of a collagen-binding chemokine fusion protein to synergistically potentiate anti-tumor treatments, the anti-tumor effect(s) of the collagen-binding chemokine fusion protein CCL11-lumican in combination with MSA-IL2 (30 µg/dose) and a tumor-targeting antibody targeting Alpha-V class of integrins (2.5F-Fc; see Kwan et al., (2017) J Exp Med 215(9):10.1084/jem.20160831) was assessed in an B16-F10 mouse melanoma model. Briefly, 0.5×10⁶ B16-F10 cells (ATCC), resuspended in 50 µL of sterile PBS, were inoculated subcutaneously into the right flank of 6-8 week old C57BL/6 female mice on day 0. Tumor-targeting antibody 2.5F-Fc and MSA-IL2 were administered intraperitoneally (i.p.) on days 5, 11, and 17. Intratumoral treatments with CCL11-lumican (5 ug/dose/mouse) was given on days 5 and 11. Tumor growth was monitored over time every other day and is shown as individual tumor areas (mm²) in FIG. 16A.

As shown in FIG. 16B, treatment of tumor-bearing mice with CCL11-lumican in combination with tumor-targeting antibody 2.5F-Fc and MSA-IL-2 decreased tumor area to a greater extent than treatment without CCL11 (lumican alone).

Collectively, the results shown in Examples 17, 18 and 19 show that lumican-chemokines induce localized inflammation, recruiting immune cells to the site of local administration and that lumican-chemokines can be used in combination with other anti-tumor therapeutic modalities to potentiate their effects and provide synergistic tumor control.

Example 20: Recombinant Expression of Collagen-Binding Antibody Fusion Proteins

To evaluate the ability to express collagen-binding antibody fusion proteins in mammalian cells, lumican fused to 5 different antibodies were generated (4420-Lumican (SEQ ID NOs: 142 and 143; anti-fluorescein), LOB12.3-Lumican (SEQ ID NOs: 146 and 147; anti-4-1BB), 3/23-Lumican (SEQ ID NOs: 184 and 185; anti-CD40), 2C11-Lumican (SEQ ID NOs: 150 and 151; anti-CD3), and OX86-Lumican (SEQ ID NOs: 148 and 149; anti-OX40) and transiently expressed in human embryonic kidney 293 (HEK293F) cells. All IgG-Lumican fusions were encoded on a single plasmid (data not shown). All IgG-lumican constructs were expressed as the light chain first (VL), with a murine kappa constant region (mκ), followed by a T2A peptide (SEQ ID NO: 152; T2A) and finally the heavy chain (VH), with a murine IgG2c constant region (mIgG2c), fused to lumican (LUM) with a short linker ((G4S)₃). The T2A peptide causes the ribosome to skip bond formation between the last two residues of the peptide, allowing for expression of two different proteins within a single open reading frame. A furin cleavage site (F) was included upstream of the T2A peptide, allowing the T2A peptide to be removed from the end of the light chain. Additionally, a GSG linker (GSG) was included upstream of the T2A peptide, which has been shown to increase the cleavage efficiency of the T2A peptide (Chng et al., (2015) mAbs 7(2):403-412). Both the light chain and heavy chain comprise a leader sequence to ensure proper trafficking of the protein to the secretory pathway. All constructs were derived with LALA-PG effector function silencing mutations, which ablate both binding to Fc gamma receptors and binding of C1q (Lo et al., (2017) J Biol Chem 292:3900-3908).

Expression and purification of the anti-fluorescein antibody (4420) alone or fused to lumican was achieved as indicated by SDS-PAGE analysis revealing protein bands located at the predicted molecular weight under both reducing (R) and non-reducing conditions (NR) (data not shown). Similarly, expression of agonist IgG-lumican fusion proteins LOB12.3-Lumican (anti-4-1BB), 3/23-Lumican (anti-CD40), 2C11-Lumican (anti-CD3), and OX86-Lumican (anti-OX40) was achieved as indicated by SDS-PAGE analysis revealing protein bands located at the predicted molecular weight under both reducing (R) and non-reducing conditions (NR) (data not shown). All IgG-lumican fusion proteins were purified using recombinant protein A resin (rProtein A Sepharose, Fast Flow resin (GE Healthcare) according to the manufacturer's recommendations.

These results demonstrate that collagen-binding antibody fusion proteins (e.g., IgG-lumican) express in mammalian cells and that the collagen-binding polypeptide fusion does not affect purification.

Example 21: Recombinant Collagen-Binding Antibody Fusion Proteins Bind Collagen In Vitro and are Retained Intratumorally In Vivo To evaluate the ability of collagen-binding antibody fusion proteins to bind collagen, the IgG-lumican fusion proteins expressed and purified as described in Example 20 were tested for their ability to bind to collagen I-coated plates by ELISA. Briefly, collagen I (Gibco) coated 96 well-plates were blocked at room temperature for 1 hour with PBS+1% wt/vol bovine serum albumin (BSA)+0.05% wt/vol Tween-20 (PBSTA) and then incubated with various concentrations of lumican in PBSTA for 2 hours at room temperature. Wells were washed with PBSTA and then incubated with a horseradish peroxidase-conjugated goat anti-mouse IgG2c heavy chain (ab98722, Abcam) at a 1:1000 dilution (0.5 µg/ml final concentration) in PBSTA for 1 hour at room temperature. Wells were washed again with PBSTA and then 1-Step Ultra TMB-ELISA Substrate Solution (Thermo Fisher Scientific) was added for 10 mins followed by 1 M sulfuric acid to stop the chromogenic reaction. Absorbance at 450 nm (corrected with a reference absorbance at 570 nm) measured using an Infinite M1000 microplate reader (Tecan). Purified collagen-binding antibody fusion proteins LOB12.3-Lumican (anti-4-1BB), 3/23-Lumican (anti-CD40), 2C11-Lumican (anti-CD3), and OX86-Lumican (anti-OX40) were evaluated by ELISA on a collagen I-coated plate. As shown in FIG. 17A, all IgG-lumican fusion proteins retain the ability to bind collagen with similar measured affinities. These results demonstrate that lumican fused to the heavy chain of IgGs retains the ability to bind to collagen I.

The ability of the 4420-Lumican fusion protein and the 4420 antibody to be intratumorally retained in vivo was also evaluated. Both proteins were purified using size exclusion chromatography then labeled with NHS-AlexaFluor 647 (Thermo Fisher) according to the manufacturer's instructions. Six to eight week old female BALB/c mice were injected with 1×10⁶ 4 T1 mammary carcinoma cells subcutaneously on day 0. On day 7 equimolar amounts of fluorescently-labeled 4420 antibody and 4420-Lumican were injected intratumorally into three mice each, along with three PBS control mice. Retention in the tumor was evaluated via measuring fluorescence on an IVIS Spectrum instrument (Perkin Elmer) at 0, 0.5, 1, 2, 4, 6, 12, 24, 48, 72, 96, 100, 124, and 148 hours (FIG. 17B).

As shown in FIG. 17B, the fluorescent signal from mice injected with the fluorescently-labeled 4420 antibody (4420 LALA-PG) decreased faster and to a greater extent than the signal from the 4420-lumican fusion protein (4420-LUM LALA-PG)

These results demonstrate that collagen-binding antibody fusion proteins (e.g., 4420-lumican fusion protein) are physically retained at the site of intratumoral injection over time. These results suggest that collagen-binding immunomodulatory molecules comprising a therapeutic antibody or antigen-binding fragment will exhibit intratumoral retention and limited systemic dissemination.

Example 22: Recombinant Expression of Collagen-Binding IgG-Binding Fusion Proteins As a strategy to localize virtually any IgG intraumorally without requiring regenerating the antibody as a direct lumican fusion, several different IgG binding proteins were fused to lumican. As with other lumican fusion proteins described herein, a mouse serum albumin (MSA) spacer was used to ensure that lumican-collagen binding did not interfere with the functionality of the IgG binding domain. Several different IgG binders were selected for screening, including a dimerized Z domain (one of the five IgG binding domains of protein A, herein referred to as "ZZ") (Jendeberg et al., (1995) J Mol Recognit 8:270-278), a dimerized IgG binding domain of protein G (herein referred to as "SpG2") (Jung et al., (2009) Anal Chem 81:936-942), an IgG binder isolated from a Sso7d yeast display library (Gera et al., (2011) J Mol Biol 409"601-616), an IgG binder isolated from a Fibronectin type III domain (Fn3) yeast display library (Hackel et al., (2010) J Mol Biol 401:84-96), and two small peptides designed to bind IgG Fc regions (herein referred to as "Fc-III-4C" and "RRGW") (Gong et al., (2015) Bioconjug Chem 27:1569-1573; Tsai et al., (2014) Anal Chem 86:2931-2938). In addition, a lumican-MSA fusion to 4m5.3 was also cloned and expressed. 4m5.3 is an scFv with femtomolar binding affinity to fluorescein (Midelfort et al., (2004) J Mol Biol 343:685-701). Fluorescein can be conjugated to antibodies with a wide range of coupling strategies borrowed from the field of antibody drug conjugates (ADCs) (Carter & Lazar (2017) Nat Rev Drug Discov 17:197-223. Using 4m5.3-MSA-Lumican with fluorescently labeled antibodies serves as an alternative strategy for localizing IgGs to the tumor. This construct also serves as a generalized platform ably to tightly bind to and localize any fluorescein (or FITC) labeled protein or small molecule.

To evaluate the ability to express collagen-binding IgG-binding fusion proteins in mammalian cells, lumican fused to 8 different IgG-binding polypeptides were generated (Lumican-MSA-Fc-III-4C (SEQ ID NO: 136; 105.7 kDa), Lumican-MSA-Fn3 (SEQ ID NO: 137; 113.7 kDa), Lumican-MSA-SpG2 (SEQ ID NO: 138; 117.7 kDa), ZZ-MSA-Lumican (SEQ ID NO: 135; 117.5 kDa), WGRR-MSA-Lumican (SEQ ID NO: 140; 104.6 kDa), RRGW-MSA-Lumican (SEQ ID NO: 139; 104.6 kDa), Sso7d-MSA-Lumican (SEQ ID NO: 134; 111.5 kDa), and 4m5.3-MSA-Lumican (SEQ ID NO: 133; 132.2 kDa)) and transiently expressed in human embryonic kidney 293 (HEK293) cells. All lumican-IgG binding fusion proteins were His-tagged to facilitate purification from HEK293 lysates using TALON Metal Affinity Resin (Takara Bio Inc.) according to the manufacturer's instructions.

Expression and purification of all 8 lumican-IgG-binding fusion proteins was achieved as indicated by SDS-PAGE analysis revealing protein bands located at the predicted molecular weights under both reducing and non-reducing conditions (data not shown).

These results demonstrate that His-tagged collagen-binding IgG-binding fusion proteins (e.g., IgG-lumican) express in mammalian cells and are able to be purified.

Example 23: Recombinant Collagen-Binding IgG-Binding Fusion Proteins Bind Collagen and IgG In Vitro To evaluate the ability of collagen-binding IgG-binding fusion proteins to bind collagen, the lumican-IgG binding fusion proteins expressed and purified as described in Example 22 were tested for their ability to bind to collagen I- and collagen IV-coated plates by ELISA. Briefly, Nunc MaxiSorp flat bottom 96 well-plates (ThermoFisher) were coated overnight with mouse IgG2a isotype control antibodies (100 µL, 2.5 µg/mL, BioXCell C1.18.4) overnight at 4C. Plates were then blocked at room temperature for 1 hour with PBS+1% wt/vol bovine serum albumin (BSA)+0.05% wt/vol Tween-20 (PBSTA) and then incubated with various concentrations of lumican in PBSTA for 2 hours at room temperature. Wells were washed with PBSTA and then incubated with a horseradish peroxidase-conjugated polyclonal anti-6×His (ab1187, Abcam) at a 1:2000 dilution (0.5 µg/ml final concentration) in PBSTA for 1 hour at room temperature. Wells were washed again with PBSTA and then 1-Step Ultra TMB-ELISA Substrate Solution (Thermo Fisher Scientific) was added for 10 mins followed by 1 M sulfuric acid to stop the chromogenic reaction. Absorbance at 450 nm (corrected with a reference absorbance at 570 nm) measured using an Infinite M1000 microplate reader (Tecan).

The purified lumican-IgG-binding fusion proteins Lumican-MSA-Fn3, Lumican-MSA-SpG2, ZZ-MSA-Lumican, and 4m5.3-MSA-Lumican were evaluated by ELISA on a collagen I-coated plate and a collagen IC-coated plate. Lumican was used as a comparator. As shown in FIG. 18A, all lumican-IgG-binding fusion proteins retain the ability to bind collagen with similar measured affinities. These results demonstrate that lumican fused to various IgG-binding polypeptides retains the ability to bind to collagen I and collagen IV.

The purified lumican-IgG-binding fusion proteins from Example 22 were tested for their ability to bind mouse IgG2a isotype control (Clone C1.18.4) as measured via ELISA. Briefly, an anti-His secondary antibody (Abcam, ab1187) conjugated to HRP was used to detect the IgG binder-lumican fusions, along with 1-step Ultra TMB-ELISA Substrate (Thermo Fischer).

As shown in FIG. 18B, all lumican-IgG-binding fusion proteins tested bind to mouse IgG2a, with a range of affinities ($K_D$).

Collectively, these results demonstrate that lumican-IgG-binding fusion protein bind to both collagen I and collagen IV and bind to IgGs. These results suggest that lumican-IgG-binding fusion proteins used in combination with IgG (e.g., therapeutic antibodies) would bind to both collagen and IgG and retain the IgG at the site of local administration.

Example 24: Collagen-binding Lumican is Retained in the Peritoneal Cavity Following Intraperitoneal Injection The aforementioned Examples have demonstrated the utility of lumican to be retained intratumorally upon intratumoral (i.tu.) administration. The peritoneal cavity is also lined by a collagen-rich mesothelium. To evaluate the ability of lumican to be retained in the peritoneal cavity upon intraperitoneal (i.p) injection, BALB/c mice were injected intraperitoneally with either *Gaussia* Luciferase (GLuc; 20 µg/dose) alone or fused to Lumican (Lumican-Gluc; 40 µg/dose). Immediately after the injection, mice were imaged by in vivo fluorescence (epi-illumination, auto-exposure). 24 hours after the injection, mice were imaged again.

Lumican-GLuc is retained in the cavity however the GLuc alone rapidly diffuses in the peritoneum immediately following injection, leading to low initial signal (data not shown). Retention of Lumican was observed in the cavity 24 hours post-injection.

Tumors embedded on this lining or the omentum of the peritoneal cavity are also collagen-rich as well. To determine if i.p. administration of lumican will result in the accumulation on tumors liking the omentum, lumican fluorescently labeled with Alexa Fluor 647 was administered to mice having ovarian tumor microcolonies in the mouse omental tissue. Briefly, mice were injected with OVCA433 cells a human ovarian tumor cell line intraperitoneally and allowed to form microcolonies on the omentum for three weeks. 20 ug of labeled lumican was injected intraperitoneally. Excised omentum tissue was imaged by fluorescence microscopy. Labeled lumican was injected intraperitoneally in tumor-bearing mice. At 1 hour, 6 hours and 24 hours post-injection, omentums of mice were excised for imaging.

As shown in FIG. 19, when Lumican is intraperitoneally injected into mice bearing ovarian tumors lining the omentum, lumican preferentially accumulates at these tumor microcolonies. One hour post injection (left panel), the fluorescent signal from lumican (shown in yellow) was distributed uniformly. After 6 hours post-injection (middle) it was largely retained only around tumor microcolonies (shown in red) in the omentum (middle panel). Retention of the lumican was observed at 24 hours (right panel) around large tumors. These results demonstrate that i.p. administration of lumican can accumulate on collagen-rich locations and that lumican is amenable to several modes of administration including intraperitoneal injection.

Example 25: Expression of Collagen-Binding IL-12 Fusion Proteins from Self-Replicating RNA In Mammalian Cells To evaluate the expression of collagen-binding immunomodulatory molecules using RNA, self-replicating RNA molecules (replicons) encoding IL12-MSA and IL12-MSA-Lumican alone or fused to a fluorescent protein (mCherry) were tested for their ability to express in B16F10 mouse melanoma cells. The replicon used in this Example was derived from an alphavirus. The replicon was deleted of capsid structural proteins, but retains the non-structural proteins. The non-structural proteins correspond to the RNA-based RNA replication and RNA transcription. The Ab1c1 is a mutant replicon that exhibits more robust expression in vitro and in vivo compared to the wild-type replicon. The Ab1c1 replicon contains four mutations in the nsP2 and nsP3 genes that prolong replicon existence in cells and subgenomic transcription.

Briefly, $0.5 \times 10^6$ B16F10 cells cultured in DMEM+10% FBS were transfected using NEOnN transfection reagents (electroporation) and the Ab1 cl replicons. The transfection efficiency was detected by FACS analyzer 24 hours later using optical settings to detect mCherry. Expression of IL-12 was quantified using cell supernatant 24 hours after the transfection and a commercial IL-12 ELISA (followed according to manufacturer's instructions). Expression of replicons was evaluated in B16F10 cells by determination of mCherry by flow cytometry (FIG. 20A). A commercial IL-12 ELISA was used to quantify IL-12 in B16F10 cell (FIG. 20B).

As shown in FIG. 20A, mCherry+ B16F10 cells transfected with IL12-MSA-mCherry or IL12-MSA-Lumican-mCherry were observed by flow cytometry. The mCherry fluorescent protein is C-terminally encoded in these replications, therefore, detection of mCherry expression is indication of full-length expression of the encoded protein.

As shown in FIG. 20B, cell supernatants shows expression of these constructs from B16F10 cells transfected with IL-12-encoding replications, but not the Ab1c1-GIM control These results demonstrate that delivery of Lumican-fusion proteins is achievable using modes of administration beyond injection, including replicon as shown.

Example 26: Synergistic Effect of Collagen-Binding Cytokine Fusion Proteins, Anti-PD-1 Antibody and TA99 in the $\text{Braf}^{V600e}/\text{Pten}^{fl/fl}$ Mouse Model To evaluate the effectiveness of lumican-cytokines in combination with anti-PD-1 blockade in a difficult-to-treat mouse melanoma model, the $\text{Braf}^{V600E}/\text{Pten}^{fl/fl}$ genetically modified mouse model (GEMM) (Spranger et al., (2015) Nature 523:231-235; Momin et al., (2019) Sci. Transl. Med. 11, eeaw2614). Melanomas in this GEMM are induced by tamoxifen-regulated Cre expression in melanocytes, which drives the activation of oncogenic $\text{Braf}^{V600E}$ and biallelic deletion of tumor suppressor Pten. $\text{Braf}^{V600E}/\text{Pten}^{fl/fl}$ melanomas have fewer neoantigens and more heterogeneity than B16F10 tumors. This model has modest T cell infiltration, but tumor growth is only slightly slowed by dual checkpoint blockade of PD-1 and cytotoxic T-lymphocyte-associated protein 4 (CTLA-4). Id.

To determine if treatment with collagen-binding IL-2 and IL-12 alongside anti-PD-1 checkpoint blockade could reinvigorate the ongoing response and prime new T cell responses, as was observed in B16F10 tumors (FIGS. 9, 10, and 13), and if de novo T cell priming and any abscopal effects could be augmented by the inclusion of an immunogenic cell death-directing agent like the tumor-targeting antibody TA99, melanoma was induced by application of 4-hydroxytamoxifen on the right flank of $\text{Braf}^{V600E}/\text{Pten}^{fl/fl}$ mice on day 0. After induction, flat black-pigment lesions are formed. The lesions will progress to large masses without therapy (data not shown). On day 25, the tumor-bearing mice are treated with PBS control (i.tu), with Lumican-MSA-IL2 (i.tu)+IL12-MSA-Lumican (i.tu)+TA99 (i.p.)+anti-PD-1 (i.p.), with Lumican-MSA-IL2 (i.tu)+IL12-MSA-Lumican (i.tu)+anti-PD-1 (i.p.), with MSA-IL2 (i.tu)+IL12-MSA (i.tu)+TA99 (i.p.)+anti-PD-1 (i.p.), or with MSA-IL2 (i.tu)+IL12-MSA(i.tu)+anti-PD-1 (i.p.) on days 25, 31, 37, 43, 49, 55, and 61.

As shown in FIG. 21A, $\text{Braf}^{V600E}/\text{Pten}^{fl/fl}$ tumor-bearing mice treated with MSA-IL2 (i.tu)+IL12-MSA (i.tu)+TA99 (i.p.)+anti-PD-1 (i.p.) display inhibited lesion development.

As shown in FIG. 21B, the overall survival of $\text{Braf}^{V600E}/\text{Pten}^{fl/fl}$ tumor-bearing mice treated with anti-PD-1 and collagen-binding IL-2 and IL-12 with or without TA99 is comparable. Thus, TA99 was not a necessary component for efficacy. These results affirm that IL-2, IL-12, and checkpoint blockade can be an effective tumor-agnostic combination treatment (FIGS. 9, 10 and 13).

Tumor control in this model could also be achieved using unanchored cytokines in lieu of collagen-anchoring cytokines, but at the cost of major and potentially lethal toxicity. One-third of the mice treated with IL12-MSA and MSA-IL2 were euthanized because of >20% loss of body weight, whereas no mice treated with IL12-MSA-Lumican and Lumican-MSA-IL2 succumbed to treatment-related toxicity (FIG. 21B). These results demonstrate that collagen binding fusion proteins can safely improve overall survival in this potent tumor-agnostic combination treatment (FIG. 21B).

Example 27: LAIR Capacity for Binding to In Vivo Tumors

In this example, the capacity of LAIR to bind excised B16F10 tumors is measured. B16F10 tumors possess little detectable collagen and therefore serves as a lower estimate for LAIR's binding-capacity to a tumor. Briefly, C57/mice were inoculated with $1 \times 10^6$ B16F10 cells injected subcutaneously into the left flank. Seven days later, tumors were carefully excised and detached from all remaining skin and subcutaneous fat. The excised tumors were then incubated in a gentle detergent (PBS+0.1% v/v Tween20) for 2 hours at 37° C. and then disaggregated/pushed through a 70 micron filter (FIG. 22A). As shown in FIG. 22B, the matrix comprises a third of the tumor's mass.

The filtered-fraction was devoid of extracellular matrix (i.e. cell fraction) while the fraction that did not pass the filter (i.e. matrix fraction) was matrix-rich, as confirmed by a hydroxyproline assay (MAK008-1KT, Millipore Sigma) performed according to the manufacturer's instructions (FIG. 22C). Hydroxyproline (4-hydroxyproline) is a non-proteinogenic amino acid formed by the post-translational hydroxylation of proline. Hydroxyproline is a major component of collagen, where it serves to stabilize the helical structure. Because hydroxyproline is largely restricted to collagen, the measurement of hydroxylproline levels is used as an indicator of collagen content. In this assay, hydroxyproline concentration is detected by the reaction of oxidized hydroxyproline with 4-(dimethylamino)benzaldehyde (DMAB), which results in development of a colorimetric (560 nm) product, proportional to the hydroxyproline present.

Each tumor's matrix fraction was then incubated in either an antigen-excess concentration (10 µM) or antigen-depleting concentration (10 µM) of AF647-labeled LAIR to quantitate LAIR binding sites in the matrix fraction. The fluorescence of the solution was monitored over time until steady-state is achieved. As shown in FIG. 22D, a decrease in fluorescence is observed with the 1 µM labeled LAIR, which corresponds to LAIR depletion from the bath upon binding to the collagen within the matrix fraction. A 20% decrease in solution concentration indicates 0.2 nmol uptake into the tumor matrix. Thus, a day 7 B16F10 tumor from a $1 \times 10^6$ cell inoculum possesses 0.2 nmol of LAIR binding sites (FIG. 22D). This number correlates to the tumor's collagen content, as measured by hydroxyproline content (FIG. 22E). This experiment shows that LAIR is capable of binding B1610, as the B1610 matrix is collagen rich.

Example 28: Collagen-Binding Fusion Proteins Using LAIR Imparts Similar Benefit Compared to Using Lumican Like Lumican, LAIR can bind to collagen type I. A LAIR cytokine fusion protein was used to determine whether the collagen-binding fusion protein could potentiate the efficacy of a fused cytokine. A LAIR-cytokine fusion protein, LAIR-MSA-IL2 (SEQ ID NO: 186), was expressed and purified as described for Lumican-MSA-IL2 (Example 1). In the B16F10 melanoma mouse model conducted as described in Example 6, LAIR-MSA-IL2 is at least as efficacious as Lumican-MSA-IL2 in reducing tumor size (compare FIG. 3B to FIG. 23A). LAIR-MSA IL-2 also increased mice survival to levels comparable to survival in mice treated with a combination of Lumican-MSA-IL2 with intraperitoneal TA99 (compare FIGS. 3B and 3C to FIG. 23B). These results demonstrate that the collagen-binding strategy can be utilized using Lumican, LAIR or other collagen-binding proteins in their class.

Example 29: LAIR-Engineering Yields Both Higher and Lower Affinity Collagen Binders In this example, a yeast display platform is utilized to engineer higher and lower affinity variants of LAIR. Briefly, the mouse LAIR gene was amplified using error prone PCR to produce a library of LAIR mutants. RJY200 yeast (in-house modified version of EBY100, ATCC) are transformed with linearized pCTCON2 vector (41843, Addgene) and the error prone PCR product is collected, and subjected to an in vivo homologous recombination event to produce the final display plasmid. The pCTCON2 plasmid is formatted such that the LAIR mutants are fused to the Aga2 protein, which is bound to the yeast surface via a disulfide linkage to the membrane bound Aga1 protein. The LAIR gene is also followed by a c-myc tag, allowing one to probe for full expression of the mutant LAIR protein. Once expression is induced on the surface, yeast can be stained with labeled antigen and an antibody against the c-myc tag (ACMYC, Exalpha). LAIR expressing clones, as determined by c-myc staining intensity, can then be sorted for lower or higher affinity using FACS. (Chao et al., (2006) Nat. Protoc. 1(2):755-768).

A soluble collagen peptide mimic (CRP, collagen related peptide) was used as the antigen for the FACS assay as the LAIR natural ligand, collagen I, is not soluble. The protein sequence for this mimic is GCO-(GPO)$_{10}$-GCOG-NH2 where O represents hydroxyproline amino acids. Similar to collagen I, these peptides spontaneously form helical structures in solution. A crosslinking reagent (cat #, company) was used to lock these helical structures in place. Following purification, the crosslinked peptide was used as our antigen (CRP-XL). Note that this peptide was used in both a biotinylated (CRP-XL-Biotin) and non-biotinylated (CRP-XL) format. (A detailed description on these peptides and their functionalization into a triple helix format can be obtained from CambCollab Inc.)

Two different strategies were used to isolate high and low affinity collagen-binding mutants. To select for low affinity mutants, equilibrium sorting was employed. In this strategy, LAIR expression was induced on the surface of the yeast library. The library was sequentially incubated with CPP-XL-biotin and chicken anti-c-myc (ACMYC, Exalpha), followed by secondary antibodies (streptavidin-AF647 (S21374, Thermo Fisher) and goat anti-chicken AF488 (A-1139, Invitrogen) until equilibrium was reached. Yeast that displayed weak or no AF647 signal but were positive for AF488, indicating that they were expressing LAIR but not binding to the collagen mimic, were sorted on a BD FACS Aria machine. After several rounds of sorting, the yeast were miniprepped to isolate the display plasmids, transformed into bacteria colonies, and submitted for sequencing. Prevalent clones (clones that appeared in sequencing at higher frequency than others (at least twice)) and/or clones that contained mutations in the collagen binding pocket were selected for downstream analysis. (Brondijk et al., (2010) Blood 115:1364-1373). These mutants were cloned into a mammalian expression vector, solubly expressed as fusions to mouse serum albumin (MSA), and tested for their ability to bind collagen I in an ELISA assays. As shown in FIGS. 24A-E and 25A-C, weakly binding clones (FIGS. 24F, 24D) contain mutations in the LAIR binding pocket. SEQ ID NOS: 187-192.

To isolate higher affinity mutants, a kinetic sort strategy was employed. After inducing expression, the yeast library was labeled with CRP-XL-biotin as described above. After equilibrium was reached, the yeast clones were washed and then incubated in 300:1 excess CRP-XL (non-biotinylated) for 3-5 days. Unlabeled CRP-XL will displace dissociated CRP-XL-biotin for LAIR binding (FIGS. 26C-D). Only the clones with the slowest off-rate, i.e., the highest affinity clones, will remain labeled. The yeast clones with highest AF647 signal were then sorted using FACS. After several rounds of sorting, high affinity clones were selected for downstream analysis in a competition assay. The isolated yeast clones were labeled with CRP-XL-biotin and then incubated with unlabeled CRP-XL. Samples were taken over time and analyzed for AF647 signal (FIGS. 26E-F). As shown in FIG. 26G, a high affinity the mutant LAIR, LAIR30.2.K1.B, has a slower off rate than WT LAIR. The mutations seen in this clone is located outside of the LAIR binding pocket (FIG. 26B, SEQ ID NO:193). These results show that mutant LAIRs with a range of binding affinities to collagen could be isolated. These LAIR1 variants provide an opportunity to engineer immunomodulatory fusion proteins comprising therapeutic agents that are have different binding affinities to collagen-rich tumors.

Summary Sequence Table

| SEQ ID NO | Description | Sequence |
|---|---|---|
| 1 | IL-2 | APTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFCQSIISTLT |
| 2 | Wild Type IL12B without signal (IL12B) Amino Acids | IWELKKDVYVVELDWYPDAPGEMVVLTCDTPEEDGITWTLDQSSEVLGSGKTLTIQVKEFGDAGQYTCHKGGEVLSHSLLLLHKKEDGIWSTDILKDQKEPKNKTFLRCEAKNYSGRFTCWWLTTISTDLTFSVKSSRGSSDPQGVTCGAATLSAERVRGDNKEYEYSVECQEDSACPAAEESLPIEVMVDAVHKLKYENYTSSFFIRDIIKPDPPKNLQLKPLKNSRQVEVSWEYPDTWSTPHSYFSLTFCVQVQGKSKREKKDRVFTDKTSATVICRKNASISVRAQDRYYSSSWSEWASVPCS |
| 3 | Wild Type IL12A without signal peptide Amino acids | RNLPVATPDPGMFPCLHHSQNLLRAVSNMLQKARQTLEFYPCTSEEIDHEDITKDKTSTVEACLPLELTKNESCLNSRETSFITNGSCLASRKTSFMMALCLSSIYEDLKMYQVEFKTMNAKLLMDPKRQIFLDQNMLAVIDELMQALNFNSETVPQKSSLEEPDFYKTKIKLCILLHAFRIRAVTIDRVMSYLNAS |
| 4 | IL-15Ra | ITCPPPMSVEHADIWVKSYSLYSRERYICNSGFKRKAGTSSLTECVLNKATNVAHWTTPSLKCIRDPALVHQRPAPPSTVTTAGVTPQPESLSPSGKEPAASSPSSNNTAATTAAIVPGSQLMPSKSPSTGTTEISSHESSHGTPSQTTAKNWELTASASHQPPGVYPQGHSDTT |
| 5 | IL-15 | NWVNVISDLKKIEDLIQSMHIDATLYTESDVHPSCKVTAMKCFLLELQVISLESGDASIHDTVENLIILANNSLSSNGNVTESGCKECEELEEKNIKEFLQSFVHIVQMFINTS |
| 6 | TNF-alpha | VRSSSRTPSDKPVAHVVANPQAEGQLQWLNRRANALLANGVELRDNQLVVPSEGLYLIYSQVLFKGQGCPSTHVLLTHTISRIAVSYQTKVNLLSAIKSPCQRETPEGAEAKPWYEPIYLCGVFQLEKGDRLSAEINRPDYLDFAESCQVYFCIIAL |
| 7 | IFN-gamma | QDPYVKEAENLKKYFNAGHSDVADNGTLFLGILKNWKEESDRKIMQSQIVSFYFKLFKNFKDDQSIQKSVETIKEDMNVKFFNSNKKKRDDFEKLTNYSVFDLNVQRKAIHELIQVMAELSPAAKTGKRKRSQMLFRG |
| 8 | IFN-alpha | CDLPQTHSLGSRRTLMLLAQMRKISLFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRAEIMRSFSLSTNLQESLRSKE |
| 9 | IL-21 | QGQDRHMIRMRQLIDIVDQLKNYVNDLVPEFLPAPEDVETNCEWSAFSCFQKAQLKSANTGNNERIINVSIKKLKRKPPSTNAGRRQKHRLTCPSCDSYEKKPPKEFLERFKSLLQKMIHQHLSSRTHGSEDS |
| 10 | IL-6 | LAPRRCPAQEVARGVLTSLPGDSVTLTCPGVEPEDNATVHWVLRKPAAGSHPSRWAGMGRRLLLRSVQLHDSGNYSCYRAGRPAGTVHLLVDVPPEEPQLSCFRKSPLSNVVCEWGPRSTPSLTTKAVLLVRKFQNSPAEDFQEPCQYSQESQKFSCQLAVPEGDSSFYIVSMCVASSVGSKFSKTQTFQGCGILQPDPPANITVTAVARNPRWLSVTWQDPHSWNSSFYRLRFELRYRAERSKTFTTWMVKDLQHHCVIHDAWSGLRHVVQLRAQEEFG |

-continued

Summary Sequence Table

| SEQ ID NO | Description | Sequence |
|---|---|---|
| | | QGEWSEWSPEAMGTPWTESRSPPAENEVSTPMQALTTNKDDDNILFRDSANATSLP VQDSSSVPLPTFLVAGGSLAFGTLLCIAIVLRFKKTWKLRALKEGKTSMHPPYSLG QLVPERPRPTPVLVPLISPPVSPSSLGSDNTSSHNRPDARDPRSPYDISNTDYFFP R |
| 11 | IL-5 | DLLPDEKISLLPPVNFTIKVTGLAQVLLQWKPNPDQEQRNVNLEYQVKINAPKEDD YETRITESKCVTILHKGFSASVRTILQNDHSLLASSWASAELHAPPGSPGISIVNL TCTTNTTEDNYSRLRSYQVSLHCTWLVGTDAPEDTQYFLYYRYGSWTEECQEYSKD TLGRNIACWFPRTFILSKGRDWLAVLVNGSSKHSAIRPFDQLFALHAIDQINPPLN VTAEIEGTRLSIQWEKPVSAFPIHCFDYEVKIHNTRNGYLQIEKLMTNAFISIIDD LSKYDVQVRAAVSSMCREAGLWSEWSQPIYVGNDEHKPLREWFVIVIMATICFILL ILSLICKICHLWIKLFPPIPAPKSNIKDLFVGGNYEKAGSSETEIEVICYIEKPGV ETLEDSVF |
| 12 | IL-8 | AVLPRSAKELRCQCIKTYSKPFHPKFIKELRVIESGPHCANTEIIVKLSDGRELCL DPKENWVQRWEKFLKRAENS |
| 13 | IL-7 | DCDIEGKDGKQYESVLMVSIDQLLDSMKEIGSNCLNNEFNFFKRHICDANKEGMFL FRAARKLRQFLKMNSTGDFDLHLLKVSEGTTILLNCTGQVKGRKPAALGEAQPTKS LEENKSLKEQKKLNDLCFLKRLLQEIKTCWNKILMGTKEH |
| 14 | IL-17A | GITIPRNPGCPNSEDKNFPRTVMVNLNIHNRNTNTNPKRSSDYYNRSTSPWNLHRN EDPERYPSVIWEAKCRHLGCINADGNVDYHMNSVPIQQEILVLRREPPHCPNSFRL EKILVSVGCTCVTPIVHHVA |
| 15 | IL-13alpha | RAVPGGSSPAWTQCQQLSQKLCTLAWSAHPLVGHMDLREEGDEETTNDVPHIQCGD GCDPQGLRDNSQFCLQRIHQGLIFYEKLLGSDIFTGEPSLLPDSPVGQLHASLLGL SQLLQPEGHHWETQQIPSLSPSQPWQRLLLRFKILRSLQAFVAVAARVFAHGAATL SP |
| 16 | IL-18 | YFGKLESKLSVIRNLNDQVLFIDQGNRPLFEDMTDSDCRDNAPRTIFIISMYKDSQ PRGMAVTISVKCEKISTLSCENKIISFKEMNPPDNIKDTKSDIIFFQRSVPGHDNK MQFESSSYEGYFLACEKERDLFKLILKKEDELGDRSIMFTVQNED |
| 17 | IL-1alpha | SAPFSFLSNVKYNFMRIIKYEFILNDALNQSIIRANDQYLTAAALHNLDEAVKFDM GAYKSSKDDAKITVILRISKTQLYVTAQDEDQPVLLKEMPEIPKTITGSETNLLFF WETHGTKNYFTSVAHPNLFIATKQDYWVCLAGGPPSITDFQILENQA |
| 18 | IL-1beta | APVRSLNCTLRDSQQKSLVMSGPYELKALHLQGQDMEQQVVFSMSFVQGEESNDKI PVALGLKEKNLYLSCVLKDDKPTLQLESVDPKNYPKKKMEKRFVFNKIEINNKLEF ESAQFPNWYISTSQAENMPVFLGGTKGGQDITDFTMQFVSS |
| 19 | IL-4 | HKCDITLQEIIKTLNSLTEQKTLCTELTVTDIFAASKNTTEKETFCRAATVLRQFY SHHEKDTRCLGATAQQFHRHKQLIRFLKRLDRNLWGLAGLNSCPVKEANQSTLENF LERLKTIMREKYSKCSS |
| 20 | IL-3 | APMTQTTPLKTSWVNCSNMIDEIITHLKQPPLPLLDFNNLNGEDQDILMENNLRRP NLEAFNRAVKSLQNASAIESILKNLLPCLPLATAAPTRHPIHIKDGDWNEFRRKLT FYLKTLENAQAQQTTLSLAIF |
| 21 | IL-10 | SPGQGTQSENSCTHFPGNLPNMLRDLRDAFSRVKTFFQMKDQLDNLLLKESLLEDF KGYLGCQALSEMIQFYLEEVMPQAENQDPDIKAHVNSLGENLKTLRLRLRRCHRFL PCENKSKAVEQVKNAFNKLQEKGIYKAMSEFDIFINYIEAYMTMKIRN |
| 22 | IL-13 | PVPPSTALRELIEELVNITQNQKAPLCNGSMVWSINLTAGMYCAALESLINVSGCS AIEKTQRMLSGFCPHKVSAGQFSSLHVRDTKIEVAQFVKDLLLHLKKLFREGRFN |
| 23 | IL-17a | GITIPRNPGCPNSEDKNFPRTVMVNLNIHNRNTNTNPKRSSDYYNRSTSPWNLHRN EDPERYPSVIWEAKCRHLGCINADGNVDYHMNSVPIQQEILVLRREPPHCPNSFRL EKILVSVGCTCVTPIVHHVA |
| 24 | IL-9 | QGCPTLAGILDINFLINKMQEDPASKCHCSANVTSCLCLGIPSDNCTRPCFSERLS QMTNTTMQTRYPLIFSRVKKSVEVLKNNKCPYFSCEQPCNQTTAGNALTFLKSLLE IFQKEKMRGMRGKI |
| 25 | IFN-gamma | QDPYVKEAENLKKYFNAGHSDVADNGTLFLGILKNWKEESDRKIMQSQIVSFYFKL FKNFKDDQSIQKSVETIKEDMNVKFFNSNKKKRDDFEKLTNYSVTDLNVQRKAIHE LIQVMAELSPAAKTGKRKRSQMLFRG |
| 26 | IFN-alpha | CDLPQTHSLGSRRTLMLLAQMRKISLFSCLKDRHDFGFPQEEFGNQFQKAETIPVL HEMIQQIFNLFSTKDSSAAWDETLLDKFYTELYQQLNDLEACVIQGVGVTETPLMK EDSILAVRKYFQRITLYLKEKKYSPCAWEVVRAEIMRSFSLSTNLQESLRSKE |

Summary Sequence Table

| SEQ ID NO | Description | Sequence |
|---|---|---|
| 27 | GM-CSF | APARSPSPSTQPWEHVNAIQEARRLLNLSRDTAAEMNETVEVISEMFDLQEPTCLQ TRLELYKQGLRGSLTKLKGPLTMMASHYKQHCPPTPETSCATQIITFESFKENLKD FLLVIPFDCWEPVQE |
| 28 | FLT3L | TQDCSFQHSPISSDFAVKIRELSDYLLQDYPVTVASNLQDEELCGGLWRLVLAQRW MERLKTVAGSKMQGLLERVNTEIHFVTKCAFQPPPSCLRFVQTNISRLLQETSEQL VALKPWITRQNFSRCLELQCQPDSSTLPPPWSPRPLEATAPTAPQPPLLLLLLLPV GLLLLAAAWCLHWQRTRRRTPRPGEQVPPVPSPQDLLLVEH |
| 29 | G-CSF | ATPLGPASSLPQSFLLKCLEQVRKIQGDGAALQEKLVSECATYKLCHPEELVLLGH SLGIPWAPLSSCPSQALQLAGCLSQLHSGLFLYQGLLQALEGISPELGPTLDTLQL DVADFATTIWQQMEELGMAPALQPTQGAMPAFASAFQRRAGGVLVASHLQSFLEVS YRVLRHLAQP |
| 30 | LIF | SPLPITPVNATCAIRHPCHNNLMNQIRSQLAQLNGSANALFILYYTAQGEPFPNNL DKLCGPNVTDFPPFHANGTEKAKLVELYRIWYLGTSLGNITRDQKILNPSALSLH SKLNATADILRGLLSNVLCRLCSKYHVGHVDVTYGPDTSGKDVFQKKKLGCQLLGK YKQIIAVLAQAF |
| 31 | M-CSF | EEVSEYCSHMIGSGHLQSLQRLIDSQMETSCQITFEFVDQEQLKDPVCYLKKAFLL VQDIMEDTMRFRDNTPNAIAIVQLQELSLRLKSCFTKDYEEHDKACVRTFYETPLQ LLEKVKNVFNETKNLLDKDWNIFSKNCNNSFAECSSQDWTKPDCNCLYPKAIPSS DPASVSPHQPLAPSMAPVAGLTWEDSEGTEGSSLLPGEQPLHTVDPGSAKQRPPRS TCQSFEPPETPWKDSTIGGSPQPRPSVGAFNPGMEDILDSAMGTNWVPEEASGEA SEIPVPQGTELSPSRPGGGSMQTEPARPSNFLSASSPLPASAKGQQPADVTGTALP RVGPVRPTGQDWNHTPQKTDHPSALLRDPPEPGSPRISSLRPQGLSNPSTLSAQPQ LSRSHSSGSVLPLGELEGRRSTRDRRSPAEPEGGPASEGAARPLPRFNSVPLTDTG HERQSEGSFSPQLQESVFHLLVPSVILVLLAVGGLLFYRWRRRSHQEPQRADSPLE QPEGSPLTQDDRQVELPV |
| 32 | MIP-2 | APLATELRCQCLQTLQGIHLKNIQSVKVKSPGPHCAQTEVIATLKNGQKACLNPAS PMVKKIIEKMLKNGKSN |
| 33 | MIP-1beta | APMGSDPPTACCFSYTARKLPRNFVVDYYETSSLCSQPAWFQTKRSKQVCADPSE SWVQEYVYDLELN |
| 34 | KP (aka CXCL1) | ASVATELRCQCLQTLQGIHPKNIQSVNVKSPGPHCAQTEVIATLKNGRKACLNPAS PIVKKIIEKMLNSDKSN |
| 35 | MIG (aka CXCL9) | TPVVRKGRCSCISTNQGTIHLQSLKDLKQFAPSPSCEKIEIIATLKNGVQTCLNPD SADVKELIKKWEKQVSQKKKQKNGKKHQKKKVLKVRKSQRSRQKKTT |
| 36 | IP-10 (CXCL10) | VPLSRTVRCTCISISNQPVNPRSLEKLEIIPASQFCPRVEIIATMKKKGEKRCLNP ESKAIKNLLKAVSKERSKRSP |
| 37 | MCP-1 | QPDAINAPVTCCYNFTNRKISVQRLASYRRITSSKCPKEAVIFKTIVAKEICADPK QKWVQDSMDHLDKQTQTPKT |
| 38 | Eotaxin | GPASVPTTCCFNLANRKIPLQRLESYRRITSGKCPQKAVIFKTKLAKDICADPKKK WVQDSMKYLDQKSPTPKP |
| 39 | RANTES | SPYSSDTTPCCFAYIARPLPRAHIKEYFYTSGKCSNPAWFVTRKNRQVCANPEKK WVREYINSLEMS |
| 40 | LIX | AGPAAAVLRELRCVCLQTTQGVHPKMISNLQVFAIGPQCSKVEWASLKNGKEICL DPEAPFLKKVIQKILDGGNKEN |
| 41 | MIP-1alpha | SLAADTPTACCFSYTSRQIPQNFIADYFETSSQCSKPGVIFLTKRSRQVCADPSEE WVQKYVSDLELSA |
| 42 | Human serum albumin amino acid sequence) | MDMRVPAQLLGLLLLWLPGARCADAHKSEVAHRFKDLGEENFKALVLIAFAQYLQQ CPFEDHVKLVNEVGEFAKTCVADESAENCDKSLHTLFGDKLCTVATLRETYGEMAD CCAKQEPERNECFLQHKDDNPNLPRLVRPEVDVMCTAFHDNEETFLKKYLYEIARR HPYFYAPELLFFAKRYKAAFTECCQAADKAACLLPKLDELRDEGKASSAKQRLKCA SLQKFGERAFKAWAVARLSQRFPKAEFAEVSKLVTDLTKVHTECCHGDLLECADDR ADLAKYICENQDSISSKLKECCEKPLLEKSHCIAEVENDEMPADLPSLAADFVESK DVCKNYAEAKDVFLGMFLYEYARRHPDYSVVLLLRLAKTYETTLEKCCAAADPHEC YAKVFDEFKPLVEEPQNLIKQNCELFEQLGEYKFQNALLVRYTKKVPQVSTPTLVE VSRNLGKVGSKCCKHPEAKRMPCAEDYLSVVLNQLCVLHEKTPVSDRVTKCCTESL |

Summary Sequence Table

| SEQ ID NO | Description | Sequence |
|---|---|---|
| | | VNRRPCFSALEVDEGYVPKEFNAETFTFHADICTLSEKERQIKKQTALVELVKHKP KATKEQLKAVMDDFAAFVEKCCKADDKETCFAEEGKKLVAASQAALGLGGGSAPTS SSTKKTQLQLEHLLLDLQMILNGINNYKNPKLTRMLTFKFYMPKKATELKHLQCLE EELKPLEEVLNLAQSKNFHLRPRDLISNINVIVLELKGSETTFMCEYADETATIVE FLNRWITFCQSIISTLGGGGS |
| 43 | Mature HSA (amino acid sequence) | DAHKSEVAHRFKDLGEENFKALVLIAFAQYLQQCPFEDHVKLVNEVTEFAKTCVAD ESAENCDKSLHTLFGDKLCTVATLRETYGEMADCCAKQEPERNECFLQHKDDNPNL PRLVRPEVDVMCTAFHDNEETFLKKYLYEIARRHPYFYAPELLFFAKRYKAAFTEC CQAADKAACLLPKLDELRDEGKASSAKQRLKCASLQKFGERAFKAWAVARLSQRFP KAEFAEVSKLVTDLTKVHTECCHGDLLECADDRADLAKYICENQDSISSKLKECCE KPLLEKSHCIAEVENDEMPADLPSLAADFVESKDVCKNYAEAKDVFLGMFLYEYAR RHPDYSVVLLLRLAKTYETTLEKCCAAADPHECYAKVFDEFKPLVEEPQNLIKQNC ELFEQLGEYKFQNALLVRYTKKVPQVSTPTLVEVSRNLGKVGSKCCKHPEAKRMPC AEDYLSVVLNQLCVLHEKTPVSDRVTKCCTESLVNRRPCFSALEVDETYVPKEFNA ETFTFHADICTLSEKERQIKKQTALVELVKHKPKATKEQLKAVMDDFAAFVEKCCK ADDKETCFAEEGKKLVAASQAALGLGGGSAPTSSSTKKTQLQLEHLLLDLQMILNG INNYKNPKLTRMLTFKFYMPKKATELKHLQCLEEELKPLEEVLNLAQSKNFHLRPR DLISNINVIVLELKGSETTFMCEYADETATIVEFLNRWITFCQSIISTLTGGGS |
| 44 | PD-1 | MQIPQAPWPVVWAVLQLGWRPGWFLDSPDPWNPPTFFPALLVVTEGDNATFTCSFS NTSESFVLNWYRMSPSNQTDKLAAFPEDRSQPGQDCRFRVTQLPNGRDFHMSVVRA RRNDSGTYLCGAISLAPKAQIKESLRAELRVTERRAEVPTAHPSPSPRPAGQFQTL VVGVVGGLLGSLVLLVWVLAVICSRAARGTIGARRTGQPLKEDPSAVPVFSVDYGE LDFQWREKTPEPPVPCVPEQTEYATIVFPSGMGTSSPARRGSADGPRSAQPLRPED GHCSWPL |
| 45 | PD-L-1 | MRIFAVFIFMTYWHLLNAFTVTVPKDLYVVEYGSNMTIECKFPVEKQLDLAALIVY WEMEDKNIIQFVHGEEDLKVQHSSYRQRARLLKDQLSLGNAALQITDVKLQDAGVY RCMISYGGADYKRITVKVNAPYNKINQRILVVDPVTSEHELTCQAEGYPKAEVIWT SSDHQVLSGKTTTTNSKREEKLFNVTSTLRINTTTNEIFYCTFRRLDPEENHTAEL VIPELPLAHPPNERTHLVTLGAILLC LGVALTFIFR LRKGRMMDVKKCGIQDTNSK KQSDTHLEET |
| 46 | CTLA-4 | MACLGFQRHKAQLNLATRTWPCTLLFFLLFIPVFCKAMHVAQPAVVLASS RGIASFVCEYASPGKATEVRVTVLRQADSQVTEVCAATYM MGNELTFLDDSICTGTSSGNQVNLTIQGLRAMDTGLYICKVELMYPPPYY LGIGNGTQIY VIDPEPCPDS DFLLWILAAVSSGLFFYSFL LYAVSLSKML KKRSPLTTGVYVKMPPTEPE CEKQFQPYFI PIN |
| 47 | LAG3 | MWEAQFLGLLFLQPLWVAPVKPLQPGAEVPVVWAQEGAPAQLPCSPTIPLQDLSLL RRAGVTWQHQPDSGPPAAAPGHPLAPGPHPAAPSSWGPRPRRYTVLSVGPGGLRSG RLPLQPRVQLDERGRQRGDFSLWLRPAR RADAGEYRAAVHLRDRALSCRLRLRLGQASMTASPPGSLR ASDWVILNCSFSRPDRPASVHWFRNRGQGRVPVRESPHHHLAESFLFLPQVSPMDS GPWGCILTYRDGFNVSIMYNLTVLGLEPPTPLTVYAGAGSRVGLPCRLPAGVGTRS FLTAKWTPPGGGPDLLVTGDNGDFTLRL EDVSQAQAGT YTCHIHLQEQ QLNATVTLAI ITVTPKSFGS PGSLGKLLCEVTPVSGQERFVWSSLDTPSQRSFSGPWLEAQEAQLLSQPWQCQLYQ GERLLGAAVYFTEL SSPGAQRSGR APGALPAGHL LLFLILGVLS LLLLVTGAFG FHLWRRQWRPRRFSALEQGI HPPQAQSKIE ELEQEPEPEP EPEPEPEPEP EPEQL |
| 48 | TIM3 | MFSHLPFDCVLLLLLLLLTRSSEVEYRAEVGQNAYLPCFYTPAAPGNLVPVCWGKG ACPVFECGNVVLRTDERDVNYWTSRYWLNGDFRKGDVSLTIENVTLADSGIYCCRI QIPGIMNDEKFNLKLVIKPAKVTPAPTR QRDFTAAFPR MLTTRGHGPA ETQTLGSLPD INLTQISTLA NELRDSRLANDLRDSGATIRGIYIGAGICAGLALALIFGALIFKWYSHSKEKIQNL SLISLANLPPSGLANAVAEGIRSEENIYTIEENVYEVEEPNEYYCYVSSRQQPSQP LGCRFAMP |
| 49 | B7-H3 | MLRRGSPGMGVHVGAALGALWFCLTGALEVQVPEDPVVALVGTDATLCC SFSPEPGFSLQLNLIWQLT DTKQLVHSFA EGQDQGSAYA NRTALFPDLLAQGNASLRLQRVRVADEGSFCFVSIRDFGSAAVSLQVAA PYSKPSMTLE PNKDLRPGDT VTITCSSYQG YPEAEVFWQD GQGVPLTGNVTTSQMANEQGLFDVHSILRWLGANGTYSCLVRNPVLQQD AHSSVTITPQRSPTGAVEVQVPEDPVVALVGTDATLRCSF SPEPGFSLAQLNLIWQLTDTKQLVHSFTEGRDQGSAYANRTALFPDLLAQ GNASLRLQRV RVADEGSFTC FVSIRDFGSA AVSLQVAAPY SKPSMTLEPNKDLRPGDTVTITCSSYRGYPEAEVFWQDGQGVPLTGNVTT SQMANEQGLFDVHSVLRVVLGANGTYSCLVRNPVLQQDAH GSVTITGQPMTFPPEALWVTVGLSVCLIALLVALAFVCWRKIKQSCEEEN AGAEDQDGEGEGSKTALQPLKHSDSKEDDGQEIA |

Summary Sequence Table

| SEQ ID NO | Description | Sequence |
|---|---|---|
| 50 | B7-H4 | MASLGQILFWSIISIIILAGAIALIIGFGISAFSMPEVNVDYNASSETLRCEAPR WFPQPTVVWASQVDQGANFSEVSNTSFELNSENVTMKVVSVLYN VTINNTYSCM IENDIAKATGDIKVTESEIKRRSHLQLLNS KASLCVSSFFAISWALLPLSPYLMLK |
| 51 | TNF-alpha extracellular domain | GPQREEFPRDLSLISPLAQAVRSSSRTPSDKPVAHVVANPQAEGQLQWLNRRANAL LANGVELRDNQLVVPSEGLYLIYSQVLFKGQGCPSTHVLLTHTISRIAVSYQTKVN LLSAIKSPCQRETPEGAEAKPWYEPIYLGGVFQLEKGDRLSAEINRPDYLDFAESG QVYFGIIAL |
| 52 | LIGHT extracellular domain | LQLHWRLGEMVTRLPDGPAGSWEQLIQERRSHEVNPAAHLTGANSSLTGSGGPLLW ETQLGLAFLRGLSYHDGALVVTKAGYYYIYSKVQLGGVGCPLGLASTITHGLYKRT PRYPEELELLVSQQSPCGRATSSSRVWWDSSFLGGVVHLEAGEKVVVRVLDERLVR LRDGTRSYFGAFMV |
| 53 | LT-alpha extracellular domain | LPGVGLTPSAAQTARQHPKMHLAHSTLKPAAHLIGDPSKQNSLLWRANTDRAFLQD GFSLSNNSLLVPTSGIYFVYSQVVFSGKAYSPKATSSPLYLAHEVQLFSSQYPFHV PLLSSQKMVYPGLQEPWLHSMYHGAAFQLTQGDQLSTHTDGIPHLVLSPSTVFFGA FAL |
| 54 | LT-beta extracellular domain | QDQGGLVTETADPGAQAQQGLGFQKLPEEEPETDLSPGLPAAHLIGAPLKGQGLGW ETTKEQAFLTSGTQFSDAEGLALPQDGLYYLYCLVGYRGRAPPGGGDPQGRSVTLR SSLYRAGGAYGPGTPELLLEGAETVTPVLDPARRQGYGPLWYTSVGFGGLVQLRRG ERVYVNISHPDMVDFARGKTFFGAVMVG |
| 55 | BTLA extracellular domain | KESCDVQLYIKRQSEHSILAGDPFELECPVKYCANRPHVTWCKLNGTTCVKLEDRQ TSWKEEKNISFFILHFEPVLPNDNGSYRCSANFQSNLIESHSTTLYVTDVKSASER PSKDEMASRPWLLYR |
| 56 | CD160 extracellular domain | INITSSASQEGTRLNLICTVWHKKEEAEGFVVFLCKDRSGDCSPETSLKQLRLKRD PGIDGVGEISSQLMFTISQVTPLHSGTYQCCARSQKSGIRLQGHFFSILFTETGNY TVTGLKQRQHLEFSHNEGTLS |
| 57 | CD40L extracellular domain | MQKGDQNPQIAAHVISEASSKTTSVLQWAEKGYYTMSNNLVTLENGKQLTVKRQGL YYIYAQVTFCSNREASSQAPFIASLCLKSPGRFERILLRAANTHSSAKPCGQQSIH LGGVFELQPGASVFVNVTDPSQVSHGTGFTSFGLLKL |
| 58 | FasL extracellular domain | QIGHPSPPPEKKELRKVAHLTGKSNSRSMPLEWEDTYGIVLLSGVKYKKGGLVINE TGLYFVYSKVYFRGQSCNNLPLSHKVYMRNSKYPQDLVMMEGKMMSYCTTGQMWAR SSYLGAVFNLTSADHLYVNVSELSLVNFEESQTFFGLYKL |
| 59 | CD30L extracellular domain | FPQDRPFEDTCHGNPSHYYDKAVRRCCYRCPMGLFPTQQCPQRPTDCRKQCEPDYY LDEADRCTACVTCSRDDLVEKTPCAWNSSRVCECRPGMFCSTSAVNSCARCFFHSV CPAGMIVKFPGTAQKNTVCEPASPGVSPACASPENCKEPSSGTIPQAKPTPVSPAT SSASTMPVRGGTRLAQEEAASKLTRAPDSPSSVGRPSSDPGLSPTQPCPEGSGDCRK QCEPDYYLDEAGRCTACVSCSRDDLVEKTPCAWNSSRTCECRPGMICATSATNSCA RCVPYPICAAETVTKPQDMAEKDTTFEAPPLGTQPDCNPTPENGEAPASTSPTQSL LVDSQASKTLPIPTSAPVALSSTGKPVLDAGPVLFWVILVLVVVVGSSAFLLCHRR ACRKRIRQKLHLCYPVQTSQPKLELVDSRPRRSSTQLRSGASVTEPVAEEERGLMSQ PLMETCHSVGAAYLESLPLQDASPAGGPSSPRDLPEPRVSTEHTNNKIEKIYIMKA DTVIVGTVKAELPEGRGLAGPAEPELEEELEADHTPHYPEQETEPPLGSCSDVMLS VEEEGKEDPLPTAASGK |
| 60 | 4-1BBL extracellular domain | ACPWAVSGARASPGSAASPRLREGPELSPDDPAGLLDLRQGMFAQLVAQNVLLIDG PLSWYSDPGLAGVSLTGGLSYKEDTKELVVAKAGVYYVFFQLELRRVVAGEGSGSV SLALHLQPLRSAAGAAALALTVDLPPASSEARNSAFGFQGRLLHLSAGQRLGVHLH TEARARHAWQLTQGATVLGLFRVTPEIPAGLPSPRSE |
| 61 | CD27L extracellular domain | ATPAPKSCPERHYWAQGKLCCQMCEPGTFLVKDCDQHRKAAQCDPCIPGVSFSPDH HTRPHCESCRHCNSGLLVRNCTITANAECACRNGWQCRDKECTECDPLPNPSLTAR SSQALSPHPQPTHLPYVSEMLEARTAGHMQTLADFRQLPARTLSTHWPPQRSLCSS DFIR |
| 62 | OX40L extracellular domain | LHCVGDTYPSNDRCCHECRPGNGMVSRCSRSQNTVCRPCGPGFYNDVVSSKPCKPC TWCNLRSGSERKQLCTATQDTVCRCRAGTQPLDSYKPGVDCAPCPPGHFSPGDNQA CKPWTNCTLAGKHTLQPASNSSDAICEDRDPPATQPQETQGPPARPITVQPTEAWP RYSQGPSTRPVEVPGGRA |
| 63 | TWEAK extracellular domain | SAPKGRKTRARRAIAAHYEVHPRPGQDGAQAGVDGTVSGWEEEARINSSSPLRYNRQ IGEFIVTRAGLYYLYCQVHFDEGKAVYLKLDLLVDGVLALRCLEEFSATAASSLGP QLRLCQVSGLLALRPGSSLRIRTLPWAHLKAAPFLTYFGLFQVH |

-continued

Summary Sequence Table

| SEQ ID NO | Description | Sequence |
|---|---|---|
| 64 | APRIL extracellular domain | AVLTQKQKKQHSVLHLVPINATSKDDSDVTEVMWQPALRRGRGLQAQGYGVRIQDA GVYLLYSQVLFQDVTFTMGVVWSREGQGRQETLFRCIRSMPSHPDRAYNSCYSAGV FHLHQGDILSVIIPRARAKLNLSPHGTFLGFVKL |
| 65 | BAFF extracellular domain | AVQGPEETVTQDCLQLIADSETPTIQKGSYTFVPWLLSFKRGSALEEKENKILVKE TGYFFIYGQVLYTDKTYAMGHLIQRKKVHVFGDELSLVTLFRCIQNMPETLPNNSC YSAGIAKLEEGDELQLAIPRENAQISLDGDVTFFGALKLL |
| 66 | RANKL extracellular domain | YFRAQMDPNRISEDGTHCIYRILRLHENADFQDTTLESQDTKLIPDSCRRIKQAFQ GAVQKELQHIVGSQHIRAEKAMVDGSWLDLAKRSKLEAQPFAHLTINATDIPSGSH KVSLSSWYHDRGWAKISNMTFSNGKLIVNQDGFYYLYANICFRHHETSGDLATEYL QLMVYVTKTSIKIPSSHTLMKGGSTKYWSGNSEFHFYSINVGGFFKLRSGEEISIE VSNPSLLDPDQDATYFGAFKVRDID |
| 67 | TRAIL extracellular domain | TNELKQMQDKYSKSGIACFLKEDDSYWDPNDEESMNSPCWQVKWQLRQLVRKMILR TSEETISTVQEKQQNISPLVRERGPQRVAAHITGTRGRSNTLSSPNSKNEKALGRK INSWESSRSGHSFLSNLHLRNGELVIHEKGFYYIYSQTYFRFQEEIKENTKNDKQM VQYIYKYTSYPDPILLMKSARNSCWSKDAEYGLYSIYQGGIFELKENDRIFVSVTN EHLIDMDHEASFFGAFLVG |
| 68 | EDA1 extracellular domain | ELRSELRRERGAESRLGGSGTPGTSGTLSSLGGLDPDSPITSHLGQPSPKQQPLEP GEAALHSDSQDGHQMALLNFFFPDEKPYSEEESRRVRRNKRSKSNEGADGPVKNKK KGKKAGPPGPNGPPGPPPGPPGPQGPPGIPGIPGTTVMGPPGPPGPPGPQGPPG LQGPSGAADKAGTRENQPAVVHLQGQGSAIQVKNDLSGGVLNDWSRITMNPKVFKL HPRSGELEVLVDGTYFIYSQVEVYYINFTDFASYEVVVDEKPFLQCTRSIETGKTN YNTCYTAGVCLLKARQKIAVKMVHADISINMSKHTTFFGAIRLGEAPAS |
| 69 | EDA2 extracellular domain | ELRSELRRERGAESRLGGSGTPGTSGTLSSLGGLDPDSPITSHLGQPSPKQQPLEP GEAALHSDSQDGHQGHQ |
| 70 | GITRL extracellular domain | QLETAKEPCMAKFGPLPSKWQMASSEPPCVNKVSDWKLEILQNGLYLIYGQVAPNA NYNDVAPFEVRLYKNKDMIQTLTNKSKIQNVGGTYELHVGDTIDLIFNSEHQVLKN NTYWGIILLANPQFIS |
| 71 | CD80 (B7-1) extracellular domain | VIHVTKEVKEVATLSCGHNVSVEELAQTRIYWQKEKKMVLTMMSGDMNIWPEYKNR TIFDITNNLSIVILALRPSDEGTYECVVLKYEKDAFKREHLAEVTLSVKADFPTPS ISDFEIPTSNIRRIICSTSGGFPEPHLSWLENGEELNAINTTVSQDPETELYAVSS KLDFNMTTNHSFMCLIKYGHLRVNQTFNWNTTKQEHFPDN |
| 72 | CD86 (B7-2) extracellular domain | APLKIQAYFNETADLPCQFANSNQSLSELVVFWQDQENLVLNEVYLGKEKFDSVH SKYMGRTSFDSDSWTLRLHNLQIKDKGLYQCIIHHKKPTGMIRIHQMNSELSVLAN FSQPEIVPISNITENVYINLTCSSIHGYPEPKKMSVLLRTKNSTIEYDGVMQKSQD NVTELYDVSISLSVSFPDVTSNMTIFCILETDKTRLLSSPFSIELEDPQPPPDHIP |
| 73 | ICOSLG extracellular domain | DTQEKEVRAMVGSDVELSCACPEGSRFDLNDVYVYWQTSESKTVVTYHIPQNSSLE NVDSRYRNRALMSPAGMLRGDFSLRLFNVTPQDEQKFHCLVLSQSLGFQEVLSVEV TLHVAANFSVPVVSAPHSPSQDELTFTCTSINGYPRPNVYWINKTDNSLLDQALQN DTVFLNMRGLYDVVSVLRIARTPSVNIGCCIENVLLQQNLTVGSQTGNDIGERDKI TENPVSTGEKNAAT |
| 74 | MICA extracellular domain | EPHSLRYNLTVLSWDGSVQSGFLTEVHLDGQPFLRCDRQKCRAKPQGQWAEDVLGN KTWDRETRDLTGNGKDLRMTLAHIKDQKEGLHSLQEIRVCEIHEDNSTRSSQHFYY DGELFLSQNLETKEWTMPQSSRAQTLAMNVRNFLKEDAMKTKTHYHAMHADCLQEL RRYLKSGVVLRRTVPPMVNVTRSEASEGNITVTCRASGFYPWNITLSWRQDGVSLS HDTQQWGDVLPDGNGTYQTWVATRICQGEEQRFTCYMEHSGNHSTHPVPSGKVLVL QSHW |
| 75 | MICB extracellular domain | AEPHSLRYNLMVLSQDESVQSGFLAEGHLDGQPFLRYDRQKRRAKPQGQWAEDVLG AKTWDTETEDLTENGQDLRRTLTHIKDQKGGLHSLQEIRVCEIHEDSSTRGSRHFY YDGELFLSQNLETQESTVPQSSRAQTLAMNVTNFWKEDAMKTKTHYRAMQADCLQK LQRYLKSGVAIRRTVPPMVNVTCSEVSEGNITVTCRASSFYPRNITLTWRQDGVSL SHNTQQWGDVLPDGNGTYQTWVATRIRQGEEQRFTCYMEHSGNHGTHPVPSGKVLV LQSQRTD |
| 76 | ULBP1 extracellular domain | GWVDTHCLCYDFIITPKSRPEPQWCEVQGLVDERPFLHYDCVNHKAKAFASLGKKV NVTKTWEEQTETLRDVVDFLKGQLLDIQVENLIPIEPLTLQARMSCEHEAHGHGRG SWQFLFNGQKFLLFDSNNRKWTALHPGAKKMTEKWEKNRDVTMFFQKISLGDCKMW LEEFLMYWEQMLDPTKPPSSLAPG |

Summary Sequence Table

| SEQ ID NO | Description | Sequence |
|---|---|---|
| 77 | ULBP2 extracellular domain | GRADPHSLCYDITVIPKFRPGPRWCAVQGQVDEKTFLHYDCGNKTVTPVSPLGKKL NVTTAWKAQNPVLREVVDILTEQLRDIQLENYTPKEPLTLQARMSCEQKAEGHSSG SWQFSFDGQIFLLFDSEKRMWTTVHPGARKMKEKVVENDKWAMSFHYFSMGDCIGW LEDFLMGMDSTLEPSAGAPLAMS |
| 78 | ULBP3 extracellular domain | DAHSLWYNFTIIHLPRHGQQWCEVQSQVDQKNFLSYDCGSDKVLSMGHLEEQLYAT DAWGKQLEMLREVGQRLRLELADTELEDFTPSGPLTLQVRMSCECEADGYIRGSWQ FSFDGRKFLLFDSNNRKWTVVHAGARRMKEKWEKDSGLTTFFKMVSMRDCKSWLRD FLMHRKKRLEPTAPPTMAPG |
| 79 | ULBP4 extracellular domain | HSLCFNFTIKSLSRPGQPWCEAQVFLNKNLFLQYNSDNNMVKPLGLLGKKVYATST WGELTQTLGEVGRDLRMLLCDIKPQIKTSDPSTLQVEMFCQREAERCTGASWQFAT NGEKSLLFDAMNMTWTVINHEASKIKETWKKDRGLEKYFRKLSKGDCDHWLREFLG HWEAMPEPTVSPVNASDIHWSSSSLPD |
| 80 | ULBP5, isoform 1 extracellular domain | GLADPHSLCYDITVIPKFRPGPRWCAVQGQVDEKTFLHYDCGSKTVTPVSPLGKKL NVTTAWKAQNPVLREVVDILTEQLLDIQLENYIPKEPLTLQARMSCEQKAEGHSSG SWQLSFDGQIFLLFDSENRMWTTVHPGARKMKEKWENDKDMTMSFHYISMGDCTGW LEDFLMGMDSTLEPSAGAPPTMSSG |
| 81 | ULBP5, isoform 2 extracellular domain | GLADPHSLCYDITVIPKFRPGPRWCAVQGQVDEKTFLHYDCGSKTVTPVSPLGKKL NVTTAWKAQNPVLREVVDILTEQLLDIQLENYIPKEPLTLQARMSCEQKAEGHSSG SWQLSFDGQIFLLFDSENRMWTTVHPGARKMKEKWENDKDMTMSFHYISMGDCTGW LEDFLMGMDSTLEPSAGGTV |
| 82 | ULBP6 extracellular domain | RRDDPHSLCYDITVIPKFRPGPRWCAVQGQVDEKTFLHYDCGNKTVTPVSPLGKKL NVTMAWKAQNPVLREVVDILTEQLLDIQLENYTPKEPLTLQARMSCEQKAEGHSSG SWQFSIDGQTFLLFDSEKRMWTTVHPGARKMKEKWENDKDVAMSFHYISMGDCIGW LEDFLMGMDSTLEPSAGAPLAMSSG |
| 83 | SLAMF1 extracellular domain | ASYGTGGRMMNCPKILRQLGSKVLLPLTYERINKSMNKSIHIVVTMAKSLENSVEN KIVSLDPSEAGPPRYLGDRYKFYLENLTLGIRESRKEDEGWYLMTLEKNVSVQRFC LQLRLYEQVSTPEIKVLNKTQENGTCTLILGCTVEKGDHVAYSWSEKAGTHPLNPA NSSHLLSLTLGPQHADNIYICTVSNPISNNSQTFSPWPGCRTDPSETKP |
| 84 | SLAMF2 extracellular domain | QGHLVHMTVVSGSNVTLNISESLPENYKQLTWFYTFDQKIVEWDSRKSKYFESKFK GRVRLDPQSGALYISKVQKEDNSTYIMRVLKKTGNEQEWKIKLQVLDPVPKPVIKI EKIEDMDDNCYLKLSCVIPGESVNYTWYGDKRPFPKELQNSVLETTLMPHNYSRCY TCQVSNSVSSKNGTVCLSPPCTLARS |
| 85 | SLAMF3 extracellular domain | KDSAPTVVSGILGGSVTLPLNISVDTEIENVIWIGPKNALAFARPKENVTIMVKSY LGRLDITKWSYSLCISNLTLNDAGSYKAQINQRNFEVTTEEEFTLFVYEQLQEPQV TMKSVKVSENFSCNITLMCSVKGAEKSVLYSWTPREPHASESNGGSILTVSRTPCD PDLPYICTAQNPVSQRSSLPVHVGQFCTDPGASRGGTTGETVVGVLGEPVTLPLAL PACRDTEKVVWLFNTSIISKEREEAATADPLIKSRDPYKNRVWVSSQDCSLKISQL KIEDAGPYHAYVCSEASSVTSMTHVTLLIYRRLRKPKITWSLRHSEDGICRISLTC SVEDGGNTVMYTWTPLQKEAVVSQGESHLNVSWRSSENHPNLTCTASNPVSRSSHQ FLSENICSGPERNTK |
| 86 | SLAMF4 extracellular domain | CQGSADHVVSISGVPLQLQPNSIQTKVDSIAWKKLLPSQNGFHHILKWENGSLPSN TSNDRFSFIVKNLSLLIKAAQQQDSGLYCLEVTSISGKVQTATFQVFVFESLLPDK VEKPRLQGQGKILDRGRCQVALSCLVSRDGNVSYAWYRGSKLIQTAGNLTYLDEEV DINGTHTYTCNVSNPVSWESHTLNLTQDCQNAHQEFRFWP |
| 87 | SLAMF5 extracellular domain | KDSEIFTVNGILGESVTFPVNIQEPRQVKIIAWTSKTSVAYVTPGDSETAPVVTVT HRNYYERIHALGPNYNLVISDLRMEDAGDYKADINTQADPYTTTKRYNLQIYRRLG KPKITQSLMASVNSTCNVTLTCSVEKEEKNVTYNWSPLGEEGNVLQIFQTPEDQEL TYTCTAQNPVSNNSDSISARQLCADIAMGFRTHHTG |
| 88 | SLAMF6 extracellular domain | QSSLTPLMVNGILGESVTLPLEFPAGEKVNFITWLFNETSLAFIVPHETKSPEIHV TNPKQGKRLNFTQSYSLQLSNLKMEDTCSYRAQISTKTSAKLSSYTLRILRQLRNI QVTNHSQLFQNMTCELHLTCSVEDADDNVSFRWEALGNTLSSQPNLTVSWDPRISS EQDYTCIAENAVSNLSFSVSAQKLCEDVKIQYTDTKM |
| 89 | SLAMF7 extracellular domain | SGPVKELVGSVGGAVTFPLKSKVKQVDSIVWTFNTTPLVTIQPEGGTIIVTQNRNR ERVDFPDGGYSLKLSKLKKNDSGIYYVGIYSSSLQQPSTQEYVLHVYEHLSKPKVT MGLQSNKNGTCVTNLTCCMEHGEEDVIYTWKALGQAANESHNGSILPISWRWGESD MTFICVARNPVSRNFSSPILARKLCEGAADDPDSSM |
| 90 | human alpha1 chain precurson of type I collagen | MFSFVDLRLLLLLAATALLTHGQEEGQVEGQDEDIPPITCVQNGLRYHDRDVWKPE PCRICVCDNGKVLCDDVICDETKNCPGAEVPEGECCPVCPDGSESPTDQETTGVEG PKGDTGPRGPRGPAGPPGRDGIPGQPGLPGPPGPPGPPGPPGLGGNFAPQLSYGYD EKSTGGISVPGPMGPSGPRGLPGPPGAPGPQGFQGPPGEPGEPGASGPMGPRGPPG |

Summary Sequence Table

| SEQ ID NO | Description | Sequence |
|---|---|---|
| | (NCBI Reference Sequence: NP_000079.2) | PPGKNGDDGEAGKPGRPGERGPPGPQGARGLPGTAGLPGMKGHRGFSGLDGAKGDA GPAGPKGEPGSPGENGAPGQMGPRGLPGERGRPGAPGPAGARGNDGATGAAGPPGP TGPAGPPGFPGAVGAKGEAGPQGPRGSEGPQGVRGEPGPPGPAGAAGPAGNPGADG QPGAKGANGAPGIAGAPGFPGARGPSGPQGPGGPPGPKGNSGEPGAPGSKGDTGAK GEPGPVGVQGPPGPAGEEGKRGARGEPGPTGLPGPPGERGGPGSRGFPGADGVAGP KGPAGERGSPGPAGPKGSPGEAGRPGEAGLPGAKGLTGSPGSPGPDGKTGPPGPAG QDGRPGPPGPPPGARGQAGVMGFPGPKGAAGEPGKAGERGVPGPPGAVGPAGKDGEA GAQGPPGPAGPAGERGEQGPAGSPGFQGLPGPAGPPGEAGKPGEQGVPGDLGAPGP SGARGERGFPGERGVQGPPGPAGPRGANGAPGNDGAKGDAGAPGAPGSQGAPGLQG MPGERGAAGLPGPKGDRGDAGPKGADGSPGKDGVRGLTGPIGPPGPAGAPGDKGES GPSGPAGPTGARGAPGDRGEPGPPGPAGFAGPPGADGQPGAKGEPGDAGAKGDAGP PGPAGPAGPPGPIGNVGAPGAKGARGSAGPPGATGFPGAAGRVGPPGPSGNAGPPG PPGPAGKEGGKPGRGETGPAGRPGEVGPPGPPGPAGEKGSPGADGPAGAPGTPGPQ GIAGQRGVVGLPGQRGERGFPGLPGPSGEPGKQGPSGASGERGPPGPMGPPGLAGP PGESGREGAPGAEGSPGRDGSPGAKGDRGETGPAGPPGAPGAPGAPGPVGPAGKSG DRGETGPAGPAGPVGPVGARGPAGPQGPRGDKGETGEQGDRGIKGHRGFSGLQGPP GPPGSPGEQGPSGASGPAGPRGPPGSAGAPGKDGLNGLPGPIGPPGPRGRTGDAGP VGPPGPPGPPGPPSAGFDFSFLPQPPQEKAHDGGRYYRADDANVVRDRDLEVD TTLKSLSQQIENIRSPEGSRKNPARTCRDLKMCHSDWKSGEYWIDPNQGCNLDAIK VFCNMETGETCVYPTQPSVAQKNWYISKNPKDKRHVWFGESMTDGFQFEYGGQGSD PADVAIQLTFLRLMSTEASQNITYHCKNSVAYMDQQTGNLKKALLLQGSNEIEIRA EGNSRFTYSVTVDGCTSHTGAWGKTVIEYKTTKTSRLPIIDVAPLDVGAPDQEFGF DVGPVCFL |
| 91 | human alpha2 chain precurson of type I collagen (NCBI Reference Sequence: NP_000080.2) | MLSFVDTRTLLLLAVTLCLATCQSLQEETVRKGPAGDRGPRGERGPPGPPGRDGED GPTGPPGPPGPPGPPGPPGLGGNFAAQYDGKGVGLGPGPMGLMGPRGPPGAAGAPGPQG FQGPAGEPGEPGQTGPAGARGPAGPPGKAGEDGHPGKPGRPGERGVVGPQGARGFP GTPGLPGFKGIRGHNGLDGLKGQPGAPGVKGEPGAPGENGTPGQTGARGLPGERGR VGAPGPAGARGSDGSVGPVGPAGPIGSAGPPGFPGAPGPKGEIGAVGNAGPAGPAG PRGEVGLPGLSGPVGPPGNPGANGLTGAKGAAGLPGVAGAPGLPGPRGIPGPVGAA GATGARGLVGEPGPAGSKGESGNKGEPGSAGPQGPPGPSGEEGKRGPNGEAGSAGP PGPPGLRGSPGSRGLPGADGRAGVMGPPGSRGASGPAGVRGPNGDAGPRGEPGLMG PRGLPGSPGNIGPAGKEGPVGLPGIDGRPGPIGPAGARGEPGNIGFPGPKGPTGDP GKNGDKGHAGLAGARGAPGPDGNNGAQGPPGPQGVQGGKGEQGPPGPPGFQGLPGP SGPAGEVGKPGERGLHGEFGLPGPAGPRGERGPPGESGAAGPTGPIGSRGPSGPPG PDGNKGEPGVVGAVGTAGPSGPSGLPGERGAAGIPGGKGEKGEPGLRGEIGNPGRD GARGAPGAVGAPGPAGATGDRGEAGAAGPAGPAGPRGSPGERGEVGPAGPNGFAGP AGAAGQPGAKGERGAKGPKGENGVVGPTGPVGAAGPAGNGPPGPAGPSGRDGGPPG MTGFPGAAGRTGPPGPSGISGPPGPPGPAGKEGLRGPRGDQGPVGRTGEVGAVGPP GFAGEKGPSGEAGTAGPPGTPGPQGLLGAPGILGLPGSRGERGLPGVAGAVGEPGP LGIAGPPGARGPPGAVGSPGVNGAPGEAGRDGNPGNDGPPGRDGQPGHKGERGYPG NIGPVGAAGAPGPHGPVGPAGKHGNRGETGPSGPVGPAGAVGPRGPSGPQGIRGDK GEPGEKGPRCLPGLKGHNGLQGLPGIAGHHGDQGAPGSVGPAGPRGPAGPSGPAGK DGRTGHPGTVGPAGIRGPQGHQGPAGPPGPPGPPGPPGVSGGGYDFGYDGDFYRAD QPRSAPSLRPKDYEVDATLKSLNNQIETLLTPEGSRKNPARTCRDLRLSHPEWSSG YYWIDPNQGCTMDAIKVYCDFSTGETCIRAQPENIPAKNWYRSSKDKKHVWLGETI NAGSQFEYNVEGVTSKEMATQLAFMRLLANYASQNITYHCKNSIAYMDEETGNLKK AVILQGSNDVELVAEGNSRFTYVLVDGCSKKTNEWGKTIIEYKTNKPSRLPFLDI APLDIGGADQEFFVDIGPVCFK |
| 92 | human alpha1 chain of type IV collagen (NCBI Reference Sequence: XP_011519350.1) | MQGPEGPQGPPGPQGQKGDTGEPGLPGTKGTRGPPGASGYPGNPGLPGIPGQDGPPGPP GIPGCNGTKGERGPLGPPGLPGFAGNPGPPGLPGMKGDPGEILGHVPGMLLKGERG FPGIPGTPGPPGLPGLQGPVGPPGFTGPPGPPGPPGEKGQMGLSFQGPKGDKG DQGVSGPPGVPGQAQVEKGDFATKGEKGQKGEPGFQGMPGVGEKGEPGKPGPRGK PGKDGDKGEKGSPGFPGEPGYPGLIGRQGPQGEKGEAGPPGPPGIVIGTGPLGEKG ERGYPGTPGPRGEPGPKGFPGLPGQPGPPGLPVPGQAGAPGFPGERGEKGDRGFPG TSLPGPSGRDGLPGPPGSPGPPGQPGYTNGIVECQPGPPGDQGPPGIPGQPGFIGE IGEKGQKGESCLICDIDGYRGPGPQGPPGEIGFPGQPGAKGDRGLPGRDGVAGVP GPQGTPGLIGQPGAKGEPGEFYFDLRLKGDKGDPGFPGQPGMPGRAGSPGRDGHPG LPGPKGSPGSVGLKGERGPPGGVGFPGSRGDTGPPGPPGYGPAGPIGDKGQAGFPG GPGSPGLPGPKGEPGKIVPLPGPPGAEGLPGSPGFPGPQGDRGFPGTGRPGLPGE KGAVGQPGIGFPGPPGPKGVDGLPGDMGPPGTPGRPGFNGLPGNPGVQGQKGEPGV GLPGLKGLPGLPGIPGTPGEKGSIGVPGVPGEHGAIGPPGLQGIRGEPGPPGLPGS VGSPGVPGIGPPGARGPPGGQGPPGLSGPPGIKGEKGPFGFPGLDMPGPKGDKGAQ GLPGITGQSLPGLPGQQGAPGIPGFPGSKGEMGVMGTPGQPGSPGPVGAPGLPGE KGDHGFPGSSGPRGDPGLKGDKGDVGLPGKPGSMDKVDMGSMKGQKGDQGEKGQIG PIGEKGSRGDPGTPGVPGKDGQAGPGQPGPKGDPGISGTPGAPGLPGPKGSVGGM GLPGTPGEKGVPGIPGPQGSPGLPGDKGAKGEKGQAGPGIGIPGLRGEKGDQGIA GFPGSPGEKGEKGSIGIPGMPGSPGLKGSPGSVGYPGSPGLPGEKGDKGLPGLDGI PGVKGEAGLPGTPGPTGPAGQKGEPGSDGIPGSAGEKGEPGLPGRGFPGFPGAKGD KGSKGEVGFPGLAGSPGIPGSKGEQGFMGPPGPQGQPGLPGSPGHATEGPKGDRGP QGQPGLPGLPGPMGPPGLPGIDGVKGDKGNPGWPGAPGVPGPKGDPGFQGMPGIGG SPGITGSKGDMGPPGVPGFQGPKGLPGLQGIKGDQGDQGVPGAKGLPGPPGPPGPY |

Summary Sequence Table

| SEQ ID NO | Description | Sequence |
|---|---|---|
| | | DIIKGEPGLPGPEGPPGLKGLQGLPGPKGQQGVTGLVGIPGPPGIPGFDGAPGQKG EMGPAGPTGPRGFPGPPGPDGLPGSMGPPGTPSVDHGFLVTRHSQTIDDPQCPSGT KILYHGYSLLYVQGNERAHGQDLGTAGSCLRKFSTMPFLFCNINNVCNFASRNDYS YWLSTPEPMPMSMAPITGENIRPFISRCAVCEAPAMVMAVHSQTIQIPPCPSGWSS LWIGYSFVMHTSAGAEGSGQALASPGSCLEEFRSAPFIECHGRGTCNYYANAYSFW LATIERSEMFKKPTPSTLKAGELRTHVSRCQVCMRRT |
| 93 | human alpha2 chain of type IV collagen (NCBI Reference Sequence: NP_001837.2) | MGRDQRAVAGPALRRWLLLGTVTVGFLAQSVLAGVKKFDVPCGGRDCSGGCQCYPE KGGRGQPGPVGPQGYNGPPGLQGFPGLQGRKGDKGERGAPGVTGPKGDVGARGVSG FPGADGIPGHPGQGGPRGRPGYDGCNGTQGDSGPQGPPGSEGFTGPPGPQGPKGQK GEPYALPKEERDRYRGEPGEPGLVGFQGPPGRPGHVGQMGPVGAPGRPGPPGPPGP KGQQGNRGLGFYGVKGEKGDVGQPGPNGIPSDTLHPIIAPTGVTFHPDQYKGEKGS EGEPGIRGISLKGEEGIMGFPGLRGYPGLSGEKGSPGQKGSRGLDGYQGPDGPRGP KGEAGDPGPPGLPAYSPHPSLAKGARGDPGFPGAQGEPGSQGEPGDPGLPGPPGLS IGDGDQRRGLPGEMGPKGFIGDPGIPALYGGPPGPDGKRGPPGPPGLPGPPGPDGF LFGLKGAKGRAGFPGLPGSPGARGPKGWKGDAGECRCTEGDEAIKGLPGLPGPKGF AGINGEPGRKGDRGDPGQHGLPGFPGLKGVPGNIGAPGPKGAKGDSRTITTKGERG QPGVPGVPGMKGDDGSPGRDGLDGFPGLPGPPGDGIKGPPGDPGYPGIPGTKGTPG EMGPPGLGLPGLKGQRGFPGDAGLPGPPGFLGPPGAGTPGQIDCDTDVKRAVGGD RQEAIQPGCIGGPKGLPGLPGPPGPTGAKGLRGIPGFAGADGPGPRGLPGDAGRE GFPGPPGFIGPRGSKGAVGLPGPDGSPGPIGLPGPDGPPGERGLPGEVLGAQPGPR GDAGVPGQPGLKGLPGDRGPPGFRGSQGMPGMVGPGLKGQPGLPGPSGQPGLYGPPGL HGFPGAPGQEGPLGLPGIPGREGLPGDRGDPGDTGAPGPVGMKGLSGDRGDAGFTG EQGHPGSPGFKGIDGMPGTPGLKGDRGSPGMDGFQGMPGLKGRPGFPGSKGEAGFF GIPGLKGLAGEPGFKGSRGDPGPPGPPPVILPGMKDIKGEKGDEGPMGLKGYLGAK GIQGMPGIPGLSGIPGLPGRPGHIKGVKGDIGVPGIPGLPGFPGVAGPPGITGFPG FIGSRGDKGAPGRAGLYGEIGATGDFGDIGDTINLPGRPGLKGERGTTGIPGLKGF FGEKGTEGDIGFPGITGVTGVQGPPGLKGQTGFPGLTGPPGSQGELGRIGLPGGKG DDGWPGAPGLPGFPGLRGIRGLHGLPGTKGFPGSPGSDIHGDPGFPGPPGERGDPG EANTLPGPVGVPGQKGDQGAPGERGPPGSPGLQGFPGITPPSNISGAPGDKGAPGI FGLKGYRGPPGPPGSAALPGSKGDTGNPGAPGTPGTKGWAGDSGPQGRPGVFGLPG EKGPRGEQGFMGNTGPTGAVGDRGPKGPKGDPGFPGAPGTVGAPGIAGIPQKIAVQ PGTVGPQGRRGPPGAPGEMGPQGPPGEPGFRGAPGKAGPQGRGGVSAVPGFRGDEG PIGHQGPIGQEGAPGRPGSPGLPGMPGRSVSIGYLLVKHSQTDQEPMCPVGMNKLW SGYSLLYFEGQEKAHNQDLGLAGSCLARFSTMPFLYCNPGDVCYYASRNDKSYWLS TTAPLPMMPVAEDEIKPYISRCSVCEAPAIAIAVHSQDVSIPHCPAGWRSLWIGYS FLMHTAAGDEGGGQSLVSPGSCLEDFRATPFIECNGGRGTCHYYANKYSFWLTTIP EQSFQGSPSADTLKAGLIRTHISRCQVCMKNL |
| 94 | human alpha3 chain of type IV collagen (NCBI Reference Sequence: NP_000082.2) | MSARTAPRPQVLLLPLLLVLLAAAPAASKGCVCKDKGQCFCDGAKGEKGEKGFPGP PGSPGQKGFTGPEGLPGPQGPKGPGLPGLTGSKGVRGISGLPGFSGSPGLPGTPG NTGPYGLVGVPGCSGSKGEQGFPGLPGTLGYPGIPGAAGLKGQKGAPAKEEDIELD AKGDPGLPGAPGPQGLPGPPGFFGPVGPPGPPGFFGFPGAMGPRGPKGHMGERVIG HKGERGVKGLTGPPGPPGTVIVTLTGPDNRTDLKGEKGDKGAMGEPGPPGPSGLPG ESYGSEKGAPGDPGLQGKPGKDGVPGFPGSEGVKGNRGFPGLMGEDGIKGKGDIG PPGFRGPTEYYDTYQEKGDEGTPGPPGPRGARGPQGPSGPPGVPGSPGSSRPGLRG APGWPGLKGSKGERGRPGKDAMGTPGSPGCAGSPGLPGSPGPPGPPGPDIVFRKGPP GDHGLPGYLGSPGIPGVDGPKGEPGLLCTQCPYIPGPPGLPGLPGLHGVKGIPGRQ GAAGLKGSPGSPGNTGLPGFPGFPGAQGDPGLKGKGEKGETLQPEGQVGVPGDPGLRG QPGRKGLDGIPGTPGVKGLPGPKGELALSGEKGDQGPPGDPGSPGSPGPAGPAGPP GYGPQGEPGLQGTQGVPGAPGPPGEAGPRGELSVSTPVPGPPGPPGPPGHPGPQGP PGIPGSLGKCGDPGLPGPDGEPGIPGIGFPGPPGPKGDQGFPGTKGSLGCPGKMGE PGLPGKPGLPGAKGEPAVAMPGGPGTPGFPGERGNSGEHGEIGLPGLPGLPGTPGN EGLDPGRGDPGQPGPPGEQGPPGRCIEGPRGAQGLPGLNGLKGQQGRRGKTGPKGD PGIPGLDRSGFPGETGSPGIPGHQGEMGPLGQRGYPGNPGILGPPGEDGVIGMMGF PGAIGPPGPPGNPGTPGQRGSPGIPGVKGQRGTPGAKGEQGDKGNPGPSEISHVIG DKGEPGLKGFAGNPGEKGNRGVPGMPGLKGLKGLPGPAGPPGPRGDLGSTGNPGEP GLRGIPGSMGNMGMPGSKGKRGTLGFPGRAGRPGLPGIHGLQGDKGEPGYSEGTRP GPPGPTGDPGLPGDMGKKGEMGQPGPPGHLGPAGPEGAPGSPGSPGLPGKPGPHGD LGFKGIKGLLGPPGIRGPPGLPGFPGSPGPMGIRGDQGRDGIPGPAGEKGETGLLR APPGPRGNPGAQGAKGDRGAPGFPGLPGRKGAMGDAGPRGPTGIEGFPGPPGLPGA IIPGQTGNRGPPGSRGSPGAPGPPGPPPGSHVIGIKGDKGSMGHPGPKGPPGTAGDM GPPGRLGAPGTPGLPGPRGDPGFQGFPGVKGEKGNPGFLGSIGPPGPIGPKGPPGV RGDPGTLKIISLPGSPGPPGTPGEPGMQGEPGPPGPPGNLGPCGPRGKPGKDGKPG TPGPAGEKGNKGSKGEPGPAGSDGLPGLKGKRGDSGSPATWTTRGFVFTRHSQTTA IPSCPEGTVPLYSGFSFLFVQGNQRAHGQDLGTLGSCLQRFTTMPFLFCNVNDVCN FASRNDYSYWLSTPALMPMNMAPITGRALEPYISRCTVCEGPAIAIAVHSQTTDIP PCPHGWISLWKGFSFIMFTSAGSEGTGQALASPGSCLEEFRASPFLECHGRGTCNY YSNSYSFWLASLNPERMFRKPIPSTVKAGELEKIISRCQVCMKKRH |
| 95 | human alpha4 chain of type IV collagen | MWSLHIVLMRCSFRLTKSLATGPWSLILILFSVQYVYGSGKKYIGPCGGRDCSVCH CVPEKGSRGPPGPPGPQGPIGPLGAPGPIGLSGEKGMRGDRGPPGAAGDKGDKGPT GVPGFPGLDGIPGHPGPPGPRGKPGMSGHNGSRGDPGFPGGRGALGPGGPLGHPGE |

Summary Sequence Table

| SEQ ID NO | Description | Sequence |
|---|---|---|
| | (NCBI Reference Sequence: NP_000083.3) | KGEKGNSVFILGAVKGIQGDRGDPGLPGLPGSWGAGGPAGPTGYPGEPGLVGPPGQ<br>PGRPGLKGNPGVGVKGQMGDPGEVGQQGSPGPTLLVEPPDFCLYKGEKGIKGIPGM<br>VGLPGPPGRKGESGIGAKGEKGIPGFPGPRGDPGSYGSPGFPGLKGELGLVGDPGL<br>FGLIGPKGDPGNRGHPGPPGVLVTPPLPLKGPPGDPGFPGRYGETGDVGPPGPPGL<br>LGRPGEACAGMIGPPGPQGFPGLPGLPGEAGIPGRPDSAPGKPGKPGSPGLPGAPG<br>LQGLPGSSVIYCSVGNPGPQGIKGKVGPPGGRGPKGEKGNEGLCACEPGPMGPPGP<br>PGLPGRQGSKGDLGLPGWLGTKGDPGPPGAEGPPGLPGKHGASGPPGNKGAKGDMV<br>VSRVKGHKGERGPDGPPGFPGQPGSHGRDGHAGEKGDPGPPGDHEDATPGGKGFPG<br>PLGPPGKAGPVGPPGLGFPGPPGERGHPGVPGHPGVRGPDGLKGQKGDTISCNVTY<br>PGRHGPPGFDGPPGPKGFPGPQGAPGLSGSDGHKGRPGTPGTAEIPGPPGFRGDMG<br>DPGFGGEKGSSPVGPPGPPGSPGVNGQKGIPGDPAFGHLGPPGKRGLSGVPGIKGP<br>RGDPGCPGAEGPAGIPGFLGLKGPKGREGHAGFPGVPGPPGHSCERGAPGIPGQPG<br>LPGYPGSPGAPGGKGQPGDVGPPGPAGMKGLPGLPGRPGAHGPPGLPGIPGPFGDD<br>GLPGPPGPKGPRGLPGFPGFPGERGKPGAEGCPGAKGEPGEKGMSGLPGDRGLRGA<br>KGAIGPPGDEGEMAIISQKGTPGEPGPPGDDGFPGERGDKGTPGMQGRRGEPGRYG<br>PPGFHRGEPGEKGQPGPPGPPGPPGSTGLRGFIGFPGLPGDQGEPGSPGPPGFSGI<br>DGARGPKGNKGDPASHFGPPGPKGEPGSPGCPGHFGASGEQGLPGIQGPRGSPGRP<br>GPPGSSGPPGCPGDHGMPGLRGQPGEMGDPGPRGLQGDPGIPGPPGIKGPSGSPGL<br>NGLHGLKGQKGTKGASGLHDVGPPGPVGIPGLKGERGDPGSPGISPPGPRGKKGPP<br>GPPGSSGPPGPAGATGRAPKDIPDPGPPGDQGPPGPDGPRGAPGPPGLPGSVDLLR<br>GEPGDCGLPGPPGPPGPPGPPGYKGFPGCDGKDGQKGPVGFPGPQGPHGFPGPPGE<br>KGLPGPPGRKGPTGLPGPRGEPGPPADVDDCPRIPGLPGAPGMRGPEGAMGLPGMR<br>GPSGPGCKGEPGLDGRRGVDGVPGSPGPPGRKGDTGEDGYPGGPGPPGPIGDPGPK<br>GFGPGYLGGFLLVLHSQTDQEPTCPLGMPRLWTGYSLLYLEGQEKAHNQDLGLAGS<br>CLPVFSTLPFAYCNIHQVCHYAQRNDRSYWLASAAPLPMMPLSEEAIRPYVSRCAV<br>CEAPAQAVAVHSQDQSIPPCPQTWRSLWIGYSFLMHTGAGDQGGGQALMSPGSCLE<br>DFRAAPFLECQGRQGTCHFFANKYSFWLTTVKADLQFSSAPAPDTLKESQAQRQKI<br>SRCQVCVKYS |
| 96 | human alpha5 chain of type IV collagen (NCBI Reference Sequence: XP_011529151.2) | MEVDSGKTENRDWEGFCYSTSAYWKNLYDGLLACYGCSPGSKCDCSGIKGEKGERG<br>FPGLEGHPGLPGFPGPEGPPGPRGQKGDDGIPGPPGPKGIRGPPGLPGFPGTPGLP<br>GMPGHDGAPGPQGIPGCNGTKGERGFPGSPGFPGLQGPPGPPGIPGMKGEPGSIIM<br>SSLPGPKGNPGYPGPPGIQGLPGPTGIPGPIGPPGPPGLMGPPGPPGLPGPKGNMG<br>LNFQGPKGEKGEQGLQGPPGPPGQISEQKRPIDVEFQKGDQGLPGDRGPPGPPGIR<br>GPPGPPGGEKGEKGEQGEPGKRGKPGKDGENGQPGIPGLPGDPGYPGEPGRDGEKG<br>QKGDTGPPGPPGLVIPRPGTGITIGEKGNIGLPGLPGEKGERGFPGIQGPPGLPGP<br>PGAAVMGPPGPPGFPGERGQKGDEGPPGISIPGPPGLDGQPGAPGLPGPPGPAGPH<br>IPPPSDEICEPGPPGPPGSPGDKGLQGEQGVKGDKGDTCFNCIGTGISGPPGQGLP<br>GLPGPPGSLGFPGQKGEKGQAGATGPKGLPGIPGAPGAPGFPGSKGEPGDILTFPG<br>MKGDKGELGSPGAPGLPGLPGTPGQDGLPGLPGPKGEPGGITFKGERGPPGNPGLP<br>GLPGNIGPMGPPGFGPPGPVGEKGIQGVAGNPGQPGIPGPKGDPGQTITQPGKPGL<br>PGNPGRDGDVGLPGDPGLPGQPGLPGIPGSKGEPGIPGIGLPGPPGPKGFPGIPGP<br>PGAPGTPGRIGLEGPPGPGFPGPKGEPGFALPGPPGPPGLPGFKGALGPKGDRGF<br>PGPPGPPGRTGLDGLPGPKGDVGPNGQPGMGPPGLPGIGVQGPPGPPGIPGPIGQ<br>PGLHGIPGEKGDPGPPGLDVPGPPGERGSPGIPGAPGPIGPPGSPGLPGKAGASGF<br>PGTKGEMGMMGPPGPPGPLGIPGRSGVPGLKGDDGLQGQPGLPGPTGEKGSKGEPG<br>LPGPPGPMDPNLLGSKGEKGEPGLPGIPGVSGPKGYQGLPGDPGQPGLSGQPGLPG<br>PPGPKGNPGLPGQPGLIGPPGLKGTIGDMGFPGPQGVEGPPGPSGVPGQPGSPGLP<br>GQKGDKGDPGISSIGLPGIPGPKGEPGLPGYPGNPGIKGSVGDPGLPGLPGTPGAK<br>GQPGLPGFPGTPGPPGPKGISGPPGNPGLPGEPGPVGGGHPGQPGPPGEKGKPGQ<br>DGIPGPAGQKGEPGQPGFGNPGPPGLPGLSGQKGDGGLPGIPGNPGLPGPKGEPGF<br>HGFPGVQGPPGPPGSPGPALEGPKGNPGPQGPPGRPGPTGFQGLPGPEGPPGLPGN<br>GGIKGEKGNPGQPGLPGLPGLKGDQGPPGLQGNPGRPGLNGMKGDPGLPGVPGFPG<br>MKGPSGVPGSAGPEGEPGLIGPGPPGLPGPSGQSIIIKGDAGPPGIPGQPGLKGL<br>PGPQGPQGLPGPTGPPGDPGRNGLPGFDGAGGRKGDPGLPGQPGTRGLDGPPGPDG<br>LQGPPGPPGTSSVAHGFLITRHSQTTDAPQCPQGTLQVYEGFSLLYVQGNKRAHGQ<br>DLGTAGSCLRRFSTMPFMFCNINNVCNFASRNDYSYWLSTPEPMPMSMQPLKGQSI<br>QPFISRCAVCEAPAVVIAVHSQTIQIPHCPQGWDSLWIGYSFMMHTSAGAEGSGQA<br>LASPGSCLEEFRSAPFIECHGRGTCNYYANSYSFWLATVDVSDMFSKPQSETLKAG<br>DLRTRISRCQVCMKRT |
| 97 | human alpha6 chain of type IV collagen (NCBI Reference Sequence: XP_006724680.1) | MLINKLWLLLVTLCLTEELAAAGEKSYGKPCGGQDCSGSCQCFPEKGARGRPGPIG<br>IQGPTGPQGFTGSTGLSGLKGERGFPGLLGPYGPKGDKGPMGVPGFLGINGIPGHP<br>GQPGPRGPPGLDGCNGTQGAVGFPGPDGYPGLLGPPGLPGQKGSKGDPVLAPGSFK<br>GMKGDPGLPGLDGITGPQGAPGFPGAVGPAGPPGLQGPPGPPGPLGPDGNMGLGFQ<br>GEKGVKGDVGLPGPAGPPPSTGELEFMGFPKGKKGSKGEPGPKGFPGISGPPGFPG<br>LGTTGEKGEKGEKGIPGLPGPRGPMGSEGVQGPPGQQKKGTLGPPGLNGFQGIEG<br>QKGDIGLPGPDVFIDIDGAVISGNPGDPGVPGLPGLKGDEGIQGLRGPSGVPGLPA<br>LSGVPGALGPQGFPGLKGDQGNPGRTTIGAAGLPGRDGLPGPPGPPGPPGSPEFETE<br>TLHNKESGFPGLRGEQGPKGNLGLKGIKGDSGFCACDGGVPNTGPPGEPGPPGPWG<br>LIGLPGLKGARGDRGSGGAQGPAGAPGLVGPLGPSGPKGKKGEPILSTIQGMPGDR<br>GDSGSQGFRGVIGEPGKDGVPGLPGLPGLPGDGQGFPGEKGLPGLPGEKGHPGPP<br>GLPGNGLPGLPGPRGLPGDKGKDGLPGQQGLPGSKGDCCCREVGKGDLDTERGITL |

Summary Sequence Table

| SEQ ID NO | Description | Sequence |
|---|---|---|
| | | PCIIPGSYGPSGFPGTPGFPGPKGSRGLPGTPGQPGSSGSKGEPGSPGLVHLPELP GFPGPRGEKGLPGFPGLPGKDGLPGMIGSPGLPGSKGATGDIFGAENGAPGEQGLQ GLTGHKGFLGDSGLPGLKGVHGKPGLLGPKGERGSPGTPGQVGQPGTPGSSGPYGI KGKSGLPGAPGFPGISGHPGKKGTRGKKGPPGSIVKKGLPGLKGLPGNPGLVGLKG SPGSPGVAGLPALSGPKGEKGSVGFVGFPGIPGLPGIPGTRGLKGIPGSTGKMGPS GRAGTPGEKGDRGNPGPVGIPSPRRPMSNLWLKGDKGSQGSAGSNGFPGPRGDKGE AGRPGPPGLPGAPGLPGIIKGVSGKPGPPGFMGIRGLPGLKGSSGITGFPGMPGES GSQGIRGSPGLPGASGLPGLKGDNGQTVEISGSPGPKGQPGESGFKGTKGRDGLIG NIGFPGNKGEDGKVGVSGDVGLPGAPGFPGVAGMRGEPGLPGSSGHQGAIGPLGSP GLIGPKGFPGFPGLHGLNGLPGTKGTHGTPGPSITGVPGPAGLPGPKGEKGYPGIG IGAPGKPGLRGQKGDRGFPGLQGPAGLPGAPGISLPSLIAGQPGDPGRPGLDGERG RPGPAGPPGPPGPSSNQGDTGDPGFPGIPGPKGPKGDQGIPGFSGLPGELGLKGMR GEPGFMGTPGKVGPPGDPGFPGMKGKAGPRGSSGLQGDPGQTPTAEAVQVPPGPLG LPGIDGIPGLTGDPGAQGPVGLQGSKGLPGIPGKDGPSGLPGPPGALGDPGLPGLQ GPPGFEGAPGQQGPFGMPGMPGQSMRVGYTLVKHSQSEQVPPCPIGMSQLWVGYSL LFVEGQEKAHNQDLGFAGSCLPRFSTMPFIYCNINEVCHYARRNDKSYWLSTTAPI PMMPVSQTQIPQYISRCSVCEAPSQAIAVHSQDITIPQCPLGWRSLWIGYSFLMHT AAGAEGGGQSLVSPGSCLEDFRATPFIECSGARGTCHYFANKYSFWLTTVEERQQF GELPVSETLKAGQLHTRVSRCQVCMKSL |
| 98 | LAIR-1 | QEEDLPRPSISAEPGTVIPLGSHVTFVCRGPVGVQTFRLERESRSTYNDTEDVSQA SPSESEARFRIDSVSEGNAGPYRCIYYKPPKWSEQSDYLELLVKETSGGPDSPDTE PGSSAGPTQRPSDNSHNEHAPASQGLKAEHLYILIGVSVVFLFCLLLLVLFCLHRQ NQIKQGPPRSKDEEQKPQQRPDLAVDVLERTADKATVNGLPEKDRETDTSALAAGS SQEVTYAQLDHWALTQRTARAVSPQSTKPMAESITYAAVARH |
| 99 | LAIR-2 | QEGALPRPSISAEPGTVISPGSHVTFMCRGPVGVQTFRLEREDRAKYKDSYNVFRL GPSESEARFHIDSVSEGNAGLYRCLYYKPPGWSEHSDFLELLVKESSGGPDSPDTE PGSSAGTVPGTEASGFDAP |
| 100 | Glycoprotein IV (CD36 extracellular domain) | GDLLIQKTIKKQVVLEEGTIAFKNWVKTGTEVYRQFWIFDVQNPQEVMMNSSNIQV KQRGPYTYRVRFLAKENVTQDAEDNTVSFLQPNGAIFEPSLSVGTEADNFTVLNLA VAAASHIYQNQFVQMILNSLINKSKSSMFQVRTLRELLWGYRDPFLSLVPYPVTTT VGLFYPYNNTADGVYKVFNGKDNISKVAIIDTYKGKRNLSYWESHCDMINGTDAAS FPPPFVEKSQVLQFFSSDICRSIYAVFESDVNLKGIPVYRFVLPSKAFASPVENPDN YCFCTEKIISKNCTSYGVLDISKCKEGRPVYISLPHFLYASPDVSEPIDGLNPNEE EHRTYLDIEPITGFTLQFAKRLQV NLLVKPSEKIQVLKNLKRNYIVPILWLNETGTIGDEKANMFRSQVTGKIN |
| 101 | Nidogen | LSRQELFPFGPGQGDLELEDGDDFVSPALELSGALRFYDRSDIDAVYVTTNGIIAT SEPPAKESHPGLFPPTFGAVAPFLADLDTTDGLGKVYYREDLSPSITQRAAECVHR GFPEISFQPSSAVVVTWESVAPYQGPSRDPDQKGKRNTFQAVLASSDSSSYAIFLY PEDGLQFHTTFSKKENNQVPAVVAFSQGSVGFLWKSNGAYNIFANDRESVENLAKS SNSGQQGVWVFEIGSPATTNGVVPADVILGTEDGAEYDDEDEDYDLATTRLGLEDV GTTPFSYKALRRGGADTYSVPSVLSPRRAATERPLGPPTERTRSFQLAVETFHQQH PQVIDVDEVEETGVVFSYNTDSRQTCANNRHQCSVHAECRDYATGFCCSCVAGYTG NGRQCVAEGSPQRVNGKVKGRIFVGSSQVPIVFENTDLHSYVVMNHGRSYTAISTI PETVGYSLLPLAPVGGIIGWMFAVEQDGFKNGFSITGGEFTRQAEVTFVGHPGNLV IKQRFSGIDEHGHLTIDTELEGRVPQIPFGSSVHIEPYTELYHYSTSVITSSSTRE YTVTEPERDGASPSRIYTYQWRQTITFQECVHDDSRPALPSTQQLSVDSVFVLYNQ EEKILRYALSNSIGPVREGSPDALQNPCYIGTHGCDTNAACRPGPRTQFTCECSIG FRGDGRTCYDIDECSEQPSVCGSHTICNNHPGTFRCECVEGYQFSDEGTCVAVVDQ RPINYCETGLHNCDIPQRAQCIYTGGSSYTCSCLPGFSGDGQACQDVDECQPSRCH PDAFCYNTPGSFTCQCKPGYQGDGFRCVPGEVEKTRCQHEREHILGAAGATDPQRP IPPGLFVPECDAHGHYAPTQCHGSTGYCWCVDRDGREVEGTRTRPGMTPPCLSTVA PPIHQGPAVPTAVIPLPPGTHLLFAQTGKIERLPLEGNTMRKTEAKAFLHVPAKVI IGLAFDCVDKMVYWTDITEPSIGRASLHGGEPTTIIRQDLSPEGIAVDHLGRNIF WTDSNLDRIEVAKLDGTQRRVLFETDLVNPRGIVTDSVRGNLYWTDWNRDNPKIET SYMDGTNRRILVQDDLGLPNGLTFDAFSSQLCWVDAGTNRAECLNPSQPSRRKALE GLQYPFAVTSYGKNLYFTDWKMNSVVALDLAISKETDAFQPHKQTRLYGITTALSQ CPQGHNYCSVNNGGCTHLCLATPGSRTCRCPDNTLGVDCIEQK |
| 102 | Perlecan | VTHGLRAYDGLSLPEDIETVTASQMRWTHSYLSDDEDMLADSISGDDLGSGDLSGG DFQMVYFRALVNFTRSIEYSPQLEDAGSREFREVSEAVVDTLESEYLKIPGDQVVS VVFIKELDGWVFVELDVGSEGNADGAQIQEMLLRVISSGSVASYVTSPQGFQFRRL GTVPQFPRACTEAEFACHSYNECVALEYRCDRRPDCRDMSDELNCEEPVLGISPTF SLLVETTSLPPRPETTIMRQPPVTHAPQPLLPGSVRPLCGPQEAACRNGHCIPRD YLCDGQEDCEDGSDELDCGPPPPCEPNEFPCGNGHCALKLWRCDGDFDCEDRTDEA NCPTKRPEEVCGPTQFRCVSTNMCIPASFHCDEESDCPDRSDEFGCMPPQVVTPPR ESIQASRGQTVTFTCVAIGVPTPIINWRLNWGHIPSHPRVTVTSEGGRGTLIIRDV KESDQGAYTCEAMNARGMVFGIPDGVLELVPQRGPCPDGHFYLEHSAACLPCFCFG ITSVCQSTRRFRDQIRLRFDQPDDFKGVNVTMPAQPGTPPLSSTQLQIDPSLHEFQ LVDLSRRFLVHDSFWALPEQFLGNKVDSYGGSLRYNVRYELARGMLEPVQRPDVVL |

Summary Sequence Table

| SEQ ID NO | Description | Sequence |
|---|---|---|
| | | MGAGYRLLSRGHTPTQPGALNQRQVQFSEEHWVHESGRPVQRAELLQVLQSLEAVL IQTVYNTKMASVGLSDIAMDTTVTHATSHGRAHSVEECRCPIGYSGLSCESCDAHF TRVPGGPYLGTCSGCNCNGHASSCDPVYGHCLNCQHNTEGPQCNKCKAGFFGDAMK ATATSCRPCPCPYIDASRRFSDTCFLDTDGQATCDACAPGYTGRRCESCAPGYEGN PIQPGGKCRPVNQEIVRCDERGSMGTSGEACRCKNNVVGRLCNECADGSFHLSTRN PDGCLKCFCMGVSRHCTSSSWSRAQLHGASEEPGHFSLTNAASTHTTNEGIFSPTP GELGFSSFHRLLSGPYFWSLPSRFLGDKVTSYGGELRFTVTQRSQPGSTPLHGQPL VVLQGNNIILEHHVAQEPSPGQPSTFIVPFREQAWQRPDGQPATREHLLMALAGID TLLIRASYAQQPAESRVSGISMDVAVPEETGQDPALEVEQCSCPPGYRGPSCQDCD TGYTRTPSGLYLGTCERCSCHGHSEACEPETGACQGCQHHTEGPRCEQCQPGYYGD AQRGTPQDCQLCPCYGDPAAGQAAHTCFLDTDGHPTCDACSPGHSGRHCERCAPGY YGNPSQGQPCQRDSQVPGPIGCNCDPQGSVSSQCDAAGQCQCKAQVEGLTCSHCRP HHFHLSASNPDGCLPCFCMGITQQCASSAYTRHLISTHFPAPGDFQGFALVNPQRNS RLTGEFTVEPVPEGAQLSFGNFAQLGHESFYWQLPETYQGDKVAAYGGKLRYTLSY TAGPQGSPLSDPDVQITGNNIMLVASQPALQGPERRSYEIMFREEFWRRPDGQPAT REHLLMALADLDELLIRATFSSVPLAASISAVSLEVAQPGPSNRPRALEVEECRCP PGYIGLSCQDCAPGYTRTGSGLYLGHCELCECNGHSDLCHPETGACSQCQHNAAGE FCELCAPGYYGDATAGTPEDCQPCACPLTNPENMFSRTCESLGAGGYRCTACEPGY TGQYCEQCGPGYVGNPSVQGGQCLPETNQAPLVVEVHPARSIVPQGGSHSLRCQVS GSPPHYFYWSREDGRPVPSGTQQRHQGSELHFPSVQPSDAGVYICTCRNLHQSNTS RAELLVTEAPSKPITVTVEEQRSQSVRPGADVTFICTAKSKSPAYTLVWTRLHNGK LPTRAMDFNGILTIRNVQLSDAGTYVCTGSNMFAMDQGTATLHVQASGTLSAPVVS IHPPQLTVQPGQLAEFRCSATGSPTPTLEWTGGPGGQLPAKAQIHGGILRLPAVEP TDQAQYLCRAHSSAGQQVARAVLHVHGGGGPRVQVSPERTQVHAGRTVRLYCRAAG VPSATITWRKEGGSLPPQARSERTDIATLLIPAITTADAGFYLCVATSPAGTAQAR IQVVVLSASDASPPPVKIESSSPSVTEGQTLDLNCVVAGSAHAQVTWYRRGGSLPP HTQVHGSRLRLPQVSPADSGEYVCRVENGSGPKEASITVSVLHGTHSGPSYTPVPG STRPIRIEPSSSHVAEGQTLDLNCVVPGQAHAQVTWHKRGGSLPARHQTHGSLLRL HQVTPADSGEYVCHVVGTSGPLEASVLVTIEASVIPGPIPPVRIESSSSTVAEGQT LDLSCVVAGQAHAQVTWYKRGGSLPARHVRGSRLYIFQASPADAGQYVCRASNGM EASITVTVTGTQGANLAYPAGSTQPIRIEPSSSQVAEGQTLDLNCVVPGQSHAQVT WHKRGGSLPVRHQTHGSLLRLYQASPADSGEYVCRVLGSSVPLEASVLVTIEPAGS VPALGVTPTVRIESSSSQVAEGQTLDLNCLVAGQAHAQVTWHKRGGSLPARHQVHG SRLRLLQVTPADSGEYVCRVVGSSGTQEASVLVTIQQRLSGSHSQGVAYPVRIESS SASLANGHTLDLNCLVASQAPHTITWYKRGGSLPSRHQIVGSRLRIPQVTPADSGE YVCHVSNGAGSRETSLIVTIQGSGSSHVPSVSPPIRIESSSPTVVEGQTLDLNCVV ARQPQAIITWYKRGGSLPSRHQTHGSHLRLHQMSVADSGEYVCRANNNIDALEASI VISVSPSAGSPSAPGSSMPIRIESSSSHVAEGETLDLNCVVPGQAHAQVTWHKRGG SLPSHHQTRGSRLRLHHVSPADSGEYVCRVMGSSGPLEASVLVTIEASGSSAVHVP APGGAPPIRIEPSSSRVAEGQTLDLKCVVPGQAHAQVTWHKRGGNLPARHQVHGPL LRLNQVSPADSGEYSCQVTGSSGTLEASVLVTIEPSSPGPIPAPGLAQPIYIEASS SHVTEGQTLDLNCVVPGQAHAQVTWYKRGGSLPARHQTHGSQLRLHLVSPADSGEY VCRAASGPGPEQEASFTVTVPPSEGSSYRLRSPVISIDPPSSTVQQGQDASFKCLI HDGAAPISLEWKTRNQELEDNVHISPNGSIITIVGTRPSNHGTYRCVASNAYGVAQ SVVNLSVHGPPTVSVLPEGPVWVKVGKAVTLECVSAGEPRSSARWTRISSSTPAKLE QRTYGLMDSHAVLQISSAKPSDAGTYVCLAQNALGTAQKQVEVIVDTGAMAPGAPQ VQAEEAELTVEAGHTATLRCSATGSPAPTIHWSKLRSPLPWQHRLEGDTLIIPRVA QQDSGQYICNATSPAGHAEATIILHVESPPYATTVPEHASVQAGETVQLQCLAHGT PPLTFQWSRVGSSLPGRATARNELLHFERAAPEDSGRYRCRVTNKVGSAEAFAQLL VQGPPGSLPATSIPAGSTPTVQVTPQLETKSIGASVEFHCAVPSDRGTQLRWFKEG GQLPPGHSVQDGVLRIQNLDQSCQGTYICQAHGPWGKAQASAQLVIQALPSVLINI RTSVQTVVVGHAVEFECLALGDPKPQVTWSKVGGHLRPGIVQSGGVVRIAHVELAD AGQYRCTATNAAGTTQSHVLLLVQALPQISMPQEVRVPAGSAAVFPCIASGYPTPD ISWSKLDGSLPPDSRLENNMLMLPSVRPQDAGTYVCTATNRQGKVKAFAHLQVPER VVPYFTQTPYSFLPLPTIKDAYRKFEIKITFRPDSADGMLLYNGQKRVPGSPTNLA NRQPDFISFGLVGGRPEFRFDAGSGMATIRHPTPLALGHFHTVTLLRSLTQGSLIV GDLAPVNGTSQGKFQGLDLNEELYLGGYPDYGAIPKAGLSSGFIGCVRELRIQGEE IVFHDLNLTAHGISHCPTCRDRPCQNGGQCHDSESSSYVCVCPAGFTGSRCEHSQA LHCHPEACGPDATCVNRPDGRGYTCRCHLGRSGLRCEEGVTVTTPSLSGAGSYLAL PALTNTHHELRLDVEFKPLAPDGVLLFSGGKSGPVEDFVSLAMVGGHLEFRYELGS GLAVLRSAEPLALGRWHRVSAERLNKDGSLRVNGGRPVLRSSPGKSQGLNLHTLLY LGGVEPSVPLSPATNMSAHFRGCVGEVSVNGKRLDLTYSFLGSQGIGQCYDSSPCE RQPCQHGATCMPAGEYEFQCLCRDGFKGDLCEHEENPCQLREPCLHGGTCQGTRCL CLPGFSGPRCQQGSGHGIAESDWHLEGSGGNDAPGQYGAYFHDDGFLAFPGHVFSR SLPEVPETIELEVRTSTASGLLLWQGVEVGEAGQGKDFISLGLQDGHLVFRYQLGS GEARLVSEDPINDGEWHRVTALREGRRGSIQVDGEELVSGRSPGPNVAVNAKGSVY IGGAPDVATLTGGRFSSGITGCVKNLVLHSARPGAPPPQPLDLQHRAQAGANTRPC PS |
| 103 | Biglycan | DEEASGADTSGVLDPDSVTPTYSAMCPFGCHCHLRVVQCSDLGLKSVPKEISPDTT LLDLQNNDISELRKDDFKGLQHLYALVLVNNKISKIHEKAFSPLRKLQKLYISKNH LVEIPPNLPSSLVELRIHDNRIRKVPKGVFSGLRNMCIEMGGNPLENSGFEPGAF DGLKLNYLRISEAKLTGIPKDLPETLNELHLDHNKIQAIELEDLLRYSKLYRLGLG |

| Summary Sequence Table | | |
|---|---|---|
| SEQ ID NO | Description | Sequence |
| | | HNQIRMIENGSLSFLPTLRELHLDNNKLARVPSGLPDLKLLQVVYLHSNNITKVGV NDFCPMGFGVKRAYYNGISLFNNPVPYWEVQPATFRCVTDRLAIQFGNYKK |
| 104 | Decorin | DEASGIGPEVPDDRDFEPSLGPVCPFRCQCHLRVVQCSDLGLDKVPKDLPPDTTLL DLQNNKITEIKDGDFKNLKNLHALILVNNKISKVSPGAFTPLVKLERLYLSKNQLK ELPEKMPKTLQELRAHENEITKVRKVTFNGLNQMIVIELGTNPLKSSGIENGAFQG MKKLSYIRIADTNITSIPQGLPPSLTELHLDGNKISRVDAASLKGLNNLAKLGLSF NSISAVDNGSLANTPHLRELHLDNNKLTRVPGGLAEHKYIQVVYLHNNNISVVGSS DFCPPGHNTKKASYSGVSLFSNPVQYWEIQPSTFRCVYVRSAIQLGNYK |
| 105 | Asporin | DMEDTDDDDDDDDDDDDDEDNSLFPTREPRSHFFPFDLFPMCPFGCQCYSRVVHC SDLGLTSVPTNIPFDTRMLDLQNNKIKEIKENDFKGLTSLYGLILNNNKLTKIHPK AFLTTKKLRRLYLSHNQLSEIPLNLPKSLAELRIHENKVKKIQKDTFKGMNALHVL EMSANPLDNNGIEPGAFEGVTVFHIRIAEAKLTSVPKGLPPTLLELHLDYNKISTV ELEDFKRYKELQRLGLGNNKITDIENGSLANIPRVREIHLENNKLKKIPSGLPELK YLQIIFLHSNSIARVGVNDFCPTVPKMKKSLYSAISLFNNPVKYWEMQPATFRCVL SRMSVQLGNFGM |
| 106 | Fibromodulin | QYEDDPHWWFHYLRSQQSTYYDPYDPYPYETYEPYPYGVDEGPAYTYGSPSPPDPR DCPQECDCPPNFPTAMYCDNRNLKYLPFVPSRMKYVYFQNNQITSIQEGVFDNATG LLWIALHGNQITSDKVGRKVFSKLRHLERLYLDHNNLTRMPGPLPRSLRELHLDHN QISRVPNNALEGLENLTALYLQHNEIQEVGSSMRGLRSLILLDLSYNHLRKVPDGL PSALEQLYMEHNNVYTVPDSYFRGAPKLLYVRLSHNSLTNNGLASNTFNSSSLLEL DLSYNQLQKIPPVNTNLENLYLQGNRINEFSISSFCTVVDVVNFSKLQVLRLDGNE IKRSAMPADAPLCLRLASLIEI |
| 107 | Lumican | QYYDYDFPLSIYGQSSPNCAPECNCPESYPSAMYCDELKLKSVPMVPPGIKYLYLR NNQIDHIDEKAFENVTDLQWLILDHNLLENSKIKGRVFSKLKQLKKLHINHNNLTE SVGPLPKSLEDLQLTHNKITKLGSFEGLVNLTFIHLQHNRLKEDAVSAAFKGLKSL EYLDLSFNQIARLPSGLPVSLLTLYLDNNKISNIPDEYFKRFNALQYLRLSHNELA DSGIPGNSFNVSSLVELDLSYNKLKNIPTVNENLENYYLEVNQLEKFDIKSFCKIL GPLSYSKIKHLRLDGNRISETSLPPDMYECLRVANEVTLN |
| 108 | PRELP | QPTRRPRPGTGPGRRPRPRPRPTPSFPQPDEPAEPTDLPPPLPPGPPSIFPDCPRE CYCPPDFPSALYCDSRNLRKVPVIPPRIHYLYLQNNFITELPVESFQNATGLRWIN LDNNRIRKIDQRVLEKLPGLVFLYMEKNQLEEVPSALPRNLEQLRLSQNHISRIPP GVFSKLENLLLLDLQHNRLSDGVFKPDTFHGLKNLMQLNLAHNILRKMPPRVPTAI HQLYLDSNKIETIPNGYFKSFPNLAFIRLNYNKLTDRGLPKNSFNISNLLVLHLSH NRISSVPAINNRLEHLYLNNNSIEKINGTQICPNDLVAFHDFSSDLENVPHLRYLR LDGNYLKPPIPLDLMMCFRLLQSV VI |
| 109 | Osteoadherin/ Osteomodulin | QYETYQWDEDYDQEPDDDYQTGFPFRQNVDYGVPFHQYTLGCVSECFCPTNFPSSM YCDNRKLKTIPNIPMHIQQLYLQFNEIEAVTANSFINATHLKEINLSHNKIKSQKI DYGVFAKLPNLLQLHLEHNNLEEFPFPLPKSLERLLLGYNEISKLQTNAMDGLVNL TMLDLCYNYLHDSLLKDKIFAKMEKLMQLNLCSNRLESMPPGLPSSLMYLSLENNS ISSIPEKYFDKLPKLHTLRMSHNKLQDIPYNIFNLPNIVELSVGHNKLKQAFYIPR NLEHLYLQNNEIEKMNLTVMCPSIDPLHYHHLTYIRVDQNKLKEPISSYIFFCFPH IHTIYYGEQRSTNGQTIQLKTQVFRRFPDDDDESEDHDDPDNAHESPEQEGAEGHF DLHYYENQE |
| 110 | Opticin | ASLPRKERKRREEQMPREGDSFEVLPLRNDVLNPDNYGEVIDLSNYEELTDYGDQL PEVKVTSLAPATSISPAKSTTAPGTPSSNPTMTRPTTAGLLLLSSQPNHGLPTCLVC VCLGSSVYCDDIDLEDIPPLPRRTAYLYARFNRISRIRAEDFKGLTKLKRIDLSNN LISSIDNDAFRLLHALQDLILPENQLEALPVLPSGIEFLDVRLNRLQSSGIQPAAF RAMEKLQFLYLSDNLLDSIPGPLPLSLRSVHLQNNLIETMQRDVFCDPEEHKHTRR QLEDIRLDGNPINLSLFPSAYFCLPRLPIGRFT |
| 111 | Osteoglycin/ Mimecan | PPTQQDSRIIYDYGTDNFEESIFSQDYEDKYLDGKNIKEKETVIIPNEKSLQLQKD EAITPLPPKKENDEMPTCLLCVCLSGSVYCEEVDIDAVPPLPKESAYLYARFNKIK KLTAKDFADIPNLRRLDFTGNLIEDIEDGTFSKLSLLEELSLAENQLLKLPVLPPK LTLFNAKYNKIKSRGIKANAFKKLNNLTFLYLDHNALESVPLNLPESLRVIHLQFN NIASITDDTFCKANDTSYIRDRIEEIRLEGNPIVLGKHPNSFICLKRLPIGSYF |
| 112 | Chondroadherin | QRCPQACICDNSRRHVACRYQNLTEVPDAIPELTQRLDLQGNLLKVIPAAAFQGVP HLTHLDLRHCEVELVAEGAFRGLGRLLLLNLASNHLRELPQEALDGLGSLRRLELE GNALEELRPGTFGALGALATLNLAHNALVYLPAMAFQGLLRVRWLRLSHNALSVLA PEALAGLPALRRLSLHHNELQALPGPVLSQARGLARLELGHNPLTYAGEEDGLALP GLRELLLDGGALQALGPRAFAHCPRLHTLPPLQGPGQLRRLRLQGN PLWCGCQARPLLEWLARARVRSDGACQGPRRLRGEALDALRPWDLRCPGDAAQEEE ELEEERAVAGPRAPPRGPPRGPEERAVAPCPRACVCVPESRHSSCEGCGLQAVPRG FPSDTQLLDLRRNHFPSVPRAAFPGLGHLVSLHLQHCGIAELEAGALAGLGRLIYL YLSDNQLAGLSAAALEGAPRLGYLYLERNRFLQVPGAALRALPSLFSLHLQDNAVD RLAPGDLGRTRALRWVYLSGNRITEVSLGALGPARELEKLHLDRNQLREVPTGALE |

Summary Sequence Table

| SEQ ID NO | Description | Sequence |
|---|---|---|
| | | GLPALLELQLSGNPLRALRDGAFQPVGRSLQHLFLNSSGLEQICPGAFSGLGPGLQ SLHLQKNQLRALPALPSLSQLELIDLSSNPFHCDCQLLPLHRWLTGLNLRVGATCA TPPNARGQRVKAAAAVFEDCPGWAARKAKRTPASRPSARRTPIKGRQCGADKVGKE KGRL |
| 113 | Podocan | GPVLAVRAPGFGRSGGHSLSPEENEFAEEEPVLVLSPEEPGPGPAAVSCPRDCACS QEGVVDCGGIDLREFPGDLPEHTNHLSLQNNQLEKIYPEELSRLHRLETLNLQNNR LTSRGLPEKAFEHLYNLNYLYLANNKLTLAPRFLPNALISVDFAANYLTKIYGLTF GQKPNLRSVYLHNNKLADAGLPDNMFNGSSNVEVLILSSNFLRHVPKHLPPALYKL HLKNNKLEKIPPGAFSELSSLRELYLQNNYLTDEGLDNETFWKLSSLEYLDLSSNN LSRVPAGLPRSLVLLHLEKNAIRSVDANVLTPIRSLEYLLLHSNQLREQGIHPLAF QGLKRLHTVHLYNNALERVPSGLPRRVRTLMILHNQITGIGREDFATTYFLEELNL SYNRITSPQVHRDAFRKLRLLRSLDLSGNRLHTLPPGLPRNVHVLKVKRNELAALA RGALVGMAQLRELYLTSNRLRSRALGPRAWVDLAHLQLLDIAGNQLTEIPEGLPES LEYLYLQNNKISAVPANAFDSTPNLKGIFLRFNKLAVGSVVDSAFRRLKHLQVLDI EGNLEFGDISKDRGRLGKEKEEEEEEEEEETR |
| 114 | Human IgG1 constant region (amino acid sequence) | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKKVEPKSCDKTHTCPPC PAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKG QPREPQVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK |
| 115 | Human IgG1 Fc domain (amino acid sequence) | EPKSCDKTHTCPPCPAPELLGGPSVFLFPPKPKDTLMISRTPEVTCVVVDVSHEDP EVKFNWYVDGVEVHNAKTKPREEQYNSTYRVVSVLTVLHQDWLNGKEYKCKVSNKA LPAPIEKTISKAKGQPREPQVYTLPPSRDELTKNQVSLTCLVKGFYPSDIAVEWES NGQPENNYKTTPPVLDSDGSFFLYSKLTVDKSRWQQGNVFSCSVMHEALHNHYTQK SLSLSPGK |
| 116 | HSA domain I | DAHKSEVAHRFKDLGEENFKALVLIAFAQYLQQCPFEDHVKLVNEVTEFAKTCVAD ESAENCDKSLHTLFGDKLCTVATLRETYGEMADCCAKQEPERNECFLQHKDDNPNL PRLVRPEVDVMCTAFHDNEETFLKKYLYEIARRHPYFYAPELLFFAKRYKAAFTEC CQAADKAACLLPKLDELRDEGKASSAKQR |
| 117 | HSA domain II | GKASSAKQRLKCASLQKFGERAFKAWAVARLSQRFPKAEFAEVSKLVTDLTKVHTE CCHGDLLECADDRADLAKYICENQDSISSKLKECCEKPLLEKSHCIAEVENDEMPA DLPSLAADFVESKDVCKNYAEAKDVFLGMFLYEYARRHPDYSVVLLLRLAKTYETT LEKCCAAADPHECYAKVFDEFKPLVEEPQ |
| 118 | HSA domain III | NLIKQNCELFEQLGEYKFQNALLVRYTKKVPQVSTPTLVEVSRNLGKVGSKCCKHP EAKRMPCAEDYLSVVLNQLCVLHEKTPVSDRVTKCCTESLVNRRPCFSALEVDETY VPKEFNAETFTFHADICTLSEKERQIKKQTALVELVKHKPKATKEQLKAVMDDFAA FVEKCCKADDKETCFAEEGKKLVAASQAALGL |
| 119 | Linker | LEA (EAAAK)₄ALEA (EAAAK)₄ALE |
| 120 | Lumican-MSA-IL2 (lumican in bold; linkers in italics; MSA underlined; IL2 bold and underline; HIS tag dotted underlined) | QYYDYDIPLFMYGQISPNCAPECNCPHSYPTAMYCDDLKLKSVPMVPPGIKYLYLR NNQIDHIDEKAFENVTDLQWLILDHNLLENSKIKGKVFSKLKQLKKLHINYNNLTE SVGPLPKSLQDLQLTNNKISKLGSFDGLVNLTFIYLQHNQLKEDAVSASLKGLKSL EYLDLSFNQMSKLPAGLPTSLLTLYLDNNKISNIPDEYFKRFTGLQYLRLSHNELA DSGVPGNSFNISSLLELDLSYNKLKSIPTVNENLENYYLEVNELEKFDVKSFCKIL GPLSYSKIKHLRLDGNPLTQSSLPPDMYECLRVANEITVN_GGGSGGGS_EAHKSEIA HRYNDLGEQHFKGLVLIAFSQYLQKCSYDEHAKLVQEVTDFAKTCVADESAANCDK SLHTLFGDKLCAIPNLRENYGELADCCTKQEPERNECFLQHKDDNPSLPPFERPEA EAMCTSFKENPTTFMGHYLEVARRHPYFYAPELLYYAEQYNEILTQCCAEADKES CLTPKLDGVKEKALVSSVRQRMKCSSMQKFGERAFKAWAVARLSQTFPNADFAEIT KLATDLTKVNKECCHGDLLECADDRAELAKYMCENQATISSKLQTCCDKPLLKKAH CLSEVEHDTMPADLPAIAADFVEDQEVCKNYAEAKDVFLGTFLYEYSRRHPDYSVS LLLRLAKKYEATLEKCCAEANPPACYGTVLAEFQPLVEEPKNLVKTNCDLYEKLGE YGFQNAILVRYTQKAPQVSTPTLVEAARNLGRVGTKCCTLPEDQRLPCVEDYLSAI LNRVCLLHEKTPVSEHVTKCCSGSLVERRPCFSALTVDETYVPKEFKAETFTFHSD ICTLPEKEKQIKKQTALAELVKHKPKATAEQLKTVMDDFAQFLDTCCKAADKDTCF STEGPNLVTRCKDALA_GGGS_APTSSSTSSSTAEAQQQQQQQQQQQHLEQLLMDLQ ELLSRMENYRNLKLPRMLTFKFYLPKQATELKDLQCLEDELGPLRHVLDLTQSKSF QLEDAENFISNIRVTVVKLKGSDNTFECQFDDESATVVDFLRRWIAFCQSIISTSP QHHHHHH |
| 121 | MSA-IL2 (MSA in bold; linkers in italics; IL2 underlined; | EAHKSEIAHRYNDLGEQHFKGLVLIAFSQYLQKCSYDEHAKLVQEVTDFAKTCVAD ESAANCDKSLHTLFGDKLCAIPNLRENYGELADCCTKQEPERNECFLQHKDDNPSL PPFERPEAEAMCTSFKENPTTFMGHYLEVARRHPYFYAPELLYYAEQYNEILTQC CAEADKESCLTPKLDGVKEKALVSSVRQRMKCSSMQKFGERAFKAWAVARLSQTFP NADFAEITKLATDLTKVNKECCHGDLLECADDRAELAKYMCENQATISSKLQTCCD |

Summary Sequence Table

| SEQ ID NO | Description | Sequence |
|---|---|---|
|  | HIS tag dotted underlined) | KPLLKKAHCLSEVEHDTMPADLPAIAADFVEDQEVCKNYAEAKDVFLGTFLYEYSR RHPDYSVSLLLRLAKKYEATLEKCCAEANPPACYGTVLAEFQPLVEEPKNLVKTNC DLYEKLGEYGFQNAILVRYTQKAPQVSTPTLVEAARNLGRVGTKCCTLPEDQRLPC VEDYLSAILNRVCLLHEKTPVSEHVTKCCSGSLVERRPCFSALTVDETYVPKEFKA ETFTFHSDICTLPEKEKQIKKQTALAELVKHKPKATAEQLKTVMDDFAQFLDTCCK AADKDTCFSTEGPNLVTRCKDALA*GGGS*SAPTSSSTSSSTAEAQQQQQQQQQQQHL EQLLMDLQELLSRMENYRNLKLPRMLTFKFYLPKQATELKDLQCLEDELGPLRHVL DLTQSKSFQLEDAENFISNIRVTVVKLKGSDNTFECQFDDESATVVDFLRRWIAFC QSIISTSPQHHHHHH |
| 122 | IL12-MSA (IL12p40 bold; linkers italics; IL12p34 underlined; MSA bold and underlined; HIS tag dotted underlined) | MWELEKDVYVVEVDWTPDAPGETVNLTCDTPEEDDITWTSDQRHGVIGSGKTLTIT VKEFLDAGQYTCHKGGETLSHSHLLLHKKENGIWSTEILKNFKNKTFLKCEAPNYS GRFTCSWLVQRNMDLKFNIKSSSSSPDSRAVTCGMASLSAEKVTLDQRDYEKYSVS CQEDVTCPTAEETLPIELALEARQQNKYENYSTSFFIRDIIKPDPPKNLQMKPLKN SQVEVSWEYPDSWSTPHSYFSLKFFVRIQRKKEKMKETEEGCNQKGAFLVEKTSTE VQCKGGNVCVQAQDRYYNSSCSKWACVPCRVRS*GGSGGGSGGGSGGGS*RVIPVSGP ARCLSQSRNLLKTTDDMVKTAREKLKHYSCTAEDIDHEDITRDQTSTLKTCLPLEL HKNESCLATRETSSTTRGSCLPPQKTSLMMTLCLGSIYEDLKMYQTEFQAINAALQ NHNHQQIILDKGMLVAIDELMQSLNHNGETLRQKPPVGEADPYRVKMKLCILLHAF STRVVTINRVMGYLSSA*GSGGGS***EAHKSEIAHRYNDLGEQHFKGLVLIAFSQYLQK CSYDEHAKLVQEVTDFAKTCVADESAANCDKSLHTLFGDKLCAIPNLRENYGELAD CCTKQEPERNECFLQHKDDNPSLPPFERPEAEAMCTSFKENPTTFMGHYLHEVARR HPYFYAPELLYYAEQYNEILTQCCAEADKESCLTPKLDGVKEKALVSSVRQRMKCS SMQKFGERAFKAWAVARLSQTFPNADFAEITKLATDLTKVNKECCHGDLLECADDR AELAKYMCENQATISSKLQTCCDKPLLKKAHCLSEVEHDTMPADLPAIAADFVEDQ EVCKNYAEAKDVFLGTFLYEYSRRHPDYSVSLLLRLAKKYEATLEKCCAEANPPAC YGTVLAEFQPLVEEPKNLVKTNCDLYEKLGEYGFQNAILVRYTQKAPQVSTPTLVE AARNLGRVGTKCCTLPEDQRLPCVEDYLSAILNRVCLLHEKTPVSEHVTKCCSGSL VERRPCFSALTVDETYVPKEFKAETFTFHSDICTLPEKEKQIKKQTALAELVKHKP KATAEQLKTVMDDFAQFLDTCCKAADKDTCFSTEGPNLVTRCKDALAHHHHHH |
| 123 | IL12-MSA-Lumican (IL12p40 bold; linkers italics; IL12p34 underlined; MSA bold and underlined; lumican bold, underlined and italc; HIS tag dotted underlined) | MWELEKDVYVVEVDWTPDAPGETVNLTCDTPEEDDITWTSDQRHGVIGSGKTLTIT VKEFLDAGQYTCHKGGETLSHSHLLLHKKENGIWSTEILKNFKNKTFLKCEAPNYS GRFTCSWLVQRNMDLKFNIKSSSSSPDSRAVTCGMASLSAEKVTLDQRDYEKYSVS CQEDVTCPTAEETLPIELALEARQQNKYENYSTSFFIRDIIKPDPPKNLQMKPLKN SQVEVSWEYPDSWSTPHSYFSLKFFVRIQRKKEKMKETEEGCNQKGAFLVEKTSTE VQCKGGNVCVQAQDRYYNSSCSKWACVPCRVRS*GGSGGGSGGGSGGGS*RVIPVSGP ARCLSQSRNLLKTTDDMVKTAREKLKHYSCTAEDIDHEDITRDQTSTLKTCLPLEL HKNESCLATRETSSTTRGSCLPPQKTSLMMTLCLGSIYEDLKMYQTEFQAINAALQ NHNHQQIILDKGMLVAIDELMQSLNHNGETLRQKPPVGEADPYRVKMKLCILLHAF STRVVTINRVMGYLSSA*GSGGGS***EAHKSEIAHRYNDLGEQHFKGLVLIAFSQYLQK CSYDEHAKLVQEVTDFAKTCVADESAANCDKSLHTLFGDKLCAIPNLRENYGELAD CCTKQEPERNECFLQHKDDNPSLPPFERPEAEAMCTSFKENPTTFMGHYLHEVARR HPYFYAPELLYYAEQYNEILTQCCAEADKESCLTPKLDGVKEKALVSSVRQRMKCS SMQKFGERAFKAWAVARLSQTFPNADFAEITKLATDLTKVNKECCHGDLLECADDR AELAKYMCENQATISSKLQTCCDKPLLKKAHCLSEVEHDTMPADLPAIAADFVEDQ EVCKNYAEAKDVFLGTFLYEYSRRHPDYSVSLLLRIAKKYEATLEKCCAEANPPAC YGTVLAEFQPLVEEPKNLVKTNCDLYEKLGEYGFQNAILVRYTQKAPQVSTPTLVE AARNLGRVGTKCCTLPEDQRLPCVEDYLSAILNRVCLLHEKTPVSEHVTKCCSGSL VERRPCFSALTVDETYVPKEFKAETFTFHSDICTLPEKEKQIKKQTALAELVKHKP KATAEQLKTVMDDFAQFLDTCCKAADKDTCFSTEGPNLVTRCKDALA_GGGSGGGSQ_ _YYDYDIPLFMYGQISPNCAPECNCPHSYPTAMYCDDLKLKSVPMVPPGIKYLYLRN_ _NQIDHIDEKAFENVTDLQWLILDHNLLENSKIKGKVFSKLKQLKKLHINYNNLTES_ _VGPLPKSLQDLQLTNNKISKLGSFDGLVNLTFIYLQHNQLKEDAVSASLKGLKSLE_ _YLDLSFNQMSKLPAGLPTSLLTLYLDNNKISNIPDEYFKRFTGLQYLRLSHNELAD_ _SGVPGNSFNISSLLELDLSYNKLKSIPTVNENLENYYLEVNELEKFDVKSFCKILG_ _PLSYSKIKHLRLDGNPLTQSSLPPDMYECLRVANEITVN_HHHHHH |
| 124 | Lumican-GGGS-(H)$_6$ | QYYDYDIPLFMYGQISPNCAPECNCPHSYPTAMYCDDLKLKSVPMVPPGIKYLYLR NNQIDHIDEKAFENVTDLQWLILDHNLLENSKIKGKVFSKLKQLKKLHINYNNLTE SVGPLPKSLQDLQLTNNKISKLGSFDGLVNLTFIYLQHNQLKEDAVSASLKGLKSL EYLDLSFNQMSKLPAGLPTSLLTLYLDNNKISNIPDEYFKRFTGLQYLRLSHNELA DSGVPGNSFNISSLLELDLSYNKLKSIPTVNENLENYYLEVNELEKFDVKSFCKIL GPLSYSKIKHLRLDGNPLTQSSLPPDMYECLRVANEITVN*GGGS*HHHHHH |

Summary Sequence Table

| SEQ ID NO | Description | Sequence |
|---|---|---|
| 125 | Lumican D213A | QYYDYDIPLFMYGQISPNCAPECNCPHSYPTAMYCDDLKLKSVPMVPPGIKYLYLR NNQIDHIDEKAFENVTDLQWLILDHNLLENSKIKGKVFSKLKQLKKLHINYNNLTE SVGPLPKSLQDLQLTNNKISKLGSFDGLVNLTFIYLQHNQLKEDAVSASLKGLKSL EYLDLSFNQMSKLPAGLPTSLLTLYLANNKISNIPDEYFKRFTGLQYLRLSHNELA DSGVPGNSFNISSLLELDLSYNKLKSIPTVNENLENYYLEVNELEKFDVKSFCKIL GPLSYSKIKHLRLDGNPLTQSSLPPDMYECLRVANEITVN*GGGS*HHHHHH |
| 126 | Lumican-MSA | QYYDYDIPLFMYGQISPNCAPECNCPHSYPTAMYCDDLKLKSVPMVPPGIKYLYLR NNQIDHIDEKAFENVTDLQWLILDHNLLENSKIKGKVFSKLKQLKKLHINYNNLTE SVGPLPKSLQDLQLTNNKISKLGSFDGLVNLTFIYLQHNQLKEDAVSASLKGLKSL EYLDLSFNQMSKLPAGLPTSLLTLYLDNNKISNIPDEYFKRFTGLQYLRLSHNELA DSGVPGNSFNISSLLELDLSYNKLKSIPTVNENLENYYLEVNELEKFDVKSFCKIL GPLSYSKIKHLRLDGNPLTQSSLPPDMYECLRVANEITVN*GGGSGGGS*EAHKSEIA HRYNDLGEQHFKGLVLIAFSQYLQKCSYDEHAKLVQEVTDFAKTCVADESAANCDK SLHTLFGDKLCAIPNLRENYGELADCCTKQEPERNECFLQHKDDNPSLPPFERPEA EAMCTSFKENPTTFMGHYLHEVARRHPYFYAPELLYYAEQYNEILTQCCAEADKES CLTPKLDGVKEKALVSSVRQRMKCSSMQKFGERAFKAWAVARLSQTFPNADFAEIT KLATDLTKVNKECCHGDLLECADDRAELAKYMCENQATISSKLQTCCDKPLLKKAH CLSEVEHDTMPADLPAIAADFVEDQEVCKNYAEAKDVFLGTFLYEYSRRHPDYSVS LLLRLAKKYEATLEKCCAEANPPACYGTVLAEFQPLVEEPKNLVKTNCDLYEKLGE YGFQNAILVRYTQKAPQVSTPTLVEAARNLGRVGTKCCTLPEDQRLPCVEDYLSAI LNRVCLLHEKTPVSEHVTKCCSGSLVERRPCFSALTVDETYVPKEFKAETFTFHSD ICTLPEKEKQIKKQTALAELVKHKPKATAEQLKTVMDDFAQFLDTCCKAADKDTCF STEGPNLVTRCKDALAHHHHHH |
| 127 | Gluc | KPTENNEDFNIVAVASNFATTDLDADRGKLPGKKLPLEVLKEMEANARKAGCTRGC LICLSHIKCTPKMKKFIPGRCHTYEGDKESAQGGIGEAIVDIPEIPGFKDLEPMEQ FIAQVDLCVDCTTGCLKGLANVQCSDLLKKWLPQRCATFASKIQGQVDKIKGAGGD *GGGS*HHHHHH |
| 128 | Lumican-Gluc | QYYDYDIPLFMYGQISPNCAPECNCPHSYPTAMYCDDLKLKSVPMVPPGIKYLYLR NNQIDHIDEKAFENVTDLQWLILDHNLLENSKIKGKVFSKLKQLKKLHINYNNLTE SVGPLPKSLQDLQLTNNKISKLGSFDGLVNLTFIYLQHNQLKEDAVSASLKGLKSL EYLDLSFNQMSKLPAGLPTSLLTLYLDNNKISNIPDEYFKRFTGLQYLRLSHNELA DSGVPGNSFNISSLLELDLSYNKLKSIPTVNENLENYYLEVNELEKFDVKSFCKIL GPLSYSKIKHLRLDGNPLTQSSLPPDMYECLRVANEITVN*GGGSGGGSGGGGS*KPTE NNEDFNIVAVASNFATTDLDADRGKLPGKKLPLEVLKEMEANARKAGCTRGCLICL SHIKCTPKMKKFIPGRCHTYEGDKESAQGGIGEAIVDIPEIPGFKDLEPMEQFIAQ VDLCVDCTTGCLKGLANVQCSDLLKKWLPQRCATFASKIQGQVDKIKGAGGD*GGGS* HHHHHH |
| 129 | CNA35-Gluc | ARDISSTNVTDLTVSPSKIEDGGKTTVKMTFDDKNGKIQNGDMIKVAWPTSGTVKI EGYSKTVPLTVKGEQVGQAVITPDGATITFNDKVEKLSDVSGFAEFEVQGRNLTQT NTSDDKVATITSGNKSTNVTVHKSEAGTSSVFYYKTGDMLPEDTTHVRWFLNINNE KSYVSKDITIKDQIQGGQQLDLSTLNINVTGTHSNYYSGQSAITDFEKAFPGSKIT VDNTKNTIDVTIPQGYGSYNSFSINYKTKITNEQQKEFVNNSQAWYQEHGKEEVNG KSFNHTVHNINANAGIEGTVKGELKVLKQDKDTK*GGGSGGGGGGGGGK*PTENNEDFN IVAVASNFATTDLDADRGKLPGKKLPLEVLKEMEANARKAGCTRGCLICLSHIKCT PKMKKFIPGRCHTYEGDKESAQGGIGEAIVDIPEIPGFKDLEPMEQFIAQVDLCVD CTTGCLKGLANVQCSDLLKKWLPQRCATFASKIQGQVDKIKGAGGD*GGGS*HHHHHH |
| 130 | ColG s3s/s3b-Gluc | PITKEMEPNDDIKEANGPIVEGVTVKGDLNGSDDADTFYFDVKEDGDVTIELPYSG SSNFTWLVYKEGDDQNHIASGIDKNNSKVGTFKSTKGRHYVFIYKHDSASNISYSL NIKGLGNEKLKEKENNDSSDKATVIPNFNTTMQGSLLGDDSRDYYSFEVKEEGEVN IELDKKDEFGVTWTLHPESNINDRITYGQVDGNKVSNKVKLRPGKYYLLVYKYSGS GNYELRVN*GGGSGGGSGGGS*KPTENNEDFNIVAVASNFATTDLDADRGKLPGKKLP LEVLKEMEANARKAGCTRGCLICLSHIKCTPKMKKFIPGRCHTYEGDKESAQGGIG EAIVDIPEIPGFKDLEPMEQFIAQVDLCVDCTTGCLKGLANVQCSDLLKKWLPQRC ATFASKIQGQVDKIKGAGGD*GGGS*HHHHHH |
| 131 | ColH_s3-Gluc | GTEKEPNNSKETASGPIVPGIPVSGTIENTSDQDYFYFDVITPGEVKIDINKLGYG GATWVVYDENNNAVSYATDDGQNLSGKFKADKPGRYYIHLYMFNGSYMPYRINIE*G GGSGGGSGGGS*KPTENNEDFNIVAVASNFATTDLDADRGKLPGKKLPLEVLKEMEA NARKAGCTRGCLICLSHIKCTPKMKKFIPGRCHTYEGDKESAQGGIGEAIVDIPEI PGFKDLEPMEQFIAQVDLCVDCTTGCLKGLANVQCSDLLKKWLPQRCATFASKIQG QVDKIKGAGGD*GGGS*HHHHHH |
| 132 | PLGF2 HBD-Gluc | RRRPKGRGKRRREKQRPTDSHL*GGGSGGGSGGGS*KPTENNEDFNIVAVASNFATTD LDADRGKLPGKKLPLEVLKEMEANARKAGCTRGCLICLSHIKCTPKMKKFIPGRCH TYEGDKESAQGGIGEAIVDIPEIPGFKDLEPMEQFIAQVDLCVDCTTGCLKGLANV QCSDLLKKWLPQRCATFASKIQGQVDKIKGAGGD*GGGS*HHHHHH |

Summary Sequence Table

| SEQ ID NO | Description | Sequence |
|---|---|---|
| 133 | 4M5.3-MSA-Lumican | ADVVMTQTPLSLPVSLGDQASISCRSSQSLVHSNGNTYLRWYLQKPGQSPKVLIYK VSNRVSGVPDRFSGSGSGTDFTLKINRVEAEDLGVYFCSQSTHVPWTFGGGTKLEI KSSADDAKKDAAKKDDAAKKDDAAKKDGGVKLDETGGGLVQPGGAMKLSCVTSGFTFG HYWMNWVRQSPEKGLEWVAQFRNKPYNYETYYSDSVKGRFTISRDDSKSSVYLQMN NLRVEDTGIYYCTGASYGMEYLGQGTSVTVS*GGGS*EAHKSEIAHRYNDLGEQHFKG LVLIAFSQYLQKCSYDEHAKLVQEVTDFAKTCVADESAANCDKSLHTLFGDKLCAI PNLRENYGELADCCTKQEPERNECFLQHKDDNPSLPPFERPEAEAMCTSFKENPTT FMGHYLHEVARRHPYFYAPELLYYAEQYNEILTQCCAEADKESCLTPKLDGVKEKA LVSSVRQRMKCSSMQKFGERAFKAWAVARLSQTFPNADFAEITKLATDLTKVNKEC CHGDLLECADDRAELAKYMCENQATISSKLQTCCDKPLLKKAHCLSEVEHDTMPAD LPAIAADFVEDQEVCKNYAEAKDVFLGTFLYEYSRRHPDYSVSLLLRLAKKYEATL EKCCAEANPPACYGTVLAEFQPLVEEPKNLVKTNCDLYEKLGEYGFQNAILVRYTQ KAPQVSTPTLVEAARNLGRVGTKCCTLPEDQRLPCVEDYLSAILNRVCLLHEKTPV SEHVTKCCSGSLVERRPCFSALTVDETYVPKEFKAETFTFHSDICTLPEKEKQIKK QTALAELVKHKPKATAEQLKTVMDDFAQFLDTCCKAADKDTCFSTEGPNLVTRCKD ALA*GGGSGGGS*QYYDYDIPLFMYGQISPNCAPECNCPHSYPTAMYCDDLKLKSVPM VPPGIKYLYLRNNQIDHIDEKAFENVTDLQWLILDHNLLENSKIKGKVFSKLKQLK KLHINYNNLTESVGPLPKSLQDLQLTNNKISKLGSFDGLVNLTFIYLQHNQLKEDA VSASLKGLKSLEYLDLSFNQMSKLPAGLPTSLLTLYLDNNKISNIPDEYFKRFTGL QYLRLSHNELADSGVPGNSFNISSLLELDLSYNKLKSIPTVNENLENYYLEVNELE KFDVKSFCKILGPLSYSKIKHLRLDGNPLTQSSLPPDMYECLRVANEITVNGGGSH HHHHH |
| 134 | Ss07d-MSA-Lumican | ATVKFKYKGEEKQVDISKIYLVLRLGKFIYFYYDLGGGKLGLGHVSEKDAPKELLQ MLEKQKK*GGGS*EAHKSEIAHRYNDLGEQHFKGLVLIAFSQYLQKCSYDEHAKLVQE VTDFAKTCVADESAANCDKSLHTLFGDKLCAIPNLRENYGELADCCTKQEPERNEC FLQHKDDNPSLPPFERPEAEAMCTSFKENPTTFMGHYLHEVARRHPYFYAPELLYY AEQYNEILTQCCAEADKESCLTPKLDGVKEKALVSSVRQRMKCSSMQKFGERAFKA WAVARLSQTFPNADFAEITKLATDLTKVNKECCHGDLLECADDRAELAKYMCENQA TISSKLQTCCDKPLLKKAHCLSEVEHDTMPADLPAIAADFVEDQEVCKNYAEAKDV FLGTFLYEYSRRHPDYSVSLLLRLAKKYEATLEKCCAEANPPACYGTVLAEFQPLV EEPKNLVKTNCDLYEKLGEYGFQNAILVRYTQKAPQVSTPTLVEAARNLGRVGTKC CTLPEDQRLPCVEDYLSAILNRVCLLHEKTPVSEHVTKCCSGSLVERRPCFSALTV DETYVPKEFKAETFTFHSDICTLPEKEKQIKKQTALAELVKHKPKATAEQLKTVMD DFAQFLDTCCKAADKDTCFSTEGPNLVTRCKDALA*GGGSGGGS*QYYDYDIPLFMYG QISPNCAPECNCPHSYPTAMYCDDLKLKSVPMVPPGIKYLYLRNNQIDHIDEKAFE NVTDLQWLILDHNLLENSKIKGKVFSKLKQLKKLHINYNNLTESVGPLPKSLQDLQ LTNNKISKLGSFDGLVNLTFIYLQHNQLKEDAVSASLKGLKSLEYLDLSFNQMSKL PAGLPTSLLTLYLDNNKISNIPDEYFKRFTGLQYLRLSHNELADSGVPGNSFNISS LLELDLSYNKLKSIPTVNENLENYYLEVNELEKFDVKSFCKILGPLSYSKIKHLRL DGNPLTQSSLPPDMYECLRVANEITVN*GGGS***HHHHHH |
| 135 | ZZ-MSA Lumican | MRVPAQLLGLLLLWLPGARCAVDNKFNKEQQNAFYEILHLPNLNEEQRNAFIQSLK DPPSQSANLLAEAKKLNDAQAPKVDNKFNKEQQNAFYEILHLPNLNEEQRNAFIQS LKDDPSQSANLLAEAKKLNDAQAPK*GGGS*EAHKSEIAHRYNDLGEQHFKGLVLIAF SQYLQKCSYDEHAKLVQEVTDFAKTCVADESAANCDKSLHTLFGDKLCAIPNLREN YGELADCCTKQEPERNECFLQHKDDNPSLPPFERPEAEAMCTSFKENPTTFMGHYL HEVARRHPYFYAPELLYYAEQYNEILTQCCAEADKESCLTPKLDGVKEKALVSSVR QRMKCSSMQKFGERAFKAWAVARLSQTFPNADFAEITKLATDLTKVNKECCHGDLL ECADDRAELAKYMCENQATISSKLQTCCDKPLLKKAHCLSEVEHDTMPADLPAIAA DFVEDQEVCKNYAEAKDVFLGTFLYEYSRRHPDYSVSLLLRLAKKYEATLEKCCAE ANPPACYGTVLAEFQPLVEEPKNLVKTNCDLYEKLGEYGFQNAILVRYTQKAPQVS TPTLVEAARNLGRVGTKCCTLPEDQRLPCVEDYLSAILNRVCLLHEKTPVSEHVTK CCSGSLVERRPCFSALTVDETYVPKEFKAETFTFHSDICTLPEKEKQIKKQTALAE LVKHKPKATAEQLKTVMDDFAQFLDTCCKAADKDTCFSTEGPNLVTRCKDALA*GGG SGGGS*QYYDYDIPLFMYGQISPNCAPECNCPHSYPTAMYCDDLKLKSVPMVPPGIK YLYLRNNQIDHIDEKAFENVTDLQWLILDHNLLENSKIKGKVFSKLKQLKKLHINY NNLTESVGPLPKSLQDLQLTNNKISKLGSFDGLVNLTFIYLQHNQLKEDAVSASLK GLKSLEYLDLSFNQMSKLPAGLPTSLLTLYLDNNKISNIPDEYFKRFTGLQYLRLS HNELADSGVPGNSFNISSLLELDLSYNKLKSIPTVNENLENYYLEVNELEKFDVKS FCKILGPLSYSKIKHLRLDGNPLTQSSLPPDMYECLRVANEITVN*GGGS*HHHHHH |
| 136 | Lumican-MSA-FcIII4C | QYYDYDIPLFMYGQISPNCAPECNCPHSYPTAMYCDDLKLKSVPMVPPGIKYLYLR NNQIDHIDEKAFENVTDLQWLILDHNLLENSKIKGKVFSKLKQLKKLHINYNNLTE SVGPLPKSLQDLQLTNNKISKLGSFDGLVNLTFIYLQHNQLKEDAVSASLKGLKSL EYLDLSFNQMSKLPAGLPTSLLTLYLDNNKISNIPDEYFKRFTGLQYLRLSHNELA DSGVPGNSFNISSLLELDLSYNKLKSIPTVNENLENYYLEVNELEKFDVKSFCKIL GPLSYSKIKHLRLDGNPLTQSSLPPDMYECLRVANEITVN*GGGSGGGS*EAHKSEIA HRYNDLGEQHFKgLVLIAFSQYLQKCSYDEHAKLVQEVTDFAKTCVADESAANCDK SLHTLFGDKLCAIPNLRENYGELADCCTKQEPERNECFLQHKDDNPSLPPFERPEA EAMCTSFKENPTIFMGHYLHEVARRHPYFYAPELLYYAEQYNEILFQCCAEADKES CLTPKLDGVKEKALVSSVRQRMKCSSMQKFGERAFKAWAVARLSQTFPNADFAEIT KLATDLTKVNKECCHGDLLECADDRAELAKYMCENQATISSKLQTCCDKPLLKKAH |

Summary Sequence Table

| SEQ ID NO | Description | Sequence |
|---|---|---|
| | | CLSEVEHDTMPADLPAIAADFVEDQEVCKNYAEAKDVFLGTFLYEYSRRHPDYSVS<br>LLLRLAKKYEATLEKCCAEANPPACYGTVLAEFQPLVEEPKNLVKTNCDLYEKLGE<br>YGFQNAILVRYTQKAPQVSTPTLVEAARNLGRVGTKCCTLPEDQRLPCVEDYLSAI<br>LNRVCLLHEKTPVSEHVTKCCSGSLVERRPCFSALTVDETYVPKEFKAETFTFHSD<br>ICTLPEKEKQIKKQTALAELVKHKPKATAEQLKTVMDDFAQFLDTCCKAADKDTCF<br>STEGPNLVTRCKDALA*GGGS*CDCAWHLGELVWCTCHHHHHH |
| 137 | Lumican-MSA-Fn3 | QYYDYDIPLFMYGQISPNCAPECNCPHSYPTAMYCDDLKLKSVPMVPPGIKYLYLR<br>NNQIDHIDEKAFENVTDLQWLILDHNLLENSKIKGKVFSKLKQLKKLHINYNNLTE<br>SVGPLPKSLQDLQLTNNKISKLGSFDGLVNLTFIYLQHNQLKEDAVSASLKGLKSL<br>EYLDLSFNQMSKLPAGLPTSLLTLYLDNNKISNIPDEYFKRFTGLQYLRLSHNELA<br>DSGVPGNSFNISSLLELDLSYNKLKSIPTVNENLENYYLEVNELEKFDVKSFCKIL<br>GPLSYSKIKHLRLDGNPLTQSSLPPDMYECLRVANEITVN*GGGSGGGS*EAEKSEIA<br>HRYNDLGEQHFKGLVLIAFSQYLQKCSYDEHAKLVQEVTDFAKTCVADESAANCDK<br>SLHTLFGDKLCAIPNLRENYGELADCCTKQEPERNECFLQHKDDNPSLPPFERPEA<br>EAMCTSFKENPTTFMGHYLHEVARRHPYFYAPELLYYAEQYNEILEQCCAEADKES<br>CLTPKLDGVKEKALVSSVRQRMKCSSMQKFGERAFKAWAVARLSQEFPNADFAEIT<br>KLATDLTKVNKECCHGDLLECADDRAELAKYMCENQATISSKLQTCCDKPLLKKAH<br>CLSEVEHDTMPADLPAIAADFVEDQEVCKNYAEAKDVFLGTFLYEYSRRHPDYSVS<br>LLLRLAKKYEATLEKCCAEANPPACYGTVLAEFQPLVEEPKNLVKTNCDLYEKLGE<br>YGFQNAILVRYTQKAPQVSTPTLVEAARNLGRVGTKCCTLPEDQRLPCVEDYLSAI<br>LNRVCLLHEKTPVSEHVTKCCSGSLVERRPCFSALTVDETYVPKEFKAETFTFHSD<br>ICTLPEKEKQIKKQTALAELVKHKPKATAEQLKTVMDDFAQFLDTCCKAADKDTCF<br>STEGPNLVTRCKDALA*GGGS*VSDVPRDLEVVAATPTSLLISWCCSDNCSNSYRITY<br>GETGGNSPVQEFTVPRSCFMATISGLKPGVDYTITAYAVTDSNGPHPISINYRTHH<br>HHHH |
| 138 | Lumican-MSA-SpG2 | QYYDYDIPLFMYGQISPNCAPECNCPHSYPTAMYCDDLKLKSVPMVPPGIKYLYLR<br>NNQIDHIDEKAFENVTDLQWLILDHNLLENSKIKGKVFSKLKQLKKLHINYNNLTE<br>SVGPLPKSLQDLQLTNNKISKLGSFDGLVNLTFIYLQHNQLKEDAVSASLKGLKSL<br>EYLDLSFNQMSKLPAGLPTSLLTLYLDNNKISNIPDEYFKRFTGLQYLRLSHNELA<br>DSGVPGNSFNISSLLELDLSYNKLKSIPTVNENLENYYLEVNELEKFDVKSFCKIL<br>GPLSYSKIKHLRLDGNPLTQSSLPPDMYECLRVANEITVN*GGGSGGGS*EAHKSEIA<br>HRYNDLGEQHFKGLVLIAFSQYLQKCSYDEHAKLVQEVTDFAKTCVADESAANCDK<br>SLHTLFGDKLCAIPNLRENYGELADCCTKQEPERNECFLQHKDDNPSLPPFERPEA<br>EAMCTSFKENPTTFMGHYLHEVARRHPYFYAPELLYYAEQYNEILTQCCAEADKES<br>CLTPKLDGVKEKALVSSVRQRMKCSSMQKFGERAFKAWAVARLSQTFPNADFAEIT<br>KLATDLTKVNKECCHGDLLECADDRAELAKYMCENQATISSKLQTCCDKPLLKKAH<br>CLSEVEHDTMPADLPAIAADFVEDQEVCKNYAEAKDVFLGTFLYEYSRRHPDYSVS<br>LLLRLAKKYEATLEKCCAEANPPACYGTVLAEFQPLVEEPKNLVKTNCDLYEKLGE<br>YGFQNAILVRYTQKAPQVSTPTLVEAARNLGRVGTKCCTLPEDQRLPCVEDYLSAI<br>LNRVCLLHEKTPVSEHVTKCCSGSLVERRPCFSALTVDETYVPKEFKAETFTFHSD<br>ICTLPEKEKQIKKQTALAELVKHKPKATAEQLKTVMDDFAQFLDTCCKAADKDTCF<br>STEGPNLVTRCKDALA*GGGS*TYKLVINGKTLKGETTTEAVDAATAEKVFKQYANDY<br>GVDGEWTYDDATKTFTVTEKPEVIDASELTPAVTTYKLVINGKTLKGETTTKAVDA<br>ETAEKAFKQYANDYGVDGVWTYDDATKTFTVTEHHHHHH |
| 139 | Lumican-MSA-RRGW | QYYDYDIPLFMYGQISPNCAPECNCPHSYPTAMYCDDLKLKSVPMVPPGIKYLYLR<br>NNQIDHIDEKAFENVTDLQWLILDHNLLENSKIKGKVFSKLKQLKKLHINYNNLTE<br>SVGPLPKSLQDLQLTNNKISKLGSFDGLVNLTFIYLQHNQLKEDAVSASLKGLKSL<br>EYLDLSFNQMSKLPAGLPTSLLTLYLDNNKISNIPDEYFKRFTGLQYLRLSHNELA<br>DSGVPGNSFNISSLLELDLSYNKLKSIPTVNENLENYYLEVNELEKFDVKSFCKIL<br>GPLSYSKIKHLRLDGNPLTQSSLPPDMYECLRVANEITVN*GGGSGGGS*EAHKSEIA<br>HRYNDLGEQHFKGLVLIAFSQYLQKCSYDEHAKLVQEVTDFAKTCVADESAANCDK<br>SLHTLFGDKLCAIPNLRENYGELADCCTKQEPERNECFLQHKDDNPSLPPFERPEA<br>EAMCTSFKENPTTFMGHYLHEVARRHPYFYAPELLYYAEQYNEILFQCCAEADKES<br>CLTPKLDGVKEKALVSSVRQRMKCSSMQKFGERAFKAWAVARLSQTFPNADFAEIT<br>KLATDLTKVNKECCHGDLLECADDRAELAKYMCENQATISSKLQTCCDKPLLKKAH<br>CLSEVEHDTMPADLPAIAADFVEDQEVCKNYAEAKDVFLGTFLYEYSRRHPDYSVS<br>LLLRLAKKYEATLEKCCAEANPPACYGTVLAEFQPLVEEPKNLVKTNCDLYEKLGE<br>YGFQNAILVRYTQKAPQVSTPTLVEAARNLGRVGTKCCTLPEDQRLPCVEDYLSAI<br>LNRVCLLHEKTPVSEHVTKCCSGSLVERRPCFSALTVDETYVPKEFKAETFTFHSD<br>ICTLPEKEKQIKKQTALAELVKHKPKATAEQLKTVMDDFAQFLDTCCKAADKDTCF<br>STEGPNLVTRCKDALA*GGGS*RRGWHHHHHH |
| 140 | Lumican-MSA-WGRR | QYYDYDIPLFMYGQISPNCAPECNCPHSYPTAMYCDDLKLKSVPMVPPGIKYLYLR<br>NNQIDHIDEKAFENVTDLQWLILDHNLLENSKIKGKVFSKLKQLKKLHINYNNLTE<br>SVGPLPKSLQDLQLTNNKISKLGSFDGLVNLTFIYLQHNQLKEDAVSASLKGLKSL<br>EYLDLSFNQMSKLPAGLPTSLLTLYLDNNKISNIPDEYFKRFTGLQYLRLSHNELA<br>DSGVPGNSFNISSLLELDLSYNKLKSIPTVNENLENYYLEVNELEKFDVKSFCKIL<br>GPLSYSKIKHLRLDGNPLTQSSLPPDMYECLRVANEITVN*GGGSGGGS*EAHKSEIA<br>HRYNDLGEQHFKGLVLIAFSQYLQKCSYDEHAKLVQEVTDFAKTCVADESAANCDK<br>SLHTLFGDKLCAIPNLRENYGELADCCTKQEPERNECFLQHKDDNPSLPPFERPEA |

Summary Sequence Table

| SEQ ID NO | Description | Sequence |
|---|---|---|
| | | EAMCTSFKENPTTFMGHYLHEVARRHPYFYAPELLYYAEQYNEILTQCCAEADKES CLTPKLDGVKEKALVSSVRQRMKCSSMQKFGERAFKAWAVARLSQEFPNADFAEIT KLATDLTKVNKECCHGDLLECADDRAELAKYMCENQATISSKLQTCCDKPLLKKAH CLSEVEHDTMPADLPAIAADFVEDQEVCKNYAEAKDVFLGTFLYEYSRRHPDYSVS LLLRLAKKYEATLEKCCAEANPPACYGTVLAEFQPLVEEPKNLVKTNCDLYEKLGE YGFQNAILVRYTQKAPQVSTPTLVEAARNLGRVGTKCCTLPEDQRLPCVEDYLSAI LNRVCLLHEKTPVSEHVTKCCSGSLVERRPCFSALTVDETYVPKEFKAETFTFHSD ICTLPEKEKQIKKQTALAELVKHKPKATAEQLKTVMDDFAQFLDTCCKAADKDTCF STEGPNLVTRCKDALA*GGGS*WGRRHHHHHH |
| 141 | 4420 LC-murine kappa chain | DVVMTQTPLSLPVSLGDQASISCRSSQSLVHSNGNTYLRWYLQKPGQSPKVLIYKV SNRFSGVPDRFSGSGSGTDFTLKISRVEAEDLGVYFCSQSTHVPWTFGGGTKLEIKRADAAPTVSIFPPSSEQLTSGGASVVCFLNNFYPKDINVKWKIDGSERQNGVLNSW TDQDSKDSTYSMSSTLTLTKDEYERHNSYTCEATHKTSTSPIVKSFNRNEC |
| 142 | 4420 HC-Lumican (LALA-PG) | DVKLDETGGGLVQPGRPMKLSCVASGFTFSDYWMNWVRQSPEKGLEWVAQIRNKPY NYETYYSDSVKGRFTISRDDSKSSVYLQMNNLRVEDMGIYYCTGSYYGMDYWGQGT SVTVSAKTTAPSVYPLAPVCGGTTGSSVTLGCLVKGYFPEPVTLTWNSGSLSSGVH TFPALLQSGLYTLSSSVTVTSNTWPSQTITCNVAHPASSTKVDKKIEPRVPITQNP CPPLKECPPCAAPDAAGGPSVFIFPPKIKDVLMISLSPMVTCVVVDSEDDPDVQI SWFVNNVEVHTAQTQTHREDYNSTLRVVSALPIQHQDWMSGKEFKCKVNNRALGSP IEKTISKPRGPVRAPQVYVLPPPAEEMTKKEFSLTCMITGFLPAEIAVDWTSNGRT EQNYKNTATVLDSDGSYFMYSKLRVQKSTWERGSLFACSVVHEGLHNHLTTKTISR SLGK*GGGGSGGGGSGGGGS*QYYDYDIPLFMYGQISPNCAPECNCPHSYPTAMYCDD LKLKSVPMVPPGIKYLYLRNNQIDHIDEKAFENVTDLQWLILDHNLLENSKIKGKV FSKLKQLKKLHINYNNLTESVGPLPKSLQDLQLTNNKISKLGSFDGLVNLTFIYLQ HNQLKEDAVSASLKGLKSLEYLDLSFNQMSKLPAGLPTSLLTLYLDNNKISNIPDE YFKRFTGLQYLRLSHNELADSGVPGNSFNISSLLELDLSYNKLKSIPTVNENLENY YLEVNELEKFDVKSFCKILGPLSYSKIKHLRLDGNPLTQSSLPPDMYECLRVANEI TVN |
| 143 | 4220 HC-mIgG2c | DVKLDETGGGLVQPGRPMKLSCVASGFTFSDYWMNWVRQSPEKGLEWVAQIRNKPY NYETYYSDSVKGRFTISRDDSKSSVYLQMNNLRVEDMGIYYCTGSYYGMDYWGQGT SVTVSAKTTAPSVYPLAPVCGGTTGSSVTLGCLVKGYFPEPVTLTWNSGSLSSGVH TFPALLQSGLYTLSSSVTVTSNTWPSQTITCNVAHPASSTKVDKKIEPRVPITQNP CPPLKECPPCAAPDAAGGPSVFIFPPKIKDVLMISLSPMVTCVVVDSEDDPDVQI SWFVNNVEVHTAQTQTHREDYNSTLRVVSALPIQHQDWMSGKEFKCKVNNRALGSP IEKTISKPRGPVRAPQVYVLPPPAEEMTKKEFSLTCMITGFLPAEIAVDWTSNGRT EQNYKNTATVLDSDGSYFMYSKLRVQKSTWERGSLFACSVVHEGLHNHLTTKTISR SLGK |
| 144 | 3/23 LC-murine kappa | METDTLLLWVLLLWVPGSTGDTVLTQSPALAVSPGERVTISCRASESVSTRMHWYQ QRPGQPPKLLIYVASRLESGVPARFS*GGGS*GTDFTLTIDPVEANDTATYFCQQSWN DPWTFGGGTKLELKRADAAPTVSIFPPSSEQLTSGGASVVCFLNNFYPKDINVKWK IDGSERQNGVLNSWTDQDSKDSTYSMSSTLTLTKDEYERHNSYTCEATHKTSTSPI VKSFNRNEC |
| 145 | 3/23 HC-lumican | MDIWLSLVFLVLFIKGVQCEVQLVESGGGLVQPGRSLKLSCAASGFTLSDYYMAWV RQAPKKGLEWVASINYEGSSTYYGESVKGRFTISRDNAKSTLYLQMNSLRSEDTAT YYCVRHDNYFDYWGQGVLVTVSSAKTTAPSVYPLAPVCGGTTGSSVTLGCLVKGYF PEPVTLTWNSGSLSSGVHTFPALLQSGLYTLSSSVTVTSNTWPSQTITCNVAHPAS STKVDKKIEPRVPITQNPCPPLKECPPCAAPDAAGGPSVFIFPPKIKDVLMISLSP MVTCVVVDSEDDPDVQISWFVNNVEVHTAQTQTHREDYNSTLRVVSALPIQHQDW MSGKEFKCKVNNRALGSPIEKTISKPRGPVRAPQVYVLPPPAEEMTKKEFSLTCMI TGFLPAEIAVDWTSNGRTEQNYKNTATVLDSDGSYFMYSKLRVQKSTWERGSLFAC SVVHEGLHNHLTTKTISRSLGK*GGGGSGGGGSGGGGS*QYYDYDIPLFMYGQISPNC APECNCPHSYPTAMYCDDLKLKSVPMVPPGIKYLYLRNNQIDHIDEKAFENVTDLQ WLILDHNLLENSKIKGKVFSKLKQLKKLHINYNNLTESVGPLPKSLQDLQLTNNKI SKLGSFDGLVNLTFIYLQHNQLKEDAVSASLKGLKSLEYLDLSFNQMSKLPAGLPT SLLTLYLDNNKISNIPDEYFKRFTGLQYLRLSHNELADSGVPGNSFNISSLLELDL SYNKLKSIPTVNENLENYYLEVNELEKFDVKSFCKILGPLSYSKIKHLRLDGNPLT QSSLPPDMYECLRVANEITVN |

Summary Sequence Table

| SEQ ID NO | Description | Sequence |
|---|---|---|
| 146 | LOB12.3 LC-murine kappa | DIQMTQSPASLSASLEEIVTITCQASQDIGNWLAWYHQKPGKSPQLLIYGSTSLAD GVPSRFSGSSSGSQYSLKISRLQVEDIGIYYCLQAYGAPWTFGGGTKLELKRADAA PTVSIFPPSSEQLTSGGASVVCFLNNFYPKDINVKWKIDGSERQNGVLNSWTDQDS KDSTYSMSSTLTLTKDEYERHNSYTCEATHKTSTSPIVKSFNRNEC |
| 147 | LOB12.3 HC-Lumican | DVQLVESGGGLVQPGRSLKLSCAASGFIFSYFDMAWVRQAPTKGLEWVASISPDGS IPYYRDSVKGRFTVSRENAKSSLYLQMDSLRSEDTATYYCARRSYGGYSEIDYWGQ GVMVTVSSAKTTAPSVYPLAPVCGGTTGSSVTLGCLVKGYFPEPVTLTWNSGSLSS GVHTFPALLQSGLYTLSSSVTVTSNTWPSQTITCNVAHPASSTKVDKKIEPRVPIT QNPCPPLKECPPCAAPDAAGGPSVFIFPPKIKDVLMISLSPMVTCVVVDVSEDDPD VQISWFVNNVEVHTAQTQTHREDYNSTLRVVSALPIQHQDWMSGKEFKCKVNNRALG SPIEKTISKPRGPVRAPQVYVLPPPAEEMTKKEFSLTCMITGFLPAEIAVDWTSN GRTEQNYKNTATVLDSDGSYFMYSKLRVQKSTWERGSLFACSVVHEGLHNHLTTKT ISRSLGK*GGGGSGGGGSGGGGS*QYYDYDIPLFMYGQISPNCAPECNCPHSYPTAMY CDDLKLKSVPMVPPGIKYLYLRNNQIDHIDEKAFENVTDLQWLILDHNLLENSKIK GKVFSKLKQLKKLHINYNNLTESVGPLPKSLQDLQLTNNKISKLGSFDGLVNLTFI YLQHNQLKEDAVSASLKGLKSLEYLDLSFNQMSKLPAGLPTSLLTLYLDNNKISNI PDEYFKRFTGLQYLRLSHNELADSGVPGNSFNISSLLELDLSYNKLKSIPTVNENL ENYYLEVNELEKFDVKSFCKILGPLSYSKIKHLRLDGNPLTQSSLPPDMYECLRVA NEITVN |
| 148 | OX86 LC-murine kappa | DIVMTQGALPNPVPSGESASITCRSSQSLVYKDGQTYLNWFLQRPGQSPQLLTYWM STRASGVSDRFSGSGSGTYFTLKISRVRAEDAGVYYCQQVREYPFTFGSGTKLEIKRADAAPTVSIFPPSSEQLTSGGASVVCFLNNFYPKDINVKWKIDGSERQNGVLNSW TDQDSKDSTYSMSSTLTLTKDEYERHNSYTCEATHKTSTSPIVKSFNRNEC |
| 149 | OX86 HC-Lumican | QVQLKESGPGLVQPSQTLSLTCTVSGFSLTGYNLHWVRQPPGKGLEWMGRMRYDGD TYYNSVLKSRLSISRDTSKNQVFLKMNSLQTDDTAIYYCTRDGRGDSFDYWGQGVM VTVSSAKTTAPSVYPLAPVCGGTTGSSVTLGCLVKGYFPEPVTLTWNSGSLSSGVH TFPALLQSGLYTLSSSVTVTSNTWPSQTITCNVAHPASSTKVDKKIEPRVPITQNP CPPLKECPPCAAPDAAGGPSVFIFPPKIKDVLMISLSPMVTCVVVDVSEDDPDVQI SWFVNNVEVHTAQTQTHREDYNSTLRVVSALPIQHQDWMSGKEFKCKVNNRALGSP IEKTISKPRGPVRAPQVYVLPPPAEEMTKKEFSLTCMITGFLPAEIAVDWTSNGRT EQNYKNTATVLDSDGSYFMYSKLRVQKSTWERGSLFACSVVHEGLHNHLTTKTISR SLGK*GGGGSGGGGSGGGGS*QYYDYDIPLFMYGQISPNCAPECNCPHSYPTAMYCDD LKLKSVPMVPPGIKYLYLRNNQIDHIDEKAFENVTDLQWLILDHNLLENSKIKGKV FSKLKQLKKLHINYNNLTESVGPLPKSLQDLQLTNNKISKLGSFDGLVNLTFIYLQ HNQLKEDAVSASLKGLKSLEYLDLSFNQMSKLPAGLPTSLLTLYLDNNKISNIPDE YFKRFTGLQYLRLSHNELADSGVPGNSFNISSLLELDLSYNKLKSIPTVNENLENY YLEVNELEKFDVKSFCKILGPLSYSKIKHLRLDGNPLTQSSLPPDMYECLRVANEI TVN |
| 150 | 2C11 LC-murine kappa | DIQMTQSPSSLPASLGDRVTINCQASQDISNYLNWYQQKPGKAPKLLIYYTNKLAD GVPSRFSGSGSGRDSSFTISSLESEDIGSYYCQQYYNYPWTFGPGTKLEIKRADA APTVSIFPPSSEQLTSGGASVVCFLNNFYPKDINVKWKIDGSERQNGVLNSWTDQD SKDSTYSMSSTLTLTKDEYERHNSYTCEATHKTSTSPIVKSFNRNEC |
| 151 | 2C11 HC-lumican | EVQLVESGGGLVQPGKSLKLSCEASGFTFSGYGMHWVRQAPGRGLESVAYITSSSI NIKYADAVKGRFTVSRDNAKNLLFLQMNILKSEDTAMYYCARFDWDKNYWGQGTMV TVSSAKTTAPSVYPLAPVCGGTTGSSVTLGCLVKGYFPEPVTLTWNSGSLSSGVHT FPALLQSGLYTLSSSVTVTSNTWPSQTITCNVAHPASSTKVDKKIEPRVPITQNPC PPLKECPPCAAPDAAGGPSVFIFPPKIKDVLMISLSPMVTCVVVDVSEDDPDVQIS WFVNNVEVHTAQTQTHREDYNSTLRVVSALPIQHQDWMSGKEFKCKVNNRALGSPI EKTISKPRGPVRAPQVYVLPPPAEEMTKKEFSLTCMITGFLPAEIAVDWTSNGRTE QNYKNTATVLDSDGSYFMYSKLRVQKSTWERGSLFACSVVHEGLHNHLTTKTISRS LGK*GGGGSGGGGSGGGGS*QYYDYDIPLFMYGQISPNCAPECNCPHSYPTAMYCDDL KLKSVPMVPPGIKYLYLRNNQIDHIDEKAFENVTDLQWLILDHNLLENSKIKGKVF SKLKQLKKLHINYNNLTESVGPLPKSLQDLQLTNNKISKLGSFDGLVNLTFIYLQH |

Summary Sequence Table

| SEQ ID NO | Description | Sequence |
|---|---|---|
| | | NQLKEDAVSASLKGLKSLEYLDLSFNQMSKLPAGLPTSLLTLYLDNNKISNIPDEY |
| | | FKRFTGLQYLRLSHNELADSGVPGNSFNISSLLELDLSYNKLKSIPTVNENLENYY |
| | | LEVNELEKFDVKSFCKILGPLSYSKIKHLRLDGNPLTQSSLPPDMYECLRVANEIT |
| | | VN |
| 152 | T2A peptide (furin cleavage site-GSG-T2A) | RRKRGSGEGRGSLLTCGDVEENPGP |
| 153 | CCL3-Lumican | APYGADTPTACCFSYSRKIPRQFIVDYFETSSLCSQPGVIFLTKRNRQICADSKET WVQEYITDLELNAGGGSGGGSGGGSQYYDYDIPLFMYGQISPNCAPECNCPHSYPT AMYCDDLKLKSVPMVPPGIKYLYLRNNQIDHIDEKAFENVTDLQWLILDHNLLENS KIKGKVFSKLKQLKKLHINYNNLTESVGPLPKSLQDLQLTNNKISKLGSFDGLVNL TFIYLQHNQLKEDAVSASLKGLKSLEYLDLSFNQMSKLPAGLPTSLLTLYLDNNKI SNIPDEYFKRFTGLQYLRLSHNELADSGVPGNSFNISSLLELDLSYNKLKSIPTVN ENLENYYLEVNELEKFDVKSFCKILGPLSYSKIKHLRLDGNPLTQSSLPPDMYECL RVANEITVNGGGSHHHHHH |
| 154 | Lumican-CCL3 | QYYDYDIPLFMYGQISPNCAPECNCPHSYPTAMYCDDLKLKSVPMVPPGIKYLYLR NNQIDHIDEKAFENVTDLQWLILDHNLLENSKIKGKVFSKLKQLKKLHINYNNLTE SVGPLPKSLQDLQLTNNKISKLGSFDGLVNLTFIYLQHNQLKEDAVSASLKGLKSL EYLDLSFNQMSKLPAGLPTSLLTLYLDNNKISNIPDEYFKRFTGLQYLRLSHNELA DSGVPGNSFNISSLLELDLSYNKLKSIPTVNENLENYYLEVNELEKFDVKSFCKIL GPLSYSKIKHLRLDGNPLTQSSLPPDMYECLRVANEITVNGGGSGGGSGGGSAPYG ADTPTACCFSYSRKIPRQFIVDYFETSSLCSQPGVIFLTKRNRQICADSKETWVQE YITDLELNAGGGSHHHHHH |
| 155 | CCL3 | APYGADTPTACCFSYSRKIPRQFIVDYFETSSLCSQPGVIFLTKRNRQICADSKET WVQEYITDLELNAGGGSHHHHHH |
| 156 | CCL4-lumican | APMGSDPPTSCCFSYTSRQLHRSFVMDYYETSSLCSKPAVVFLTKRGRQICANPSE PWVTEYMSDLELNGGGSGGGSGGGSQYYDYDIPLFMYGQISPNCAPECNCPHSYPT AMYCDDLKLKSVPMVPPGIKYLYLRNNQIDHIDEKAFENVTDLQWLILDHNLLENS KIKGKVFSKLKQLKKLHINYNNLTESVGPLPKSLQDLQLTNNKISKLGSFDGLVNL TFIYLQHNQLKEDAVSASLKGLKSLEYLDLSFNQMSKLPAGLPTSLLTLYLDNNKI SNIPDEYFKRFTGLQYLRLSHNELADSGVPGNSFNISSLLELDLSYNKLKSIPTVN ENLENYYLEVNELEKFDVKSFCKILGPLSYSKIKHLRLDGNPLTQSSLPPDMYECL RVANEITVNGGGSHHHHHH |
| 157 | Lumican-CCL4 | QYYDYDIPLFMYGQISPNCAPECNCPHSYPTAMYCDDLKLKSVPMVPPGIKYLYLR NNQIDHIDEKAFENVTDLQWLILDHNLLENSKIKGKVFSKLKQLKKLHINYNNLTE SVGPLPKSLQDLQLTNNKISKLGSFDGLVNLTFIYLQHNQLKEDAVSASLKGLKSL EYLDLSFNQMSKLPAGLPTSLLTLYLDNNKISNIPDEYFKRFTGLQYLRLSHNELA DSGVPGNSFNISSLLELDLSYNKLKSIPTVNENLENYYLEVNELEKFDVKSFCKIL GPLSYSKIKHLRLDGNPLTQSSLPPDMYECLRVANEITVNGGGSGGGSGGGSAPMG SDPPTSCCFSYTSRQLHRSFVMDYYETSSLCSKPAVVFLTKRGRQICANPSEPWVT EYMSDLELNGGGSHHHHHH |
| 158 | CCL4 | APMGSDPPTSCCFSYTSRQLHRSFVMDYYETSSLCSKPAVVFLTKRGRQICANPSE PWVTEYMSDLELNGGGSHHHHHH |
| 159 | CCL5-lumican | SPYGSDTTPCCFAYLSLALPRAHVKEYFYTSSKCSNLAVVFVTRRNRQVCANPEKK WVQEYINYLEMSGGGSGGGSGGGSQYYDYDIPLFMYGQISPNCAPECNCPHSYPTA MYCDDLKLKSVPMVPPGIKYLYLRNNQIDHIDEKAFENVTDLQWLILDHNLLENSK IKGKVFSKLKQLKKLHINYNNLTESVGPLPKSLQDLQLTNNKISKLGSFDGLVNLT FIYLQHNQLKEDAVSASLKGLKSLEYLDLSFNQMSKLPAGLPTSLLTLYLDNNKIS NIPDEYFKRFTGLQYLRLSHNELADSGVPGNSFNISSLLELDLSYNKLKSIPTVNE NLENYYLEVNELEKFDVKSFCKILGPLSYSKIKHLRLDGNPLTQSSLPPDMYECLR VANEITVNGGGSHHHHHH |
| 160 | Lumican-CCL5 | QYYDYDIPLFMYGQISPNCAPECNCPHSYPTAMYCDDLKLKSVPMVPPGIKYLYLR NNQIPHIDEKAFENVTDLQWLILDHNLLENSKIKGKVFSKLKQLKKLHINYNNLTE SVGPLPKSLQDLQLTNNKISKLGSFDGLVNLTFIYLQHNQLKEDAVSASLKGLKSL EYLDLSFNQMSKLPAGLPTSLLTLYLDNNKISNIPDEYFKRFTGLQYLRLSHNELA DSGVPGNSFNISSLLELDLSYNKLKSIPTVNENLENYYLEVNELEKFDVKSFCKIL GPLSYSKIKHLRLDGNPLTQSSLPPDMYECLRVANEITVNGGGSGGGSGGGSSPYG SDTTPCCFAYLSLALPRAHVKEYFYTSSKCSNLAVVFVTRRNRQVCANPEKKWVQE YINYLEMSGGGSHHHHHH |

-continued

Summary Sequence Table

| SEQ ID NO | Description | Sequence |
|---|---|---|
| 161 | CCL5 | SPYGSDTTPCCFAYLSLALPRAHVKEYFYTSSKCSNLAWFVTRRNRQVCANPEKK WVQEYINYLEMS*GGGS*HHHHHH |
| 162 | CCL19-Lumican | GANDAEDCCLSVTQRPIPGNIVKAFRYLLNEDGCRVPAVVFTTLRGYQLCAPPDQP WVDRIIRRLKKSSAKNKGNSTRRSPVS*GGGSGGGSGGGS*QYYDYDIPLFMYGQISP NCAPECNCPHSYPTAMYCDDLKLKSVPMVPPGIKYLYLRNNQIDHIDEKAFENVTD LQWLILDHNLLENSKIKGKVFSKLKQLKKLHINYNNLTESVGPLPKSLQDLQLTNN KISKLGSFDGLVNLTFIYLQHNQLKEDAVSASLKGLKSLEYLDLSFNQMSKLPAGL PTSLLTLYLDNNKISNIPDEYFKRFTGLQYLRLSHNELADSGVPGNSFNISSLLEL DLSYNKLKSIPTVNENLENYYLEVNELEKFDVKSFCKILGPLSYSKIKHLRLDGNP LTQSSLPPDMYECLRVANEITVN*GGGS*HHHHHH |
| 163 | Lumican-CCL19 | QYYDYDIPLFMYGQISPNCAPECNCPHSYPTAMYCDDLKLKSVPMVPPGIKYLYLR NNQIPHIDEKAFENVTDLQWLILDHNLLENSKIKGKVFSKLKQLKKLHINYNNLTE SVGPLPKSLQDLQLTNNKISKLGSFDGLVNLTFIYLQHNQLKEDAVSASLKGLKSL EYLDLSFNQMSKLPAGLPTSLLTLYLDNNKISNIPDEYFKRFTGLQYLRLSHNELA DSGVPGNSFNISSLLELDLSYNKLKSIPTVNENLENYYLEVNELEKFDVKSFCKIL GPLSYSKIKHLRLDGNPLTQSSLPPDMYECLRVANEITVN*GGGSGGGSGGG*GANDA EDCCLSVTQRPIPGNIVKAFRYLLNEDGCRVPAVVFTTLRGYQLCAPPDQPWVDRI IRRLKKSSAKNKGNSTRRSPVS*GGGS*HHHHHH |
| 164 | CCL19 | GANDAEDCCLSVTQRPIPGNIVKAFRYLLNEDGCRVPAVVFTTLRGYQLCAPPDQP WVDRIIRRLKKSSAKNKGNSTRRSPVS*GGGS*HHHHHH |
| 165 | CCL21c-Lumican | SDGGGQDCCLKYSQKKIPYSIVRGYRKQEPSLGCPIPAILFLPRKHSKPELCANPE EGWVQNLMRRLDQPPAPGKQSPGCRKNRGTSKSGKKGKGSKGCKRTEQTQPSRG*GG GSGGGSGGGS*QYYDYDIPLFMYGQISPNCAPECNCPHSYPTAMYCDDLKLKSVPMV PPGIKYLYLRNNQIDHIDEKAFENVTDLQWLILDHNLLENSKIKGKVFSKLKQLKK LHINYNNLTESVGPLPKSLQDLQLTNNKISKLGSFDGLVNLTFIYLQHNQLKEDAV SASLKGLKSLEYLDLSFNQMSKLPAGLPTSLLTLYLDNNKISNIPDEYFKRFTGLQ YLRLSHNELADSGVPGNSFNISSLLELDLSYNKLKSIPTVNENLENYYLEVNELEK FDVKSFCKILGPLSYSKIKHLRLDGNPLTQSSLPPDMYECLRVANEITVN*GGGS*HH HHHH |
| 166 | Lumican-CCL21c | QYYDYDIPLFMYGQISPNCAPECNCPHSYPTAMYCDDLKLKSVPMVPPGIKYLYLR NNQIPHIDEKAFENVTDLQWLILDHNLLENSKIKGKVFSKLKQLKKLHINYNNLTE SVGPLPKSLQDLQLTNNKISKLGSFDGLVNLTFIYLQHNQLKEDAVSASLKGLKSL EYLDLSFNQMSKLPAGLPTSLLTLYLDNNKISNIPDEYFKRFTGLQYLRLSHNELA DSGVPGNSFNISSLLELDLSYNKLKSIPTVNENLENYYLEVNELEKFDVKSFCKIL GPLSYSKIKHLRLDGNPLTQSSLPPDMYECLRVANEITVN*GGGSGGGSGGG*SDGGG QDCCLKYSQKKIPYSIVRGYRKQEPSLGCPIPAILFLPRKHSKPELCANPEEGWVQ NLMRRLDQPPAPGKQSPGCRKNRGTSKSGKKGKGSKGCKRTEQTQPSRG*GGGS*HHH HHH |
| 167 | CCL21c | SDGGGQDCCLKYSQKKIPYSIVRGYRKQEPSLGCPIPAILFLPRKHSKPELCANPE EGWVQNLMRRLDQPPAPGKQSPGCRKNRGTSKSGKKGKGSKGCKRTEQTQPSRG*GG GS*HHHHHH |
| 168 | truncated CCL21c-Lumican | SDGGGQDCCLKYSQKKIPYSIVRGYRKQEPSLGCPIPAILFLPRKHSKPELCANPE EGWVQNLMRRLDQPPAPGK*GGGSGGGSGGGS*QYYDYDIPLFMYGQISPNCAPECNC PHSYPTAMYCDDLKLKSVPMVPPGIKYLYLRNNQIDHIDEKAFENVTDLQWLILDH NLLENSKIKGKVFSKLKQLKKLHINYNNLTESVGPLPKSLQDLQLTNNKISKLGSF DGLVNLTFIYLQHNQLKEDAVSASLKGLKSLEYLDLSFNQMSKLPAGLPTSLLTLY LDNNKISNIPDEYFKRFTGLQYLRLSHNELADSGVPGNSFNISSLLELDLSYNKLK SIPTVNENLENYYLEVNELEKFDVKSFCKILGPLSYSKIKHLRLDGNPLTQSSLPP DMYECLRVANEITVN*GGGS*HHHHHH |
| 169 | Lumican-truncated CCL21c | QYYDYDIPLFMYGQISPNCAPECNCPHSYPTAMYCDDLKLKSVPMVPPGIKYLYLR NNQIPHIDEKAFENVTDLQWLILDHNLLENSKIKGKVFSKLKQLKKLHINYNNLTE SVGPLPKSLQDLQLTNNKISKLGSFDGLVNLTFIYLQHNQLKEDAVSASLKGLKSL EYLDLSFNQMSKLPAGLPTSLLTLYLDNNKISNIPDEYFKRFTGLQYLRLSHNELA DSGVPGNSFNISSLLELDLSYNKLKSIPTVNENLENYYLEVNELEKFDVKSFCKIL GPLSYSKIKHLRLDGNPLTQSSLPPDMYECLRVANEITVN*GGGSGGGSGGGS*SDGG GQDCCLKYSQKKIPYSIVRGYRKQEPSLGCPIPAILFLPRKHSKPELCANPEEGWV QNLMRRLDQPPAPGK*GGGS*HHHHHH |
| 170 | truncated CCL21c | SDGGGQDCCLKYSQKKIPYSIVRGYRKQEPSLGCPIPAILFLPRKHSKPELCANPE EGWVQNLMRRLDQPPAPGK*GGGS*HHHHHH |
| 171 | CCL11 | HPGSIPTSCCFIMTSKKIPNTLLKSYKRITNNRCTLKAIVFKTRLGKEICADPKKK WVQDATKHLDQKLQTPKP*GGGS*HHHHHH |

Summary Sequence Table

| SEQ ID NO | Description | Sequence |
|---|---|---|
| 172 | CCL11-Lumican | HPGSIPTSCCFIMTSKKIPNTLLKSYKRITNNRCTLKAIVFKTRLGKEICADPKKK WVQDATKHLDQKLQTPKP_GGGSGGGSGGGS_QYYDYDIPLFMYGQISPNCAPECNCP HSYPTAMYCDDLKLKSVPMVPPGIKYLYLRNNQIDHIDEKAFENVTDLQWLILDHN LLENSKIKGKVFSKLKQLKKLHINYNNLTESVGPLPKSLQDLQLTNNKISKLGSFD GLVNLTFIYLQHNQLKEDAVSASLKGLKSLEYLDLSFNQMSKLPAGLPTSLLTLYL DNNKISNIPDEYFKRFTGLQYLRLSHNELADSGVPGNSFNISSLLELDLSYNKLKS IPTVNENLENYYLEVNELEKFDVKSFCKILGPLSYSKIKHLRLDGNPLTQSSLPPD MYECLRVANEITVN_GGGS_HHHHHH |
| 173 | CLEC2-MSA-lumican | QQKYLLAEKENLSATLQQLAKKFCQELIRQSEIKTKSTFEHKCSPCATKWRYHGDS CYGFFRRNLTWEESKQYCTEQNATLVKTASQSTLDYIAERITSVRWIGLSRQNSKK DWMWEDSSVLRKNGINLSGNTEENMNCAYLHNGKIHPASCKERHYLICERNAGMTR VDQLL_GGGGGGGGGGGGS_EAHKSEIAHRYNDLGEQHFKGLVLIAFSQYLQKCSYDEH AKLVQEVTDFAKTCVADESAANCDKSLHTLFGDKLCAIPNLRENYGELADCCTKQE PERNECFLQHKDDNPSLPPFERPEAEAMCTSFKENPTTFMGHYLHEVARRHPYFYA PELLYYAEQYNEILTQCCAEADKESCLTPKLDGVKEKALVSSVRQRMKCSSMQKFG ERAFKAWAVARLSQTFPNADFAEITKLATDLTKVNKECCHGDLLECADDRAELAKY MCENQATISSKLQTCCDKPLLKKAHCLSEVEHDTMPADLPAIAADFVEDQEVCKNY AEAKDVFLGTFLYEYSRRHPDYSVSLLLRLAKKYEATLEKCCAEANPPACYGTVLA EFQPLVEEPKNLVKTNCDLYEKLGEYGFQNAILVRYTQKAPQVSTPTLVEAARNLG RVGTKCCTLPEDQRLPCVEDYLSAILNRVCLLHEKTPVSEHVTKCCSGSLVERRPC FSALTVDETYVPKEFKAETFTFHSDICTLPEKEKQIKKQTALAELVKHKPKATAEQ LKTVMDDFAQFLDTCCKAADKDTCFSTEGPNLVTRCKDALA_GGGSGGGS_QYYDYDI PLFMYGQISPNCAPECNCPHSYPTAMYCDDLKLKSVPMVPPGIKYLYLRNNQIDHI DEKAFENVTDLQWLILDHNLLENSKIKGKVFSKLKQLKKLHINYNNLTESVGPLPK SLQDLQLTNNKISKLGSFDGLVNLTFIYLQHNQLKEDAVSASLKGLKSLEYLDLSF NQMSKLPAGLPTSLLTLYLDNNKISNIPDEYFKRFTGLQYLRLSHNELADSGVPGN SFNISSLLELDLSYNKLKSIPTVNENLENYYLEVNELEKFDVKSFCKILGPLSYSK IKHLRLDGNPLTQSSLPPDMYECLRVANEITVN_GGGS_HHHHHH |
| 174 | CLEC2-MSA | QQKYLLAEKENLSATLQQLAKKFCQELIRQSEIKTKSTFEHKCSPCATKWRYHGDS CYGFFRRNLTWEESKQYCTEQNATLVKTASQSTLDYIAERITSVRWIGLSRQNSKK DWMWEDSSVLRKNGINLSGNTEENMNCAYLHNGKIHPASCKERHYLICERNAGMTR VDQLL_GGGSGGGSGGGS_EAHKSEIAHRYNDLGEQHFKGLVLIAFSQYLQKCSYDEH AKLVQEVTDFAKTCVADESAANCDKSLHTLFGDKLCAIPNLRENYGELADCCTKQE PERNECFLQHKDDNPSLPPFERPEAEAMCTSFKENPTTFMGHYLHEVARRHPYFYA PELLYYAEQYNEILTQCCAEADKESCLTPKLDGVKEKALVSSVRQRMKCSSMQKFG ERAFKAWAVARLSQTFPNADFAEITKLATDLTKVNKECCHGDLLECADDRAELAKY MCENQATISSKLQTCCDKPLLKKAHCLSEVEHDTMPADLPAIAADFVEDQEVCKNY AEAKDVFLGTFLYEYSRRHPDYSVSLLLRLAKKYEATLEKCCAEANPPACYGTVLA EFQPLVEEPKNLVKTNCDLYEKLGEYGFQNAILVRYTQKAPQVSTPTLVEAARNLG RVGTKCCTLPEDQRLPCVEDYLSAILNRVCLLHEKTPVSEHVTKCCSGSLVERRPC FSALTVDETYVPKEFKAETFTFHSDICTLPEKEKQIKKQTALAELVKHKPKATAEQ LKTVMDDFAQFLDTCCKAADKDTCFSTEGPNLVTRCKDALAHHHHHH |
| 175 | IFNg-MSA-lumican | HGTVIESLESLNNYFNSSGIDVEEKSLFLDIWRNWQKDGDMKILQSQIISFYLRLF EVLKDNQAISNNISVIESHLITTFFSNSKAKKDAFMSIAKFEVNNPQVQRQAFNEL IRVVHQLLPESSLRKRKRSRC_GSGGGS_EAHKSEIAHRYNDLGEQHFKGLVLIAFSQ YLQKCSYDEHAKLVQEVTDFAKTCVADESAANCDKSLHTLFGDKLCAIPNLRENYG ELADCCTKQEPERNECFLQHKDDNPSLPPFERPEAEAMCTSFKENPTTFMGHYLHE VARRHPYFYAPELLYYAEQYNEILTQCCAEADKESCLTPKLDGVKEKALVSSVRQR MKCSSMQKFGERAFKAWAVARLSQTFPNADFAEITKLATDLTKVNKECCHGDLLEC ADDRAELAKYMCENQATISSKLQTCCDKPLLKKAHCLSEVEHDTMPADLPAIAADF VEDQEVCKNYAEAKDVFLGTFLYEYSRRHPDYSVSLLLRLAKKYEATLEKCCAEAN PPACYGTVLAEFQPLVEEPKNLVKTNCDLYEKLGEYGFQNAILVRYTQKAPQVSTP TLVEAARNLGRVGTKCCTLPEDQRLPCVEDYLSAILNRVCLLHEKTPVSEHVTKCC SGSLVERRPCFSALTVDETYVPKEFKAETFTFHSDICTLPEKEKQIKKQTALAELV KHKPKATAEQLKTVMDDFAQFLDTCCKAADKDTCFSTEGPNLVTRCKDALA_GGGSG GGS_QYYDYDIPLFMYGQISPNCAPECNCPHSYPTAMYCDDLKLKSVPMVPPGIKYL YLRNNQIDHIDEKAFENVTDLQWLILDHNLLENSKIKGKVFSKLKQLKKLHINYNN |

Summary Sequence Table

| SEQ ID NO | Description | Sequence |
|---|---|---|
| | | LTESVGPLPKSLQDLQLTNNKISKLGSFDGLVNLTFIYLQHNQLKEDAVSASLKGL |
| | | KSLEYLDLSFNQMSKLPAGLPTSLLTLYLDNNKISNIPDEYFKRFTGLQYLRLSHN |
| | | ELADSGVPGNSFNISSLLELDLSYNKLKSIPTVNENLENYYLEVNELEKFDVKSFC |
| | | KILGPLSYSKIKHLRLDGNPLTQSSLPPDMYECLRVANEITVN*GGGS*HHHHHH |
| 176 | IFNg-IFNg-MSA-lumican | HGTVIESLESLNNYFNSSGIDVEEKSLFLDIWRNWQKDGDMKILQSQIISFYLRLF EVLKDNQAISNNISVIESHLITTFFSNSKAKKDAFMSIAKFEVNNPQVQRQAFNEL IRVVHQLLPESSLRKRKRSRC*GGGSGGGSGGGSGGGS*HGTVIESLESLNNYFNSSG IDVEEKSLFLDIWRNWQKDGDMKILQSQIISFYLRLFEVLKDNQAISNNISVIESH LITTFFSNSKAKKDAFMSIAKFEVNNPQVQRQAFNELIRVVHQLLPESSLRKRKRS RC*GSGGGS*EAHKSEIAHRYNDLGEQHFKGLVLIAFSQYLQKCSYDEHAKLVQEVTD FAKTCVADESAANCDKSLHTLFGDKLCAIPNLRENYGELADCCTKQEPERNECFLQ HKDDNPSLPPFERPEAEAMCTSFKENPTTFMGHYLHEVARRHPYFAPELLYYAEQ YNEILTQCCAEADKESCLTPKLDGVKEKALVSSVRQRMKCSSMQKFGERAFKAWAV ARLSQTFPNADFAEITKLATDLTKVNKECCHGDLLECADDRAELAKYMCENQATIS SKLQTCCDKPLLKKAHCLSEVEHDTMPADLPAIAADFVEDQEVCKNYAEAKDVFLG TFLYEYSRRHPDYSVSLLLRLAKKYEATLEKCCAEANPPACYGTVLAEFQPLVEEP KNLVKTNCDLYEKLGEYGFQNAILVRYTQKAPQVSTPTLVEAARNLGRVGTKCCTL PEDQRLPCVEDYLSAILNRVCLLHEKTPVSEHVTKCCSGSLVERRPCFSALTVDET YVPKEFKAETFTFHSDICTLPEKEKQIKKQTALAELVKHKPKATAEQLKTVMDDFA QFLDTCCKAADKDTCFSTEGPNLVTRCKDALA*GGGSGGGS*QYYDYDIPLFMYGQIS PNCAPECNCPHSYPTAMYCDDLKLKSVPMVPPGIKYLYLRNNQIDHIDEKAFENVT DLQWLILDHNLLENSKIKGKVFSKLKQLKKLHINYNNLTESVGPLPKSLQDLQLTN NKISKLGSFDGLVNLTFIYLQHNQLKEDAVSASLKGLKSLEYLDLSFNQMSKLPAG LPTSLLTLYLDNNKISNIPDEYFKRFTGLQYLRLSHNELADSGVPGNSFNISSLLE LDLSYNKLKSIPTVNENLENYYLEVNELEKFDVKSFCKILGPLSYSKIKHLRLDGN PLTQSSLPPDMYECLRVANEITVN*GGGS*HHHHHH |
| 177 | IFNg-IFNg-MSA | HGTVIESLESLNNYFNSSGIDVEEKSLFLDIWRNWQKDGDMKILQSQIISFYLRLF EVLKDNQAISNNISVIESHLITTFFSNSKAKKDAFMSIAKFEVNNPQVQRQAFNEL IRVVHQLLPESSLRKRKRSRC*GGGSGGGSGGGSGGGS*HGTVIESLESLNNYFNSSG IDVEEKSLFLDIWRNWQKDGDMKILQSQIISFYLRLFEVLKDNQAISNNISVIESH LITTFFSNSKAKKDAFMSIAKFEVNNPQVQRQAFNELIRVVHQLLPESSLRKRKRS RC*GSGGGS*EAHKSEIAHRYNDLGEQHFKGLVLIAFSQYLQKCSYDEHAKLVQEVTD FAKTCVADESAANCDKSLHTLFGDKLCAIPNLRENYGELADCCTKQEPERNECFLQ HKDDNPSLPPFERPEAEAMCTSFKENPTTFMGHYLHEVARRHPYFAPELLYYAEQ YNEILTQCCAEADKESCLTPKLDGVKEKALVSSVRQRMKCSSMQKFGERAFKAWAV ARLSQTFPNADFAEITKLATDLTKVNKECCHGDLLECADDRAELAKYMCENQATIS SKLQTCCDKPLLKKAHCLSEVEHDTMPADLPAIAADFVEDQEVCKNYAEAKDVFLG TFLYEYSRRHPDYSVSLLLRLAKKYEATLEKCCAEANPPACYGTVLAEFQPLVEEP KNLVKTNCDLYEKLGEYGFQNAILVRYTQKAPQVSTPTLVEAARNLGRVGTKCCTL PEDQRLPCVEDYLSAILNRVCLLHEKTPVSEHVTKCCSGSLVERRPCFSALTVDET YVPKEFKAETFTFHSDICTLPEKEKQIKKQTALAELVKHKPKATAEQLKTVMDDFA QFLDTCCKAADKDTCFSTEGPNLVTRCKDALAHHHHHH |
| 178 | Lumican-MSA-IFNg | QYYDYDIPLFMYGQISPNCAPECNCPHSYPTAMYCDDLKLKSVPMVPPGIKYLYLR NNQIDHIDEKAFENVTDLQWLILDHNLLENSKIKGKVFSKLKQLKKLHINYNNLTE SVGPLPKSLQDLQLTNNKISKLGSFDGLVNLTFIYLQHNQLKEDAVSASLKGLKSL EYLDLSFNQMSKLPAGLPTSLLTLYLDNNKISNIPDEYFKRFTGLQYLRLSHNELA DSGVPGNSFNISSLLELDLSYNKLKSIPTVNENLENYYLEVNELEKFDVKSFCKIL GPLSYSKIKHLRLDGNPLTQSSLPPDMYECLRVANEITVN*GGGSGGS*EAHKSEIA HRYNDLGEQHFKGLVLIAFSQYLQKCSYDEHAKLVQEVTDFAKTCVADESAANCDK SLHTLFGDKLCAIPNLRENYGELADCCTKQEPERNECFLQHKDDNPSLPPFERPEA EAMCTSFKENPTTFMGHYLHEVARRHPYFAPELLYYAEQYNEILTQCCAEADKES CLTPKLDGVKEKALVSSVRQRMKCSSMQKFGERAFKAWAVARLSQTFPNADFAEIT KLATDLTKVNKECCHGDLLECADDRAELAKYMCENQATISSKLQTCCDKPLLKKAH CLSEVEHDTMPADLPAIAADFVEDQEVCKNYAEAKDVFLGTFLYEYSRRHPDYSVS LLLRLAKKYEATLEKCCAEANPPACYGTVLAEFQPLVEEPKNLVKTNCDLYEKLGE YGFQNAILVRYTQKAPQVSTPTLVEAARNLGRVGTKCCTLPKDQRLPCVEDYLSAI |

-continued

Summary Sequence Table

| SEQ ID NO | Description | Sequence |
|---|---|---|
| | | LNRVCLLHEKTPVSEHVTKCCSGSLVERRPCFSALTVDETYVPKEFKAETFTFHSD ICTLPEKEKQIKKQTALAELVKHKPKATAEQLKTVMDDFAQFLDTCCKAADKDTCF STEGPNLVTRCKDALA*GGGS*HGTVIESLESLNNYFNSSGIDVEEKSLFLDIWRNWQ KDGDMKILQSQIISFYLRLFEVLKDNQAISNNISVIESHLITTFFSNSKAKKDAFM SIAKFEVNNPQVQRQAFNELIRWHQLLPESSLRKRKRSRCHHHHHH |
| 179 | Lumican-MSA-IFNg-IFNg | QYYDYDIPLFMYGQISPNCAPECNCPHSYPTAMYCDDLKLKSVPMVPPGIKYLYLR NNQIDHIDEKAFENVTDLQWLILDHNLLENSKIKGKVFSKLKQLKKLHINYNNLTE SVGPLPKSLQDLQLTNNKISKLGSFDGLVNLTFIYLQHNQLKEDAVSASLKGLKSL EYLDLSFNQMSKLPAGLPTSLLTLYLDNNKISNIPDEYFKRFTGLQYLRLSHNELA DSGVPGNSFNISSLLELDLSYNKLKSIPTVNENLENYYLEVNELEKFDVKSFCKIL GPLSYSKIKHLRLDGNPLTQSSLPPDMYECLRVANEITVN*GGGSGGGS*EAHKSEIA HRYNDLGEQHFKGLVLIAFSQYLQKCSYDEHAKLVQEVTDFAKTCVADESAANCDK SLHTLFGDKLCAIPNLRENYGELADCCTKQEPERNECFLQHKDDNPSLPPFERPEA EAMCTSFKENPTTFMGHYLHEVARRHPYFYAPELLYYAEQYNEILTQCCAEADKES CLTPKLDGVKEKALVSSVRQRMKCSSMQKFGERAFKAWAVARLSQTFPNADFAEIT KLATDLTKVNKECCHGDLLECADDRAELAKYMCENQATISSKLQTCCDKPLLKKAH CLSEVEHDTMPADLPAIAADFVEDQEVCKNYAEAKDVFLGTFLYEYSRRHPDYSVS LLLRLAKKYEATLEKCCAEANPPACYGTVLAEFQPLVEEPKNLVKTNCDLYEKLGE YGFQNAILVRYTQKAPQVSTPTLVEAARNLGRVGTKCCTLPEDQRLPCVEDYLSAI LNRVCLLHEKTPVSEHVTKCCSGSLVERRPCFSALTVDETYVPKEFKAETFTFHSD ICTLPEKEKQIKKQTALAELVKHKPKATAEQLKTVMDDFAQFLDTCCKAADKDTCF STEGPNLVTRCKDALA*GGGS*HGTVIESLESLNNYFNSSGIDVEEKSLFLDIWRNWQ KDGDMKILQSQIISFYLRLFEVLKDNQAISNNISVIESHLITTFFSNSKAKKDAFM SIAKFEVNNPQVQRQAFNELIRVVHQLLPESSLRKRKRSRCGGGSGGGSGGGSGGG SHGTVIESLESLNNYFNSSGIDVEEKSLFLDIWRNWQKDGDMKILQSQIISFYLRL FEVLKDNQAISNNISVIESHLITTFFSNSKAKKDAFMSIAKFEVNNPQVQRQAFNE LIRVVHQLLPESSLRKRKRSRCHHHHHH |
| 180 | MSA-IFNg-IFNg | EAHKSEIAHRYNDLGEQHFKGLVLIAFSQYLQKCSYDEHAKLVQEVTDFAKTCVAD ESAANCDKSLHTLFGDKLCAIPNLRENYGELADCCTKQEPERNECFLQHKDDNPSL PPFERPEAEAMCTSFKENPTYFMGHYLHEVARRHPYFYAPKLLYYAEQYNEILTQC CAEADKESCLTPKLDGVKEKALVSSVRQRMKCSSMQKFGERAFKAWAVARLSQTFP NADFAEITKLATDLTKVNKECCHGDLLECADDRAELAKYMCENQATISSKLQTCCD KPLLKKAHCLSEVEHDTMPADLPAIAADFVEDQEVCKNYAEAKDVFLGTFLYEYSR RHPDYSVSLLLRLAKKYEATLEKCCAEANPPACYGTVLAEFQPLVEEPKNLVKTNC DLYEKLGEYGFQNAILVRYTQKAPQVSTPTLVEAARNLGRVGTKCCTLPEDQRLPC VEDYLSAILNRVCLLHEKTPVSEHVTKCCSGSLVERRPCFSALTVDETYVPKEFKA ETFTFHSDICTLPEKEKQIKKQTALAELVKHKPKATAEQLKTVMDDFAQFLDTCCK AADKDTCFSTEGPNLVTRCKDALA*GGGS*HGTVIESLESLNNYFNSSGIDVEEKSLF LDIWRNWQKDGDMKILQSQIISFYLRLFEVLKDNQAISNNISVIESHLITTFFSNS KAKKDAFMSIAKFEVNNPQVQRQAFNELIRVVHQLLPESSLRKRKRSRCGGGSGGG SGGGGSGGGSHGTVIESLESLNNYFNSSGIDVEEKSLFLDIWRNWQKDGDMKILQSQ IISFYLRLFEVLKDNQAISNNISVIESHLITTFFSNSKAKKDAFMSIAKFEVNNPQ VQRQAFNELIRVVHQLLPESSLRKRKRSRCHHHHHH |
| 181 | LAIR-(H)6 | QEGSLPDITIFPNSSLMISQGTFVTVVCSYSDKHDLYNMVRLEKDGSTFMEKSTEP YKTEDEFEIGPVNETITGHYSCIYSKGITWSERSKTLELKVIKENVIQTPAPGPTS DTSWLKTYSIYHHHHHH |
| 182 | Lumican (murine) | YYDYDIPLFMYGQISPNCAPECNCPHSYPTAMYCDDLKLKSVPMVPPGIKYLYLRN NQIDHIDEKAFENVTDLQWLILDHNLLENSKIKGKVFSKLKQLKKLHINYNNLTES VGPLPKSLQDLQLTNNKISKLGSFDGLVNLTFIYLQHNQLKEDAVSASLKGLKSLE YLDLSFNQMSKLPAGLPTSLLTLYLDNNKISNIPDEYFKRFTGLQYLRLSHNELAD SGVPGNSFNISSLLELDLSYNKLKSIPTVNENLENYYLEVNELEKFDVKSFCKILG PLSYSKIKHLRLDGNPLTQSSLPPDMYECLRVANEITVN |
| 183 | murine MSA | EAHKSEIAHRYNDLGEQHFKGLVLIAFSQYLQKCSYDEHAKLVQEVTDFAKTCVAD ESAANCDKSLHTLFGDKLCAIPNLRENYGELADCCTKQEPERNECFLQHKDDNPSL PPFERPEAEAMCTSFKENPTTFMGHYLHEVARRHPYFYAPELLYYAEQYNEILTQC CAEADKESCLTPKLDGVKEKALVSSVRQRMKCSSMQKFGERAFKAWAVARLSQTFP NADFAEITKLATDLTKVNKECCHGDLLECADDRAELAKYMCENQATISSKLQTCCD KPLLKKAHCLSEVEHDTMPADLPAIAADFVEDQEVCKNYAEAKDVFLGTFLYEYSR RHPDYSVSLLLRLAKKYEATLEKCCAEANPPACYGTVLAEFQPLVEEPKNLVKTNC DLYEKLGEYGFQNAILVRYTQKAPQVSTPTLVEAARNLGRVGTKCCTLPEDQRLPC VEDYLSAILNRVCLLHEKTPVSEHVTKCCSGSLVERRPCFSALTVDETYVPKEFKA ETFTFHSDICTLPEKEKQIKKQTALAELVKHKPKATAEQLKTVMDDFAQFLDTCCK AADKDTCFSTEGPNLVTRCKDALA |

Summary Sequence Table

| SEQ ID NO | Description | Sequence |
|---|---|---|
| 184 | 3/23 LC-murine kappa (3/23 LC bold; murine kappa chain underlined) | DTVLTQSPALAVSPGERVTISCRASESVSTRMHWYQQRPGQPPKLLIYVASRLESG<br>VPARFSGGGSGTDFTLTIDPVEANDTATYFCQQSWNDPWTFGGGTKLELKRADAAP<br>TVSIFPPSSEQLTSGGASVVGFLNNFYPKDINVKWKIDGSERQNGVLNSWTDQDSK<br>DSTYSMSSTLTLTKDEYERHNSYTCEATHKTSTSPIVKSFNRNEC |
| 185 | 3/23 HC-lumican (LALA-PG) (3/23 HC bold; mIgG2c underline; LALA-PG silencing mutation bold underline; Lumican dotted underline) | EVQLVESGGGLVQPGRSLKLSCAASGFTLSDYYMAWVRQAPKKGLEWVASINYEGS<br>STYYGESVKGRFTISRDNAKSTLYLQMNSLRSEDTATYYCVRHDNYFDYWGQGVLV<br>TVSSAKTTAPSVYPLAPVCGGTTGSSVTLGCLVKGYFPEPVTLTWNSGSLSSGVHT<br>FPALLQSGLYTLSSSVTVTSNTWPSQTITCNVAHPASSTKVDKKIEPRVPITQNPC<br>PPLKECPPCAAPDAAGGPSVF1FPPPKIKDVLMISLSPMVTCVVVDVSEDDPDVQIS<br>WFVNNVEVHTAQTQTHREDYNSTLRVVSALPIQHQDWMSGKEFKCKVNNRALGSPI<br>EKTISKPRGPVRAPQVYVLPPPAEEMTKKEFSLTCMITGFLPAEIAVDWTSNGRTE<br>QNYKNTATVLDSDGSYFMYSKLRVQKSTWERGSLFACSVVHEGLHNHLTTKTISRS<br>LGK*GGGGSGGGGSGGGGS*QYYDYDIPLFMYGQISPNCAPECNCPHSYPTAMYCDDL<br>KLKSVPMVPPGIKYLYLRNNQIDHIDEKAFENVTDLQWLILDHNLLENSKIKGKVF<br>SKLKQLKKLHINYNNLTESVGPLPKSLQDLQLTNNKISKLGSFDGLVNLTFIYLQH<br>NQLKEDAVSASLKGLKSLEYLDLSFNQMSKLPAGLPTSLLTLYLDNNKISNIPDEY<br>FKRFTGLQYLRLSHNELADSGVPGNSFNISSLLELDLSYNKLKSIPTVNENLENYY<br>LEVNELEKFDVKSFCKILGPLSYSKIKHLRLDGNPLTQSSLPPDMYECLRVANEIT<br>VN |
| 186 | LAIR-MSA-IL2 (LAIR bold;-(GGGS)1 italc; MSA underline; (GGGS)1 italic; IL-2; (H)6 dotted underline) | QEGSLPDITIFPNSSLMISQGTFVTVVCSYSDKHDLYNMVRLEKDGSTFMEKSTEP<br>YKTEDEFEIGPVNETITGHYSCIYSKGITWSERSKTLELKVIKENVIQTPAPGPTS<br>DTSWLKTYSIY*GGS*EAHKSEIAHRYNDLGEQHFKGLVLIAFSQYLQKCSYDEHAKL<br>VQEVTDFAKTCVADESAANCDKSLHTLFGDKLCAIPNLRENYGELADCCTKQEPER<br>NECFLQHKDDNPSLPPFERPEAEAMCTSFKENPTTFMGHYLHEVARRHPYFYAPEL<br>LYYAEQYNEILTQCCAEADKESCLTPKLDGVKEKALVSSVRQRMKCSSMQKFGERA<br>FKAWAVARLSQTFPNADFAEITKLATDLTKVNKECCHGDLLECADDRAELAKYMCE<br>NQATISSKLQTCCDKPLLKKAHCLSEVEHDTMPADLPAIAADFVEDQEVCKNYAEA<br>KDVFLGTFLYEYSRRHPDYSVSLLLRLAKKYEATLEKCCAEANPPACYGTVLAEFQ<br>PLVEEPKNLVKTNCDLYEKLGEYGFQNAILVRYTQKAPQVSTPTLVEAARNLGRVG<br>TKCCTLPEDQRLPCVEDYLSAILNRVCLLHEKTPVSEHVTKCCSGSLVERRPCFSA<br>LTVDETYVPKEFKAETFTFHSDICTLPEKEKQIKKQTALAELVKHKPKATAEQLKT<br>VMDDFAQFLDTCCKAADKDTCFSTEGPNLVTRCKDALA*GGGS*APTSSSTSSSTAEA<br>QQQQQQQQQQQHLEQLLMDLQELLSRMENYRNLKLPRMLTFKFYLPKQATELKDL<br>QCLEDELGPLRHVLDLTQSKSFQLEDAENFISNIRVTVVKLKGSDNTFECQFDDES<br>ATVVDFLRRWIAFCQSIISTSPQHHHHHH |
| 187 | LAIR30.w.A | QEGSLPDITIFPNSSLMISQGTFVTVACSYSDKHDLYNMVRLEKGGSTFMEKSTEP<br>YKTEDEFEIGPVNETITGHYSCIYSKGITWSERSKTLELKVIKENVIQTPAPGPTS<br>DTSWLKTYSIY |
| 188 | LAIR30.w.B | QEGSLPDITIFPNSSLMISQGTFVTVVCSYSDKHDLYNMVRLEKDGSTSMEKSTEP<br>YKTEDEFEIGPVNETITGHYSCIYSKGITWSERSKTLELKVTKENVIQTPAPGPTS<br>DTSWLKTYSIY |
| 189 | LAIR30.w.C | QEGSLPDITIFPNSSLMISQGTFVTVVCSYSDKHDLYNMVRLEKDGSTFMGKSTEP<br>YKTEDEFEIGPVNETITGHYSCIYSKGITWSERSKTLELKVIKENVIQTPAPGPTS<br>DTSWLKTYSIY |
| 190 | LAIR30.w.D | QEGSLPDITIFPNSSLMISQGTFVTVVCSYSDKHDLYNMVRLAKDGSTFMEKSTEP<br>YKTEDEFEIGPVNETITGHYSCIYSKGITWSERSKTLELKVIKENVIQTPAPGPTS<br>DTSWLKTYSIY |
| 191 | LAIR30.w.E | QEGSLPDITIFPNSSLMISQGTFVTVVCSYSDKHDLYNMVRLEKDGSTFMEKSTEP<br>YKTEDEFEIGPVNETITGHYSCIYSKGITWSERAKTLELKVIKENVIQTPAPGPTS<br>DTSWLKTYSIY |
| 192 | LAIR30.w.F | QEGSLPDITIFPNSSLMISQGTFVTVVCSYSDKHDLYNMVRLEKDGSTFMEKSTEP<br>YKTEDEFEIGPVNETITGHYSCIYSKGITWSERAKTLELKVIKENVIQTPAPGPTS<br>DTSWLKTYSIY |

Summary Sequence Table

| SEQ ID NO | Description | Sequence |
|---|---|---|
| 193 | LAIR30.2.K1.B | QEGSLPDITIFPNSSLVISQGTFVTVVCSYSDKHDLYNMVRLEKDGSTFMEKSTAP YKTEDEFEIGPVNETITGHYSCIYSKGITWSERSKTLELKVIKENVIQTPAPGPTS DTLWLKTYSIY |
| 194 | LAIR-MSA (LAIR bold; (GGGS)1 italic-IL-2-(H)6 dotted underline) | QEGSLPDITIFPNSSLMISQGTFVTVVCSYSDKHDLYNMVRLEKDGSTFMEKSTEP YKTEDEFEIGPVNETITGHYSCIYSKGITWSERSKTLELKVIKENVIQTPAPGPTS DTSWLKTYSIY*GGS*EAHKSEIAHRYNDLGEQHFKGLVLIAFSQYLQKCSYDEHAKL VQEVTDFAKTCVADESAANCDKSLHTLFGDKLCAIPNLRENYGELADCCTKQEPER NECFLQHKDDNPSLPPFERPEAEAMCTSFKENPTTFMGHYLHEVARRHPYFYAPEL LYYAEQYNEILTQCCAEADKESCLTPKLDGVKEKALVSSVRQRMKCSSMQKFGERA FKAWAVARLSQTFPNADFAEITKLATDLTKVNKECCHGDLLECADDRAELAKYMCE NQATISSKLQTCCDKPLLKKAHCLSEVEHDTMPADLPAIAADFVEDQEVCKNYAEA KDVFLGTFLYEYSRRHPDYSVSLLLRLAKKYEATLEKCCAEANPPACYGTVLAEFQ PLVEEPKNLVKTNCDLYEKLGEYGFQNAILVRYTQKAPQVSTPTLVEAARNLGRVG TKCCTLPEDQRLPCVEDYLSAILNRVCLLHEKTPVSEHVTKCCSGSLVERRPCFSA LTVDETYVPKEFKAETFTFHSDICTLPEKEKQIKKQTALAELVKHKPKATAEQLKT VMDDFAQFLDTCCKAADKDTCFSTEGPNLVTRCKDALA*GGGS*HHHHHH |
| 195 | 4420 HC-LAIR (4420 HC bold; mIgG1; (GGGGS)3 italic; LAIR underline) | DVKLDETGGGLVQPGRPMKLSCVASGFTFSDYWMNWVRQSPEKGLEWVAQIRNKPY NYETYYSDSVKGRFTISRDDSKSSVYLQMNNLRVEDMGIYYCTGSYYGMDYWGQGT SVTVSATTKGPSVYPLAPGSAAQTNSMVTLGCLVKGYFPEPVTVTWNSGSLSSGVH TFPAVLQSDLYTLSSSVTVPSSTWPSQTVTCNVAHPASSTKVDKKIVPRDCGCKPC ICTVPEVSSVFIFPPKPKDVLTITLTPKVTCVVVDISKDDPEVQFSWFVDDVEVHT AQTKPREEQINSTFRSVSELPIMHQDWLNGKEFKCRVNSAAFPAPIEKTISKTKGR PK*GGGGSGGGGSGGGGS*<u>QEGSLPDITIFPNSSLMISQGTFVTVVCSYSDKHDLYNM VRLEKDGSTFMEKSTEPYKTEDEFEIGPVNETITGHYSCIYSKGITWSERSKTLEL KVIKENVIQTPAPGPTSDTSWLKTYSIY</u> |
| 196 | 3/23 HC-LAIR (3/23 HC bold; mIgG1; (GGGGS)3 italic; LAIR underline) | EVQLVESGGGLVQPGRSLKLSCAASGFTLSDYYMAWVRQAPKKGLEWVASINYEGS STYYGESVKGRFTISRDNAKSTLYLQMNSLRSEDTATYYCVRHDNYFDYWGQGVLV TVSSATTKGPSVYPLAPGSAAQTNSMVTLGCLVKGYFPEPVTVTWNSGSLSSGVHT FPAVLQSDLYTLSSSVTVPSSTWPSQTVTCNVAHPASSTKVDKKIVPRDCGCKPCI CTVPEVSSVFIFPPKPKDVLTITLTPKVTCVVVDISKDDPEVQFSWFVDDVEVHTA QTKPREEQINSTFRSVSELPIMHQDWLNGKEFKCRVNSAAFPAPIEKTISKTKGRP K*GGGGSGGGGSGGGGS*<u>QEGSLPDITIFPNSSLMISQGTFVTVVCSYSDKHDLYNMV RLEKDGSTFMEKSTEPYKTEDEFEIGPVNETITGHYSCIYSKGITWSERSKTLELK VIKENVIQTPAPGPTSDTSWLKTYSIY</u> |
| 197 | LOB12.3 HC-LAIR (LOB12.3 HC bold; mIgG1; (GGGGS)3 italic; LAIR underline) | DVQLVESGGGLVQPGRSLKLSCAASGFIFSYFDMAWVRQAPTKGLEWVASISPDGS IPYYRDSVKGRFTVSRENAKSSLYLQMDSLRSEDTATYYCARRSYGGYSEIDYWGQ GVMVTVSSATTKGPSVYPLAPGSAAQTNSMVTLGCLVKGYFPEPVTVTWNSGSLSS GVHTFPAVLQSDLYTLSSSVTVPSSTWPSQTVTCNVAHPASSTKVDKKIVPRDCGC KPCICTVPEVSSVFIFPPKPKDVLTITLTPKVTCVVVDISKDDPEVQFSWFVDDVE VHTAQTKPREEQINSTFRSVSELPIMHQDWLNGKEFKCRVNSAAFPAPIEKTISKT KGRPK*GGGGSGGGGSGGGGS*<u>QEGSLPDITIFPNSSLMISQGTFVTVVCSYSDKHDL YNMVRLEKDGSTFMEKSTEPYKTEDEFEIGPVNETITGHYSCIYSKGITWSERSKT LELKVIKENVIQTPAPGPTSDTSWLKTYSIY</u> |
| 198 | OX86 HC-LAIR (OX86 HC bold; mIgG1; (GGGGS)3 italic; LAIR underline) | QVQLKESGPGLVQPSQTLSLTCTVSGFSLTGYNLHWVRQPPGKGLEWMGRMRYDGD TYYNSVLKSRLSISRDTSKNQVFLKMNSLQTDDTAIYYCTRDGRGDSFDYWGQGVM VTVSSATTKGPSVYPLAPGSAAQTNSMVTLGCLVKGYFPEPVTVTWNSGSLSSGVH TFPAVLQSDLYTLSSSVTVPSSTWPSQTVTCNVAHPASSTKVDKKIVPRDCGCKPC ICTVPEVSSVFIFPPKPKDVLTITLTPKVTCVVVDISKDDPEVQFSWFVDDVEVHT AQTKPREEQINSTFRSVSELPIMHQDWLNGKEFKCRVNSAAFPAPIEKTISKTKGR PK*GGGGSGGGGSGGGGS*<u>QEGSLPDITIFPNSSLMISQGTFVTVVCSYSDKHDLYNM VRLEKDGSTFMEKSTEPYKTEDEFEIGPV</u>NETITGHYSCIYSKGITWSERSKTLEL KVIKENVIQTPAPGPTSDTSWLKTYSIY |
| 199 | 2C11 HC-LAIR (2C11 HC bold; mIgG1; (GGGGS)3 italic; LAIR underline) | EVQLVESGGGLVQPGKSLKLSCEASGFTFSGYGMHWVRQAPGRGLESVAYITSSSI NIKYADAVKGRFTVSRDNAKNLLFLQMNILKSEDTAMYYCARFDWDKNYWGQGTMV TVSSATTKGPSVYPLAPGSAAQTNSMVTLGCLVKGYFPEPVTVTWNSGSLSSGVHT FPAVLQSDLYTLSSSVTVPSSTWPSQTVTCNVAHPASSTKVDKKIVPRDCGCKPCI CTVPEVSSVFIFPPKPKDVLTITLTPKVTCVVVDISKDDPEVQFSWFVDDVEVHTA QTKPREEQINSTFRSVSELPIMHQDWLNGKEFKCRVNSAAFPAPIEKTISKTKGRP K*GGGGSGGGGSGGGGS*<u>QEGSLPDITIFPNSSLMISQGTFVTVVCSYSDKHDLYNMV RLEKDGSTFMEKSTEPYKTEDEFEIGPVNETITGHYSCIYSKGITWSERSKTLELK VIKENVIQTPAPGPTSDTSWLKTYSIY</u> |

What is claimed is:

1. An immunomodulatory fusion protein comprising:

(i) an immunomodulatory domain comprising IL-2;

(ii) a collagen-binding domain comprising LAIR 1 having the amino acid sequence of SEQ ID NO: 98; and (iii) an albumin linker, wherein the immunomodulatory domain is operably linked with the linker to the collagen-binding domain;

wherein the fusion protein binds type I and/or type IV collagen upon administration in vivo and the collagen-binding domain increases tumor retention and prevents systemic exposure to the cytokine.

2. The immunomodulatory fusion protein of claim 1, wherein the immunomodulatory domain comprises a polypeptide that activates, enhances or promotes a response by an immune cell, or wherein the immunomodulatory domain comprises a polypeptide that inhibits, reduces or suppresses a response by an immune cell.

3. The immunomodulatory fusion protein of claim 1, wherein the linker is mouse serum albumin or human serum albumin.

4. The immunomodulatory fusion protein of claim 1, wherein: the fusion protein is >60 kDa.

5. The immunomodulatory fusion protein of claim 1, wherein the fusion protein is of sufficient mass to reduce size dependent escape by diffusion or convection upon administration in vivo.

6. A pharmaceutical composition comprising an immunomodulatory fusion protein of claim 1, and a pharmaceutically acceptable carrier.

7. A method for activating, enhancing, or promoting a response by an immune cell in a subject, comprising administering to a subject in need thereof, an effective amount of an immunomodulatory fusion protein of claim 1.

8. A method for reducing or inhibiting tumor growth, comprising administering to a subject in need thereof, an effective amount of an immunomodulatory fusion protein of claim 1.

9. A method for treating cancer in a subject, comprising administering to a subject in need thereof, an effective amount of an immunomodulatory fusion protein of claim 1.

10. The immunomodulatory fusion protein of claim 1, wherein the immunomodulatory fusion protein has the amino acid sequence of SEQ ID NO: 186.

* * * * *

```
                              SEQUENCE LISTING

Sequence total quantity: 212
SEQ ID NO: 1                  moltype = AA  length = 133
FEATURE                       Location/Qualifiers
REGION                        1..133
                              note = Synthetic: IL-2
source                        1..133
                              mol_type = protein
                              organism = synthetic construct
SEQUENCE: 1
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR   120
WITFCQSIIS TLT                                                      133

SEQ ID NO: 2                  moltype = AA  length = 306
FEATURE                       Location/Qualifiers
REGION                        1..306
                              note = Synthetic: Wild Type IL12B without signal (IL12B)
                              Amino Acids
source                        1..306
                              mol_type = protein
                              organism = synthetic construct
SEQUENCE: 2
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCS                                                              306

SEQ ID NO: 3                  moltype = AA  length = 197
FEATURE                       Location/Qualifiers
REGION                        1..197
                              note = Synthetic: Wild Type IL12A without signal peptide
                              Amino acids
source                        1..197
                              mol_type = protein
                              organism = synthetic construct
SEQUENCE: 3
RNLPVATPDP GMFPCLHHSQ NLLRAVSNML QKARQTLEFY PCTSEEIDHE DITKDKTSTV   60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRAVTIDRV MSYLNAS                                                  197

SEQ ID NO: 4                  moltype = AA  length = 175
FEATURE                       Location/Qualifiers
REGION                        1..175
                              note = Synthetic: IL-15Ra
source                        1..175
                              mol_type = protein
                              organism = synthetic construct
SEQUENCE: 4
ITCPPPMSVE HADIWVKSYS LYSRERYICN SGFKRKAGTS SLTECVLNKA TNVAHWTTPS   60
LKCIRDPALV HQRPAPPSTV TTAGVTPQPE SLSPSGKEPA ASSPSSNNTA ATTAAIVPGS   120
QLMPSKSPST GTTEISSHES SHGTPSQTTA KNWELTASAS HQPPGVYPQG HSDTT        175

SEQ ID NO: 5                  moltype = AA  length = 114
FEATURE                       Location/Qualifiers
REGION                        1..114
                              note = Synthetic: IL-15
source                        1..114
                              mol_type = protein
                              organism = synthetic construct
SEQUENCE: 5
NWVNVISDLK KIEDLIQSMH IDATLYTESD VHPSCKVTAM KCFLLELQVI SLESGDASIH   60
DTVENLIILA NNSLSSNGNV TESGCKECEE LEEKNIKEFL QSFVHIVQMF INTS         114

SEQ ID NO: 6                  moltype = AA  length = 157
FEATURE                       Location/Qualifiers
REGION                        1..157
                              note = Synthetic: TNF-alpha
source                        1..157
                              mol_type = protein
                              organism = synthetic construct
SEQUENCE: 6
VRSSSRTPSD KPVAHVVANP QAEGQLQWLN RRANALLANG VELRDNQLVV PSEGLYLIYS   60
QVLFKGQGCP STHVLLTHTI SRIAVSYQTK VNLLSAIKSP CQRETPEGAE AKPWYEPIYL   120
GGVFQLEKGD RLSAEINRPD YLDFAESGQV YFGIIAL                            157
```

```
SEQ ID NO: 7              moltype = AA   length = 138
FEATURE                   Location/Qualifiers
REGION                    1..138
                          note = Synthetic: IFN-gamma
source                    1..138
                          mol_type = protein
                          organism = synthetic construct
SEQUENCE: 7
QDPYVKEAEN LKKYFNAGHS DVADNGTLFL GILKNWKEES DRKIMQSQIV SFYFKLFKNF    60
KDDQSIQKSV ETIKEDMNVK FFNSNKKKRD DFEKLTNYSV TDLNVQRKAI HELIQVMAEL   120
SPAAKTGKRK RSQMLFRG                                                 138

SEQ ID NO: 8              moltype = AA   length = 165
FEATURE                   Location/Qualifiers
REGION                    1..165
                          note = Synthetic: IFN-alpha
source                    1..165
                          mol_type = protein
                          organism = synthetic construct
SEQUENCE: 8
CDLPQTHSLG SRRTLMLLAQ MRKISLFSCL KDRHDFGFPQ EEFGNQFQKA ETIPVLHEMI    60
QQIFNLFSTK DSSAAWDETL LDKFYTELYQ QLNDLEACVI QGVGVTETPL MKEDSILAVR   120
KYFQRITLYL KEKKYSPCAW EVVRAEIMRS FSLSTNLQES LRSKE                   165

SEQ ID NO: 9              moltype = AA   length = 133
FEATURE                   Location/Qualifiers
REGION                    1..133
                          note = Synthetic: IL-21
source                    1..133
                          mol_type = protein
                          organism = synthetic construct
SEQUENCE: 9
QGQDRHMIRM RQLIDIVDQL KNYVNDLVPE FLPAPEDVET NCEWSAFSCF QKAQLKSANT    60
GNNERIINVS IKKLKRKPPS TNAGRRQKHR LTCPSCDSYE KKPPKEFLER FKSLLQKMIH   120
QHLSSRTHGS EDS                                                      133

SEQ ID NO: 10             moltype = AA   length = 449
FEATURE                   Location/Qualifiers
REGION                    1..449
                          note = Synthetic: IL-6
source                    1..449
                          mol_type = protein
                          organism = synthetic construct
SEQUENCE: 10
LAPRRCPAQE VARGVLTSLP GDSVTLTCPG VEPEDNATVH WVLRKPAAGS HPSRWAGMGR    60
RLLLRSVQLH DSGNYSCYRA GRPAGTVHLL VDVPPEEPQL SCFRKSPLSN VVCEWGPRST   120
PSLTTKAVLL VRKFQNSPAE DFQEPCQYSQ ESQKFSCQLA VPEGDSSFYI VSMCVASSVG   180
SKFSKTQTFQ GCGILQPDPP ANITVTAVAR NPRWLSVTWQ DPHSWNSSFY RLRFELRYRA   240
ERSKTFTTWM VKDLQHHCVI HDAWSGLRHV VQLRAQEEFG QGEWSEWSPE AMGTPWTESR   300
SPPAENEVST PMQALTTNKD DDNILFRDSA NATSLPVQDS SSVPLPTFLV AGGSLAFGTL   360
LCIAIVLRFK KTWKLRALKE GKTSMHPPYS LGQLVPERPR PTPVLVPLIS PPVSPSSLGS   420
DNTSSHNRPD ARDPRSPYDI SNTDYFFPR                                     449

SEQ ID NO: 11             moltype = AA   length = 400
FEATURE                   Location/Qualifiers
REGION                    1..400
                          note = Synthetic: IL-5
source                    1..400
                          mol_type = protein
                          organism = synthetic construct
SEQUENCE: 11
DLLPDEKISL LPPVNFTIKV TGLAQVLLQW KPNPDQEQRN VNLEYQVKIN APKEDDYETR    60
ITESKCVTIL HKGFSASVRT ILQNDHSLLA SSWASAELHA PPGSPGTSIV NLTCTTNTTE   120
DNYSRLRSYQ VSLHCTWLVG TDAPEDTQYF LYYRYGSWTE ECQEYSKDTL GRNIACWFPR   180
TFILSKGRDW LAVLVNGSSK HSAIRPFDQL FALHAIDQIN PPLNVTAEIE GTRLSIQWEK   240
PVSAFPIHCF DYEVKIHNTR NGYLQIEKLM TNAFISIIDD LSKYDVQVRA AVSSMCREAG   300
LWSEWSQPIY VGNDEHKPLR EWFVIVIMAT ICFILLILSL ICKICHLWIK LFPPIPAPKS   360
NIKDLFVTTN YEKAGSSETE IEVICYIEKP GVETLEDSVF                         400

SEQ ID NO: 12             moltype = AA   length = 77
FEATURE                   Location/Qualifiers
REGION                    1..77
                          note = Synthetic: IL-8
source                    1..77
                          mol_type = protein
                          organism = synthetic construct
SEQUENCE: 12
AVLPRSAKEL RCQCIKTYSK PFHPKFIKEL RVIESGPHCA NTEIIVKLSD GRELCLDPKE    60
NWVQRVVEKF LKRAENS                                                   77
```

```
SEQ ID NO: 13              moltype = AA  length = 152
FEATURE                    Location/Qualifiers
REGION                     1..152
                           note = Synthetic: IL-7
source                     1..152
                           mol_type = protein
                           organism = synthetic construct
SEQUENCE: 13
DCDIEGKDGK QYESVLMVSI DQLLDSMKEI GSNCLNNEFN FFKRHICDAN KEGMFLFRAA    60
RKLRQFLKMN STGDFDLHLL KVSEGTTILL NCTGQVKGRK PAALGEAQPT KSLEENKSLK   120
EQKKLNDLCF LKRLLQEIKT CWNKILMGTK EH                                 152

SEQ ID NO: 14              moltype = AA  length = 132
FEATURE                    Location/Qualifiers
REGION                     1..132
                           note = Synthetic: IL-17A
source                     1..132
                           mol_type = protein
                           organism = synthetic construct
SEQUENCE: 14
GITIPRNPGC PNSEDKNFPR TVMVNLNIHN RNTNTNPKRS SDYYNRSTSP WNLHRNEDPE    60
RYPSVIWEAK CRHLGCINAD GNVDYHMNSV PIQQEILVLR REPPHCPNSF RLEKILVSVG   120
CTCVTPIVHH VA                                                       132

SEQ ID NO: 15              moltype = AA  length = 170
FEATURE                    Location/Qualifiers
REGION                     1..170
                           note = Synthetic: IL-23alpha
source                     1..170
                           mol_type = protein
                           organism = synthetic construct
SEQUENCE: 15
RAVPGGSSPA WTQCQQLSQK LCTLAWSAHP LVGHMDLREE GDEETTNDVP HIQCGDGCDP    60
QGLRDNSQFC LQRIHQGLIF YEKLLGSDIF TGEPSLLPDS PVGQLHASLL GLSQLLQPEG   120
HHWETQQIPS LSPSQPWQRL LLRFKILRSL QAFVAVAARV FAHGAATLSP              170

SEQ ID NO: 16              moltype = AA  length = 157
FEATURE                    Location/Qualifiers
REGION                     1..157
                           note = Synthetic: IL-18
source                     1..157
                           mol_type = protein
                           organism = synthetic construct
SEQUENCE: 16
YFGKLESKLS VIRNLNDQVL FIDQGNRPLF EDMTDSDCRD NAPRTIFIIS MYKDSQPRGM    60
AVTISVKCEK ISTLSCENKI ISFKEMNPPD NIKDTKSDII FFQRSVPGHD NKMQFESSSY   120
EGYFLACEKE RDLFKLILKK EDELGDRSIM FTVQNED                            157

SEQ ID NO: 17              moltype = AA  length = 159
FEATURE                    Location/Qualifiers
REGION                     1..159
                           note = Synthetic: IL-1alpha
source                     1..159
                           mol_type = protein
                           organism = synthetic construct
SEQUENCE: 17
SAPFSFLSNV KYNFMRIIKY EFILNDALNQ SIIRANDQYL TAAALHNLDE AVKFDMGAYK    60
SSKDDAKITV ILRISKTQLY VTAQDEDQPV LLKEMPEIPK TITGSETNLL FFWETHGTKN   120
YFTSVAHPNL FIATKQDYWV CLAGGPPSIT DFQILENQA                          159

SEQ ID NO: 18              moltype = AA  length = 153
FEATURE                    Location/Qualifiers
REGION                     1..153
                           note = Synthetic: IL-1beta
source                     1..153
                           mol_type = protein
                           organism = synthetic construct
SEQUENCE: 18
APVRSLNCTL RDSQQKSLVM SGPYELKALH LQGQDMEQQV VFSMSFVQGE ESNDKIPVAL    60
GLKEKNLYLS CVLKDDKPTL QLESVDPKNY PKKKMEKRFV FNKIEINNKL EFESAQFPNW   120
YISTSQAENM PVFLGGTKGG QDITDFTMQF VSS                                153

SEQ ID NO: 19              moltype = AA  length = 129
FEATURE                    Location/Qualifiers
REGION                     1..129
                           note = Synthetic: IL-4
source                     1..129
                           mol_type = protein
```

```
                                  organism = synthetic construct
SEQUENCE: 19
HKCDITLQEI IKTLNSLTEQ KTLCTELTVT DIFAASKNTT EKETFCRAAT VLRQFYSHHE    60
KDTRCLGATA QQFHRHKQLI RFLKRLDRNL WGLAGLNSCP VKEANQSTLE NFLERLKTIM   120
REKYSKCSS                                                          129

SEQ ID NO: 20             moltype = AA  length = 133
FEATURE                   Location/Qualifiers
REGION                    1..133
                          note = Synthetic: IL-3
source                    1..133
                          mol_type = protein
                          organism = synthetic construct
SEQUENCE: 20
APMTQTTPLK TSWVNCSNMI DEIITHLKQP PLPLLDFNNL NGEDQDILME NNLRRPNLEA    60
FNRAVKSLQN ASAIESILKN LLPCLPLATA APTRHPIHIK DGDWNEFRRK LTFYLKTLEN   120
AQAQQTTLSL AIF                                                     133

SEQ ID NO: 21             moltype = AA  length = 160
FEATURE                   Location/Qualifiers
REGION                    1..160
                          note = Synthetic: IL-10
source                    1..160
                          mol_type = protein
                          organism = synthetic construct
SEQUENCE: 21
SPGQGTQSEN SCTHFPGNLP NMLRDLRDAF SRVKTFFQMK DQLDNLLLKE SLLEDFKGYL    60
GCQALSEMIQ FYLEEVMPQA ENQDPDIKAH VNSLGENLKT LRLRLRRCHR FLPCENKSKA   120
VEQVKNAFNK LQEKGIYKAM SEFDIFINYI EAYMTMKIRN                        160

SEQ ID NO: 22             moltype = AA  length = 111
FEATURE                   Location/Qualifiers
REGION                    1..111
                          note = Synthetic: IL-13
source                    1..111
                          mol_type = protein
                          organism = synthetic construct
SEQUENCE: 22
PVPPSTALRE LIEELVNITQ NQKAPLCNGS MVWSINLTAG MYCAALESLI NVSGCSAIEK    60
TQRMLSGFCP HKVSAGQFSS LHVRDTKIEV AQFVKDLLLH LKKLFREGRF N           111

SEQ ID NO: 23             moltype = AA  length = 132
FEATURE                   Location/Qualifiers
REGION                    1..132
                          note = Synthetic: IL-17a
source                    1..132
                          mol_type = protein
                          organism = synthetic construct
SEQUENCE: 23
GITIPRNPGC PNSEDKNFPR TVMVNLNIHN RNTNTNPKRS SDYYNRSTSP WNLHRNEDPE    60
RYPSVIWEAK CRHLGCINAD GNVDYHMNSV PIQQEILVLR REPPHCPNSF RLEKILVSVG   120
CTCVTPIVHH VA                                                      132

SEQ ID NO: 24             moltype = AA  length = 126
FEATURE                   Location/Qualifiers
REGION                    1..126
                          note = Synthetic: IL-9
source                    1..126
                          mol_type = protein
                          organism = synthetic construct
SEQUENCE: 24
QGCPTLAGIL DINFLINKMQ EDPASKCHCS ANVTSCLCLG IPSDNCTRPC FSERLSQMTN    60
TTMQTRYPLI FSRVKKSVEV LKNNKCPYFS CEQPCNQTTA GNALTFLKSL LEIFQKEKMR   120
GMRGKI                                                             126

SEQ ID NO: 25             moltype = AA  length = 138
FEATURE                   Location/Qualifiers
REGION                    1..138
                          note = Synthetic: IFN-gamma
source                    1..138
                          mol_type = protein
                          organism = synthetic construct
SEQUENCE: 25
QDPYVKEAEN LKKYFNAGHS DVADNGTLFL GILKNWKEES DRKIMQSQIV SFYFKLFKNF    60
KDDQSIQKSV ETIKEDMNVK FFNSNKKKRD DFEKLTNYSV TDLNVQRKAI HELIQVMAEL  120
SPAAKTGKRK RSQMLFRG                                                138

SEQ ID NO: 26             moltype = AA  length = 165
FEATURE                   Location/Qualifiers
```

```
REGION                  1..165
                        note = Synthetic: IFN-alpha
source                  1..165
                        mol_type = protein
                        organism = synthetic construct
SEQUENCE: 26
CDLPQTHSLG SRRTLMLLAQ MRKISLFSCL KDRHDFGFPQ EEFGNQFQKA ETIPVLHEMI    60
QQIFNLFSTK DSSAAWDETL LDKFYTELYQ QLNDLEACVI QGVGVTETPL MKEDSILAVR   120
KYFQRITLYL KEKKYSPCAW EVVRAEIMRS FSLSTNLQES LRSKE                  165

SEQ ID NO: 27           moltype = AA  length = 127
FEATURE                 Location/Qualifiers
REGION                  1..127
                        note = Synthetic: GM-CSF
source                  1..127
                        mol_type = protein
                        organism = synthetic construct
SEQUENCE: 27
APARSPSPST QPWEHVNAIQ EARRLLNLSR DTAAEMNETV EVISEMFDLQ EPTCLQTRLE    60
LYKQGLRGSL TKLKGPLTMM ASHYKQHCPP TPETSCATQI ITFESFKENL KDFLLVIPFD   120
CWEPVQE                                                            127

SEQ ID NO: 28           moltype = AA  length = 209
FEATURE                 Location/Qualifiers
REGION                  1..209
                        note = Synthetic: FLT3L
source                  1..209
                        mol_type = protein
                        organism = synthetic construct
SEQUENCE: 28
TQDCSFQHSP ISSDFAVKIR ELSDYLLQDY PVTVASNLQD EELCGGLWRL VLAQRWMERL    60
KTVAGSKMQG LLERVNTEIH FVTKCAFQPP PSCLRFVQTN ISRLLQETSE QLVALKPWIT   120
RQNFSRCLEL QCQPDSSTLP PPWSPRPLEA TAPTAPQPPL LLLLLLPVGL LLLAAAWCLH   180
WQRTRRRTPR PGEQVPPVPS PQDLLLVEH                                    209

SEQ ID NO: 29           moltype = AA  length = 178
FEATURE                 Location/Qualifiers
REGION                  1..178
                        note = Synthetic: G-CSF
source                  1..178
                        mol_type = protein
                        organism = synthetic construct
SEQUENCE: 29
ATPLGPASSL PQSFLLKCLE QVRKIQGDGA ALQEKLVSEC ATYKLCHPEE LVLLGHSLGI    60
PWAPLSSCPS QALQLAGCLS QLHSGLFLYQ GLLQALEGIS PELGPTLDTL QLDVADFATT   120
IWQQMEELGM APALQPTQGA MPAFASAFQR RAGGVLVASH LQSFLEVSYR VLRHLAQP    178

SEQ ID NO: 30           moltype = AA  length = 180
FEATURE                 Location/Qualifiers
REGION                  1..180
                        note = Synthetic: LIF
source                  1..180
                        mol_type = protein
                        organism = synthetic construct
SEQUENCE: 30
SPLPITPVNA TCAIRHPCHN NLMNQIRSQL AQLNGSANAL FILYYTAQGE PFPNNLDKLC    60
GPNVTDFPPF HANGTEKAKL VELYRIVVYL GTSLGNITRD QKILNPSALS LHSKLNATAD   120
ILRGLLSNVL CRLCSKYHVG HVDVTYGPDT SGKDVFQKKK LGCQLLGKYK QIIAVLAQAF   180

SEQ ID NO: 31           moltype = AA  length = 522
FEATURE                 Location/Qualifiers
REGION                  1..522
                        note = Synthetic: M-CSF
source                  1..522
                        mol_type = protein
                        organism = synthetic construct
SEQUENCE: 31
EEVSEYCSHM IGSGHLQSLQ RLIDSQMETS CQITFEFVDQ EQLKDPVCYL KKAFLLVQDI    60
MEDTMRFRDN TPNAIAIVQL QELSLRLKSC FTKDYEEHDK ACVRTFYETP LQLLEKVKNV   120
FNETKNLLDK DWNIFSKNCN NSFAECSSQD VVTKPDCNCL YPKAIPSSDP ASVSPHQPLA   180
PSMAPVAGLT WEDSEGTEGS SLLPGEQPLH TVDPGSAKQR PPRSTCQSFE PPETPVVKDS   240
TIGGSPQPRP SVGAFNPGME DILDSAMGTN WVPEEASGEA SEIPVPQGTE LSPSRPGGGS   300
MQTEPARPSN FLSASSSLPA SAKGQQPADV TGTALPRVGP VRPTGQDWNH TPQKTDHPSA   360
LLRDPEPEPGS PRISSLRPQG LSNPSTLSAQ PQLSRSHSSG SVLPLGELEG RRSTRDRRSP   420
AEPEGGPASE GAARPLPRFN SVPLTDTGHE RQSEGSFSPQ LQESVFHLLV PSVILVLLAV   480
GGLLFYRWRR RSHQEPQRAD SPLEQPEGSP LTQDDRQVEL PV                     522

SEQ ID NO: 32           moltype = AA  length = 73
FEATURE                 Location/Qualifiers
```

```
REGION                      1..73
                            note = Synthetic: MIP-2
source                      1..73
                            mol_type = protein
                            organism = synthetic construct
SEQUENCE: 32
APLATELRCQ CLQTLQGIHL KNIQSVKVKS PGPHCAQTEV IATLKNGQKA CLNPASPMVK    60
KIIEKMLKNG KSN                                                      73

SEQ ID NO: 33               moltype = AA  length = 69
FEATURE                     Location/Qualifiers
REGION                      1..69
                            note = Synthetic: MIP-1beta
source                      1..69
                            mol_type = protein
                            organism = synthetic construct
SEQUENCE: 33
APMGSDPPTA CCFSYTARKL PRNFVVDYYE TSSLCSQPAV VFQTKRSKQV CADPSESWVQ    60
EYVYDLELN                                                           69

SEQ ID NO: 34               moltype = AA  length = 73
FEATURE                     Location/Qualifiers
REGION                      1..73
                            note = Synthetic: KP (aka CXCL1)
source                      1..73
                            mol_type = protein
                            organism = synthetic construct
SEQUENCE: 34
ASVATELRCQ CLQTLQGIHP KNIQSVNVKS PGPHCAQTEV IATLKNGRKA CLNPASPIVK    60
KIIEKMLNSD KSN                                                      73

SEQ ID NO: 35               moltype = AA  length = 103
FEATURE                     Location/Qualifiers
REGION                      1..103
                            note = Synthetic: MIG (aka CXCL9)
source                      1..103
                            mol_type = protein
                            organism = synthetic construct
SEQUENCE: 35
TPVVRKGRCS CISTNQGTIH LQSLKDLKQF APSPSCEKIE IIATLKNGVQ TCLNPDSADV    60
KELIKKWEKQ VSQKKKQKNG KKHQKKKVLK VRKSQRSRQK KTT                      103

SEQ ID NO: 36               moltype = AA  length = 77
FEATURE                     Location/Qualifiers
REGION                      1..77
                            note = Synthetic: IP-10 (CXCL10)
source                      1..77
                            mol_type = protein
                            organism = synthetic construct
SEQUENCE: 36
VPLSRTVRCT CISISNQPVN PRSLEKLEII PASQFCPRVE IIATMKKKGE KRCLNPESKA    60
IKNLLKAVSK ERSKRSP                                                  77

SEQ ID NO: 37               moltype = AA  length = 76
FEATURE                     Location/Qualifiers
REGION                      1..76
                            note = Synthetic: MCP-1
source                      1..76
                            mol_type = protein
                            organism = synthetic construct
SEQUENCE: 37
QPDAINAPVT CCYNFTNRKI SVQRLASYRR ITSSKCPKEA VIFKTIVAKE ICADPKQKWV    60
QDSMDHLDKQ TQTPKT                                                   76

SEQ ID NO: 38               moltype = AA  length = 74
FEATURE                     Location/Qualifiers
REGION                      1..74
                            note = Synthetic: Eotaxin
source                      1..74
                            mol_type = protein
                            organism = synthetic construct
SEQUENCE: 38
GPASVPTTCC FNLANRKIPL QRLESYRRIT SGKCPQKAVI FKTKLAKDIC ADPKKKWVQD    60
SMKYLDQKSP TPKP                                                     74

SEQ ID NO: 39               moltype = AA  length = 68
FEATURE                     Location/Qualifiers
REGION                      1..68
                            note = Synthetic: RANTES
```

```
                        source          1..68
                                        mol_type = protein
                                        organism = synthetic construct
SEQUENCE: 39
SPYSSDTTPC CFAYIARPLP RAHIKEYFYT SGKCSNPAVV FVTRKNRQVC ANPEKKWVRE    60
YINSLEMS                                                             68

SEQ ID NO: 40           moltype = AA    length = 78
FEATURE                 Location/Qualifiers
REGION                  1..78
                        note = Synthetic: LIX
source                  1..78
                        mol_type = protein
                        organism = synthetic construct
SEQUENCE: 40
AGPAAAVLRE LRCVCLQTTQ GVHPKMISNL QVFAIGPQCS KVEVVASLKN GKEICLDPEA    60
PFLKKVIQKI LDGGNKEN                                                  78

SEQ ID NO: 41           moltype = AA    length = 69
FEATURE                 Location/Qualifiers
REGION                  1..69
                        note = Synthetic: MIP-1alpha
source                  1..69
                        mol_type = protein
                        organism = synthetic construct
SEQUENCE: 41
SLAADTPTAC CFSYTSRQIP QNFIADYFET SSQCSKPGVI FLTKRSRQVC ADPSEEWVQK    60
YVSDLELSA                                                            69

SEQ ID NO: 42           moltype = AA    length = 749
FEATURE                 Location/Qualifiers
REGION                  1..749
                        note = misc_feature - Human serum albumin (amino acid
                         sequence)
source                  1..749
                        mol_type = protein
                        organism = Homo sapiens
SEQUENCE: 42
MDMRVPAQLL GLLLLWLPGA RCADAHKSEV AHRFKDLGEE NFKALVLIAF AQYLQQCPFE    60
DHVKLVNEVT EFAKTCVADE SAENCDKSLH TLFGDKLCTV ATLRETYGEM ADCCAKQEPE   120
RNECFLQHKD DNPNLPRLVR PEVDVMCTAF HDNEETFLKK YLYEIARRHP YFYAPELLFF   180
AKRYKAAFTE CCQAADKAAC LLPKLDELRD EGKASSAKQR LKCASLQKFG ERAFKAWAVA   240
RLSQRFPKAE FAEVSKLVTD LTKVHTECCH GDLLECADDR ADLAKYICEN QDSISSKLKE   300
CCEKPLLEKS HCIAEVENDE MPADLPSLAA DFVESKDVCK NYAEAKDVFL GMFLYEYARR   360
HPDYSVVLLL RLAKTYETTL EKCCAAADPH ECYAKVFDEF KPLVEEPQNL IKQNCELFEQ   420
LGEYKFQNAL LVRYTKKVPQ VSTPTLVEVS RNLGKVGSKC CKHPEAKRMP CAEDYLSVVL   480
NQLCVLHEKT PVSDRVTKCC TESLVNRRPC FSALEVDETY VPKEFNAETF TFHADICTLS   540
EKERQIKKQT ALVELVKHKP KATKEQLKAV MDDFAAFVEK CCKADDKETC FAEEGKKLVA   600
ASQAALGLGG GSAPTSSSTK KTQLQLEHLL LDLQMILNGI NNYKNPKLTR MLTFKFYMPK   660
KATELKHLQC LEEELKPLEE VLNLAQSKNF HLRPRDLISN INVIVLELKG SETTFMCEYA   720
DETATIVEFL NRWITFCQSI ISTLTGGGS                                     749

SEQ ID NO: 43           moltype = AA    length = 726
FEATURE                 Location/Qualifiers
REGION                  1..726
                        note = misc_feature - Mature HSA (amino acid sequence)
source                  1..726
                        mol_type = protein
                        organism = Homo sapiens
SEQUENCE: 43
DAHKSEVAHR FKDLGEENFK ALVLIAFAQY LQQCPFEDHV KLVNEVTEFA KTCVADESAE    60
NCDKSLHTLF GDKLCTVATL RETYGEMADC CAKQEPERNE CFLQHKDDNP NLPRLVRPEV   120
DVMCTAFHDN EETFLKKYLY EIARRHPYFY APELLFFAKR YKAAFTECCQ AADKAACLLP   180
KLDELRDEGK ASSAKQRLKC ASLQKFGERA FKAWAVARLS QRFPKAEFAE VSKLVTDLTK   240
VHTECCHGDL LECADDRADL AKYICENQDS ISSKLKECCE KPLLEKSHCI AEVENDEMPA   300
DLPSLAADFV ESKDVCKNYA EAKDVFLGMF LYEYARRHPD YSVVLLLRLA KTYETTLEKC   360
CAAADPHECY AKVFDEFKPL VEEPQNLIKQ NCELFEQLGE YKFQNALLVR YTKKVPQVST   420
PTLVEVSRNL GKVGSKCCKH PEAKRMPCAE DYLSVVNQL CVLHEKTPVS DRVTKCCTES    480
LVNRRPCFSA LEVDETYVPK EFNAETFTFH ADICTLSEKE RQIKKQTALV ELVKHKPKAT   540
KEQLKAVMDD FAAFVEKCCK ADDKETCFAE EGKKLVAASQ AALGLGGGSA PTSSSTKKTQ   600
LQLEHLLLDL QMILNGINNY KNPKLTRMLT FKFYMPKKAT ELKHLQCLEE ELKPLEEVLN   660
LAQSKNFHLR PRDLISNINV IVLELKGSET TFMCEYADET ATIVEFLNRW ITFCQSIIST   720
LTGGGS                                                              726

SEQ ID NO: 44           moltype = AA    length = 287
FEATURE                 Location/Qualifiers
REGION                  1..287
                        note = Synthetic: PD-1
source                  1..287
```

```
                        mol_type = protein
                        organism = synthetic construct
SEQUENCE: 44
MQIPQAPWPV VWAVLQLGWR PGWFLDSPDP WNPPTFFPAL LVVTEGDNAT FTCSFSNTSE    60
SFVLNWYRMS PSNQTDKLAA FPEDRSQPGQ DCRFRVTQLP NGRDFHMSVV RARRNDSGTY   120
LCGAISLAPK AQIKESLRAE LRVTERRAEV PTAHPSPSPR PAGQFQTLVV GVVGGLLGSL   180
VLLVWVLAVI CSRAARGTIG ARRTGQPLKE DPSAVPVFSV DYGELDFQWR EKTPEPPVPC   240
VPEQTEYATI VFPSGMGTSS PARRGSADGP RSAQPLRPED GHCSWPL                 287

SEQ ID NO: 45           moltype = AA  length = 290
FEATURE                 Location/Qualifiers
REGION                  1..290
                        note = Synthetic: PD-L-1
source                  1..290
                        mol_type = protein
                        organism = synthetic construct
SEQUENCE: 45
MRIFAVFIFM TYWHLLNAFT VTVPKDLYVV EYGSNMTIEC KFPVEKQLDL AALIVYWEME    60
DKNIIQFVHG EEDLKVQHSS YRQRARLLKD QLSLGNAALQ ITDVKLQDAG VYRCMISYGG   120
ADYKRITVKV NAPYNKINQR ILVVDPVTSE HELTCQAEGY PKAEVIWTSS DHQVLSGKTT   180
TTNSKREEKL FNVTSTLRIN TTTNEIFYCT FRRLDPEENH TAELVIPELP LAHPPNERTH   240
LVILGAILLC LGVALTFIFR LRKGRMMDVK KCGIQDTNSK KQSDTHLEET              290

SEQ ID NO: 46           moltype = AA  length = 223
FEATURE                 Location/Qualifiers
REGION                  1..223
                        note = Synthetic: CTLA-4
source                  1..223
                        mol_type = protein
                        organism = synthetic construct
SEQUENCE: 46
MACLGFQRHK AQLNLATRTW PCTLLFFLLF IPVFCKAMHV AQPAVVLASS RGIASFVCEY    60
ASPGKATEVR VTVLRQADSQ VTEVCAATYM MGNELTFLDD SICTGTSSGN QVNLTIQGLR   120
AMDTGLYICK VELMYPPPYY LGIGNGTQIY VIDPEPCPDS DFLLWILAAV SSGLFFYSFL   180
LTAVSLSKML KKRSPLTTGV YVKMPPTEPE CEKQFQPYFI PIN                     223

SEQ ID NO: 47           moltype = AA  length = 525
FEATURE                 Location/Qualifiers
REGION                  1..525
                        note = Synthetic: LAG3
source                  1..525
                        mol_type = protein
                        organism = synthetic construct
SEQUENCE: 47
MWEAQFLGLL FLQPLWVAPV KPLQPGAEVP VVWAQEGAPA QLPCSPTIPL QDLSLLRRAG    60
VTWQHQPDSG PPAAAPGHPL APGPHPAAPS SWGPRPRRYT VLSVGPGGLR SGRLPLQPRV   120
QLDERGRQRG DFSLWLRPAR RADAGEYRAA VHLRDRALSC RLRLRLGQAS MTASPPGSLR   180
ASDWVILNCS FSRPDRPASV HWFRNRGQGR VPVRESPHHH LAESFLFLPQ VSPMDSGPWG   240
CILTYRDGFN VSIMYNLTVL GLEPPTPLTV YAGAGSRVGL PCRLPAGVGT RSFLTAKWTP   300
PGGGPDLLVT GDNGDFTLRL EDVSQAQAGT YTCHIHLQEQ QLNATVTLAI ITVTPKSFGS   360
PGSLGKLLCE VTPVSGQERF VWSSLDTPSQ RSFSGPWLEA QEAQLLSQPW QCQLYQGERL   420
LGAAVYFTEL SSPGAQRSGR APGALPAGHL LLFLILGVLS LLLLLVTGAFG FHLWRRQWRP   480
RRFSALEQGI HPPQAQSKIE ELEQEPEPEP EPEPEPEPEP EPEQL                   525

SEQ ID NO: 48           moltype = AA  length = 300
FEATURE                 Location/Qualifiers
REGION                  1..300
                        note = Synthetic: TIM3
source                  1..300
                        mol_type = protein
                        organism = synthetic construct
SEQUENCE: 48
MFSHLPFDCV LLLLLLLLTR SSEVEYRAEV GQNAYLPCFY TPAAPGNLVP VCWGKGACPV    60
FECGNVVLRT DERDVNYWTS RYWLNGDFRK GDVSLTIENV TLADSGIYCC RIQIPGIMND   120
EKFNLKLVIK PAKVTPAPTR QRDFTAAFPR MLTTRGHGPA ETQTLGSLPD INLTQISTLA   180
NELRDSRLAN DLRDSGATIR GIYIGAGICA GLALALIFGA LIFKWYSHSK EKIQNLSLIS   240
LANLPPSGLA NAVAEGIRSE ENIYTIEENV YEVEEPNEYY CYVSSRQQPS QPLGCRFAMP   300

SEQ ID NO: 49           moltype = AA  length = 532
FEATURE                 Location/Qualifiers
REGION                  1..532
                        note = Synthetic: B7-H3
source                  1..532
                        mol_type = protein
                        organism = synthetic construct
SEQUENCE: 49
MLRRRGSPGM GVHVGAALGA LWFCLTGALE VQVPEDPVVA LVGTDATLCC SFSPEPGFSL    60
QLNLIWQLTD TKQLVHSFAE GQDQGSAYAN RTALFPDLLA QGNASLRLQR VRVADEGSFC   120
FVSIRDFGSA AVSLQVAAPY SKPSMTLEPN KDLRPGDTVT ITCSSYQGYP EAEVFWQDGQ   180
```

```
GVPLTGNVTT SQMANEQGLF DVHSILRVVL GANGTYSCLV RNPVLQQDAH SSVTITPQRS    240
PTGAVEVQVP EDPVVALVGT DATLRCSFSP EPGFSLAQLN LIWQLTDTKQ LVHSFTEGRD    300
QGSAYANRTA LFPDLLAQGN ASLRLQRVRV ADEGSFTCFV SIRDFGSAAV SLQVAAPYSK    360
PSMTLEPNKD LRPGDTVTIT CSSYRGYPEA EVFWQDGQGV PLTGNVTTSQ MANEQGLFDV    420
HSVLRVVLGA NGTYSCLVRN PVLQQDAHGS VTITGQPMTF PPEALWVTVG LSVCLIALLV    480
ALAFVCWRKI KQSCEEENAG AEDQDGEGEG SKTALQPLKH SDSKEDDGQE IA            532

SEQ ID NO: 50           moltype = AA  length = 166
FEATURE                 Location/Qualifiers
REGION                  1..166
                        note = Synthetic: B7-H4
source                  1..166
                        mol_type = protein
                        organism = synthetic construct
SEQUENCE: 50
MASLGQILFW SIISIIIILA GAIALIIGFG ISAFSMPEVN VDYNASSETL RCEAPRWFPQ    60
PTVVWASQVD QGANFSEVSN TSFELNSENV TMKVVSVLYN VTINNTYSCM IENDIAKATG   120
DIKVTESEIK RRSHLQLLNS KASLCVSSFF AISWALLPLS PYLMLK                  166

SEQ ID NO: 51           moltype = AA  length = 177
FEATURE                 Location/Qualifiers
REGION                  1..177
                        note = Synthetic: TNF-alpha extracellular domain
source                  1..177
                        mol_type = protein
                        organism = synthetic construct
SEQUENCE: 51
GPQREEFPRD LSLISPLAQA VRSSSRTPSD KPVAHVVANP QAEGQLQWLN RRANALLANG    60
VELRDNQLVV PSEGLYLIYS QVLFKGQGCP STHVLLTHTI SRIAVSYQTK VNLLSAIKSP   120
CQRETPEGAE AKPWYEPIYL GGVFQLEKGD RLSAEINRPD YLDFAESGQV YFGIIAL      177

SEQ ID NO: 52           moltype = AA  length = 182
FEATURE                 Location/Qualifiers
REGION                  1..182
                        note = Synthetic: LIGHT extracellular domain
source                  1..182
                        mol_type = protein
                        organism = synthetic construct
SEQUENCE: 52
LQLHWRLGEM VTRLPDGPAG SWEQLIQERR SHEVNPAAHL TGANSSLTGS GGPLLWETQL    60
GLAFLRGLSY HDGALVVTKA GYYYIYSKVQ LGGVGCPLGL ASTITHGLYK RTPRYPEELE   120
LLVSQQSPCG RATSSSRVWW DSSFLGGVVH LEAGEKVVVR VLDERLVRLR DGTRSYFGAF   180
MV                                                                  182

SEQ ID NO: 53           moltype = AA  length = 171
FEATURE                 Location/Qualifiers
REGION                  1..171
                        note = Synthetic: LT-alpha extracellular domain
source                  1..171
                        mol_type = protein
                        organism = synthetic construct
SEQUENCE: 53
LPGVGLTPSA AQTARQHPKM HLAHSTLKPA AHLIGDPSKQ NSLLWRANTD RAFLQDGFSL    60
SNNSLLVPTS GIYFVYSQVV FSGKAYSPKA TSSPLYLAHE VQLFSSQYPF HVPLLSSQKM   120
VYPGLQEPWL HSMYHGAAFQ LTQGDQLSTH TDGIPHLVLS PSTVFFGAFA L            171

SEQ ID NO: 54           moltype = AA  length = 196
FEATURE                 Location/Qualifiers
REGION                  1..196
                        note = Synthetic: LT-beta extracellular domain
source                  1..196
                        mol_type = protein
                        organism = synthetic construct
SEQUENCE: 54
QDQGGLVTET ADPGAQAQQG LGFQKLPEEE PETDLSPGLP AAHLIGAPLK GQGLGWETTK    60
EQAFLTSGTQ FSDAEGLALP QDGLYYLYCL VGYRGRAPPG GGDPQGRSVT LRSSLYRAGG   120
AYGPGTPELL LEGAETVTPV LDPARRQGYG PLWYTSVGFG GLVQLRRGER VYVNISHPDM   180
VDFARGKTFF GAVMVG                                                   196

SEQ ID NO: 55           moltype = AA  length = 127
FEATURE                 Location/Qualifiers
REGION                  1..127
                        note = Synthetic: BTLA extracellular domain
source                  1..127
                        mol_type = protein
                        organism = synthetic construct
SEQUENCE: 55
KESCDVQLYI KRQSEHSILA GDPFELECPV KYCANRPHVT WCKLNGTTCV KLEDRQTSWK    60
EEKNISFFIL HFEPVLPNDN GSYRCSANFQ SNLIESHSTT LYVTDVKSAS ERPSKDEMAS   120
```

```
RPWLLYR                                                                    127

SEQ ID NO: 56           moltype = AA  length = 133
FEATURE                 Location/Qualifiers
REGION                  1..133
                        note = Synthetic: CD160 extracellular domain
source                  1..133
                        mol_type = protein
                        organism = synthetic construct
SEQUENCE: 56
INITSSASQE GTRLNLICTV WHKKEEAEGF VVFLCKDRSG DCSPETSLKQ LRLKRDPGID    60
GVGEISSQLM FTISQVTPLH SGTYQCCARS QKSGIRLQGH FFSILFTETG NYTVTGLKQR   120
QHLEFSHNEG TLS                                                     133

SEQ ID NO: 57           moltype = AA  length = 149
FEATURE                 Location/Qualifiers
REGION                  1..149
                        note = Synthetic: CD40L extracellular domain
source                  1..149
                        mol_type = protein
                        organism = synthetic construct
SEQUENCE: 57
MQKGDQNPQI AAHVISEASS KTTSVLQWAE KGYYTMSNNL VTLENGKQLT VKRQGLYYIY    60
AQVTFCSNRE ASSQAPFIAS LCLKSPGRFE RILLRAANTH SSAKPCGQQS IHLGGVFELQ   120
PGASVFVNVT DPSQVSHGTG FTSFGLLKL                                    149

SEQ ID NO: 58           moltype = AA  length = 152
FEATURE                 Location/Qualifiers
REGION                  1..152
                        note = Synthetic: FasL extracellular domain
source                  1..152
                        mol_type = protein
                        organism = synthetic construct
SEQUENCE: 58
QIGHPSPPPE KKELRKVAHL TGKSNSRSMP LEWEDTYGIV LLSGVKYKKG GLVINETGLY    60
FVYSKVYFRG QSCNNLPLSH KVYMRNSKYP QDLVMMEGKM MSYCTTGQMW ARSSYLGAVF   120
NLTSADHLYV NVSELSLVNF EESQTFFGLY KL                                152

SEQ ID NO: 59           moltype = AA  length = 577
FEATURE                 Location/Qualifiers
REGION                  1..577
                        note = Synthetic: CD30L extracellular domain
source                  1..577
                        mol_type = protein
                        organism = synthetic construct
SEQUENCE: 59
FPQDRPFEDT CHGNPSHYYD KAVRRCCYRC PMGLFPTQQC PQRPTDCRKQ CEPDYYLDEA    60
DRCTACVTCS RDDLVEKTPC AWNSSRVCEC RPGMFCSTSA VNSCARCFFH SVCPAGMIVK   120
FPGTAQKNTV CEPASPGVSP ACASPENCKE PSSGTIPQAK PTPVSPATSS ASTMPVRGGT   180
RLAQEAASKL TRAPDSPSSV GRPSSDPGLS PTQPCPEGSG DCRKQCEPDY YLDEAGRCTA   240
CVSCSRDDLV EKTPCAWNSS RTCECRPGMI CATSATNSCA RCVPYPICAA ETVTKPQDMA   300
EKDTTFEAPP LGTQPDCNPT PENGEAPAST SPTQSLLVDS QASKTLPIPT SAPVALSSTG   360
KPVLDAGPVL FWVILVLVVV VGSSAFLLCH RRACRKRIRQ KLHLCYPVQT SQPKLELVDS   420
RPRRSSTQLR SGASVTEPVA EERGLMSQPL METCHSVGAA YLESLPLQDA SPAGGPSSPR   480
DLPEPRVSTE HTNNKIEKIY IMKADTVIVG TVKAELPEGR GLAGPAEPEL EEELEADHTP   540
HYPEQETEPP LGSCSDVMLS VEEEGKEDPL PTAASGK                           577

SEQ ID NO: 60           moltype = AA  length = 205
FEATURE                 Location/Qualifiers
REGION                  1..205
                        note = Synthetic: 4-1BBL extracellular domain
source                  1..205
                        mol_type = protein
                        organism = synthetic construct
SEQUENCE: 60
ACPWAVSGAR ASPGSAASPR LREGPELSPD DPAGLLDLRQ GMFAQLVAQN VLLIDGPLSW    60
YSDPGLAGVS LTGGLSYKED TKELVVAKAG VYYVFFQLEL RRVVAGEGSG SVSLALHLQP   120
LRSAAGAAAL ALTVDLPPAS SEARNSAFGF QGRLLHLSAG QRLGVHLHTE ARARHAWQLT   180
QGATVLGLFR VTPEIPAGLP SPRSE                                        205

SEQ ID NO: 61           moltype = AA  length = 172
FEATURE                 Location/Qualifiers
REGION                  1..172
                        note = Synthetic: CD27L extracellular domain
source                  1..172
                        mol_type = protein
                        organism = synthetic construct
SEQUENCE: 61
ATPAPKSCPE RHYWAQGKLC CQMCEPGTFL VKDCDQHRKA AQCDPCIPGV SFSPDHHTRP    60
```

```
HCESCRHCNS GLLVRNCTIT ANAECACRNG WQCRDKECTE CDPLPNPSLT ARSSQALSPH    120
PQPTHLPYVS EMLEARTAGH MQTLADFRQL PARTLSTHWP PQRSLCSSDF IR            172

SEQ ID NO: 62            moltype = AA  length = 186
FEATURE                  Location/Qualifiers
REGION                   1..186
                         note = Synthetic: OX40L extracellular domain
source                   1..186
                         mol_type = protein
                         organism = synthetic construct
SEQUENCE: 62
LHCVGDTYPS NDRCCHECRP GNGMVSRCSR SQNTVCRPCG PGFYNDVVSS KPCKPCTWCN    60
LRSGSERKQL CTATQDTVCR CRAGTQPLDS YKPGVDCAPC PPGHFSPGDN QACKPWTNCT    120
LAGKHTLQPA SNSSDAICED RDPPATQPQE TQGPPARPIT VQPTEAWPRT SQGPSTRPVE    180
VPGGRA                                                                186

SEQ ID NO: 63            moltype = AA  length = 156
FEATURE                  Location/Qualifiers
REGION                   1..156
                         note = Synthetic: TWEAK extracellular domain
source                   1..156
                         mol_type = protein
                         organism = synthetic construct
SEQUENCE: 63
SAPKGRKTRA RRAIAAHYEV HPRPGQDGAQ AGVDGTVSGW EEARINSSSP LRYNRQIGEF    60
IVTRAGLYYL YCQVHFDEGK AVYLKLDLLV DGVLALRCLE EFSATAASSL GPQLRLCQVS    120
GLLALRPGSS LRIRTLPWAH LKAAPFLTYF GLFQVH                               156

SEQ ID NO: 64            moltype = AA  length = 146
FEATURE                  Location/Qualifiers
REGION                   1..146
                         note = Synthetic: APRIL extracellular domain
source                   1..146
                         mol_type = protein
                         organism = synthetic construct
SEQUENCE: 64
AVLTQKQKKQ HSVLHLVPIN ATSKDDSDVT EVMWQPALRR GRGLQAQGYG VRIQDAGVYL    60
LYSQVLFQDV TFTMGQVVSR EGQGRQETLF RCIRSMPSHP DRAYNSCYSA GVFHLHQGDI    120
LSVIIPRARA KLNLSPHGTF LGFVKL                                         146

SEQ ID NO: 65            moltype = AA  length = 152
FEATURE                  Location/Qualifiers
REGION                   1..152
                         note = Synthetic: BAFF extracellular domain
source                   1..152
                         mol_type = protein
                         organism = synthetic construct
SEQUENCE: 65
AVQGPEETVT QDCLQLIADS ETPTIQKGSY TFVPWLLSFK RGSALEEKEN KILVKETGYF    60
FIYGQVLYTD KTYAMGHLIQ RKKVHVFGDE LSLVTLFRCI QNMPETLPNN SCYSAGIAKL    120
EEGDELQLAI PRENAQISLD GDVTFFGALK LL                                   152

SEQ ID NO: 66            moltype = AA  length = 249
FEATURE                  Location/Qualifiers
REGION                   1..249
                         note = Synthetic: RANKL extracellular domain
source                   1..249
                         mol_type = protein
                         organism = synthetic construct
SEQUENCE: 66
YFRAQMDPNR ISEDGTHCIY RILRLHENAD FQDTTLESQD TKLIPDSCRR IKQAFQGAVQ    60
KELQHIVGSQ HIRAEKAMVD GSWLDLAKRS KLEAQPFAHL TINATDIPSG SHKVSLSSWY    120
HDRGWAKISN MTFSNGKLIV NQDGFYYLYA NICFRHHETS GDLATEYLQL MVYVTKTSIK    180
IPSSHTLMKG GSTKYWSGNS EHFHFYSINVG GFFKLRSGEE ISIEVSNPSL LDPDQDATYF   240
GAFKVRDID                                                             249

SEQ ID NO: 67            moltype = AA  length = 243
FEATURE                  Location/Qualifiers
REGION                   1..243
                         note = Synthetic: TRAIL extracellular domain
source                   1..243
                         mol_type = protein
                         organism = synthetic construct
SEQUENCE: 67
TNELKQMQDK YSKSGIACFL KEDDSYWDPN DEESMNSPCW QVKWQLRQLV RKMILRTSEE    60
TISTVQEKQQ NISPLVRERG PQRVAAHITG TRGRSNTLSS PNSKNEKALG RKINSWESSR    120
SGHSFLSNLH LRNGELVIHE KGFYYIYSQT YFRFQEEIKE NTKNDKQMVQ YIYKYTSYPD    180
PILLMKSARN SCWSKDAEYG LYSIYQGGIF ELKENDRIFV SVTNEHLIDM DHEASFFGAF    240
LVG                                                                   243
```

```
SEQ ID NO: 68            moltype = AA   length = 329
FEATURE                  Location/Qualifiers
REGION                   1..329
                         note = Synthetic: EDA1 extracellular domain
source                   1..329
                         mol_type = protein
                         organism = synthetic construct
SEQUENCE: 68
ELRSELRRER GAESRLGGSG TPGTSGTLSS LGGLDPDSPI TSHLGQPSPK QQPLEPGEAA   60
LHSDSQDGHQ MALLNFFFPD EKPYSEEESR RVRRNKRSKS NEGADGPVKN KKKGKKAGPP  120
GPNGPPGPPG PPGPQGPPGI PGIPGIPGTT VMGPPGPPGP PGPQGPPGLQ GPSGAADKAG  180
TRENQPAVVH LQGQGSAIQV KNDLSGGVLN DWSRITMNPK VFKLHPRSGE LEVLVDGTYF  240
IYSQVEVYYI NFTDFASYEV VVDEKPFLQC TRSIETGKTN YNTCYTAGVC LLKARQKIAV  300
KMVHADISIN MSKHTTFFGA IRLGEAPAS                                   329

SEQ ID NO: 69            moltype = AA   length = 73
FEATURE                  Location/Qualifiers
REGION                   1..73
                         note = Synthetic: EDA2 extracellular domain
source                   1..73
                         mol_type = protein
                         organism = synthetic construct
SEQUENCE: 69
ELRSELRRER GAESRLGGSG TPGTSGTLSS LGGLDPDSPI TSHLGQPSPK QQPLEPGEAA   60
LHSDSQDGHQ GHQ                                                     73

SEQ ID NO: 70            moltype = AA   length = 128
FEATURE                  Location/Qualifiers
REGION                   1..128
                         note = Synthetic: GITRL extracellular domain
source                   1..128
                         mol_type = protein
                         organism = synthetic construct
SEQUENCE: 70
QLETAKEPCM AKFGPLPSKW QMASSEPPCV NKVSDWKLEI LQNGLYLIYG QVAPNANYND   60
VAPFEVRLYK NKDMIQTLTN KSKIQNVGGT YELHVGDTID LIFNSEHQVL KNNTYWGIIL  120
LANPQFIS                                                          128

SEQ ID NO: 71            moltype = AA   length = 208
FEATURE                  Location/Qualifiers
REGION                   1..208
                         note = Synthetic: CD80 (B7-1) extracellular domain
source                   1..208
                         mol_type = protein
                         organism = synthetic construct
SEQUENCE: 71
VIHVTKEVKE VATLSCGHNV SVEELAQTRI YWQKEKKMVL TMMSGDMNIW PEYKNRTIFD   60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                    208

SEQ ID NO: 72            moltype = AA   length = 224
FEATURE                  Location/Qualifiers
REGION                   1..224
                         note = Synthetic: CD86 (B7-2) extracellular domain
source                   1..224
                         mol_type = protein
                         organism = synthetic construct
SEQUENCE: 72
APLKIQAYFN ETADLPCQFA NSQNQSLSEL VVFWQDQENL VLNEVYLGKE KFDSVHSKYM   60
GRTSFDSDSW TLRLHNLQIK DKGLYQCIIH HKKPTGMIRI HQMNSELSVL ANFSQPEIVP  120
ISNITENVYI NLTCSSIHGY PEPKKMSVLL RTKNSTIEYD GVMQKSQDNV TELYDVSISL  180
SVSFPDVTSN MTIFCILETD KTRLLSSPFS IELEDPQPPP DHIP                  224

SEQ ID NO: 73            moltype = AA   length = 238
FEATURE                  Location/Qualifiers
REGION                   1..238
                         note = Synthetic: ICOSLG extracellular domain
source                   1..238
                         mol_type = protein
                         organism = synthetic construct
SEQUENCE: 73
DTQEKEVRAM VGSDVELSCA CPEGSRFDLN DVYVYWQTSE SKTVVTYHIP QNSSLENVDS   60
RYRNRALMSP AGMLRGDFSL RLFNVTPQDE QKFHCLVLSQ SLGFQEVLSV EVTLHVAANF  120
SVPVVSAPHS PSQDELTFTC TSINGYPRPN VYWINKTDNS LLDQALQNDT VPLNMRGLYD  180
VVSVLRIART PSVNIGCCIE NVLLQQNLTV GSQTGNDIGE RDKITENPVS TGEKNAAT   238

SEQ ID NO: 74            moltype = AA   length = 284
```

```
FEATURE                 Location/Qualifiers
REGION                  1..284
                        note = Synthetic: MICA extracellular domain
source                  1..284
                        mol_type = protein
                        organism = synthetic construct
SEQUENCE: 74
EPHSLRYNLT VLSWDGSVQS GFLTEVHLDG QPFLRCDRQK CRAKPQGQWA EDVLGNKTWD    60
RETRDLTGNG KDLRMTLAHI KDQKEGLHSL QEIRVCEIHE DNSTRSSQHF YYDGELFLSQ  120
NLETKEWTMP QSSRAQTLAM NVRNFLKEDA MKTKTHYHAM HADCLQELRR YLKSGVVLRR  180
TVPPMVNVTR SEASEGNITV TCRASGFYPW NITLSWRQDG VSLSHDTQQW GDVLPDGNGT  240
YQTWVATRIC QGEEQRFTCY MEHSGNHSTH PVPSGKVLVL QSHW                   284

SEQ ID NO: 75           moltype = AA  length = 287
FEATURE                 Location/Qualifiers
REGION                  1..287
                        note = Synthetic: MICB extracellular domain
source                  1..287
                        mol_type = protein
                        organism = synthetic construct
SEQUENCE: 75
AEPHSLRYNL MVLSQDESVQ SGFLAEGHLD GQPFLRYDRQ KRRAKPQGQW AEDVLGAKTW    60
DTETEDLTEN GQDLRRTLTH IKDQKGGLHS LQEIRVCEIH EDSSTRGSRH FYYDGELFLS  120
QNLETQESTV PQSSRAQTLA MNVTNFWKED AMKTKTHYRA MQADCLQKLQ RYLKSGVAIR  180
RTVPPMVNVT CSEVSEGNIT VTCRASSFYP RNITLTWRQD GVSLSHNTQQ WGDVLPDGNG  240
TYQTWVATRI RQGEEQRFTC YMEHSGNHGT HPVPSGKVLV LQSQRTD                287

SEQ ID NO: 76           moltype = AA  length = 191
FEATURE                 Location/Qualifiers
REGION                  1..191
                        note = Synthetic: ULBP1 extracellular domain
source                  1..191
                        mol_type = protein
                        organism = synthetic construct
SEQUENCE: 76
GWVDTHCLCY DFIITPKSRP EPQWCEVQGL VDERPFLHYD CVNHKAKAFA SLGKKVNVTK    60
TWEEQTETLR DVVDFLKGQL LDIQVENLIP IEPLTLQARM SCEHEAHGHG RGSWQFLFNG  120
QKFLLFDSNN RKWTALHPGA KKMTEKWEKN RDVTMFFQKI SLGDCKMWLE EFLMYWEQML  180
DPTKPPSLAP G                                                       191

SEQ ID NO: 77           moltype = AA  length = 191
FEATURE                 Location/Qualifiers
REGION                  1..191
                        note = Synthetic: ULBP2 extracellular domain
source                  1..191
                        mol_type = protein
                        organism = synthetic construct
SEQUENCE: 77
GRADPHSLCY DITVIPKFRP GPRWCAVQGQ VDEKTFLHYD CGNKTVTPVS PLGKKLNVTT    60
AWKAQNPVLR EVVDILTEQL RDIQLENYTP KEPLTLQARM SCEQKAEGHS SGSWQFSFDG  120
QIFLLFDSEK RMWTTVHPGA RKMKEKWEND KVVAMSFHYF SMGDCIGWLE DFLMGMDSTL  180
EPSAGAPLAM S                                                       191

SEQ ID NO: 78           moltype = AA  length = 188
FEATURE                 Location/Qualifiers
REGION                  1..188
                        note = Synthetic: ULBP3 extracellular domain
source                  1..188
                        mol_type = protein
                        organism = synthetic construct
SEQUENCE: 78
DAHSLWYNFT IIHLPRHGQQ WCEVQSQVDQ KNFLSYDCGS DKVLSMGHLE EQLYATDAWG    60
KQLEMLREVG QRLRLELADT ELEDFTPSGP LTLQVRMSCE CEADGYIRGS WQFSFDGRKF  120
LLFDSNNRKW TVVHAGARRM KEKWEKDSGL TTFFKMVSMR DCKSWLRDFL MHRKKRLEPT  180
APPTMAPG                                                           188

SEQ ID NO: 79           moltype = AA  length = 195
FEATURE                 Location/Qualifiers
REGION                  1..195
                        note = Synthetic: ULBP4 extracellular domain
source                  1..195
                        mol_type = protein
                        organism = synthetic construct
SEQUENCE: 79
HSLCFNFTIK SLSRPGQPWC EAQVFLNKNL FLQYNSDNNM VKPLGLLGKK VYATSTWGEL    60
TQTLGEVGRD LRMLLCDIKP QIKTSDPSTL QVEMFCQREA ERCTGASWQF ATNGEKSLLF  120
DAMNMTWTVI NHEASKIKET WKKDRGLEKY FRKLSKGDCD HWLREFLGHW EAMPEPTVSP  180
VNASDIHWSS SSLPD                                                   195
```

```
SEQ ID NO: 80            moltype = AA  length = 193
FEATURE                  Location/Qualifiers
REGION                   1..193
                         note = Synthetic: ULBP5, isoform 1 extracellular domain
source                   1..193
                         mol_type = protein
                         organism = synthetic construct
SEQUENCE: 80
GLADPHSLCY DITVIPKFRP GPRWCAVQGQ VDEKTFLHYD CGSKTVTPVS PLGKKLNVTT    60
AWKAQNPVLR EVVDILTEQL LDIQLENYIP KEPLTLQARM SCEQKAEGHG SGSWQLSFDG   120
QIFLLFDSEN RMWTTVHPGA RKMKEKWEND KDMTMSFHYI SMGDCTGWLE DFLMGMDSTL   180
EPSAGAPPTM SSG                                                     193

SEQ ID NO: 81            moltype = AA  length = 188
FEATURE                  Location/Qualifiers
REGION                   1..188
                         note = Synthetic: ULBP5, isoform 2 extracellular domain
source                   1..188
                         mol_type = protein
                         organism = synthetic construct
SEQUENCE: 81
GLADPHSLCY DITVIPKFRP GPRWCAVQGQ VDEKTFLHYD CGSKTVTPVS PLGKKLNVTT    60
AWKAQNPVLR EVVDILTEQL LDIQLENYIP KEPLTLQARM SCEQKAEGHG SGSWQLSFDG   120
QIFLLFDSEN RMWTTVHPGA RKMKEKWEND KDMTMSFHYI SMGDCTGWLE DFLMGMDSTL   180
EPSAGGTV                                                           188

SEQ ID NO: 82            moltype = AA  length = 193
FEATURE                  Location/Qualifiers
REGION                   1..193
                         note = Synthetic: ULBP6 extracellular domain
source                   1..193
                         mol_type = protein
                         organism = synthetic construct
SEQUENCE: 82
RRDDPHSLCY DITVIPKFRP GPRWCAVQGQ VDEKTFLHYD CGNKTVTPVS PLGKKLNVTM    60
AWKAQNPVLR EVVDILTEQL LDIQLENYTP KEPLTLQARM SCEQKAEGHS SGSWQFSIDG   120
QTFLLFDSEK RMWTTVHPGA RKMKEKWEND KDVAMSFHYI SMGDCIGWLE DFLMGMDSTL   180
EPSAGAPLAM SSG                                                     193

SEQ ID NO: 83            moltype = AA  length = 217
FEATURE                  Location/Qualifiers
REGION                   1..217
                         note = Synthetic: SLAMF1 extracellular domain
source                   1..217
                         mol_type = protein
                         organism = synthetic construct
SEQUENCE: 83
ASYGTGGRMM NCPKILRQLG SKVLLPLTYE RINKSMNKSI HIVVTMAKSL ENSVENKIVS    60
LDPSEAGPPR YLGDRYKFYL ENLTLGIRES RKEDEGWYLM TLEKNVSVQR FCLQLRLYEQ   120
VSTPEIKVLN KTQENGTCTL ILGCTVEKGD HVAYSWSEKA GTHPLNPANS SHLLSLTLGP   180
QHADNIYICT VSNPISNNSQ TFSPWPGCRT DPSETKP                           217

SEQ ID NO: 84            moltype = AA  length = 194
FEATURE                  Location/Qualifiers
REGION                   1..194
                         note = Synthetic: SLAMF2 extracellular domain
source                   1..194
                         mol_type = protein
                         organism = synthetic construct
SEQUENCE: 84
QGHLVHMTVV SGSNVTLNIS ESLPENYKQL TWFYTFDQKI VEWDSRKSKY FESKFKGRVR    60
LDPQSGALYI SKVQKEDNST YIMRVLKKTG NEQEWKIKLQ VLDPVPKPVI KIEKIEDMDD   120
NCYLKLSCVI PGESVNYTWY GDKRPFPKEL QNSVLETTLM PHNYSRCYTC QVSNSVSSKN   180
GTVCLSPPCT LARS                                                    194

SEQ ID NO: 85            moltype = AA  length = 407
FEATURE                  Location/Qualifiers
REGION                   1..407
                         note = Synthetic: SLAMF3 extracellular domain
source                   1..407
                         mol_type = protein
                         organism = synthetic construct
SEQUENCE: 85
KDSAPTVVSG ILGGSVTLPL NISVDTEIEN VIWIGPKNAL AFARPKENVT IMVKSYLGRL    60
DITKWSYSLC ISNLTLNDAG SYKAQINQRN FEVTTEEEFT LFVYEQLQEP QVTMKSVKVS   120
ENFSCNITLM CSVKGAEKSV LYSWTPREPH ASESNGGSIL TVSRTPCDPD LPYICTAQNP   180
VSQRSSLPVH VGQFCTDPGA SRGGTTGETV VGVLGEPVTL PLALPACRDT EKVVWLFNTS   240
IISKEREEAA TADPLIKSRD PYKNRVWVSS QDCSLKISQL KIEDAGPYHA YVCSEASSVT   300
SMTHVTLLIY RRLRKPKITW SLRHSEDGIC RISLTCSVED GGNTVMYTWT PLQKEAVVSQ   360
```

```
GESHLNVSWR SSENHPNLTC TASNPVSRSS HQFLSENICS GPERNTK              407

SEQ ID NO: 86           moltype = AA  length = 208
FEATURE                 Location/Qualifiers
REGION                  1..208
                        note = Synthetic: SLAMF4 extracellular domain
source                  1..208
                        mol_type = protein
                        organism = synthetic construct
SEQUENCE: 86
CQGSADHVVS ISGVPLQLQP NSIQTKVDSI AWKKLLPSQN GFHHILKWEN GSLPSNTSND  60
RFSFIVKNLS LLIKAAQQQD SGLYCLEVTS ISGKVQTATF QVFVFESLLP DKVEKPRLQG 120
QGKILDRGRC QVALSCLVSR DGNVSYAWYR GSKLIQTAGN LTYLDEEVDI NGTHTYTCNV 180
SNPVSWESHT LNLTQDCQNA HQEFRFWP                                   208

SEQ ID NO: 87           moltype = AA  length = 204
FEATURE                 Location/Qualifiers
REGION                  1..204
                        note = Synthetic: SLAMF5 extracellular domain
source                  1..204
                        mol_type = protein
                        organism = synthetic construct
SEQUENCE: 87
KDSEIFTVNG ILGESVTFPV NIQEPRQVKI IAWTSKTSVA YVTPGDSETA PVVTVTHRNY  60
YERIHALGPN YNLVISDLRM EDAGDYKADI NTQADPYTTT KRYNLQIYRR LGKPKITQSL 120
MASVNSTCNV TLTCSVEKEE KNVTYNWSPL GEEGNVLQIF QTPEDQELTY TCTAQNPVSN 180
NSDSISARQL CADIAMGFRT HHTG                                       204

SEQ ID NO: 88           moltype = AA  length = 205
FEATURE                 Location/Qualifiers
REGION                  1..205
                        note = Synthetic: SLAMF6 extracellular domain
source                  1..205
                        mol_type = protein
                        organism = synthetic construct
SEQUENCE: 88
QSSLTPLMVN GILGESVTLP LEFPAGEKVN FITWLFNETS LAFIVPHETK SPEIHVTNPK  60
QGKRLNFTQS YSLQLSNLKM EDTGSYRAQI STKTSAKLSS YTLRILRQLR NIQVTNHSQL 120
FQNMTCELHL TCSVEDADDN VSFRWEALGN TLSSQPNLTV SWDPRISSEQ DYTCIAENAV 180
SNLSFSVSAQ KLCEDVKIQY TDTKM                                      205

SEQ ID NO: 89           moltype = AA  length = 204
FEATURE                 Location/Qualifiers
REGION                  1..204
                        note = Synthetic: SLAMF7 extracellular domain
source                  1..204
                        mol_type = protein
                        organism = synthetic construct
SEQUENCE: 89
SGPVKELVGS VGGAVTFPLK SKVKQVDSIV WTFNTTPLVT IQPEGGTIIV TQNRNRERVD  60
FPDGGYSLKL SKLKKNDSGI YYVGIYSSSL QQPSTQEYVL HVYEHLSKPK VTMGLQSNKN 120
GTCVTNLTCC MEHGEEDVIY TWKALGQAAN ESHNGSILPI SWRWGESDMT FICVARNPVS 180
RNFSSPILAR KLCEGAADDP DSSM                                       204

SEQ ID NO: 90           moltype = AA  length = 1464
FEATURE                 Location/Qualifiers
REGION                  1..1464
                        note = misc_feature - human alpha1 chain precursor of type
                        I collagen
source                  1..1464
                        mol_type = protein
                        organism = Homo sapiens
SEQUENCE: 90
MFSFVDLRLL LLLAATALLT HGQEEGQVEG QDEDIPPITC VQNGLRYHDR DVWKPEPCRI  60
CVCDNGKVLC DDVICDETKN CPGAEVPEGE CCPVCPDGSE SPTDQETTGV EGPKGDTGPR 120
GPRGPAGPPG RDGIPGQPGL PGPPGPPGPP GPPGLGGNFA PQLSYGYDEK STGGISVPGP 180
MGPSGPRGLP GPPGAPGPQG FQGPPGEPGE PGASGPMGPR GPPGPPGKNG DDGEAGKPGR 240
PGERGPPGPQ GARGLPGTAG LPGMKGHRGF SGLDGAKGDA GPAGPKGEPG SPGENGAPGQ 300
MGPRGLPGER GRPGAPGPAG ARGNDGATGA AGPPGPTGPA GPPGFPGAVG AKGEAGPQGP 360
RGSEGPQGVR GEPGPPGPAG AAGPAGNPGA DGQPGAKGAN GAPGIAGAPG FPGARGPSGP 420
QGPGGPPGPK GNSGEPGAPG SKGDTGAKGE PGPVGVQGPP GPAGEEGKRG ARGEPGPTGL 480
PGPPGERGGP GSRGFPGADG VAGPKGPAGE RGSPGPAGPK GSPGEAGRPG EAGLPGAKGL 540
TGSPGSPGPD GKTGPPGPAG QDGRPGPPGP PGARGQAGVM PPGEAGAAGA EPGKAGERGV 600
PGPPGAVGPA GKDGEAGAQG PPGPAGPAGE RGEQGPAGSP GFQGLPGPAG PPGEAGKPGE 660
QGVPGDLGAP GPSGARGERG FPGERGVQGP PGPAGPRGAN GAPGNDGAKG DAGAPGAPGS 720
QGAPGLQGMP GERGAAGLPG PKGDRGDAGP KGADGSPGKD GVRGLTGPIG PPGPAGAPGD 780
KGESGPSGPA GPTGARGAPG DRGEPGPPGP AGFAGPPGAD GQPGAKGEPG DAGAKGDAGP 840
PGPAGPAGPP GPIGNVGAPG AKGARGSAGP PGATGFPGAA GRVGPPGPSG NAGPPGPPGP 900
AGKEGGKGPR GETGPAGRPG EVGPPGPPGP AGEKGSPGAD GPAGAPGTPG PQGIAGQRGV 960
```

```
VGLPGQRGER GFPGLPGPSG EPGKQGPSGA SGERGPPGPM GPPGLAGPPG ESGREGAPGA   1020
EGSPGRDGSP GAKGDRGETG PAGPPGAPGA PGAGPGVGPA GKSGDRGETG PAGPAGVGP    1080
VGARGPAGPQ GPRGDKGETG EQGDRGIKGH RGFSGLQGPP GPPGSPGEQG PSGASGPAGP   1140
RGPPGSAGAP GKDGLNGLPG PIGPPGPRGR TGDAGPVGPP GPPGPPGPPG PPSAGFDFSF   1200
LPQPPQEKAH DGGRYYRADD ANVVRDRDLE VDTTLKSLSQ QIENIRSPEG SRKNPARTCR   1260
DLKMCHSDWK SGEYWIDPNQ GCNLDAIKVF CNMETGETCV YPTQPSVAQK NWYISKNPKD   1320
KRHVWFGESM TDGFQFEYGG QGSDPADVAI QLTFLRLMST EASQNITYHC KNSVAYMDQQ   1380
TGNLKKALLL QGSNEIEIRA EGNSRFTYSV TVDGCTSHTG AWGKTVIEYK TTKTSRLPII   1440
DVAPLDVGAP DQEFGFDVGP VCFL                                         1464

SEQ ID NO: 91            moltype = AA   length = 1366
FEATURE                  Location/Qualifiers
REGION                   1..1366
                         note = misc_feature - human alpha2 chain precursor of type
                         I collagen
source                   1..1366
                         mol_type = protein
                         organism = Homo sapiens
SEQUENCE: 91
MLSFVDTRTL LLLAVTLCLA TCQSLQEETV RKGPAGDRGP RGERGPPGPP GRDGEDGPTG   60
PPGPPGPPGP PGLGGNFAAQ YDGKGVGLGP GPMGLMGPRG PPGAAGAPGP QGFQGPAGEP   120
GEPGQTGPAG ARGPAGPPGK AGEDGHPGKP GRPGERGVVG PGPGARGFPGT PGLPGFKGIR   180
GHNGLDGLKG QPGAPGVKGE PGAPGENGTP GQTGARGLPG ERGRVGAPGP AGARGSDGSV   240
GPVGPAGPIG SAGPPGFPGA PGPKGEIGAV GNAGPAGPAG PRGEVGLPGL SGPVGPPGNP   300
GANGLTGAKG AAGLPGVAGA PGLPGPRGIP GPVGAAGATG ARGLVGEPGP AGSKGESGNK   360
GEPGSAGPQG PPGPSGEEGK RGPNGEAGSA GPPGPPGLRG PGSRGLPGA DGRAGVMGPP    420
GSRGASGPAG VRGPNGDAGR PGEPGLMGPR GLPGSPGNIG PAGKEGPVGL PGIDGRPGPI   480
GPAGARGEPG NIGFPGPKGP TGDPGKNGDK GHAGLAGARG APGPDGNNGA QGPPGPQGVQ   540
GGKGEQGPPG PPGFQGLPGP SGPAGEVGKP GERGLHGEFG LPGPAGPRGE RGPPGESGAA   600
GPTGPIGSRG PSGPPGPDGN KGEPGVVGAV GTAGPSGPSG IGPERGAAGI PGGKGEKGEP   660
GLRGEIGNPG RDGARGAPGA VGAPGPAGAT GDRGEAGAAG PAGPAGPRGS PGERGEVGPA   720
GPNGFAGPAG AAGQPGAKGE RGAKGPKGEN GVVGPTGPVG AAGPAGPNGP PGPAGSRGDG   780
GPPGMTGFPG AAGRTGPPGP SGISGPPGPP GPAGKEGLRG PRGDQGPVGR TGEVGAVGPP   840
GFAGEKGPSG EAGTAGPPGT PGPQGLLGAP GILGLPGSRG ERGLPGVAGA VGEPGPLGIA   900
GPPGARGPPG AVGSPGVNGA PGEAGRDGNP GNDGPPGRDG QPGHKGERGY PGNIGPVGAA   960
GAPGPHGPVG PAGKHGNRGE TGPSGPVGPA GAVGPRGPSG PQGIRGDKGE PGEKGPRGLP   1020
GLKGHNGLQG LPGIAGHHGD QGAPGSVGPA GPRGPAGPSG PAGKDGRTGH PGTVGPAGIR   1080
GPQGHQGPAG PPGPPGPPGP PGVSGGGYDF GYDGDFYRAD QPRSAPSLRP KDYEVDATLK   1140
SLNNQIETLL TPEGSRKNPA RTCRDLRLSH PEWSSGYYWI DPNQGCTMDA IKVYCDFSTG   1200
ETCIRAQPEN IPAKNWYRSS KDKKHVWLGE TINAGSQFEY NVEGVTSKEM ATQLAFMRLL   1260
ANYASQNITY HCKNSIAYMD EETGNLKKAV ILQGSNDVEL VAEGNSRFTY TVLVDGCSKK   1320
TNEWGKTIIE YKTNKPSRLP FLDIAPLDIG GADQEFFVDI GPVCFK                  1366

SEQ ID NO: 92            moltype = AA   length = 1605
FEATURE                  Location/Qualifiers
REGION                   1..1605
                         note = misc_feature - human alpha1 chain of type IV collagen
source                   1..1605
                         mol_type = protein
                         organism = Homo sapiens
SEQUENCE: 92
MQGPEGPQGP PGQKGDTGEP GLPGTKGTRG PPGASGYPGN PGLPGIPGQD GPPGPPGIPG   60
CNGTKGERGP LGPPGLPGFA GNPGPPGLPG MKGDPGEILG HVPGMLLKGE RGFPGIPGTP   120
GPPGLPGLQG PVGPPGFTGP PGPPGPPGPP GEKGQMGLSF QGPKGDKGDQ GVSGPPGVPG   180
QAQVQEKGDF ATKGEKGQKG EPGFQGMPGV GEKGEPGKPG PRGKPGKDGD KGEKGSPGFP   240
GEPGYPGLIG RQGPQGEKGE AGPPGPPGIV IGTGPLGEKG ERGYPGTPGP REGPGPKGFP   300
GLPGQPGPPG LPVPGQAGAP GFPGERGEKG DRGFPGTSLP GPSGRDGLPG PPGSPGPPGQ   360
PGYTNGIVEC QPGPPGDQGP PGIPGQPGFI GEIGEKGQKG ESCLICDIDG YRGPPGPQGP   420
PGEIGFPGQP GAKGDRGLPG RDGVAGVPGP QGTPGLIGQP GAKGEPGEFY FDLRLKGDKG   480
DPGFPGQPGM PGRAGSPGRD GHPGLPGPKG SPGSVGLKGE RGPPGGVGFP GSRGDTGPPG   540
PPGYGPAGPI GDKGQAGFPG GPGSPGLPGP KGEPGKIVPL PGPPGAEGLP GSPGFPGPQG   600
DRGFPGTPGR PGLPGEKGAV GQPGIGFPGP PGPKGVDGLP GDMGPPGTPG RPGFNGLPGN   660
PGVQGQPGGP GVGLPGLKGL PGLPGIPGTP GEKGSIGVPG VPGEHGAIGP PGLQGIPGLP   720
GPPGLPGSVG SPGVPGIGPP GARGPPGGQG PPGLSGPPGI KGEKGFPGFP GLDMPGPKGD   780
KGAQGLPGIT GQSGLPGLPG QQGAPGIPGF PGSKGEMGVM GTPGQPGSPG PVGAPGLPGE   840
KGDHGFPGSS GPRGDPGLKG DKGDVGLPGK PGSMDKVDMG SMKGQKGDQG EKGQIGPIGE   900
KGSRGDPGTP GVPGKDGQAG QPGQPGPKGD PGISGTPGAP GLPGPKGSVG GMGLPGTPGE   960
KGVPGIPGPQ GSPGLPGDKG AKGEKGQAGP PGIGIPGLRG EKGDQGIAGF PGSPGEKGEK   1020
GSIGIPGMPG SPGLKGSPGS VGYPGSPGLP GEKGDKGLPG LDGIPGVKGE AGLPGTPGPT   1080
GPAGQKGEPG SDGIPGSAGE KGEPGLPGRG FPGFPGAKGD KGSKGEVGFP GLAGSPGIPG   1140
SKGEQGFMGP PGPQGQPGLP GSPGHATEGP KGDRGPQGQP GLPGLPGPMG PPGLPGIDGV   1200
KGDKGNPGWP GAPGVPGPKG DPGFQGMPGI GGSPGITGSK GDMGPPGVPG FQGPKGLPGL   1260
QGIKGDQGDQ GVPGAKGLPG PPGPPGPYDI IKGEPGLPGP EGPPGLKGLQ GLPGPKGQQG   1320
VTGLVGIPGP PGIPGFDGAP GQKGEMGPAG PTGPRGFPGP PGPDGLPGSM GPPGTPSVDH   1380
GFLVTRHSQT IDDPQCPSGT KILYHGYSLL YVQGNERAHG QDLGTAGSCL RKFSTMPFLF   1440
CNINNVCNFA SRNDYSYWLS TPEPMPMSMA PITGENIRPF ISRCAVCEAP AMVMAVHSQT   1500
IQIPPCPSGW SSLWIGYSFV MHTSAGAEGS GQALASPGSC LEEFRSAPFI ECHGRGTCNY   1560
YANAYSFWLA TIERSEMFKK PTPSTLKAGE LRTHVSRCQV CMRRT                   1605
```

```
SEQ ID NO: 93           moltype = AA  length = 1712
FEATURE                 Location/Qualifiers
REGION                  1..1712
                        note = misc_feature - human alpha2 chain of type IV collagen
source                  1..1712
                        mol_type = protein
                        organism = Homo sapiens
SEQUENCE: 93
MGRDQRAVAG PALRRWLLLG TVTVGFLAQS VLAGVKKFDV PCGGRDCSGG CQCYPEKGGR   60
GQPGPVGPQG YNGPPGLQGF PGLQGRKGDK GERGAPGVTG PKGDVGARGV SGFPGADGIP  120
GHPGQGGPRG RPGYDGCNGT QGDSGPQGPP GSEGFTGPPG PQGPKGQKGE PYALPKEERD  180
RYRGEPGEPG LVGFQGPPGR PGHVGQMGPV GAPGRPGPPG PPGPKGQQGN RGLGFYGVKG  240
EKGDVGQPGP NGIPSDTLHP IIAPTGVTFH PDQYKGEKGS EGEPGIRGIS LKGEEGIMGF  300
PGLRGYPGLS GEKGSPGQKG SRGLDGYQGP DGPRGPKGEA GDPGPPGLPA YSPHPSLAKG  360
ARGDPGFPGA QGEPGSQGEP GDPGLPGPPG LSIGDGDQRR GLPGEMGPKG FIGDPGIPAL  420
YGGPPGPDGK RGPPGPPGLP GPPGPDGFLF GLKGAKGRAG FPGLPGSPGA RGPKGWKGDA  480
GECRCTEGDE AIKGLPGLPG PKGFAGINGE PGRKGDRGDP GQHGLPGFPG LKGVPGNIGA  540
PGPKGAKGDS RTITTKGERG QPGVPGVPGM KGDDGSPGRD GLDGFPGLPG PPGDGIKGPP  600
GDPGYPGIPG TKGTPGEMGP PGLGLPGLKG QRGFPGDAGL PGPPGFLGPP GPAGTPGQID  660
CDTDVKRAVG GDRQEAIQPG CIGGPKGLPG LPGPPGPTGA KGLRGIPGFA GADGGPGPRG  720
LPGDAGREGF PGPPGFIGPR GSKGAVGLPG PDGSPGPIGL PGPDGPPGER GLPGEVLGAQ  780
PGPRGDAGVP GQPGLKGLPG DRGPPGFRGS QGMPGMPGLG ESYGSKEGAP GDTGNPGAPG  840
HGFPGAPGQE GPLGLPGIPG REGLPGDRGD PGDTGAPGPV GMKGLSGDRG DAGFTGEQGH  900
PGSPGFKGSR GMPGTPGLKG DRGSPGMDGF QGMPGLKGRP GFPGSKGEAG FFGIPGLKGL  960
AGEPGFKGSR GDPGPPGPPP VILPGMKDIK GEKGDEGPMG LKGYLGAKGI QGMPGIPGLS 1020
GIPGLPGRPG HIKGVKGDIG VPGIPGLPGF PGVAGPPGIT GFPGFIGSRG DKGAPGRAGL 1080
YGEIGATGDF GDIGDTINLP GRPGLKGERG TTGIPGLKGF FGEKGTEGDI GFPGITGVTG 1140
VQGPPGLKGQ TGFPGLTGPP GSQGELGRIG LPGGKGDDGW PGAPGLPGFP GLRGIRGLHG 1200
LPGTKGFPGS PGSDIHGDPG FPGPPGERGD PGEANTLPGP VGVPGQKGDQ GAPGERGPPG 1260
SPGLQGFPGI TPPSNISGAP GDKGAPGIFG LKGYRGPPGF PGSAALPGSK GDTGNPGAPG 1320
TPGTKGWAGD SGPQGRPGVF GLPGEKGPRG EQGFMGNTGP TGAVGDRGPK GPKGDPGFPG 1380
APGTVGAPGI AGIPQKIAVQ PGTVGPQGRR GPPGAPGEMG PQGPPGEPGF RGAPGKAGPQ 1440
GRGGVSAVPG FRGDEGPIGH QGPIGQEGAP GRPGSPGLPG MPGRSVSIGY LLVKHSQTDQ 1500
EPMCPVGMNK LWSGYSLLYF EGQEKAHNQD LGLAGSCLAR FSTMPFLYCN PGDVCYYASR 1560
NDKSYWLSTT APLPMMPVAE DEIKPYISRC SVCEAPAIAI AVHSQDVSIP HCPAGWRSLW 1620
IGYSFLMHTA AGDEGGGQSL VSPGSCLEDF RATPFIECNG GRGTCHYYAN KYSFWLTTIP 1680
EQSFQGSPSA DTLKAGLIRT HISRCQVCMK NL                             1712

SEQ ID NO: 94           moltype = AA  length = 1670
FEATURE                 Location/Qualifiers
REGION                  1..1670
                        note = misc_feature - human alpha3 chain of type IV collagen
source                  1..1670
                        mol_type = protein
                        organism = Homo sapiens
SEQUENCE: 94
MSARTAPRPQ VLLLPLLLVL LAAAPAASKG CVCKDKGQCF CDGAKGEKGE KGFPGPPGSP   60
GQKGFTGPEG LPGPQGPKGF PGLPGLTGSK GVRGISGLPG FSGSPGLPGT PGNTGPYGLV  120
GVPGCSGSKG EQGFPGLPGT LGYPGIPGAA GLKGQKGAPA KEEDIELDAK GDPGLPGAPG  180
PQGLPGPPGF PGPVGPPGPP GFFGFPGAMG PRGPKGHMGE RVIGHKGERG VKGLTGPPGP  240
PGTVIVTLTG PDNRTDLKGE KGDKGAMGEP GPPGPSGLPG ESYGSEKGAP GDPGLQGKPG  300
KDGVPGFPGS EGVKGNRGFP GLMGEDGIKG QKGDIGPPGF RGPTEYYDTY QEKGDEGTPG  360
PPGPRGARGP QGPSGPPGVP GSPGSSRPGL RGAPGWPGLK GSKGERGRPG KDAMGTPGSP  420
GCAGSPGLPG SPGPPGPPGD IVFRKGPPGD HGLPGYLGSP GIPGVDGPKG EPGLLCTQCP  480
YIPGPPGLPG LPGLHGVKGI PGRQGAAGLK GSPGSPGNTG LPGFPGFPGA QGDPGLKGEK  540
GETLQPEGQV GVPGDPGLRG QPGRKGLDGI PGTPGVKGLP GPKGELALSG EKGDQGPPGD  600
PGSPGSPGPA GPAGPPGYGP QGEPGLQGTQ GVPGAPGPPG EAGPRGELSV STPVPGPPGP  660
PGPPGHPGPQ GPPGIPGSLG KCGDPGLPGP DGEPGIPGIG FPGPPGPKGD QGFPGTKGSL  720
GCPGKMGEPG LPGKPGLPGA KGEPAVAMPG GPGTPGFPGE RGNSGEHGEI GLPGLPGLPG  780
TPGNEGLDGP RGDPGQPGPP GEQGPPGRCI EGPRGAQGLP GLNGLKGQQG RRGKTGPKGD  840
PGIPGLDRSG FPGETGSPGI PGHQGEMGPL GQRYPGNPG ILGPPGEDGV IGMMGFPGAI  900
GPPGPPGNPG TPGQRGSPGI PGVKGQRGTP GAKGEQGDKG NPGPSEISHV IGDKGEPGLK  960
GFAGNPGEKG NRGVPGMPGL KGLKGLPGPA GPPGPRGDLG STGNPGEPGL RGIPGSMGNM 1020
GMPGSKGKRG TLGFPGRAGR PGLPGIHGLQ GDKGEPGYSE GTRPGPPGPT GDPGLPGDMG 1080
KKGEMGQPGP PGHLGPAGPE GAPGSPGSPG LPGKPGPHGD LGFKGIKGLL GPPGIRGPPG 1140
LPGFPGSPGM MGIRGDQGRD GIPGPAGEKG ETGLLRAPPG PRGNPGAQGA KGDRGAPGFP 1200
GLPGRKGAMG DAGPRGPTGI EGFPGPPGLP GAIIPGQTGN RGPPGSRGSP GAPGPPGPPG 1260
SHVIGIKGDK GSMGHPGPKG PPGTAGDMGP PGRLGAPGTP GGRLGAPGTP FQGFPGVKGE 1320
KGNPGFLGSI GPPGPIGPKG PPGVRGDPGT LKIISLPGSP GPPGTPGEPG MQGEPGPPGP 1380
PGNLGPCGPR GKPGKDGKPG TPGPAGEKGN KGSKGEPGPA GSDGLPGLKG KRGDSGSPAT 1440
WTTRGFVFTR HSQTTAIPSC PEGTVPLYSG FSFLFVQGNQ RAHGQDLGTL GSCLQRFTTM 1500
PFLFCNVNDV CNFASRNDYS YWLSTPALMP MNMAPITGRA LEPYISRCTV CEGPAIAIAV 1560
HSQTTDIPPC PHGWISLWKG FSFIMFTSAG SEGTGQALAS PGSCLEEFRA SPFLECHGRG 1620
TCNYYSNSYS FWLASLNPER MFRKPIPSTV KAGELEKIIS RCQVCMKKRH           1670

SEQ ID NO: 95           moltype = AA  length = 1690
FEATURE                 Location/Qualifiers
REGION                  1..1690
                        note = misc_feature - human alpha4 chain of type IV collagen
```

```
source                  1..1690
                        mol_type = protein
                        organism = Homo sapiens
SEQUENCE: 95
MWSLHIVLMR CSFRLTKSLA TGPWSLILIL FSVQYVYGSG KKYIGPCGGR DCSVCHCVPE    60
KGSRGPPGPP GPQGPIGPLG APGPIGLSGE KGMRGDRGPP GAAGDKGDKG PTGVPGFPGL   120
DGIPGHPGPP GPRGKPGMSG HNGSRGDPGF PGGRGALGPG GPLGHPGEKG EKGNSVFILG   180
AVKGIQGDRG DPGLPGLPGS WGAGGPAGPT GYPGEPGLVG PPGQPGRPGL KGNPGVGVKG   240
QMGDPGEVGQ QGSPGPTLLV EPPDFCLYKG EKGIKGIPGM VGLPGPPGRK GESGIGAKGE   300
KGIPGFPGPR GDPGSYGSPG FPGLKGELGL VGDPGLFGLI GPKGDPGNRG HPGPPGVLVT   360
PPLPLKGPPG DPGFPGRYGE TGDVGPPGPP GLLGRPGEAC AGMIGPPGPQ GFPGLPGLPG   420
EAGIPGRPDS APGKPGKPGS PGLPGAPGLQ GLPGSSVIYC SVGNPGPQGI KGKVGPPGGR   480
GPKGEKGNEG LCACEPGPMG PPGPPGLPGR QGSKGDLGLP GWLGTKGDPG PPGAEGPPGL   540
PGKHGASGPP GNKGAKGDMV VSRVKGHKGE RGPDGPPGFP GQPGSHGRDG HAGEKGDPGP   600
PGDHEDATPG GKGFPGPLGP PGKAGPVGPP GLGFPGPPGE RGHPGVPGHP GVRGPDGLKG   660
QKGDTISCNV TYPGRHGPPG FDGPPGPKGF PGPQGAPGLS GSDGHKGRPG TPGTAEIPGP   720
PGFRGDMGDP GFGGEKGSSP VGPPGPPGSP GVNGQKGIPG DPAFGHLGPP GKRGLSGVPG   780
IKGPRGDPGC PGAEGPAGIP GFLGLKGPKG REGHAGFPGV PGPPGHSCER GAPGIPGQPG   840
LPGYPGSPGA PGGKGQPGDV GPPGPAGMKG LPGLPGRPGA HGPPGLPGIP GPFGDDGLPG   900
PPGPKGPRGL PGFPGFPGER GKPGAEGCPG AKGEPGEKGM SGLPGDRGLR GAKGAIGPPG   960
DEGEMAIISQ KGTPGEPGPP GDDGFPGERG DKGTPGMQGR RGEPGRYGPP GFHRGEPGEK  1020
GQPGPPGPPG PPGSTGLRGF IGFPGLPGDQ GEPGSPGGPP FSGIDGARGP KGNKGDPASH  1080
FGPPGPKGEP GSPGCPGHFG ASGEQGLPGI QGPRGSPGRP GPPGSSGPPG CPGDHGMPGL  1140
RGQPGEMGDP GPRGLQGDPG IPGPGIKGP SGSPGLNGLH GLKGQKGTKG ASGLHDVGPP  1200
GPVGIPGLKG ERGDPGSPGI SPPGPRGKKG PPGPPGSSGP PGPAGATGRA PKDIPDPGPP  1260
GDQGPPGPDG PRGAPGPPGL PGSVDLLRGE PGDCGLPGPP GPGEKGLPGP YKGFPGCDGK  1320
DGQKGPVGFP GPQGPHGFPG PPGEKGLPGP PGRKGPTGLP GPRGEPGPPA DVDDCPRIPG  1380
LPGAPGMRGP EGAMGLPGMR GPSGPGCKGE PGLDGRRGVD GVPGSPGPPG RKGDTGEDGY  1440
PGGPGPPGPI GDPGPKGFGP GYLGGFLLVL HSQTDQEPTC PLGMPRLWTG YSLLYLEGQE  1500
KAHNQDLGLA GSCLPVFSTL PFAYCNIHQV CHYAQRNDRS YWLASAAPLP MMPLSEEAIR  1560
PYVSRCAVCE APAQAVAVHS QDQSIPPCPQ TWRSLWIGYS FLMHTGAGDQ GGGQALMSPG  1620
SCLEDFRAAP FLECQGRQGT CHFFANKYSF WLTTVKADLQ FSSAPAPDTL KESQAQRQKI  1680
SRCQVCVKYS                                                        1690

SEQ ID NO: 96           moltype = AA  length = 1696
FEATURE                 Location/Qualifiers
REGION                  1..1696
                        note = misc_feature - human alpha5 chain of type IV collagen
source                  1..1696
                        mol_type = protein
                        organism = Homo sapiens
SEQUENCE: 96
MEVDSGKTEN RDWEGFCYST SAYWKNLYDG LLACYGCSPG SKCDCSGIKG EKGERGFPGL    60
EGHPGLPGFP GPEGPPGPRG QKGDDGIPGP PGPKGIRGPP GLPGFPGTPG LPGMPGHDGA   120
PGPQGIPGCN GTKGERGFPG SPGFPGLQGP PGPPGIPGMK GEPGSIIMSS LPGPKGNPGY   180
PGPPGIQGLP GPTGIPGPIG PPGPPGLMGP PGPPGLPGPK GNMGLNFQGP KGEKGEQGLQ   240
GPPGPPGQIS EQKRPIDVEF QKGDQGLPGD RGPPGPPGER GPPGPPGGEK GEKGEQGEPG   300
KRGKPGKDGE NGQPGIPGLP GDPGYPGEPG RDGEKGQKGD TGPPGPPGLV IPRPGTGITI   360
GEKGNIGLPG LPGEKGERGF PGIQGPPGLP GPPGAAVMGP PGPGPFPGER GQKGDEGPPG   420
ISIPGPPGLD GQPGAPGLPG PPGPAGPHIP PSDEICEPGP PGPPGSPGDK GLQGEQGVKG   480
DKGDTCFNCI GTGISGPPGQ PGLPGLPGPP GSLGFPGGKG EKGQAGATGP KGLPGIPGAP   540
GAPGFPGSKG EPGDILTFPG MKGDKGELGS PGAPGLPGLP GTPGQDLPG LPGPKGEPGG   600
ITFKGERGPP GNPGLPGLPG NIGPMGPPGF GPPGPVGEKG IQGVAGNPGQ PGIPGPKGDP   660
GQTITQPGKG GLPGNPGRDG DVGLPGDPGL PGQPGLPGIP GSKGEPGIPG IGLPGPPGPK   720
GPFGIPGPPG APGTPGRIGL EGPPGPPGFP GPKGEPGFAL PGPKGALGPKG              780
DRGFPGPPGP PGRTGLDGLP GPKGDVPGNG QPGPMGPPGL PGIGVQGPPG PPGIPGPIGQ   840
PGLHGIPGEK GDPGPPGLDV PGPPGERGSP GIPGAPGPIG PPGSPGLPGK AGASGFPGTK   900
GEMGMMGPPG PPGPLGIPGR SGVPGLKGDD GLQGQPGLPG PTGEKGSKGE PGLPGPPGPM   960
DPNLLGSKGE KGEPGLPGIP GVSGPKGYQG LPGDPGQPGL SGPLPGP GPKGNPGLPG     1020
QPGLIGPPGL KGTIGDMGFP GPQGVEGPPG PSGVPGQPGS PGLPGQKGDK GDPGISSIGL  1080
PGLPGPKGEP GLPGYPGNPG IKGSVGDPGL PGLPGTPGAK GQPGLPGPPG TPGPPGPKGI  1140
SGPPGNPGLP GEPGPVGGGG HPGQPGPPGE KGKPGQDGIP GPAGQKGEPG QPGFGNPGPP  1200
GLPGLSGQKG DGGLPGIPGN PGLPGPKGEP GFHGFPGVQG PGPPGPSPGP ALEGPKGNPG  1260
PQGPPGRPGP TGFQGLPGPE GPPGLPGNGG IKGEKGNPGQ PGLPGLPGLK GDQGPPGLQG  1320
NPGRPGLNGM KGDPGLPGVP GFPGMKGPSG VPGSAGPEGE PGLIGPPGPP GLPGPSGQSI  1380
IIKGDAGPPG IPGQPGLKGL PGPQGPQGLP GPTGPPGDPG RNGLPGFDGA GGRKGDPGLP  1440
GQPGTRGLDG PPGPDGLQGP PGPPGTSSVA HGFLITRHSQ TTDAPQCPQG TLQVYEGFSL  1500
LYVQGNKRAH GQDLGTAGSC LRRFSTMPFM FCNINNVCNF ASRNDYSYWL STPEPMPMSM  1560
QPLKGQSIQP FISRCAVCEA PAVVIAVHSQ TIQIPHCPQG WDSLWIGYSF MMHTSAGAEG  1620
SGQALASPGS CLEEFRSAPF IECHGRGTCN YYANSYSFWL ATVDVSMFS KPQSETLKAG  1680
DLRTRISRCQ VCMKRT                                                 1696

SEQ ID NO: 97           moltype = AA  length = 1708
FEATURE                 Location/Qualifiers
REGION                  1..1708
                        note = misc_feature - human alpha6 chain of type IV collagen
source                  1..1708
                        mol_type = protein
                        organism = Homo sapiens
```

```
SEQUENCE: 97
MLINKLWLLL VTLCLTEELA AAGEKSYGKP CGGQDCSGSC QCFPEKGARG RPGPIGIQGP    60
TGPQGFTGST GLSGLKGERG FPGLLGPYGP KGDKGPMGVP GFLGINGIPG HPGQPGPRGP   120
PGLDGCNGTQ GAVGFPGPDG YPGLLGPPGL PGQKGSKGDP VLAPGSFKGM KGDPGLPGLD   180
GITGPQGAPG FPGAVGPAGP PGLQGPPGPP GPLGPDGLPG LGFGGEKGVK GDVGLPGPAG   240
PPPSTGELEF MGFPKGKKGS KGEPGPKGFP GISGPPGFPG LGTTGEKGEK GEKGIPGLPG   300
PRGPMGSEGV QGPPGQQGKK GTLGFPGLNG FQGIEGQKGD IGLPGPDVFI DIDGAVISGN   360
PGDPGVPGLP GLKGDEGIQG LRGPSGVPGL PALSGVPGAL GPQGFPGLKG DQGNPGRTTI   420
GAAGLPGRDG LPGPPGPPGP PSPEFETETL HNKESGFPGL RGEQGPKGNL GLKGIKGDSG   480
FCACDGGVPN TGPPGEPGPP GPWGLIGLPG LKGARGDRGS GGAQGPAGAP GLVGPLGPSG   540
PKGKKGEPIL STIQGMPGDR GDSGSQGFRG VIGEPGKDGV PGLPGLPGLP GDGGQGFPGE   600
KGLPGLPGEK GHPGPPGLPG NGLPGLPGPR GLPGDKGKDG LPGQQGLPGS KGDCCCREVG   660
KGDLDTERGI TLPCIIPGSY GPSGFPGTPG FPGPKGSRGL NGFPGPQPGSS GSKGEPGSPG   720
LVHLPELPGF PGPRGEKGLP GFPGLPGKDG LPGMIGSPGL PGSKGATGDI FGAENGAPGE   780
QGLQGLTGHK GFLGDSGLPG LKGVHGKPGL LGPKGERGSP GTPGQVGQPG TPGSSGPYGI   840
KGKSGLPGAP GFPGISGHPG KKGTRGKKGP PGSIVKKGLP GLKGLPGNPG LVGLKGSPGS   900
PGVAGLPALS GPKGEKGSVG FVGFPGIPGL PGIPGTRGLK GIPGSTGKMG PSGRAGTPGE   960
KGDRGNPGPV GIPSPRRPMS NLWLKGDKGS QGSAGSNGFP GPRGDKGEAG RPGPPGLPGA  1020
PGLPGIIKGV SGKPGPPGFM GIRGLPGLKG SSGITGFPGM PGESGSQGIR GSPGLPGASG  1080
LPGLKGDNGQ TVEISGSPGP KGQPGESGFK GTKGRDGLIG NIGFPGNKGE DGKVGVSGDV  1140
GLPGAPGFPG VAGMRGEPGL PGSSGHQGAI GPLGSPGLIG PKGFPGFPGL HGLNGLPGTK  1200
GTHGTPGPSI TGVPGPAGLP GPKGEKGYPG IGIGAPGKPG PGLQGPAGLP PGLQGPAGLP  1260
GAPGISLPSL IAGQPGDPGR PGLDGERGRP GPAGPPGPPG PSSNQGDTGD PGFPGIPGPK  1320
GPKGDQGIPG FSGLPGELGL KGMRGEPGFM GTPGKVGPPG DPGFPGMKGK AGPRGSSGLQ  1380
GDPGQTPTAE AVQVPPGPLG LPGIDGIPGL TGDPGAQGPV GLQGSKGLPG IPGKDGPSGL  1440
PGPPGALGDP GLPGLQGPPG FEGAPGQQGP FGMPGMPGQS MRVGYTLVKH SQSEQVPPCP  1500
IGMSQLWVGY SLLFVEGQEK AHNQDLGFAG SCLPRFSTMP FIYCNINEVC HYARRNDKSY  1560
WLSTTAPIPM MPVSQTQIPQ YISRCSVCEA PSQAIAVHSQ DITIPQCPLG WRSLWIGYSF  1620
LMHTAAGAEG GGQSLVSPGS CLEDFRATPF IECSGARGTC HYFANKYSFW LTTVEERQQF  1680
GELPVSETLK AGQLHTRVSR CQVCMKSL                                    1708

SEQ ID NO: 98            moltype = AA  length = 266
FEATURE                  Location/Qualifiers
REGION                   1..266
                         note = Synthetic: LAIR-1
source                   1..266
                         mol_type = protein
                         organism = synthetic construct
SEQUENCE: 98
QEEDLPRPSI SAEPGTVIPL GSHVTFVCRG PVGVQTFRLE RESRSTYNDT EDVSQASPSE    60
SEARFRIDSV SEGNAGPYRC IYYKPPKWSE QSDYLELLVK ETSGGPDSPD TEPGSSAGPT   120
QRPSDNSHNE HAPASQGLKA EHLYILIGVS VVFLFCLLLL VLFCLHRQNQ IKQGPPRSKD   180
EEQKPQQRPD LAVDVLERTA DKATVNGLPE KDRETDTSAL AAGSSQEVTY AQLDHWALTQ   240
RTARAVSPQS TKPMAESITY AAVARH                                       266

SEQ ID NO: 99            moltype = AA  length = 131
FEATURE                  Location/Qualifiers
REGION                   1..131
                         note = Synthetic: LAIR-2
source                   1..131
                         mol_type = protein
                         organism = synthetic construct
SEQUENCE: 99
QEGALPRPSI SAEPGTVISP GSHVTFMCRG PVGVQTFRLE REDRAKYKDS YNVFRLGPSE    60
SEARFHIDSV SEGNAGLYRC LYYKPPGWSE HSDFLELLVK ESSGGPDSPD TEPGSSAGTV   120
PGTEASGFDA P                                                       131

SEQ ID NO: 100           moltype = AA  length = 410
FEATURE                  Location/Qualifiers
REGION                   1..410
                         note = Synthetic: Glycoprotein IV (CD36 extracellular
                          domain)
source                   1..410
                         mol_type = protein
                         organism = synthetic construct
SEQUENCE: 100
GDLLIQKTIK KQVVLEEGTI AFKNWVKTGT EVYRQFWIFD VQNPQEVMMN SSNIQVKQRG    60
PYTYRVRFLA KENVTQDAED NTVSFLQPNG AIFEPSLSVG TEADNFTVLN LAVAAASHIY   120
QNQFVQMILN SLINKSKSSM FQVRTLRELL WGYRDPFLSL VPYPVTTTVG LFYPYNNTAD   180
GVYKVFNGKD NISKVAIIDT YKGKRNLSYW ESHCDMINGT DAASFPPFVE KSQVLQFFSS   240
DICRSIYAVF ESDVNLKGIP VYRFVLPSKA FASPVENPDN YCFCTEKIIS KNCTSYGVLD   300
ISKCKEGRPV YISLPHFLYA SPDVSEPIDG LNPNEEEHRT YLDIEPITGF TLQFAKRLQV   360
NLLVKPSEKI QVLKNLKRNY IVPILWLNET GTIGDEKANM FRSQVTGKIN              410

SEQ ID NO: 101           moltype = AA  length = 1219
FEATURE                  Location/Qualifiers
REGION                   1..1219
                         note = Synthetic: Nidogen
source                   1..1219
```

|  | mol_type = protein |  |  |  |  |
|---|---|---|---|---|---|
|  | organism = synthetic construct |  |  |  |  |

SEQUENCE: 101

```
LSRQELFPFG PGQGDLELED GDDFVSPALE LSGALRFYDR SDIDAVYVTT NGIIATSEPP    60
AKESHPGLFP PTFGAVAPFL ADLDTTDGLG KVYYREDLSP SITQRAAECV HRGFPEISFQ   120
PSSAVVVTWE SVAPYQGPSR DPDQKGKRNT FQAVLASSDS SSYAIFLYPE DGLQFHTTFS   180
KKENNQVPAV VAFSQGSVGF LWKSNGAYNI FANDRESVEN LAKSSNSGQQ GVWVFEIGSP   240
ATTNGVVPAD VILGTEDGAE YDDEDEDYDL ATTRLGLEDV GTTPFSYKAL RRGGADTYSV   300
PSVLSPRRAA TERPLGPPTE RTRSFQLAVE TFHQQHPQVI DVDEVEETGV VFSYNTDSRQ   360
TCANNRHQCS VHAECRDYAT GFCCSCVAGY TGNGRQCVAE GSPQRVNGKV KGRIFVGSSQ   420
VPIVFENTDL HSYVVMNHGR SYTAISTIPE TVGYSLLPLA PVGGIIGWMF AVEQDGFKNG   480
FSITGGEFTR QAEVTFVGHP GNLVIKQRFS GIDEHGHLTI DTELEGRVPQ IPFGSSVHIE   540
PYTELYHYST SVITSSSTRE YTVTEPERDG ASPSRIYTYQ WRQTITFQEC VHDDSRPALP   600
STQQLSVDSV FVLYNQEEKI LRYALSNSIG PVREGSPDAL QNPCYIGTHG CDTNAACRPG   660
PRTQFTCECS IGFRGDGRTC YDIDECSEQP SVCGSHTICN NHPGTFRCEC VEGYQFSDEG   720
TCVAVVDQRP INYCETGLHN CDIPQRAQCI YTGGSSYTCS CLPGFSGDGQ ACQDVDECQP   780
SRCHPDAFCY NTPGSFTCQC KPGYQGDGFR CVPGEVEKTR CQHEREHILG AAGATDPQRP   840
IPPGLFVPEC DAHGHYAPTQ CHGSTGYCWC VDRDGREVEG TRTRPGMTPP CLSTVAPPIH   900
QGPAVPTAVI PLPPGTHLLF AQTGKIERLP LEGNTMRKTE AKAFLHVPAK VIIGLAFDCV   960
DKMVYWTDIT EPSIGRASLH GGEPTTIIRQ DLGSPEGIAV DHLGRNIFWT DSNLDRIEVA  1020
KLDGTQRRVL FETDLVNPRG IVTDSVRGNL YWTDWNRDNP KIETSYMDGT NRRILVQDDL  1080
GLPNGLTFDA FSSQLCWVDA GTNRAECLNP SQPSRRKALE GLQYPFAVTS YGKNLYFTDW  1140
KMNSVVALDL AISKETDAFQ PHKQTRLYGI TTALSQCPQG HNYCSVNNGG CTHLCLATPG  1200
SRTCRCPDNT LGVDCIEQK                                              1219
```

```
SEQ ID NO: 102      moltype = AA  length = 4370
FEATURE             Location/Qualifiers
REGION              1..4370
                    note = Synthetic: Perlecan
source              1..4370
                    mol_type = protein
                    organism = synthetic construct
```

SEQUENCE: 102

```
VTHGLRAYDG LSLPEDIETV TASQMRWTHS YLSDDEDMLA DSISGDDLGS GDLSGDFQM     60
VYFRALVNFT RSIEYSPQLE DAGSREFREV SEAVVDTLES EYLKIPGDQV VSVVFIKELD   120
GWVFVELDVG SEGNADGAQI QEMLLRVISS GSVASYVTSP QGFQFRRLGT VPQFPPRACTE  180
AEFACHSYNE CVALEYRCDR RPDCRDMSDE LNCEEPVLGI SPTFSLLVET TSLPPRPETT   240
IMRQPPVTHA PQPLLPGSVR PLPCGPQEAA CRNGHCIPRD YLCDGQEDCE DGSDELDCGP   300
PPPCEPNEFP CGNGHCALKL WRCDGDFDCE DRTDEANCPT KRPEEVCGPT QFRCVSTNMC   360
IPASFHCDEE SDCPDRSDEF GCMPPQVVTP PRESIQASRG QTVTFTCVAI GVPTPIIINWR  420
LNWGHIPSHP RVTVTSEGGR GTLIIRDVKE SDQGAYTCEA MNARGMVFGI PDGVLELVPQ   480
RGPCPDGHFY LEHSAACLPC FCFGITSVCQ STRRFRDQIR LRFDQPDDFK GVNVTMPAQP   540
GTPPLSSTQL QIDPSLHEFQ LVDLSRRFLV HDSFWALPEQ FLGNKVDSYG GSLRYNVRYE   600
LARGMLEPVQ RPDVVLMGAG YRLLSRGHTP TQPGALNQRQ VQFSEEHWVH ESGRPVQRAE   660
LLQVLQSLEA VLIQTVYNTK MASVGLSDIA MDTTVTHATS HGRAHSVEEC RCPIGYSGLS   720
CESCDAHFTR VPGGPYLGTC SGCNCNGHAS SCDPVYGHCL NCQHNTEGPQ CNKCKAGFFG   780
DAMKATATSC RPCPCPYIDA SRRFSDTCFL DTDGQATCDA CAPGYTGRRC ESCAPGYEGN   840
PIQPGGKCRP VNQEIVRCDE RGSMGTSGEA CRCKNNVVGR LCNECADGSF HLSTRNPDGC   900
LKCFCMGVSR HCTSSSWSRA QLHGASEEPG HFSLTNAAST HTTNEGIFSP TPGELGFSSF   960
HRLLSGPYFW SLPSRFLGDK VTSYGGELRF TVTQRSQPGS TPLHGQPLVV LQGNNIILEH  1020
HVAQEPSPGQ PSTFIVPFRE QAWQRPDGQP ATREHLLMAL AGIDTLLIRA SYAQQPEASR  1080
VSGISMDVAV PEETGQDPAL EVEQCSCPPG YRGPSCQDCD TGYTRTPSGL YLGTCERCSC  1140
HGHSEACEPE TGACQGCQHH TEGPRCEQCQ PGYYGDAQRG TPQDCQLCPC YGDPAAGQAA  1200
HTCFLDTDGH PTCDACSPGH SGRHCERCAP GYYGNPSQGQ PCQRDSQVPG PIGCNCDPQG  1260
SVSSQCDAAG QCQCKAQVEG LTCSHCRPHH FHLSASNDGN GCLPCFCMGIT QQCASSAYTR  1320
HLISTHFAPG DFQGFALVNP QRNSRLTGEF TVEPVPEGAQ LSFGNFAQLG HESFYWQLPE  1380
TYQGDKVAAY GGKLRYTLSY TAGPQGSPLS DPDVQITGNN IMLVASQPAL QGPERRSYEI  1440
MFREEFWRRP DGQPATREHL LMALADLDEL LIRATFSSVP LAASISAVSL EVAQPGPSNR  1500
PRALEVEECR CPPGYIGLSC QDCAPGYTRT GSGLYLGHCE LCECNGHSDL CHPETGACSQ  1560
CQHNAAGEFC ELCAPGYYGD ATAGTPEDCQ PCACPLTNPE NMFSRTCESL GAGGYRCTAC  1620
EPGYTGQYCE QCGPGYVGNP SVQGGQCLPE TNQAPLVVEV HPARSIVPQG GSHSLRCQVS  1680
GSPPHYFYWS REDGRPVPSG TQQRHQGSEL HFPSVQPSDA GVYICTCRNL HQSNTSRAEL  1740
LVTEAPSKPI TVTVEEQRSQ SVRPGADVTF ICTAKSKSPA YTLVWTRLHN GKLPTRAMDF  1800
NGILTIRNVQ LSDAGTYVCT GSNMFAMDQG TATLHVQASG TLSAPVVSIH PPQLTVQPGQ  1860
LAEFRCSATG SPTPTLEWTG GPGGQLPAKA QIHGGILRLP AVEPTDQAQY LCRAHSSAGQ  1920
QVARAVLHVH GGGGPRVQVS PERTQVHAGR TVRLYCRAAG VPSATITWRK EGGSLPPQAR  1980
SERTDIATLL IPAITTADAG FYLCVATSPA GTAQARIQVV VLSASDASPP PVKIESSSPS  2040
VTEGQTLDLN CVVAGSAHAQ VTWYRRGGSL PPHTQVHGSR LRLPQVSPAD SGEYVCRVEN  2100
GSGPKEASIT VSVLHGTHSG PSYTPVPGST RPIRIEPSSS HVAEGQTLDL NCVVPGQAHA  2160
QVTWHKRGGS LPARHQTHGS LLRLHQVTPA DSGEYVCHVV GTSGPLEASV LVTIEASVIP  2220
GPIPPVRIES SSSTVAEGQT LDLSCVVAGQ AHAQVTWYKR GGSLPARHQV RGSRLYIFQA  2280
SPADAGQYVC RASNGMEASI TVTVGTQGA NLAYPAGSTQ PIRIEPSSSQ VAEGQTLDLN  2340
CVVPGQSHAQ VTWHKRGGSL PVRHQTHGSL LRLYQASPAD SGEYVCRVLG SSVPLEASVL  2400
VTIEPAGSVP ALGVTPTVRI ESSSSQVAEG QTLDLNCLVA GQAHAQVTWH KRGGSLPARH  2460
QVHGSRLRLL QVTSPADSGEY VCRVVGSSGT QEASVLVTIQ QRLSGSHSQG VAYPVRIESS  2520
SASLANGHTL DLNCLVASQA PHTITWYKRG GSLPSRHQIV GSRLRIPDSG PTPADSGEYVCH  2580
VSNGAGSRET SLIVTIQGSG SSHVPSVSPP IRIESSSPTV VEGQTLDLNC VVARQPQAII  2640
TWYKRGGSLP SRHQTHGSHL RLHQMSVADS GEYVCRANNN IDALEASIVI SVSPSAGSPS  2700
APGSSMPIRI ESSSHVAEG ETLDLNCVVP GQAHAQVTWH KRGGSLPSHH QTRGSRLRLH  2760
```

```
HVSPADSGEY VCRVMGSSGP LEASVLVTIE ASGSSAVHVP APGGAPPIRI EPSSSRVAEG    2820
QTLDLKCVVP GQAHAQVTWH KRGGNLPARH QVHGPLLRLN QVSPADSGEY SCQVTGSSGT    2880
LEASVLVTIE PSSPGPIPAP GLAQPIYIEA SSSHVTEGQT LDLNCVVPGQ AHAQVTWYKR    2940
GGSLPARHQT HGSQLRLHLV SPADSGEYVC RAASGPGPEQ EASFTVTVPP SEGSSYRLRS    3000
PVISIDPPSS TVQQGQDASF KCLIHDGAAP ISLEWKTRNQ ELEDNVHISP NGSIITIVGT    3060
RPSNHGTYRC VASNAYGVAQ SVVNLSVHGP PTVSVLPEGP VWVKVGKAVT LECVSAGEPR    3120
SSARWTRISS TPAKLEQRTY GLMDSHAVLQ ISSAKPSDAG TYVCLAQNAL GTAQKQVEVI    3180
VDTGAMAPGA PQVQAEEEAEL TVEAGHTATL RCSATGSPAP TIHWSKLRSP LPWQHRLEGD    3240
TLIIPRVAQQ DSGQYICNAT SPAGHAEATI ILHVESPPYA TTVPEHASVQ AGETVQLQCL    3300
AHGTPPLTFQ WSRVGSSLPG RATARNELLH FERAAPEDSG RYRCRVTNKV GSAEAFAQLL    3360
VQGPPGSLPA TSIPAGSTPT VQVTPQLETK SIGASVEPHC AVPSDRGTQL RWFKEGGQLP    3420
PGHSVQDGVL RIQNLDQSCQ GTYICQAHGP WGKAQASAQL VIQALPSVLI NIRTSVQTVV    3480
VGHAVEFECL ALGDKPQVT WSKVGGHLRP GIVQSGGVVR IAHVELADAG QYRCTATNAA    3540
GTTQSHVLLL VQALPQISMP QEVRVPAGSA AVFPCIASGY PTPDISWSKL DGSLPPDSRL    3600
ENNMLMLPSV RPQDAGTYVC TATNRQGKVK AFAHLQVPER VVPYFTQTPY SFLPLPTIKD    3660
AYRKFEIKIT FRPDSADGML LYNGQKRVPG SPTNLANRQP DFISFGLVGG RPEFRFDAGS    3720
GMATIRHPTP LALGHFHTVT LLRSLTQGSL IVGDLAPVNG TSQGKFQGLD LNEELYLGGY    3780
PDYGAIPKAG LSSGFIGCVR ELRIQGEEIV FHDLNLTAHG ISHCPTCRDR PCQNGGACHD    3840
SESSSYVCVC PAGFTGSRCE HSQALHCHPE ACGPDATCVN RPDGRGYTCR CHLGRSGLRC    3900
EEGVTVTTPS LSGAGSYLAL PALTNTHHEL RLDVEFKPLA PDGVLLFSGG KSGPVEDFVS    3960
LAMVGGHLEF RYELGSGLAV LRSAEPLALG RWHRVSAERL NKDGSLRVNG GRPVLRSSPG    4020
KSQGLNLHTL LYLGGVEPSV PLSPATNMSA HFRGCVGEVS VNGKRLDLTY SFLGSQGIGQ    4080
CYDSSPCERQ PCQHGATCMP AGEYEFQCLC RDGFKGDLCE HEENPCQLRE PCLHGGTCQG    4140
TRCLCLPGFS GPRCQQGSGH GIAESDWHLE GSGGNDAPGQ YGAYFHDDGF LAFPGHVFSR    4200
SLPEVPETIE LEVRTSTASG LLLWQGVEVG EAGQGKDFIS LGLQDGHLVF RYQLGSGEAR    4260
LVSEDPINDG EWHRVTALRE GRRGSIQVDG EELVSGRSPG PNVAVNAKGS VYIGGAPDVA    4320
TLTGGRFSSG ITGCVKNLVL HSARPGAPPP QPLDLQHRAQ AGANTRPCPS              4370

SEQ ID NO: 103         moltype = AA  length = 331
FEATURE                Location/Qualifiers
REGION                 1..331
                       note = Synthetic: Biglycan
source                 1..331
                       mol_type = protein
                       organism = synthetic construct
SEQUENCE: 103
DEEASGADTS GVLDPDSVTP TYSAMCPFGC HCHLRVVQCS DLGLKSVPKE ISPDTTLLDL     60
QNNDISELRK DDFKGLQHLY ALVLVNNKIS KIHEKAFSPL RKLQKLYISK NHLVEIPPNL    120
PSSLVELRIH DNRIRKVPKG VFSGLRNMNC IEMGGNPLEN SGFEPGAFDG LKLNYLRISE    180
AKLTGIPKDL PETLNELHLD HNKIQAIELE DLLRYSKLYR LGLGHNQIRM IENGSLSFLP    240
TLRELHLDNN KLARVPSGLP DLKLLQVVYL HSNNITKVGV NDFCPMGFGV KRAYYNGISL    300
FNNPVPYWEV QPATFRCVTD RLAIQFGNYK K                                  331

SEQ ID NO: 104         moltype = AA  length = 329
FEATURE                Location/Qualifiers
REGION                 1..329
                       note = Synthetic: Decorin
source                 1..329
                       mol_type = protein
                       organism = synthetic construct
SEQUENCE: 104
DEASGIGPEV PDDRDFEPSL GPVCPFRCQC HLRVVQCSDL GLDKVPKDLP PDTTLLDLQN     60
NKITEIKDGD FKNLKNLHAL ILVNNKISKV SPGAFTPLVK LERLYLSKNQ LKELPEKMPK    120
TLQELRAHEN EITKVRKVTF NGLNQMIVIE LGTNPLKSSG IENGAFQGMK KLSYIRIADT    180
NITSIPQGLP PSLTELHLDG NKISRVDAAS LKGLNNLAKL GLSFNSISAV DNGSLANTPH    240
LRELHLDNNK LTRVPGGLAE HKYIQVVYLH NNNISVGSS DFCPPGHNTK KASYSGVSLF    300
SNPVQYWEIQ PSTFRCVYVR SAIQLGNYK                                    329

SEQ ID NO: 105         moltype = AA  length = 348
FEATURE                Location/Qualifiers
REGION                 1..348
                       note = Synthetic: Asporin
source                 1..348
                       mol_type = protein
                       organism = synthetic construct
SEQUENCE: 105
DMEDTDDDDD DDDDDDDDE DNSLFPTREP RSHFFPFDLF PMCPFGCQCY SRVVHCSDLG     60
LTSVPTNIPF DTRMLDLQNN KIKEIKENDF KGLTSLYGLI LNNNKLTKIH PKAFLTTKKL    120
RRLYLSHNQL SEIPLNLPKS LAELRIHENK VKKIQKDTFK GMNALHVLEM SANPLDNNGI    180
EPGAFEGVTV FHIRIAEAKL TSVPKGLPPT LLELHLDYNK ISTVELEDFK RYKELQRLGL    240
GNNKITDIEN GSLANIPRVR EIHLENNKLK KIPSGLPELK YLQIIFLHSN SIARVGVNDF    300
CPTVPKMKKS LYSAISLFNN PVKYWEMQPA TFRCVLSRMS VQLGNFGM                348

SEQ ID NO: 106         moltype = AA  length = 358
FEATURE                Location/Qualifiers
REGION                 1..358
                       note = Synthetic: Fibromodulin
source                 1..358
                       mol_type = protein
```

```
                        organism = synthetic construct
SEQUENCE: 106
QYEDDPHWWF  HYLRSQQSTY  YDPYDPYPYE  TYEPYPYGVD  EGPAYTYGSP  SPPDPRDCPQ    60
ECDCPPNFPT  AMYCDNRNLK  YLPFVPSRMK  YVYFQNNQIT  SIQEGVFDNA  TGLLWIALHG   120
NQITSDKVGR  KVFSKLRHLE  RLYLDHNNLT  RMPGPLPRSL  RELHLDHNQI  SRVPNNALEG   180
LENLTALYLQ  HNEIQEVGSS  MRGLRSLILL  DLSYNHLRKV  PDGLPSALEQ  LYMEHNNVYT   240
VPDSYFRGAP  KLLYVRLSHN  SLTNNGLASN  TFNSSSLLEL  DLSYNQLQKI  PPVNTNLENL   300
YLQGNRINEF  SISSFCTVVD  VVNFSKLQVL  RLDGNEIKRS  AMPADAPLCL  RLASLIEI    358

SEQ ID NO: 107           moltype = AA  length = 320
FEATURE                  Location/Qualifiers
REGION                   1..320
                         note = Synthetic: Lumican
source                   1..320
                         mol_type = protein
                         organism = synthetic construct
SEQUENCE: 107
QYYDYDFPLS  IYGQSSPNCA  PECNCPESYP  SAMYCDELKL  KSVPMVPPGI  KYLYLRNNQI    60
DHIDEKAFEN  VTDLQWLILD  HNLLENSKIK  GRVFSKLKQL  KKLHINHNNL  TESVGPLPKS   120
LEDLQLTHNK  ITKLGSFEGL  VNLTFIHLQH  NRLKEDAVSA  AFKGLKSLEY  LDLSFNQIAR   180
LPSGLPVSLL  TLYLDNNKIS  NIPDEYFKRF  NALQYLRLSH  NELADSGIPG  NSFNVSSLVE   240
LDLSYNKLKN  IPTVNENLEN  YYLEVNQLEK  FDIKSFCKIL  GPLSYSKIKH  LRLDGNRISE   300
TSLPPDMYEC  LRVANEVTLN                                                  320

SEQ ID NO: 108           moltype = AA  length = 362
FEATURE                  Location/Qualifiers
REGION                   1..362
                         note = Synthetic: PRELP
source                   1..362
                         mol_type = protein
                         organism = synthetic construct
SEQUENCE: 108
QPTRRPRPGT  GPGRRPRPRP  RPTPSFPQPD  EPAEPTDLPP  PLPPGPPSIF  PDCPRECYCP    60
PDFPSALYCD  SRNLRKVPVI  PPRIHYLYLQ  NNFITELPVE  SFQNATGLRW  INLDNNRIRK   120
IDQRVLEKLP  GLVFLYMEKN  QLEEVPSALP  RNLEQLRLSQ  NHISRIPPGV  FSKLENLLLL   180
DLQHNRLSDG  VFKPDTFHGL  KNLMQLNLAH  NILRKMPPRV  PTAIHQLYLD  SNKIETIPNG   240
YFKSFPNLAF  IRLNYNKLTD  RGLPKNSFNI  SNLLVLHLSH  NRISSVPAIN  NRLEHLYLNN   300
NSIEKINGTQ  ICPNDLVAFH  DFSSDLENVP  HLRYLRLDGN  YLKPPIPLDL  MMCFRLLQSV   360
VI                                                                      362

SEQ ID NO: 109           moltype = AA  length = 401
FEATURE                  Location/Qualifiers
REGION                   1..401
                         note = Synthetic: Osteoadherin/Osteomodulin
source                   1..401
                         mol_type = protein
                         organism = synthetic construct
SEQUENCE: 109
QYETYQWDED  YDQEPDDDYQ  TGFPFRQNVD  YGVPFHQYTL  GCVSECFCPT  NFPSSMYCDN    60
RKLKTIPNIP  MHIQQLYLQF  NEIEAVTANS  FINATHLKEI  NLSHNKIKSQ  KIDYGVFAKL   120
PNLLQLHLEH  NNLEEFPFPL  PKSLERLLLG  YNEISKLQTN  AMDGLVNLTM  LDLCYNYLHD   180
SLLKDKIFAK  MEKLMQLNLC  SNRLESMPPG  LPSSLMYLSL  ENNSISSIPE  KYFDKLPKLH   240
TLRMSHNKLQ  DIPYNIFNLP  NIVELSVGHN  KLKQAFYIPR  NLEHLYLQNN  EIEKMNLTVM   300
CPSIDPLHYH  HLTYIRVDQN  KLKEPISSYI  FFCFPHIHTI  YYGEQRSTNG  QTIQLKTQVF   360
RRFPDDDDES  EDHDDPDNAH  ESPEQEGAEG  HFDLHYYENQ  E                       401

SEQ ID NO: 110           moltype = AA  length = 313
FEATURE                  Location/Qualifiers
REGION                   1..313
                         note = Synthetic: Opticin
source                   1..313
                         mol_type = protein
                         organism = synthetic construct
SEQUENCE: 110
ASLPRKERKR  REEQMPREGD  SFEVLPLRND  VLNPDNYGEV  IDLSNYEELT  DYGDQLPEVK    60
VTSLAPATSI  SPAKSTTAPG  TPSSNPTMTR  PTTAGLLLSS  QPNHGLPTCL  VCVCLGSSVY   120
CDDIDLEDIP  PLPRRTAYLY  ARFNRISRIR  AEDFKGLTKL  KRIDLSNNLI  SSIDNDAFRL   180
LHALQDLILP  ENQLEALPVL  PSGIEFLDVR  LNRLQSSGIQ  PAAFRAMEKL  QFLYLSDNLL   240
DSIPGPLPLS  LRSVHLQNNL  IETMQRDVFC  DPEEHKHTRR  QLEDIRLDGN  PINLSLFPSA   300
YFCLPRLPIG  RFT                                                         313

SEQ ID NO: 111           moltype = AA  length = 278
FEATURE                  Location/Qualifiers
REGION                   1..278
                         note = Synthetic: Osteoglycin/Mimecan
source                   1..278
                         mol_type = protein
                         organism = synthetic construct
SEQUENCE: 111
```

```
PPTQQDSRII YDYGTDNFEE SIFSQDYEDK YLDGKNIKEK ETVIIPNEKS LQLQKDEAIT      60
PLPPKKENDE MPTCLLCVCL SGSVYCEEVD IDAVPPLPKE SAYLYARFNK IKKLTAKDFA     120
DIPNLRRLDF TGNLIEDIED GTFSKLSLLE ELSLAENQLL KLPVLPPKLT LFNAKYNKIK     180
SRGIKANAFK KLNNLTFLYL DHNALESVPL NLPESLRVIH LQFNNIASIT DDTFCKANDT     240
SYIRDRIEEI RLEGNPIVLG KHPNSFICLK RLPIGSYF                             278

SEQ ID NO: 112          moltype = AA  length = 732
FEATURE                 Location/Qualifiers
REGION                  1..732
                        note = Synthetic: Chondroadherin
source                  1..732
                        mol_type = protein
                        organism = synthetic construct
SEQUENCE: 112
QRCPQACICD NSRRHVACRY QNLTEVPDAI PELTQRLDLQ GNLLKVIPAA AFQGVPHLTH      60
LDLRHCEVEL VAEGAFRGLG RLLLLNLASN HLRELPQEAL DGLGSLRRLE LEGNALEELR     120
PGTFGALGAL ATLNLAHNAL VYLPAMAFQG LLRVRWLRLS HNALSVLAPE ALAGLPALRR     180
LSLHHNELQA LPGPVLSQAR GLARLELGHN PLTYAGEEDG LALPGLRELL LDGGALQALG     240
PRAFAHCPRL HTLDLRGNQL DTLPPLQGPG QLRRLRLQGN PLWCGCQARP LLEWLARARV     300
RSDGACQGPR RLRGEALDAL RPWDLRCPGD AAQEEEELEE RAVAGPRAPP RGPPRGPGEE     360
RAVAPCPRAC VCVPESRHSS CEGCGLQAVP RGFPSDTQLL DLRRNHFPSV PRAAFPGLGH     420
LVSLHLQHCG IAELEAGALA GLGRLIYLYL SDNQLAGLSA AALEGAPRLG YLYLERNRFL     480
QVPGAALRAL PSLFSLHLQD NAVDRLAPGD LGRTRALRWV YLSGNRITEV SLGALGPARE     540
LEKLHLDRNQ LREVPTGALE GLPALLELQL SGNPLRALRD GAFQPVGRSL QHLFLNSSGL     600
EQICPGAFSG LGPGLQSLHL QKNQLRALPA LPSLSQLELI DLSSNPFHCD CQLLPLHRWL     660
TGLNLRVGAT CATPPNARGQ RVKAAAAVFE DCPGWAARKA KRTPASRPSA RRTPIKGRQC     720
GADKVGKEKG RL                                                        732

SEQ ID NO: 113          moltype = AA  length = 594
FEATURE                 Location/Qualifiers
REGION                  1..594
                        note = Synthetic: Podocan
source                  1..594
                        mol_type = protein
                        organism = synthetic construct
SEQUENCE: 113
GPVLAVRAPG FGRSGGHSLS PEENEFAEEE PVLVLSPEEP GPGPAAVSCP RDCACSQEGV      60
VDCCGIDLRE FPGDLPEHTN HLSLQNNQLE KIYPEELSRL HRLETLNLQN NRLTSRGLPE     120
KAFEHLTNLN YLYLANNKLT LAPRFLPNAL ISVDFAANYL TKIYGLTFGQ KPNLRSVYLH     180
NNKLADAGLP DNMFGSSNV EVLILSSNFL RHVPKHLPPA LYKLHLKNNK LEKIPPGAFS     240
ELSSLRELYL QNNYLTDEGL DNETFWKLSS LEYLDLSSNN LSRVPAGLPR SLVLLHLEKN     300
AIRSVDANVL TPIRSLEYLL LHSNQLREQG IHPLAFQGLK RLHTVHLYNN ALERVPSGLP     360
RRVRTLMILH NQITGIGRED FATTYFLEEL NLSYNRITSP QVHRDAFRKL RLLRSLDLSG     420
NRLHTLPPGL PRNVHLVKVK RNELAALARG ALVGMAQLRE LYLTSNRLRS RALGPRAWVD     480
LAHLQLLDIA GNQLTEIPEG LPESLEYLYL QNNKISAVPA NAFDSTPNLK GIFLRFNKLA     540
VGSVVDSAFR RLKHLQVLDI EGNLEFGDIS KDRGRLGKEK EEEEEEEEEE EETR           594

SEQ ID NO: 114          moltype = AA  length = 330
FEATURE                 Location/Qualifiers
REGION                  1..330
                        note = misc_feature - Human IgG1 constant region (amino
                         acid sequence)
source                  1..330
                        mol_type = protein
                        organism = Homo sapiens
SEQUENCE: 114
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKKVEP KSCDKTHTCP PCPAPELLGG     120
PSVFLFPPKP KDTLMISRTP EVTCVVVDVS HEDPEVKFNW YVDGVEVHNA KTKPREEQYN     180
STYRVVSVLT VLHQDWLNGK EYKCKVSNKA LPAPIEKTIS KAKGQPREPQ VYTLPPSRDE     240
LTKNQVSLTC LVKGFYPSDI AVEWESNGQP ENNYKTTPPV LDSDGSFFLY SKLTVDKSRW     300
QQGNVFSCSV MHEALHNHYT QKSLSLSPGK                                     330

SEQ ID NO: 115          moltype = AA  length = 232
FEATURE                 Location/Qualifiers
REGION                  1..232
                        note = misc_feature - Human IgG1 Fc domain (amino acid
                         sequence)
source                  1..232
                        mol_type = protein
                        organism = Homo sapiens
SEQUENCE: 115
EPKSCDKTHT CPPCPAPELL GGPSVFLFPP KPKDTLMISR TPEVTCVVVD VSHEDPEVKF      60
NWYVDGVEVH NAKTKPREEQ YNSTYRVVSV LTVLHQDWLN GKEYKCKVSN KALPAPIEKT     120
ISKAKGQPRE PQVYTLPPSR DELTKNQVSL TCLVKGFYPS DIAVEWESNG QPENNYKTTP     180
PVLDSDGSFF LYSKLTVDKS RWQQGNVFSC SVMHEALHNH YTQKSLSLSP GK             232

SEQ ID NO: 116          moltype = AA  length = 197
FEATURE                 Location/Qualifiers
```

```
REGION                       1..197
                             note = Synthetic: HSA domain I
source                       1..197
                             mol_type = protein
                             organism = synthetic construct
SEQUENCE: 116
DAHKSEVAHR FKDLGEENFK ALVLIAFAQY LQQCPFEDHV KLVNEVTEFA KTCVADESAE    60
NCDKSLHTLF GDKLCTVATL RETYGEMADC CAKQEPERNE CFLQHKDDNP NLPRLVRPEV   120
DVMCTAFHDN EETFLKKYLY EIARRHPYFY APELLFFAKR YKAAFTECCQ AADKAACLLP   180
KLDELRDEGK ASSAKQR                                                  197

SEQ ID NO: 117               moltype = AA  length = 197
FEATURE                      Location/Qualifiers
REGION                       1..197
                             note = Synthetic: HSA domain II
source                       1..197
                             mol_type = protein
                             organism = synthetic construct
SEQUENCE: 117
GKASSAKQRL KCASLQKFGE RAFKAWAVAR LSQRFPKAEF AEVSKLVTDL TKVHTECCHG    60
DLLECADDRA DLAKYICENQ DSISSKLKEC CEKPLLEKSH CIAEVENDEM PADLPSLAAD   120
FVESKDVCKN YAEAKDVFLG MFLYEYARRH PDYSVVLLLR LAKTYETTLE KCCAAADPHE   180
CYAKVFDEFK PLVEEPQ                                                  197

SEQ ID NO: 118               moltype = AA  length = 200
FEATURE                      Location/Qualifiers
REGION                       1..200
                             note = Synthetic: HSA domain III
source                       1..200
                             mol_type = protein
                             organism = synthetic construct
SEQUENCE: 118
NLIKQNCELF EQLGEYKFQN ALLVRYTKKV PQVSTPTLVE VSRNLGKVGS KCCKHPEAKR    60
MPCAEDYLSV VLNQLCVLHE KTPVSDRVTK CCTESLVNRR PCFSALEVDE TYVPKEFNAE   120
TFTFHADICT LSEKERQIKK QTALVELVKH KPKATKEQLK AVMDDFAAFV EKCCKADDKE   180
TCFAEEGKKL VAASQAALGL                                               200

SEQ ID NO: 119               moltype = AA  length = 50
FEATURE                      Location/Qualifiers
REGION                       1..50
                             note = Synthetic: Linker
source                       1..50
                             mol_type = protein
                             organism = synthetic construct
SEQUENCE: 119
LEAEAAAKEA AAKEAAAKEA AAKALEAEAA AKEAAAKEAA AKEAAAKALE               50

SEQ ID NO: 120               moltype = AA  length = 1071
FEATURE                      Location/Qualifiers
REGION                       1..1071
                             note = Synthetic: Lumican-MSA-IL2
source                       1..1071
                             mol_type = protein
                             organism = synthetic construct
SEQUENCE: 120
QYYDYDIPLF MYGQISPNCA PECNCPHSYP TAMYCDDLKL KSVPMVPPGI KYLYLRNNQI    60
DHIDEKAFEN VTDLQWLILD HNLLENSKIK GKVFSKLKQL KKLHINYNNL TESVGPLPKS   120
LQDLQLTNNK ISKLGSFDGL VNLTFIYLQH NQLKEDAVSA SLKGLKSLEY LDLSFNQMSK   180
LPAGLPTSLL TLYLDNNKIS NIPDEYFKRF TGLQYLRLSH NELADSGVPG NSFNISSLLE   240
LDLSYNKLKS IPTVNENLEN YYLEVNELEK FDVKSFCKIL GPLSYSKIKH LRLDGNPLTQ   300
SSLPPDMYEC LRVANEITVN GGGSGGGSEA HKSEIAHRYN DLGEQHFKGL VLIAFSQYLQ   360
KCSYDEHAKL VQEVTDFAKT CVADESAANC DKSLHTLFGD KLCAIPNLRE NYGELADCCT   420
KQEPERNECF LQHKDDNPSL PPFERPEAEA MCTSFKENPT TFMGHYLHEV ARRHPYFYAP   480
ELLYYAEQYN EILTQCCAEA DKESCLTPKL DGVKEKALVS SVRQRMKCSS MQKFGERAFK   540
AWAVARLSQT FPNADFAEIT KLATDLTKVN KECCHGDLLE CADDRAELAK YMCENQATIS   600
SKLQTCCDKP LLKKAHCLSE VEHDTMPADL PAIAADFVED QEVCKNYAEA KDVFLGTFLY   660
EYSRRHPDYS VSLLLRLAKK YEATLEKCCA EANPPACYGT VLAEFQPLVE EPKNLVKTNC   720
DLYEKLGEYG FQNAILVRYT QKAPQVSTPT LVEAARNLGR VGTKCCTLPE DQRLPCVEDY   780
LSAILNRVCL LHEKTPVSEH VTKCCSGSLV ERRPCFSALT VDETYVPKEF KAETFTFHSD   840
ICTLPEKEKQ IKKQTALAEL VKHKPKATAE QLKTVMDDFA QFLDTCCKAA DKDTCFSTEG   900
PNLVTRCKDA LAGGGSAPTS SSTSSSTAEA QQQQQQQQQQ QQHLEQLLMD LQELLSRMEN   960
YRNLKLPRML TFKFYLPKQA TELKDLQCLE DELGPLRHVL DLTQSKSFQL EDAENFISNI  1020
RVTVVKLKGS DNTFECQFDD ESATVVDFLR RWIAFCQSII STSPQHHHHH H           1071

SEQ ID NO: 121               moltype = AA  length = 743
FEATURE                      Location/Qualifiers
REGION                       1..743
                             note = Synthetic: MSA-IL2
source                       1..743
```

```
                        mol_type = protein
                        organism = synthetic construct
SEQUENCE: 121
EAHKSEIAHR YNDLGEQHFK GLVLIAFSQY LQKCSYDEHA KLVQEVTDFA KTCVADESAA    60
NCDKSLHTLF GDKLCAIPNL RENYGELADC CTKQEPERNE CFLQHKDDNP SLPPFERPEA   120
EAMCTSFKEN PTTFMGHYLH EVARRHPYFY APELLYYAEQ YNEILTQCCA EADKESCLTP   180
KLDGVKEKAL VSSVRQRMKC SSMQKFGERA FKAWAVARLS QTFPNADFAE ITKLATDLTK   240
VNKECCHGDL LECADDRAEL AKYMCENQAT ISSKLQTCCD KPLLKKAHCL SEVEHDTMPA   300
DLPAIAADFV EDQEVCKNYA EAKDVFLGTF LYEYSRRHPD YSVSLLLRLA KKYEATLEKC   360
CAEANPPACY GTVLAEFQPL VEEPKNLVKT NCDLYEKLGE YGFQNAILVR YTQKAPQVST   420
PTLVEAARNL GRVGTKCCTL PEDQRLPCVE DYLSAILNRV CLLHEKTPVS EHVTKCCSGS   480
LVERRPCFSA LTVDETYVPK EFKAETFTFH SDICTLPEKE KQIKKQTALA ELVKHKPKAT   540
AEQLKTVMDD FAQFLDTCCK AADKDTCFST EGPNLVTRCK DALAGGGSAP TSSSTSSSTA   600
EAQQQQQQQQ QQQQHLEQLL MDLQELLSRM ENYRNLKLPR MLTFKFYLPK QATELKDLQC   660
LEDELGPLRH VLDLTQSKSF QLEDAENFIS NIRVTVVKLK GSDNTFECQF DDESATVVDF   720
LRRWIAFCQS IISTSPQHHH HHH                                           743

SEQ ID NO: 122          moltype = AA  length = 1117
FEATURE                 Location/Qualifiers
REGION                  1..1117
                        note = Synthetic: IL12-MSA
source                  1..1117
                        mol_type = protein
                        organism = synthetic construct
SEQUENCE: 122
MWELEKDVYV VEVDWTPDAP GETVNLTCDT PEEDDITWTS DQRHGVIGSG KTLTITVKEF    60
LDAGQYTCHK GGETLSHSHL LLHKKENGIW STEILKNFKN KTFLKCEAPN YSGRFTCSWL   120
VQRNMDLKFN IKSSSSSPDS RAVTCGMASL SAEKVTLDQR DYEKYSVSCQ EDVTCPTAEE   180
TLPIELALEA RQQNKYENYS TSFFIRDIIK PDPPKNLQMK PLKNSQVEVS WEYPDSWSTP   240
HSYFSLKFFV RIQRKKEKMK ETEEGCNQKG AFLVEKTSTE VQCKGGNVCV QAQDRYYNSS   300
CSKWACVPCR VRSGGSGGGS GGGSGGGSRV IPVSGPARCL SQSRNLLKTT DDMVKTAREK   360
LKHYSCTAED IDHEDITRDQ TSTLKTCLPL ELHKNESCLA TRETSSTTRG SCLPPQKTSL   420
MMTLCLGSIY EDLKMYQTEF QAINAALQNH NHQQIILDKG MLVAIDELMQ SLNHNGETLR   480
QKPPVGEADP YRVKMKLCIL LHAFSTRVVT INRVMGYLSS AGSGGGSEAH KSEIAHRYND   540
LGEQHFKGLV LIAFSQYLQK CSYDEHAKLV QEVTDFAKTC VADESAANCD KSLHTLFGDK   600
LCAIPNLREN YGELADCCTK QEPERNECFL QHKDDNPSLP PFERPEAEAM CTSFKENPTT   660
FMGHYLHEVA RRHPYFYAPE LLYYAEQYNE ILTQCCAEAD KESCLTPKLD GVKEKALVSS   720
VRQRMKCSSM QKFGERAFKA WAVARLSQTF PNADFAEITK LATDLTKVNK ECCHGDLLEC   780
ADDRAELAKY MCENQATISS KLQTCCDKPL LKKAHCLSEV EHDTMPADLP AIAADFVEDQ   840
EVCKNYAEAK DVFLGTFLYE YSRRHPDYSV SLLLRLAKKY EATLEKCCAE ANPPACYGTV   900
LAEFQPLVEE PKNLVKTNCD LYEKLGEYGF QNAILVRYTQ KAPQVSTPTL VEAARNLGRV   960
GTKCCTLPED QRLPCVEDYL SAILNRVCLL HEKTPVSEHV TKCCSGSLVE RRPCFSALTV  1020
DETYVPKEFK AETFTFHSDI CTLPEKEKQI KKQTALAELV KHKPKATAEQ LKTVMDDFAQ  1080
FLDTCCKAAD KDTCFSTEGP NLVTRCKDAL AHHHHHH                          1117

SEQ ID NO: 123          moltype = AA  length = 1445
FEATURE                 Location/Qualifiers
REGION                  1..1445
                        note = Synthetic: IL12-MSA-Lumican
source                  1..1445
                        mol_type = protein
                        organism = synthetic construct
SEQUENCE: 123
MWELEKDVYV VEVDWTPDAP GETVNLTCDT PEEDDITWTS DQRHGVIGSG KTLTITVKEF    60
LDAGQYTCHK GGETLSHSHL LLHKKENGIW STEILKNFKN KTFLKCEAPN YSGRFTCSWL   120
VQRNMDLKFN IKSSSSSPDS RAVTCGMASL SAEKVTLDQR DYEKYSVSCQ EDVTCPTAEE   180
TLPIELALEA RQQNKYENYS TSFFIRDIIK PDPPKNLQMK PLKNSQVEVS WEYPDSWSTP   240
HSYFSLKFFV RIQRKKEKMK ETEEGCNQKG AFLVEKTSTE VQCKGGNVCV QAQDRYYNSS   300
CSKWACVPCR VRSGGSGGGS GGGSGGGSRV IPVSGPARCL SQSRNLLKTT DDMVKTAREK   360
LKHYSCTAED IDHEDITRDQ TSTLKTCLPL ELHKNESCLA TRETSSTTRG SCLPPQKTSL   420
MMTLCLGSIY EDLKMYQTEF QAINAALQNH NHQQIILDKG MLVAIDELMQ SLNHNGETLR   480
QKPPVGEADP YRVKMKLCIL LHAFSTRVVT INRVMGYLSS AGSGGGSEAH KSEIAHRYND   540
LGEQHFKGLV LIAFSQYLQK CSYDEHAKLV QEVTDFAKTC VADESAANCD KSLHTLFGDK   600
LCAIPNLREN YGELADCCTK QEPERNECFL QHKDDNPSLP PFERPEAEAM CTSFKENPTT   660
FMGHYLHEVA RRHPYFYAPE LLYYAEQYNE ILTQCCAEAD KESCLTPKLD GVKEKALVSS   720
VRQRMKCSSM QKFGERAFKA WAVARLSQTF PNADFAEITK LATDLTKVNK ECCHGDLLEC   780
ADDRAELAKY MCENQATISS KLQTCCDKPL LKKAHCLSEV EHDTMPADLP AIAADFVEDQ   840
EVCKNYAEAK DVFLGTFLYE YSRRHPDYSV SLLLRLAKKY EATLEKCCAE ANPPACYGTV   900
LAEFQPLVEE PKNLVKTNCD LYEKLGEYGF QNAILVRYTQ KAPQVSTPTL VEAARNLGRV   960
GTKCCTLPED QRLPCVEDYL SAILNRVCLL HEKTPVSEHV TKCCSGSLVE RRPCFSALTV  1020
DETYVPKEFK AETFTFHSDI CTLPEKEKQI KKQTALAELV KHKPKATAEQ LKTVMDDFAQ  1080
FLDTCCKAAD KDTCFSTEGP NLVTRCKDAL AGGGSGGGSQ YYDYDIPLFM YGQISPNCAP  1140
ECNCPHSYPT AMYCDDLKLK SVPMVPPGIK YLYLRNNQID HIDEKAFENV TDLQWLILDH  1200
NLLENSKIKG KVFSKLKQLK KLHINYNNLT ESVGPLPKSL QDLQLTNNKI SKLGSFDGLV  1260
NLTFIYLQHN QLKEDAVSAS LKGLKSSEYL DLSFNQMSKL PAGLPTSLLT LYLDNNKISN  1320
IPDEYFKRFT GLQYLRLSHN ELADSGVPGN SFNISSLLEL DLSYNKLKSI PTVNENLENY  1380
YLEVNELEKF DVKSFCKILG PLSYSKIKHL RLDGNPLTQS SLPPDMYECL RVANEITVNH  1440
HHHHH                                                             1445
```

```
SEQ ID NO: 124          moltype = AA    length = 330
FEATURE                 Location/Qualifiers
REGION                  1..330
                        note = Synthetic: Lumican-GGGS-(H)6
source                  1..330
                        mol_type = protein
                        organism = synthetic construct
SEQUENCE: 124
QYYDYDIPLF MYGQISPNCA PECNCPHSYP TAMYCDDLKL KSVPMVPPGI KYLYLRNNQI    60
DHIDEKAFEN VTDLQWLILD HNLLENSKIK GKVFSKLKQL KKLHINYNNL TESVGPLPKS   120
LQDLQLTNNK ISKLGSFDGL VNLTFIYLQH NQLKEDAVSA SLKGLKSLEY LDLSFNQMSK   180
LPAGLPTSLL TLYLDNNKIS NIPDEYFKRF TGLQYLRLSH NELADSGVPG NSFNISSLLE   240
LDLSYNKLKS IPTVNENLEN YYLEVNELEK FDVKSFCKIL GPLSYSKIKH LRLDGNPLTQ   300
SSLPPDMYEC LRVANEITVN GGGSHHHHHH                                   330

SEQ ID NO: 125          moltype = AA    length = 330
FEATURE                 Location/Qualifiers
REGION                  1..330
                        note = Synthetic: Lumican D213A
source                  1..330
                        mol_type = protein
                        organism = synthetic construct
SEQUENCE: 125
QYYDYDIPLF MYGQISPNCA PECNCPHSYP TAMYCDDLKL KSVPMVPPGI KYLYLRNNQI    60
DHIDEKAFEN VTDLQWLILD HNLLENSKIK GKVFSKLKQL KKLHINYNNL TESVGPLPKS   120
LQDLQLTNNK ISKLGSFDGL VNLTFIYLQH NQLKEDAVSA SLKGLKSLEY LDLSFNQMSK   180
LPAGLPTSLL TLYLANNKIS NIPDEYFKRF TGLQYLRLSH NELADSGVPG NSFNISSLLE   240
LDLSYNKLKS IPTVNENLEN YYLEVNELEK FDVKSFCKIL GPLSYSKIKH LRLDGNPLTQ   300
SSLPPDMYEC LRVANEITVN GGGSHHHHHH                                   330

SEQ ID NO: 126          moltype = AA    length = 918
FEATURE                 Location/Qualifiers
REGION                  1..918
                        note = Synthetic: Lumican-MSA
source                  1..918
                        mol_type = protein
                        organism = synthetic construct
SEQUENCE: 126
QYYDYDIPLF MYGQISPNCA PECNCPHSYP TAMYCDDLKL KSVPMVPPGI KYLYLRNNQI    60
DHIDEKAFEN VTDLQWLILD HNLLENSKIK GKVFSKLKQL KKLHINYNNL TESVGPLPKS   120
LQDLQLTNNK ISKLGSFDGL VNLTFIYLQH NQLKEDAVSA SLKGLKSLEY LDLSFNQMSK   180
LPAGLPTSLL TLYLDNNKIS NIPDEYFKRF TGLQYLRLSH NELADSGVPG NSFNISSLLE   240
LDLSYNKLKS IPTVNENLEN YYLEVNELEK FDVKSFCKIL GPLSYSKIKH LRLDGNPLTQ   300
SSLPPDMYEC LRVANEITVN GGGSGGGSEA HKSEIAHRYN DLGEQHFKGL VLIAFSQYLQ   360
KCSYDEHAKL VQEVTDFAKT CVADESAANC DKSLHTLFGD KLCAIPNLRE NYGELADCCT   420
KQEPERNECF LQHKDDNPSL PPFERPEAEA MCTSFKENPT TFMGHYLHEV ARRHPYFYAP   480
ELLYYAEQYN EILTQCCAEA DKESCLTPKL DGVKEKALVS SVRQRMKCSS MQKFGERAFK   540
AWAVARLSQT FPNADFAEIT KLATDLTKVN KECCHGDLLE CADDRAELAK YMCENQATIS   600
SKLQTCCDKP LLKKAHCLSE VEHDTMPADL PAIAADFVED QEVCKNYAEA KDVFLGTFLY   660
EYSRRHPDYS VSLLLRLAKK YEATLEKCCA EANPPACYGT VLAEFQPLVE EPKNLVKTNC   720
DLYEKLGEYG FQNAILVRYT QKAPQVSTPT LVEAARNLGR VGTKCCTLPE DQRLPCVEDY   780
LSAILNRVCL LHEKTPVSEH VTKCCSGSLV ERRPCFSALT VDETYVPKEF KAETFTFHSD   840
ICTLPEKEKQ IKKQTALAEL VKHKPKATAE QLKTVMDDFA QFLDTCCKAA DKDTCFSTEG   900
PNLVTRCKDA LAHHHHHH                                                918

SEQ ID NO: 127          moltype = AA    length = 178
FEATURE                 Location/Qualifiers
REGION                  1..178
                        note = Synthetic: Gluc
source                  1..178
                        mol_type = protein
                        organism = synthetic construct
SEQUENCE: 127
KPTENNEDFN IVAVASNFAT TDLDADRGKL PGKKLPLEVL KEMEANARKA GCTRGCLICL    60
SHIKCTPKMK KFIPGRCHTY EGDKESAQGG IGEAIVDIPE IPGFKDLEPM EQFIAQVDLC   120
VDCTTGCLKG LANVQCSDLL KKWLPQRCAT FASKIQGQVD KIKGAGGDGG GSHHHHHH    178

SEQ ID NO: 128          moltype = AA    length = 510
FEATURE                 Location/Qualifiers
REGION                  1..510
                        note = Synthetic: Lumican-Gluc
source                  1..510
                        mol_type = protein
                        organism = synthetic construct
SEQUENCE: 128
QYYDYDIPLF MYGQISPNCA PECNCPHSYP TAMYCDDLKL KSVPMVPPGI KYLYLRNNQI    60
DHIDEKAFEN VTDLQWLILD HNLLENSKIK GKVFSKLKQL KKLHINYNNL TESVGPLPKS   120
LQDLQLTNNK ISKLGSFDGL VNLTFIYLQH NQLKEDAVSA SLKGLKSLEY LDLSFNQMSK   180
LPAGLPTSLL TLYLDNNKIS NIPDEYFKRF TGLQYLRLSH NELADSGVPG NSFNISSLLE   240
```

```
LDLSYNKLKS IPTVNENLEN YYLEVNELEK FDVKSFCKIL GPLSYSKIKH LRLDGNPLTQ    300
SSLPPDMYEC LRVANEITVN GGGSGGGSGG GSKPTENNED FNIVAVASNF ATTDLDADRG    360
KLPGKKLPLE VLKEMEANAR KAGCTRGCLI CLSHIKCTPK MKKFIPGRCH TYEGDKESAQ    420
GGIGEAIVDI PEIPGFKDLE PMEQFIAQVD LCVDCTTGCL KGLANVQCSD LLKKWLPQRC    480
ATFASKIQGQ VDKIKGAGGD GGGSHHHHHH                                    510

SEQ ID NO: 129           moltype = AA   length = 504
FEATURE                  Location/Qualifiers
REGION                   1..504
                         note = Synthetic: CNA35-Gluc
source                   1..504
                         mol_type = protein
                         organism = synthetic construct
SEQUENCE: 129
ARDISSTNVT DLTVSPSKIE DGGKTTVKMT FDDKNGKIQN GDMIKVAWPT SGTVKIEGYS     60
KTVPLTVKGE QVGQAVITPD GATITFNDKV EKLSDVSGFA EFEVQGRNLT QTNTSDDKVA    120
TITSGNKSTN VTVHKSEAGT SSVFYYKTGD MLPEDTTHVR WFLNINNEKS YVSKDITIKD    180
QIQGGQQLDL STLNINVTGT HSNYYSGQSA ITDFEKAFPG SKITVDNTKN TIDVTIPQGY    240
GSYNSFSINY KTKITNEQQK EFVNNSQAWY QEHGKEEVNG KSFNHTVHNI NANAGIEGTV    300
KGELKVLKQD KDTKGGGSGG GSGGGSKPTE NNEDFNIVAV ASNFATTDLD ADRGKLPGKK    360
LPLEVLKEME ANARKAGCTR GCLICLSHIK CTPKMKKFIP GRCHTYEGDK ESAQGGIGEA    420
IVDIPEIPGF KDLEPMEQFI AQVDLCVDCT TGCLKGLANV QCSDLLKKWL PQRCATFASK    480
IQGQVDKIKG AGGDGGGSHH HHHH                                          504

SEQ ID NO: 130           moltype = AA   length = 422
FEATURE                  Location/Qualifiers
REGION                   1..422
                         note = Synthetic: ColG s3a/s3b-Gluc
source                   1..422
                         mol_type = protein
                         organism = synthetic construct
SEQUENCE: 130
PITKEMEPND DIKEANGPIV EGVTVKGDLN GSDDADTFYF DVKEDGDVTI ELPYSGSSNF     60
TWLVYKEGDD QNHIASGIDK NNSKVGTFKS TKGRHYVFIY KHDSASNISY SLNIKGLGNE    120
KLKEKENNDS SDKATVIPNF NTTMQGSLLG DDSRDYYSFE VKEEGEVNIE LDKKDEFGVT    180
WTLHPESNIN DRITYGQVDG NKVSNKVKLR PGKYYLLVYK YSGSGNYELR VNGGGSGGGS    240
GGGSKPTENN EDFNIVAVAS NFATTDLDAD RGKLPGKKLP LEVLKEMEAN ARKAGCTRGC    300
LICLSHIKCT PKMKKFIPGR CHTYEGDKES AQGGIGEAIV DIPEIPGFKD LEPMEQFIAQ    360
VDLCVDCTTG CLKGLANVQC SDLLKKWLPQ RCATFASKIQ GQVDKIKGAG GDGGGSHHHH    420
HH                                                                  422

SEQ ID NO: 131           moltype = AA   length = 301
FEATURE                  Location/Qualifiers
REGION                   1..301
                         note = Synthetic: ColH_s3-Gluc
source                   1..301
                         mol_type = protein
                         organism = synthetic construct
SEQUENCE: 131
GTEKEPNNSK ETASGPIVPG IPVSGTIENT SDQDYFYFDV ITPGEVKIDI NKLGYGGATW     60
VVYDENNNAV SYATDDGQNL SGKFKADKPG RYYIHLYMFN GSYMPYRINI EGGGSGGGSG    120
GGSKPTENNE DFNIVAVASN FATTDLDADR GKLPGKKLPL EVLKEMEANA RKAGCTRGCL    180
ICLSHIKCTP KMKKFIPGRC HTYEGDKESA QGGIGEAIVD IPEIPGFKDL EPMEQFIAQV    240
DLCVDCTTGC LKGLANVQCS DLLKKWLPQR CATFASKIQG QVDKIKGAGG DGGGSHHHHH    300
H                                                                   301

SEQ ID NO: 132           moltype = AA   length = 212
FEATURE                  Location/Qualifiers
REGION                   1..212
                         note = Synthetic: PLGF2 HBD-Gluc
source                   1..212
                         mol_type = protein
                         organism = synthetic construct
SEQUENCE: 132
RRRPKGRGKR RREKQRPTDS HLGGGSGGGS GGGSKPTENN EDFNIVAVAS NFATTDLDAD     60
RGKLPGKKLP LEVLKEMEAN ARKAGCTRGC LICLSHIKCT PKMKKFIPGR CHTYEGDKES    120
AQGGIGEAIV DIPEIPGFKD LEPMEQFIAQ VDLCVDCTTG CLKGLANVQC SDLLKKWLPQ    180
RCATFASKIQ GQVDKIKGAG GDGGGSHHHH HH                                  212

SEQ ID NO: 133           moltype = AA   length = 1181
FEATURE                  Location/Qualifiers
REGION                   1..1181
                         note = Synthetic: 4M5.3-MSA-Lumican
source                   1..1181
                         mol_type = protein
                         organism = synthetic construct
SEQUENCE: 133
ADVVMTQTPL SLPVSLGDQA SISCRSSQSL VHSNGNTYLR WYLQKPGQSP KVLIYKVSNR     60
VSGVPDRFSG SGSGTDFTLK INRVEAEDLG VYFCSQSTHV PWTFGGGTKL EIKSSADDAK    120
```

```
KDAAKKDDAK KDDAKKDGGV KLDETGGGLV QPGGAMKLSC VTSGFTFGHY WMNWVRQSPE   180
KGLEWVAQFR NKPYNYETYY SDSVKGRFTI SRDDSKSSVY LQMNNLRVED TGIYYCTGAS   240
YGMEYLQGGT SVTVSGGGSE AHKSEIAHRY NDLGEQHFKG LVLIAFSQYL QKCSYDEHAK   300
LVQEVTDFAK TCVADESAAN CDKSLHTLFG DKLCAIPNLR ENYGELADCC TKQEPERNEC   360
FLQHKDDNPS LPPFERPEAE AMCTSFKENP TTFMGHYLHE VARRHPYFYA PELLYYAEQY   420
NEILTQCCAE ADKESCLTPK LDGVKEKALV SSVRQRMKCS SMQKFGERAF KAWAVARLSQ   480
TFPNADFAEI TKLATDLTKV NKECCHGDLL ECADDRAELA KYMCENQATI SSKLQTCCDK   540
PLLKKAHCLS EVEHDTMPAD LPAIAADFVE DQEVCKNYAE AKDVFLGTFL YEYSRRHPDY   600
SVSLLLRLAK KYEATLEKCC AEANPPACYG TVLAEFQPLV EEPKNLVKTN CDLYEKLGEY   660
GFQNAILVRY TQKAPQVSTP TLVEAARNLG RVGTKCCTLP EDQRLPCVED YLSAILNRVC   720
LLHEKTPVSE HVTKCCSGSL VERRPCFSAL TVDETYVPKE FKAETFTFHS DICTLPEKEK   780
QIKKQTALAE LVKHKPKATA EQLKTVMDDF AQFLDTCCKA ADKDTCFSTE GPNLVTRCKD   840
ALAGGGSGGG SQYYDYDIPL FMYGQISPNC APECNCPHSY PTAMYCDDLK LKSVPMVPPG   900
IKYLYLRNNQ IDHIDEKAFE NVTDLQWLIL DHNLLENSKI KGKVFSKLKQ LKKLHINYNN   960
LTESVGPLPK SLQDLQLTNN KISKLGSFDG LVNLTFIYLQ HNQLKEDAVS ASLKGLKSLE  1020
YLDLSFNQMS KLPAGLPTSL LTLYLDNNKI SNIPDEYFKR FTGLQYLRLS HNELADSGVP  1080
GNSFNISSLL ELDLSYNKLK SIPTVNENLE NYYLEVNELE KFDVKSFCKI LGPLSYSKIK  1140
HLRLDGNPLT QSSLPPDMYE CLRVANEITV NGGGSHHHHH H                     1181

SEQ ID NO: 134           moltype = AA   length = 989
FEATURE                  Location/Qualifiers
REGION                   1..989
                         note = Synthetic: Ss07d-MSA-Lumican
source                   1..989
                         mol_type = protein
                         organism = synthetic construct
SEQUENCE: 134
ATVKFKYKGE EKQVDISKIY LVLRLGKFIY FYYDLGGGKL GLGHVSEKDA PKELLQMLEK    60
QKKGGGSEAH KSEIAHRYND LGEQHFKGLV LIAFSQYLQK CSYDEHAKLV QEVTDFAKTC   120
VADESAANCD KSLHTLFGDK LCAIPNLREN YGELADCCTK QEPERNECFL QHKDDNPSLP   180
PFERPEAEAM CTSFKENPTT FMGHYLHEVA RRHPYFYAPE LLYYAEQYNE ILTQCCAEAD   240
KESCLTPKLD GVKEKALVSS VRQRMKCSSM QKFGERAFKA WAVARLSQTF PNADFAEITK   300
LATDLTKVNK ECCHGDLLEC ADDRAELAKY MCENQATISS KLQTCCDKPL LKKAHCLSEV   360
EHDTMPADLP AIAADFVEDQ EVCKNYAEAK DVFLGTFLYE YSRRHPDYSV SLLLRLAKKY   420
EATLEKCCAE ANPPACYGTV LAEFQPLVEE PKNLVKTNCD LYEKLGEYGF QNAILVRYTQ   480
KAPQVSTPTL VEAARNLGRV GTKCCTLPED QRLPCVEDYL SAILNRVCLL HEKTPVSEHV   540
TKCCSGSLVE RRPCFSALTV DETYVPKEFK AETFTFHSDI CTLPEKEKQI KKQTALAELV   600
KHKPKATAEQ LKTVMDDFAQ FLDTCCKAAD KDTCFSTEGP NLVTRCKDAL AGGGSGGGSQ   660
YYDYDIPLFM YGQISPNCAP ECNCPHSYPT AMYCDDLKLK SVPMVPPGIK YLYLRNNQID   720
HIDEKAFENV TDLQWLILDH NLLENSKIKG KVFSKLKQLK KLHINYNNLT ESVGPLPKSL   780
QDLQLTNNKI SKLGSFDGLV NLTFIYLQHN QLKEDAVSAS LKGLKSLEYL DLSFNQMSKL   840
PAGLPTSLLT LYLDNNKISN IPDEYFKRFT GLQYLRLSHN ELADSGVPGN SFNISSLLEL   900
DLSYNKLKSI PTVNENLENY YLEVNELEKF DVKSFCKILG PLSYSKIKHL RLDGNPLTQS   960
SLPPDMYECL RVANEITVNG GGSHHHHHH                                    989

SEQ ID NO: 135           moltype = AA   length = 1063
FEATURE                  Location/Qualifiers
REGION                   1..1063
                         note = Synthetic: ZZ-MSA Lumican
source                   1..1063
                         mol_type = protein
                         organism = synthetic construct
SEQUENCE: 135
MRVPAQLLGL LLLWLPGARC AVDNKFNKEQ QNAFYEILHL PNLNEEQRNA FIQSLKDDPS    60
QSANLLAEAK KLNDAQAPKV DNKFNKEQQN AFYEILHLPN LNEEQRNAFI QSLKDDPSQS   120
ANLLAEAKKL NDAQAPKGGG SEAHKSEIAH RYNDLGEQHF KGLVLIAFSQ YLQKCSYDEH   180
AKLVQEVTDF AKTCVADESA ANCDKSLHTL FGDKLCAIPN LRENYGELAD CCTKQEPERN   240
ECFLQHKDDN PSLPPFERPE AEAMCTSFKE NPTTFMGHYL HEVARRHPYF YAPELLYYAE   300
QYNEILTQCC AEADKESCLT PKLDGVKEKA LVSSVRQRMK CSSMQKFGER AFKAWAVARL   360
SQTFPNADFA EITKLATDLT KVNKECCHGD LLECADDRAE LAKYMCENQA TISSKLQTCC   420
DKPLLKKAHC LSEVEHDTMP ADLPAIAADF VEDQEVCKNY AEAKDVFLGT FLYEYSRRHP   480
DYSVSLLLRL AKKYEATLEK CCAEANPPAC YGTVLAEFQP LVEEPKNLVK TNCDLYEKLG   540
EYGFQNAILV RYTQKAPQVS TPTLVEAARN LGRVGTKCCT LPEDQRLPCV EDYLSAILNR   600
VCLLHEKTPV SEHVTKCCSG SLVERRPCFS ALTVDETYVP KEFKAETFTF HSDICTLPEK   660
EKQIKKQTAL AELVKHKPKA TAEQLKTVMD DFAQFLDTCC KAADKDTCFS TEGPNLVTRC   720
KDALAGGGSG GGSQYYDYDI PLFMYGQISP NCAPECNCPH SYPTAMYCDD LKLKSVPMVP   780
PGIKYLYLRN NQIDHIDEKA FENVTDLQWL ILDHNLLENS KIKGKVFSKL KQLKKLHINY   840
NNLTESVGPL PKSLQDLQLT NNKISKLGSF DGLVNLTFIY LQHNQLKEDA VSASLKGLKS   900
LEYLDLSFNQ MSKLPAGLPT SLLTLYLDNN KISNIPDEYF KRFTGLQYLR LSHNELADSG   960
VPGNSFNISS LLELDLSYNK LKSIPTVNEN LENYYLEVNE LEKFDVKSFC KILGPLSYSK  1020
IKHLRLDGNP LTQSSLPPDM YECLRVANEI TVNGGGSHHH HHH                   1063

SEQ ID NO: 136           moltype = AA   length = 937
FEATURE                  Location/Qualifiers
REGION                   1..937
                         note = Synthetic: Lumican-MSA-FcIII4C
source                   1..937
                         mol_type = protein
                         organism = synthetic construct
```

```
SEQUENCE: 136
QYYDYDIPLF MYGQISPNCA PECNCPHSYP TAMYCDDLKL KSVPMVPPGI KYLYLRNNQI    60
DHIDEKAFEN VTDLQWLILD HNLLENSKIK GKVFSKLKQL KKLHINYNNL TESVGPLPKS   120
LQDLQLTNNK ISKLGSFDGL VNLTFIYLQH NQLKEDAVSA SLKGLKSLEY LDLSFNQMSK   180
LPAGLPTSLL TLYLDNNKIS NIPDEYFKRF TGLQYLRLSH NELADSGVPG NSFNISSLLE   240
LDLSYNKLKS IPTVNENLEN YYLEVNELEK FDVKSFCKIL GPLSYSKIKH LRLDGNPLTQ   300
SSLPPDMYEC LRVANEITVN GGGSGGGSEA HKSEIAHRYN DLGEQHFKGL VLIAFSQYLQ   360
KCSYDEHAKL VQEVTDFAKT CVADESAANC DKSLHTLFGD KLCAIPNLRE NYGELADCCT   420
KQEPERNECF LQHKDDNPSL PPFERPEAEA MCTSFKENPT TFMGHYLHEV ARRHPYFYAP   480
ELLYYAEQYN EILTQCCAEA DKESCLTPKL DGVKEKALVS SVRQRMKCSS MQKFGERAFK   540
AWAVARLSQT FPNADFAEIT KLATDLTKVN KECCHGDLLE CADDRAELAK YMCENQATIS   600
SKLQTCCDKP LLKKAHCLSE VEHDTMPADL PAIAADFVED QEVCKNYAEA KDVFLGTFLY   660
EYSRRHPDYS VSLLLRLAKK YEATLEKCCA EANPPACYGT VLAEFQPLVE EPKNLVKTNC   720
DLYEKLGEYG FQNAILVRYT QKAPQVSTPT LVEAARNLGR VGTKCCTLPE DQRLPCVEDY   780
LSAILNRVCL LHEKTPVSEH VTKCCSGSLV ERRPCFSALT VDETYVPKEF KAETFTFHSD   840
ICTLPEKEKQ IKKQTALAEL VKHKPKATAE QLKTVMDDFA QFLDTCCKAA DKDTCFSTEG   900
PNLVTRCKDA LAGGGSCDCA WHLGELVWCT CHHHHHH                           937

SEQ ID NO: 137         moltype = AA length = 1012
FEATURE                Location/Qualifiers
REGION                 1..1012
                       note = Synthetic: Lumican-MSA-Fn3
source                 1..1012
                       mol_type = protein
                       organism = synthetic construct
SEQUENCE: 137
QYYDYDIPLF MYGQISPNCA PECNCPHSYP TAMYCDDLKL KSVPMVPPGI KYLYLRNNQI    60
DHIDEKAFEN VTDLQWLILD HNLLENSKIK GKVFSKLKQL KKLHINYNNL TESVGPLPKS   120
LQDLQLTNNK ISKLGSFDGL VNLTFIYLQH NQLKEDAVSA SLKGLKSLEY LDLSFNQMSK   180
LPAGLPTSLL TLYLDNNKIS NIPDEYFKRF TGLQYLRLSH NELADSGVPG NSFNISSLLE   240
LDLSYNKLKS IPTVNENLEN YYLEVNELEK FDVKSFCKIL GPLSYSKIKH LRLDGNPLTQ   300
SSLPPDMYEC LRVANEITVN GGGSGGGSEA HKSEIAHRYN DLGEQHFKGL VLIAFSQYLQ   360
KCSYDEHAKL VQEVTDFAKT CVADESAANC DKSLHTLFGD KLCAIPNLRE NYGELADCCT   420
KQEPERNECF LQHKDDNPSL PPFERPEAEA MCTSFKENPT TFMGHYLHEV ARRHPYFYAP   480
ELLYYAEQYN EILTQCCAEA DKESCLTPKL DGVKEKALVS SVRQRMKCSS MQKFGERAFK   540
AWAVARLSQT FPNADFAEIT KLATDLTKVN KECCHGDLLE CADDRAELAK YMCENQATIS   600
SKLQTCCDKP LLKKAHCLSE VEHDTMPADL PAIAADFVED QEVCKNYAEA KDVFLGTFLY   660
EYSRRHPDYS VSLLLRLAKK YEATLEKCCA EANPPACYGT VLAEFQPLVE EPKNLVKTNC   720
DLYEKLGEYG FQNAILVRYT QKAPQVSTPT LVEAARNLGR VGTKCCTLPE DQRLPCVEDY   780
LSAILNRVCL LHEKTPVSEH VTKCCSGSLV ERRPCFSALT VDETYVPKEF KAETFTFHSD   840
ICTLPEKEKQ IKKQTALAEL VKHKPKATAE QLKTVMDDFA QFLDTCCKAA DKDTCFSTEG   900
PNLVTRCKDA LAGGGSVSDV PRDLEVVAAT PTSLLISWCC SDNCSNSYRI TYGETGGNSP   960
VQEFTVPRSC FMATISGLKP GVDYTITAYA VTDSNGHPPI SINYRTHHHH HH         1012

SEQ ID NO: 138         moltype = AA length = 1047
FEATURE                Location/Qualifiers
REGION                 1..1047
                       note = Synthetic: Lumican-MSA-SpG2
source                 1..1047
                       mol_type = protein
                       organism = synthetic construct
SEQUENCE: 138
QYYDYDIPLF MYGQISPNCA PECNCPHSYP TAMYCDDLKL KSVPMVPPGI KYLYLRNNQI    60
DHIDEKAFEN VTDLQWLILD HNLLENSKIK GKVFSKLKQL KKLHINYNNL TESVGPLPKS   120
LQDLQLTNNK ISKLGSFDGL VNLTFIYLQH NQLKEDAVSA SLKGLKSLEY LDLSFNQMSK   180
LPAGLPTSLL TLYLDNNKIS NIPDEYFKRF TGLQYLRLSH NELADSGVPG NSFNISSLLE   240
LDLSYNKLKS IPTVNENLEN YYLEVNELEK FDVKSFCKIL GPLSYSKIKH LRLDGNPLTQ   300
SSLPPDMYEC LRVANEITVN GGGSGGGSEA HKSEIAHRYN DLGEQHFKGL VLIAFSQYLQ   360
KCSYDEHAKL VQEVTDFAKT CVADESAANC DKSLHTLFGD KLCAIPNLRE NYGELADCCT   420
KQEPERNECF LQHKDDNPSL PPFERPEAEA MCTSFKENPT TFMGHYLHEV ARRHPYFYAP   480
ELLYYAEQYN EILTQCCAEA DKESCLTPKL DGVKEKALVS SVRQRMKCSS MQKFGERAFK   540
AWAVARLSQT FPNADFAEIT KLATDLTKVN KECCHGDLLE CADDRAELAK YMCENQATIS   600
SKLQTCCDKP LLKKAHCLSE VEHDTMPADL PAIAADFVED QEVCKNYAEA KDVFLGTFLY   660
EYSRRHPDYS VSLLLRLAKK YEATLEKCCA EANPPACYGT VLAEFQPLVE EPKNLVKTNC   720
DLYEKLGEYG FQNAILVRYT QKAPQVSTPT LVEAARNLGR VGTKCCTLPE DQRLPCVEDY   780
LSAILNRVCL LHEKTPVSEH VTKCCSGSLV ERRPCFSALT VDETYVPKEF KAETFTFHSD   840
ICTLPEKEKQ IKKQTALAEL VKHKPKATAE QLKTVMDDFA QFLDTCCKAA DKDTCFSTEG   900
PNLVTRCKDA LAGGGSTYKL VINGKTLKGE TTTEAVDAAT AEKVFKQYAN DYGVDGEWTY   960
DDATKTFTVT EKPEVIDASE LTPAVTTYKL VINGKTLKGE TTTKAVDAET AEKAFKQYAN  1020
DYGVDGVWTY DDATKTFTVT EHHHHHH                                     1047

SEQ ID NO: 139         moltype = AA length = 926
FEATURE                Location/Qualifiers
REGION                 1..926
                       note = Synthetic: Lumican-MSA-RRGW
source                 1..926
                       mol_type = protein
                       organism = synthetic construct
SEQUENCE: 139
```

```
QYYDYDIPLF MYGQISPNCA PECNCPHSYP TAMYCDDLKL KSVPMVPPGI KYLYLRNNQI    60
DHIDEKAFEN VTDLQWLILD HNLLENSKIK GKVFSKLKQL KKLHINYNNL TESVGPLPKS   120
LQDLQLTNNK ISKLGSFDGL VNLTFIYLQH NQLKEDAVSA SLKGLKSLEY LDLSFNQMSK   180
LPAGLPTSLL TLYLDNNKIS NIPDEYFKRF TGLQYLRLSH NELADSGVPG NSFNISSLLE   240
LDLSYNKLKS IPTVNENLEN YYLEVNELEK FDVKSFCKIL GPLSYSKIKH LRLDGNPLTQ   300
SSLPPDMYEC LRVANEITVN GGGSGGGSEA HKSEIAHRYN DLGEQHFKGL VLIAFSQYLQ   360
KCSYDEHAKL VQEVTDFAKT CVADESAANC DKSLHTLFGD KLCAIPNLRE NYGELADCCT   420
KQEPERNECF LQHKDDNPSL PPFERPEAEA MCTSFKENPT TFMGHYLHEV ARRHPYFYAP   480
ELLYYAEQYN EILTQCCAEA DKESCLTPKL DGVKEKALVS SVRQRMKCSS MQKFGERAFK   540
AWAVARLSQT FPNADFAEIT KLATDLTKVN KECCHGDLLE CADDRAELAK YMCENQATIS   600
SKLQTCCDKP LLKKAHCLSE VEHDTMPADL PAIAADFVED QEVCKNYAEA KDVFLGTFLY   660
EYSRRHPDYS VSLLLRLAKK YEATLEKCCA EANPPACYGT VLAEFQPLVE EPKNLVKTNC   720
DLYEKLGEYG FQNAILVRYT QKAPQVSTPT LVEAARNLGR VGTKCCTLPE DQRLPCVEDY   780
LSAILNRVCL LHEKTPVSEH VTKCCSGSLV ERRPCFSALT VDETYVPKEF KAETFTFHSD   840
ICTLPEKEKQ IKKQTALAEL VKHKPKATAE QLKTVMDDFA QFLDTCCKAA DKDTCFSTEG   900
PNLVTRCKDA LAGGGSRRGW HHHHHH                                       926

SEQ ID NO: 140          moltype = AA   length = 926
FEATURE                 Location/Qualifiers
REGION                  1..926
                        note = Synthetic: Lumican-MSA-WGRR
source                  1..926
                        mol_type = protein
                        organism = synthetic construct
SEQUENCE: 140
QYYDYDIPLF MYGQISPNCA PECNCPHSYP TAMYCDDLKL KSVPMVPPGI KYLYLRNNQI    60
DHIDEKAFEN VTDLQWLILD HNLLENSKIK GKVFSKLKQL KKLHINYNNL TESVGPLPKS   120
LQDLQLTNNK ISKLGSFDGL VNLTFIYLQH NQLKEDAVSA SLKGLKSLEY LDLSFNQMSK   180
LPAGLPTSLL TLYLDNNKIS NIPDEYFKRF TGLQYLRLSH NELADSGVPG NSFNISSLLE   240
LDLSYNKLKS IPTVNENLEN YYLEVNELEK FDVKSFCKIL GPLSYSKIKH LRLDGNPLTQ   300
SSLPPDMYEC LRVANEITVN GGGSGGGSEA HKSEIAHRYN DLGEQHFKGL VLIAFSQYLQ   360
KCSYDEHAKL VQEVTDFAKT CVADESAANC DKSLHTLFGD KLCAIPNLRE NYGELADCCT   420
KQEPERNECF LQHKDDNPSL PPFERPEAEA MCTSFKENPT TFMGHYLHEV ARRHPYFYAP   480
ELLYYAEQYN EILTQCCAEA DKESCLTPKL DGVKEKALVS SVRQRMKCSS MQKFGERAFK   540
AWAVARLSQT FPNADFAEIT KLATDLTKVN KECCHGDLLE CADDRAELAK YMCENQATIS   600
SKLQTCCDKP LLKKAHCLSE VEHDTMPADL PAIAADFVED QEVCKNYAEA KDVFLGTFLY   660
EYSRRHPDYS VSLLLRLAKK YEATLEKCCA EANPPACYGT VLAEFQPLVE EPKNLVKTNC   720
DLYEKLGEYG FQNAILVRYT QKAPQVSTPT LVEAARNLGR VGTKCCTLPE DQRLPCVEDY   780
LSAILNRVCL LHEKTPVSEH VTKCCSGSLV ERRPCFSALT VDETYVPKEF KAETFTFHSD   840
ICTLPEKEKQ IKKQTALAEL VKHKPKATAE QLKTVMDDFA QFLDTCCKAA DKDTCFSTEG   900
PNLVTRCKDA LAGGGSWGRR HHHHHH                                       926

SEQ ID NO: 141          moltype = AA   length = 219
FEATURE                 Location/Qualifiers
REGION                  1..219
                        note = Synthetic: 4420 LC murine kappa chain
source                  1..219
                        mol_type = protein
                        organism = synthetic construct
SEQUENCE: 141
DVVMTQTPLS LPVSLGDQAS ISCRSSQSLV HSNGNTYLRW YLQKPGQSPK VLIYKVSNRF    60
SGVPDRFSGS GSGTDFTLKI SRVEAEDLGV YFCSQSTHVP WTFGGGTKLE IKRADAAPTV   120
SIFPPSSEQL TSGGASVVCF LNNFYPKDIN VKWKIDGSER QNGVLNSWTD QDSKDSTYSM   180
SSTLTLTKDE YERHNSYTCE ATHKTSTSPI VKSFNRNEC                          219

SEQ ID NO: 142          moltype = AA   length = 787
FEATURE                 Location/Qualifiers
REGION                  1..787
                        note = Synthetic: 4220 HC-Lumican (LALA-PG)
source                  1..787
                        mol_type = protein
                        organism = synthetic construct
SEQUENCE: 142
DVKLDETGGG LVQPGRPMKL SCVASGFTFS DYWMNWVRQS PEKGLEWVAQ IRNKPYNYET    60
YYSDSVKGRF TISRDDSKSS VYLQMNNLRV EDMGIYYCTG SYYGMDYWGQ GTSVTVSAKT   120
TAPSVYPLAP VCGGTTGSSV TLGCLVKGYF PEPVTLTWNS GSLSSGVHTF PALLQSGLYT   180
LSSSVTVTSN TWPSQTITCN VAHPASSTKV DKKIEPRVPI TQNPCPPLKE CPPCAAPDAA   240
GGPSVFIFPP KIKDVLMISL SPMVTCVVVD VSEDDPDVQI SWFVNNVEVH TAQTQTHRED   300
YNSTLRVVSA LPIQHQDWMS GKEFKCKVNN RALGSPIEKT ISKPRGPVRA PQVYVLPPPA   360
EEMTKKEFSL TCMITGFLPA EIAVDWTSNG RTEQNYKNTA TVLDSDGSYF MYSKLRVQKS   420
TWERGSLFAC SVVHEGLHNH LTTKTISRSL GKGGGGSGGG GSGGGGSQYY DYDIPLFMYG   480
QISPNCAPEC NCPHSYPTAM YCDDLKLKSV PMVPPGIKYL YLRNNQIDHI DEKAFENVTD   540
LQWLILDHNL LENSKIKGKV FSKLKQLKKL HINYNNLTES VGPLPKSLQD LQLTNNKISK   600
LGSFDGLVNL TFIYLQHNQL KEDAVSASLK GLKSLEYLDL SFNQMSKLPA GLPTSLLTLY   660
LDNNKISNIP DEYFKRFTGL QYLRLSHNEL ADSGVPGNSF NISSLLELDL SYNKLKSIPT   720
VNENLENYYL EVNELEKFDV KSFCKILGPL SYSKIKHLRL DGNPLTQSSL PPDMYECLRV   780
ANEITVN                                                            787

SEQ ID NO: 143          moltype = AA   length = 452
```

```
FEATURE            Location/Qualifiers
REGION             1..452
                   note = Synthetic: 4220 HC mIgG2c
source             1..452
                   mol_type = protein
                   organism = synthetic construct
SEQUENCE: 143
DVKLDETGGG LVQPGRPMKL SCVASGFTFS DYWMNWVRQS PEKGLEWVAQ IRNKPYNYET   60
YYSDSVKGRF TISRDDSKSS VYLQMNNLRV EDMGIYYCTG SYYGMDYWGQ GTSVTVSAKT  120
TAPSVYPLAP VCGGTTGSSV TLGCLVKGYF PEPVTLTWNS GSLSSGVHTF PALLQSGLYT  180
LSSSVTVTSN TWPSQTITCN VAHPASSTKV DKKIEPRVPI TQNPCPPLKE CPPCAAPDAA  240
GGPSVFIFPP KIKDVLMISL SPMVTCVVVD VSEDDPDVQI SWFVNNVEVH TAQTQTHRED  300
YNSTLRVVSA LPIQHQDWMS GKEFKCKVNN RALGSPIEKT ISKPRGPVRA PQVYVLPPPA  360
EEMTKKEFSL TCMITGFLPA EIAVDWTSNG RTEQNYKNTA TVLDSDGSYF MYSKLRVQKS  420
TWERGSLFAC SVVHEGLHNH LTTKTISRSL GK                               452

SEQ ID NO: 144     moltype = AA  length = 233
FEATURE            Location/Qualifiers
REGION             1..233
                   note = Synthetic: 3/23 LC murine kappa
source             1..233
                   mol_type = protein
                   organism = synthetic construct
SEQUENCE: 144
METDTLLLWV LLLWVPGSTG DTVLTQSPAL AVSPGERVTI SCRASESVST RMHWYQQRPG   60
QPPKLLIYVA SRLESGVPAR FSGGGSGTDF TLTIDPVEAN DTATYFCQQS WNDPWTFGGG  120
TKLELKRADA APTVSIFPPS SEQLTSGGAS VVCFLNNFYP KDINVKWKID GSERQNGVLN  180
SWTDQDSKDS TYSMSSTLTL TKDEYERHNS YTCEATHKTS TSPIVKSFNR NEC         233

SEQ ID NO: 145     moltype = AA  length = 805
FEATURE            Location/Qualifiers
REGION             1..805
                   note = Synthetic: 3/23 HC-lumican
source             1..805
                   mol_type = protein
                   organism = synthetic construct
SEQUENCE: 145
MDIWLSLVFL VLFIKGVQCE VQLVESGGGL VQPGRSLKLS CAASGFTLSD YYMAWVRQAP   60
KKGLEWVASI NYEGSSTYYG ESVKGRFTIS RDNAKSTLYL QMNSLRSEDT ATYYCVRHDN  120
YFDYWGQGVL VTVSSAKTTA PSVYPLAPVC GGTTGSSVTL GCLVKGYFPE PVTLTWNSGS  180
LSSGVHTFPA LLQSGLYTLS SSVTVTSNTW PSQTITCNVA HPASSTKVDK KIEPRVPITQ  240
NPCPPLKECP PCAAPDAAGG PSVFIFPPKI KDVLMISLSP MVTCVVVDVS EDDPDVQISW  300
FVNNVEVHTA QTQTHREDYN STLRVVSALP IQHQDWMSGK EFKCKVNNRA LGSPIEKTIS  360
KPRGPVRAPQ VYVLPPPAEE MTKKEFSLTC MITGFLPAEI AVDWTSNGRT EQNYKNTATV  420
LDSDGSYFMY SKLRVQKSTW ERGSLFACSV VHEGLHNHLT TKTISRSLGK GGGGSGGGGS  480
GGGGSQYYDY DIPLFMYGQI SPNCAPECNC PHSYPTAMYC DDLKLKSVPM VPPGIKYLYL  540
RNNQIDHIDE KAFENVTDLQ WLILDHNLLE NSKIKGKVFS KLKQLKKLHI NYNNLTESVG  600
PLPKSLQDLQ LTNNKISKLG SFDGLVNLTF IYLQHNQLKE DAVSASLKGL KSLEYLDLSF  660
NQMSKLPAGL PTSLLTLYLD NNKISNIPDE YFKRFTGLQY LRLSHNELAD SGVPGNSFNI  720
SSLLELDLSY NKLKSIPTVN ENLENYYLEV NELEKFDVKS FCKILGPLSY SKIKHLRLDG  780
NPLTQSSLPP DMYECLRVAN EITVN                                       805

SEQ ID NO: 146     moltype = AA  length = 214
FEATURE            Location/Qualifiers
REGION             1..214
                   note = Synthetic: LOB12.3 LC murine kappa
source             1..214
                   mol_type = protein
                   organism = synthetic construct
SEQUENCE: 146
DIQMTQSPAS LSASLEEIVT ITCQASQDIG NWLAWYHQKP GKSPQLLIYG STSLADGVPS   60
RFSGSSSGSQ YSLKISRLQV EDIGIYYCLQ AYGAPWTFGG GTKLELKRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                              214

SEQ ID NO: 147     moltype = AA  length = 790
FEATURE            Location/Qualifiers
REGION             1..790
                   note = Synthetic: LOB12.3 HC- Lumican
source             1..790
                   mol_type = protein
                   organism = synthetic construct
SEQUENCE: 147
DVQLVESGGG LVQPGRSLKL SCAASGFIFS YFDMAWVRQA PTKGLEWVAS ISPDGSIPYY   60
RDSVKGRFTV SRENAKSSLY LQMDSLRSED TATYYCARRS YGGYSEIDYW GQGVMVTVSS  120
AKTTAPSVYP LAPVCGGTTG SSVTLGCLVK GYFPEPVTLT WNSGSLSSGV HTFPALLQSG  180
LYTLSSSVTV TSNTWPSQTI TCNVAHPASS TKVDKKIEPR VPITQNPCPP LKECPPCAAP  240
DAAGGPSVFI FPPKIKDVLM ISLSPMVTCV VVDVSEDDPD VQISWFVNNV EVHTAQTQTH  300
REDYNSTLRV VSALPIQHQD WMSGKEFKCK VNNRALGSPI EKTISKPRGP VRAPQVYVLP  360
```

```
PPAEEMTKKE FSLTCMITGF LPAEIAVDWT SNGRTEQNYK NTATVLDSDG SYFMYSKLRV    420
QKSTWERGSL FACSVVHEGL HNHLTTKTIS RSLGKGGGGS GGGGSGGGGS QYYDYDIPLF    480
MYGQISPNCA PECNCPHSYP TAMYCDDLKL KSVPMVPPGI KYLYLRNNQI DHIDEKAFEN    540
VTDLQWLILD HNLLENSKIK GKVFSKLKQL KKLHINYNNL TESVGPLPKS LQDLQLTNNK    600
ISKLGSFDGL VNLTFIYLQH NQLKEDAVSA SLKGLKSLEY LDLSFNQMSK LPAGLPTSLL    660
TLYLDNNKIS NIPDEYFKRF TGLQYLRLSH NELADSGVPG NSFNISSLLE LDLSYNKLKS    720
IPTVNENLEN YYLEVNELEK FDVKSFCKIL GPLSYSKIKH LRLDGNPLTQ SSLPPDMYEC    780
LRVANEITVN                                                          790

SEQ ID NO: 148          moltype = AA  length = 219
FEATURE                 Location/Qualifiers
REGION                  1..219
                        note = Synthetic: OX86 LC murine kappa
source                  1..219
                        mol_type = protein
                        organism = synthetic construct
SEQUENCE: 148
DIVMTQGALP NPVPSGESAS ITCRSSQSLV YKDGQTYLNW FLQRPGQSPQ LLTYWMSTRA     60
SGVSDRFSGS GSGTYFTLKI SRVRAEDAGV YYCQQVREYP FTFGSGTKLE IKRADAAPTV    120
SIFPPSSEQL TSGGASVVCF LNNFYPKDIN VKWKIDGSER QNGVLNSWTD QDSKDSTYSM    180
SSTLTLTKDE YERHNSYTCE ATHKTSTSPI VKSFNRNEC                           219

SEQ ID NO: 149          moltype = AA  length = 787
FEATURE                 Location/Qualifiers
REGION                  1..787
                        note = Synthetic: OX86 HC-Lumican
source                  1..787
                        mol_type = protein
                        organism = synthetic construct
SEQUENCE: 149
QVQLKESGPG LVQPSQTLSL TCTVSGFSLT GYNLHWVRQP PGKGLEWMGR MRYDGDTYYN     60
SVLKSRLSIS RDTSKNQVFL KMNSLQTDDT AIYYCTRDGR GDSFDYWGQG VMVTVSSAKT    120
TAPSVYPLAP VCGGTTGSSV TLGCLVKGYF PEPVTLTWNS GSLSSGVHTF PALLQSGLYT    180
LSSSVTVTSN TWPSQTITCN VAHPASSTKV DKKIEPRVPI TQNPCPPLKE CPPCAAPDAA    240
GGPSVFIFPP KIKDVLMISL SPMVTCVVVD VSEDDPDVQI SWFVNNVEVH TAQTQTHRED    300
YNSTLRVVSA LPIQHQDWMS GKEFKCKVNN RALGSPIEKT ISKPRGPVRA PQVYVLPPPA    360
EEMTKKEFSL TCMITGFLPA EIAVDWTSNG RTEQNYKNTA TVLDSDGSYF MYSKLRVQKS    420
TWERGSLFAC SVVHEGLHNH LTTKTISRSL GKGGGGSGGG GSGGGGSQYY DYDIPLFMYG    480
QISPNCAPEC NCPHSYPTAM YCDDLKLKSV PMVPPGIKYL YLRNNQIDHI DEKAFENVTD    540
LQWLILDHNL LENSKIKGKV FSKLKQLKKL HINYNNLTES VGPLPKSLQD LQLTNNKISK    600
LGSFDGLVNL TFIYLQHNQL KEDAVSASLK GLKSLEYLDL SFNQMSKLPA GLPTSLLTLY    660
LDNNKISNIP DEYFKRFTGL QYLRLSHNEL ADSGVPGNSF NISSLLELDL SYNKLKSIPT    720
VNENLENYYL EVNELEKFDV KSFCKILGPL SYSKIKHLRL DGNPLTQSSL PPDMYECLRV    780
ANEITVN                                                             787

SEQ ID NO: 150          moltype = AA  length = 215
FEATURE                 Location/Qualifiers
REGION                  1..215
                        note = Synthetic: 2C11 LC murine kappa
source                  1..215
                        mol_type = protein
                        organism = synthetic construct
SEQUENCE: 150
DIQMTQSPSS LPASLGDRVT INCQASQDIS NYLNWYQQKP GKAPKLLIYY TNKLADGVPS     60
RFSGSGSGRD SSFTISSLES EDIGSYYCQQ YYNYPWTFGP GTKLEIKRRA DAAPTVSIFP    120
PSSEQLTSGG ASVVCFLNNF YPKDINVKWK IDGSERQNGV LNSWTDQDSK DSTYSMSSTL    180
TLTKDEYERH NSYTCEATHK TSTSPIVKSF NRNEC                               215

SEQ ID NO: 151          moltype = AA  length = 786
FEATURE                 Location/Qualifiers
REGION                  1..786
                        note = Synthetic: 2C11 HC- lumican
source                  1..786
                        mol_type = protein
                        organism = synthetic construct
SEQUENCE: 151
EVQLVESGGG LVQPGKSLKL SCEASGFTFS GYGMHWVRQA PGRGLESVAY ITSSSINIKY     60
ADAVKGRFTV SRDNAKNLLF LQMNILKSED TAMYYCARPD WDKNYWGQGT MVTVSSAKTT    120
APSVYPLAPV CGGTTGSSVT LGCLVKGYFP EPVTLTWNSG SLSSGVHTFP ALLQSGLYTL    180
SSSVTVTSNT WPSQTITCNV AHPASSTKVD KKIEPRVPIT QNPCPPLKEC PPCAAPDAAG    240
GPSVFIFPPK IKDVLMISLS PMVTCVVVDV SEDDPDVQIS WFVNNVEVHT AQTQTHREDY    300
NSTLRVVSAL PIQHQDWMSG KEFKCKVNNR ALGSPIEKTI SKPRGPVRAP QVYVLPPPAE    360
EMTKKEFSLT CMITGFLPAE IAVDWTSNGR TEQNYKNTAT VLDSDGSYFM YSKLRVQKST    420
WERGSLFACS VVHEGLHNHL TTKTISRSLG KGGGGSGGGG SGGGGSQYYD YDIPLFMYGQ    480
ISPNCAPECN CPHSYPTAMY CDDLKLKSVP MVPPGIKYLY LRNNQIDHID EKAFENVTDL    540
QWLILDHNLL ENSKIKGKVF SKLKQLKKLH INYNNLTESV GPLPKSLQDL QLTNNKISKL    600
GSFDGLVNLT FIYLQHNQLK EDAVSASLKG LKSLEYLDLS FNQMSKLPAG LPTSLLTLYL    660
DNNKISNIPD EYFKRFTGLQ YLRLSHNELA DSGVPGNSFN ISSLLELDLS YNKLKSIPTV    720
NENLENYYLE VNELEKFDVK SFCKILGPLS YSKIKHLRLD GNPLTQSSLP PDMYECLRVA    780
```

```
                                                      -continued

NEITVN                                                                786

SEQ ID NO: 152           moltype = AA   length = 25
FEATURE                  Location/Qualifiers
REGION                   1..25
                         note = Synthetic: T2A peptide (furin cleavage site GSG T2A)
source                   1..25
                         mol_type = protein
                         organism = synthetic construct
SEQUENCE: 152
RRKRGSGEGR GSLLTCGDVE ENPGP                                           25

SEQ ID NO: 153           moltype = AA   length = 411
FEATURE                  Location/Qualifiers
REGION                   1..411
                         note = Synthetic: CCL3- Lumican
source                   1..411
                         mol_type = protein
                         organism = synthetic construct
SEQUENCE: 153
APYGADTPTA CCFSYSRKIP RQFIVDYFET SSLCSQPGVI FLTKRNRQIC ADSKETWVQE      60
YITDLELNAG GGSGGGSGGG SQYYDYDIPL FMYGQISPNC APECNCPHSY PTAMYCDDLK      120
LKSVPMVPPG IKYLYLRNNQ IDHIDEKAFE NVTDLQWLIL DHNLLENSKI KGKVFSKLKQ      180
LKKLHINYNN LTESVGPLPK SLQDLQLTNN KISKLGSFDG LVNLTFIYLQ HNQLKEDAVS      240
ASLKGLKSLE YLDLSFNQMS KLPAGLPTSL LTLYLDNNKI SNIPDEYFKR FTGLQYLRLS      300
HNELADSGVP GNSFNISSLL ELDLSYNKLK SIPTVNENLE NYYLEVNELE KFDVKSFCKI      360
LGPLSYSKIK HLRLDGNPLT QSSLPPDMYE CLRVANEITV NGGGSHHHHH H              411

SEQ ID NO: 154           moltype = AA   length = 411
FEATURE                  Location/Qualifiers
REGION                   1..411
                         note = Synthetic: Lumican CCL3
source                   1..411
                         mol_type = protein
                         organism = synthetic construct
SEQUENCE: 154
QYYDYDIPLF MYGQISPNCA PECNCPHSYP TAMYCDDLKL KSVPMVPPGI KYLYLRNNQI      60
DHIDEKAFEN VTDLQWLILD HNLLENSKIK GKVFSKLKQL KKLHINYNNL TESVGPLPKS      120
LQDLQLTNNK ISKLGSFDGL VNLTFIYLQH NQLKEDAVSA SLKGLKSLEY LDLSFNQMSK      180
LPAGLPTSLL TLYLDNNKIS NIPDEYFKRF TGLQYLRLSH NELADSGVPG NSFNISSLLE      240
LDLSYNKLKS IPTVNENLEN YYLEVNELEK FDVKSFCKIL GPLSYSKIKH LRLDGNPLTQ      300
SSLPPDMYEC LRVANEITVN GGGSGGGSGG GSAPYGADTP TACCFSYSRK IPRQFIVDYF      360
ETSSLCSQPG VIFLTKRNRQ ICADSKETWV QEYITDLELN AGGGSHHHHH H              411

SEQ ID NO: 155           moltype = AA   length = 79
FEATURE                  Location/Qualifiers
REGION                   1..79
                         note = Synthetic: CCL3
source                   1..79
                         mol_type = protein
                         organism = synthetic construct
SEQUENCE: 155
APYGADTPTA CCFSYSRKIP RQFIVDYFET SSLCSQPGVI FLTKRNRQIC ADSKETWVQE      60
YITDLELNAG GGSHHHHHH                                                  79

SEQ ID NO: 156           moltype = AA   length = 411
FEATURE                  Location/Qualifiers
REGION                   1..411
                         note = Synthetic: CCL4- lumican
source                   1..411
                         mol_type = protein
                         organism = synthetic construct
SEQUENCE: 156
APMGSDPPTS CCFSYTSRQL HRSFVMDYYE TSSLCSKPAV VFLTKRGRQI CANPSEPWVT      60
EYMSDLELNG GGSGGGSGGG SQYYDYDIPL FMYGQISPNC APECNCPHSY PTAMYCDDLK      120
LKSVPMVPPG IKYLYLRNNQ IDHIDEKAFE NVTDLQWLIL DHNLLENSKI KGKVFSKLKQ      180
LKKLHINYNN LTESVGPLPK SLQDLQLTNN KISKLGSFDG LVNLTFIYLQ HNQLKEDAVS      240
ASLKGLKSLE YLDLSFNQMS KLPAGLPTSL LTLYLDNNKI SNIPDEYFKR FTGLQYLRLS      300
HNELADSGVP GNSFNISSLL ELDLSYNKLK SIPTVNENLE NYYLEVNELE KFDVKSFCKI      360
LGPLSYSKIK HLRLDGNPLT QSSLPPDMYE CLRVANEITV NGGGSHHHHH H              411

SEQ ID NO: 157           moltype = AA   length = 411
FEATURE                  Location/Qualifiers
REGION                   1..411
                         note = Synthetic: Lumican CCL4
source                   1..411
                         mol_type = protein
                         organism = synthetic construct
SEQUENCE: 157
```

```
QYYDYDIPLF MYGQISPNCA PECNCPHSYP TAMYCDDLKL KSVPMVPPGI KYLYLRNNQI    60
DHIDEKAFEN VTDLQWLILD HNLLENSKIK GKVFSKLKQL KKLHINYNNL TESVGPLPKS   120
LQDLQLTNNK ISKLGSFDGL VNLTFIYLQH NQLKEDAVSA SLKGLKSLEY LDLSFNQMSK   180
LPAGLPTSLL TLYLDNNKIS NIPDEYFKRF TGLQYLRLSH NELADSGVPG NSFNISSLLE   240
LDLSYNKLKS IPTVNENLEN YYLEVNELEK FDVKSFCKIL GPLSYSKIKH LRLDGNPLTQ   300
SSLPPDMYEC LRVANEITVN GGGSGGGSGG GSAPMGSDPP TSCCFSYTSR QLHRSFVMDY   360
YETSSLCSKP AVVFLTKRGR QICANPSEPW VTEYMSDLEL NGGGSHHHHH H            411

SEQ ID NO: 158             moltype = AA   length = 79
FEATURE                    Location/Qualifiers
REGION                     1..79
                           note = Synthetic: CCL4
source                     1..79
                           mol_type = protein
                           organism = synthetic construct
SEQUENCE: 158
APMGSDPPTS CCFSYTSRQL HRSFVMDYYE TSSLCSKPAV VFLTKRGRQI CANPSEPWVT    60
EYMSDLELNG GGSHHHHHH                                                 79

SEQ ID NO: 159             moltype = AA   length = 410
FEATURE                    Location/Qualifiers
REGION                     1..410
                           note = Synthetic: CCL5- lumican
source                     1..410
                           mol_type = protein
                           organism = synthetic construct
SEQUENCE: 159
SPYGSDTTPC CFAYLSLALP RAHVKEYFYT SSKCSNLAVV FVTRRNRQVC ANPEKKWVQE    60
YINYLEMSGG GSGGGSGGGS QYYDYDIPLF MYGQISPNCA PECNCPHSYP TAMYCDDLKL   120
KSVPMVPPGI KYLYLRNNQI DHIDEKAFEN VTDLQWLILD HNLLENSKIK GKVFSKLKQL   180
KKLHINYNNL TESVGPLPKS LQDLQLTNNK ISKLGSFDGL VNLTFIYLQH NQLKEDAVSA   240
SLKGLKSLEY LDLSFNQMSK LPAGLPTSLL TLYLDNNKIS NIPDEYFKRF TGLQYLRLSH   300
NELADSGVPG NSFNISSLLE LDLSYNKLKS IPTVNENLEN YYLEVNELEK FDVKSFCKIL   360
GPLSYSKIKH LRLDGNPLTQ SSLPPDMYEC LRVANEITVN GGGSHHHHHH              410

SEQ ID NO: 160             moltype = AA   length = 410
FEATURE                    Location/Qualifiers
REGION                     1..410
                           note = Synthetic: Lumican CCL5
source                     1..410
                           mol_type = protein
                           organism = synthetic construct
SEQUENCE: 160
QYYDYDIPLF MYGQISPNCA PECNCPHSYP TAMYCDDLKL KSVPMVPPGI KYLYLRNNQI    60
DHIDEKAFEN VTDLQWLILD HNLLENSKIK GKVFSKLKQL KKLHINYNNL TESVGPLPKS   120
LQDLQLTNNK ISKLGSFDGL VNLTFIYLQH NQLKEDAVSA SLKGLKSLEY LDLSFNQMSK   180
LPAGLPTSLL TLYLDNNKIS NIPDEYFKRF TGLQYLRLSH NELADSGVPG NSFNISSLLE   240
LDLSYNKLKS IPTVNENLEN YYLEVNELEK FDVKSFCKIL GPLSYSKIKH LRLDGNPLTQ   300
SSLPPDMYEC LRVANEITVN GGGSGGGSGG GSSPYGSDTT PCCFAYLSLA LPRAHVKEYF   360
YTSSKCSNLA VVFVTRRNRQ VCANPEKKWV QEYINYLEMS GGGSHHHHHH              410

SEQ ID NO: 161             moltype = AA   length = 78
FEATURE                    Location/Qualifiers
REGION                     1..78
                           note = Synthetic: CCL5
source                     1..78
                           mol_type = protein
                           organism = synthetic construct
SEQUENCE: 161
SPYGSDTTPC CFAYLSLALP RAHVKEYFYT SSKCSNLAVV FVTRRNRQVC ANPEKKWVQE    60
YINYLEMSGG GSHHHHHH                                                  78

SEQ ID NO: 162             moltype = AA   length = 425
FEATURE                    Location/Qualifiers
REGION                     1..425
                           note = Synthetic: CCL19-Lumican
source                     1..425
                           mol_type = protein
                           organism = synthetic construct
SEQUENCE: 162
GANDAEDCCL SVTQRPIPGN IVKAFRYLLN EDGCRVPAVV FTTLRGYQLC APPDQPWVDR    60
IIRRLKKSSA KNKGNSTRRS PVSGGGSGGG SGGGSQYYDY DIPLFMYGQI SPNCAPECNC   120
PHSYPTAMYC DDLKLKSVPM VPPGIKYLYL RNNQIDHIDE KAFENVTDLQ WLILDHNLLE   180
NSKIKGKVFS KLKQLKKLHI NYNNLTESVG PLPKSLQDLQ LTNNKISKLG SFDGLVNLTF   240
IYLQHNQLKE DAVSASLKGL KSLEYLDLSF NQMSKLPAGL PTSLLTLYLD NNKISNIPDE   300
YFKRFTGLQY LRLSHNELAD SGVPGNSFNI SSLELDLSY NKLKSIPTVN ENLENYYLEV   360
NELEKFDVKS FCKILGPLSY SKIKHLRLDG NPLTQSSLPP DMYECLRVAN EITVNGGGSH   420
HHHH                                                                 425
```

```
SEQ ID NO: 163            moltype = AA   length = 424
FEATURE                   Location/Qualifiers
REGION                    1..424
                          note = Synthetic: Lumican CCL19
source                    1..424
                          mol_type = protein
                          organism = synthetic construct
SEQUENCE: 163
QYYDYDIPLF MYGQISPNCA PECNCPHSYP TAMYCDDLKL KSVPMVPPGI KYLYLRNNQI    60
DHIDEKAFEN VTDLQWLILD HNLLENSKIK GKVFSKLKQL KKLHINYNNL TESVGPLPKS   120
LQDLQLTNNK ISKLGSFDGL VNLTFIYLQH NQLKEDAVSA SLKGLKSLEY LDLSFNQMSK   180
LPAGLPTSLL TLYLDNNKIS NIPDEYFKRF TGLQYLRLSH NELADSGVPG NSFNISSLLE   240
LDLSYNKLKS IPTVNENLEN YYLEVNELEK FDVKSFCKIL GPLSYSKIKH LRLDGNPLTQ   300
SSLPPDMYEC LRVANEITVN GGGSGGGSGG GGANDAEDCC LSVTQRPIPG NIVKAFRYLL   360
NEDGCRVPAV VFTTLRGYQL CAPPDQPWVD RIIRRLKKSS AKNKGNSTRR SPVSGGGSHH   420
HHHH                                                                424

SEQ ID NO: 164            moltype = AA   length = 93
FEATURE                   Location/Qualifiers
REGION                    1..93
                          note = Synthetic: CCL19
source                    1..93
                          mol_type = protein
                          organism = synthetic construct
SEQUENCE: 164
GANDAEDCCL SVTQRPIPGN IVKAFRYLLN EDGCRVPAVV FTTLRGYQLC APPDQPWVDR    60
IIRRLKKSSA KNKGNSTRRS PVSGGGSHHH HHH                                 93

SEQ ID NO: 165            moltype = AA   length = 452
FEATURE                   Location/Qualifiers
REGION                    1..452
                          note = Synthetic: CCL21c - Lumican
source                    1..452
                          mol_type = protein
                          organism = synthetic construct
SEQUENCE: 165
SDGGGQDCCL KYSQKKIPYS IVRGYRKQEP SLGCPIPAIL FLPRKHSKPE LCANPEEGWV    60
QNLMRRLDQP PAPGKQSPGC RKNRGTSKSG KKGKGSKGCK RTEQTQPSRG GGGSGGGSGG   120
GSQYYDYDIP LFMYGQISPN CAPECNCPHS YPTAMYCDDL KLKSVPMVPP GIKYLYLRNN   180
QIDHIDEKAF ENVTDLQWLI LDHNLLENSK IKGKVFSKLK QLKKLHINYN NLTESVGPLP   240
KSLQDLQLTN NKISKLGSFD GLVNLTFIYL QHNQLKEDAV SASLKGLKSL EYLDLSFNQM   300
SKLPAGLPTS LLTLYLDNNK ISNIPDEYFK RFTGLQYLRL SHNELADSGV PGNSFNISSL   360
LELDLSYNKL KSIPTVNENL ENYYLEVNEL EKFDVKSFCK ILGPLSYSKI KHLRLDGNPL   420
TQSSLPPDMY ECLRVANEIT VNGGGSHHHH HH                                 452

SEQ ID NO: 166            moltype = AA   length = 451
FEATURE                   Location/Qualifiers
REGION                    1..451
                          note = Synthetic: Lumican CCL21c
source                    1..451
                          mol_type = protein
                          organism = synthetic construct
SEQUENCE: 166
QYYDYDIPLF MYGQISPNCA PECNCPHSYP TAMYCDDLKL KSVPMVPPGI KYLYLRNNQI    60
DHIDEKAFEN VTDLQWLILD HNLLENSKIK GKVFSKLKQL KKLHINYNNL TESVGPLPKS   120
LQDLQLTNNK ISKLGSFDGL VNLTFIYLQH NQLKEDAVSA SLKGLKSLEY LDLSFNQMSK   180
LPAGLPTSLL TLYLDNNKIS NIPDEYFKRF TGLQYLRLSH NELADSGVPG NSFNISSLLE   240
LDLSYNKLKS IPTVNENLEN YYLEVNELEK FDVKSFCKIL GPLSYSKIKH LRLDGNPLTQ   300
SSLPPDMYEC LRVANEITVN GGGSGGGSGG GSDGGGQDCC LKYSQKKIPY SIVRGYRKQE   360
PSLGCPIPAI LFLPRKHSKP ELCANPEEGW VQNLMRRLDQ PPAPGKQSPG CRKNRGTSKS   420
GKKGKGSKGC KRTEQTQPSR GGGGSHHHHH H                                  451

SEQ ID NO: 167            moltype = AA   length = 120
FEATURE                   Location/Qualifiers
REGION                    1..120
                          note = Synthetic: CCL21c
source                    1..120
                          mol_type = protein
                          organism = synthetic construct
SEQUENCE: 167
SDGGGQDCCL KYSQKKIPYS IVRGYRKQEP SLGCPIPAIL FLPRKHSKPE LCANPEEGWV    60
QNLMRRLDQP PAPGKQSPGC RKNRGTSKSG KKGKGSKGCK RTEQTQPSRG GGGSHHHHHH   120

SEQ ID NO: 168            moltype = AA   length = 417
FEATURE                   Location/Qualifiers
REGION                    1..417
                          note = Synthetic: truncated CCL21c-Lumican
source                    1..417
                          mol_type = protein
```

```
                        organism = synthetic construct
SEQUENCE: 168
SDGGGQDCCL KYSQKKIPYS IVRGYRKQEP SLGCPIPAIL FLPRKHSKPE LCANPEEGWV    60
QNLMRRLDQP PAPGKGGGSG GGSGGGSQYY DYDIPLFMYG QISPNCAPEC NCPHSYPTAM   120
YCDDLKLKSV PMVPPGIKYL YLRNNQIDHI DEKAFENVTD LQWLILDHNL LENSKIKGKV   180
FSKLKQLKKL HINYNNLTES VGPLPKSLQD LQLTNNKISK LGSFDGLVNL TFIYLQHNQL   240
KEDAVSASLK GLKSLEYLDL SFNQMSKLPA GLPTSLLTLY LDNNKISNIP DEYFKRFTGL   300
QYLRLSHNEL ADSGVPGNSF NISSLLELDL SYNKLKSIPT VNENLENYYL EVNELEKFDV   360
KSFCKILGPL SYSKIKHLRL DGNPLTQSSL PPDMYECLRV ANEITVNGGG SHHHHHH      417

SEQ ID NO: 169          moltype = AA  length = 417
FEATURE                 Location/Qualifiers
REGION                  1..417
                        note = Synthetic: Lumican truncated CCL21c
source                  1..417
                        mol_type = protein
                        organism = synthetic construct
SEQUENCE: 169
QYYDYDIPLF MYGQISPNCA PECNCPHSYP TAMYCDDLKL KSVPMVPPGI KYLYLRNNQI    60
DHIDEKAFEN VTDLQWLILD HNLLENSKIK GKVFSKLKQL KKLHINYNNL TESVGPLPKS   120
LQDLQLTNNK ISKLGSFDGL VNLTFIYLQH NQLKEDAVSA SLKGLKSLEY LDLSFNQMSK   180
LPAGLPTSLL TLYLDNNKIS NIPDEYFKRF TGLQYLRLSH NELADSGVPG NSFNISSLLE   240
LDLSYNKLKS IPTVNENLEN YYLEVNELEK FDVKSFCKIL GPLSYSKIKH LRLDGNPLTQ   300
SSLPPDMYEC LRVANEITVN GGGSGGGSGG GSSDGGGQDC CLKYSQKKIP YSIVRGYRKQ   360
EPSLGCPIPA ILFLPRKHSK PELCANPEEG WVQNLMRRLD QPPAPGKGGG SHHHHHH      417

SEQ ID NO: 170          moltype = AA  length = 85
FEATURE                 Location/Qualifiers
REGION                  1..85
                        note = Synthetic: truncated CCL21c
source                  1..85
                        mol_type = protein
                        organism = synthetic construct
SEQUENCE: 170
SDGGGQDCCL KYSQKKIPYS IVRGYRKQEP SLGCPIPAIL FLPRKHSKPE LCANPEEGWV    60
QNLMRRLDQP PAPGKGGGSH HHHH                                          85

SEQ ID NO: 171          moltype = AA  length = 84
FEATURE                 Location/Qualifiers
REGION                  1..84
                        note = Synthetic: CCL11
source                  1..84
                        mol_type = protein
                        organism = synthetic construct
SEQUENCE: 171
HPGSIPTSCC FIMTSKKIPN TLLKSYKRIT NNRCTLKAIV FKTRLGKEIC ADPKKKWVQD    60
ATKHLDQKLQ TPKPGGGSHH HHHH                                          84

SEQ ID NO: 172          moltype = AA  length = 416
FEATURE                 Location/Qualifiers
REGION                  1..416
                        note = Synthetic: CCL11 Lumican
source                  1..416
                        mol_type = protein
                        organism = synthetic construct
SEQUENCE: 172
HPGSIPTSCC FIMTSKKIPN TLLKSYKRIT NNRCTLKAIV FKTRLGKEIC ADPKKKWVQD    60
ATKHLDQKLQ TPKPGGGSGG GSGGGSQYYD YDIPLFMYGQ ISPNCAPECN CPHSYPTAMY   120
CDDLKLKSVP MVPPGIKYLY LRNNQIDHID EKAFENVTDL QWLILDHNLL ENSKIKGKVF   180
SKLKQLKKLH INYNNLTESV GPLPKSLQDL QLTNNKISKL GSFDGLVNLT FIYLQHNQLK   240
EDAVSASLKG LKSLEYLDLS FNQMSKLPAG LPTSLLTLYL DNNKISNIPD EYFKRFTGLQ   300
YLRLSHNELA DSGVPGNSFN ISSLLELDLS YNKLKSIPTV NENLENYYLE VNELEKFDVK   360
SFCKILGPLS YSKIKHLRLD GNPLTQSSLP DMYECLRVA NEITVNGGGS HHHHHH        416

SEQ ID NO: 173          moltype = AA  length = 1107
FEATURE                 Location/Qualifiers
REGION                  1..1107
                        note = Synthetic: CLEC2- MSA- lumican
source                  1..1107
                        mol_type = protein
                        organism = synthetic construct
SEQUENCE: 173
QQKYLLAEKE NLSATLQQLA KKFCQELIRQ SEIKTKSTFE HKCSPCATKW RYHGDSCYGF    60
FRRNLTWEES KQYCTEQNAT LVKTASQSTL DYIAERITSV RWIGLSRQNS KKDWMWEDSS   120
VLRKNGINLS GNTEENMNCA YLHNGKIHPA SCKERHYLIC ERNAGMTRVD QLLGGGSGGG   180
SGGGSEAHKS EIAHRYNDLG EQHFKGLVLI AFSQYLQKCS YDEHAKLVQE VTDFAKTCVA   240
DESAANCDKS LHTLFGDKLC AIPNLRENYG ELADCCTKQE PERNECFLQH KDDNPSLPPF   300
ERPEAEAMCT SFKENPTTFM GHYLHEVARR HPYFYAPELL YYAEQYNEIL TQCCAEADKE   360
SCLTPKLDGV KEKALVSSVR QRMKCSSMQK FGERAFKAWA VARLSQTFPN ADFAEITKLA   420
```

```
TDLTKVNKEC CHGDLLECAD DRAELAKYMC ENQATISSKL QTCCDKPLLK KAHCLSEVEH      480
DTMPADLPAI AADFVEDQEV CKNYAEAKDV FLGTFLYEYS RRHPDYSVSL LLRLAKKYEA      540
TLEKCCAEAN PPACYGTVLA EFQPLVEEPK NLVKTNCDLY EKLGEYGFQN AILVRYTQKA      600
PQVSTPTLVE AARNLGRVGT KCCTLPEDQR LPCVEDYLSA ILNRVCLLHE KTPVSEHVTK      660
CCSGSLVERR PCFSALTVDE TYVPKEFKAE TFTFHSDICT LPEKEKQIKK QTALAELVKH      720
KPKATAEQLK TVMDDFAQFL DTCCKAADKD TCFSTEGPNL VTRCKDALAG GGSGGGSQYY      780
DYDIPLFMYG QISPNCAPEC NCPHSYPTAM YCDDLKLKSV PMVPPGIKYL YLRNNQIDHI      840
DEKAFENVTD LQWLILDHNL LENSKIKGKV FSKLKQLKKL HINYNNLTES VGPLPKSLQD      900
LQLTNNKISK LGSFDGLVNL TFIYLQHNQL KEDAVSASLK GLKSLEYLDL SFNQMSKLPA      960
GLPTSLLTLY LDNNKISNIP DEYFKRFTGL QYLRLSHNEL ADSGVPGNSF NISSLLELDL     1020
SYNKLKSIPT VNENLENYYL EVNELEKFDV QSFCKILGPL SYSKIKHLRL DGNPLTQSSL     1080
PPDMYECLRV ANEITVNGGG SHHHHHH                                        1107

SEQ ID NO: 174          moltype = AA   length = 775
FEATURE                 Location/Qualifiers
REGION                  1..775
                        note = Synthetic: CLEC2- MSA
source                  1..775
                        mol_type = protein
                        organism = synthetic construct
SEQUENCE: 174
QQKYLLAEKE NLSATLQQLA KKFCQELIRQ SEIKTKSTFE HKCSPCATKW RYHGDSCYGF       60
FRRNLTWEES KQYCTEQNAT LVKTASQSTL DYIAERITSV RWIGLSRQNS KKDWMWEDSS      120
VLRKNGINLS GNTEENMNCA YLHNGKIHPA SCKERHYLIC ERNAGMTRVD QLLGGGSGGG      180
SGGGSEAHKS EIAHRYNDLG EQHFKGLVLI AFSQYLQKCS YDEHAKLVQE VTDFAKTCVA      240
DESAANCDKS LHTLFGDKLC AIPNLRENYG ELADCCTKQE PERNECFLQH KDDNPSLPPF      300
ERPEAEAMCT SFKENPTTFM GHYLHEVARR HPYFYAPELL YYAEQYNEIL TQCCAEADKE      360
SCLTPKLDGV KEKALVSSVR QRMKCSSMQK FGERAFKAWA VARLSQTFPN ADFAEITKLA      420
TDLTKVNKEC CHGDLLECAD DRAELAKYMC ENQATISSKL QTCCDKPLLK KAHCLSEVEH      480
DTMPADLPAI AADFVEDQEV CKNYAEAKDV FLGTFLYEYS RRHPDYSVSL LLRLAKKYEA      540
TLEKCCAEAN PPACYGTVLA EFQPLVEEPK NLVKTNCDLY EKLGEYGFQN AILVRYTQKA      600
PQVSTPTLVE AARNLGRVGT KCCTLPEDQR LPCVEDYLSA ILNRVCLLHE KTPVSEHVTK      660
CCSGSLVERR PCFSALTVDE TYVPKEFKAE TFTFHSDICT LPEKEKQIKK QTALAELVKH      720
KPKATAEQLK TVMDDFAQFL DTCCKAADKD TCFSTEGPNL VTRCKDALAH HHHHH          775

SEQ ID NO: 175          moltype = AA   length = 1061
FEATURE                 Location/Qualifiers
REGION                  1..1061
                        note = Synthetic: IFNg-MSA-lumican
source                  1..1061
                        mol_type = protein
                        organism = synthetic construct
SEQUENCE: 175
HGTVIESLES LNNYFNSSGI DVEEKSLFLD IWRNWQKDGD MKILQSQIIS FYLRLFEVLK       60
DNQAISNNIS VIESHLITTF FSNSKAKKDA FMSIAKFEVN NPQVQRQAFN ELIRVVHQLL      120
PESSLRKRKR SRCGSGGGSE AHKSEIAHRY NDLGEQHFKG LVLIAFSQYL QKCSYDEHAK      180
LVQEVTDFAK TCVADESAAN CDKSLHTLFG DKLCAIPNLR ENYGELADCC TKQEPERNEC      240
FLQHKDDNPS LPPFERPEAE AMCTSFKENP TTFMGHYLHE VARRHPYFYA PELLYYAEQY      300
NEILTQCCAE ADKESCLTPK LDGVKEKALV SSVRQRMKCS SMQKFGERAF KAWAVARLSQ      360
TFPNADFAEI TKLATDLTKV NKECCHGDLL ECADDRAELA KYMCENQATI SSKLQTCCDK      420
PLLKKAHCLS EVEHDTMPAD LPAIAADFVE DQEVCKNYAE AKDVFLGTFL YEYSRRHPDY      480
SVSLLLRLAK KYEATLEKCC AEANPPACYG TVLAEFQPLV EEPKNLVKTN CDLYEKLGEY      540
GFQNAILVRY TQKAPQVSTP TLVEAARNLG RVGTKCCTLP EDQRLPCVED YLSAILNRVC      600
LLHEKTPVSE HVTKCCSGSL VERRPCFSAL TVDETYVPKE FKAETFTFHS DICTLPEKEK      660
QIKKQTALAE LVKHKPKATA EQLKTVMDDF AQFLDTCCKA ADKDTCFSTE GPNLVTRCKD      720
ALAGGGSGGG SQYYDYDIPL FMYGQISPNC APECNCPHSY PTAMYCDDLK LKSVPMVPPG      780
IKYLYLRNNQ IDHIDEKAFE NVTDLQWLIL DHNLLENSKI KGKVFSKLKQ LKKLHINYNN      840
LTESVGPLPK SLQDLQLTNN KISKLGSFDG LVNLTFIYLQ HNQLKEDAVS ASLKGLKSLE      900
YLDLSFNQMS KLPAGLPTSL LTLYLDNNKI SNIPDEYFKR FTGLQYLRLS HNELADSGVP      960
GNSFNISSLL ELDLSYNKLK SIPTVNENLE NYYLEVNELE KFDVKSFCKI LGPLSYSKIK     1020
HLRLDGNPLT QSSLPPDMYE CLRVANEITV NGGGSHHHHH H                        1061

SEQ ID NO: 176          moltype = AA   length = 1210
FEATURE                 Location/Qualifiers
REGION                  1..1210
                        note = Synthetic: IFNg IFNg MSA- lumican
source                  1..1210
                        mol_type = protein
                        organism = synthetic construct
SEQUENCE: 176
HGTVIESLES LNNYFNSSGI DVEEKSLFLD IWRNWQKDGD MKILQSQIIS FYLRLFEVLK       60
DNQAISNNIS VIESHLITTF FSNSKAKKDA FMSIAKFEVN NPQVQRQAFN ELIRVVHQLL      120
PESSLRKRKR SRCGGGSGGG SGGGSGGGSH GTVIESLESL NNYFNSSGID VEEKSLFLDI      180
WRNWQKDGDM KILQSQIISF YLRLFEVLKD NQAISNNISV IESHLITTFF SNSKAKKDAF      240
MSIAKFEVNN PQVQRQAFNE LIRVVHQLLP ESSLRKRKRS RCGSGGGSEA HKSEIAHRYN      300
DLGEQHFKGL VLIAFSQYLQ KCSYDEHAKL VQEVTDFAKT CVADESAANC DKSLHTLFGD      360
KLCAIPNLRE NYGELADCCT KQEPERNECF LQHKDDNPSL PPFERPEAEA MCTSFKENPT      420
TFMGHYLHEV ARRHPYFYAP ELLYYAEQYN EILTQCCAEA DKESCLTPKL DGVKEKALVS      480
SVRQRMKCSS MQKFGERAFK AWAVARLSQT FPNADFAEIT KLATDLTKVN KECCHGDLLE      540
```

```
CADDRAELAK YMCENQATIS SKLQTCCDKP LLKKAHCLSE VEHDTMPADL PAIAADFVED    600
QEVCKNYAEA KDVFLGTFLY EYSRRHPDYS VSLLLRLAKK YEATLEKCCA EANPPACYGT    660
VLAEFQPLVE EPKNLVKTNC DLYEKLGEYG FQNAILVRYT QKAPQVSTPT LVEAARNLGR    720
VGTKCCTLPE DQRLPCVEDY LSAILNRVCL LHEKTPVSEH VTKCCSGSLV ERRPCFSALT    780
VDETYVPKEF KAETFTFHSD ICTLPEKEKQ IKKQTALAEL VKHKPKATAE QLKTVMDDFA    840
QFLDTCCKAA DKDTCFSTEG PNLVTRCKDA LAGGGSGGGS QYYDYDIPLF MYGQISPNCA    900
PECNCPHSYP TAMYCDDLKL KSVPMVPPGI KYLYLRNNQI DHIDEKAFEN VTDLQWLILD    960
HNLLENSKIK GKVFSKLKQL KKLHINYNNL TESVGPLPKS LQDLQLTNNK ISKLGSFDGL   1020
VNLTFIYLQH NQLKEDAVSA SLKGLKSLEY LDLSFNQMSK LPAGLPTSLL TLYLDNNKIS   1080
NIPDEYFKRF TGLQYLRLSH NELADSGVPG NSFNISSLLE LDLSYNKLKS IPTVNENLEN   1140
YYLEVNELEK FDVKSFCKIL GPLSYSKIKH LRLDGNPLTQ SSLPPDMYEC LRVANEITVN   1200
GGGSHHHHHH                                                          1210

SEQ ID NO: 177          moltype = AA  length = 878
FEATURE                 Location/Qualifiers
REGION                  1..878
                        note = Synthetic: IFNg IFNg MSA
source                  1..878
                        mol_type = protein
                        organism = synthetic construct
SEQUENCE: 177
HGTVIESLES LNNYFNSSGI DVEEKSLFLD IWRNWQKDGD MKILQSQIIS FYLRLFEVLK     60
DNQAISNNIS VIESHLITTF FSNSKAKKDA FMSIAKFEVN NPQVQRQAFN ELIRVVHQLL    120
PESSLRKRKR SRCGGGSGGG SGGGSGGGSH GTVIESLESL NNYFNSSGID VEEKSLFLDI    180
WRNWQKDGDM KILQSQIISF YLRLFEVLKD NQAISNNISV IESHLITTFF SNSKAKKDAF    240
MSIAKFEVNN PQVQRQAFNE LIRVVHQLLP ESSLRKRKRS RCGSGGGSEA HKSEIAHRYN    300
DLGEQHFKGL VLIAFSQYLQ KCSYDEHAKL VQEVTDFAKT CVADESAANC DKSLHTLFGD    360
KLCAIPNLRE NYGELADCCT KQEPERNECF LQHKDDNPSL PPFERPEAEA MCTSFKENPT    420
TFMGHYLHEV ARRHPYFYAP ELLYYAEQYN EILTQCCAEA DKESCLTPKL DGVKEKALVS    480
SVRQRMKCSS MQKFGERAFK AWAVARLSQT FPNADFAEIT KLATDLTKVN KECCHGDLLE    540
CADDRAELAK YMCENQATIS SKLQTCCDKP LLKKAHCLSE VEHDTMPADL PAIAADFVED    600
QEVCKNYAEA KDVFLGTFLY EYSRRHPDYS VSLLLRLAKK YEATLEKCCA EANPPACYGT    660
VLAEFQPLVE EPKNLVKTNC DLYEKLGEYG FQNAILVRYT QKAPQVSTPT LVEAARNLGR    720
VGTKCCTLPE DQRLPCVEDY LSAILNRVCL LHEKTPVSEH VTKCCSGSLV ERRPCFSALT    780
VDETYVPKEF KAETFTFHSD ICTLPEKEKQ IKKQTALAEL VKHKPKATAE QLKTVMDDFA    840
QFLDTCCKAA DKDTCFSTEG PNLVTRCKDA LAHHHHHH                            878

SEQ ID NO: 178          moltype = AA  length = 1055
FEATURE                 Location/Qualifiers
REGION                  1..1055
                        note = Synthetic: Lumican MSA - IFNg
source                  1..1055
                        mol_type = protein
                        organism = synthetic construct
SEQUENCE: 178
QYYDYDIPLF MYGQISPNCA PECNCPHSYP TAMYCDDLKL KSVPMVPPGI KYLYLRNNQI     60
DHIDEKAFEN VTDLQWLILD HNLLENSKIK GKVFSKLKQL KKLHINYNNL TESVGPLPKS    120
LQDLQLTNNK ISKLGSFDGL VNLTFIYLQH NQLKEDAVSA SLKGLKSLEY LDLSFNQMSK    180
LPAGLPTSLL TLYLDNNKIS NIPDEYFKRF TGLQYLRLSH NELADSGVPG NSFNISSLLE    240
LDLSYNKLKS IPTVNENLEN YYLEVNELEK FDVKSFCKIL GPLSYSKIKH LRLDGNPLTQ    300
SSLPPDMYEC LRVANEITVN GGGSGGGSEA HKSEIAHRYN DLGEQHFKGL VLIAFSQYLQ    360
KCSYDEHAKL VQEVTDFAKT CVADESAANC DKSLHTLFGD KLCAIPNLRE NYGELADCCT    420
KQEPERNECF LQHKDDNPSL PPFERPEAEA MCTSFKENPT TFMGHYLHEV ARRHPYFYAP    480
ELLYYAEQYN EILTQCCAEA DKESCLTPKL DGVKEKALVS SVRQRMKCSS MQKFGERAFK    540
AWAVARLSQT FPNADFAEIT KLATDLTKVN KECCHGDLLE CADDRAELAK YMCENQATIS    600
SKLQTCCDKP LLKKAHCLSE VEHDTMPADL PAIAADFVED QEVCKNYAEA KDVFLGTFLY    660
EYSRRHPDYS VSLLLRLAKK YEATLEKCCA EANPPACYGT VLAEFQPLVE EPKNLVKTNC    720
DLYEKLGEYG FQNAILVRYT QKAPQVSTPT LVEAARNLGR VGTKCCTLPE DQRLPCVEDY    780
LSAILNRVCL LHEKTPVSEH VTKCCSGSLV ERRPCFSALT VDETYVPKEF KAETFTFHSD    840
ICTLPEKEKQ IKKQTALAEL VKHKPKATAE QLKTVMDDFA QFLDTCCKAA DKDTCFSTEG    900
PNLVTRCKDA LAGGGSHGTV IESLESLNNY FNSSGIDVEE KSLFLDIWRN WQKDGDMKIL    960
QSQIISFYLR LFEVLKDNQA ISNNISVIES HLITTFFSNS KAKKDAFMSI AKFEVNNPQV   1020
QRQAFNELIR VVHQLLPESS LRKRKRSRCH HHHHH                              1055

SEQ ID NO: 179          moltype = AA  length = 1204
FEATURE                 Location/Qualifiers
REGION                  1..1204
                        note = Synthetic: Lumican MSA IFNg - IFNg
source                  1..1204
                        mol_type = protein
                        organism = synthetic construct
SEQUENCE: 179
QYYDYDIPLF MYGQISPNCA PECNCPHSYP TAMYCDDLKL KSVPMVPPGI KYLYLRNNQI     60
DHIDEKAFEN VTDLQWLILD HNLLENSKIK GKVFSKLKQL KKLHINYNNL TESVGPLPKS    120
LQDLQLTNNK ISKLGSFDGL VNLTFIYLQH NQLKEDAVSA SLKGLKSLEY LDLSFNQMSK    180
LPAGLPTSLL TLYLDNNKIS NIPDEYFKRF TGLQYLRLSH NELADSGVPG NSFNISSLLE    240
LDLSYNKLKS IPTVNENLEN YYLEVNELEK FDVKSFCKIL GPLSYSKIKH LRLDGNPLTQ    300
SSLPPDMYEC LRVANEITVN GGGSGGGSEA HKSEIAHRYN DLGEQHFKGL VLIAFSQYLQ    360
KCSYDEHAKL VQEVTDFAKT CVADESAANC DKSLHTLFGD KLCAIPNLRE NYGELADCCT    420
```

```
KQEPERNECF LQHKDDNPSL PPFERPEAEA MCTSFKENPT TFMGHYLHEV ARRHPYFYAP    480
ELLYYAEQYN EILTQCCAEA DKESCLTPKL DGVKEKALVS SVRQRMKCSS MQKFGERAFK    540
AWAVARLSQT FPNADFAEIT KLATDLTKVN KECCHGDLLE CADDRAELAK YMCENQATIS    600
SKLQTCCDKP LLKKAHCLSE VEHDTMPADL PAIAADFVED QEVCKNYAEA KDVFLGTFLY    660
EYSRRHPDYS VSLLLRLAKK YEATLEKCCA EANPPACYGT VLAEFQPLVE EPKNLVKTNC    720
DLYEKLGEYG FQNAILVRYT QKAPQVSTPT LVEAARNLGR VGTKCCTLPE DQRLPCVEDY    780
LSAILNRVCL LHEKTPVSEH VTKCCSGSLV ERRPCFSALT VDETYVPKEF KAETFTFHSD    840
ICTLPEKEKQ IKKQTALAEL VKHKPKATAE QLKTVMDDFA QFLDTCCKAA DKDTCFSTEG    900
PNLVTRCKDA LAGGGSHGTV IESLESLNNY FNSSGIDVEE KSLFLDIWRN WQKDGDMKIL    960
QSQIISFYLR LFEVLKDNQA ISNNISVIES HLITTFFSNS KAKKDAFMSI AKFEVNNPQV   1020
QRQAFNELIR VVHQLLPESS LRKRKRSRCG GGSGGGSGGG SGGSHGTVI ESLESLNNYF   1080
NSSGIDVEEK SLFLDIWRNW QKDGDMKILQ SQIISFYLRL FEVLKDNQAI SNNISVIESH   1140
LITTFFSNSK AKKDAFMSIA KFEVNNPQVQ RQAFNELIRV VHQLLPESSL RKRKRSRCHH   1200
HHHH                                                                1204

SEQ ID NO: 180          moltype = AA  length = 876
FEATURE                 Location/Qualifiers
REGION                  1..876
                        note = Synthetic: MSA- IFNg - IFNg
source                  1..876
                        mol_type = protein
                        organism = synthetic construct
SEQUENCE: 180
EAHKSEIAHR YNDLGEQHFK GLVLIAFSQY LQKCSYDEHA KLVQEVTDFA KTCVADESAA     60
NCDKSLHTLF GDKLCAIPNL RENYGELADC CTKQEPERNE CFLQHKDDNP SLPPFERPEA    120
EAMCTSFKEN PTTFMGHYLH EVARRHPYFY APELLYYAEQ YNEILTQCCA EADKESCLTP    180
KLDGVKEKAL VSSVRQRMKC SSMQKFGERA FKAWAVARLS QTFPNADFAE ITKLATDLTK    240
VNKECCHGDL LECADDRAEL AKYMCENQAT ISSKLQTCCD KPLLKKAHCL SEVEHDTMPA    300
DLPAIAADFV EDQEVCKNYA EAKDVFLGTF LYEYSRRHPD YSVSLLLRLA KKYEATLEKC    360
CAEANPPACY GTVLAEFQPL VEEPKNLVKT NCDLYEKLGE YGFQNAILVR YTQKAPQVST    420
PTLVEAARNL GRVGTKCCTL PEDQRLPCVE DYLSAILNRV CLLHEKTPVS EHVTKCCSGS    480
LVERRPCFSA LTVDETYVPK EFKAETFTPH SDICTLPEKE KQIKKQTALA ELVKHKPKAT    540
AEQLKTVMDD FAQFLDTCCK AADKDTCFST EGPNLVTRCK DALAGGGSHG TVIESLESLN    600
NYFNSSGIDV EEKSLFLDIW RNWQKDGDMK ILQSQIISFY LRLFEVLKDN QAISNNISVI    660
ESHLITTFFS NSKAKKDAFM SIAKFEVNNP QVQRQAFNEL IRVVHQLLPE SSLRKRKRSR    720
CGGGSGGGSG GGSGGGSHGT VIESLESLNN YFNSSGIDVE EKSLFLDIWR NWQKDGDMKI    780
LQSQIISFYL RLFEVLKDNQ AISNNISVIE SHLITTFFSN SKAKKDAFMS IAKFEVNNPQ    840
VQRQAFNELI RVVHQLLPES SLRKRKRSRC HHHHHH                              876

SEQ ID NO: 181          moltype = AA  length = 129
FEATURE                 Location/Qualifiers
REGION                  1..129
                        note = Synthetic: LAIR (H)6
source                  1..129
                        mol_type = protein
                        organism = synthetic construct
SEQUENCE: 181
QEGSLPDITI FPNSSLMISQ GTFVTVVCSY SDKHDLYNMV RLEKDGSTFM EKSTEPYKTE     60
DEFEIGPVNE TITGHYSCIY SKGITWSERS KTLELKVIKE NVIQTPAPGP TSDTSWLKTY    120
SIYHHHHHH                                                            129

SEQ ID NO: 182          moltype = AA  length = 319
FEATURE                 Location/Qualifiers
REGION                  1..319
                        note = misc_feature - Lumican (murine)
source                  1..319
                        mol_type = protein
                        organism = Mus musculus
SEQUENCE: 182
YYDYDIPLFM YGQISPNCAP ECNCPHSYPT AMYCDDLKLK SVPMVPPGIK YLYLRNNQID     60
HIDEKAFENV TDLQWLILDH NLLENSKIKG KVFSKLKQLK KLHINYNNLT ESVGPLPKSL    120
QDLQLTNNKI SKLGSFDGLV NLTFIYLQHN QLKEDAVSAS LKGLKSLEYL DLSFNQMSKL    180
PAGLPTSLLT LYLDNNKISN IPDEYFKRFT GLQYLRLSHN ELADSGVPGN SFNISSLLEL    240
DLSYNKLKSI PTVNENLENY YLEVNELEKF DVKSFCKILG PLSYSKIKHL RLDGNPLTQS    300
SLPPDMYECL RVANEITVN                                                 319

SEQ ID NO: 183          moltype = AA  length = 584
FEATURE                 Location/Qualifiers
REGION                  1..584
                        note = misc_feature - murine MSA
source                  1..584
                        mol_type = protein
                        organism = Mus musculus
SEQUENCE: 183
EAHKSEIAHR YNDLGEQHFK GLVLIAFSQY LQKCSYDEHA KLVQEVTDFA KTCVADESAA     60
NCDKSLHTLF GDKLCAIPNL RENYGELADC CTKQEPERNE CFLQHKDDNP SLPPFERPEA    120
EAMCTSFKEN PTTFMGHYLH EVARRHPYFY APELLYYAEQ YNEILTQCCA EADKESCLTP    180
KLDGVKEKAL VSSVRQRMKC SSMQKFGERA FKAWAVARLS QTFPNADFAE ITKLATDLTK    240
VNKECCHGDL LECADDRAEL AKYMCENQAT ISSKLQTCCD KPLLKKAHCL SEVEHDTMPA    300
```

```
DLPAIAADFV EDQEVCKNYA EAKDVFLGTF LYEYSRRHPD YSVSLLLRLA KKYEATLEKC    360
CAEANPPACY GTVLAEFQPL VEEPKNLVKT NCDLYEKLGE YGFQNAILVR YTQKAPQVST    420
PTLVEAARNL GRVGTKCCTL PEDQRLPCVE DYLSAILNRV CLLHEKTPVS EHVTKCCSGS    480
LVERRPCFSA LTVDETYVPK EFKAETFTFH SDICTLPEKE KQIKKQTALA ELVKHKPKAT    540
AEQLKTVMDD FAQFLDTCCK AADKDTCFST EGPNLVTRCK DALA                    584

SEQ ID NO: 184            moltype = AA   length = 213
FEATURE                   Location/Qualifiers
REGION                    1..213
                          note = Synthetic: 3/23 LC murine kappa
source                    1..213
                          mol_type = protein
                          organism = synthetic construct
SEQUENCE: 184
DTVLTQSPAL AVSPGERVTI SCRASESVST RMHWYQQRPG QPPKLLIYVA SRLESGVPAR     60
FSGGGSGTDF TLTIDPVEAN DTATYFCQQS WNDPWTFGGG TKLELKRADA APTVSIFPPS    120
SEQLTSGGAS VVCFLNNFYP KDINVKWKID GSERQNGVLN SWTDQDSKDS TYSMSSTLTL    180
TKDEYERHNS YTCEATHKTS TSPIVKSFNR NEC                                 213

SEQ ID NO: 185            moltype = AA   length = 786
FEATURE                   Location/Qualifiers
REGION                    1..786
                          note = Synthetic: 3/23 HC-lumican
source                    1..786
                          mol_type = protein
                          organism = synthetic construct
SEQUENCE: 185
EVQLVESGGG LVQPGRSLKL SCAASGFTLS DYYMAWVRQA PKKGLEWVAS INYEGSSTYY     60
GESVKGRFTI SRDNAKSTLY LQMNSLRSED TATYYCVRHD NYFDYWGQGV LVTVSSAKTT    120
APSVYPLAPV CGGTTGSSVT LGCLVKGYFP EPVTLTWNSG SLSSGVHTFP ALLQSGLYTL    180
SSSVTVTSNT WPSQTITCNV AHPASSTKVD KKIEPRVPIT QNPCPPLKEC PPCAAPDAAG    240
GPSVFIFPPK IKDVLMISLS PMVTCVVVDV SEDDPDVQIS WFVNNVEVHT AQTQTHREDY    300
NSTLRVVSAL PIQHQDWMSG KEFKCKVNNR ALGSPIEKTI SKPRGPVRAP QVYVLPPPAE    360
EMTKKEFSLT CMITGFLPAE IAVDWTSNGR TEQNYKNTAT VLDSDGSYFM YSKLRVQKST    420
WERGSLFACS VVHEGLHNHL TTKTISRSLG KGGGGSGGGG SGGGGSQYYD YDIPLFMYGQ    480
ISPNCAPECN CPHSYPTAMY CDDLKLKSVP MVPPGIKYLY LRNNQIDHID EKAFENVTDL    540
QWLILDHNLL ENSKIKGKVF SKLKQLKKLH INYNNLTESV GPLPKSLQDL QLTNNKISKL    600
GSFDGLVNLT FIYLQHNQLK EDAVSASLKG LKSLEYLDLS FNQMSKLPAG LPTSLLTLYL    660
DNNKISNIPD EYFKRFTGLQ YLRLSHNELA DSGVPGNSFN ISSLLELDLS YNKLKSIPTV    720
NENLENYYLE VNELEKFDVK SFCKILGPLS YSKIKHLRLD GNPLTQSSLP PDMYECLRVA    780
NEITVN                                                               786

SEQ ID NO: 186            moltype = AA   length = 869
FEATURE                   Location/Qualifiers
REGION                    1..869
                          note = Synthetic: LAIR-MSA-IL2
source                    1..869
                          mol_type = protein
                          organism = synthetic construct
SEQUENCE: 186
QEGSLPDITI FPNSSLMISQ GTFVTVVCSY SDKHDLYNMV RLEKDGSTFM EKSTEPYKTE     60
DEFEIGPVNE TITGHYSCIY SKGITWSERS KTLELKVIKE NVIQTPAPGP TSDTSWLKTY    120
SIYGGSEAHK SEIAHRYNDL GEQHFKGLVL IAFSQYLQKC SYDEHAKLVQ EVTDFAKTCV    180
ADESAANCDK SLHTLFGDKL CAIPNLRENY GELADCCTKQ EPERNECFLQ HKDDNPSLPP    240
FERPEAEAMC TSFKENPTTF MGHYLHEVAR RHPYFYAPEL LYYAEQYNEI LTQCCAEADK    300
ESCLTPKLDG VKEKALVSSV RQRMKCSSMQ KFGERAFKAW AVARLSQTFP NADFAEITKL    360
ATDLTKVNKE CCHGDLLECA DDRAELAKYM CENQATISSK LQTCCDKPLL KKAHCLSEVE    420
HDTMPADLPA IAADFVEDQE VCKNYAEAKD VFLGTFLYEY SRRHPDYSVS LLLRLAKKYE    480
ATLEKCCAEA NPPACYGTVL AEFQPLVEEP KNLVKTNCDL YEKLGEYGFQ NAILVRYTQK    540
APQVSTPTLV EAARNLGRVG TKCCTLPEDQ RLPCVEDYLS AILNRVCLLH EKTPVSEHVT    600
KCCSGSLVER RPCFSALTVD ETYVPKEFKA ETFTFHSDIC TLPEKEKQIK KQTALAELVK    660
HKPKATAEQL KTVMDDFAQF LDTCCKAADK DTCFSTEGPN LVTRCKDALA GGGSAPTSSS    720
TSSSTAEAQQ QQQQQQQQQQ HLEQLLMDLQ ELLSRMENYR NLKLPRMLTF KFYLPKQATE    780
LKDLQCLEDE LGPLRHVLDL TQSKSFQLED AENFISNIRV TVVKLKGSDN TFECQFDDES    840
ATVVDFLRRW IAFCQSIIST SPQHHHHHH                                      869

SEQ ID NO: 187            moltype = AA   length = 123
FEATURE                   Location/Qualifiers
REGION                    1..123
                          note = Synthetic: LAIR30.w.A
source                    1..123
                          mol_type = protein
                          organism = synthetic construct
SEQUENCE: 187
QEGSLPDITI FPNSSLMISQ GTFVTVACSY SDKHDLYNMV RLEKGGSTFM EKSTEPYKTE     60
DEFEIGPVNE TITGHYSCIY SKGITWSERS KTLELKVIKE NVIQTPAPGP TSDTSWLKTY    120
SIY                                                                  123

SEQ ID NO: 188            moltype = AA   length = 123
```

```
                        -continued
FEATURE                 Location/Qualifiers
REGION                  1..123
                        note = Synthetic: LAIR30.w.B
source                  1..123
                        mol_type = protein
                        organism = synthetic construct
SEQUENCE: 188
QEGSLPDITI FPNSSLMISQ GTFVTVVCSY SDKHDLYNMV RLEKDGSTSM EKSTEPYKTE   60
DEFEIGPVNE TITGHYSCIY SKGITWSERS KTLELKVIKE NVIQTPAPGP TSDTSWLKTY  120
SIY                                                                123

SEQ ID NO: 189          moltype = AA  length = 123
FEATURE                 Location/Qualifiers
REGION                  1..123
                        note = Synthetic: LAIR30.w.C
source                  1..123
                        mol_type = protein
                        organism = synthetic construct
SEQUENCE: 189
QEGSLPDITI FPNSSLMISQ GTFVTVVCSY SDKHDLYNMV RLEKDGSTFM GKSTEPYKTE   60
DEFEIGPVNE TITGHYSCIY SKGITWSERS KTLELKVIKE NVIQTPAPGP TSDTSWLKTY  120
SIY                                                                123

SEQ ID NO: 190          moltype = AA  length = 123
FEATURE                 Location/Qualifiers
REGION                  1..123
                        note = Synthetic: LAIR30.d.D
source                  1..123
                        mol_type = protein
                        organism = synthetic construct
SEQUENCE: 190
QEGSLPDITI FPNSSLMISQ GTFVTVVCSY SDKHDLYNMV RLAKDGSTFM EKSTEPYKTE   60
DEFEIGPVNE TITGHYSCIY SKGITWSERS KTLELKVIKE NVIQTPAPGP TSDTSWLKTY  120
SIY                                                                123

SEQ ID NO: 191          moltype = AA  length = 123
FEATURE                 Location/Qualifiers
REGION                  1..123
                        note = Synthetic: LAIR30.w.E
source                  1..123
                        mol_type = protein
                        organism = synthetic construct
SEQUENCE: 191
QEGSLPDITI FPNSSLMISQ GTFVTVVCSY SDKHDLYNMV RLEKDGSTFM EKSTEPYKTE   60
DELEIGPVNE TITGHYSCIY SKGITWSERS KTLELKVIKE NVIQTPAPGP TSDTSWLKTY  120
SIY                                                                123

SEQ ID NO: 192          moltype = AA  length = 123
FEATURE                 Location/Qualifiers
REGION                  1..123
                        note = Synthetic: LAIR30.w.F
source                  1..123
                        mol_type = protein
                        organism = synthetic construct
SEQUENCE: 192
QEGSLPDITI FPNSSLMISQ GTFVTVVCSY SDKHDLYNMV RLEKDGSTFM EKSTEPYKTE   60
DEFEIGPVNE TITGHYSCIY SKGITWSERA KTLELKVIKE NVIQTPAPGP TSDTSWLKTY  120
SIY                                                                123

SEQ ID NO: 193          moltype = AA  length = 123
FEATURE                 Location/Qualifiers
REGION                  1..123
                        note = Synthetic: LAIR30.2.K1.B
source                  1..123
                        mol_type = protein
                        organism = synthetic construct
SEQUENCE: 193
QEGSLPDITI FPNSSLVISQ GTFVTVVCSY SDKHDLYNMV RLEKDGSTFM EKSTAPYKTE   60
DEFEIGPVNE TITGHYSCIY SKGITWSERS KTLELKVIKE NVIQTPAPGP TSDTLWLKTY  120
SIY                                                                123

SEQ ID NO: 194          moltype = AA  length = 720
FEATURE                 Location/Qualifiers
REGION                  1..720
                        note = Synthetic: LAIR-MSA
source                  1..720
                        mol_type = protein
                        organism = synthetic construct
SEQUENCE: 194
```

```
QEGSLPDITI FPNSSLMISQ GTFVTVVCSY SDKHDLYNMV RLEKDGSTFM EKSTEPYKTE  60
DEFEIGPVNE TITGHYSCIY SKGITWSERS KTLELKVIKE NVIQTPAPGP TSDTSWLKTY 120
SIYGGSEAHK SEIAHRYNDL GEQHFKGLVL IAFSQYLQKC SYDEHAKLVQ EVTDFAKTCV 180
ADESAANCDK SLHTLFGDKL CAIPNLRENY GELADCCTKQ EPERNECFLQ HKDDNPSLPP 240
FERPEAEAMC TSFKENPTTF MGHYLHEVAR RHPFYAPEL LYYAEQYNEI LTQCCAEADK 300
ESCLTPKLDG VKEKALVSSV RQRMKCSSMQ KFGERAFKAW AVARLSQTFP NADFAEITKL 360
ATDLTKVNKE CCHGDLLECA DDRAELAKYM CENQATISSK LQTCCDKPLL KKAHCLSEVE 420
HDTMPADLPA IAADFVEDQE VCKNYAEAKD VFLGTFLYEY SRRHPDYSVS LLLRLAKKYE 480
ATLEKCCAEA NPPACYGTVL AEFQPLVEEP KNLVKTNCDL YEKLGEYGFQ NAILVRYTQK 540
APQVSTPTLV EAARNLGRVG TKCCTLPEDQ RLPCVEDYLS AILNRVCLLH EKTPVSEHVT 600
KCCSGSLVER RPCFSALTVD ETYVPKEFKA ETFTFHSDIC TLPEKEKQIK KQTALAELVK 660
HKPKATAEQL KTVMDDFAQF LDTCCKAADK DTCFSTEGPN LVTRCKDALA GGGSHHHHHH 720

SEQ ID NO: 195         moltype = AA   length = 476
FEATURE                Location/Qualifiers
REGION                 1..476
                       note = Synthetic: 4420 HC-LAIR
source                 1..476
                       mol_type = protein
                       organism = synthetic construct
SEQUENCE: 195
DVKLDETGGG LVQPGRPMKL SCVASGFTFS DYWMNWVRQS PEKGLEWVAQ IRNKPYNYET  60
YYSDSVKGRF TISRDDSKSS VYLQMNNLRV EDMGIYYCTG SYYGMDYWGQ GTSVTVSATT 120
KGPSVYPLAP GSAAQTNSMV TLGCLVKGYF PEPVTVTWNS GSLSSGVHTF PAVLQSDLYT 180
LSSSVTVPSS TWPSQTVTCN VAHPASSTKV DKKIVPRDCG CKPCICTVPE VSSVFIFPPK 240
PKDVLTITLT PKVTCVVVDI SKDDPEVQFS WFVDDVEVHT AQTKPREEQI NSTFRSVSEL 300
PIMHQDWLNG KEFKCRVNSA AFPAPIEKTI SKTKGRPKGG GGSGGGSGG GGSQEGSLPD 360
ITIFPNSSLM ISQGTFVTVV CSYSDKHDLY NMVRLEKDGS TFMEKSTEPY KTEDEFEIGP 420
VNETITGHYS CIYSKGITWS ERSKTLELKV IKENVIQTPA PGPTSDTSWL KTYSIY     476

SEQ ID NO: 196         moltype = AA   length = 475
FEATURE                Location/Qualifiers
REGION                 1..475
                       note = Synthetic: 3/23 HC-LAIR
source                 1..475
                       mol_type = protein
                       organism = synthetic construct
SEQUENCE: 196
EVQLVESGGG LVQPGRSLKL SCAASGFTLS DYYMAWVRQA PKKGLEWVAS INYEGSSTYY  60
GESVKGRFTI SRDNAKSTLY LQMNSLRSED TATYYCVRHD NYFDYWGQGV LVTVSSATTK 120
GPSVYPLAPG SAAQTNSMVT LGCLVKGYFP EPVTVTWNSG SLSSGVHTFP AVLQSDLYTL 180
SSSVTVPSST WPSQTVTCNV AHPASSTKVD KKIVPRDCGC KPCICTVPEV SSVFIFPPKP 240
KDVLTITLTP KVTCVVVDIS KDDPEVQFSW FVDDVEVHTA QTKPREEQIN STFRSVSELP 300
IMHQDWLNGK EFKCRVNSAA FPAPIEKTIS KTKGRPKGGG GSGGGSGGG GSQEGSLPDI 360
TIFPNSSLMI SQGTFVTVVC SYSDKHDLYN MVRLEKDGST FMEKSTEPYK TEDEFEIGPV 420
NETITGHYSC IYSKGITWSE RSKTLELKVI KENVIQTPAP GPTSDTSWLK TYSIY      475

SEQ ID NO: 197         moltype = AA   length = 479
FEATURE                Location/Qualifiers
REGION                 1..479
                       note = Synthetic: LOB12.3 HC-LAIR
source                 1..479
                       mol_type = protein
                       organism = synthetic construct
SEQUENCE: 197
DVQLVESGGG LVQPGRSLKL SCAASGFIFS YFDMAWVRQA PTKGLEWVAS ISPDGSIPYY  60
RDSVKGRFTV SRENAKSSLY LQMDSLRSED TATYYCARRS YGGYSEIDYW GQGVMVTVSS 120
ATTKGPSVYP LAPGSAAQTN SMVTLGCLVK GYFPEPVTVT WNSGSLSSGV HTFPAVLQSD 180
LYTLSSSVTV PSSTWPSQTV TCNVAHPASS TKVDKKIVPR DCGCKPCICT VPEVSSVFIF 240
PPKPKDVLTI TLTPKVTCVV VDISKDDPEV QFSWFVDDVE VHTAQTKPRE EQINSTFRSV 300
SELPIMHQDW LNGKEFKCRV NSAAFPAPIE KTISKTKGRP KGGGGSGGG SGGGGSQEGS 360
LPDITIFPNS SLMISQGTFV TVVCSYSDKH DLYNMVRLEK DGSTFMEKST EPYKTEDEFE 420
IGPVNETITG HYSCIYSKGI TWSERSKTLE LKVIKENVIQ TPAPGPTSDT SWLKTYSIY  479

SEQ ID NO: 198         moltype = AA   length = 476
FEATURE                Location/Qualifiers
REGION                 1..476
                       note = Synthetic: OX86 HC-LAIR
source                 1..476
                       mol_type = protein
                       organism = synthetic construct
SEQUENCE: 198
QVQLKESGPG LVQPSQTLSL TCTVSGFSLT GYNLHWVRQP PGKGLEWMGR MRYDGDTYYN  60
SVLKSRLSIS RDTSKNQVFL KMNSLQTDDT AIYYCTRDGR GDSFDYWGQG VMVTVSSATT 120
KGPSVYPLAP GSAAQTNSMV TLGCLVKGYF PEPVTVTWNS GSLSSGVHTF PAVLQSDLYT 180
LSSSVTVPSS TWPSQTVTCN VAHPASSTKV DKKIVPRDCG CKPCICTVPE VSSVFIFPPK 240
PKDVLTITLT PKVTCVVVDI SKDDPEVQFS WFVDDVEVHT AQTKPREEQI NSTFRSVSEL 300
PIMHQDWLNG KEFKCRVNSA AFPAPIEKTI SKTKGRPKGG GGSGGGSGG GGSQEGSLPD 360
ITIFPNSSLM ISQGTFVTVV CSYSDKHDLY NMVRLEKDGS TFMEKSTEPY KTEDEFEIGP 420
```

```
VNETITGHYS CIYSKGITWS ERSKTLELKV IKENVIQTPA PGPTSDTSWL KTYSIY        476

SEQ ID NO: 199              moltype = AA  length = 475
FEATURE                     Location/Qualifiers
REGION                      1..475
                            note = Synthetic: 2C11 HC-LAIR
source                      1..475
                            mol_type = protein
                            organism = synthetic construct
SEQUENCE: 199
EVQLVESGGG LVQPGKSLKL SCEASGFTFS GYGMHWVRQA PGRGLESVAY ITSSSINIKY     60
ADAVKGRFTV SRDNAKNLLF LQMNILKSED TAMYYCARFD WDKNYWGQGT MVTVSSATTK    120
GPSVYPLAPG SAAQTNSMVT LGCLVKGYFP EPVTVTWNSG SLSSGVHTFP AVLQSDLYTL    180
SSSVTVPSST WPSQTVTCNV AHPASSTKVD KKIVPRDCGC KPCICTVPEV SSVFIFPPKP    240
KDVLTITLTP KVTCVVVDIS KDDPEVQFSW FVDDVEVHTA QTKPREEQIN STFRSVSELP    300
IMHQDWLNGK EFKCRVNSAA FPAPIEKTIS KTKGRPKGGG GSGGGGSGGG GSQEGSLPDI    360
TIFPNSSLMI SQGTFVTVVC SYSDKHDLYN MVRLEKDGST FMEKSTEPYK TEDEFEIGPV    420
NETITGHYSC IYSKGITWSE RSKTLELKVI KENVIQTPAP GPTSDTSWLK TYSIY         475

SEQ ID NO: 200              moltype = AA  length = 27
FEATURE                     Location/Qualifiers
REGION                      1..27
                            note = Synthetic: Linker
REGION                      12..26
                            note = misc_feature - "Glu Ala Ala Ala Lys" may or may not
                             be present
source                      1..27
                            mol_type = protein
                            organism = synthetic construct
SEQUENCE: 200
AEAAAKEAAA KEAAAKEAAA KEAAAKA                                         27

SEQ ID NO: 201              moltype = AA  length = 4
FEATURE                     Location/Qualifiers
REGION                      1..4
                            note = Synthetic: Linker
source                      1..4
                            mol_type = protein
                            organism = synthetic construct
SEQUENCE: 201
GGSG                                                                   4

SEQ ID NO: 202              moltype = AA  length = 20
FEATURE                     Location/Qualifiers
REGION                      1..20
                            note = Synthetic: Linker
REGION                      5..20
                            note = misc_feature - "Gly Gly Ser Gly" may or may not be
                             present
source                      1..20
                            mol_type = protein
                            organism = synthetic construct
SEQUENCE: 202
GGSGGGSGGG SGGGSGGGSG                                                  20

SEQ ID NO: 203              moltype = AA  length = 4
FEATURE                     Location/Qualifiers
REGION                      1..4
                            note = Synthetic: Linker
source                      1..4
                            mol_type = protein
                            organism = synthetic construct
SEQUENCE: 203
GSAT                                                                   4

SEQ ID NO: 204              moltype = AA  length = 30
FEATURE                     Location/Qualifiers
REGION                      1..30
                            note = Synthetic: Linker
REGION                      7..30
                            note = misc_feature - "Gly Gly Ser Gly Gly Ser" may or may
                             not be present
source                      1..30
                            mol_type = protein
                            organism = synthetic construct
SEQUENCE: 204
GGSGGSGGSG GSGGSGGSGG SGGSGGSGGS                                       30

SEQ ID NO: 205              moltype = DNA  length = 25
```

| | |
|---|---|
| FEATURE | Location/Qualifiers |
| misc_feature | 1..25 |
| | note = Synthetic: lipophilic-CpG oligonucleotide |
| misc_feature | 1 |
| | note = 5 lipophilic compound, such as diacyl lipid |
| misc_feature | 1 |
| | note = 5' lipophilic compound, such as diacyl lipid |
| misc_feature | 2..5 |
| | note = g may or may not be present |
| source | 1..25 |
| | mol_type = other DNA |
| | organism = synthetic construct |

SEQUENCE: 205
ggggggtccat gacgttcctg acgtt                                25

| | |
|---|---|
| SEQ ID NO: 206 | moltype = DNA   length = 12 |
| FEATURE | Location/Qualifiers |
| misc_feature | 1..12 |
| | note = Synthetic: oligonucleotide linker |
| misc_feature | 1 |
| | note = 5' lipo |
| source | 1..12 |
| | mol_type = other DNA |
| | organism = synthetic construct |

SEQUENCE: 206
tttttttttt cg                                12

| | |
|---|---|
| SEQ ID NO: 207 | moltype = DNA   length = 12 |
| FEATURE | Location/Qualifiers |
| misc_feature | 1..12 |
| | note = Synthetic: oligonucleotide linker |
| misc_feature | 1 |
| | note = 5' lipo |
| source | 1..12 |
| | mol_type = other DNA |
| | organism = synthetic construct |

SEQUENCE: 207
ggtttttttt cg                                12

| | |
|---|---|
| SEQ ID NO: 208 | moltype = DNA   length = 12 |
| FEATURE | Location/Qualifiers |
| misc_feature | 1..12 |
| | note = Synthetic: oligonucleotide linker |
| misc_feature | 1 |
| | note = 5' lipo |
| source | 1..12 |
| | mol_type = other DNA |
| | organism = synthetic construct |

SEQUENCE: 208
ggggtttttt cg                                12

| | |
|---|---|
| SEQ ID NO: 209 | moltype = DNA   length = 12 |
| FEATURE | Location/Qualifiers |
| misc_feature | 1..12 |
| | note = Synthetic: oligonucleotide linker |
| misc_feature | 1 |
| | note = 5' lipo |
| source | 1..12 |
| | mol_type = other DNA |
| | organism = synthetic construct |

SEQUENCE: 209
ggggggtttt cg                                12

| | |
|---|---|
| SEQ ID NO: 210 | moltype = DNA   length = 12 |
| FEATURE | Location/Qualifiers |
| misc_feature | 1..12 |
| | note = Synthetic: oligonucleotide linker |
| misc_feature | 1 |
| | note = 5' lipo |
| source | 1..12 |
| | mol_type = other DNA |
| | organism = synthetic construct |

SEQUENCE: 210
gggggggggtt cg                                12

| | |
|---|---|
| SEQ ID NO: 211 | moltype = DNA   length = 12 |
| FEATURE | Location/Qualifiers |
| misc_feature | 1..12 |
| | note = Synthetic: oligonucleotide linker |

-continued

```
misc_feature        1
                    note = 5' lipo
source              1..12
                    mol_type = other DNA
                    organism = synthetic construct
SEQUENCE: 211
gggggggggg cg                                                        12

SEQ ID NO: 212      moltype = AA  length = 37
FEATURE             Location/Qualifiers
REGION              1..37
                    note = Synthetic: soluble collagen peptide mimic
SITE                3
                    note = misc_feature - Xaa is a hydroxyproline amino acid
SITE                6
                    note = misc_feature - Xaa is a hydroxyproline amino acid
SITE                9
                    note = misc_feature - Xaa is a hydroxyproline amino acid
SITE                12
                    note = misc_feature - Xaa is a hydroxyproline amino acid
SITE                15
                    note = misc_feature - Xaa is a hydroxyproline amino acid
SITE                18
                    note = misc_feature - Xaa is a hydroxyproline amino acid
SITE                21
                    note = misc_feature - Xaa is a hydroxyproline amino acid
SITE                24
                    note = misc_feature - Xaa is a hydroxyproline amino acid
SITE                27
                    note = misc_feature - Xaa is a hydroxyproline amino acid
SITE                30
                    note = misc_feature - Xaa is a hydroxyproline amino acid
SITE                33
                    note = misc_feature - Xaa is a hydroxyproline amino acid
SITE                36
                    note = misc_feature - Xaa is a hydroxyproline amino acid
SITE                37
                    note = misc_feature - NH2 group at 3' end
source              1..37
                    mol_type = protein
                    organism = synthetic construct
SEQUENCE: 212
GCXGPXGPXG PXGPXGPXGP XGPXGPXGPX GPXGCXG                             37
```